US006733993B2

(12) United States Patent
Emini et al.

(10) Patent No.: US 6,733,993 B2
(45) Date of Patent: May 11, 2004

(54) ENHANCED FIRST GENERATION ADENOVIRUS VACCINES EXPRESSING CODON OPTIMIZED HIV1-GAG, POL, NEF AND MODIFICATIONS

(75) Inventors: Emilio A. Emini, Wayne, PA (US); Rima Youil, North Wales, PA (US); Andrew J. Bett, Landsdale, PA (US); Ling Chen, Blue Bell, PA (US); David C. Kaslow, Bryn Mawr, PA (US); John W. Shiver, Doylestown, PA (US); Timothy J. Toner, Marlton, NJ (US); Danilo R. Casimiro, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 20 days.

(21) Appl. No.: 09/952,060

(22) Filed: Sep. 14, 2001

(65) Prior Publication Data

US 2003/0044421 A1 Mar. 6, 2003

Related U.S. Application Data

(60) Provisional application No. 60/233,180, filed on Sep. 15, 2000, provisional application No. 60/279,056, filed on Mar. 27, 2001, and provisional application No. 60/317,814, filed on Sep. 7, 2001.

(51) Int. Cl.$^7$ .......................... C12P 21/06; C12Q 1/70; G01N 33/53; C07K 16/00; C07H 21/04

(52) U.S. Cl. .......................... 435/69.1; 435/5; 435/7.1; 435/325; 435/339.1; 530/388.35; 536/23.1; 424/199.1; 424/208.1

(58) Field of Search .......................... 435/5, 7.1, 69.1, 435/325, 339.1; 530/388.35; 536/23.1; 424/199.1, 208.1

(56) References Cited

U.S. PATENT DOCUMENTS

| | | | |
|---|---|---|---|
| 5,643,579 | A | 7/1997 | Hung et al. |
| 5,672,508 | A | 9/1997 | Gyuris et al. |
| 5,716,613 | A | 2/1998 | Guber et al. |
| 5,859,193 | A | 1/1999 | Devare et al. |
| 6,019,978 | A | 2/2000 | Ertl et al. |
| 6,033,908 | A | 3/2000 | Bout et al. |
| 6,287,571 | B1 | 9/2001 | Ertl et al. |
| 2002/0155127 | A1 | 10/2002 | Wang |

FOREIGN PATENT DOCUMENTS

| | | |
|---|---|---|
| EP | 0 586 076 | 7/1993 |
| EP | 0 638 316 | 7/1994 |
| EP | 0 707 071 | 8/1995 |
| WO | WO 96/21015 | 7/1996 |
| WO | WO 96/39178 | 12/1996 |
| WO | WO 97/00326 | 1/1997 |
| WO | WO 97/31115 | 8/1997 |
| WO | WO 97/39771 | 10/1997 |
| WO | WO 97/48370 | 12/1997 |
| WO | WO 98/34640 | 8/1998 |
| WO | WO 98/56919 | 12/1998 |
| WO | WO 01/02607 | 7/2000 |
| WO | WO 01/21201 | 9/2000 |
| WO | WO 01/02067 | 1/2001 |
| WO | WO 01/43693 | 3/2001 |
| WO | WO 01/45748 | 6/2001 |

OTHER PUBLICATIONS

Bruce, C. et al. "Replication–deficient recombinant adenoviruses expressing the human immunodeficiency virus Env antigen can induce both humoral and CTL immune responses in mice", Journal of General Virology, 1999, vol. 80, pp. 2621–2628.

Fallaux, F. et al. "New Helper Cells and Matched Early Region 1–Deleted Adenovirus Vectors Prevent Generation of Replication–Competent Adenoviruses", Human Gene Therapy, 1998, vol. 9, pp. 1909–1917.

Flanagan, B. et al., "A recombinant human adenovirus expressing the simian immunodeficiency virus Gag antigen can induce long–lived immune responses in mice", Journal of General Virology, 1997, vol. 78, pp. 991–997.

Lubeck, M. et al. "Immunogenicity of Recombinant Adenovirus–Human Immunodeficiency Virus Vaccines in Chimpanzees Following Intranasal Administration", AIDS Research and Human Retroviruses, 1994, vol. 10, pp. 1443–1449.

(List continued on next page.)

*Primary Examiner*—Hankyel T. Park
(74) *Attorney, Agent, or Firm*—Anna L. Cocuzzo; Jack L. Tribble

(57) ABSTRACT

First generation adenoviral vectors and associated recombinant adenovirus-based HIV vaccines which show enhanced stability and growth properties and greater cellular-mediated immunity are described within this specification. These adenoviral vectors are utilized to generate and produce through cell culture various adenoviral-based HIV-1 vaccines which contain HIV-1 gag, HIV-1 pol and/or HIV-1 nef polynucleotide pharmaceutical products, and biologically relevant modifications thereof. These adenovirus vaccines, when directly introduced into living vertebrate tissue, preferably a mammalian host such as a human or a non-human mammal of commercial or domestic veterinary importance, express the HIV1-Gag, Pol and/or Nef protein or biologically modification thereof, inducing a cellular immune response which specifically recognizes HIV-1. The exemplified polynucleotides of the present invention are synthetic DNA molecules encoding HIV-1 Gag, encoding codon optimized HIV-1 Pol, derivatives of optimized HIV-1 Pol (including constructs wherein protease, reverse transcriptase, RNAse H and integrase activity of HIV-1 Pol is inactivated), HIV-1 Nef and derivatives of optimized HIV-1 Nef, including nef mutants which effect wild type characteristics of Nef, such as myristylation and down regulation of host CD4. The adenoviral vaccines of the present invention, when administered alone or in a combined modality regime, will offer a prophylactic advantage to previously uninfected individuals and/or provide a therapeutic effect by reducing viral load levels within an infected individual, thus prolonging the asymptomatic phase of HIV-1 infection.

57 Claims, 176 Drawing Sheets

OTHER PUBLICATIONS

Vernon, S. et al. "Ultrastructural characterization of human immunodeficiency virus type 1 Gag–containing particles assembled in a recombinant adenovirus vector system", Journal of General Virology, 1991, vol. 72, pp. 1243–1251.

Wilkinson, G. et al. "Constitutive and enhanced expression from the CMV major IE promoter in a defective adenovirus vector", Nucleic Acids Research, 192, vol. 20, pp. 2233–2239.

Grable, M. et al. "Adenovirus Type 5 Packaging Domain Is Composed of a Repeated Element That Is Functionally Redundant", Journal of Virology, 1990, vol. 64, pp. 2047–2056.

Grable, M. et al. "*cis* and *trans* Requirements for the Selective Packaging of Adenovirus Type 5 DNA", Journal of Virology, 1992, vol. 66, pp. 723–731.

Wang, Y. et al. "The Use of an E1–Deleted, Replication–Defective Adenovirus Recombinant Expressing the Rabies Virus Glycoprotein for Early Vaccination of Mice against Rabies Virus", Journal of Virology, 1997, vol. 71, pp. 3677–3583.

Natuk, R. et al. "Immunogenicity of Recombinant Human Adenovirus–Human Immunodeficiency Virus Vaccines in Chimpanzees", AIDS Research and Human Retroviruses, 1993, vol. 9, pp. 395–404.

Prevec, L. et al. "Immune Response to HIV–1 gag Antigens Induced by Recombinant Adenovirus Vectors in Mice and Rhesus Macaque Monkeys", Journal of Acquired Immune Deficiency Syndrome, 1991, vol. 4, pp. 568–576.

Lori, F. et al. "Rapid protection against human immunodeficiency virus type 1 (HIV–1) replication mediated by high efficiency non–retroviral delivery of genes interfering with HIV–1 tat and gag", Gene Therapy, 1994, vol. 1, pp. 27–31.

Pfarr, D. et al. "Differential Effects of Polyadenylation Regions on Gene Expression in Mammalian Cells", DNA, 1986, vol. 5, pp. 115–122.

Natuk, R. et al. "Adenovirus Vectored Vaccines", Developments in Biological Standardization, 1994, vol. 82, pp. 71–77.

Aiken, C. et al. "Nef Induces CD4 Endocytosis: Requirement for a Critical Dileucine Motif in the Membrane–Proximal CD4 Cytoplasmic Domain", Cell, 1994, vol. 76, pp. 853–864.

Chapman, B. et al. "Effect of intron A from human cytomegalovirus (Towne) immediate–early gene on heterologous expression in mammalian cells", Nucleic Acids Research, 1991, vol. 19, pp. 3979–3986.

Chroboczek, J. et al. "The Sequence of the Genome of Adenovirus Type 5 and Its Comparison with the Genome of Adenovirus Type 2", 1992, Virology, vol. 186, pp. 280–285.

Davies, J. et al. "Crystal Structure of the Ribonuclease H Domain of HIV–1 Reverse Transcriptase", Science, 1991, vol. 252, pp. 88–95.

Franchini, G. et al. "Cytoplasmic Localization of the HTLV–III 3'orf Protein in Cultured T Cells", Virology, 1986, vol. 155, pp. 593–599.

Graham, F. et al. "Characteristics of a Human Cell Line Transformed by DNA from Human Adenovirus Type 5", Journal General Virology, 1977, vol. 36, pp. 59–72.

Hitt, M. et al. "Human Adenovirus Vectors for Gene Transfer into Mammalian Cells", 1997, Advances in Pharmacology, vol. 40, pp. 137–206.

Larder, B. et al. "Infectious potential of human immunodeficiency virus type 1 reverse transcriptase mutants with altered inhibitor sensitivity", Proc. Natl. Acad. Sci. USA, 1989, vol. 86, pp. 4803–4807.

Larder, B. et al. "Site–specific mutagenesis of AIDS virus reverse transcriptase", Nature, 1987, vol. 327, pp. 716–717.

Lathe, R. "Synthetic Oligonucleotide Probes Deduced from Amino Acid Sequence Data Theoretical and Practical Considerations", Journal Molecular Biology, 1985, vol. 183, pp. 1–12.

Leavitt, A. et al. "Site–directed Mutagenesis of HIV–1 Integrase Demonstrates Differential Effects on Integrase Functions in Vitro", The Journal of Biological Chemistry, 1993, vol. 268, pp. 2113–2119.

Miyahira, Y. et al. "Quantification of antigen specific CD8+ T cells using an ELISPOT assay", Journal of Immunological Methods, 1995, vol. 181, pp. 45–54.

Mizrahi, V. et al. "Site–directed mutagenesis of the conserved Asp–443 and Asp–498 carboxy–terminal residues of HIV–1 reverse transcriptase", Nucleic Acids Research, vol. 18, p. 5359–5363.

Montgomery, D. et al. "Heterologous and Homologous Protection Against Influenza A by DNA Vaccination: Optimization of DNA Vectors", DNA and Cell Biology, 1993, vol. 12, pp. 777–783.

Myers, G. et al. "Human Retroviruses and AIDS 1995 : A compilation and Analysis of Nucleic Acid and Amino Acid Sequences", 1995, Part II, A3–A19.

Ondoa, P. et al. "Evaluation of Different V3 Peptides in an Enzyme Immunoassay for Specific HIV Type 1 Group O Antibody Detection", Aids Research and Human Retroviruses, 1998, vol. 14, pp. 963–972.

Schatz, O. et al. Point mutations in conserved amino acid residues within the C–terminal domain of HIV–1 reverse transcriptase specifically repress RNase H function, FEBS Letters, 1989, vol. 257, pp. 311–314.

Schwartz, O. et al. "Endocytosis of major histocompatibility complex I molecules is induced by the HIV–1 Nef protein", Nature Medicine, 1996, vol. 2, pp. 338–342.

Wiskerchen, M. et al. "Human Immunodeficiency Virus Type 1 Integrase: Effects of Mutations on Viral Ability to Integrate, Direct Viral Gene Expression from Unintegrated Viral DNA Templates, and Sustain Viral Propagation in Primary Cells", Journal of Virology, 1995, vol. 69, pp. 376–386.

ORIGINAL ADENOVECTOR CONSTRUCT:

ORIGINAL HIV-1 gag ADENOVECTOR.

Sequence of the open reading frame for FL-gag (human codon optimized)

atgggtgctagggcttctgtgctgtctggtggtgagctggacaagtgggagaagatcaggctgaggcctggtgg
caagaagaagtacaagctaaagcacattgtgtgggcctccagggagctggagaggtttgctgtgaaccctggc
ctgctggagacctctgaggggtgcaggcagatcctgggccagctccagccctccctgcaaacaggctctgagg
agctgaggtccctgtacaacacagtggctaccctgtactgtgtgcaccagaagattgatgtgaaggacaccaag
gaggccctggagaagattgaggaggagcagaacaagtccaagaagaaggcccagcaggctgctgctggc
acaggcaactccagccaggtgtcccagaactaccccattgtgcagaacctccagggccagatggtgcaccag
gccatctcccccggaccctgaatgcctgggtgaaggtggtggaggagaaggccttctcccctgaggtgatccc
catgttctctgccctgtctgagggtgccacccccaggacctgaacaccatgctgaacacagtgggggccatc
aggctgccatgcagatgctgaaggagaccatcaatgaggaggctgctgagtgggacaggctgcatcctgtgc
acgctggccccattgcccccggccagatgagggagcccaggggctctgacattgctggcaccacctccaccct
ccaggagcagattggctggatgaccaacaacccccccatccctgtgggggaaatctacaagaggtggatcat
cctgggcctgaacaagattgtgaggatgtactcccccacctccatcctggacatcaggcagggccccaaggag
cccttcagggactatgtggacaggttctacaagaccctgagggctgagcaggcctcccaggaggtgaagaact
ggatgacagagaccctgctggtgcagaatgccaaccctgactgcaagaccatcctgaaggccctgggccctg
ctgccaccctggaggagatgatgacagcctgccaggggtgggggccctggtcacaaggccagggtgctg
gctgaggccatgtcccaggtgaccaactccgccaccatcatgatgcagaggggcaacttcaggaaccagag
gaagacagtgaagtgcttcaactgtggcaaggtgggccacattgccaagaactgtagggcccccaggaaga
agggctgctggaagtgtggcaaggagggccaccagatgaaggactgcaatgagaggcaggccaacttcctg
ggcaaaatctggccctcccacaagggcaggcctggcaacttcctccagtccaggcctgagcccacagcccct
cccgaggagtccttcaggtttggggaggagaagaccacccccagccagaagcaggagcccattgacaagg
agctgtacccccctggcctccctgaggtccctgtttggcaacgacccctcctcccagtaaaataaagcccgggca
gat (SEQ ID NO: 27)

FIG.2

DIAGRAMMATIC REPRESENTATION OF THE ORIGINAL HIV-1 GAG TRANSGENE AND THE SERIES OF NEW TRANSGENE CONSTRUCTIONS.

MODIFICATIONS MADE TO THE CURRENT ADENOVECTOR BACKBONE IN THE GENERATION OF THE NEW VECTOR.

VIRUS MIXING EXPERIMENTS TO DETERMINE THE EFFECTS OF THE ADDITION MADE TO THE PACKAGING SIGNAL REGION (EXPT #1) AND ANALYSIS OF THE EFFECTS OF THE E3 GENE ON VIRAL GROWTH (EXPT. #2). THE RED BARS DENOTE THE REGION OF MODIFICATIONS MADE TO THE E1 DELETION.

hCMV-FLgag-bGHpA ADENOVECTORS CONSTRUCTED WITHIN THE "MRK" BACKBONE. E1 PARALLEL AND E1 ANTIPARALLEL TRANSGENE ORIENTATION WITHIN THE E3− AND E3+ BACKBONES WERE CONSTRUCTED.

hCMV-FLgag-SPA ADENOVECTORS CONSTRUCTED WITHIN THE "MRK" BACKBONE. E1 PARALLEL AND E1 ANTIPARALLEL TRANSGENE ORIENTATION WITHIN THE E3− AND E3+ BACKBONES WERE CONSTRUCTED.

mCMV–FLgag–bGHpA ADENOVECTORS CONSTRUCTED WITHIN THE "MRK" BACKBONE. E1 PARALLEL AND E1 ANTIPARALLEL TRANSGENE ORIENTATION WITHIN THE E3– AND E3+ BACKBONES WERE CONSTRUCTED.

PLASMID MIXING EXPT: (POLY A SIGNAL)

EFFECT OF POLYADENYLATION SIGNAL

```
        PacI
      ~~~~~~~~~~
  1  TTCTTAATTA ACATCATCAA TAATATACCT TATTTTGGAT TGAAGCCAAT
     AAGAATTAAT TGTAGTAGTT ATTATATGGA ATAAAACCTA ACTTCGGTTA

 51  ATGATAATGA GGGGGTGGAG TTTGTGACGT GGCGCGGGGC GTGGGAACGG
     TACTATTACT CCCCCACCTC AAACACTGCA CCGCGCCCCG CACCCTTGCC

101  GGCGGGTGAC GTAGTAGTGT GGCGGAAGTG TGATGTTGCA AGTGTGGCGG
     CCGCCCACTG CATCATCACA CCGCCTTCAC ACTACAACGT TCACACCGCC

151  AACACATGTA AGCGACGGAT GTGGCAAAAG TGACGTTTTT GGTGTGCGCC
     TTGTGTACAT TCGCTGCCTA CACCGTTTTC ACTGCAAAAA CCACACGCGG

201  GGTGTACACA GGAAGTGACA ATTTTCGCGC GGTTTTAGGC GGATGTTGTA
     CCACATGTGT CCTTCACTGT TAAAAGCGCG CCAAAATCCG CCTACAACAT

251  GTAAATTTGG GCGTAACCGA GTAAGATTTG GCCATTTTCG CGGGAAAACT
     CATTTAAACC CGCATTGGCT CATTCTAAAC CGGTAAAAGC GCCCTTTTGA

301  GAATAAGAGG AAGTGAAATC TGAATAATTT TGTGTTACTC ATAGCGCGTA
     CTTATTCTCC TTCACTTTAG ACTTATTAAA ACACAATGAG TATCGCGCAT

351  ATATTTGTCT AGGGCCGCGG GGACTTTGAC CGTTTACGTG GAGACTCGCC
     TATAAACAGA TCCCGGCGCC CCTGAAACTG GCAAATGCAC CTCTGAGCGG

401  CAGGTGTTTT TCTCAGGTGT TTTCCGCGTT CCGGGTCAAA GTTGGCGTTT
     GTCCACAAAA AGAGTCCACA AAAGGCGCAA GGCCCAGTTT CAACCGCAAA

451  TATTATTATA GGCGGCCGCG ATCCATTGCA TACGTTGTAT CCATATCATA
     ATAATAATAT CCGCCGGCGC TAGGTAACGT ATGCAACATA GGTATAGTAT

501  ATATGTACAT TTATATTGGC TCATGTCCAA CATTACCGCC ATGTTGACAT
     TATACATGTA AATATAACCG AGTACAGGTT GTAATGGCGG TACAACTGTA

551  TGATTATTGA CTAGTTATTA ATAGTAATCA ATTACGGGGT CATTAGTTCA
     ACTAATAACT GATCAATAAT TATCATTAGT TAATGCCCCA GTAATCAAGT

601  TAGCCCATAT ATGGAGTTCC GCGTTACATA ACTTACGGTA AATGGCCCGC
     ATCGGGTATA TACCTCAAGG CGCAATGTAT TGAATGCCAT TTACCGGGCG

651  CTGGCTGACC GCCCAACGAC CCCCGCCCAT TGACGTCAAT AATGACGTAT
     GACCGACTGG CGGGTTGCTG GGGGCGGGTA ACTGCAGTTA TTACTGCATA

701  GTTCCCATAG TAACGCCAAT AGGGACTTTC CATTGACGTC AATGGGTGGA
     CAAGGGTATC ATTGCGGTTA TCCCTGAAAG GTAACTGCAG TTACCCACCT

751  GTATTTACGG TAAACTGCCC ACTTGGCAGT ACATCAAGTG TATCATATGC
     CATAAATGCC ATTTGACGGG TGAACCGTCA TGTAGTTCAC ATAGTATACG
```

FIG.15A-1

```
801  CAAGTACGCC CCCTATTGAC GTCAATGACG GTAAATGGCC CGCCTGGCAT
     GTTCATGCGG GGGATAACTG CAGTTACTGC CATTTACCGG GCGGACCGTA

851  TATGCCCAGT ACATGACCTT ATGGGACTTT CCTACTTGGC AGTACATCTA
     ATACGGGTCA TGTACTGGAA TACCCTGAAA GGATGAACCG TCATGTAGAT

901  CGTATTAGTC ATCGCTATTA CCATGGTGAT GCGGTTTTGG CAGTACATCA
     GCATAATCAG TAGCGATAAT GGTACCACTA CGCCAAAACC GTCATGTAGT

951  ATGGGCGTGG ATAGCGGTTT GACTCACGGG GATTTCCAAG TCTCCACCCC
     TACCCGCACC TATCGCCAAA CTGAGTGCCC CTAAAGGTTC AGAGGTGGGG

1001 ATTGACGTCA ATGGGAGTTT GTTTTGGCAC CAAAATCAAC GGGACTTTCC
     TAACTGCAGT TACCCTCAAA CAAAACCGTG GTTTTAGTTG CCCTGAAAGG

1051 AAAATGTCGT AACAACTCCG CCCCATTGAC GCAAATGGGC GGTAGGCGTG
     TTTTACAGCA TTGTTGAGGC GGGGTAACTG CGTTTACCCG CCATCCGCAC

1101 TACGGTGGGA GGTCTATATA AGCAGAGCTC GTTTAGTGAA CCGTCAGATC
     ATGCCACCCT CCAGATATAT TCGTCTCGAG CAAATCACTT GGCAGTCTAG

1151 GCCTGGAGAC GCCATCCACG CTGTTTTGAC CTCCATAGAA GACACCGGGA
     CGGACCTCTG CGGTAGGTGC GACAAAACTG GAGGTATCTT CTGTGGCCCT

1201 CCGATCCAGC CTCCGCGGCC GGGAACGGTG CATTGGAACG CGGATTCCCC
     GGCTAGGTCG GAGGCGCCGG CCCTTGCCAC GTAACCTTGC GCCTAAGGGG

1251 GTGCCAAGAG TGAGATCTAC CATGGGTGCT AGGGCTTCTG TGCTGTCTGG
     CACGGTTCTC ACTCTAGATG GTACCCACGA TCCCGAAGAC ACGACAGACC

1301 TGGTGAGCTG GACAAGTGGG AGAAGATCAG GCTGAGGCCT GGTGGCAAGA
     ACCACTCGAC CTGTTCACCC TCTTCTAGTC CGACTCCGGA CCACCGTTCT

1351 AGAAGTACAA GCTAAAGCAC ATTGTGTGGG CCTCCAGGGA GCTGGAGAGG
     TCTTCATGTT CGATTTCGTG TAACACACCC GGAGGTCCCT CGACCTCTCC

1401 TTTGCTGTGA ACCCTGGCCT GCTGGAGACC TCTGAGGGGT GCAGGCAGAT
     AAACGACACT TGGGACCGGA CGACCTCTGG AGACTCCCCA CGTCCGTCTA

1451 CCTGGGCCAG CTCCAGCCCT CCCTGCAAAC AGGCTCTGAG GAGCTGAGGT
     GGACCCGGTC GAGGTCGGGA GGGACGTTTG TCCGAGACTC CTCGACTCCA

1501 CCCTGTACAA CACAGTGGCT ACCCTGTACT GTGTGCACCA GAAGATTGAT
     GGGACATGTT GTGTCACCGA TGGGACATGA CACACGTGGT CTTCTAACTA

1551 GTGAAGGACA CCAAGGAGGC CCTGGAGAAG ATTGAGGAGG AGCAGAACAA
     CACTTCCTGT GGTTCCTCCG GGACCTCTTC TAACTCCTCC TCGTCTTGTT

1601 GTCCAAGAAG AAGGCCCAGC AGGCTGCTGC TGGCACAGGC AACTCCAGCC
     CAGGTTCTTC TTCCGGGTCG TCCGACGACG ACCGTGTCCG TTGAGGTCGG
```

FIG. 15A-2

```
1651 AGGTGTCCCA GAACTACCCC ATTGTGCAGA ACCTCCAGGG CCAGATGGTG
     TCCACAGGGT CTTGATGGGG TAACACGTCT TGGAGGTCCC GGTCTACCAC

1701 CACCAGGCCA TCTCCCCCCG GACCCTGAAT GCCTGGGTGA AGGTGGTGGA
     GTGGTCCGGT AGAGGGGGGC CTGGGACTTA CGGACCCACT TCCACCACCT

1751 GGAGAAGGCC TTCTCCCCTG AGGTGATCCC CATGTTCTCT GCCCTGTCTG
     CCTCTTCCGG AAGAGGGGAC TCCACTAGGG GTACAAGAGA CGGGACAGAC

1801 AGGGTGCCAC CCCCCAGGAC CTGAACACCA TGCTGAACAC AGTGGGGGGC
     TCCCACGGTG GGGGGTCCTG GACTTGTGGT ACGACTTGTG TCACCCCCCG

1851 CATCAGGCTG CCATGCAGAT GCTGAAGGAG ACCATCAATG AGGAGGCTGC
     GTAGTCCGAC GGTACGTCTA CGACTTCCTC TGGTAGTTAC TCCTCCGACG

1901 TGAGTGGGAC AGGCTGCATC CTGTGCACGC TGGCCCCATT GCCCCCGGCC
     ACTCACCCTG TCCGACGTAG GACACGTGCG ACCGGGGTAA CGGGGGCCGG

1951 AGATGAGGGA GCCCAGGGGC TCTGACATTG CTGGCACCAC CTCCACCCTC
     TCTACTCCCT CGGGTCCCCG AGACTGTAAC GACCGTGGTG GAGGTGGGAG

2001 CAGGAGCAGA TTGGCTGGAT GACCAACAAC CCCCCCATCC CTGTGGGGGA
     GTCCTCGTCT AACCGACCTA CTGGTTGTTG GGGGGGTAGG GACACCCCCT

2051 AATCTACAAG AGGTGGATCA TCCTGGGCCT GAACAAGATT GTGAGGATGT
     TTAGATGTTC TCCACCTAGT AGGACCCGGA CTTGTTCTAA CACTCCTACA

2101 ACTCCCCCAC CTCCATCCTG GACATCAGGC AGGGCCCCAA GGAGCCCTTC
     TGAGGGGGTG GAGGTAGGAC CTGTAGTCCG TCCCGGGGTT CCTCGGGAAG

2151 AGGGACTATG TGGACAGGTT CTACAAGACC CTGAGGGCTG AGCAGGCCTC
     TCCCTGATAC ACCTGTCCAA GATGTTCTGG GACTCCCGAC TCGTCCGGAG

2201 CCAGGAGGTG AAGAACTGGA TGACAGAGAC CCTGCTGGTG CAGAATGCCA
     GGTCCTCCAC TTCTTGACCT ACTGTCTCTG GGACGACCAC GTCTTACGGT

2251 ACCCTGACTG CAAGACCATC CTGAAGGCCC TGGGCCCTGC TGCCACCCTG
     TGGGACTGAC GTTCTGGTAG GACTTCCGGG ACCCGGGACG ACGGTGGGAC

2301 GAGGAGATGA TGACAGCCTG CCAGGGGGTG GGGGGCCCTG GTCACAAGGC
     CTCCTCTACT ACTGTCGGAC GGTCCCCCAC CCCCCGGGAC CAGTGTTCCG

2351 CAGGGTGCTG GCTGAGGCCA TGTCCCAGGT GACCAACTCC GCCACCATCA
     GTCCCACGAC CGACTCCGGT ACAGGGTCCA CTGGTTGAGG CGGTGGTAGT

2401 TGATGCAGAG GGGCAACTTC AGGAACCAGA GGAAGACAGT GAAGTGCTTC
     ACTACGTCTC CCCGTTGAAG TCCTTGGTCT CCTTCTGTCA CTTCACGAAG

2451 AACTGTGGCA AGGTGGGCCA CATTGCCAAG AACTGTAGGG CCCCCAGGAA
     TTGACACCGT TCCACCCGGT GTAACGGTTC TTGACATCCC GGGGGTCCTT
```

FIG.15A-3

2501 GAAGGGCTGC TGGAAGTGTG GCAAGGAGGG CCACCAGATG AAGGACTGCA
CTTCCCGACG ACCTTCACAC CGTTCCTCCC GGTGGTCTAC TTCCTGACGT

2551 ATGAGAGGCA GGCCAACTTC CTGGGCAAAA TCTGGCCCTC CCACAAGGGC
TACTCTCCGT CCGGTTGAAG GACCCGTTTT AGACCGGGAG GGTGTTCCCG

2601 AGGCCTGGCA ACTTCCTCCA GTCCAGGCCT GAGCCCACAG CCCCTCCCGA
TCCGGACCGT TGAAGGAGGT CAGGTCCGGA CTCGGGTGTC GGGGAGGGCT

2651 GGAGTCCTTC AGGTTTGGGG AGGAGAAGAC CACCCCCAGC CAGAAGCAGG
CCTCAGGAAG TCCAAACCCC TCCTCTTCTG GTGGGGGTCG GTCTTCGTCC

2701 AGCCCATTGA CAAGGAGCTG TACCCCCTGG CCTCCCTGAG GTCCCTGTTT
TCGGGTAACT GTTCCTCGAC ATGGGGGACC GGAGGGACTC CAGGGACAAA

2751 GGCAACGACC CCTCCTCCCA GTAAAATAAA GCCCGGGCAG ATCTGCTGTG
CCGTTGCTGG GGAGGAGGGT CATTTTATTT CGGGCCCGTC TAGACGACAC

2801 CCTTCTAGTT GCCAGCCATC TGTTGTTTGC CCCTCCCCCG TGCCTTCCTT
GGAAGATCAA CGGTCGGTAG ACAACAAACG GGGAGGGGGC ACGGAAGGAA

2851 GACCCTGGAA GGTGCCACTC CCACTGTCCT TTCCTAATAA AATGAGGAAA
CTGGGACCTT CCACGGTGAG GGTGACAGGA AAGGATTATT TTACTCCTTT

2901 TTGCATCGCA TTGTCTGAGT AGGTGTCATT CTATTCTGGG GGGTGGGGTG
AACGTAGCGT AACAGACTCA TCCACAGTAA GATAAGACCC CCCACCCCAC

2951 GGGCAGGACA GCAAGGGGGA GGATTGGGAA GACAATAGCA GGCATGCTGG
CCCGTCCTGT CGTTCCCCCT CCTAACCCTT CTGTTATCGT CCGTACGACC

3001 GGATGCGGTG GGCTCTATGG CCGATCGGCG CGCCGTACTG AAATGTGTGG
CCTACGCCAC CCGAGATACC GGCTAGCCGC GCGGCATGAC TTTACACACC

3051 GCGTGGCTTA AGGGTGGGAA AGAATATATA AGGTGGGGGT CTTATGTAGT
CGCACCGAAT TCCCACCCTT TCTTATATAT TCCACCCCCA GAATACATCA

3101 TTTGTATCTG TTTTGCAGCA GCCGCCGCCG CCATGAGCAC CAACTCGTTT
AAACATAGAC AAAACGTCGT CGGCGGCGGC GGTACTCGTG GTTGAGCAAA

3151 GATGGAAGCA TTGTGAGCTC ATATTTGACA ACGCGCATGC CCCCATGGGC
CTACCTTCGT AACACTCGAG TATAAACTGT TGCGCGTACG GGGGTACCCG

3201 CGGGGTGCGT CAGAATGTGA TGGGCTCCAG CATTGATGGT CGCCCCGTCC
GCCCCACGCA GTCTTACACT ACCCGAGGTC GTAACTACCA GCGGGGCAGG

3251 TGCCCGCAAA CTCTACTACC TTGACCTACG AGACCGTGTC TGGAACGCCG
ACGGGCGTTT GAGATGATGG AACTGGATGC TCTGGCACAG ACCTTGCGGC

3301 TTGGAGACTG CAGCCTCCGC CGCCGCTTCA GCCGCTGCAG CCACCGCCCG
AACCTCTGAC GTCGGAGGCG GCGGCGAAGT CGGCGACGTC GGTGGCGGGC

FIG.15A-4

```
3351 CGGGATTGTG ACTGACTTTG CTTTCCTGAG CCCGCTTGCA AACAGTGCAG
     GCCCTAACAC TGACTGAAAC GAAAGGACTC GGGCGAACGT TTGTCACGTC

3401 CTTCCCGTTC ATCCGCCCGC GATGACAAGT TGACGGCTCT TTTGGCACAA
     GAAGGGCAAG TAGGCGGGCG CTACTGTTCA ACTGCCGAGA AAACCGTGTT

3451 TTGGATTCTT TGACCCGGGA ACTTAATGTC GTTTCTCAGC AGCTGTTGGA
     AACCTAAGAA ACTGGGCCCT TGAATTACAG CAAAGAGTCG TCGACAACCT

3501 TCTGCGCCAG CAGGTTTCTG CCCTGAAGGC TTCCTCCCCT CCCAATGCGG
     AGACGCGGTC GTCCAAAGAC GGGACTTCCG AAGGAGGGGA GGGTTACGCC

3551 TTTAAAACAT AAATAAAAAA CCAGACTCTG TTTGGATTTG GATCAAGCAA
     AAATTTTGTA TTTATTTTTT GGTCTGAGAC AAACCTAAAC CTAGTTCGTT

3601 GTGTCTTGCT GTCTTTATTT AGGGGTTTTG CGCGCGCGGT AGGCCCGGGA
     CACAGAACGA CAGAAATAAA TCCCCAAAAC GCGCGCGCCA TCCGGGCCCT

3651 CCAGCGGTCT CGGTCGTTGA GGGTCCTGTG TATTTTTTCC AGGACGTGGT
     GGTCGCCAGA GCCAGCAACT CCCAGGACAC ATAAAAAAGG TCCTGCACCA

3701 AAAGGTGACT CTGGATGTTC AGATACATGG GCATAAGCCC GTCTCTGGGG
     TTTCCACTGA GACCTACAAG TCTATGTACC CGTATTCGGG CAGAGACCCC

3751 TGGAGGTAGC ACCACTGCAG AGCTTCATGC TGCGGGGTGG TGTTGTAGAT
     ACCTCCATCG TGGTGACGTC TCGAAGTACG ACGCCCCACC ACAACATCTA

3801 GATCCAGTCG TAGCAGGAGC GCTGGGCGTG GTGCCTAAAA ATGTCTTTCA
     CTAGGTCAGC ATCGTCCTCG CGACCCGCAC CACGGATTTT TACAGAAAGT

3851 GTAGCAAGCT GATTGCCAGG GGCAGGCCCT TGGTGTAAGT GTTTACAAAG
     CATCGTTCGA CTAACGGTCC CCGTCCGGGA ACCACATTCA CAAATGTTTC

3901 CGGTTAAGCT GGGATGGGTG CATACGTGGG GATATGAGAT GCATCTTGGA
     GCCAATTCGA CCCTACCCAC GTATGCACCC CTATACTCTA CGTAGAACCT

3951 CTGTATTTTT AGGTTGGCTA TGTTCCCAGC CATATCCCTC CGGGGATTCA
     GACATAAAAA TCCAACCGAT ACAAGGGTCG GTATAGGGAG GCCCCTAAGT

4001 TGTTGTGCAG AACCACCAGC ACAGTGTATC CGGTGCACTT GGGAAATTTG
     ACAACACGTC TTGGTGGTCG TGTCACATAG GCCACGTGAA CCCTTTAAAC

4051 TCATGTAGCT TAGAAGGAAA TGCGTGGAAG AACTTGGAGA CGCCCTTGTG
     AGTACATCGA ATCTTCCTTT ACGCACCTTC TTGAACCTCT GCGGGAACAC

4101 ACCTCCAAGA TTTTCCATGC ATTCGTCCAT AATGATGGCA ATGGGCCCAC
     TGGAGGTTCT AAAAGGTACG TAAGCAGGTA TTACTACCGT TACCCGGGTG

4151 GGGCGGCGGC CTGGGCGAAG ATATTTCTGG GATCACTAAC GTCATAGTTG
     CCCGCCGCCG GACCCGCTTC TATAAAGACC CTAGTGATTG CAGTATCAAC
```

FIG.15A-5

```
4201 TGTTCCAGGA TGAGATCGTC ATAGGCCATT TTTACAAAGC GCGGGCGGAG
     ACAAGGTCCT ACTCTAGCAG TATCCGGTAA AAATGTTTCG CGCCCGCCTC

4251 GGTGCCAGAC TGCGGTATAA TGGTTCCATC CGGCCCAGGG GCGTAGTTAC
     CCACGGTCTG ACGCCATATT ACCAAGGTAG GCCGGGTCCC CGCATCAATG

4301 CCTCACAGAT TTGCATTTCC CACGCTTTGA GTTCAGATGG GGGGATCATG
     GGAGTGTCTA AACGTAAAGG GTGCGAAACT CAAGTCTACC CCCCTAGTAC

4351 TCTACCTGCG GGGCGATGAA GAAAACGGTT TCCGGGGTAG GGGAGATCAG
     AGATGGACGC CCCGCTACTT CTTTTGCCAA AGGCCCCATC CCCTCTAGTC

4401 CTGGGAAGAA AGCAGGTTCC TGAGCAGCTG CGACTTACCG CAGCCGGTGG
     GACCCTTCTT TCGTCCAAGG ACTCGTCGAC GCTGAATGGC GTCGGCCACC

4451 GCCCGTAAAT CACACCTATT ACCGGCTGCA ACTGGTAGTT AAGAGAGCTG
     CGGGCATTTA GTGTGGATAA TGGCCGACGT TGACCATCAA TTCTCTCGAC

4501 CAGCTGCCGT CATCCCTGAG CAGGGGGGCC ACTTCGTTAA GCATGTCCCT
     GTCGACGGCA GTAGGGACTC GTCCCCCCGG TGAAGCAATT CGTACAGGGA

4551 GACTCGCATG TTTTCCCTGA CCAAATCCGC CAGAAGGCGC TCGCCGCCCA
     CTGAGCGTAC AAAAGGGACT GGTTTAGGCG GTCTTCCGCG AGCGGCGGGT

4601 GCGATAGCAG TTCTTGCAAG GAAGCAAAGT TTTTCAACGG TTTGAGACCG
     CGCTATCGTC AAGAACGTTC CTTCGTTTCA AAAAGTTGCC AAACTCTGGC

4651 TCCGCCGTAG GCATGCTTTT GAGCGTTTGA CCAAGCAGTT CCAGGCGGTC
     AGGCGGCATC CGTACGAAAA CTCGCAAACT GGTTCGTCAA GGTCCGCCAG

4701 CCACAGCTCG GTCACCTGCT CTACGGCATC TCGATCCAGC ATATCTCCTC
     GGTGTCGAGC CAGTGGACGA GATGCCGTAG AGCTAGGTCG TATAGAGGAG

4751 GTTTCGCGGG TTGGGGCGGC TTTCGCTGTA CGGCAGTAGT CGGTGCTCGT
     CAAAGCGCCC AACCCCGCCG AAAGCGACAT GCCGTCATCA GCCACGAGCA

4801 CCAGACGGGC CAGGGTCATG TCTTTCCACG GGCGCAGGGT CCTCGTCAGC
     GGTCTGCCCG GTCCCAGTAC AGAAAGGTGC CCGCGTCCCA GGAGCAGTCG

4851 GTAGTCTGGG TCACGGTGAA GGGGTGCGCT CCGGGCTGCG CGCTGGCCAG
     CATCAGACCC AGTGCCACTT CCCCACGCGA GGCCCGACGC GCGACCGGTC

4901 GGTGCGCTTG AGGCTGGTCC TGCTGGTGCT GAAGCGCTGC CGGTCTTCGC
     CCACGCGAAC TCCGACCAGG ACGACCACGA CTTCGCGACG GCCAGAAGCG

4951 CCTGCGCGTC GGCCAGGTAG CATTTGACCA TGGTGTCATA GTCCAGCCCC
     GGACGCGCAG CCGGTCCATC GTAAACTGGT ACCACAGTAT CAGGTCGGGG

5001 TCCGCGGCGT GGCCCTTGGC GCGCAGCTTG CCCTTGGAGG AGGCGCCGCA
     AGGCGCCGCA CCGGGAACCG CGCGTCGAAC GGGAACCTCC TCCGCGGCGT
```

FIG.15A-6

```
5051 CGAGGGGCAG TGCAGACTTT TGAGGGCGTA GAGCTTGGGC GCGAGAAATA
     GCTCCCCGTC ACGTCTGAAA ACTCCCGCAT CTCGAACCCG CGCTCTTTAT

5101 CCGATTCCGG GGAGTAGGCA TCCGCGCCGC AGGCCCCGCA GACGGTCTCG
     GGCTAAGGCC CCTCATCCGT AGGCGCGGCG TCCGGGGCGT CTGCCAGAGC

5151 CATTCCACGA GCCAGGTGAG CTCTGGCCGT TCGGGGTCAA AAACCAGGTT
     GTAAGGTGCT CGGTCCACTC GAGACCGGCA AGCCCCAGTT TTTGGTCCAA

5201 TCCCCCATGC TTTTTGATGC GTTTCTTACC TCTGGTTTCC ATGAGCCGGT
     AGGGGGTACG AAAAACTACG CAAAGAATGG AGACCAAAGG TACTCGGCCA

5251 GTCCACGCTC GGTGACGAAA AGGCTGTCCG TGTCCCCGTA TACAGACTTG
     CAGGTGCGAG CCACTGCTTT TCCGACAGGC ACAGGGGCAT ATGTCTGAAC

5301 AGAGGCCTGT CCTCGAGCGG TGTTCCGCGG TCCTCCTCGT ATAGAAACTC
     TCTCCGGACA GGAGCTCGCC ACAAGGCGCC AGGAGGAGCA TATCTTTGAG

5351 GGACCACTCT GAGACAAAGG CTCGCGTCCA GGCCAGCACG AAGGAGGCTA
     CCTGGTGAGA CTCTGTTTCC GAGCGCAGGT CCGGTCGTGC TTCCTCCGAT

5401 AGTGGGAGGG GTAGCGGTCG TTGTCCACTA GGGGGTCCAC TCGCTCCAGG
     TCACCCTCCC CATCGCCAGC AACAGGTGAT CCCCCAGGTG AGCGAGGTCC

5451 GTGTGAAGAC ACATGTCGCC CTCTTCGGCA TCAAGGAAGG TGATTGGTTT
     CACACTTCTG TGTACAGCGG GAGAAGCCGT AGTTCCTTCC ACTAACCAAA

5501 GTAGGTGTAG GCCACGTGAC CGGGTGTTCC TGAAGGGGGG CTATAAAAGG
     CATCCACATC CGGTGCACTG GCCCACAAGG ACTTCCCCCC GATATTTTCC

5551 GGGTGGGGGC GCGTTCGTCC TCACTCTCTT CCGCATCGCT GTCTGCGAGG
     CCCACCCCCG CGCAAGCAGG AGTGAGAGAA GGCGTAGCGA CAGACGCTCC

5601 GCCAGCTGTT GGGGTGAGTA CTCCCTCTGA AAAGCGGGCA TGACTTCTGC
     CGGTCGACAA CCCCACTCAT GAGGGAGACT TTTCGCCCGT ACTGAAGACG

5651 GCTAAGATTG TCAGTTTCCA AAAACGAGGA GGATTTGATA TTCACCTGGC
     CGATTCTAAC AGTCAAAGGT TTTTGCTCCT CCTAAACTAT AAGTGGACCG

5701 CCGCGGTGAT GCCTTTGAGG GTGGCCGCAT CCATCTGGTC AGAAAAGACA
     GGCGCCACTA CGGAAACTCC CACCGGCGTA GGTAGACCAG TCTTTTCTGT

5751 ATCTTTTTGT TGTCAAGCTT GGTGGCAAAC GACCCGTAGA GGGCGTTGGA
     TAGAAAAACA ACAGTTCGAA CCACCGTTTG CTGGGCATCT CCCGCAACCT

5801 CAGCAACTTG GCGATGGAGC GCAGGGTTTG GTTTTTGTCG CGATCGGCGC
     GTCGTTGAAC CGCTACCTCG CGTCCCAAAC CAAAAACAGC GCTAGCCGCG

5851 GCTCCTTGGC CGCGATGTTT AGCTGCACGT ATTCGCGCGC AACGCACCGC
     CGAGGAACCG GCGCTACAAA TCGACGTGCA TAAGCGCGCG TTGCGTGGCG
```

FIG. 15A-7

5901 CATTCGGGAA AGACGGTGGT GCGCTCGTCG GGCACCAGGT GCACGCGCCA
GTAAGCCCTT TCTGCCACCA CGCGAGCAGC CCGTGGTCCA CGTGCGCGGT

5951 ACCGCGGTTG TGCAGGGTGA CAAGGTCAAC GCTGGTGGCT ACCTCTCCGC
TGGCGCCAAC ACGTCCCACT GTTCCAGTTG CGACCACCGA TGGAGAGGCG

6001 GTAGGCGCTC GTTGGTCCAG CAGAGGCGGC CGCCCTTGCG CGAGCAGAAT
CATCCGCGAG CAACCAGGTC GTCTCCGCCG GCGGGAACGC GCTCGTCTTA

6051 GGCGGTAGGG GGTCTAGCTG CGTCTCGTCC GGGGGGTCTG CGTCCACGGT
CCGCCATCCC CCAGATCGAC GCAGAGCAGG CCCCCCAGAC GCAGGTGCCA

6101 AAAGACCCCG GGCAGCAGGC GCGCGTCGAA GTAGTCTATC TTGCATCCTT
TTTCTGGGGC CCGTCGTCCG CGCGCAGCTT CATCAGATAG AACGTAGGAA

6151 GCAAGTCTAG CGCCTGCTGC CATGCGCGGG CGGCAAGCGC GCGCTCGTAT
CGTTCAGATC GCGGACGACG GTACGCGCCC GCCGTTCGCG CGCGAGCATA

6201 GGGTTGAGTG GGGGACCCCA TGGCATGGGG TGGGTGAGCG CGGAGGCGTA
CCCAACTCAC CCCCTGGGGT ACCGTACCCC ACCCACTCGC GCCTCCGCAT

6251 CATGCCGCAA ATGTCGTAAA CGTAGAGGGG CTCTCTGAGT ATTCCAAGAT
GTACGGCGTT TACAGCATTT GCATCTCCCC GAGAGACTCA TAAGGTTCTA

6301 ATGTAGGGTA GCATCTTCCA CCGCGGATGC TGGCGCGCAC GTAATCGTAT
TACATCCCAT CGTAGAAGGT GGCGCCTACG ACCGCGCGTG CATTAGCATA

6351 AGTTCGTGCG AGGGAGCGAG GAGGTCGGGA CCGAGGTTGC TACGGGCGGG
TCAAGCACGC TCCCTCGCTC CTCCAGCCCT GGCTCCAACG ATGCCCGCCC

6401 CTGCTCTGCT CGGAAGACTA TCTGCCTGAA GATGGCATGT GAGTTGGATG
GACGAGACGA GCCTTCTGAT AGACGGACTT CTACCGTACA CTCAACCTAC

6451 ATATGGTTGG ACGCTGGAAG ACGTTGAAGC TGGCGTCTGT GAGACCTACC
TATACCAACC TGCGACCTTC TGCAACTTCG ACCGCAGACA CTCTGGATGG

6501 GCGTCACGCA CGAAGGAGGC GTAGGAGTCG CGCAGCTTGT TGACCAGCTC
CGCAGTGCGT GCTTCCTCCG CATCCTCAGC GCGTCGAACA ACTGGTCGAG

6551 GGCGGTGACC TGCACGTCTA GGGCGCAGTA GTCCAGGGTT TCCTTGATGA
CCGCCACTGG ACGTGCAGAT CCCGCGTCAT CAGGTCCCAA AGGAACTACT

6601 TGTCATACTT ATCCTGTCCC TTTTTTTTCC ACAGCTCGCG GTTGAGGACA
ACAGTATGAA TAGGACAGGG AAAAAAAAGG TGTCGAGCGC CAACTCCTGT

6651 AACTCTTCGC GGTCTTTCCA GTACTCTTGG ATCGGAAACC CGTCGGCCTC
TTGAGAAGCG CCAGAAAGGT CATGAGAACC TAGCCTTTGG GCAGCCGGAG

6701 CGAACGGTAA GAGCCTAGCA TGTAGAACTG GTTGACGGCC TGGTAGGCGC
GCTTGCCATT CTCGGATCGT ACATCTTGAC CAACTGCCGG ACCATCCGCG

FIG.15A-8

```
6751 AGCATCCCTT TTCTACGGGT AGCGCGTATG CCTGCGCGGC CTTCCGGAGC
     TCGTAGGGAA AAGATGCCCA TCGCGCATAC GGACGCGCCG GAAGGCCTCG

6801 GAGGTGTGGG TGAGCGCAAA GGTGTCCCTG ACCATGACTT TGAGGTACTG
     CTCCACACCC ACTCGCGTTT CCACAGGGAC TGGTACTGAA ACTCCATGAC

6851 GTATTTGAAG TCAGTGTCGT CGCATCCGCC CTGCTCCCAG AGCAAAAAGT
     CATAAACTTC AGTCACAGCA GCGTAGGCGG GACGAGGGTC TCGTTTTTCA

6901 CCGTGCGCTT TTTGGAACGC GGATTTGGCA GGGCGAAGGT GACATCGTTG
     GGCACGCGAA AAACCTTGCG CCTAAACCGT CCCGCTTCCA CTGTAGCAAC

6951 AAGAGTATCT TTCCCGCGCG AGGCATAAAG TTGCGTGTGA TGCGGAAGGG
     TTCTCATAGA AAGGGCGCGC TCCGTATTTC AACGCACACT ACGCCTTCCC

7001 TCCCGGCACC TCGGAACGGT TGTTAATTAC CTGGGCGGCG AGCACGATCT
     AGGGCCGTGG AGCCTTGCCA ACAATTAATG GACCCGCCGC TCGTGCTAGA

7051 CGTCAAAGCC GTTGATGTTG TGGCCCACAA TGTAAAGTTC CAAGAAGCGC
     GCAGTTTCGG CAACTACAAC ACCGGGTGTT ACATTTCAAG GTTCTTCGCG

7101 GGGATGCCCT TGATGGAAGG CAATTTTTTA AGTTCCTCGT AGGTGAGCTC
     CCCTACGGGA ACTACCTTCC GTTAAAAAAT TCAAGGAGCA TCCACTCGAG

7151 TTCAGGGGAG CTGAGCCCGT GCTCTGAAAG GGCCCAGTCT GCAAGATGAG
     AAGTCCCCTC GACTCGGGCA CGAGACTTTC CCGGGTCAGA CGTTCTACTC

7201 GGTTGGAAGC GACGAATGAG CTCCACAGGT CACGGGCCAT TAGCATTTGC
     CCAACCTTCG CTGCTTACTC GAGGTGTCCA GTGCCCGGTA ATCGTAAACG

7251 AGGTGGTCGC GAAAGGTCCT AAACTGGCGA CCTATGGCCA TTTTTTCTGG
     TCCACCAGCG CTTTCCAGGA TTTGACCGCT GGATACCGGT AAAAAAGACC

7301 GGTGATGCAG TAGAAGGTAA GCGGGTCTTG TTCCCAGCGG TCCCATCCAA
     CCACTACGTC ATCTTCCATT CGCCCAGAAC AAGGGTCGCC AGGGTAGGTT

7351 GGTTCGCGGC TAGGTCTCGC GCGGCAGTCA CTAGAGGCTC ATCTCCGCCG
     CCAAGCGCCG ATCCAGAGCG CGCCGTCAGT GATCTCCGAG TAGAGGCGGC

7401 AACTTCATGA CCAGCATGAA GGGCACGAGC TGCTTCCCAA AGGCCCCCAT
     TTGAAGTACT GGTCGTACTT CCCGTGCTCG ACGAAGGGTT TCCGGGGGTA

7451 CCAAGTATAG GTCTCTACAT CGTAGGTGAC AAAGAGACGC TCGGTGCGAG
     GGTTCATATC CAGAGATGTA GCATCCACTG TTTCTCTGCG AGCCACGCTC

7501 GATGCGAGCC GATCGGGAAG AACTGGATCT CCCGCCACCA ATTGGAGGAG
     CTACGCTCGG CTAGCCCTTC TTGACCTAGA GGGCGGTGGT TAACCTCCTC

7551 TGGCTATTGA TGTGGTGAAA GTAGAAGTCC CTGCGACGGG CCGAACACTC
     ACCGATAACT ACACCACTTT CATCTTCAGG GACGCTGCCC GGCTTGTGAG
```

FIG. 15A-9

```
7601  GTGCTGGCTT TTGTAAAAAC GTGCGCAGTA CTGGCAGCGG TGCACGGGCT
      CACGACCGAA AACATTTTTG CACGCGTCAT GACCGTCGCC ACGTGCCCGA

7651  GTACATCCTG CACGAGGTTG ACCTGACGAC CGCGCACAAG GAAGCAGAGT
      CATGTAGGAC GTGCTCCAAC TGGACTGCTG GCGCGTGTTC CTTCGTCTCA

7701  GGGAATTTGA GCCCCTCGCC TGGCGGGTTT GGCTGGTGGT CTTCTACTTC
      CCCTTAAACT CGGGGAGCGG ACCGCCCAAA CCGACCACCA GAAGATGAAG

7751  GGCTGCTTGT CCTTGACCGT CTGGCTGCTC GAGGGGAGTT ACGGTGGATC
      CCGACGAACA GGAACTGGCA GACCGACGAG CTCCCCTCAA TGCCACCTAG

7801  GGACCACCAC GCCGCGCGAG CCCAAAGTCC AGATGTCCGC GCGCGGCGGT
      CCTGGTGGTG CGGCGCGCTC GGGTTTCAGG TCTACAGGCG CGCGCCGCCA

7851  CGGAGCTTGA TGACAACATC GCGCAGATGG GAGCTGTCCA TGGTCTGGAG
      GCCTCGAACT ACTGTTGTAG CGCGTCTACC CTCGACAGGT ACCAGACCTC

7901  CTCCCGCGGC GTCAGGTCAG GCGGGAGCTC CTGCAGGTTT ACCTCGCATA
      GAGGGCGCCG CAGTCCAGTC CGCCCTCGAG GACGTCCAAA TGGAGCGTAT

7951  GACGGGTCAG GGCGCGGGCT AGATCCAGGT GATACCTAAT TTCCAGGGGC
      CTGCCCAGTC CCGCGCCCGA TCTAGGTCCA CTATGGATTA AAGGTCCCCG

8001  TGGTTGGTGG CGGCGTCGAT GGCTTGCAAG AGGCCGCATC CCCGCGGCGC
      ACCAACCACC GCCGCAGCTA CCGAACGTTC TCCGGCGTAG GGGCGCCGCG

8051  GACTACGGTA CCGCGCGGCG GGCGGTGGGC CGCGGGGGTG TCCTTGGATG
      CTGATGCCAT GGCGCGCCGC CCGCCACCCG GCGCCCCCAC AGGAACCTAC

8101  ATGCATCTAA AAGCGGTGAC GCGGGCGAGC CCCCGGAGGT AGGGGGGGCT
      TACGTAGATT TTCGCCACTG CGCCCGCTCG GGGGCCTCCA TCCCCCCCGA

8151  CCGGACCCGC CGGGAGAGGG GGCAGGGGCA CGTCGGCGCC GCGCGCGGGC
      GGCCTGGGCG GCCCTCTCCC CCGTCCCCGT GCAGCCGCGG CGCGCGCCCG

8201  AGGAGCTGGT GCTGCGCGCG TAGGTTGCTG GCGAACGCGA CGACGCGGCG
      TCCTCGACCA CGACGCGCGC ATCCAACGAC CGCTTGCGCT GCTGCGCCGC

8251  GTTGATCTCC TGAATCTGGC GCCTCTGCGT GAAGACGACG GGCCCGGTGA
      CAACTAGAGG ACTTAGACCG CGGAGACGCA CTTCTGCTGC CCGGGCCACT

8301  GCTTGAACCT GAAAGAGAGT TCGACAGAAT CAATTTCGGT GTCGTTGACG
      CGAACTTGGA CTTTCTCTCA AGCTGTCTTA GTTAAAGCCA CAGCAACTGC

8351  GCGGCCTGGC GCAAAATCTC CTGCACGTCT CCTGAGTTGT CTTGATAGGC
      CGCCGGACCG CGTTTTAGAG GACGTGCAGA GGACTCAACA GAACTATCCG

8401  GATCTCGGCC ATGAACTGCT CGATCTCTTC CTCCTGGAGA TCTCCGCGTC
      CTAGAGCCGG TACTTGACGA GCTAGAGAAG GAGGACCTCT AGAGGCGCAG
```

FIG. 15A-10

```
8451 CGGCTCGCTC CACGGTGGCG GCGAGGTCGT TGGAAATGCG GGCCATGAGC
     GCCGAGCGAG GTGCCACCGC CGCTCCAGCA ACCTTTACGC CCGGTACTCG

8501 TGCGAGAAGG CGTTGAGGCC TCCCTCGTTC CAGACGCGGC TGTAGACCAC
     ACGCTCTTCC GCAACTCCGG AGGGAGCAAG GTCTGCGCCG ACATCTGGTG

8551 GCCCCCTTCG GCATCGCGGG CGCGCATGAC CACCTGCGCG AGATTGAGCT
     CGGGGGAAGC CGTAGCGCCC GCGCGTACTG GTGGACGCGC TCTAACTCGA

8601 CCACGTGCCG GGCGAAGACG GCGTAGTTTC GCAGGCGCTG AAAGAGGTAG
     GGTGCACGGC CCGCTTCTGC CGCATCAAAG CGTCCGCGAC TTTCTCCATC

8651 TTGAGGGTGG TGGCGGTGTG TTCTGCCACG AAGAAGTACA TAACCCAGCG
     AACTCCCACC ACCGCCACAC AAGACGGTGC TTCTTCATGT ATTGGGTCGC

8701 TCGCAACGTG GATTCGTTGA TATCCCCCAA GGCCTCAAGG CGCTCCATGG
     AGCGTTGCAC CTAAGCAACT ATAGGGGGTT CCGGAGTTCC GCGAGGTACC

8751 CCTCGTAGAA GTCCACGGCG AAGTTGAAAA ACTGGGAGTT GCGCGCCGAC
     GGAGCATCTT CAGGTGCCGC TTCAACTTTT TGACCCTCAA CGCGCGGCTG

8801 ACGGTTAACT CCTCCTCCAG AAGACGGATG AGCTCGGCGA CAGTGTCGCG
     TGCCAATTGA GGAGGAGGTC TTCTGCCTAC TCGAGCCGCT GTCACAGCGC

8851 CACCTCGCGC TCAAAGGCTA CAGGGGCCTC TTCTTCTTCT TCAATCTCCT
     GTGGAGCGCG AGTTTCCGAT GTCCCCGGAG AAGAAGAAGA AGTTAGAGGA

8901 CTTCCATAAG GGCCTCCCCT TCTTCTTCTT CTGGCGGCGG TGGGGGAGGG
     GAAGGTATTC CCGGAGGGGA AGAAGAAGAA GACCGCCGCC ACCCCCTCCC

8951 GGGACACGGC GGCGACGACG GCGCACCGGG AGGCGGTCGA CAAAGCGCTC
     CCCTGTGCCG CCGCTGCTGC CGCGTGGCCC TCCGCCAGCT GTTTCGCGAG

9001 GATCATCTCC CCGCGGCGAC GGCGCATGGT CTCGGTGACG GCGCGGCCGT
     CTAGTAGAGG GGCGCCGCTG CCGCGTACCA GAGCCACTGC CGCGCCGGCA

9051 TCTCGCGGGG GCGCAGTTGG AAGACGCCGC CCGTCATGTC CCGGTTATGG
     AGAGCGCCCC CGCGTCAACC TTCTGCGGCG GGCAGTACAG GGCCAATACC

9101 GTTGGCGGGG GGCTGCCATG CGGCAGGGAT ACGGCGCTAA CGATGCATCT
     CAACCGCCCC CCGACGGTAC GCCGTCCCTA TGCCGCGATT GCTACGTAGA

9151 CAACAATTGT TGTGTAGGTA CTCCGCCGCC GAGGGACCTG AGCGAGTCCG
     GTTGTTAACA ACACATCCAT GAGGCGGCGG CTCCCTGGAC TCGCTCAGGC

9201 CATCGACCGG ATCGGAAAAC CTCTCGAGAA AGGCGTCTAA CCAGTCACAG
     GTAGCTGGCC TAGCCTTTTG GAGAGCTCTT TCCGCAGATT GGTCAGTGTC

9251 TCGCAAGGTA GGCTGAGCAC CGTGGCGGGC GGCAGCGGGC GGCGGTCGGG
     AGCGTTCCAT CCGACTCGTG GCACCGCCCG CCGTCGCCCG CCGCCAGCCC
```

FIG.15A-11

9301 GTTGTTTCTG GCGGAGGTGC TGCTGATGAT GTAATTAAAG TAGGCGGTCT
CAACAAAGAC CGCCTCCACG ACGACTACTA CATTAATTTC ATCCGCCAGA

9351 TGAGACGGCG GATGGTCGAC AGAAGCACCA TGTCCTTGGG TCCGGCCTGC
ACTCTGCCGC CTACCAGCTG TCTTCGTGGT ACAGGAACCC AGGCCGGACG

9401 TGAATGCGCA GGCGGTCGGC CATGCCCCAG GCTTCGTTTT GACATCGGCG
ACTTACGCGT CCGCCAGCCG GTACGGGGTC CGAAGCAAAA CTGTAGCCGC

9451 CAGGTCTTTG TAGTAGTCTT GCATGAGCCT TTCTACCGGC ACTTCTTCTT
GTCCAGAAAC ATCATCAGAA CGTACTCGGA AAGATGGCCG TGAAGAAGAA

9501 CTCCTTCCTC TTGTCCTGCA TCTCTTGCAT CTATCGCTGC GGCGGCGGCG
GAGGAAGGAG AACAGGACGT AGAGAACGTA GATAGCGACG CCGCCGCCGC

9551 GAGTTTGGCC GTAGGTGGCG CCCTCTTCCT CCCATGCGTG TGACCCCGAA
CTCAAACCGG CATCCACCGC GGGAGAAGGA GGGTACGCAC ACTGGGGCTT

9601 GCCCCTCATC GGCTGAAGCA GGGCTAGGTC GGCGACAACG CGCTCGGCTA
CGGGGAGTAG CCGACTTCGT CCCGATCCAG CCGCTGTTGC GCGAGCCGAT

9651 ATATGGCCTG CTGCACCTGC GTGAGGGTAG ACTGGAAGTC ATCCATGTCC
TATACCGGAC GACGTGGACG CACTCCCATC TGACCTTCAG TAGGTACAGG

9701 ACAAAGCGGT GGTATGCGCC CGTGTTGATG GTGTAAGTGC AGTTGGCCAT
TGTTTCGCCA CCATACGCGG GCACAACTAC CACATTCACG TCAACCGGTA

9751 AACGGACCAG TTAACGGTCT GGTGACCCGG CTGCGAGAGC TCGGTGTACC
TTGCCTGGTC AATTGCCAGA CCACTGGGCC GACGCTCTCG AGCCACATGG

9801 TGAGACGCGA GTAAGCCCTC GAGTCAAATA CGTAGTCGTT GCAAGTCCGC
ACTCTGCGCT CATTCGGGAG CTCAGTTTAT GCATCAGCAA CGTTCAGGCG

9851 ACCAGGTACT GGTATCCCAC CAAAAAGTGC GGCGGCGGCT GGCGGTAGAG
TGGTCCATGA CCATAGGGTG GTTTTTCACG CCGCCGCCGA CCGCCATCTC

9901 GGGCCAGCGT AGGGTGGCCG GGGCTCCGGG GGCGAGATCT TCCAACATAA
CCCGGTCGCA TCCCACCGGC CCCGAGGCCC CCGCTCTAGA AGGTTGTATT

9951 GGCGATGATA TCCGTAGATG TACCTGGACA TCCAGGTGAT GCCGGCGGCG
CCGCTACTAT AGGCATCTAC ATGGACCTGT AGGTCCACTA CGGCCGCCGC

10001 GTGGTGGAGG CGCGCGGAAA GTCGCGGACG CGGTTCCAGA TGTTGCGCAG
CACCACCTCC GCGCGCCTTT CAGCGCCTGC GCCAAGGTCT ACAACGCGTC

10051 CGGCAAAAAG TGCTCCATGG TCGGGACGCT CTGGCCGGTC AGGCGCGCGC
GCCGTTTTTC ACGAGGTACC AGCCCTGCGA GACCGGCCAG TCCGCGCGCG

10101 AATCGTTGAC GCTCTAGACC GTGCAAAAGG AGAGCCTGTA AGCGGGCACT
TTAGCAACTG CGAGATCTGG CACGTTTTCC TCTCGGACAT TCGCCCGTGA

FIG.15A-12

```
10151 CTTCCGTGGT CTGGTGGATA AATTCGCAAG GGTATCATGG CGGACGACCG
      GAAGGCACCA GACCACCTAT TTAAGCGTTC CCATAGTACC GCCTGCTGGC

10201 GGGTTCGAGC CCCGTATCCG GCCGTCCGCC GTGATCCATG CGGTTACCGC
      CCCAAGCTCG GGGCATAGGC CGGCAGGCGG CACTAGGTAC GCCAATGGCG

10251 CCGCGTGTCG AACCCAGGTG TGCGACGTCA GACAACGGGG GAGTGCTCCT
      GGCGCACAGC TTGGGTCCAC ACGCTGCAGT CTGTTGCCCC CTCACGAGGA

10301 TTTGGCTTCC TTCCAGGCGC GGCGGCTGCT GCGCTAGCTT TTTTGGCCAC
      AAACCGAAGG AAGGTCCGCG CCGCCGACGA CGCGATCGAA AAAACCGGTG

10351 TGGCCGCGCG CAGCGTAAGC GGTTAGGCTG GAAAGCGAAA GCATTAAGTG
      ACCGGCGCGC GTCGCATTCG CCAATCCGAC CTTTCGCTTT CGTAATTCAC

10401 GCTCGCTCCC TGTAGCCGGA GGGTTATTTT CCAAGGGTTG AGTCGCGGGA
      CGAGCGAGGG ACATCGGCCT CCCAATAAAA GGTTCCCAAC TCAGCGCCCT

10451 CCCCCGGTTC GAGTCTCGGA CCGGCCGGAC TGCGGCGAAC GGGGGTTTGC
      GGGGGCCAAG CTCAGAGCCT GGCCGGCCTG ACGCCGCTTG CCCCCAAACG

10501 CTCCCCGTCA TGCAAGACCC CGCTTGCAAA TTCCTCCGGA AACAGGGACG
      GAGGGGCAGT ACGTTCTGGG GCGAACGTTT AAGGAGGCCT TTGTCCCTGC

10551 AGCCCCTTTT TTGCTTTTCC CAGATGCATC CGGTGCTGCG GCAGATGCGC
      TCGGGGAAAA AACGAAAAGG GTCTACGTAG GCCACGACGC CGTCTACGCG

10601 CCCCCTCCTC AGCAGCGGCA AGAGCAAGAG CAGCGGCAGA CATGCAGGGC
      GGGGGAGGAG TCGTCGCCGT TCTCGTTCTC GTCGCCGTCT GTACGTCCCG

10651 ACCCTCCCCT CCTCCTACCG CGTCAGGAGG GGCGACATCC GCGGTTGACG
      TGGGAGGGGA GGAGGATGGC GCAGTCCTCC CCGCTGTAGG CGCCAACTGC

10701 CGGCAGCAGA TGGTGATTAC GAACCCCCGC GGCGCCGGGC CCGGCACTAC
      GCCGTCGTCT ACCACTAATG CTTGGGGGCG CCGCGGCCCG GGCCGTGATG

10751 CTGGACTTGG AGGAGGGCGA GGGCCTGGCG CGGCTAGGAG CGCCCTCTCC
      GACCTGAACC TCCTCCCGCT CCCGGACCGC GCCGATCCTC GCGGGAGAGG

10801 TGAGCGGCAC CCAAGGGTGC AGCTGAAGCG TGATACGCGT GAGGCGTACG
      ACTCGCCGTG GGTTCCCACG TCGACTTCGC ACTATGCGCA CTCCGCATGC

10851 TGCCGCGGCA GAACCTGTTT CGCGACCGCG AGGGAGAGGA GCCCGAGGAG
      ACGGCGCCGT CTTGGACAAA GCGCTGGCGC TCCCTCTCCT CGGGCTCCTC

10901 ATGCGGGATC GAAAGTTCCA CGCAGGGCGC GAGCTGCGGC ATGGCCTGAA
      TACGCCCTAG CTTTCAAGGT GCGTCCCGCG CTCGACGCCG TACCGGACTT

10951 TCGCGAGCGG TTGCTGCGCG AGGAGGACTT TGAGCCCGAC GCGCGAACCG
      AGCGCTCGCC AACGACGCGC TCCTCCTGAA ACTCGGGCTG CGCGCTTGGC
```

FIG.15A-13

11001 GGATTAGTCC CGCGCGCGCA CACGTGGCGG CCGCCGACCT GGTAACCGCA
CCTAATCAGG GCGCGCGCGT GTGCACCGCC GGCGGCTGGA CCATTGGCGT

11051 TACGAGCAGA CGGTGAACCA GGAGATTAAC TTTCAAAAAA GCTTTAACAA
ATGCTCGTCT GCCACTTGGT CCTCTAATTG AAAGTTTTTT CGAAATTGTT

11101 CCACGTGCGT ACGCTTGTGG CGCGCGAGGA GGTGGCTATA GGACTGATGC
GGTGCACGCA TGCGAACACC GCGCGCTCCT CCACCGATAT CCTGACTACG

11151 ATCTGTGGGA CTTTGTAAGC GCGCTGGAGC AAAACCCAAA TAGCAAGCCG
TAGACACCCT GAAACATTCG CGCGACCTCG TTTTGGGTTT ATCGTTCGGC

11201 CTCATGGCGC AGCTGTTCCT TATAGTGCAG CACAGCAGGG ACAACGAGGC
GAGTACCGCG TCGACAAGGA ATATCACGTC GTGTCGTCCC TGTTGCTCCG

11251 ATTCAGGGAT GCGCTGCTAA ACATAGTAGA GCCCGAGGGC CGCTGGCTGC
TAAGTCCCTA CGCGACGATT TGTATCATCT CGGGCTCCCG GCGACCGACG

11301 TCGATTTGAT AAACATCCTG CAGAGCATAG TGGTGCAGGA GCGCAGCTTG
AGCTAAACTA TTTGTAGGAC GTCTCGTATC ACCACGTCCT CGCGTCGAAC

11351 AGCCTGGCTG ACAAGGTGGC CGCCATCAAC TATTCCATGC TTAGCCTGGG
TCGGACCGAC TGTTCCACCG GCGGTAGTTG ATAAGGTACG AATCGGACCC

11401 CAAGTTTTAC GCCCGCAAGA TATACCATAC CCCTTACGTT CCCATAGACA
GTTCAAAATG CGGGCGTTCT ATATGGTATG GGGAATGCAA GGGTATCTGT

11451 AGGAGGTAAA GATCGAGGGG TTCTACATGC GCATGGCGCT GAAGGTGCTT
TCCTCCATTT CTAGCTCCCC AAGATGTACG CGTACCGCGA CTTCCACGAA

11501 ACCTTGAGCG ACGACCTGGG CGTTTATCGC AACGAGCGCA TCCACAAGGC
TGGAACTCGC TGCTGGACCC GCAAATAGCG TTGCTCGCGT AGGTGTTCCG

11551 CGTGAGCGTG AGCCGGCGGC GCGAGCTCAG CGACCGCGAG CTGATGCACA
GCACTCGCAC TCGGCCGCCG CGCTCGAGTC GCTGGCGCTC GACTACGTGT

11601 GCCTGCAAAG GGCCCTGGCT GGCACGGGCA GCGGCGATAG AGAGGCCGAG
CGGACGTTTC CCGGGACCGA CCGTGCCCGT CGCCGCTATC TCTCCGGCTC

11651 TCCTACTTTG ACGCGGGCGC TGACCTGCGC TGGGCCCCAA GCCGACGCGC
AGGATGAAAC TGCGCCCGCG ACTGGACGCG ACCCGGGGTT CGGCTGCGCG

11701 CCTGGAGGCA GCTGGGGCCG GACCTGGGCT GGCGGTGGCA CCCGCGCGCG
GGACCTCCGT CGACCCCGGC CTGGACCCGA CCGCCACCGT GGGCGCGCGC

11751 CTGGCAACGT CGGCGGCGTG GAGGAATATG ACGAGGACGA TGAGTACGAG
GACCGTTGCA GCCGCCGCAC CTCCTTATAC TGCTCCTGCT ACTCATGCTC

11801 CCAGAGGACG GCGAGTACTA AGCGGTGATG TTTCTGATCA GATGATGCAA
GGTCTCCTGC CGCTCATGAT TCGCCACTAC AAAGACTAGT CTACTACGTT

FIG. 15A-14

```
11851 GACGCAACGG ACCCGGCGGT GCGGGCGGCG CTGCAGAGCC AGCCGTCCGG
      CTGCGTTGCC TGGGCCGCCA CGCCCGCCGC GACGTCTCGG TCGGCAGGCC

11901 CCTTAACTCC ACGGACGACT GGCGCCAGGT CATGGACCGC ATCATGTCGC
      GGAATTGAGG TGCCTGCTGA CCGCGGTCCA GTACCTGGCG TAGTACAGCG

11951 TGACTGCGCG CAATCCTGAC GCGTTCCGGC AGCAGCCGCA GGCCAACCGG
      ACTGACGCGC GTTAGGACTG CGCAAGGCCG TCGTCGGCGT CCGGTTGGCC

12001 CTCTCCGCAA TTCTGGAAGC GGTGGTCCCG GCGCGCGCAA ACCCCACGCA
      GAGAGGCGTT AAGACCTTCG CCACCAGGGC CGCGCGCGTT TGGGGTGCGT

12051 CGAGAAGGTG CTGGCGATCG TAAACGCGCT GGCCGAAAAC AGGGCCATCC
      GCTCTTCCAC GACCGCTAGC ATTTGCGCGA CCGGCTTTTG TCCCGGTAGG

12101 GGCCCGACGA GGCCGGCCTG GTCTACGACG CGCTGCTTCA GCGCGTGGCT
      CCGGGCTGCT CCGGCCGGAC CAGATGCTGC GCGACGAAGT CGCGCACCGA

12151 CGTTACAACA GCGGCAACGT GCAGACCAAC CTGGACCGGC TGGTGGGGGA
      GCAATGTTGT CGCCGTTGCA CGTCTGGTTG GACCTGGCCG ACCACCCCCT

12201 TGTGCGCGAG GCCGTGGCGC AGCGTGAGCG CGCGCAGCAG CAGGGCAACC
      ACACGCGCTC CGGCACCGCG TCGCACTCGC GCGCGTCGTC GTCCCGTTGG

12251 TGGGCTCCAT GGTTGCACTA AACGCCTTCC TGAGTACACA GCCCGCCAAC
      ACCCGAGGTA CCAACGTGAT TTGCGGAAGG ACTCATGTGT CGGGCGGTTG

12301 GTGCCGCGGG GACAGGAGGA CTACACCAAC TTTGTGAGCG CACTGCGGCT
      CACGGCGCCC CTGTCCTCCT GATGTGGTTG AAACACTCGC GTGACGCCGA

12351 AATGGTGACT GAGACACCGC AAAGTGAGGT GTACCAGTCT GGGCCAGACT
      TTACCACTGA CTCTGTGGCG TTTCACTCCA CATGGTCAGA CCCGGTCTGA

12401 ATTTTTTCCA GACCAGTAGA CAAGGCCTGC AGACCGTAAA CCTGAGCCAG
      TAAAAAAGGT CTGGTCATCT GTTCCGGACG TCTGGCATTT GGACTCGGTC

12451 GCTTTCAAAA ACTTGCAGGG GCTGTGGGGG GTGCGGGCTC CCACAGGCGA
      CGAAAGTTTT TGAACGTCCC CGACACCCCC CACGCCCGAG GGTGTCCGCT

12501 CCGCGCGACC GTGTCTAGCT TGCTGACGCC CAACTCGCGC CTGTTGCTGC
      GGCGCGCTGG CACAGATCGA ACGACTGCGG GTTGAGCGCG GACAACGACG

12551 TGCTAATAGC GCCCTTCACG GACAGTGGCA GCGTGTCCCG GGACACATAC
      ACGATTATCG CGGGAAGTGC CTGTCACCGT CGCACAGGGC CCTGTGTATG

12601 CTAGGTCACT TGCTGACACT GTACCGCGAG GCCATAGGTC AGGCGCATGT
      GATCCAGTGA ACGACTGTGA CATGGCGCTC CGGTATCCAG TCCGCGTACA

12651 GGACGAGCAT ACTTTCCAGG AGATTACAAG TGTCAGCCGC GCGCTGGGGC
      CCTGCTCGTA TGAAAGGTCC TCTAATGTTC ACAGTCGGCG CGCGACCCCG
```

FIG.15A-15

```
12701 AGGAGGACAC GGGCAGCCTG GAGGCAACCC TAAACTACCT GCTGACCAAC
      TCCTCCTGTG CCCGTCGGAC CTCCGTTGGG ATTTGATGGA CGACTGGTTG

12751 CGGCGGCAGA AGATCCCCTC GTTGCACAGT TTAAACAGCG AGGAGGAGCG
      GCCGCCGTCT TCTAGGGGAG CAACGTGTCA AATTTGTCGC TCCTCCTCGC

12801 CATTTTGCGC TACGTGCAGC AGAGCGTGAG CCTTAACCTG ATGCGCGACG
      GTAAAACGCG ATGCACGTCG TCTCGCACTC GGAATTGGAC TACGCGCTGC

12851 GGGTAACGCC CAGCGTGGCG CTGGACATGA CCGCGCGCAA CATGGAACCG
      CCCATTGCGG GTCGCACCGC GACCTGTACT GGCGCGCGTT GTACCTTGGC

12901 GGCATGTATG CCTCAAACCG GCCGTTTATC AACCGCCTAA TGGACTACTT
      CCGTACATAC GGAGTTTGGC CGGCAAATAG TTGGCGGATT ACCTGATGAA

12951 GCATCGCGCG GCCGCCGTGA ACCCCGAGTA TTTCACCAAT GCCATCTTGA
      CGTAGCGCGC CGGCGGCACT TGGGGCTCAT AAAGTGGTTA CGGTAGAACT

13001 ACCCGCACTG GCTACCGCCC CCTGGTTTCT ACACCGGGGG ATTCGAGGTG
      TGGGCGTGAC CGATGGCGGG GGACCAAAGA TGTGGCCCCC TAAGCTCCAC

13051 CCCGAGGGTA ACGATGGATT CCTCTGGGAC GACATAGACG ACAGCGTGTT
      GGGCTCCCAT TGCTACCTAA GGAGACCCTG CTGTATCTGC TGTCGCACAA

13101 TTCCCCGCAA CCGCAGACCC TGCTAGAGTT GCAACAGCGC GAGCAGGCAG
      AAGGGGCGTT GGCGTCTGGG ACGATCTCAA CGTTGTCGCG CTCGTCCGTC

13151 AGGCGGCGCT GCGAAAGGAA AGCTTCCGCA GGCCAAGCAG CTTGTCCGAT
      TCCGCCGCGA CGCTTTCCTT TCGAAGGCGT CCGGTTCGTC GAACAGGCTA

13201 CTAGGCGCTG CGGCCCCGCG GTCAGATGCT AGTAGCCCAT TTCCAAGCTT
      GATCCGCGAC GCCGGGGCGC CAGTCTACGA TCATCGGGTA AAGGTTCGAA

13251 GATAGGGTCT CTTACCAGCA CTCGCACCAC CCGCCCGCGC CTGCTGGGCG
      CTATCCCAGA GAATGGTCGT GAGCGTGGTG GGCGGGCGCG GACGACCCGC

13301 AGGAGGAGTA CCTAAACAAC TCGCTGCTGC AGCCGCAGCG CGAAAAAAAC
      TCCTCCTCAT GGATTTGTTG AGCGACGACG TCGGCGTCGC GCTTTTTTTG

13351 CTGCCTCCGG CATTTCCCAA CAACGGGATA GAGAGCCTAG TGGACAAGAT
      GACGGAGGCC GTAAAGGGTT GTTGCCCTAT CTCTCGGATC ACCTGTTCTA

13401 GAGTAGATGG AAGACGTACG CGCAGGAGCA CAGGGACGTG CCAGGCCCGC
      CTCATCTACC TTCTGCATGC GCGTCCTCGT GTCCCTGCAC GGTCCGGGCG

13451 GCCCGCCCAC CCGTCGTCAA AGGCACGACC GTCAGCGGGG TCTGGTGTGG
      CGGGCGGGTG GGCAGCAGTT TCCGTGCTGG CAGTCGCCCC AGACCACACC

13501 GAGGACGATG ACTCGGCAGA CGACAGCAGC GTCCTGGATT TGGGAGGGAG
      CTCCTGCTAC TGAGCCGTCT GCTGTCGTCG CAGGACCTAA ACCCTCCCTC
```

FIG. 15A-16

```
13551 TGGCAACCCG TTTGCGCACC TTCGCCCCAG GCTGGGGAGA ATGTTTTAAA
      ACCGTTGGGC AAACGCGTGG AAGCGGGGTC CGACCCCTCT TACAAAATTT

13601 AAAAAAAAAA GCATGATGCA AAATAAAAAA CTCACCAAGG CCATGGCACC
      TTTTTTTTTT CGTACTACGT TTTATTTTTT GAGTGGTTCC GGTACCGTGG

13651 GAGCGTTGGT TTTCTTGTAT TCCCCTTAGT ATGCGGCGCG CGGCGATGTA
      CTCGCAACCA AAAGAACATA AGGGGAATCA TACGCCGCGC GCCGCTACAT

13701 TGAGGAAGGT CCTCCTCCCT CCTACGAGAG TGTGGTGAGC GCGGCGCCAG
      ACTCCTTCCA GGAGGAGGGA GGATGCTCTC ACACCACTCG CGCCGCGGTC

13751 TGGCGGCGGC GCTGGGTTCT CCCTTCGATG CTCCCCTGGA CCCGCCGTTT
      ACCGCCGCCG CGACCCAAGA GGGAAGCTAC GAGGGGACCT GGGCGGCAAA

13801 GTGCCTCCGC GGTACCTGCG GCCTACCGGG GGGAGAAACA GCATCCGTTA
      CACGGAGGCG CCATGGACGC CGGATGGCCC CCCTCTTTGT CGTAGGCAAT

13851 CTCTGAGTTG GCACCCCTAT TCGACACCAC CCGTGTGTAC CTGGTGGACA
      GAGACTCAAC CGTGGGGATA AGCTGTGGTG GGCACACATG GACCACCTGT

13901 ACAAGTCAAC GGATGTGGCA TCCCTGAACT ACCAGAACGA CCACAGCAAC
      TGTTCAGTTG CCTACACCGT AGGGACTTGA TGGTCTTGCT GGTGTCGTTG

13951 TTTCTGACCA CGGTCATTCA AAACAATGAC TACAGCCCGG GGGAGGCAAG
      AAAGACTGGT GCCAGTAAGT TTTGTTACTG ATGTCGGGCC CCCTCCGTTC

14001 CACACAGACC ATCAATCTTG ACGACCGGTC GCACTGGGGC GGCGACCTGA
      GTGTGTCTGG TAGTTAGAAC TGCTGGCCAG CGTGACCCCG CCGCTGGACT

14051 AAACCATCCT GCATACCAAC ATGCCAAATG TGAACGAGTT CATGTTTACC
      TTTGGTAGGA CGTATGGTTG TACGGTTTAC ACTTGCTCAA GTACAAATGG

14101 AATAAGTTTA AGGCGCGGGT GATGGTGTCG CGCTTGCCTA CTAAGGACAA
      TTATTCAAAT TCCGCGCCCA CTACCACAGC GCGAACGGAT GATTCCTGTT

14151 TCAGGTGGAG CTGAAATACG AGTGGGTGGA GTTCACGCTG CCCGAGGGCA
      AGTCCACCTC GACTTTATGC TCACCCACCT CAAGTGCGAC GGGCTCCCGT

14201 ACTACTCCGA GACCATGACC ATAGACCTTA TGAACAACGC GATCGTGGAG
      TGATGAGGCT CTGGTACTGG TATCTGGAAT ACTTGTTGCG CTAGCACCTC

14251 CACTACTTGA AAGTGGGCAG ACAGAACGGG GTTCTGGAAA GCGACATCGG
      GTGATGAACT TTCACCCGTC TGTCTTGCCC CAAGACCTTT CGCTGTAGCC

14301 GGTAAAGTTT GACACCCGCA ACTTCAGACT GGGGTTTGAC CCCGTCACTG
      CCATTTCAAA CTGTGGGCGT TGAAGTCTGA CCCCAAACTG GGGCAGTGAC

14351 GTCTTGTCAT GCCTGGGGTA TATACAAACG AAGCCTTCCA TCCAGACATC
      CAGAACAGTA CGGACCCCAT ATATGTTTGC TTCGGAAGGT AGGTCTGTAG
```

FIG.15A-17

```
14401 ATTTTGCTGC CAGGATGCGG GGTGGACTTC ACCCACAGCC GCCTGAGCAA
      TAAAACGACG GTCCTACGCC CCACCTGAAG TGGGTGTCGG CGGACTCGTT

14451 CTTGTTGGGC ATCCGCAAGC GGCAACCCTT CCAGGAGGGC TTTAGGATCA
      GAACAACCCG TAGGCGTTCG CCGTTGGGAA GGTCCTCCCG AAATCCTAGT

14501 CCTACGATGA TCTGGAGGGT GGTAACATTC CCGCACTGTT GGATGTGGAC
      GGATGCTACT AGACCTCCCA CCATTGTAAG GGCGTGACAA CCTACACCTG

14551 GCCTACCAGG CGAGCTTGAA AGATGACACC GAACAGGGCG GGGGTGGCGC
      CGGATGGTCC GCTCGAACTT TCTACTGTGG CTTGTCCCGC CCCCACCGCG

14601 AGGCGGCAGC AACAGCAGTG GCAGCGGCGC GGAAGAGAAC TCCAACGCGG
      TCCGCCGTCG TTGTCGTCAC CGTCGCCGCG CCTTCTCTTG AGGTTGCGCC

14651 CAGCCGCGGC AATGCAGCCG GTGGAGGACA TGAACGATCA TGCCATTCGC
      GTCGGCGCCG TTACGTCGGC CACCTCCTGT ACTTGCTAGT ACGGTAAGCG

14701 GGCGACACCT TTGCCACACG GGCTGAGGAG AAGCGCGCTG AGGCCGAAGC
      CCGCTGTGGA AACGGTGTGC CCGACTCCTC TTCGCGCGAC TCCGGCTTCG

14751 AGCGGCCGAA GCTGCCGCCC CCGCTGCGCA ACCCGAGGTC GAGAAGCCTC
      TCGCCGGCTT CGACGGCGGG GGCGACGCGT TGGGCTCCAG CTCTTCGGAG

14801 AGAAGAAACC GGTGATCAAA CCCCTGACAG AGGACAGCAA GAAACGCAGT
      TCTTCTTTGG CCACTAGTTT GGGGACTGTC TCCTGTCGTT CTTTGCGTCA

14851 TACAACCTAA TAAGCAATGA CAGCACCTTC ACCCAGTACC GCAGCTGGTA
      ATGTTGGATT ATTCGTTACT GTCGTGGAAG TGGGTCATGG CGTCGACCAT

14901 CCTTGCATAC AACTACGGCG ACCCTCAGAC CGGAATCCGC TCATGGACCC
      GGAACGTATG TTGATGCCGC TGGGAGTCTG GCCTTAGGCG AGTACCTGGG

14951 TGCTTTGCAC TCCTGACGTA ACCTGCGGCT CGGAGCAGGT CTACTGGTCG
      ACGAAACGTG AGGACTGCAT TGGACGCCGA GCCTCGTCCA GATGACCAGC

15001 TTGCCAGACA TGATGCAAGA CCCCGTGACC TTCCGCTCCA CGCGCCAGAT
      AACGGTCTGT ACTACGTTCT GGGGCACTGG AAGGCGAGGT GCGCGGTCTA

15051 CAGCAACTTT CCGGTGGTGG GCGCCGAGCT GTTGCCCGTG CACTCCAAGA
      GTCGTTGAAA GGCCACCACC CGCGGCTCGA CAACGGGCAC GTGAGGTTCT

15101 GCTTCTACAA CGACCAGGCC GTCTACTCCC AACTCATCCG CCAGTTTACC
      CGAAGATGTT GCTGGTCCGG CAGATGAGGG TTGAGTAGGC GGTCAAATGG

15151 TCTCTGACCC ACGTGTTCAA TCGCTTTCCC GAGAACCAGA TTTTGGCGCG
      AGAGACTGGG TGCACAAGTT AGCGAAAGGG CTCTTGGTCT AAAACCGCGC

15201 CCCGCCAGCC CCCACCATCA CCACCGTCAG TGAAAACGTT CCTGCTCTCA
      GGGCGGTCGG GGGTGGTAGT GGTGGCAGTC ACTTTTGCAA GGACGAGAGT
```

FIG.15A-18

```
15251  CAGATCACGG GACGCTACCG CTGCGCAACA GCATCGGAGG AGTCCAGCGA
       GTCTAGTGCC CTGCGATGGC GACGCGTTGT CGTAGCCTCC TCAGGTCGCT

15301  GTGACCATTA CTGACGCCAG ACGCCGCACC TGCCCCTACG TTTACAAGGC
       CACTGGTAAT GACTGCGGTC TGCGGCGTGG ACGGGGATGC AAATGTTCCG

15351  CCTGGGCATA GTCTCGCCGC GCGTCCTATC GAGCCGCACT TTTTGAGCAA
       GGACCCGTAT CAGAGCGGCG CGCAGGATAG CTCGGCGTGA AAAACTCGTT

15401  GCATGTCCAT CCTTATATCG CCCAGCAATA ACACAGGCTG GGGCCTGCGC
       CGTACAGGTA GGAATATAGC GGGTCGTTAT TGTGTCCGAC CCCGGACGCG

15451  TTCCCAAGCA AGATGTTTGG CGGGGCCAAG AAGCGCTCCG ACCAACACCC
       AAGGGTTCGT TCTACAAACC GCCCCGGTTC TTCGCGAGGC TGGTTGTGGG

15501  AGTGCGCGTG CGCGGGCACT ACCGCGCGCC CTGGGGCGCG CACAAACGCG
       TCACGCGCAC GCGCCCGTGA TGGCGCGCGG GACCCCGCGC GTGTTTGCGC

15551  GCCGCACTGG GCGCACCACC GTCGATGACG CCATCGACGC GGTGGTGGAG
       CGGCGTGACC CGCGTGGTGG CAGCTACTGC GGTAGCTGCG CCACCACCTC

15601  GAGGCGCGCA ACTACACGCC CACGCCGCCA CCAGTGTCCA CAGTGGACGC
       CTCCGCGCGT TGATGTGCGG GTGCGGCGGT GGTCACAGGT GTCACCTGCG

15651  GGCCATTCAG ACCGTGGTGC GCGGAGCCCG GCGCTATGCT AAAATGAAGA
       CCGGTAAGTC TGGCACCACG CGCCTCGGGC CGCGATACGA TTTTACTTCT

15701  GACGGCGGAG GCGCGTAGCA CGTCGCCACC GCCGCCGACC CGGCACTGCC
       CTGCCGCCTC CGCGCATCGT GCAGCGGTGG CGGCGGCTGG GCCGTGACGG

15751  GCCCAACGCG CGGCGGCGGC CCTGCTTAAC CGCGCACGTC GCACCGGCCG
       CGGGTTGCGC GCCGCCGCCG GGACGAATTG GCGCGTGCAG CGTGGCCGGC

15801  ACGGGCGGCC ATGCGGGCCG CTCGAAGGCT GGCCGCGGGT ATTGTCACTG
       TGCCCGCCGG TACGCCCGGC GAGCTTCCGA CCGGCGCCCA TAACAGTGAC

15851  TGCCCCCCAG GTCCAGGCGA CGAGCGGCCG CCGCAGCAGC CGCGGCCATT
       ACGGGGGGTC CAGGTCCGCT GCTCGCCGGC GGCGTCGTCG GCGCCGGTAA

15901  AGTGCTATGA CTCAGGGTCG CAGGGGCAAC GTGTATTGGG TGCGCGACTC
       TCACGATACT GAGTCCCAGC GTCCCCGTTG CACATAACCC ACGCGCTGAG

15951  GGTTAGCGGC CTGCGCGTGC CCGTGCGCAC CCGCCCCCCG CGCAACTAGA
       CCAATCGCCG GACGCGCACG GGCACGCGTG GGCGGGGGGC GCGTTGATCT

16001  TTGCAAGAAA AAACTACTTA GACTCGTACT GTTGTATGTA TCCAGCGGCG
       AACGTTCTTT TTTGATGAAT CTGAGCATGA CAACATACAT AGGTCGCCGC

16051  GCGGCGCGCA ACGAAGCTAT GTCCAAGCGC AAAATCAAAG AAGAGATGCT
       CGCCGCGCGT TGCTTCGATA CAGGTTCGCG TTTTAGTTTC TTCTCTACGA
```

FIG.15A-19

```
16101 CCAGGTCATC GCGCCGGAGA TCTATGGCCC CCCGAAGAAG GAAGAGCAGG
      GGTCCAGTAG CGCGGCCTCT AGATACCGGG GGGCTTCTTC CTTCTCGTCC

16151 ATTACAAGCC CCGAAAGCTA AAGCGGGTCA AAAAGAAAAA GAAAGATGAT
      TAATGTTCGG GGCTTTCGAT TTCGCCCAGT TTTTCTTTTT CTTTCTACTA

16201 GATGATGAAC TTGACGACGA GGTGGAACTG CTGCACGCTA CCGCGCCCAG
      CTACTACTTG AACTGCTGCT CCACCTTGAC GACGTGCGAT GGCGCGGGTC

16251 GCGACGGGTA CAGTGGAAAG GTCGACGCGT AAAACGTGTT TTGCGACCCG
      CGCTGCCCAT GTCACCTTTC CAGCTGCGCA TTTTGCACAA AACGCTGGGC

16301 GCACCACCGT AGTCTTTACG CCCGGTGAGC GCTCCACCCG CACCTACAAG
      CGTGGTGGCA TCAGAAATGC GGGCCACTCG CGAGGTGGGC GTGGATGTTC

16351 CGCGTGTATG ATGAGGTGTA CGGCGACGAG GACCTGCTTG AGCAGGCCAA
      GCGCACATAC TACTCCACAT GCCGCTGCTC CTGGACGAAC TCGTCCGGTT

16401 CGAGCGCCTC GGGGAGTTTG CCTACGGAAA GCGGCATAAG GACATGCTGG
      GCTCGCGGAG CCCCTCAAAC GGATGCCTTT CGCCGTATTC CTGTACGACC

16451 CGTTGCCGCT GGACGAGGGC AACCCAACAC CTAGCCTAAA GCCCGTAACA
      GCAACGGCGA CCTGCTCCCG TTGGGTTGTG GATCGGATTT CGGGCATTGT

16501 CTGCAGCAGG TGCTGCCCGC GCTTGCACCG TCCGAAGAAA AGCGCGGCCT
      GACGTCGTCC ACGACGGGCG CGAACGTGGC AGGCTTCTTT TCGCGCCGGA

16551 AAAGCGCGAG TCTGGTGACT TGGCACCCAC CGTGCAGCTG ATGGTACCCA
      TTTCGCGCTC AGACCACTGA ACCGTGGGTG GCACGTCGAC TACCATGGGT

16601 AGCGCCAGCG ACTGGAAGAT GTCTTGGAAA AAATGACCGT GGAACCTGGG
      TCGCGGTCGC TGACCTTCTA CAGAACCTTT TTTACTGGCA CCTTGGACCC

16651 CTGGAGCCCG AGGTCCGCGT GCGGCCAATC AAGCAGGTGG CGCCGGGACT
      GACCTCGGGC TCCAGGCGCA CGCCGGTTAG TTCGTCCACC GCGGCCCTGA

16701 GGGCGTGCAG ACCGTGGACG TTCAGATACC CACTACCAGT AGCACCAGTA
      CCCGCACGTC TGGCACCTGC AAGTCTATGG GTGATGGTCA TCGTGGTCAT

16751 TTGCCACCGC CACAGAGGGC ATGGAGACAC AAACGTCCCC GGTTGCCTCA
      AACGGTGGCG GTGTCTCCCG TACCTCTGTG TTTGCAGGGG CCAACGGAGT

16801 GCGGTGGCGG ATGCCGCGGT GCAGGCGGTC GCTGCGGCCG CGTCCAAGAC
      CGCCACCGCC TACGGCGCCA CGTCCGCCAG CGACGCCGGC GCAGGTTCTG

16851 CTCTACGGAG GTGCAAACGG ACCCGTGGAT GTTTCGCGTT TCAGCCCCCC
      GAGATGCCTC CACGTTTGCC TGGGCACCTA CAAAGCGCAA AGTCGGGGGG

16901 GGCGCCCGCG CCGTTCGAGG AAGTACGGCG CCGCCAGCGC GCTACTGCCC
      CCGCGGGCGC GGCAAGCTCC TTCATGCCGC GGCGGTCGCG CGATGACGGG
```

FIG. 15A-20

```
16951 GAATATGCCC TACATCCTTC CATTGCGCCT ACCCCCGGCT ATCGTGGCTA
      CTTATACGGG ATGTAGGAAG GTAACGCGGA TGGGGGCCGA TAGCACCGAT

17001 CACCTACCGC CCCAGAAGAC GAGCAACTAC CCGACGCCGA ACCACCACTG
      GTGGATGGCG GGGTCTTCTG CTCGTTGATG GGCTGCGGCT TGGTGGTGAC

17051 GAACCCGCCG CCGCCGTCGC CGTCGCCAGC CCGTGCTGGC CCCGATTTCC
      CTTGGGCGGC GGCGGCAGCG GCAGCGGTCG GGCACGACCG GGGCTAAAGG

17101 GTGCGCAGGG TGGCTCGCGA AGGAGGCAGG ACCCTGGTGC TGCCAACAGC
      CACGCGTCCC ACCGAGCGCT TCCTCCGTCC TGGGACCACG ACGGTTGTCG

17151 GCGCTACCAC CCCAGCATCG TTTAAAAGCC GGTCTTTGTG GTTCTTGCAG
      CGCGATGGTG GGGTCGTAGC AAATTTTCGG CCAGAAACAC CAAGAACGTC

17201 ATATGGCCCT CACCTGCCGC CTCCGTTTCC CGGTGCCGGG ATTCCGAGGA
      TATACCGGGA GTGGACGGCG GAGGCAAAGG GCCACGGCCC TAAGGCTCCT

17251 AGAATGCACC GTAGGAGGGG CATGGCCGGC CACGGCCTGA CGGGCGGCAT
      TCTTACGTGG CATCCTCCCC GTACCGGCCG GTGCCGGACT GCCCGCCGTA

17301 GCGTCGTGCG CACCACCGGC GGCGGCGCGC GTCGCACCGT CGCATGCGCG
      CGCAGCACGC GTGGTGGCCG CCGCCGCGCG CAGCGTGGCA GCGTACGCGC

17351 GCGGTATCCT GCCCCTCCTT ATTCCACTGA TCGCCGCGGC GATTGGCGCC
      CGCCATAGGA CGGGGAGGAA TAAGGTGACT AGCGGCGCCG CTAACCGCGG

17401 GTGCCCGGAA TTGCATCCGT GGCCTTGCAG GCGCAGAGAC ACTGATTAAA
      CACGGGCCTT AACGTAGGCA CCGGAACGTC CGCGTCTCTG TGACTAATTT

17451 AACAAGTTGC ATGTGGAAAA ATCAAAATAA AAAGTCTGGA CTCTCACGCT
      TTGTTCAACG TACACCTTTT TAGTTTTATT TTTCAGACCT GAGAGTGCGA

17501 CGCTTGGTCC TGTAACTATT TTGTAGAATG GAAGACATCA ACTTTGCGTC
      GCGAACCAGG ACATTGATAA AACATCTTAC CTTCTGTAGT TGAAACGCAG

17551 TCTGGCCCCG CGACACGGCT CGCGCCCGTT CATGGGAAAC TGGCAAGATA
      AGACCGGGGC GCTGTGCCGA GCGCGGGCAA GTACCCTTTG ACCGTTCTAT

17601 TCGGCACCAG CAATATGAGC GGTGGCGCCT TCAGCTGGGG CTCGCTGTGG
      AGCCGTGGTC GTTATACTCG CCACCGCGGA AGTCGACCCC GAGCGACACC

17651 AGCGGCATTA AAAATTTCGG TTCCACCGTT AAGAACTATG GCAGCAAGGC
      TCGCCGTAAT TTTTAAAGCC AAGGTGGCAA TTCTTGATAC CGTCGTTCCG

17701 CTGGAACAGC AGCACAGGCC AGATGCTGAG GGATAAGTTG AAAGAGCAAA
      GACCTTGTCG TCGTGTCCGG TCTACGACTC CCTATTCAAC TTTCTCGTTT

17751 ATTTCCAACA AAAGGTGGTA GATGGCCTGG CCTCTGGCAT TAGCGGGGTG
      TAAAGGTTGT TTTCCACCAT CTACCGGACC GGAGACCGTA ATCGCCCCAC
```

FIG.15A-21

17801 GTGGACCTGG CCAACCAGGC AGTGCAAAAT AAGATTAACA GTAAGCTTGA
CACCTGGACC GGTTGGTCCG TCACGTTTTA TTCTAATTGT CATTCGAACT

17851 TCCCCGCCCT CCCGTAGAGG AGCCTCCACC GGCCGTGGAG ACAGTGTCTC
AGGGGCGGGA GGGCATCTCC TCGGAGGTGG CCGGCACCTC TGTCACAGAG

17901 CAGAGGGGCG TGGCGAAAAG CGTCCGCGCC CCGACAGGGA AGAAACTCTG
GTCTCCCCGC ACCGCTTTTC GCAGGCGCGG GGCTGTCCCT TCTTTGAGAC

17951 GTGACGCAAA TAGACGAGCC TCCCTCGTAC GAGGAGGCAC TAAAGCAAGG
CACTGCGTTT ATCTGCTCGG AGGGAGCATG CTCCTCCGTG ATTTCGTTCC

18001 CCTGCCCACC ACCCGTCCCA TCGCGCCCAT GGCTACCGGA GTGCTGGGCC
GGACGGGTGG TGGGCAGGGT AGCGCGGGTA CCGATGGCCT CACGACCCGG

18051 AGCACACACC CGTAACGCTG GACCTGCCTC CCCCCGCCGA CACCCAGCAG
TCGTGTGTGG GCATTGCGAC CTGGACGGAG GGGGGCGGCT GTGGGTCGTC

18101 AAACCTGTGC TGCCAGGCCC GACCGCCGTT GTTGTAACCC GTCCTAGCCG
TTTGGACACG ACGGTCCGGG CTGGCGGCAA CAACATTGGG CAGGATCGGC

18151 CGCGTCCCTG CGCCGCGCCG CCAGCGGTCC GCGATCGTTG CGGCCCGTAG
GCGCAGGGAC GCGGCGCGGC GGTCGCCAGG CGCTAGCAAC GCCGGGCATC

18201 CCAGTGGCAA CTGGCAAAGC ACACTGAACA GCATCGTGGG TCTGGGGGTG
GGTCACCGTT GACCGTTTCG TGTGACTTGT CGTAGCACCC AGACCCCCAC

18251 CAATCCCTGA AGCGCCGACG ATGCTTCTGA TAGCTAACGT GTCGTATGTG
GTTAGGGACT TCGCGGCTGC TACGAAGACT ATCGATTGCA CAGCATACAC

18301 TGTCATGTAT GCGTCCATGT CGCCGCCAGA GGAGCTGCTG AGCCGCCGCG
ACAGTACATA CGCAGGTACA GCGGCGGTCT CCTCGACGAC TCGGCGGCGC

18351 CGCCCGCTTT CCAAGATGGC TACCCCTTCG ATGATGCCGC AGTGGTCTTA
GCGGGCGAAA GGTTCTACCG ATGGGGAAGC TACTACGGCG TCACCAGAAT

18401 CATGCACATC TCGGGCCAGG ACGCCTCGGA GTACCTGAGC CCCGGGCTGG
GTACGTGTAG AGCCCGGTCC TGCGGAGCCT CATGGACTCG GGGCCCGACC

18451 TGCAGTTTGC CCGCGCCACC GAGACGTACT TCAGCCTGAA TAACAAGTTT
ACGTCAAACG GGCGCGGTGG CTCTGCATGA AGTCGGACTT ATTGTTCAAA

18501 AGAAACCCCA CGGTGGCGCC TACGCACGAC GTGACCACAG ACCGGTCCCA
TCTTTGGGGT GCCACCGCGG ATGCGTGCTG CACTGGTGTC TGGCCAGGGT

18551 GCGTTTGACG CTGCGGTTCA TCCCTGTGGA CCGTGAGGAT ACTGCGTACT
CGCAAACTGC GACGCCAAGT AGGGACACCT GGCACTCCTA TGACGCATGA

18601 CGTACAAGGC GCGGTTCACC CTAGCTGTGG GTGATAACCG TGTGCTGGAC
GCATGTTCCG CGCCAAGTGG GATCGACACC CACTATTGGC ACACGACCTG

FIG. 15A-22

```
18651 ATGGCTTCCA CGTACTTTGA CATCCGCGGC GTGCTGGACA GGGGCCCTAC
      TACCGAAGGT GCATGAAACT GTAGGCGCCG CACGACCTGT CCCCGGGATG

18701 TTTTAAGCCC TACTCTGGCA CTGCCTACAA CGCCCTGGCT CCCAAGGGTG
      AAAATTCGGG ATGAGACCGT GACGGATGTT GCGGGACCGA GGGTTCCCAC

18751 CCCCAAATCC TTGCGAATGG GATGAAGCTG CTACTGCTCT TGAAATAAAC
      GGGGTTTAGG AACGCTTACC CTACTTCGAC GATGACGAGA ACTTTATTTG

18801 CTAGAAGAAG AGGACGATGA CAACGAAGAC GAAGTAGACG AGCAAGCTGA
      GATCTTCTTC TCCTGCTACT GTTGCTTCTG CTTCATCTGC TCGTTCGACT

18851 GCAGCAAAAA ACTCACGTAT TTGGGCAGGC GCCTTATTCT GGTATAAATA
      CGTCGTTTTT TGAGTGCATA AACCCGTCCG CGGAATAAGA CCATATTTAT

18901 TTACAAAGGA GGGTATTCAA ATAGGTGTCG AAGGTCAAAC ACCTAAATAT
      AATGTTTCCT CCCATAAGTT TATCCACAGC TTCCAGTTTG TGGATTTATA

18951 GCCGATAAAA CATTTCAACC TGAACCTCAA ATAGGAGAAT CTCAGTGGTA
      CGGCTATTTT GTAAAGTTGG ACTTGGAGTT TATCCTCTTA GAGTCACCAT

19001 CGAAACAGAA ATTAATCATG CAGCTGGGAG AGTCCTAAAA AAGACTACCC
      GCTTTGTCTT TAATTAGTAC GTCGACCCTC TCAGGATTTT TTCTGATGGG

19051 CAATGAAACC ATGTTACGGT TCATATGCAA AACCCACAAA TGAAAATGGA
      GTTACTTTGG TACAATGCCA AGTATACGTT TTGGGTGTTT ACTTTTACCT

19101 GGGCAAGGCA TTCTTGTAAA GCAACAAAAT GGAAAGCTAG AAAGTCAAGT
      CCCGTTCCGT AAGAACATTT CGTTGTTTTA CCTTTCGATC TTTCAGTTCA

19151 GGAAATGCAA TTTTTCTCAA CTACTGAGGC AGCCGCAGGC AATGGTGATA
      CCTTTACGTT AAAAAGAGTT GATGACTCCG TCGGCGTCCG TTACCACTAT

19201 ACTTGACTCC TAAAGTGGTA TTGTACAGTG AAGATGTAGA TATAGAAACC
      TGAACTGAGG ATTTCACCAT AACATGTCAC TTCTACATCT ATATCTTTGG

19251 CCAGACACTC ATATTTCTTA CATGCCCACT ATTAAGGAAG GTAACTCACG
      GGTCTGTGAG TATAAAGAAT GTACGGGTGA TAATTCCTTC CATTGAGTGC

19301 AGAACTAATG GGCCAACAAT CTATGCCCAA CAGGCCTAAT TACATTGCTT
      TCTTGATTAC CCGGTTGTTA GATACGGGTT GTCCGGATTA ATGTAACGAA

19351 TTAGGGACAA TTTTATTGGT CTAATGTATT ACAACAGCAC GGGTAATATG
      AATCCCTGTT AAAATAACCA GATTACATAA TGTTGTCGTG CCCATTATAC

19401 GGTGTTCTGG CGGGCCAAGC ATCGCAGTTG AATGCTGTTG TAGATTTGCA
      CCACAAGACC GCCCGGTTCG TAGCGTCAAC TTACGACAAC ATCTAAACGT

19451 AGACAGAAAC ACAGAGCTTT CATACCAGCT TTTGCTTGAT TCCATTGGTG
      TCTGTCTTTG TGTCTCGAAA GTATGGTCGA AAACGAACTA AGGTAACCAC
```

FIG.15A-23

```
19501 ATAGAACCAG GTACTTTTCT ATGTGGAATC AGGCTGTTGA CAGCTATGAT
      TATCTTGGTC CATGAAAAGA TACACCTTAG TCCGACAACT GTCGATACTA

19551 CCAGATGTTA GAATTATTGA AAATCATGGA ACTGAAGATG AACTTCCAAA
      GGTCTACAAT CTTAATAACT TTTAGTACCT TGACTTCTAC TTGAAGGTTT

19601 TTACTGCTTT CCACTGGGAG GTGTGATTAA TACAGAGACT CTTACCAAGG
      AATGACGAAA GGTGACCCTC CACACTAATT ATGTCTCTGA GAATGGTTCC

19651 TAAAACCTAA AACAGGTCAG GAAAATGGAT GGGAAAAAGA TGCTACAGAA
      ATTTTGGATT TTGTCCAGTC CTTTTACCTA CCCTTTTTCT ACGATGTCTT

19701 TTTTCAGATA AAAATGAAAT AAGAGTTGGA AATAATTTTG CCATGGAAAT
      AAAAGTCTAT TTTTACTTTA TTCTCAACCT TTATTAAAAC GGTACCTTTA

19751 CAATCTAAAT GCCAACCTGT GGAGAAATTT CCTGTACTCC AACATAGCGC
      GTTAGATTTA CGGTTGGACA CCTCTTTAAA GGACATGAGG TTGTATCGCG

19801 TGTATTTGCC CGACAAGCTA AAGTACAGTC CTTCCAACGT AAAAATTTCT
      ACATAAACGG GCTGTTCGAT TTCATGTCAG GAAGGTTGCA TTTTTAAAGA

19851 GATAACCCAA ACACCTACGA CTACATGAAC AAGCGAGTGG TGGCTCCCGG
      CTATTGGGTT TGTGGATGCT GATGTACTTG TTCGCTCACC ACCGAGGGCC

19901 GCTAGTGGAC TGCTACATTA ACCTTGGAGC ACGCTGGTCC CTTGACTATA
      CGATCACCTG ACGATGTAAT TGGAACCTCG TGCGACCAGG GAACTGATAT

19951 TGGACAACGT CAACCCATTT AACCACCACC GCAATGCTGG CCTGCGCTAC
      ACCTGTTGCA GTTGGGTAAA TTGGTGGTGG CGTTACGACC GGACGCGATG

20001 CGCTCAATGT TGCTGGGCAA TGGTCGCTAT GTGCCCTTCC ACATCCAGGT
      GCGAGTTACA ACGACCCGTT ACCAGCGATA CACGGGAAGG TGTAGGTCCA

20051 GCCTCAGAAG TTCTTTGCCA TTAAAAACCT CCTTCTCCTG CCGGGCTCAT
      CGGAGTCTTC AAGAAACGGT AATTTTTGGA GGAAGAGGAC GGCCCGAGTA

20101 ACACCTACGA GTGGAACTTC AGGAAGGATG TTAACATGGT TCTGCAGAGC
      TGTGGATGCT CACCTTGAAG TCCTTCCTAC AATTGTACCA AGACGTCTCG

20151 TCCCTAGGAA ATGACCTAAG GGTTGACGGA GCCAGCATTA AGTTTGATAG
      AGGGATCCTT TACTGGATTC CCAACTGCCT CGGTCGTAAT TCAAACTATC

20201 CATTTGCCTT TACGCCACCT TCTTCCCCAT GGCCCACAAC ACCGCCTCCA
      GTAAACGGAA ATGCGGTGGA AGAAGGGGTA CCGGGTGTTG TGGCGGAGGT

20251 CGCTTGAGGC CATGCTTAGA AACGACACCA ACGACCAGTC CTTTAACGAC
      GCGAACTCCG GTACGAATCT TTGCTGTGGT TGCTGGTCAG GAAATTGCTG

20301 TATCTCTCCG CCGCCAACAT GCTCTACCCT ATACCCGCCA ACGCTACCAA
      ATAGAGAGGC GGCGGTTGTA CGAGATGGGA TATGGGCGGT TGCGATGGTT
```

FIG.15A-24

```
20351  CGTGCCCATA TCCATCCCCT CCCGCAACTG GGCGGCTTTC CGCGGCTGGG
       GCACGGGTAT AGGTAGGGGA GGGCGTTGAC CCGCCGAAAG GCGCCGACCC

20401  CCTTCACGCG CCTTAAGACT AAGGAAACCC CATCACTGGG CTCGGGCTAC
       GGAAGTGCGC GGAATTCTGA TTCCTTTGGG GTAGTGACCC GAGCCCGATG

20451  GACCCTTATT ACACCTACTC TGGCTCTATA CCCTACCTAG ATGGAACCTT
       CTGGGAATAA TGTGGATGAG ACCGAGATAT GGGATGGATC TACCTTGGAA

20501  TTACCTCAAC CACACCTTTA AGAAGGTGGC CATTACCTTT GACTCTTCTG
       AATGGAGTTG GTGTGGAAAT TCTTCCACCG GTAATGGAAA CTGAGAAGAC

20551  TCAGCTGGCC TGGCAATGAC CGCCTGCTTA CCCCCAACGA GTTTGAAATT
       AGTCGACCGG ACCGTTACTG GCGGACGAAT GGGGGTTGCT CAAACTTTAA

20601  AAGCGCTCAG TTGACGGGGA GGGTTACAAC GTTGCCCAGT GTAACATGAC
       TTCGCGAGTC AACTGCCCCT CCCAATGTTG CAACGGGTCA CATTGTACTG

20651  CAAAGACTGG TTCCTGGTAC AAATGCTAGC TAACTATAAC ATTGGCTACC
       GTTTCTGACC AAGGACCATG TTTACGATCG ATTGATATTG TAACCGATGG

20701  AGGGCTTCTA TATCCCAGAG AGCTACAAGG ACCGCATGTA CTCCTTCTTT
       TCCCGAAGAT ATAGGGTCTC TCGATGTTCC TGGCGTACAT GAGGAAGAAA

20751  AGAAACTTCC AGCCCATGAG CCGTCAGGTG GTGGATGATA CTAAATACAA
       TCTTTGAAGG TCGGGTACTC GGCAGTCCAC CACCTACTAT GATTTATGTT

20801  GGACTACCAA CAGGTGGGCA TCCTACACCA ACACAACAAC TCTGGATTTG
       CCTGATGGTT GTCCACCCGT AGGATGTGGT TGTGTTGTTG AGACCTAAAC

20851  TTGGCTACCT TGCCCCCACC ATGCGCGAAG GACAGGCCTA CCCTGCTAAC
       AACCGATGGA ACGGGGGTGG TACGCGCTTC CTGTCCGGAT GGGACGATTG

20901  TTCCCCTATC CGCTTATAGG CAAGACCGCA GTTGACAGCA TTACCCAGAA
       AAGGGGATAG GCGAATATCC GTTCTGGCGT CAACTGTCGT AATGGGTCTT

20951  AAAGTTTCTT TGCGATCGCA CCCTTTGGCG CATCCCATTC TCCAGTAACT
       TTTCAAAGAA ACGCTAGCGT GGGAAACCGC GTAGGGTAAG AGGTCATTGA

21001  TTATGTCCAT GGGCGCACTC ACAGACCTGG GCCAAAACCT TCTCTACGCC
       AATACAGGTA CCCGCGTGAG TGTCTGGACC CGGTTTTGGA AGAGATGCGG

21051  AACTCCGCCC ACGCGCTAGA CATGACTTTT GAGGTGGATC CCATGGACGA
       TTGAGGCGGG TGCGCGATCT GTACTGAAAA CTCCACCTAG GGTACCTGCT

21101  GCCCACCCTT CTTTATGTTT TGTTTGAAGT CTTTGACGTG GTCCGTGTGC
       CGGGTGGGAA GAAATACAAA ACAAACTTCA GAAACTGCAC CAGGCACACG

21151  ACCAGCCGCA CCGCGGCGTC ATCGAAACCG TGTACCTGCG CACGCCCTTC
       TGGTCGGCGT GGCGCCGCAG TAGCTTTGGC ACATGGACGC GTGCGGGAAG
```

FIG. 15A-25

```
21201 TCGGCCGGCA ACGCCACAAC ATAAAGAAGC AAGCAACATC AACAACAGCT
      AGCCGGCCGT TGCGGTGTTG TATTTCTTCG TTCGTTGTAG TTGTTGTCGA

21251 GCCGCCATGG GCTCCAGTGA GCAGGAACTG AAAGCCATTG TCAAAGATCT
      CGGCGGTACC CGAGGTCACT CGTCCTTGAC TTTCGGTAAC AGTTTCTAGA

21301 TGGTTGTGGG CCATATTTTT TGGGCACCTA TGACAAGCGC TTTCCAGGCT
      ACCAACACCC GGTATAAAAA ACCCGTGGAT ACTGTTCGCG AAAGGTCCGA

21351 TTGTTTCTCC ACACAAGCTC GCCTGCGCCA TAGTCAATAC GGCCGGTCGC
      AACAAAGAGG TGTGTTCGAG CGGACGCGGT ATCAGTTATG CCGGCCAGCG

21401 GAGACTGGGG GCGTACACTG GATGGCCTTT GCCTGGAACC CGCACTCAAA
      CTCTGACCCC CGCATGTGAC CTACCGGAAA CGGACCTTGG GCGTGAGTTT

21451 AACATGCTAC CTCTTTGAGC CCTTTGGCTT TTCTGACCAG CGACTCAAGC
      TTGTACGATG GAGAAACTCG GGAAACCGAA AAGACTGGTC GCTGAGTTCG

21501 AGGTTTACCA GTTTGAGTAC GAGTCACTCC TGCGCCGTAG CGCCATTGCT
      TCCAAATGGT CAAACTCATG CTCAGTGAGG ACGCGGCATC GCGGTAACGA

21551 TCTTCCCCCG ACCGCTGTAT AACGCTGGAA AAGTCCACCC AAAGCGTACA
      AGAAGGGGGC TGGCGACATA TTGCGACCTT TTCAGGTGGG TTTCGCATGT

21601 GGGGCCCAAC TCGGCCGCCT GTGGACTATT CTGCTGCATG TTTCTCCACG
      CCCCGGGTTG AGCCGGCGGA CACCTGATAA GACGACGTAC AAAGAGGTGC

21651 CCTTTGCCAA CTGGCCCCAA ACTCCCATGG ATCACAACCC CACCATGAAC
      GGAAACGGTT GACCGGGGTT TGAGGGTACC TAGTGTTGGG GTGGTACTTG

21701 CTTATTACCG GGGTACCCAA CTCCATGCTC AACAGTCCCC AGGTACAGCC
      GAATAATGGC CCCATGGGTT GAGGTACGAG TTGTCAGGGG TCCATGTCGG

21751 CACCCTGCGT CGCAACCAGG AACAGCTCTA CAGCTTCCTG GAGCGCCACT
      GTGGGACGCA GCGTTGGTCC TTGTCGAGAT GTCGAAGGAC CTCGCGGTGA

21801 CGCCCTACTT CCGCAGCCAC AGTGCGCAGA TTAGGAGCGC CACTTCTTTT
      GCGGGATGAA GGCGTCGGTG TCACGCGTCT AATCCTCGCG GTGAAGAAAA

21851 TGTCACTTGA AAAACATGTA AAAATAATGT ACTAGAGACA CTTTCAATAA
      ACAGTGAACT TTTTGTACAT TTTTATTACA TGATCTCTGT GAAAGTTATT

21901 AGGCAAATGC TTTTATTTGT ACACTCTCGG GTGATTATTT ACCCCCACCC
      TCCGTTTACG AAAATAAACA TGTGAGAGCC CACTAATAAA TGGGGGTGGG

21951 TTGCCGTCTG CGCCGTTTAA AAATCAAAGG GGTTCTGCCG CGCATCGCTA
      AACGGCAGAC GCGGCAAATT TTTAGTTTCC CCAAGACGGC GCGTAGCGAT

22001 TGCGCCACTG GCAGGGACAC GTTGCGATAC TGGTGTTTAG TGCTCCACTT
      ACGCGGTGAC CGTCCCTGTG CAACGCTATG ACCACAAATC ACGAGGTGAA
```

FIG. 15A-26

```
22051 AAACTCAGGC ACAACCATCC GCGGCAGCTC GGTGAAGTTT TCACTCCACA
      TTTGAGTCCG TGTTGGTAGG CGCCGTCGAG CCACTTCAAA AGTGAGGTGT

22101 GGCTGCGCAC CATCACCAAC GCGTTTAGCA GGTCGGGCGC CGATATCTTG
      CCGACGCGTG GTAGTGGTTG CGCAAATCGT CCAGCCCGCG GCTATAGAAC

22151 AAGTCGCAGT TGGGGCCTCC GCCCTGCGCG CGCGAGTTGC GATACACAGG
      TTCAGCGTCA ACCCCGGAGG CGGGACGCGC GCGCTCAACG CTATGTGTCC

22201 GTTGCAGCAC TGGAACACTA TCAGCGCCGG GTGGTGCACG CTGGCCAGCA
      CAACGTCGTG ACCTTGTGAT AGTCGCGGCC CACCACGTGC GACCGGTCGT

22251 CGCTCTTGTC GGAGATCAGA TCCGCGTCCA GGTCCTCCGC GTTGCTCAGG
      GCGAGAACAG CCTCTAGTCT AGGCGCAGGT CCAGGAGGCG CAACGAGTCC

22301 GCGAACGGAG TCAACTTTGG TAGCTGCCTT CCCAAAAAGG GCGCGTGCCC
      CGCTTGCCTC AGTTGAAACC ATCGACGGAA GGGTTTTTCC CGCGCACGGG

22351 AGGCTTTGAG TTGCACTCGC ACCGTAGTGG CATCAAAAGG TGACCGTGCC
      TCCGAAACTC AACGTGAGCG TGGCATCACC GTAGTTTTCC ACTGGCACGG

22401 CGGTCTGGGC GTTAGGATAC AGCGCCTGCA TAAAAGCCTT GATCTGCTTA
      GCCAGACCCG CAATCCTATG TCGCGGACGT ATTTTCGGAA CTAGACGAAT

22451 AAAGCCACCT GAGCCTTTGC GCCTTCAGAG AAGAACATGC CGCAAGACTT
      TTTCGGTGGA CTCGGAAACG CGGAAGTCTC TTCTTGTACG GCGTTCTGAA

22501 GCCGGAAAAC TGATTGGCCG GACAGGCCGC GTCGTGCACG CAGCACCTTG
      CGGCCTTTTG ACTAACCGGC CTGTCCGGCG CAGCACGTGC GTCGTGGAAC

22551 CGTCGGTGTT GGAGATCTGC ACCACATTTC GGCCCCACCG GTTCTTCACG
      GCAGCCACAA CCTCTAGACG TGGTGTAAAG CCGGGGTGGC CAAGAAGTGC

22601 ATCTTGGCCT TGCTAGACTG CTCCTTCAGC GCGCGCTGCC CGTTTTCGCT
      TAGAACCGGA ACGATCTGAC GAGGAAGTCG CGCGCGACGG GCAAAAGCGA

22651 CGTCACATCC ATTTCAATCA CGTGCTCCTT ATTTATCATA ATGCTTCCGT
      GCAGTGTAGG TAAAGTTAGT GCACGAGGAA TAAATAGTAT TACGAAGGCA

22701 GTAGACACTT AAGCTCGCCT TCGATCTCAG CGCAGCGGTG CAGCCACAAC
      CATCTGTGAA TTCGAGCGGA AGCTAGAGTC GCGTCGCCAC GTCGGTGTTG

22751 GCGCAGCCCG TGGGCTCGTG ATGCTTGTAG GTCACCTCTG CAAACGACTG
      CGCGTCGGGC ACCCGAGCAC TACGAACATC CAGTGGAGAC GTTTGCTGAC

22801 CAGGTACGCC TGCAGGAATC GCCCCATCAT CGTCACAAAG GTCTTGTTGC
      GTCCATGCGG ACGTCCTTAG CGGGGTAGTA GCAGTGTTTC CAGAACAACG

22851 TGGTGAAGGT CAGCTGCAAC CCGCGGTGCT CCTCGTTCAG CCAGGTCTTG
      ACCACTTCCA GTCGACGTTG GGCGCCACGA GGAGCAAGTC GGTCCAGAAC
```

FIG.15A-27

```
22901 CATACGGCCG CCAGAGCTTC CACTTGGTCA GGCAGTAGTT TGAAGTTCGC
      GTATGCCGGC GGTCTCGAAG GTGAACCAGT CCGTCATCAA ACTTCAAGCG

22951 CTTTAGATCG TTATCCACGT GGTACTTGTC CATCAGCGCG CGCGCAGCCT
      GAAATCTAGC AATAGGTGCA CCATGAACAG GTAGTCGCGC GCGCGTCGGA

23001 CCATGCCCTT CTCCCACGCA GACACGATCG GCACACTCAG CGGGTTCATC
      GGTACGGGAA GAGGGTGCGT CTGTGCTAGC CGTGTGAGTC GCCCAAGTAG

23051 ACCGTAATTT CACTTTCCGC TTCGCTGGGC TCTTCCTCTT CCTCTTGCGT
      TGGCATTAAA GTGAAAGGCG AAGCGACCCG AGAAGGAGAA GGAGAACGCA

23101 CCGCATACCA CGCGCCACTG GGTCGTCTTC ATTCAGCCGC CGCACTGTGC
      GGCGTATGGT GCGCGGTGAC CCAGCAGAAG TAAGTCGGCG GCGTGACACG

23151 GCTTACCTCC TTTGCCATGC TTGATTAGCA CCGGTGGGTT GCTGAAACCC
      CGAATGGAGG AAACGGTACG AACTAATCGT GGCCACCCAA CGACTTTGGG

23201 ACCATTTGTA GCGCCACATC TTCTCTTTCT TCCTCGCTGT CCACGATTAC
      TGGTAAACAT CGCGGTGTAG AAGAGAAAGA AGGAGCGACA GGTGCTAATG

23251 CTCTGGTGAT GGCGGGCGCT CGGGCTTGGG AGAAGGGCGC TTCTTTTTCT
      GAGACCACTA CCGCCCGCGA GCCCGAACCC TCTTCCCGCG AAGAAAAAGA

23301 TCTTGGGCGC AATGGCCAAA TCCGCCGCCG AGGTCGATGG CCGCGGGCTG
      AGAACCCGCG TTACCGGTTT AGGCGGCGGC TCCAGCTACC GGCGCCCGAC

23351 GGTGTGCGCG GCACCAGCGC GTCTTGTGAT GAGTCTTCCT CGTCCTCGGA
      CCACACGCGC CGTGGTCGCG CAGAACACTA CTCAGAAGGA GCAGGAGCCT

23401 CTCGATACGC CGCCTCATCC GCTTTTTTGG GGGCGCCCGG GGAGGCGGCG
      GAGCTATGCG GCGGAGTAGG CGAAAAAACC CCCGCGGGCC CCTCCGCCGC

23451 GCGACGGGGA CGGGGACGAC ACGTCCTCCA TGGTTGGGGG ACGTCGCGCC
      CGCTGCCCCT GCCCCTGCTG TGCAGGAGGT ACCAACCCCC TGCAGCGCGG

23501 GCACCGCGTC CGCGCTCGGG GGTGGTTTCG CGCTGCTCCT CTTCCCGACT
      CGTGGCGCAG GCGCGAGCCC CCACCAAAGC GCGACGAGGA GAAGGGCTGA

23551 GGCCATTTCC TTCTCCTATA GGCAGAAAAA GATCATGGAG TCAGTCGAGA
      CCGGTAAAGG AAGAGGATAT CCGTCTTTTT CTAGTACCTC AGTCAGCTCT

23601 AGAAGGACAG CCTAACCGCC CCCTCTGAGT TCGCCACCAC CGCCTCCACC
      TCTTCCTGTC GGATTGGCGG GGGAGACTCA AGCGGTGGTG GCGGAGGTGG

23651 GATGCCGCCA ACGCGCCTAC CACCTTCCCC GTCGAGGCAC CCCCGCTTGA
      CTACGGCGGT TGCGCGGATG GTGGAAGGGG CAGCTCCGTG GGGGCGAACT

23701 GGAGGAGGAA GTGATTATCG AGCAGGACCC AGGTTTTGTA AGCGAAGACG
      CCTCCTCCTT CACTAATAGC TCGTCCTGGG TCCAAAACAT TCGCTTCTGC
```

FIG.15A-28

23751 ACGAGGACCG CTCAGTACCA ACAGAGGATA AAAAGCAAGA CCAGGACAAC
TGCTCCTGGC GAGTCATGGT TGTCTCCTAT TTTTCGTTCT GGTCCTGTTG

23801 GCAGAGGCAA ACGAGGAACA AGTCGGGCGG GGGGACGAAA GGCATGGCGA
CGTCTCCGTT TGCTCCTTGT TCAGCCCGCC CCCCTGCTTT CCGTACCGCT

23851 CTACCTAGAT GTGGGAGACG ACGTGCTGTT GAAGCATCTG CAGCGCCAGT
GATGGATCTA CACCCTCTGC TGCACGACAA CTTCGTAGAC GTCGCGGTCA

23901 GCGCCATTAT CTGCGACGCG TTGCAAGAGC GCAGCGATGT GCCCCTCGCC
CGCGGTAATA GACGCTGCGC AACGTTCTCG CGTCGCTACA CGGGGAGCGG

23951 ATAGCGGATG TCAGCCTTGC CTACGAACGC CACCTATTCT CACCGCGCGT
TATCGCCTAC AGTCGGAACG GATGCTTGCG GTGGATAAGA GTGGCGCGCA

24001 ACCCCCCAAA CGCCAAGAAA ACGGCACATG CGAGCCCAAC CCGCGCCTCA
TGGGGGGTTT GCGGTTCTTT TGCCGTGTAC GCTCGGGTTG GGCGCGGAGT

24051 ACTTCTACCC CGTATTTGCC GTGCCAGAGG TGCTTGCCAC CTATCACATC
TGAAGATGGG GCATAAACGG CACGGTCTCC ACGAACGGTG GATAGTGTAG

24101 TTTTTCCAAA ACTGCAAGAT ACCCCTATCC TGCCGTGCCA ACCGCAGCCG
AAAAAGGTTT TGACGTTCTA TGGGGATAGG ACGGCACGGT TGGCGTCGGC

24151 AGCGGACAAG CAGCTGGCCT TGCGGCAGGG CGCTGTCATA CCTGATATCG
TCGCCTGTTC GTCGACCGGA ACGCCGTCCC GCGACAGTAT GGACTATAGC

24201 CCTCGCTCAA CGAAGTGCCA AAAATCTTTG AGGGTCTTGG ACGCGACGAG
GGAGCGAGTT GCTTCACGGT TTTTAGAAAC TCCCAGAACC TGCGCTGCTC

24251 AAGCGCGCGG CAAACGCTCT GCAACAGGAA AACAGCGAAA ATGAAAGTCA
TTCGCGCGCC GTTTGCGAGA CGTTGTCCTT TTGTCGCTTT TACTTTCAGT

24301 CTCTGGAGTG TTGGTGGAAC TCGAGGGTGA CAACGCGCGC CTAGCCGTAC
GAGACCTCAC AACCACCTTG AGCTCCCACT GTTGCGCGCG GATCGGCATG

24351 TAAAACGCAG CATCGAGGTC ACCCACTTTG CCTACCCGGC ACTTAACCTA
ATTTTGCGTC GTAGCTCCAG TGGGTGAAAC GGATGGGCCG TGAATTGGAT

24401 CCCCCCAAGG TCATGAGCAC AGTCATGAGT GAGCTGATCG TGCGCCGTGC
GGGGGGTTCC AGTACTCGTG TCAGTACTCA CTCGACTAGC ACGCGGCACG

24451 GCAGCCCCTG GAGAGGGATG CAAATTTGCA AGAACAAACA GAGGAGGGCC
CGTCGGGGAC CTCTCCCTAC GTTTAAACGT TCTTGTTTGT CTCCTCCCGG

24501 TACCCGCAGT TGGCGACGAG CAGCTAGCGC GCTGGCTTCA AACGCGCGAG
ATGGGCGTCA ACCGCTGCTC GTCGATCGCG CGACCGAAGT TTGCGCGCTC

24551 CCTGCCGACT TGGAGGAGCG ACGCAAACTA ATGATGGCCG CAGTGCTCGT
GGACGGCTGA ACCTCCTCGC TGCGTTTGAT TACTACCGGC GTCACGAGCA

FIG.15A-29

```
24601  TACCGTGGAG CTTGAGTGCA TGCAGCGGTT CTTTGCTGAC CCGGAGATGC
       ATGGCACCTC GAACTCACGT ACGTCGCCAA GAAACGACTG GGCCTCTACG

24651  AGCGCAAGCT AGAGGAAACA TTGCACTACA CCTTTCGACA GGGCTACGTA
       TCGCGTTCGA TCTCCTTTGT AACGTGATGT GGAAAGCTGT CCCGATGCAT

24701  CGCCAGGCCT GCAAGATCTC CAACGTGGAG CTCTGCAACC TGGTCTCCTA
       GCGGTCCGGA CGTTCTAGAG GTTGCACCTC GAGACGTTGG ACCAGAGGAT

24751  CCTTGGAATT TTGCACGAAA ACCGCCTTGG GCAAAACGTG CTTCATTCCA
       GGAACCTTAA AACGTGCTTT TGGCGGAACC CGTTTTGCAC GAAGTAAGGT

24801  CGCTCAAGGG CGAGGCGCGC CGCGACTACG TCCGCGACTG CGTTTACTTA
       GCGAGTTCCC GCTCCGCGCG GCGCTGATGC AGGCGCTGAC GCAAATGAAT

24851  TTTCTATGCT ACACCTGGCA GACGGCCATG GGCGTTTGGC AGCAGTGCTT
       AAAGATACGA TGTGGACCGT CTGCCGGTAC CCGCAAACCG TCGTCACGAA

24901  GGAGGAGTGC AACCTCAAGG AGCTGCAGAA ACTGCTAAAG CAAAACTTGA
       CCTCCTCACG TTGGAGTTCC TCGACGTCTT TGACGATTTC GTTTTGAACT

24951  AGGACCTATG GACGGCCTTC AACGAGCGCT CCGTGGCCGC GCACCTGGCG
       TCCTGGATAC CTGCCGGAAG TTGCTCGCGA GGCACCGGCG CGTGGACCGC

25001  GACATCATTT TCCCCGAACG CCTGCTTAAA ACCCTGCAAC AGGGTCTGCC
       CTGTAGTAAA AGGGGCTTGC GGACGAATTT TGGGACGTTG TCCCAGACGG

25051  AGACTTCACC AGTCAAAGCA TGTTGCAGAA CTTTAGGAAC TTTATCCTAG
       TCTGAAGTGG TCAGTTTCGT ACAACGTCTT GAAATCCTTG AAATAGGATC

25101  AGCGCTCAGG AATCTTGCCC GCCACCTGCT GTGCACTTCC TAGCGACTTT
       TCGCGAGTCC TTAGAACGGG CGGTGGACGA CACGTGAAGG ATCGCTGAAA

25151  GTGCCCATTA AGTACCGCGA ATGCCCTCCG CCGCTTTGGG GCCACTGCTA
       CACGGGTAAT TCATGGCGCT TACGGGAGGC GGCGAAACCC CGGTGACGAT

25201  CCTTCTGCAG CTAGCCAACT ACCTTGCCTA CCACTCTGAC ATAATGGAAG
       GGAAGACGTC GATCGGTTGA TGGAACGGAT GGTGAGACTG TATTACCTTC

25251  ACGTGAGCGG TGACGGTCTA CTGGAGTGTC ACTGTCGCTG CAACCTATGC
       TGCACTCGCC ACTGCCAGAT GACCTCACAG TGACAGCGAC GTTGGATACG

25301  ACCCCGCACC GCTCCCTGGT TTGCAATTCG CAGCTGCTTA ACGAAAGTCA
       TGGGGCGTGG CGAGGGACCA AACGTTAAGC GTCGACGAAT TGCTTTCAGT

25351  AATTATCGGT ACCTTTGAGC TGCAGGGTCC CTCGCCTGAC GAAAAGTCCG
       TTAATAGCCA TGGAAACTCG ACGTCCCAGG GAGCGGACTG CTTTTCAGGC

25401  CGGCTCCGGG GTTGAAACTC ACTCCGGGGC TGTGGACGTC GGCTTACCTT
       GCCGAGGCCC CAACTTTGAG TGAGGCCCCG ACACCTGCAG CCGAATGGAA
```

FIG. 15A-30

```
25451 CGCAAATTTG TACCTGAGGA CTACCACGCC CACGAGATTA GGTTCTACGA
      GCGTTTAAAC ATGGACTCCT GATGGTGCGG GTGCTCTAAT CCAAGATGCT

25501 AGACCAATCC CGCCCGCCTA ATGCGGAGCT TACCGCCTGC GTCATTACCC
      TCTGGTTAGG GCGGGCGGAT TACGCCTCGA ATGGCGGACG CAGTAATGGG

25551 AGGGCCACAT TCTTGGCCAA TTGCAAGCCA TCAACAAAGC CCGCCAAGAG
      TCCCGGTGTA AGAACCGGTT AACGTTCGGT AGTTGTTTCG GGCGGTTCTC

25601 TTTCTGCTAC GAAAGGGACG GGGGGTTTAC TTGGACCCCC AGTCCGGCGA
      AAAGACGATG CTTTCCCTGC CCCCCAAATG AACCTGGGGG TCAGGCCGCT

25651 GGAGCTCAAC CCAATCCCCC CGCCGCCGCA GCCCTATCAG CAGCAGCCGC
      CCTCGAGTTG GGTTAGGGGG GCGGCGGCGT CGGGATAGTC GTCGTCGGCG

25701 GGGCCCTTGC TTCCCAGGAT GGCACCCAAA AAGAAGCTGC AGCTGCCGCC
      CCCGGGAACG AAGGGTCCTA CCGTGGGTTT TTCTTCGACG TCGACGGCGG

25751 GCCACCCACG GACGAGGAGG AATACTGGGA CAGTCAGGCA GAGGAGGTTT
      CGGTGGGTGC CTGCTCCTCC TTATGACCCT GTCAGTCCGT CTCCTCCAAA

25801 TGGACGAGGA GGAGGAGGAC ATGATGGAAG ACTGGGAGAG CCTAGACGAG
      ACCTGCTCCT CCTCCTCCTG TACTACCTTC TGACCCTCTC GGATCTGCTC

25851 GAAGCTTCCG AGGTCGAAGA GGTGTCAGAC GAAACACCGT CACCCTCGGT
      CTTCGAAGGC TCCAGCTTCT CCACAGTCTG CTTTGTGGCA GTGGGAGCCA

25901 CGCATTCCCC TCGCCGGCGC CCCAGAAATC GGCAACCGGT TCCAGCATGG
      GCGTAAGGGG AGCGGCCGCG GGGTCTTTAG CCGTTGGCCA AGGTCGTACC

25951 CTACAACCTC CGCTCCTCAG GCGCCGCCGG CACTGCCCGT TCGCCGACCC
      GATGTTGGAG GCGAGGAGTC CGCGGCGGCC GTGACGGGCA AGCGGCTGGG

26001 AACCGTAGAT GGGACACCAC TGGAACCAGG GCCGGTAAGT CCAAGCAGCC
      TTGGCATCTA CCCTGTGGTG ACCTTGGTCC CGGCCATTCA GGTTCGTCGG

26051 GCCGCCGTTA GCCCAAGAGC AACAACAGCG CCAAGGCTAC CGCTCATGGC
      CGGCGGCAAT CGGGTTCTCG TTGTTGTCGC GGTTCCGATG GCGAGTACCG

26101 GCGGGCACAA GAACGCCATA GTTGCTTGCT TGCAAGACTG TGGGGGCAAC
      CGCCCGTGTT CTTGCGGTAT CAACGAACGA ACGTTCTGAC ACCCCCGTTG

26151 ATCTCCTTCG CCCGCCGCTT TCTTCTCTAC CATCACGGCG TGGCCTTCCC
      TAGAGGAAGC GGGCGGCGAA AGAAGAGATG GTAGTGCCGC ACCGGAAGGG

26201 CCGTAACATC CTGCATTACT ACCGTCATCT CTACAGCCCA TACTGCACCG
      GGCATTGTAG GACGTAATGA TGGCAGTAGA GATGTCGGGT ATGACGTGGC

26251 GCGGCAGCGG CAGCAACAGC AGCGGCCACA CAGAAGCAAA GGCGACCGGA
      CGCCGTCGCC GTCGTTGTCG TCGCCGGTGT GTCTTCGTTT CCGCTGGCCT
```

FIG.15A-31

```
26301 TAGCAAGACT CTGACAAAGC CCAAGAAATC CACAGCGGCG GCAGCAGCAG
      ATCGTTCTGA GACTGTTTCG GGTTCTTTAG GTGTCGCCGC CGTCGTCGTC

26351 GAGGAGGAGC GCTGCGTCTG GCGCCCAACG AACCCGTATC GACCCGCGAG
      CTCCTCCTCG CGACGCAGAC CGCGGGTTGC TTGGGCATAG CTGGGCGCTC

26401 CTTAGAAACA GGATTTTTCC CACTCTGTAT GCTATATTTC AACAGAGCAG
      GAATCTTTGT CCTAAAAAGG GTGAGACATA CGATATAAAG TTGTCTCGTC

26451 GGGCCAAGAA CAAGAGCTGA AAATAAAAAA CAGGTCTCTG CGATCCCTCA
      CCCGGTTCTT GTTCTCGACT TTTATTTTTT GTCCAGAGAC GCTAGGGAGT

26501 CCCGCAGCTG CCTGTATCAC AAAAGCGAAG ATCAGCTTCG GCGCACGCTG
      GGGCGTCGAC GGACATAGTG TTTTCGCTTC TAGTCGAAGC CGCGTGCGAC

26551 GAAGACGCGG AGGCTCTCTT CAGTAAATAC TGCGCGCTGA CTCTTAAGGA
      CTTCTGCGCC TCCGAGAGAA GTCATTTATG ACGCGCGACT GAGAATTCCT

26601 CTAGTTTCGC GCCCTTTCTC AAATTTAAGC GCGAAAACTA CGTCATCTCC
      GATCAAAGCG CGGGAAAGAG TTTAAATTCG CGCTTTTGAT GCAGTAGAGG

26651 AGCGGCCACA CCCGGCGCCA GCACCTGTTG TCAGCGCCAT TATGAGCAAG
      TCGCCGGTGT GGGCCGCGGT CGTGGACAAC AGTCGCGGTA ATACTCGTTC

26701 GAAATTCCCA CGCCCTACAT GTGGAGTTAC CAGCCACAAA TGGGACTTGC
      CTTTAAGGGT GCGGGATGTA CACCTCAATG GTCGGTGTTT ACCCTGAACG

26751 GGCTGGAGCT GCCCAAGACT ACTCAACCCG AATAAACTAC ATGAGCGCGG
      CCGACCTCGA CGGGTTCTGA TGAGTTGGGC TTATTTGATG TACTCGCGCC

26801 GACCCCACAT GATATCCCGG GTCAACGGAA TACGCGCCCA CCGAAACCGA
      CTGGGGTGTA CTATAGGGCC CAGTTGCCTT ATGCGCGGGT GGCTTTGGCT

26851 ATTCTCCTGG AACAGGCGGC TATTACCACC ACACCTCGTA ATAACCTTAA
      TAAGAGGACC TTGTCCGCCG ATAATGGTGG TGTGGAGCAT TATTGGAATT

26901 TCCCCGTAGT TGGCCCGCTG CCCTGGTGTA CCAGGAAAGT CCCGCTCCCA
      AGGGGCATCA ACCGGGCGAC GGGACCACAT GGTCCTTTCA GGGCGAGGGT

26951 CCACTGTGGT ACTTCCCAGA GACGCCCAGG CCGAAGTTCA GATGACTAAC
      GGTGACACCA TGAAGGGTCT CTGCGGGTCC GGCTTCAAGT CTACTGATTG

27001 TCAGGGGCGC AGCTTGCGGG CGGCTTTCGT CACAGGGTGC GGTCGCCCGG
      AGTCCCCGCG TCGAACGCCC GCCGAAAGCA GTGTCCCACG CCAGCGGGCC

27051 GCAGGGTATA ACTCACCTGA CAATCAGAGG GCGAGGTATT CAGCTCAACG
      CGTCCCATAT TGAGTGGACT GTTAGTCTCC CGCTCCATAA GTCGAGTTGC

27101 ACGAGTCGGT GAGCTCCTCG CTTGGTCTCC GTCCGGACGG GACATTTCAG
      TGCTCAGCCA CTCGAGGAGC GAACCAGAGG CAGGCCTGCC CTGTAAAGTC
```

FIG.15A-32

```
27151 ATCGGCGGCG CCGGCCGCTC TTCATTCACG CCTCGTCAGG CAATCCTAAC
      TAGCCGCCGC GGCCGGCGAG AAGTAAGTGC GGAGCAGTCC GTTAGGATTG

27201 TCTGCAGACC TCGTCCTCTG AGCCGCGCTC TGGAGGCATT GGAACTCTGC
      AGACGTCTGG AGCAGGAGAC TCGGCGCGAG ACCTCCGTAA CCTTGAGACG

27251 AATTTATTGA GGAGTTTGTG CCATCGGTCT ACTTTAACCC CTTCTCGGGA
      TTAAATAACT CCTCAAACAC GGTAGCCAGA TGAAATTGGG GAAGAGCCCT

27301 CCTCCCGGCC ACTATCCGGA TCAATTTATT CCTAACTTTG ACGCGGTAAA
      GGAGGGCCGG TGATAGGCCT AGTTAAATAA GGATTGAAAC TGCGCCATTT

27351 GGACTCGGCG GACGGCTACG ACTGAATGTT AAGTGGAGAG GCAGAGCAAC
      CCTGAGCCGC CTGCCGATGC TGACTTACAA TTCACCTCTC CGTCTCGTTG

27401 TGCGCCTGAA ACACCTGGTC CACTGTCGCC GCCACAAGTG CTTTGCCCGC
      ACGCGGACTT TGTGGACCAG GTGACAGCGG CGGTGTTCAC GAAACGGGCG

27451 GACTCCGGTG AGTTTTGCTA CTTTGAATTG CCCGAGGATC ATATCGAGGG
      CTGAGGCCAC TCAAAACGAT GAAACTTAAC GGGCTCCTAG TATAGCTCCC

27501 CCCGGCGCAC GGCGTCCGGC TTACCGCCCA GGGAGAGCTT GCCCGTAGCC
      GGGCCGCGTG CCGCAGGCCG AATGGCGGGT CCCTCTCGAA CGGGCATCGG

27551 TGATTCGGGA GTTTACCCAG CGCCCCCTGC TAGTTGAGCG GGACAGGGGA
      ACTAAGCCCT CAAATGGGTC GCGGGGGACG ATCAACTCGC CCTGTCCCCT

27601 CCCTGTGTTC TCACTGTGAT TTGCAACTGT CCTAACCCTG GATTACATCA
      GGGACACAAG AGTGACACTA AACGTTGACA GGATTGGGAC CTAATGTAGT

27651 AGATCTTTGT TGCCATCTCT GTGCTGAGTA TAATAAATAC AGAAATTAAA
      TCTAGAAACA ACGGTAGAGA CACGACTCAT ATTATTTATG TCTTTAATTT

27701 ATATACTGGG GCTCCTATCG CCATCCTGTA AACGCCACCG TCTTCACCCG
      TATATGACCC CGAGGATAGC GGTAGGACAT TTGCGGTGGC AGAAGTGGGC

27751 CCCAAGCAAA CCAAGGCGAA CCTTACCTGG TACTTTTAAC ATCTCTCCCT
      GGGTTCGTTT GGTTCCGCTT GGAATGGACC ATGAAAATTG TAGAGAGGGA

27801 CTGTGATTTA CAACAGTTTC AACCCAGACG GAGTGAGTCT ACGAGAGAAC
      GACACTAAAT GTTGTCAAAG TTGGGTCTGC CTCACTCAGA TGCTCTCTTG

27851 CTCTCCGAGC TCAGCTACTC CATCAGAAAA AACACCACCC TCCTTACCTG
      GAGAGGCTCG AGTCGATGAG GTAGTCTTTT TTGTGGTGGG AGGAATGGAC

27901 CCGGGAACGT ACGAGTGCGT CACCGGCCGC TGCACCACAC CTACCGCCTG
      GGCCCTTGCA TGCTCACGCA GTGGCCGGCG ACGTGGTGTG GATGGCGGAC

27951 ACCGTAAACC AGACTTTTTC CGGACAGACC TCAATAACTC TGTTTACCAG
      TGGCATTTGG TCTGAAAAAG GCCTGTCTGG AGTTATTGAG ACAAATGGTC
```

FIG.15A-33

```
28001 AACAGGAGGT GAGCTTAGAA AACCCTTAGG GTATTAGGCC AAAGGCGCAG
      TTGTCCTCCA CTCGAATCTT TTGGGAATCC CATAATCCGG TTTCCGCGTC

28051 CTACTGTGGG GTTTATGAAC AATTCAAGCA ACTCTACGGG CTATTCTAAT
      GATGACACCC CAAATACTTG TTAAGTTCGT TGAGATGCCC GATAAGATTA

28101 TCAGGTTTCT CTAGAATCGG GGTTGGGGTT ATTCTCTGTC TTGTGATTCT
      AGTCCAAAGA GATCTTAGCC CCAACCCCAA TAAGAGACAG AACACTAAGA

28151 CTTTATTCTT ATACTAACGC TTCTCTGCCT AAGGCTCGCC GCCTGCTGTG
      GAAATAAGAA TATGATTGCG AAGAGACGGA TTCCGAGCGG CGGACGACAC

28201 TGCACATTTG CATTTATTGT CAGCTTTTTA AACGCTGGGG TCGCCACCCA
      ACGTGTAAAC GTAAATAACA GTCGAAAAAT TTGCGACCCC AGCGGTGGGT

28251 AGATGATTAG GTACATAATC CTAGGTTTAC TCACCCTTGC GTCAGCCCAC
      TCTACTAATC CATGTATTAG GATCCAAATG AGTGGGAACG CAGTCGGGTG

28301 GGTACCACCC AAAAGGTGGA TTTTAAGGAG CCAGCCTGTA ATGTTACATT
      CCATGGTGGG TTTTCCACCT AAAATTCCTC GGTCGGACAT TACAATGTAA

28351 CGCAGCTGAA GCTAATGAGT GCACCACTCT TATAAAATGC ACCACAGAAC
      GCGTCGACTT CGATTACTCA CGTGGTGAGA ATATTTTACG TGGTGTCTTG

28401 ATGAAAAGCT GCTTATTCGC CACAAAAACA AAATTGGCAA GTATGCTGTT
      TACTTTTCGA CGAATAAGCG GTGTTTTTGT TTTAACCGTT CATACGACAA

28451 TATGCTATTT GGCAGCCAGG TGACACTACA GAGTATAATG TTACAGTTTT
      ATACGATAAA CCGTCGGTCC ACTGTGATGT CTCATATTAC AATGTCAAAA

28501 CCAGGGTAAA AGTCATAAAA CTTTTATGTA TACTTTTCCA TTTTATGAAA
      GGTCCCATTT TCAGTATTTT GAAAATACAT ATGAAAAGGT AAAATACTTT

28551 TGTGCGACAT TACCATGTAC ATGAGCAAAC AGTATAAGTT GTGGCCCCCA
      ACACGCTGTA ATGGTACATG TACTCGTTTG TCATATTCAA CACCGGGGGT

28601 CAAAATTGTG TGGAAAACAC TGGCACTTTC TGCTGCACTG CTATGCTAAT
      GTTTTAACAC ACCTTTTGTG ACCGTGAAAG ACGACGTGAC GATACGATTA

28651 TACAGTGCTC GCTTTGGTCT GTACCCTACT CTATATTAAA TACAAAAGCA
      ATGTCACGAG CGAAACCAGA CATGGGATGA GATATAATTT ATGTTTTCGT

28701 GACGCAGCTT TATTGAGGAA AAGAAAATGC CTTAATTTAC TAAGTTACAA
      CTGCGTCGAA ATAACTCCTT TTCTTTTACG GAATTAAATG ATTCAATGTT

28751 AGCTAATGTC ACCACTAACT GCTTTACTCG CTGCTTGCAA AACAAATTCA
      TCGATTACAG TGGTGATTGA CGAAATGAGC GACGAACGTT TTGTTTAAGT

28801 AAAAGTTAGC ATTATAATTA GAATAGGATT TAAACCCCCC GGTCATTTCC
      TTTTCAATCG TAATATTAAT CTTATCCTAA ATTTGGGGGG CCAGTAAAGG
```

FIG. 15A-34

28851 TGCTCAATAC CATTCCCCTG AACAATTGAC TCTATGTGGG ATATGCTCCA
ACGAGTTATG GTAAGGGGAC TTGTTAACTG AGATACACCC TATACGAGGT

28901 GCGCTACAAC CTTGAAGTCA GGCTTCCTGG ATGTCAGCAT CTGACTTTGG
CGCGATGTTG GAACTTCAGT CCGAAGGACC TACAGTCGTA GACTGAAACC

28951 CCAGCACCTG TCCCGCGGAT TTGTTCCAGT CCAACTACAG CGACCCACCC
GGTCGTGGAC AGGGCGCCTA AACAAGGTCA GGTTGATGTC GCTGGGTGGG

29001 TAACAGAGAT GACCAACACA ACCAACGCGG CCGCCGCTAC CGGACTTACA
ATTGTCTCTA CTGGTTGTGT TGGTTGCGCC GGCGGCGATG GCCTGAATGT

29051 TCTACCACAA ATACACCCCA AGTTTCTGCC TTTGTCAATA ACTGGGATAA
AGATGGTGTT TATGTGGGGT TCAAAGACGG AAACAGTTAT TGACCCTATT

29101 CTTGGGCATG TGGTGGTTCT CCATAGCGCT TATGTTTGTA TGCCTTATTA
GAACCCGTAC ACCACCAAGA GGTATCGCGA ATACAAACAT ACGGAATAAT

29151 TTATGTGGCT CATCTGCTGC CTAAAGCGCA AACGCGCCCG ACCACCCATC
AATACACCGA GTAGACGACG GATTTCGCGT TTGCGCGGGC TGGTGGGTAG

29201 TATAGTCCCA TCATTGTGCT ACACCCAAAC AATGATGGAA TCCATAGATT
ATATCAGGGT AGTAACACGA TGTGGGTTTG TTACTACCTT AGGTATCTAA

29251 GGACGGACTG AAACACATGT TCTTTTCTCT TACAGTATGA TTAAATGAGA
CCTGCCTGAC TTTGTGTACA AGAAAAGAGA ATGTCATACT AATTTACTCT

29301 CATGATTCCT CGAGTTTTTA TATTACTGAC CCTTGTTGCG CTTTTTTGTG
GTACTAAGGA GCTCAAAAAT ATAATGACTG GGAACAACGC GAAAAAACAC

29351 CGTGCTCCAC ATTGGCTGCG GTTTCTCACA TCGAAGTAGA CTGCATTCCA
GCACGAGGTG TAACCGACGC CAAAGAGTGT AGCTTCATCT GACGTAAGGT

29401 GCCTTCACAG TCTATTTGCT TTACGGATTT GTCACCCTCA CGCTCATCTG
CGGAAGTGTC AGATAAACGA AATGCCTAAA CAGTGGGAGT GCGAGTAGAC

29451 CAGCCTCATC ACTGTGGTCA TCGCCTTTAT CCAGTGCATT GACTGGGTCT
GTCGGAGTAG TGACACCAGT AGCGGAAATA GGTCACGTAA CTGACCCAGA

29501 GTGTGCGCTT TGCATATCTC AGACACCATC CCCAGTACAG GGACAGGACT
CACACGCGAA ACGTATAGAG TCTGTGGTAG GGGTCATGTC CCTGTCCTGA

29551 ATAGCTGAGC TTCTTAGAAT TCTTTAATTA TGAAATTTAC TGTGACTTTT
TATCGACTCG AAGAATCTTA AGAAATTAAT ACTTTAAATG ACACTGAAAA

29601 CTGCTGATTA TTTGCACCCT ATCTGCGTTT TGTTCCCCGA CCTCCAAGCC
GACGACTAAT AAACGTGGGA TAGACGCAAA ACAAGGGGCT GGAGGTTCGG

29651 TCAAAGACAT ATATCATGCA GATTCACTCG TATATGGAAT ATTCCAAGTT
AGTTTCTGTA TATAGTACGT CTAAGTGAGC ATATACCTTA TAAGGTTCAA

FIG. 15A-35

```
29701 GCTACAATGA AAAAAGCGAT CTTTCCGAAG CCTGGTTATA TGCAATCATC
      CGATGTTACT TTTTTCGCTA GAAAGGCTTC GGACCAATAT ACGTTAGTAG

29751 TCTGTTATGG TGTTCTGCAG TACCATCTTA GCCCTAGCTA TATATCCCTA
      AGACAATACC ACAAGACGTC ATGGTAGAAT CGGGATCGAT ATATAGGGAT

29801 CCTTGACATT GGCTGGAACG CAATAGATGC CATGAACCAC CCAACTTTCC
      GGAACTGTAA CCGACCTTGC GTTATCTACG GTACTTGGTG GGTTGAAAGG

29851 CCGCGCCCGC TATGCTTCCA CTGCAACAAG TTGTTGCCGG CGGCTTTGTC
      GGCGCGGGCG ATACGAAGGT GACGTTGTTC AACAACGGCC GCCGAAACAG

29901 CCAGCCAATC AGCCTCGCCC ACCTTCTCCC ACCCCCACTG AAATCAGCTA
      GGTCGGTTAG TCGGAGCGGG TGGAAGAGGG TGGGGGTGAC TTTAGTCGAT

29951 CTTTAATCTA ACAGGAGGAG ATGACTGACA CCCTAGATCT AGAAATGGAC
      GAAATTAGAT TGTCCTCCTC TACTGACTGT GGGATCTAGA TCTTTACCTG

30001 GGAATTATTA CAGAGCAGCG CCTGCTAGAA AGACGCAGGG CAGCGGCCGA
      CCTTAATAAT GTCTCGTCGC GGACGATCTT TCTGCGTCCC GTCGCCGGCT

30051 GCAACAGCGC ATGAATCAAG AGCTCCAAGA CATGGTTAAC TTGCACCAGT
      CGTTGTCGCG TACTTAGTTC TCGAGGTTCT GTACCAATTG AACGTGGTCA

30101 GCAAAAGGGG TATCTTTTGT CTCGTAAAGC AGGCCAAAGT CACCTACGAC
      CGTTTTCCCC ATAGAAAACA GAGCATTTCG TCCGGTTTCA GTGGATGCTG

30151 AGTAATACCA CCGGACACCG CCTTAGCTAC AAGTTGCCAA CCAAGCGTCA
      TCATTATGGT GGCCTGTGGC GGAATCGATG TTCAACGGTT GGTTCGCAGT

30201 GAAATTGGTG GTCATGGTGG GAGAAAAGCC CATTACCATA ACTCAGCACT
      CTTTAACCAC CAGTACCACC CTCTTTTCGG GTAATGGTAT TGAGTCGTGA

30251 CGGTAGAAAC CGAAGGCTGC ATTCACTCAC CTTGTCAAGG ACCTGAGGAT
      GCCATCTTTG GCTTCCGACG TAAGTGAGTG GAACAGTTCC TGGACTCCTA

30301 CTCTGCACCC TTATTAAGAC CCTGTGCGGT CTCAAAGATC TTATTCCCTT
      GAGACGTGGG AATAATTCTG GGACACGCCA GAGTTTCTAG AATAAGGGAA

30351 TAACTAATAA AAAAAAATAA TAAAGCATCA CTTACTTAAA ATCAGTTAGC
      ATTGATTATT TTTTTTTATT ATTTCGTAGT GAATGAATTT TAGTCAATCG

30401 AAATTTCTGT CCAGTTTATT CAGCAGCACC TCCTTGCCCT CCTCCCAGCT
      TTTAAAGACA GGTCAAATAA GTCGTCGTGG AGGAACGGGA GGAGGGTCGA

30451 CTGGTATTGC AGCTTCCTCC TGGCTGCAAA CTTTCTCCAC AATCTAAATG
      GACCATAACG TCGAAGGAGG ACCGACGTTT GAAAGAGGTG TTAGATTTAC

30501 GAATGTCAGT TTCCTCCTGT TCCTGTCCAT CCGCACCCAC TATCTTCATG
      CTTACAGTCA AAGGAGGACA AGGACAGGTA GGCGTGGGTG ATAGAAGTAC
```

FIG. 15A-36

30551 TTGTTGCAGA TGAAGCGCGC AAGACCGTCT GAAGATACCT TCAACCCCGT
AACAACGTCT ACTTCGCGCG TTCTGGCAGA CTTCTATGGA AGTTGGGGCA

30601 GTATCCATAT GACACGGAAA CCGGTCCTCC AACTGTGCCT TTTCTTACTC
CATAGGTATA CTGTGCCTTT GGCCAGGAGG TTGACACGGA AAAGAATGAG

30651 CTCCCTTTGT ATCCCCCAAT GGGTTTCAAG AGAGTCCCCC TGGGGTACTC
GAGGGAAACA TAGGGGGTTA CCCAAAGTTC TCTCAGGGGG ACCCCATGAG

30701 TCTTTGCGCC TATCCGAACC TCTAGTTACC TCCAATGGCA TGCTTGCGCT
AGAAACGCGG ATAGGCTTGG AGATCAATGG AGGTTACCGT ACGAACGCGA

30751 CAAAATGGGC AACGGCCTCT CTCTGGACGA GGCCGGCAAC CTTACCTCCC
GTTTTACCCG TTGCCGGAGA GAGACCTGCT CCGGCCGTTG GAATGGAGGG

30801 AAAATGTAAC CACTGTGAGC CCACCTCTCA AAAAAACCAA GTCAAACATA
TTTTACATTG GTGACACTCG GGTGGAGAGT TTTTTTGGTT CAGTTTGTAT

30851 AACCTGGAAA TATCTGCACC CCTCACAGTT ACCTCAGAAG CCCTAACTGT
TTGGACCTTT ATAGACGTGG GGAGTGTCAA TGGAGTCTTC GGGATTGACA

30901 GGCTGCCGCC GCACCTCTAA TGGTCGCGGG CAACACACTC ACCATGCAAT
CCGACGGCGG CGTGGAGATT ACCAGCGCCC GTTGTGTGAG TGGTACGTTA

30951 CACAGGCCCC GCTAACCGTG CACGACTCCA AACTTAGCAT TGCCACCCAA
GTGTCCGGGG CGATTGGCAC GTGCTGAGGT TTGAATCGTA ACGGTGGGTT

31001 GGACCCCTCA CAGTGTCAGA AGGAAAGCTA GCCCTGCAAA CATCAGGCCC
CCTGGGGAGT GTCACAGTCT TCCTTTCGAT CGGGACGTTT GTAGTCCGGG

31051 CCTCACCACC ACCGATAGCA GTACCCTTAC TATCACTGCC TCACCCCCTT
GGAGTGGTGG TGGCTATCGT CATGGGAATG ATAGTGACGG AGTGGGGGAA

31101 TAACTACTGC CACTGGTAGC TTGGGCATTG ACTTGAAAGA GCCCATTTAT
ATTGATGACG GTGACCATCG AACCCGTAAC TGAACTTTCT CGGGTAAATA

31151 ACACAAAATG GAAAACTAGG ACTAAAGTAC GGGGCTCCTT TGCATGTAAC
TGTGTTTTAC CTTTTGATCC TGATTTCATG CCCCGAGGAA ACGTACATTG

31201 AGACGACCTA AACACTTTGA CCGTAGCAAC TGGTCCAGGT GTGACTATTA
TCTGCTGGAT TTGTGAAACT GGCATCGTTG ACCAGGTCCA CACTGATAAT

31251 ATAATACTTC CTTGCAAACT AAAGTTACTG GAGCCTTGGG TTTTGATTCA
TATTATGAAG GAACGTTTGA TTTCAATGAC CTCGGAACCC AAAACTAAGT

31301 CAAGGCAATA TGCAACTTAA TGTAGCAGGA GGACTAAGGA TTGATTCTCA
GTTCCGTTAT ACGTTGAATT ACATCGTCCT CCTGATTCCT AACTAAGAGT

31351 AAACAGACGC CTTATACTTG ATGTTAGTTA TCCGTTTGAT GCTCAAAACC
TTTGTCTGCG GAATATGAAC TACAATCAAT AGGCAAACTA CGAGTTTTGG

FIG.15A-37

```
31401 AACTAAATCT AAGACTAGGA CAGGGCCCTC TTTTTATAAA CTCAGCCCAC
      TTGATTTAGA TTCTGATCCT GTCCCGGGAG AAAAATATTT GAGTCGGGTG

31451 AACTTGGATA TTAACTACAA CAAAGGCCTT TACTTGTTTA CAGCTTCAAA
      TTGAACCTAT AATTGATGTT GTTTCCGGAA ATGAACAAAT GTCGAAGTTT

31501 CAATTCCAAA AAGCTTGAGG TTAACCTAAG CACTGCCAAG GGGTTGATGT
      GTTAAGGTTT TTCGAACTCC AATTGGATTC GTGACGGTTC CCCAACTACA

31551 TTGACGCTAC AGCCATAGCC ATTAATGCAG GAGATGGGCT TGAATTTGGT
      AACTGCGATG TCGGTATCGG TAATTACGTC CTCTACCCGA ACTTAAACCA

31601 TCACCTAATG CACCAAACAC AAATCCCCTC AAAACAAAAA TTGGCCATGG
      AGTGGATTAC GTGGTTTGTG TTTAGGGGAG TTTTGTTTTT AACCGGTACC

31651 CCTAGAATTT GATTCAAACA AGGCTATGGT TCCTAAACTA GGAACTGGCC
      GGATCTTAAA CTAAGTTTGT TCCGATACCA AGGATTTGAT CCTTGACCGG

31701 TTAGTTTTGA CAGCACAGGT GCCATTACAG TAGGAAACAA AAATAATGAT
      AATCAAAACT GTCGTGTCCA CGGTAATGTC ATCCTTTGTT TTTATTACTA

31751 AAGCTAACTT TGTGGACCAC ACCAGCTCCA TCTCCTAACT GTAGACTAAA
      TTCGATTGAA ACACCTGGTG TGGTCGAGGT AGAGGATTGA CATCTGATTT

31801 TGCAGAGAAA GATGCTAAAC TCACTTTGGT CTTAACAAAA TGTGGCAGTC
      ACGTCTCTTT CTACGATTTG AGTGAAACCA GAATTGTTTT ACACCGTCAG

31851 AAATACTTGC TACAGTTTCA GTTTTGGCTG TTAAAGGCAG TTTGGCTCCA
      TTTATGAACG ATGTCAAAGT CAAAACCGAC AATTTCCGTC AAACCGAGGT

31901 ATATCTGGAA CAGTTCAAAG TGCTCATCTT ATTATAAGAT TTGACGAAAA
      TATAGACCTT GTCAAGTTTC ACGAGTAGAA TAATATTCTA AACTGCTTTT

31951 TGGAGTGCTA CTAAACAATT CCTTCCTGGA CCCAGAATAT TGGAACTTTA
      ACCTCACGAT GATTTGTTAA GGAAGGACCT GGGTCTTATA ACCTTGAAAT

32001 GAAATGGAGA TCTTACTGAA GGCACAGCCT ATACAAACGC TGTTGGATTT
      CTTTACCTCT AGAATGACTT CCGTGTCGGA TATGTTTGCG ACAACCTAAA

32051 ATGCCTAACC TATCAGCTTA TCCAAAATCT CACGGTAAAA CTGCCAAAAG
      TACGGATTGG ATAGTCGAAT AGGTTTTAGA GTGCCATTTT GACGGTTTTC

32101 TAACATTGTC AGTCAAGTTT ACTTAAACGG AGACAAAACT AAACCTGTAA
      ATTGTAACAG TCAGTTCAAA TGAATTTGCC TCTGTTTTGA TTTGGACATT

32151 CACTAACCAT TACACTAAAC GGTACACAGG AAACAGGAGA CACAACTCCA
      GTGATTGGTA ATGTGATTTG CCATGTGTCC TTTGTCCTCT GTGTTGAGGT

32201 AGTGCATACT CTATGTCATT TTCATGGGAC TGGTCTGGCC ACAACTACAT
      TCACGTATGA GATACAGTAA AAGTACCCTG ACCAGACCGG TGTTGATGTA
```

FIG. 15A-38

```
32251 TAATGAAATA TTTGCCACAT CCTCTTACAC TTTTTCATAC ATTGCCCAAG
      ATTACTTTAT AAACGGTGTA GGAGAATGTG AAAAAGTATG TAACGGGTTC

32301 AATAAAGAAT CGTTTGTGTT ATGTTTCAAC GTGTTTATTT TTCAATTGCA
      TTATTTCTTA GCAAACACAA TACAAAGTTG CACAAATAAA AAGTTAACGT

32351 GAAAATTTCA AGTCATTTTT CATTCAGTAG TATAGCCCCA CCACCACATA
      CTTTTAAAGT TCAGTAAAAA GTAAGTCATC ATATCGGGGT GGTGGTGTAT

32401 GCTTATACAG ATCACCGTAC CTTAATCAAA CTCACAGAAC CCTAGTATTC
      CGAATATGTC TAGTGGCATG GAATTAGTTT GAGTGTCTTG GGATCATAAG

32451 AACCTGCCAC CTCCCTCCCA ACACACAGAG TACACAGTCC TTTCTCCCCG
      TTGGACGGTG GAGGGAGGGT TGTGTGTCTC ATGTGTCAGG AAAGAGGGGC

32501 GCTGGCCTTA AAAAGCATCA TATCATGGGT AACAGACATA TTCTTAGGTG
      CGACCGGAAT TTTTCGTAGT ATAGTACCCA TTGTCTGTAT AAGAATCCAC

32551 TTATATTCCA CACGGTTTCC TGTCGAGCCA AACGCTCATC AGTGATATTA
      AATATAAGGT GTGCCAAAGG ACAGCTCGGT TTGCGAGTAG TCACTATAAT

32601 ATAAACTCCC CGGGCAGCTC ACTTAAGTTC ATGTCGCTGT CCAGCTGCTG
      TATTTGAGGG GCCCGTCGAG TGAATTCAAG TACAGCGACA GGTCGACGAC

32651 AGCCACAGGC TGCTGTCCAA CTTGCGGTTG CTTAACGGGC GGCGAAGGAG
      TCGGTGTCCG ACGACAGGTT GAACGCCAAC GAATTGCCCG CCGCTTCCTC

32701 AAGTCCACGC CTACATGGGG GTAGAGTCAT AATCGTGCAT CAGGATAGGG
      TTCAGGTGCG GATGTACCCC CATCTCAGTA TTAGCACGTA GTCCTATCCC

32751 CGGTGGTGCT GCAGCAGCGC GCGAATAAAC TGCTGCCGCC GCCGCTCCGT
      GCCACCACGA CGTCGTCGCG CGCTTATTTG ACGACGGCGG CGGCGAGGCA

32801 CCTGCAGGAA TACAACATGG CAGTGGTCTC CTCAGCGATG ATTCGCACCG
      GGACGTCCTT ATGTTGTACC GTCACCAGAG GAGTCGCTAC TAAGCGTGGC

32851 CCCGCAGCAT AAGGCGCCTT GTCCTCCGGG CACAGCAGCG CACCCTGATC
      GGGCGTCGTA TTCCGCGGAA CAGGAGGCCC GTGTCGTCGC GTGGGACTAG

32901 TCACTTAAAT CAGCACAGTA ACTGCAGCAC AGCACCACAA TATTGTTCAA
      AGTGAATTTA GTCGTGTCAT TGACGTCGTG TCGTGGTGTT ATAACAAGTT

32951 AATCCCACAG TGCAAGGCGC TGTATCCAAA GCTCATGGCG GGGACCACAG
      TTAGGGTGTC ACGTTCCGCG ACATAGGTTT CGAGTACCGC CCCTGGTGTC

33001 AACCCACGTG GCCATCATAC CACAAGCGCA GGTAGATTAA GTGGCGACCC
      TTGGGTGCAC CGGTAGTATG GTGTTCGCGT CCATCTAATT CACCGCTGGG

33051 CTCATAAACA CGCTGGACAT AAACATTACC TCTTTTGGCA TGTTGTAATT
      GAGTATTTGT GCGACCTGTA TTTGTAATGG AGAAAACCGT ACAACATTAA
```

FIG. 15A-39

```
33101 CACCACCTCC CGGTACCATA TAAACCTCTG ATTAAACATG GCGCCATCCA
      GTGGTGGAGG GCCATGGTAT ATTTGGAGAC TAATTTGTAC CGCGGTAGGT

33151 CCACCATCCT AAACCAGCTG GCCAAAACCT GCCCGCCGGC TATACACTGC
      GGTGGTAGGA TTTGGTCGAC CGGTTTTGGA CGGGCGGCCG ATATGTGACG

33201 AGGGAACCGG GACTGGAACA ATGACAGTGG AGAGCCCAGG ACTCGTAACC
      TCCCTTGGCC CTGACCTTGT TACTGTCACC TCTCGGGTCC TGAGCATTGG

33251 ATGGATCATC ATGCTCGTCA TGATATCAAT GTTGGCACAA CACAGGCACA
      TACCTAGTAG TACGAGCAGT ACTATAGTTA CAACCGTGTT GTGTCCGTGT

33301 CGTGCATACA CTTCCTCAGG ATTACAAGCT CCTCCCGCGT TAGAACCATA
      GCACGTATGT GAAGGAGTCC TAATGTTCGA GGAGGGCGCA ATCTTGGTAT

33351 TCCCAGGGAA CAACCCATTC CTGAATCAGC GTAAATCCCA CACTGCAGGG
      AGGGTCCCTT GTTGGGTAAG GACTTAGTCG CATTTAGGGT GTGACGTCCC

33401 AAGACCTCGC ACGTAACTCA CGTTGTGCAT TGTCAAAGTG TTACATTCGG
      TTCTGGAGCG TGCATTGAGT GCAACACGTA ACAGTTTCAC AATGTAAGCC

33451 GCAGCAGCGG ATGATCCTCC AGTATGGTAG CGCGGGTTTC TGTCTCAAAA
      CGTCGTCGCC TACTAGGAGG TCATACCATC GCGCCCAAAG ACAGAGTTTT

33501 GGAGGTAGAC GATCCCTACT GTACGGAGTG CGCCGAGACA ACCGAGATCG
      CCTCCATCTG CTAGGGATGA CATGCCTCAC GCGGCTCTGT TGGCTCTAGC

33551 TGTTGGTCGT AGTGTCATGC CAAATGGAAC GCCGGACGTA GTCATATTTC
      ACAACCAGCA TCACAGTACG GTTTACCTTG CGGCCTGCAT CAGTATAAAG

33601 CTGAAGCAAA ACCAGGTGCG GGCGTGACAA ACAGATCTGC GTCTCCGGTC
      GACTTCGTTT TGGTCCACGC CCGCACTGTT TGTCTAGACG CAGAGGCCAG

33651 TCGCCGCTTA GATCGCTCTG TGTAGTAGTT GTAGTATATC CACTCTCTCA
      AGCGGCGAAT CTAGCGAGAC ACATCATCAA CATCATATAG GTGAGAGAGT

33701 AAGCATCCAG GCGCCCCCTG GCTTCGGGTT CTATGTAAAC TCCTTCATGC
      TTCGTAGGTC CGCGGGGGAC CGAAGCCCAA GATACATTTG AGGAAGTACG

33751 GCCGCTGCCC TGATAACATC CACCACCGCA GAATAAGCCA CACCCAGCCA
      CGGCGACGGG ACTATTGTAG GTGGTGGCGT CTTATTCGGT GTGGGTCGGT

33801 ACCTACACAT TCGTTCTGCG AGTCACACAC GGGAGGAGCG GGAAGAGCTG
      TGGATGTGTA AGCAAGACGC TCAGTGTGTG CCCTCCTCGC CCTTCTCGAC

33851 GAAGAACCAT GTTTTTTTTT TTATTCCAAA AGATTATCCA AAACCTCAAA
      CTTCTTGGTA CAAAAAAAAA AATAAGGTTT TCTAATAGGT TTTGGAGTTT

33901 ATGAAGATCT ATTAAGTGAA CGCGCTCCCC TCCGGTGGCG TGGTCAAACT
      TACTTCTAGA TAATTCACTT GCGCGAGGGG AGGCCACCGC ACCAGTTTGA
```

FIG. 15A-40

```
33951 CTACAGCCAA AGAACAGATA ATGGCATTTG TAAGATGTTG CACAATGGCT
      GATGTCGGTT TCTTGTCTAT TACCGTAAAC ATTCTACAAC GTGTTACCGA

34001 TCCAAAAGGC AAACGGCCCT CACGTCCAAG TGGACGTAAA GGCTAAACCC
      AGGTTTTCCG TTTGCCGGGA GTGCAGGTTC ACCTGCATTT CCGATTTGGG

34051 TTCAGGGTGA ATCTCCTCTA TAAACATTCC AGCACCTTCA ACCATGCCCA
      AAGTCCCACT TAGAGGAGAT ATTTGTAAGG TCGTGGAAGT TGGTACGGGT

34101 AATAATTCTC ATCTCGCCAC CTTCTCAATA TATCTCTAAG CAAATCCCGA
      TTATTAAGAG TAGAGCGGTG GAAGAGTTAT ATAGAGATTC GTTTAGGGCT

34151 ATATTAAGTC CGGCCATTGT AAAAATCTGC TCCAGAGCGC CCTCCACCTT
      TATAATTCAG GCCGGTAACA TTTTTAGACG AGGTCTCGCG GGAGGTGGAA

34201 CAGCCTCAAG CAGCGAATCA TGATTGCAAA AATTCAGGTT CCTCACAGAC
      GTCGGAGTTC GTCGCTTAGT ACTAACGTTT TTAAGTCCAA GGAGTGTCTG

34251 CTGTATAAGA TTCAAAAGCG GAACATTAAC AAAAATACCG CGATCCCGTA
      GACATATTCT AAGTTTTCGC CTTGTAATTG TTTTTATGGC GCTAGGGCAT

34301 GGTCCCTTCG CAGGGCCAGC TGAACATAAT CGTGCAGGTC TGCACGGACC
      CCAGGGAAGC GTCCCGGTCG ACTTGTATTA GCACGTCCAG ACGTGCCTGG

34351 AGCGCGGCCA CTTCCCCGCC AGGAACCATG ACAAAAGAAC CCACACTGAT
      TCGCGCCGGT GAAGGGGCGG TCCTTGGTAC TGTTTTCTTG GGTGTGACTA

34401 TATGACACGC ATACTCGGAG CTATGCTAAC CAGCGTAGCC CCGATGTAAG
      ATACTGTGCG TATGAGCCTC GATACGATTG GTCGCATCGG GGCTACATTC

34451 CTTGTTGCAT GGGCGGCGAT ATAAAATGCA AGGTGCTGCT CAAAAAATCA
      GAACAACGTA CCCGCCGCTA TATTTTACGT TCCACGACGA GTTTTTTAGT

34501 GGCAAAGCCT CGCGCAAAAA AGAAAGCACA TCGTAGTCAT GCTCATGCAG
      CCGTTTCGGA GCGCGTTTTT TCTTTCGTGT AGCATCAGTA CGAGTACGTC

34551 ATAAAGGCAG GTAAGCTCCG GAACCACCAC AGAAAAAGAC ACCATTTTTC
      TATTTCCGTC CATTCGAGGC CTTGGTGGTG TCTTTTTCTG TGGTAAAAAG

34601 TCTCAAACAT GTCTGCGGGT TTCTGCATAA ACACAAAATA AAATAACAAA
      AGAGTTTGTA CAGACGCCCA AAGACGTATT TGTGTTTTAT TTTATTGTTT

34651 AAAACATTTA AACATTAGAA GCCTGTCTTA CAACAGGAAA AACAACCCTT
      TTTTGTAAAT TTGTAATCTT CGGACAGAAT GTTGTCCTTT TTGTTGGGAA

34701 ATAAGCATAA GACGGACTAC GGCCATGCCG GCGTGACCGT AAAAAAACTG
      TATTCGTATT CTGCCTGATG CCGGTACGGC CGCACTGGCA TTTTTTTGAC

34751 GTCACCGTGA TTAAAAAGCA CCACCGACAG CTCCTCGGTC ATGTCCGGAG
      CAGTGGCACT AATTTTTCGT GGTGGCTGTC GAGGAGCCAG TACAGGCCTC
```

FIG. 15A-41

```
34801  TCATAATGTA AGACTCGGTA AACACATCAG GTTGATTCAC ATCGGTCAGT
       AGTATTACAT TCTGAGCCAT TTGTGTAGTC CAACTAAGTG TAGCCAGTCA

34851  GCTAAAAAGC GACCGAAATA GCCCGGGGGA ATACATACCC GCAGGCGTAG
       CGATTTTTCG CTGGCTTTAT CGGGCCCCCT TATGTATGGG CGTCCGCATC

34901  AGACAACATT ACAGCCCCCA TAGGAGGTAT AACAAAATTA ATAGGAGAGA
       TCTGTTGTAA TGTCGGGGGT ATCCTCCATA TTGTTTTAAT TATCCTCTCT

34951  AAAACACATA AACACCTGAA AAACCCTCCT GCCTAGGCAA AATAGCACCC
       TTTTGTGTAT TTGTGGACTT TTTGGGAGGA CGGATCCGTT TTATCGTGGG

35001  TCCCGCTCCA GAACAACATA CAGCGCTTCC ACAGCGGCAG CCATAACAGT
       AGGGCGAGGT CTTGTTGTAT GTCGCGAAGG TGTCGCCGTC GGTATTGTCA

35051  CAGCCTTACC AGTAAAAAAG AAAACCTATT AAAAAAACAC CACTCGACAC
       GTCGGAATGG TCATTTTTTC TTTTGGATAA TTTTTTTGTG GTGAGCTGTG

35101  GGCACCAGCT CAATCAGTCA CAGTGTAAAA AAGGGCCAAG TGCAGAGCGA
       CCGTGGTCGA GTTAGTCAGT GTCACATTTT TTCCCGGTTC ACGTCTCGCT

35151  GTATATATAG GACTAAAAAA TGACGTAACG GTTAAAGTCC ACAAAAAACA
       CATATATATC CTGATTTTTT ACTGCATTGC CAATTTCAGG TGTTTTTTGT

35201  CCCAGAAAAC CGCACGCGAA CCTACGCCCA GAAACGAAAG CCAAAAAACC
       GGGTCTTTTG GCGTGCGCTT GGATGCGGGT CTTTGCTTTC GGTTTTTTGG

35251  CACAACTTCC TCAAATCGTC ACTTCCGTTT TCCCACGTTA CGTCACTTCC
       GTGTTGAAGG AGTTTAGCAG TGAAGGCAAA AGGGTGCAAT GCAGTGAAGG

35301  CATTTTAAGA AAACTACAAT TCCCAACACA TACAAGTTAC TCCGCCCTAA
       GTAAAATTCT TTTGATGTTA AGGGTTGTGT ATGTTCAATG AGGCGGGATT

35351  AACCTACGTC ACCCGCCCCG TTCCCACGCC CCGCGCCACG TCACAAACTC
       TTGGATGCAG TGGGCGGGGC AAGGGTGCGG GGCGCGGTGC AGTGTTTGAG

35401  CACCCCCTCA TTATCATATT GGCTTCAATC CAAAATAAGG TATATTATTG
       GTGGGGGAGT AATAGTATAA CCGAAGTTAG GTTTTATTCC ATATAATAAC

                   PacI
                 ~~~~~~~~~
35451  ATGATGTTAA TTAAGAATTC GGATCTGCGA CGCGAGGCTG GATGGCCTTC
       TACTACAATT AATTCTTAAG CCTAGACGCT GCGCTCCGAC CTACCGGAAG

35501  CCCATTATGA TTCTTCTCGC TTCCGGCGGC ATCGGGATGC CCGCGTTGCA
       GGGTAATACT AAGAAGAGCG AAGGCCGCCG TAGCCCTACG GGCGCAACGT

35551  GGCCATGCTG TCCAGGCAGG TAGATGACGA CCATCAGGGA CAGCTTCAAG
       CCGGTACGAC AGGTCCGTCC ATCTACTGCT GGTAGTCCCT GTCGAAGTTC
```

FIG.15A-42

```
35601  GCCAGCAAAA GGCCAGGAAC CGTAAAAAGG CCGCGTTGCT GGCGTTTTTC
       CGGTCGTTTT CCGGTCCTTG GCATTTTTCC GGCGCAACGA CCGCAAAAAG

35651  CATAGGCTCC GCCCCCCTGA CGAGCATCAC AAAAATCGAC GCTCAAGTCA
       GTATCCGAGG CGGGGGGACT GCTCGTAGTG TTTTTAGCTG CGAGTTCAGT

35701  GAGGTGGCGA AACCCGACAG GACTATAAAG ATACCAGGCG TTTCCCCCTG
       CTCCACCGCT TTGGGCTGTC CTGATATTTC TATGGTCCGC AAAGGGGGAC

35751  GAAGCTCCCT CGTGCGCTCT CCTGTTCCGA CCCTGCCGCT TACCGGATAC
       CTTCGAGGGA GCACGCGAGA GGACAAGGCT GGGACGGCGA ATGGCCTATG

35801  CTGTCCGCCT TTCTCCCTTC GGGAAGCGTG GCGCTTTCTC ATAGCTCACG
       GACAGGCGGA AAGAGGGAAG CCCTTCGCAC CGCGAAAGAG TATCGAGTGC

35851  CTGTAGGTAT CTCAGTTCGG TGTAGGTCGT TCGCTCCAAG CTGGGCTGTG
       GACATCCATA GAGTCAAGCC ACATCCAGCA AGCGAGGTTC GACCCGACAC

35901  TGCACGAACC CCCCGTTCAG CCCGACCGCT GCGCCTTATC CGGTAACTAT
       ACGTGCTTGG GGGGCAAGTC GGGCTGGCGA CGCGGAATAG GCCATTGATA

35951  CGTCTTGAGT CCAACCCGGT AAGACACGAC TTATCGCCAC TGGCAGCAGC
       GCAGAACTCA GGTTGGGCCA TTCTGTGCTG AATAGCGGTG ACCGTCGTCG

36001  CACTGGTAAC AGGATTAGCA GAGCGAGGTA TGTAGGCGGT GCTACAGAGT
       GTGACCATTG TCCTAATCGT CTCGCTCCAT ACATCCGCCA CGATGTCTCA

36051  TCTTGAAGTG GTGGCCTAAC TACGGCTACA CTAGAAGGAC AGTATTTGGT
       AGAACTTCAC CACCGGATTG ATGCCGATGT GATCTTCCTG TCATAAACCA

36101  ATCTGCGCTC TGCTGAAGCC AGTTACCTTC GGAAAAAGAG TTGGTAGCTC
       TAGACGCGAG ACGACTTCGG TCAATGGAAG CCTTTTTCTC AACCATCGAG

36151  TTGATCCGGC AAACAAACCA CCGCTGGTAG CGGTGGTTTT TTTGTTTGCA
       AACTAGGCCG TTTGTTTGGT GGCGACCATC GCCACCAAAA AAACAAACGT

36201  AGCAGCAGAT TACGCGCAGA AAAAAAGGAT CTCAAGAAGA TCCTTTGATC
       TCGTCGTCTA ATGCGCGTCT TTTTTTCCTA GAGTTCTTCT AGGAAACTAG

36251  TTTTCTACGG GGTCTGACGC TCAGTGGAAC GAAAACTCAC GTTAAGGGAT
       AAAAGATGCC CCAGACTGCG AGTCACCTTG CTTTTGAGTG CAATTCCCTA

36301  TTTGGTCATG AGATTATCAA AAAGGATCTT CACCTAGATC CTTTTAAATC
       AAACCAGTAC TCTAATAGTT TTTCCTAGAA GTGGATCTAG GAAAATTTAG

36351  AATCTAAAGT ATATATGAGT AAACTTGGTC TGACAGTTAC CAATGCTTAA
       TTAGATTTCA TATATACTCA TTTGAACCAG ACTGTCAATG GTTACGAATT

36401  TCAGTGAGGC ACCTATCTCA GCGATCTGTC TATTTCGTTC ATCCATAGTT
       AGTCACTCCG TGGATAGAGT CGCTAGACAG ATAAAGCAAG TAGGTATCAA
```

FIG.15A-43

```
36451 GCCTGACTCC CCGTCGTGTA GATAACTACG ATACGGGAGG GCTTACCATC
      CGGACTGAGG GGCAGCACAT CTATTGATGC TATGCCCTCC CGAATGGTAG

36501 TGGCCCCAGT GCTGCAATGA TACCGCGAGA CCCACGCTCA CCGGCTCCAG
      ACCGGGGTCA CGACGTTACT ATGGCGCTCT GGGTGCGAGT GGCCGAGGTC

36551 ATTTATCAGC AATAAACCAG CCAGCCGGAA GGGCCGAGCG CAGAAGTGGT
      TAAATAGTCG TTATTTGGTC GGTCGGCCTT CCCGGCTCGC GTCTTCACCA

36601 CCTGCAACTT TATCCGCCTC CATCCAGTCT ATTAATTGTT GCCGGGAAGC
      GGACGTTGAA ATAGGCGGAG GTAGGTCAGA TAATTAACAA CGGCCCTTCG

36651 TAGAGTAAGT AGTTCGCCAG TTAATAGTTT GCGCAACGTT GTTGCCATTG
      ATCTCATTCA TCAAGCGGTC AATTATCAAA CGCGTTGCAA CAACGGTAAC

36701 CTACAGGCAT CGTGGTGTCA CGCTCGTCGT TTGGTATGGC TTCATTCAGC
      GATGTCCGTA GCACCACAGT GCGAGCAGCA AACCATACCG AAGTAAGTCG

36751 TCCGGTTCCC AACGATCAAG GCGAGTTACA TGATCCCCCA TGTTGTGCAA
      AGGCCAAGGG TTGCTAGTTC CGCTCAATGT ACTAGGGGGT ACAACACGTT

36801 AAAAGCGGTT AGCTCCTTCG GTCCTCCGAT CGTTGTCAGA AGTAAGTTGG
      TTTTCGCCAA TCGAGGAAGC CAGGAGGCTA GCAACAGTCT TCATTCAACC

36851 CCGCAGTGTT ATCACTCATG GTTATGGCAG CACTGCATAA TTCTCTTACT
      GGCGTCACAA TAGTGAGTAC CAATACCGTC GTGACGTATT AAGAGAATGA

36901 GTCATGCCAT CCGTAAGATG CTTTTCTGTG ACTGGTGAGT ACTCAACCAA
      CAGTACGGTA GGCATTCTAC GAAAAGACAC TGACCACTCA TGAGTTGGTT

36951 GTCATTCTGA GAATAGTGTA TGCGGCGACC GAGTTGCTCT TGCCCGGCGT
      CAGTAAGACT CTTATCACAT ACGCCGCTGG CTCAACGAGA ACGGGCCGCA

37001 CAACACGGGA TAATACCGCG CCACATAGCA GAACTTTAAA AGTGCTCATC
      GTTGTGCCCT ATTATGGCGC GGTGTATCGT CTTGAAATTT TCACGAGTAG

37051 ATTGGAAAAC GTTCTTCGGG GCGAAAACTC TCAAGGATCT TACCGCTGTT
      TAACCTTTTG CAAGAAGCCC CGCTTTTGAG AGTTCCTAGA ATGGCGACAA

37101 GAGATCCAGT TCGATGTAAC CCACTCGTGC ACCCAACTGA TCTTCAGCAT
      CTCTAGGTCA AGCTACATTG GGTGAGCACG TGGGTTGACT AGAAGTCGTA

37151 CTTTTACTTT CACCAGCGTT TCTGGGTGAG CAAAAACAGG AAGGCAAAAT
      GAAAATGAAA GTGGTCGCAA AGACCCACTC GTTTTTGTCC TTCCGTTTTA

37201 GCCGCAAAAA AGGGAATAAG GGCGACACGG AAATGTTGAA TACTCATACT
      CGGCGTTTTT TCCCTTATTC CCGCTGTGCC TTTACAACTT ATGAGTATGA

37251 CTTCCTTTTT CAATATTATT GAAGCATTTA TCAGGGTTAT TGTCTCATGA
      GAAGGAAAAA GTTATAATAA CTTCGTAAAT AGTCCCAATA ACAGAGTACT
```

FIG. 15A-44

```
37301  GCGGATACAT ATTTGAATGT ATTTAGAAAA ATAAACAAAT AGGGGTTCCG
       CGCCTATGTA TAAACTTACA TAAATCTTTT TATTTGTTTA TCCCCAAGGC

37351  CGCACATTTC CCCGAAAAGT GCCACCTGAC GTCTAAGAAA CCATTATTAT
       GCGTGTAAAG GGGCTTTTCA CGGTGGACTG CAGATTCTTT GGTAATAATA

37401  CATGACATTA ACCTATAAAA ATAGGCGTAT CACGAGGCCC TTTCGTCTTC
       GTACTGTAAT TGGATATTTT TATCCGCATA GTGCTCCGGG AAAGCAGAAG

37451  AAGAATTGGA TCCGAATTCT TAAT (SEQ ID NO: 25)
       TTCTTAACCT AGGCTTAAGA ATTA (SEQ ID NO: 26)
```

FIG.15A-45

```
AGATCTACCATGGCCCCCATCTCCCCCATTGAGACTGTGCCTGTGAAGCTGAAGCCTGGCATGGATGGCCCCAAGGTGAA
BglII    MetAlaProIleSerProIleGluThrValProValLysLeuLysProGlyMetAspGlyProLysValLy
           1                       10                        20

GCAGTGGCCCCTGACTGAGGAGAAGATCAAGGCCCTGGTGGAAATCTGCACTGAGATGGAGAAGGAGGGCAAAATCTCCA
sGlnTrpProLeuThrGluGluLysIleLysAlaLeuValGluIleCysThrGluMetGluLysGluGlyLysIleSerL
            30                        40                        50

AGATTGGCCCCGAGAACCCCTACAACACCCCTGTGTTTGCCATCAAGAAGAAGGACTCCACCAAGTGGAGGAAGCTGGTG
ysIleGlyProGluAsnProTyrAsnThrProValPheAlaIleLysLysLysAspSerThrLysTrpArgLysLeuVal
                     60                        70

GACTTCAGGGAGCTGAACAAGAGGACCCAGGACTTCTGGGAGGTGCAGCTGGGCATCCCCCACCCCGCTGGCCTGAAGAA
AspPheArgGluLeuAsnLysArgThrGlnAspPheTrpGluValGlnLeuGlyIleProHisProAlaGlyLeuLysLy
      80                        90                        100

GAAGAAGTCTGTGACTGTGCTGGCTGTGGGGGATGCCTACTTCTCTGTGCCCCTGGATGAGGACTTCAGGAAGTACACTG
sLysLysSerValThrValLeuAlaValGlyAspAlaTyrPheSerValProLeuAspGluAspPheArgLysTyrThrA
            110                       120                       130

CCTTCACCATCCCCTCCATCAACAATGAGACCCCTGGCATCAGGTACCAGTACAATGTGCTGCCCCAGGGCTGGAAGGGC
laPheThrIleProSerIleAsnAsnGluThrProGlyIleArgTyrGlnTyrAsnValLeuProGlnGlyTrpLysGly
                     140                       150

TCCCCTGCCATCTTCCAGTCCTCCATGACCAAGATCCTGGAGCCCTTCAGGAAGCAGAACCCTGACATTGTGATCTACCA
SerProAlaIlePheGlnSerSerMetThrLysIleLeuGluProPheArgLysGlnAsnProAspIleValIleTyrGl
      160                       170                       180

GTACATGGCTGCCCTGTATGTGGGCTCTGACCTGGAGATTGGGCAGCACAGGACCAAGATTGAGGAGCTGAGGCAGCACC
nTyrMetAlaAlaLeuTyrValGlySerAspLeuGluIleGlyGlnHisArgThrLysIleGluGluLeuArgGlnHisL
            190                       200                       210

TGCTGAGGTGGGGCCTGACCACCCCTGACAAGAAGCACCAGAAGGAGCCCCCCTTCCTGTGGATGGGCTATGAGCTGCAC
euLeuArgTrpGlyLeuThrThrProAspLysLysHisGlnLysGluProProPheLeuTrpMetGlyTyrGluLeuHis
                     220                       230

CCCGACAAGTGGACTGTGCAGCCCATTGTGCTGCCTGAGAAGGACTCCTGGACTGTGAATGACATCCAGAAGCTGGTGGG
ProAspLysTrpThrValGlnProIleValLeuProGluLysAspSerTrpThrValAsnAspIleGlnLysLeuValGl
      240                       250                       260

CAAGCTGAACTGGGCCTCCCAAATCTACCCTGGCATCAAGGTGAGGCAGCTGTGCAAGCTGCTGAGGGGCACCAAGGCCC
yLysLeuAsnTrpAlaSerGlnIleTyrProGlyIleLysValArgGlnLeuCysLysLeuLeuArgGlyThrLysAlaL
            270                       280                       290

TGACTGAGGTGATCCCCCTGACTGAGGAGGCTGAGCTGGAGCTGGCTGAGAACAGGGAGATCCTGAAGGAGCCTGTGCAT
euThrGluValIleProLeuThrGluGluAlaGluLeuGluLeuAlaGluAsnArgGluIleLeuLysGluProValHis
                     300                       310

GGGGTGTACTATGACCCCTCCAAGGACCTGATTGCTGAGATCCAGAAGCAGGGCCAGGGCCAGTGGACCTACCAAATCTA
GlyValTyrTyrAspProSerLysAspLeuIleAlaGluIleGlnLysGlnGlyGlnGlyGlnTrpThrTyrGlnIleTy
      320                       330                       340

CCAGGAGCCCTTCAAGAACCTGAAGACTGGCAAGTATGCCAGGATGAGGGGGGCCCACACCAATGATGTGAAGCAGCTGA
rGlnGluProPheLysAsnLeuLysThrGlyLysTyrAlaArgMetArgGlyAlaHisThrAsnAspValLysGlnLeuT
            350                       360                       370

CTGAGGCTGTGCAGAAGATCACCACTGAGTCCATTGTGATCTGGGGCAAGACCCCCAAGTTCAAGCTGCCCATCCAGAAG
hrGluAlaValGlnLysIleThrThrGluSerIleValIleTrpGlyLysThrProLysPheLysLeuProIleGlnLys
                     380                       390
```

FIG. 17A-1

```
GAGACCTGGGAGACCTGGTGGACTGAGTACTGGCAGGCCACCTGGATCCCTGAGTGGGAGTTTGTGAACACCCCCCCCCT
GluThrTrpGluThrTrpTrpThrGluTyrTrpGlnAlaThrTrpIleProGluTrpGluPheValAsnThrProProLe
       400                                 410                                 420

GGTGAAGCTGTGGTACCAGCTGGAGAAGGAGCCCATTGTGGGGGCTGAGACCTTCTATGTGGCTGGGGCTGCCAACAGGG
uValLysLeuTrpTyrGlnLeuGluLysGluProIleValGlyAlaGluThrPheTyrValAlaGlyAlaAlaAsnArgG
                   430                                 440                                 450

AGACCAAGCTGGGCAAGGCTGGCTATGTGACCAACAGGGGCAGGCAGAAGGTGGTGACCCTGACTGACACCACCAACCAG
luThrLysLeuGlyLysAlaGlyTyrValThrAsnArgGlyArgGlnLysValValThrLeuThrAspThrThrAsnGln
                               460                                 470

AAGACTGCCCTCCAGGCCATCTACCTGGCCCTCCAGGACTCTGGCCTGGAGGTGAACATTGTGACTGCCTCCCAGTATGC
LysThrAlaLeuGlnAlaIleTyrLeuAlaLeuGlnAspSerGlyLeuGluValAsnIleValThrAlaSerGlnTyrAl
       480                                 490                                 500

CCTGGGCATCATCCAGGCCCAGCCTGATCAGTCTGAGTCTGAGCTGGTGAACCAGATCATTGAGCAGCTGATCAAGAAGG
aLeuGlyIleIleGlnAlaGlnProAspGlnSerGluSerGluLeuValAsnGlnIleIleGluGlnLeuIleLysLysG
                   510                                 520                                 530

AGAAGGTGTACCTGGCCTGGGTGCCTGCCCACAAGGGCATTGGGGGCAATGAGCAGGTGGACAAGCTGGTGTCTGCTGGC
luLysValTyrLeuAlaTrpValProAlaHisLysGlyIleGlyGlyAsnGluGlnValAspLysLeuValSerAlaGly
                               540                                 550

ATCAGGAAGGTGCTGTTCCTGGATGGCATTGACAAGGCCCAGGATGAGCATGAGAAGTACCACTCCAACTGGAGGGCTAT
IleArgLysValLeuPheLeuAspGlyIleAspLysAlaGlnAspGluHisGluLysTyrHisSerAsnTrpArgAlaMe
       560                                 570                                 580

GGCCTCTGACTTCAACCTGCCCCCTGTGGTGGCTAAGGAGATTGTGGCCTCCTGTGACAAGTGCCAGCTGAAGGGGGAGG
tAlaSerAspPheAsnLeuProProValValAlaLysGluIleValAlaSerCysAspLysCysGlnLeuLysGlyGluA
                   590                                 600                                 610

CCATGCATGGGCAGGTGGACTGCTCCCCTGGCATCTGGCAGCTGGCCTGCACCCACCTGGAGGGCAAGGTGATCCTGGTG
laMetHisGlyGlnValAspCysSerProGlyIleTrpGlnLeuAlaCysThrHisLeuGluGlyLysValIleLeuVal
                               620                                 630

GCTGTGCATGTGGCCTCCGGCTACATTGAGGCTGAGGTGATCCCTGCTGAGACAGGCCAGGAGACTGCCTACTTCCTGCT
AlaValHisValAlaSerGlyTyrIleGluAlaGluValIleProAlaGluThrGlyGlnGluThrAlaTyrPheLeuLe
       640                                 650                                 660

GAAGCTGGCTGGCAGGTGGCCTGTGAAGACCATCCACACTGCCAATGGCTCCAACTTCACTGGGGCCACAGTGAGGGCTG
uLysLeuAlaGlyArgTrpProValLysThrIleHisThrAlaAsnGlySerAsnPheThrGlyAlaThrValArgAlaA
                   670                                 680                                 690

CCTGCTGGTGGGCTGGCATCAAGCAGGAGTTTGGCATCCCCTACAACCCCCAGTCCCAGGGGGTGGTGGCCTCCATGAAC
laCysTrpTrpAlaGlyIleLysGlnGluPheGlyIleProTyrAsnProGlnSerGlnGlyValValAlaSerMetAsn
                               700                                 710

AAGGAGCTGAAGAAGATCATTGGGCAGGTGAGGGACCAGGCTGAGCACCTGAAGACAGCTGTGCAGATGGCTGTGTTCAT
LysGluLeuLysLysIleIleGlyGlnValArgAspGlnAlaGluHisLeuLysThrAlaValGlnMetAlaValPheIl
       720                                 730                                 740

CCACAACTTCAAGAGGAAGGGGGGCATCGGGGGCTACTCCGCTGGGGAGAGGATTGTGGACATCATTGCCACAGACATCC
eHisAsnPheLysArgLysGlyGlyIleGlyGlyTyrSerAlaGlyGluArgIleValAspIleIleAlaThrAspIleG
                   750                                 760                                 770

AGACCAAGGAGCTCCAGAAGCAGATCACCAAGATCCAGAACTTCAGGGTGTACTACAGGGACTCCAGGAACCCCCTGTGG
lnThrLysGluLeuGlnLysGlnIleThrLysIleGlnAsnPheArgValTyrTyrArgAspSerArgAsnProLeuTrp
                               780                                 790
```

FIG. 17A-2

```
AAGGGCCCTGCCAAGCTGCTGTGGAAGGGGGAGGGGGCTGTGGTGATCCAGGACAACTCTGACATCAAGGTGGTGCCCAG
LysGlyProAlaLysLeuLeuTrpLysGlyGluGlyAlaValValIleGlnAspAsnSerAspIleLysValValProAr
      800                            810                            820

GAGGAAGGCCAAGATCATCAGGGACTATGGCAAGCAGATGGCTGGGGATGACTGTGTGGCCTCCAGGCAGGATGAGGACT
gArgLysAlaLysIleIleArgAspTyrGlyLysGlnMetAlaGlyAspAspCysValAlaSerArgGlnAspGluAspx
                830                            840                            850

AAAGCCCGGGCAGATCT   (SEQ ID NO: 3)
Xx         BglII    (SEQ ID NO: 4)
```

FIG. 17A-3

```
GATCACCATGGATGCAATGAAGAGAGGGCTCTGCTGTGTGCTGCTGCTGTGTGGAGCAGTCTTCGTTTCGC
       MetAspAlaMetLysArgGlyLeuCysCysValLeuLeuLeuCysGlyAlaValPheValSerP
       -25            -20                           -10

CCAGCGAGATCTCCGCCCCCATCTCCCCCATTGAGACTGTGCCTGTGAAGCTGAAGCCTGGCATGGATGGC     (within SEQ ID NO: 7)
RoSerGluIleSerAlaProIleSerProIleGluThrValProValLysLeuLysProGlyMetAspGly     (within SEQ ID NO: 8)
           -1  2                      10                            20
```

FIG. 18

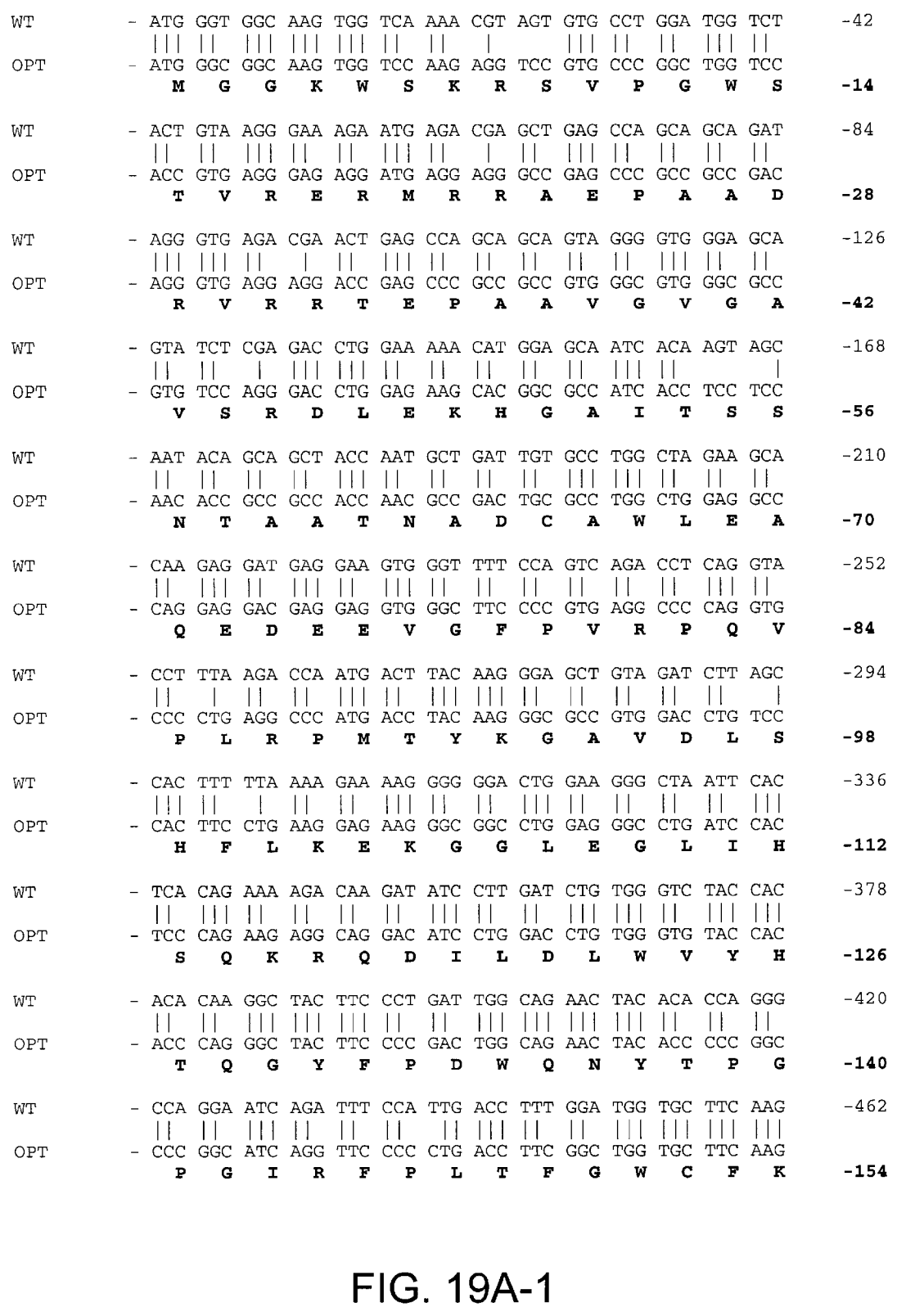

```
WT   - ATG GGT GGC AAG TGG TCA AAA CGT AGT GTG CCT GGA TGG TCT   -42
OPT  - ATG GGC GGC AAG TGG TCC AAG AGG TCC GTG CCC GGC TGG TCC
        M   G   G   K   W   S   K   R   S   V   P   G   W   S   -14

WT   - ACT GTA AGG GAA AGA ATG AGA CGA GCT GAG CCA GCA GCA GAT   -84
OPT  - ACC GTG AGG GAG AGG ATG AGG AGG GCC GAG CCC GCC GCC GAC
        T   V   R   E   R   M   R   R   A   E   P   A   A   D   -28

WT   - AGG GTG AGA CGA ACT GAG CCA GCA GCA GTA GGG GTG GGA GCA   -126
OPT  - AGG GTG AGG AGG ACC GAG CCC GCC GCC GTG GGC GTG GGC GCC
        R   V   R   R   T   E   P   A   A   V   G   V   G   A   -42

WT   - GTA TCT CGA GAC CTG GAA AAA CAT GGA GCA ATC ACA AGT AGC   -168
OPT  - GTG TCC AGG GAC CTG GAG AAG CAC GGC GCC ATC ACC TCC TCC
        V   S   R   D   L   E   K   H   G   A   I   T   S   S   -56

WT   - AAT ACA GCA GCT ACC AAT GCT GAT TGT GCC TGG CTA GAA GCA   -210
OPT  - AAC ACC GCC GCC ACC AAC GCC GAC TGC GCC TGG CTG GAG GCC
        N   T   A   A   T   N   A   D   C   A   W   L   E   A   -70

WT   - CAA GAG GAT GAG GAA GTG GGT TTT CCA GTC AGA CCT CAG GTA   -252
OPT  - CAG GAG GAC GAG GAG GTG GGC TTC CCC GTG AGG CCC CAG GTG
        Q   E   D   E   E   V   G   F   P   V   R   P   Q   V   -84

WT   - CCT TTA AGA CCA ATG ACT TAC AAG GGA GCT GTA GAT CTT AGC   -294
OPT  - CCC CTG AGG CCC ATG ACC TAC AAG GGC GCC GTG GAC CTG TCC
        P   L   R   P   M   T   Y   K   G   A   V   D   L   S   -98

WT   - CAC TTT TTA AAA GAA AAG GGG GGA CTG GAA GGG CTA ATT CAC   -336
OPT  - CAC TTC CTG AAG GAG AAG GGC GGC CTG GAG GGC CTG ATC CAC
        H   F   L   K   E   K   G   G   L   E   G   L   I   H   -112

WT   - TCA CAG AAA AGA CAA GAT ATC CTT GAT CTG TGG GTC TAC CAC   -378
OPT  - TCC CAG AAG AGG CAG GAC ATC CTG GAC CTG TGG GTG TAC CAC
        S   Q   K   R   Q   D   I   L   D   L   W   V   Y   H   -126

WT   - ACA CAA GGC TAC TTC CCT GAT TGG CAG AAC TAC ACA CCA GGG   -420
OPT  - ACC CAG GGC TAC TTC CCC GAC TGG CAG AAC TAC ACC CCC GGC
        T   Q   G   Y   F   P   D   W   Q   N   Y   T   P   G   -140

WT   - CCA GGA ATC AGA TTT CCA TTG ACC TTT GGA TGG TGC TTC AAG   -462
OPT  - CCC GGC ATC AGG TTC CCC CTG ACC TTC GGC TGG TGC TTC AAG
        P   G   I   R   F   P   L   T   F   G   W   C   F   K   -154
```

FIG. 19A-1

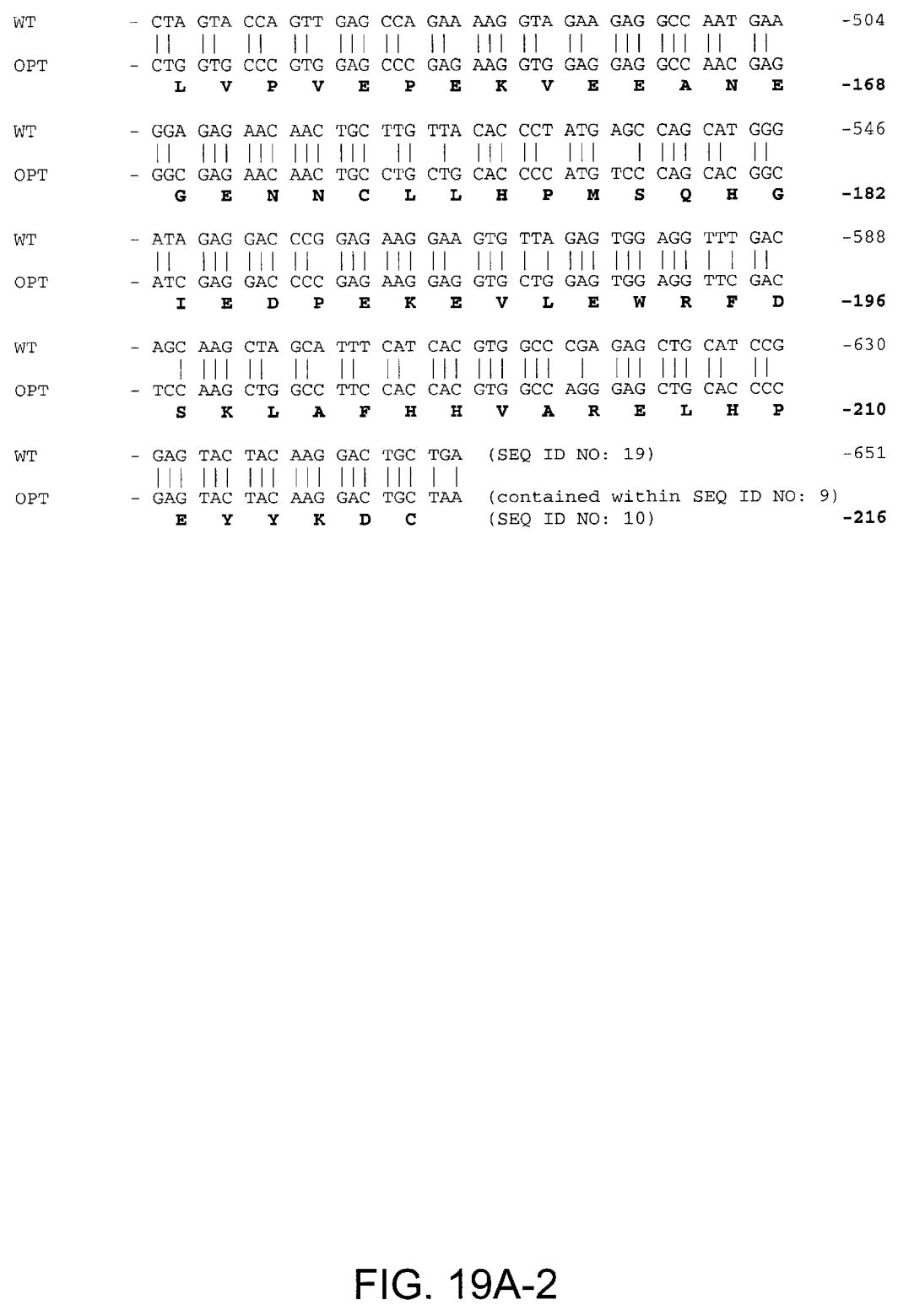

```
WT    - CTA GTA CCA GTT GAG CCA GAA AAG GTA GAA GAG GCC AAT GAA    -504
        ||  ||  ||  ||  |||  ||  ||  |||  ||  ||  |||  |||  ||  ||
OPT   - CTG GTG CCC GTG GAG CCC GAG AAG GTG GAG GAG GCC AAC GAG
        L   V   P   V   E   P   E   K   V   E   E   A   N   E    -168

WT    - GGA GAG AAC AAC TGC TTG TTA CAC CCT ATG AGC CAG CAT GGG    -546
        ||  |||  |||  |||  |||  ||  |   |||  ||  |||  |   |||  ||  ||
OPT   - GGC GAG AAC AAC TGC CTG CTG CAC CCC ATG TCC CAG CAC GGC
        G   E   N   N   C   L   L   H   P   M   S   Q   H   G    -182

WT    - ATA GAG GAC CCG GAG AAG GAA GTG TTA GAG TGG AGG TTT GAC    -588
        ||  |||  |||  ||  |||  |||  ||  |||  |  |  |||  |||  |||  |  |  ||
OPT   - ATC GAG GAC CCC GAG AAG GAG GTG CTG GAG TGG AGG TTC GAC
        I   E   D   P   E   K   E   V   L   E   W   R   F   D    -196

WT    - AGC AAG CTA GCA TTT CAT CAC GTG GCC CGA GAG CTG CAT CCG    -630
        |  |||  ||  ||  ||  ||  |||  |||  |||  |   |||  |||  ||  ||
OPT   - TCC AAG CTG GCC TTC CAC CAC GTG GCC AGG GAG CTG CAC CCC
        S   K   L   A   F   H   H   V   A   R   E   L   H   P    -210

WT    - GAG TAC TAC AAG GAC TGC TGA    (SEQ ID NO: 19)              -651
        |||  |||  |||  |||  |||  |||  |  |
OPT   - GAG TAC TAC AAG GAC TGC TAA    (contained within SEQ ID NO: 9)
        E   Y   Y   K   D   C          (SEQ ID NO: 10)              -216
```

FIG. 19A-2

V1Jns/nef

A

```
              PstI            BglII
CATGGGTCTTTTCTGCAGTCACCGTCCTTGAGATCTGCCACC ATG GGC GGC AAG TGG TCC AAG AGG TCC GTG CCC . . . .
                                            M   G   G   K   W   S   K   R   S   V   P

                                             SrfI  BglII
. . . . . CAC CCC GAG TAC TAC AAG GAC TGC TAA AGCCCGGGCAGATCTGCTGTGCCTTCTAGTTGCCAGC (SEQ ID NO: 36)
           H   P   E   Y   Y   K   D   C   * (contained within SEQ ID NO: 10)
```

V1Jns/nef(G2A,LLAA)

B

```
              PstI            BglII
CATGGGTCTTTTCTGCAGTCACCGTCCTTGAGATCTGCCACC ATG GCC GGC AAG TGG TCC AAG AGG TCC GTG CCC . . . .
                                            M   A   G   K   W   S   K   R   S   V   P

                                             SrfI  BglII
. . . . . CAC CCC GAG TAC TAC AAG GAC TGC TAA AGCCCGGGCAGATCTGCTGTGCCTTCTAGTTGCCAGC (SEQ ID NO: 37)
           H   P   E   Y   Y   K   D   C   *  (contained within SEQ ID NO: 14)
```

V1Jns/tpanef & V1Jns/tpanef(LLAA)

C

```
              PstI
CATGGGTCTTTTCTGCAGTCACCGTCCTTATATCTAGATCACC ATG GAT GCA ATG AAG AGA GGG CTC TGC TGT GTG
                                             M   D   A   M   K   R   G   L   C   C   V

                                                  BglII
CTG CTG CTG TGT GGA GCA GTC TTC GTT TCG CCC AGC GAG ATC TCC TCC AAG AGG TCC GTG CCC . . . .
 L   L   L   C   G   A   V   F   V   S   P   S   E   I   S   S   K   R   S   V   P

                                             SrfI  BglII
. . . . . CAC CCC GAG TAC TAC AAG GAC TGC TAA AGCCCGGGCAGATCTGCTGTGCCTTCTAGTTGCCAGC (SEQ ID NO: 38)
           H   P   E   Y   Y   K   D   C   *  (contained within SEQ ID NO: 16)
```

FIGS. 20A-C

Figure 1: Construction of pre-plasmid "pMRKAd5pol"

Figure 2: Construction of pre-plasmid "pMRKAd5nef".

Comparison of Clade B vs. Clade C Anti-gag T Cell Responses in Clade B HIV-Infected Subjects

Comparison of Clade B vs. Clade C Anti-nef T Cell Responses in Clade B HIV-Infected Subjects nef c = 131.132 + 0.8646 nef b

| Summary of Fit | |
|---|---|
| RSquare | 0.91685 |
| RSquare Adj | 0.91289 |
| Root Mean Square Error | 289.7718 |
| Mean of Response | 1096.435 |
| Observations (or Sum Wgts) | 23 |

```
1    CATCATCAAT AATATACCTT ATTTTGGATT GAAGCCAATA TGATAATGAG
     GTAGTAGTTA TTATATGGAA TAAAACCTAA CTTCGGTTAT ACTATTACTC

51   GGGGTGGAGT TTGTGACGTG GCGCGGGGCG TGGGAACGGG GCGGGTGACG
     CCCCACCTCA AACACTGCAC CGCGCCCCGC ACCCTTGCCC CGCCCACTGC

101  TAGTAGTGTG GCGGAAGTGT GATGTTGCAA GTGTGGCGGA ACACATGTAA
     ATCATCACAC CGCCTTCACA CTACAACGTT CACACCGCCT TGTGTACATT

151  GCGACGGATG TGGCAAAAGT GACGTTTTTG GTGTGCGCCG GTGTACACAG
     CGCTGCCTAC ACCGTTTTCA CTGCAAAAAC CACACGCGGC CACATGTGTC

201  GAAGTGACAA TTTTCGCGCG GTTTTAGGCG GATGTTGTAG TAAATTTGGG
     CTTCACTGTT AAAAGCGCGC CAAAATCCGC CTACAACATC ATTTAAACCC

251  CGTAACCGAG TAAGATTTGG CCATTTTCGC GGGAAAACTG AATAAGAGGA
     GCATTGGCTC ATTCTAAACC GGTAAAAGCG CCCTTTTGAC TTATTCTCCT

301  AGTGAAATCT GAATAATTTT GTGTTACTCA TAGCGCGTAA TATTTGTCTA
     TCACTTTAGA CTTATTAAAA CACAATGAGT ATCGCGCATT ATAAACAGAT

351  GGGCCGCGGG GACTTTGACC GTTTACGTGG AGACTCGCCC AGGTGTTTTT
     CCCGGCGCCC CTGAAACTGG CAAATGCACC TCTGAGCGGG TCCACAAAAA

401  CTCAGGTGTT TTCCGCGTTC CGGGTCAAAG TTGGCGTTTT ATTATTATAG
     GAGTCCACAA AAGGCGCAAG GCCCAGTTTC AACCGCAAAA TAATAATATC

451  GCGGCCGCGA TCCATTGCAT ACGTTGTATC CATATCATAA TATGTACATT
     CGCCGGCGCT AGGTAACGTA TGCAACATAG GTATAGTATT ATACATGTAA

501  TATATTGGCT CATGTCCAAC ATTACCGCCA TGTTGACATT GATTATTGAC
     ATATAACCGA GTACAGGTTG TAATGGCGGT ACAACTGTAA CTAATAACTG

551  TAGTTATTAA TAGTAATCAA TTACGGGGTC ATTAGTTCAT AGCCCATATA
     ATCAATAATT ATCATTAGTT AATGCCCCAG TAATCAAGTA TCGGGTATAT

601  TGGAGTTCCG CGTTACATAA CTTACGGTAA ATGGCCCGCC TGGCTGACCG
     ACCTCAAGGC GCAATGTATT GAATGCCATT TACCGGGCGG ACCGACTGGC

651  CCCAACGACC CCCGCCCATT GACGTCAATA ATGACGTATG TTCCCATAGT
     GGGTTGCTGG GGGCGGGTAA CTGCAGTTAT TACTGCATAC AAGGGTATCA

701  AACGCCAATA GGGACTTTCC ATTGACGTCA ATGGGTGGAG TATTTACGGT
     TTGCGGTTAT CCCTGAAAGG TAACTGCAGT TACCCACCTC ATAAATGCCA

751  AAACTGCCCA CTTGGCAGTA CATCAAGTGT ATCATATGCC AAGTACGCCC
     TTTGACGGGT GAACCGTCAT GTAGTTCACA TAGTATACGG TTCATGCGGG

801  CCTATTGACG TCAATGACGG TAAATGGCCC GCCTGGCATT ATGCCCAGTA
     GGATAACTGC AGTTACTGCC ATTTACCGGG CGGACCGTAA TACGGGTCAT
```

FIG. 26A-1

```
 851  CATGACCTTA TGGGACTTTC CTACTTGGCA GTACATCTAC GTATTAGTCA
      GTACTGGAAT ACCCTGAAAG GATGAACCGT CATGTAGATG CATAATCAGT

 901  TCGCTATTAC CATGGTGATG CGGTTTTGGC AGTACATCAA TGGGCGTGGA
      AGCGATAATG GTACCACTAC GCCAAAACCG TCATGTAGTT ACCCGCACCT

 951  TAGCGGTTTG ACTCACGGGG ATTTCCAAGT CTCCACCCCA TTGACGTCAA
      ATCGCCAAAC TGAGTGCCCC TAAAGGTTCA GAGGTGGGGT AACTGCAGTT

1001  TGGGAGTTTG TTTTGGCACC AAAATCAACG GGACTTTCCA AAATGTCGTA
      ACCCTCAAAC AAAACCGTGG TTTTAGTTGC CCTGAAAGGT TTTACAGCAT

1051  ACAACTCCGC CCCATTGACG CAAATGGGCG GTAGGCGTGT ACGGTGGGAG
      TGTTGAGGCG GGGTAACTGC GTTTACCCGC CATCCGCACA TGCCACCCTC

1101  GTCTATATAA GCAGAGCTCG TTTAGTGAAC CGTCAGATCG CCTGGAGACG
      CAGATATATT CGTCTCGAGC AAATCACTTG GCAGTCTAGC GGACCTCTGC

1151  CCATCCACGC TGTTTTGACC TCCATAGAAG ACACCGGGAC CGATCCAGCC
      GGTAGGTGCG ACAAAACTGG AGGTATCTTC TGTGGCCCTG GCTAGGTCGG

1201  TCCGCGGCCG GGAACGGTGC ATTGGAACGC GGATTCCCCG TGCCAAGAGT
      AGGCGCCGGC CCTTGCCACG TAACCTTGCG CCTAAGGGGC ACGGTTCTCA

1251  GAGATCTACC ATGGCCCCCA TCTCCCCCAT TGAGACTGTG CCTGTGAAGC
      CTCTAGATGG TACCGGGGGT AGAGGGGGTA ACTCTGACAC GGACACTTCG

1301  TGAAGCCTGG CATGGATGGC CCCAAGGTGA AGCAGTGGCC CCTGACTGAG
      ACTTCGGACC GTACCTACCG GGGTTCCACT TCGTCACCGG GGACTGACTC

1351  GAGAAGATCA AGGCCCTGGT GGAAATCTGC ACTGAGATGG AGAAGGAGGG
      CTCTTCTAGT TCCGGGACCA CCTTTAGACG TGACTCTACC TCTTCCTCCC

1401  CAAAATCTCC AAGATTGGCC CCGAGAACCC CTACAACACC CCTGTGTTTG
      GTTTTAGAGG TTCTAACCGG GGCTCTTGGG GATGTTGTGG GGACACAAAC

1451  CCATCAAGAA GAAGGACTCC ACCAAGTGGA GGAAGCTGGT GGACTTCAGG
      GGTAGTTCTT CTTCCTGAGG TGGTTCACCT CCTTCGACCA CCTGAAGTCC

1501  GAGCTGAACA AGAGGACCCA GGACTTCTGG GAGGTGCAGC TGGGCATCCC
      CTCGACTTGT TCTCCTGGGT CCTGAAGACC CTCCACGTCG ACCCGTAGGG

1551  CCACCCCGCT GGCCTGAAGA AGAAGAAGTC TGTGACTGTG CTGGCTGTGG
      GGTGGGGCGA CCGGACTTCT TCTTCTTCAG ACACTGACAC GACCGACACC

1601  GGGATGCCTA CTTCTCTGTG CCCCTGGATG AGGACTTCAG GAAGTACACT
      CCCTACGGAT GAAGAGACAC GGGGACCTAC TCCTGAAGTC CTTCATGTGA

1651  GCCTTCACCA TCCCCTCCAT CAACAATGAG ACCCCTGGCA TCAGGTACCA
      CGGAAGTGGT AGGGGAGGTA GTTGTTACTC TGGGGACCGT AGTCCATGGT
```

FIG. 26A-2

```
1701  GTACAATGTG CTGCCCCAGG GCTGGAAGGG CTCCCCTGCC ATCTTCCAGT
      CATGTTACAC GACGGGGTCC CGACCTTCCC GAGGGGACGG TAGAAGGTCA

1751  CCTCCATGAC CAAGATCCTG GAGCCCTTCA GGAAGCAGAA CCCTGACATT
      GGAGGTACTG GTTCTAGGAC CTCGGGAAGT CCTTCGTCTT GGGACTGTAA

1801  GTGATCTACC AGTACATGGC TGCCCTGTAT GTGGGCTCTG ACCTGGAGAT
      CACTAGATGG TCATGTACCG ACGGGACATA CACCCGAGAC TGGACCTCTA

1851  TGGGCAGCAC AGGACCAAGA TTGAGGAGCT GAGGCAGCAC CTGCTGAGGT
      ACCCGTCGTG TCCTGGTTCT AACTCCTCGA CTCCGTCGTG GACGACTCCA

1901  GGGGCCTGAC CACCCCTGAC AAGAAGCACC AGAAGGAGCC CCCCTTCCTG
      CCCCGGACTG GTGGGGACTG TTCTTCGTGG TCTTCCTCGG GGGGAAGGAC

1951  TGGATGGGCT ATGAGCTGCA CCCCGACAAG TGGACTGTGC AGCCCATTGT
      ACCTACCCGA TACTCGACGT GGGGCTGTTC ACCTGACACG TCGGGTAACA

2001  GCTGCCTGAG AAGGACTCCT GGACTGTGAA TGACATCCAG AAGCTGGTGG
      CGACGGACTC TTCCTGAGGA CCTGACACTT ACTGTAGGTC TTCGACCACC

2051  GCAAGCTGAA CTGGGCCTCC CAAATCTACC CTGGCATCAA GGTGAGGCAG
      CGTTCGACTT GACCCGGAGG GTTTAGATGG GACCGTAGTT CCACTCCGTC

2101  CTGTGCAAGC TGCTGAGGGG CACCAAGGCC CTGACTGAGG TGATCCCCCT
      GACACGTTCG ACGACTCCCC GTGGTTCCGG GACTGACTCC ACTAGGGGGA

2151  GACTGAGGAG GCTGAGCTGG AGCTGGCTGA GAACAGGGAG ATCCTGAAGG
      CTGACTCCTC CGACTCGACC TCGACCGACT CTTGTCCCTC TAGGACTTCC

2201  AGCCTGTGCA TGGGGTGTAC TATGACCCCT CCAAGGACCT GATTGCTGAG
      TCGGACACGT ACCCCACATG ATACTGGGGA GGTTCCTGGA CTAACGACTC

2251  ATCCAGAAGC AGGGCCAGGG CCAGTGGACC TACCAAATCT ACCAGGAGCC
      TAGGTCTTCG TCCCGGTCCC GGTCACCTGG ATGGTTTAGA TGGTCCTCGG

2301  CTTCAAGAAC CTGAAGACTG GCAAGTATGC CAGGATGAGG GGGGCCCACA
      GAAGTTCTTG GACTTCTGAC CGTTCATACG GTCCTACTCC CCCCGGGTGT

2351  CCAATGATGT GAAGCAGCTG ACTGAGGCTG TGCAGAAGAT CACCACTGAG
      GGTTACTACA CTTCGTCGAC TGACTCCGAC ACGTCTTCTA GTGGTGACTC

2401  TCCATTGTGA TCTGGGGCAA GACCCCCAAG TTCAAGCTGC CCATCCAGAA
      AGGTAACACT AGACCCCGTT CTGGGGGTTC AAGTTCGACG GGTAGGTCTT

2451  GGAGACCTGG GAGACCTGGT GGACTGAGTA CTGGCAGGCC ACCTGGATCC
      CCTCTGGACC CTCTGGACCA CCTGACTCAT GACCGTCCGG TGGACCTAGG

2501  CTGAGTGGGA GTTTGTGAAC ACCCCCCCCC TGGTGAAGCT GTGGTACCAG
      GACTCACCCT CAAACACTTG TGGGGGGGGG ACCACTTCGA CACCATGGTC
```

FIG. 26A-3

```
2551  CTGGAGAAGG AGCCCATTGT GGGGGCTGAG ACCTTCTATG TGGCTGGGGC
      GACCTCTTCC TCGGGTAACA CCCCCGACTC TGGAAGATAC ACCGACCCCG

2601  TGCCAACAGG GAGACCAAGC TGGGCAAGGC TGGCTATGTG ACCAACAGGG
      ACGGTTGTCC CTCTGGTTCG ACCCGTTCCG ACCGATACAC TGGTTGTCCC

2651  GCAGGCAGAA GGTGGTGACC CTGACTGACA CCACCAACCA GAAGACTGCC
      CGTCCGTCTT CCACCACTGG GACTGACTGT GGTGGTTGGT CTTCTGACGG

2701  CTCCAGGCCA TCTACCTGGC CCTCCAGGAC TCTGGCCTGG AGGTGAACAT
      GAGGTCCGGT AGATGGACCG GGAGGTCCTG AGACCGGACC TCCACTTGTA

2751  TGTGACTGCC TCCCAGTATG CCCTGGGCAT CATCCAGGCC CAGCCTGATC
      ACACTGACGG AGGGTCATAC GGGACCCGTA GTAGGTCCGG GTCGGACTAG

2801  AGTCTGAGTC TGAGCTGGTG AACCAGATCA TTGAGCAGCT GATCAAGAAG
      TCAGACTCAG ACTCGACCAC TTGGTCTAGT AACTCGTCGA CTAGTTCTTC

2851  GAGAAGGTGT ACCTGGCCTG GGTGCCTGCC CACAAGGGCA TTGGGGGCAA
      CTCTTCCACA TGGACCGGAC CCACGGACGG GTGTTCCCGT AACCCCCGTT

2901  TGAGCAGGTG GACAAGCTGG TGTCTGCTGG CATCAGGAAG GTGCTGTTCC
      ACTCGTCCAC CTGTTCGACC ACAGACGACC GTAGTCCTTC CACGACAAGG

2951  TGGATGGCAT TGACAAGGCC CAGGATGAGC ATGAGAAGTA CCACTCCAAC
      ACCTACCGTA ACTGTTCCGG GTCCTACTCG TACTCTTCAT GGTGAGGTTG

3001  TGGAGGGCTA TGGCCTCTGA CTTCAACCTG CCCCCTGTGG TGGCTAAGGA
      ACCTCCCGAT ACCGGAGACT GAAGTTGGAC GGGGGACACC ACCGATTCCT

3051  GATTGTGGCC TCCTGTGACA AGTGCCAGCT GAAGGGGGAG GCCATGCATG
      CTAACACCGG AGGACACTGT TCACGGTCGA CTTCCCCCTC CGGTACGTAC

3101  GGCAGGTGGA CTGCTCCCCT GGCATCTGGC AGCTGGCCTG CACCCACCTG
      CCGTCCACCT GACGAGGGGA CCGTAGACCG TCGACCGGAC GTGGGTGGAC

3151  GAGGGCAAGG TGATCCTGGT GGCTGTGCAT GTGGCCTCCG GCTACATTGA
      CTCCCGTTCC ACTAGGACCA CCGACACGTA CACCGGAGGC CGATGTAACT

3201  GGCTGAGGTG ATCCCTGCTG AGACAGGCCA GGAGACTGCC TACTTCCTGC
      CCGACTCCAC TAGGGACGAC TCTGTCCGGT CCTCTGACGG ATGAAGGACG

3251  TGAAGCTGGC TGGCAGGTGG CCTGTGAAGA CCATCCACAC TGCCAATGGC
      ACTTCGACCG ACCGTCCACC GGACACTTCT GGTAGGTGTG ACGGTTACCG

3301  TCCAACTTCA CTGGGGCCAC AGTGAGGGCT GCCTGCTGGT GGGCTGGCAT
      AGGTTGAAGT GACCCCGGTG TCACTCCCGA CGGACGACCA CCCGACCGTA

3351  CAAGCAGGAG TTTGGCATCC CCTACAACCC CCAGTCCCAG GGGGTGGTGG
      GTTCGTCCTC AAACCGTAGG GGATGTTGGG GGTCAGGGTC CCCCACCACC
```

FIG. 26A-4

```
3401  CCTCCATGAA CAAGGAGCTG AAGAAGATCA TTGGGCAGGT GAGGGACCAG
      GGAGGTACTT GTTCCTCGAC TTCTTCTAGT AACCCGTCCA CTCCCTGGTC

3451  GCTGAGCACC TGAAGACAGC TGTGCAGATG GCTGTGTTCA TCCACAACTT
      CGACTCGTGG ACTTCTGTCG ACACGTCTAC CGACACAAGT AGGTGTTGAA

3501  CAAGAGGAAG GGGGGCATCG GGGGCTACTC CGCTGGGGAG AGGATTGTGG
      GTTCTCCTTC CCCCCGTAGC CCCCGATGAG GCGACCCCTC TCCTAACACC

3551  ACATCATTGC CACAGACATC CAGACCAAGG AGCTCCAGAA GCAGATCACC
      TGTAGTAACG GTGTCTGTAG GTCTGGTTCC TCGAGGTCTT CGTCTAGTGG

3601  AAGATCCAGA ACTTCAGGGT GTACTACAGG GACTCCAGGA ACCCCCTGTG
      TTCTAGGTCT TGAAGTCCCA CATGATGTCC CTGAGGTCCT TGGGGGACAC

3651  GAAGGGCCCT GCCAAGCTGC TGTGGAAGGG GGAGGGGGCT GTGGTGATCC
      CTTCCCGGGA CGGTTCGACG ACACCTTCCC CCTCCCCCGA CACCACTAGG

3701  AGGACAACTC TGACATCAAG GTGGTGCCCA GGAGGAAGGC CAAGATCATC
      TCCTGTTGAG ACTGTAGTTC CACCACGGGT CCTCCTTCCG GTTCTAGTAG

3751  AGGGACTATG GCAAGCAGAT GGCTGGGGAT GACTGTGTGG CCTCCAGGCA
      TCCCTGATAC CGTTCGTCTA CCGACCCCTA CTGACACACC GGAGGTCCGT

3801  GGATGAGGAC TAAAGCCCGG GCAGATCTGC TGTGCCTTCT AGTTGCCAGC
      CCTACTCCTG ATTTCGGGCC CGTCTAGACG ACACGGAAGA TCAACGGTCG

3851  CATCTGTTGT TTGCCCCTCC CCCGTGCCTT CCTTGACCCT GGAAGGTGCC
      GTAGACAACA AACGGGGAGG GGGCACGGAA GGAACTGGGA CCTTCCACGG

3901  ACTCCCACTG TCCTTTCCTA ATAAAATGAG GAAATTGCAT CGCATTGTCT
      TGAGGGTGAC AGGAAAGGAT TATTTTACTC CTTTAACGTA GCGTAACAGA

3951  GAGTAGGTGT CATTCTATTC TGGGGGGTGG GGTGGGGCAG GACAGCAAGG
      CTCATCCACA GTAAGATAAG ACCCCCCACC CCACCCCGTC CTGTCGTTCC

4001  GGGAGGATTG GGAAGACAAT AGCAGGCATG CTGGGGATGC GGTGGGCTCT
      CCCTCCTAAC CCTTCTGTTA TCGTCCGTAC GACCCCTACG CCACCCGAGA

4051  ATGGCCGATC GGCGCGCCGT ACTGAAATGT GTGGGCGTGG CTTAAGGGTG
      TACCGGCTAG CCGCGCGGCA TGACTTTACA CACCCGCACC GAATTCCCAC

4101  GGAAAGAATA TATAAGGTGG GGGTCTTATG TAGTTTTGTA TCTGTTTTGC
      CCTTTCTTAT ATATTCCACC CCCAGAATAC ATCAAAACAT AGACAAAACG

4151  AGCAGCCGCC GCCGCCATGA GCACCAACTC GTTTGATGGA AGCATTGTGA
      TCGTCGGCGG CGGCGGTACT CGTGGTTGAG CAAACTACCT TCGTAACACT

4201  GCTCATATTT GACAACGCGC ATGCCCCCAT GGGCCGGGGT GCGTCAGAAT
      CGAGTATAAA CTGTTGCGCG TACGGGGGTA CCCGGCCCCA CGCAGTCTTA
```

FIG. 26A-5

```
4251  GTGATGGGCT CCAGCATTGA TGGTCGCCCC GTCCTGCCCG CAAACTCTAC
      CACTACCCGA GGTCGTAACT ACCAGCGGGG CAGGACGGGC GTTTGAGATG

4301  TACCTTGACC TACGAGACCG TGTCTGGAAC GCCGTTGGAG ACTGCAGCCT
      ATGGAACTGG ATGCTCTGGC ACAGACCTTG CGGCAACCTC TGACGTCGGA

4351  CCGCCGCCGC TTCAGCCGCT GCAGCCACCG CCCGCGGGAT TGTGACTGAC
      GGCGGCGGCG AAGTCGGCGA CGTCGGTGGC GGGCGCCCTA ACACTGACTG

4401  TTTGCTTTCC TGAGCCCGCT TGCAAACAGT GCAGCTTCCC GTTCATCCGC
      AAACGAAAGG ACTCGGGCGA ACGTTTGTCA CGTCGAAGGG CAAGTAGGCG

4451  CCGCGATGAC AAGTTGACGG CTCTTTTGGC ACAATTGGAT TCTTTGACCC
      GGCGCTACTG TTCAACTGCC GAGAAAACCG TGTTAACCTA AGAAACTGGG

4501  GGGAACTTAA TGTCGTTTCT CAGCAGCTGT TGGATCTGCG CCAGCAGGTT
      CCCTTGAATT ACAGCAAAGA GTCGTCGACA ACCTAGACGC GGTCGTCCAA

4551  TCTGCCCTGA AGGCTTCCTC CCCTCCCAAT GCGGTTTAAA ACATAAATAA
      AGACGGGACT TCCGAAGGAG GGGAGGGTTA CGCCAAATTT TGTATTTATT

4601  AAAACCAGAC TCTGTTTGGA TTTGGATCAA GCAAGTGTCT TGCTGTCTTT
      TTTTGGTCTG AGACAAACCT AAACCTAGTT CGTTCACAGA ACGACAGAAA

4651  ATTTAGGGGT TTTGCGCGCG CGGTAGGCCC GGGACCAGCG GTCTCGGTCG
      TAAATCCCCA AAACGCGCGC GCCATCCGGG CCCTGGTCGC CAGAGCCAGC

4701  TTGAGGGTCC TGTGTATTTT TTCCAGGACG TGGTAAAGGT GACTCTGGAT
      AACTCCCAGG ACACATAAAA AAGGTCCTGC ACCATTTCCA CTGAGACCTA

4751  GTTCAGATAC ATGGGCATAA GCCCGTCTCT GGGGTGGAGG TAGCACCACT
      CAAGTCTATG TACCCGTATT CGGGCAGAGA CCCCACCTCC ATCGTGGTGA

4801  GCAGAGCTTC ATGCTGCGGG GTGGTGTTGT AGATGATCCA GTCGTAGCAG
      CGTCTCGAAG TACGACGCCC CACCACAACA TCTACTAGGT CAGCATCGTC

4851  GAGCGCTGGG CGTGGTGCCT AAAAATGTCT TTCAGTAGCA AGCTGATTGC
      CTCGCGACCC GCACCACGGA TTTTTACAGA AAGTCATCGT TCGACTAACG

4901  CAGGGGCAGG CCCTTGGTGT AAGTGTTTAC AAAGCGGTTA AGCTGGGATG
      GTCCCCGTCC GGGAACCACA TTCACAAATG TTTCGCCAAT TCGACCCTAC

4951  GGTGCATACG TGGGGATATG AGATGCATCT TGGACTGTAT TTTTAGGTTG
      CCACGTATGC ACCCCTATAC TCTACGTAGA ACCTGACATA AAAATCCAAC

5001  GCTATGTTCC CAGCCATATC CCTCCGGGGA TTCATGTTGT GCAGAACCAC
      CGATACAAGG GTCGGTATAG GGAGGCCCCT AAGTACAACA CGTCTTGGTG

5051  CAGCACAGTG TATCCGGTGC ACTTGGGAAA TTTGTCATGT AGCTTAGAAG
      GTCGTGTCAC ATAGGCCACG TGAACCCTTT AAACAGTACA TCGAATCTTC
```

FIG. 26A-6

```
5101  GAAATGCGTG GAAGAACTTG GAGACGCCCT TGTGACCTCC AAGATTTTCC
      CTTTACGCAC CTTCTTGAAC CTCTGCGGGA ACACTGGAGG TTCTAAAAGG

5151  ATGCATTCGT CCATAATGAT GGCAATGGGC CCACGGGCGG CGGCCTGGGC
      TACGTAAGCA GGTATTACTA CCGTTACCCG GGTGCCCGCC GCCGGACCCG

5201  GAAGATATTT CTGGGATCAC TAACGTCATA GTTGTGTTCC AGGATGAGAT
      CTTCTATAAA GACCCTAGTG ATTGCAGTAT CAACACAAGG TCCTACTCTA

5251  CGTCATAGGC CATTTTTACA AAGCGCGGGC GGAGGGTGCC AGACTGCGGT
      GCAGTATCCG GTAAAAATGT TTCGCGCCCG CCTCCCACGG TCTGACGCCA

5301  ATAATGGTTC CATCCGGCCC AGGGGCGTAG TTACCCTCAC AGATTTGCAT
      TATTACCAAG GTAGGCCGGG TCCCCGCATC AATGGGAGTG TCTAAACGTA

5351  TTCCCACGCT TTGAGTTCAG ATGGGGGGAT CATGTCTACC TGCGGGGCGA
      AAGGGTGCGA AACTCAAGTC TACCCCCCTA GTACAGATGG ACGCCCCGCT

5401  TGAAGAAAAC GGTTTCCGGG GTAGGGGAGA TCAGCTGGGA AGAAAGCAGG
      ACTTCTTTTG CCAAAGGCCC CATCCCCTCT AGTCGACCCT TCTTTCGTCC

5451  TTCCTGAGCA GCTGCGACTT ACCGCAGCCG GTGGGCCCGT AAATCACACC
      AAGGACTCGT CGACGCTGAA TGGCGTCGGC CACCCGGGCA TTTAGTGTGG

5501  TATTACCGGC TGCAACTGGT AGTTAAGAGA GCTGCAGCTG CCGTCATCCC
      ATAATGGCCG ACGTTGACCA TCAATTCTCT CGACGTCGAC GGCAGTAGGG

5551  TGAGCAGGGG GGCCACTTCG TTAAGCATGT CCCTGACTCG CATGTTTTCC
      ACTCGTCCCC CCGGTGAAGC AATTCGTACA GGGACTGAGC GTACAAAAGG

5601  CTGACCAAAT CCGCCAGAAG GCGCTCGCCG CCCAGCGATA GCAGTTCTTG
      GACTGGTTTA GGCGGTCTTC CGCGAGCGGC GGGTCGCTAT CGTCAAGAAC

5651  CAAGGAAGCA AAGTTTTTCA ACGGTTTGAG ACCGTCCGCC GTAGGCATGC
      GTTCCTTCGT TTCAAAAAGT TGCCAAACTC TGGCAGGCGG CATCCGTACG

5701  TTTTGAGCGT TTGACCAAGC AGTTCCAGGC GGTCCCACAG CTCGGTCACC
      AAAACTCGCA AACTGGTTCG TCAAGGTCCG CCAGGGTGTC GAGCCAGTGG

5751  TGCTCTACGG CATCTCGATC CAGCATATCT CCTCGTTTCG CGGGTTGGGG
      ACGAGATGCC GTAGAGCTAG GTCGTATAGA GGAGCAAAGC GCCCAACCCC

5801  CGGCTTTCGC TGTACGGCAG TAGTCGGTGC TCGTCCAGAC GGGCCAGGGT
      GCCGAAAGCG ACATGCCGTC ATCAGCCACG AGCAGGTCTG CCCGGTCCCA

5851  CATGTCTTTC CACGGGCGCA GGGTCCTCGT CAGCGTAGTC TGGGTCACGG
      GTACAGAAAG GTGCCCGCGT CCCAGGAGCA GTCGCATCAG ACCCAGTGCC

5901  TGAAGGGGTG CGCTCCGGGC TGCGCGCTGG CCAGGGTGCG CTTGAGGCTG
      ACTTCCCCAC GCGAGGCCCG ACGCGCGACC GGTCCCACGC GAACTCCGAC
```

FIG. 26A-7

```
5951  GTCCTGCTGG TGCTGAAGCG CTGCCGGTCT TCGCCCTGCG CGTCGGCCAG
      CAGGACGACC ACGACTTCGC GACGGCCAGA AGCGGGACGC GCAGCCGGTC

6001  GTAGCATTTG ACCATGGTGT CATAGTCCAG CCCCTCCGCG GCGTGGCCCT
      CATCGTAAAC TGGTACCACA GTATCAGGTC GGGGAGGCGC CGCACCGGGA

6051  TGGCGCGCAG CTTGCCCTTG GAGGAGGCGC CGCACGAGGG GCAGTGCAGA
      ACCGCGCGTC GAACGGGAAC CTCCTCCGCG GCGTGCTCCC CGTCACGTCT

6101  CTTTTGAGGG CGTAGAGCTT GGGCGCGAGA AATACCGATT CCGGGGAGTA
      GAAAACTCCC GCATCTCGAA CCCGCGCTCT TTATGGCTAA GGCCCCTCAT

6151  GGCATCCGCG CCGCAGGCCC CGCAGACGGT CTCGCATTCC ACGAGCCAGG
      CCGTAGGCGC GGCGTCCGGG GCGTCTGCCA GAGCGTAAGG TGCTCGGTCC

6201  TGAGCTCTGG CCGTTCGGGG TCAAAAACCA GGTTTCCCCC ATGCTTTTTG
      ACTCGAGACC GGCAAGCCCC AGTTTTTGGT CCAAAGGGGG TACGAAAAAC

6251  ATGCGTTTCT TACCTCTGGT TTCCATGAGC CGGTGTCCAC GCTCGGTGAC
      TACGCAAAGA ATGGAGACCA AAGGTACTCG GCCACAGGTG CGAGCCACTG

6301  GAAAAGGCTG TCCGTGTCCC CGTATACAGA CTTGAGAGGC CTGTCCTCGA
      CTTTTCCGAC AGGCACAGGG GCATATGTCT GAACTCTCCG GACAGGAGCT

6351  GCGGTGTTCC GCGGTCCTCC TCGTATAGAA ACTCGGACCA CTCTGAGACA
      CGCCACAAGG CGCCAGGAGG AGCATATCTT TGAGCCTGGT GAGACTCTGT

6401  AAGGCTCGCG TCCAGGCCAG CACGAAGGAG GCTAAGTGGG AGGGGTAGCG
      TTCCGAGCGC AGGTCCGGTC GTGCTTCCTC CGATTCACCC TCCCCATCGC

6451  GTCGTTGTCC ACTAGGGGGT CCACTCGCTC CAGGGTGTGA AGACACATGT
      CAGCAACAGG TGATCCCCCA GGTGAGCGAG GTCCCACACT TCTGTGTACA

6501  CGCCCTCTTC GGCATCAAGG AAGGTGATTG GTTTGTAGGT GTAGGCCACG
      GCGGGAGAAG CCGTAGTTCC TTCCACTAAC CAAACATCCA CATCCGGTGC

6551  TGACCGGGTG TTCCTGAAGG GGGGCTATAA AAGGGGGTGG GGGCGCGTTC
      ACTGGCCCAC AAGGACTTCC CCCCGATATT TTCCCCCACC CCCGCGCAAG

6601  GTCCTCACTC TCTTCCGCAT CGCTGTCTGC GAGGGCCAGC TGTTGGGGTG
      CAGGAGTGAG AGAAGGCGTA GCGACAGACG CTCCCGGTCG ACAACCCCAC

6651  AGTACTCCCT CTGAAAAGCG GGCATGACTT CTGCGCTAAG ATTGTCAGTT
      TCATGAGGGA GACTTTTCGC CCGTACTGAA GACGCGATTC TAACAGTCAA

6701  TCCAAAAACG AGGAGGATTT GATATTCACC TGGCCCGCGG TGATGCCTTT
      AGGTTTTTGC TCCTCCTAAA CTATAAGTGG ACCGGGCGCC ACTACGGAAA

6751  GAGGGTGGCC GCATCCATCT GGTCAGAAAA GACAATCTTT TTGTTGTCAA
      CTCCCACCGG CGTAGGTAGA CCAGTCTTTT CTGTTAGAAA AACAACAGTT
```

FIG. 26A-8

```
6801  GCTTGGTGGC AAACGACCCG TAGAGGGCGT TGGACAGCAA CTTGGCGATG
      CGAACCACCG TTTGCTGGGC ATCTCCCGCA ACCTGTCGTT GAACCGCTAC

6851  GAGCGCAGGG TTTGGTTTTT GTCGCGATCG GCGCGCTCCT TGGCCGCGAT
      CTCGCGTCCC AAACCAAAAA CAGCGCTAGC CGCGCGAGGA ACCGGCGCTA

6901  GTTTAGCTGC ACGTATTCGC GCGCAACGCA CCGCCATTCG GGAAAGACGG
      CAAATCGACG TGCATAAGCG CGCGTTGCGT GGCGGTAAGC CCTTTCTGCC

6951  TGGTGCGCTC GTCGGGCACC AGGTGCACGC GCCAACCGCG GTTGTGCAGG
      ACCACGCGAG CAGCCCGTGG TCCACGTGCG CGGTTGGCGC CAACACGTCC

7001  GTGACAAGGT CAACGCTGGT GGCTACCTCT CCGCGTAGGC GCTCGTTGGT
      CACTGTTCCA GTTGCGACCA CCGATGGAGA GGCGCATCCG CGAGCAACCA

7051  CCAGCAGAGG CGGCCGCCCT TGCGCGAGCA GAATGGCGGT AGGGGGTCTA
      GGTCGTCTCC GCCGGCGGGA ACGCGCTCGT CTTACCGCCA TCCCCCAGAT

7101  GCTGCGTCTC GTCCGGGGGG TCTGCGTCCA CGGTAAAGAC CCCGGGCAGC
      CGACGCAGAG CAGGCCCCCC AGACGCAGGT GCCATTTCTG GGGCCCGTCG

7151  AGGCGCGCGT CGAAGTAGTC TATCTTGCAT CCTTGCAAGT CTAGCGCCTG
      TCCGCGCGCA GCTTCATCAG ATAGAACGTA GGAACGTTCA GATCGCGGAC

7201  CTGCCATGCG CGGGCGGCAA GCGCGCGCTC GTATGGGTTG AGTGGGGGAC
      GACGGTACGC GCCCGCCGTT CGCGCGCGAG CATACCCAAC TCACCCCCTG

7251  CCCATGGCAT GGGGTGGGTG AGCGCGGAGG CGTACATGCC GCAAATGTCG
      GGGTACCGTA CCCCACCCAC TCGCGCCTCC GCATGTACGG CGTTTACAGC

7301  TAAACGTAGA GGGGCTCTCT GAGTATTCCA AGATATGTAG GGTAGCATCT
      ATTTGCATCT CCCCGAGAGA CTCATAAGGT TCTATACATC CCATCGTAGA

7351  TCCACCGCGG ATGCTGGCGC GCACGTAATC GTATAGTTCG TGCGAGGGAG
      AGGTGGCGCC TACGACCGCG CGTGCATTAG CATATCAAGC ACGCTCCCTC

7401  CGAGGAGGTC GGGACCGAGG TTGCTACGGG CGGGCTGCTC TGCTCGGAAG
      GCTCCTCCAG CCCTGGCTCC AACGATGCCC GCCCGACGAG ACGAGCCTTC

7451  ACTATCTGCC TGAAGATGGC ATGTGAGTTG GATGATATGG TTGGACGCTG
      TGATAGACGG ACTTCTACCG TACACTCAAC CTACTATACC AACCTGCGAC

7501  GAAGACGTTG AAGCTGGCGT CTGTGAGACC TACCGCGTCA CGCACGAAGG
      CTTCTGCAAC TTCGACCGCA GACACTCTGG ATGGCGCAGT GCGTGCTTCC

7551  AGGCGTAGGA GTCGCGCAGC TTGTTGACCA GCTCGGCGGT GACCTGCACG
      TCCGCATCCT CAGCGCGTCG AACAACTGGT CGAGCCGCCA CTGGACGTGC

7601  TCTAGGGCGC AGTAGTCCAG GGTTTCCTTG ATGATGTCAT ACTTATCCTG
      AGATCCCGCG TCATCAGGTC CCAAAGGAAC TACTACAGTA TGAATAGGAC
```

FIG. 26A-9

```
7651  TCCCTTTTTT TTCCACAGCT CGCGGTTGAG GACAAACTCT TCGCGGTCTT
      AGGGAAAAAA AAGGTGTCGA GCGCCAACTC CTGTTTGAGA AGCGCCAGAA

7701  TCCAGTACTC TTGGATCGGA AACCCGTCGG CCTCCGAACG GTAAGAGCCT
      AGGTCATGAG AACCTAGCCT TTGGGCAGCC GGAGGCTTGC CATTCTCGGA

7751  AGCATGTAGA ACTGGTTGAC GGCCTGGTAG GCGCAGCATC CCTTTTCTAC
      TCGTACATCT TGACCAACTG CCGGACCATC CGCGTCGTAG GGAAAAGATG

7801  GGGTAGCGCG TATGCCTGCG CGGCCTTCCG GAGCGAGGTG TGGGTGAGCG
      CCCATCGCGC ATACGGACGC GCCGGAAGGC CTCGCTCCAC ACCCACTCGC

7851  CAAAGGTGTC CCTGACCATG ACTTTGAGGT ACTGGTATTT GAAGTCAGTG
      GTTTCCACAG GGACTGGTAC TGAAACTCCA TGACCATAAA CTTCAGTCAC

7901  TCGTCGCATC CGCCCTGCTC CCAGAGCAAA AAGTCCGTGC GCTTTTTGGA
      AGCAGCGTAG GCGGGACGAG GGTCTCGTTT TTCAGGCACG CGAAAAACCT

7951  ACGCGGATTT GGCAGGGCGA AGGTGACATC GTTGAAGAGT ATCTTTCCCG
      TGCGCCTAAA CCGTCCCGCT TCCACTGTAG CAACTTCTCA TAGAAAGGGC

8001  CGCGAGGCAT AAAGTTGCGT GTGATGCGGA AGGGTCCCGG CACCTCGGAA
      GCGCTCCGTA TTTCAACGCA CACTACGCCT TCCCAGGGCC GTGGAGCCTT

8051  CGGTTGTTAA TTACCTGGGC GGCGAGCACG ATCTCGTCAA AGCCGTTGAT
      GCCAACAATT AATGGACCCG CCGCTCGTGC TAGAGCAGTT TCGGCAACTA

8101  GTTGTGGCCC ACAATGTAAA GTTCCAAGAA GCGCGGGATG CCCTTGATGG
      CAACACCGGG TGTTACATTT CAAGGTTCTT CGCGCCCTAC GGGAACTACC

8151  AAGGCAATTT TTTAAGTTCC TCGTAGGTGA GCTCTTCAGG GGAGCTGAGC
      TTCCGTTAAA AAATTCAAGG AGCATCCACT CGAGAAGTCC CCTCGACTCG

8201  CCGTGCTCTG AAAGGGCCCA GTCTGCAAGA TGAGGGTTGG AAGCGACGAA
      GGCACGAGAC TTTCCCGGGT CAGACGTTCT ACTCCCAACC TTCGCTGCTT

8251  TGAGCTCCAC AGGTCACGGG CCATTAGCAT TTGCAGGTGG TCGCGAAAGG
      ACTCGAGGTG TCCAGTGCCC GGTAATCGTA AACGTCCACC AGCGCTTTCC

8301  TCCTAAACTG GCGACCTATG GCCATTTTTT CTGGGGTGAT GCAGTAGAAG
      AGGATTTGAC CGCTGGATAC CGGTAAAAAA GACCCCACTA CGTCATCTTC

8351  GTAAGCGGGT CTTGTTCCCA GCGGTCCCAT CCAAGGTTCG CGGCTAGGTC
      CATTCGCCCA GAACAAGGGT CGCCAGGGTA GGTTCCAAGC GCCGATCCAG

8401  TCGCGCGGCA GTCACTAGAG GCTCATCTCC GCCGAACTTC ATGACCAGCA
      AGCGCGCCGT CAGTGATCTC CGAGTAGAGG CGGCTTGAAG TACTGGTCGT

8451  TGAAGGGCAC GAGCTGCTTC CCAAAGGCCC CCATCCAAGT ATAGGTCTCT
      ACTTCCCGTG CTCGACGAAG GGTTTCCGGG GGTAGGTTCA TATCCAGAGA
```

FIG. 26A-10

```
8501  ACATCGTAGG TGACAAAGAG ACGCTCGGTG CGAGGATGCG AGCCGATCGG
      TGTAGCATCC ACTGTTTCTC TGCGAGCCAC GCTCCTACGC TCGGCTAGCC

8551  GAAGAACTGG ATCTCCCGCC ACCAATTGGA GGAGTGGCTA TTGATGTGGT
      CTTCTTGACC TAGAGGGCGG TGGTTAACCT CCTCACCGAT AACTACACCA

8601  GAAAGTAGAA GTCCCTGCGA CGGGCCGAAC ACTCGTGCTG GCTTTTGTAA
      CTTTCATCTT CAGGGACGCT GCCCGGCTTG TGAGCACGAC CGAAAACATT

8651  AAACGTGCGC AGTACTGGCA GCGGTGCACG GGCTGTACAT CCTGCACGAG
      TTTGCACGCG TCATGACCGT CGCCACGTGC CCGACATGTA GGACGTGCTC

8701  GTTGACCTGA CGACCGCGCA CAAGGAAGCA GAGTGGGAAT TTGAGCCCCT
      CAACTGGACT GCTGGCGCGT GTTCCTTCGT CTCACCCTTA AACTCGGGGA

8751  CGCCTGGCGG GTTTGGCTGG TGGTCTTCTA CTTCGGCTGC TTGTCCTTGA
      GCGGACCGCC CAAACCGACC ACCAGAAGAT GAAGCCGACG AACAGGAACT

8801  CCGTCTGGCT GCTCGAGGGG AGTTACGGTG GATCGGACCA CCACGCCGCG
      GGCAGACCGA CGAGCTCCCC TCAATGCCAC CTAGCCTGGT GGTGCGGCGC

8851  CGAGCCCAAA GTCCAGATGT CCGCGCGCGG CGGTCGGAGC TTGATGACAA
      GCTCGGGTTT CAGGTCTACA GGCGCGCGCC GCCAGCCTCG AACTACTGTT

8901  CATCGCGCAG ATGGGAGCTG TCCATGGTCT GGAGCTCCCG CGGCGTCAGG
      GTAGCGCGTC TACCCTCGAC AGGTACCAGA CCTCGAGGGC GCCGCAGTCC

8951  TCAGGCGGGA GCTCCTGCAG GTTTACCTCG CATAGACGGG TCAGGGCGCG
      AGTCCGCCCT CGAGGACGTC CAAATGGAGC GTATCTGCCC AGTCCCGCGC

9001  GGCTAGATCC AGGTGATACC TAATTTCCAG GGGCTGGTTG GTGGCGGCGT
      CCGATCTAGG TCCACTATGG ATTAAAGGTC CCCGACCAAC CACCGCCGCA

9051  CGATGGCTTG CAAGAGGCCG CATCCCCGCG GCGCGACTAC GGTACCGCGC
      GCTACCGAAC GTTCTCCGGC GTAGGGGCGC CGCGCTGATG CCATGGCGCG

9101  GGCGGGCGGT GGGCCGCGGG GGTGTCCTTG GATGATGCAT CTAAAAGCGG
      CCGCCCGCCA CCCGGCGCCC CCACAGGAAC CTACTACGTA GATTTTCGCC

9151  TGACGCGGGC GAGCCCCCGG AGGTAGGGGG GGCTCCGGAC CCGCCGGGAG
      ACTGCGCCCG CTCGGGGGCC TCCATCCCCC CCGAGGCCTG GGCGGCCCTC

9201  AGGGGGCAGG GGCACGTCGG CGCCGCGCGC GGGCAGGAGC TGGTGCTGCG
      TCCCCCGTCC CCGTGCAGCC GCGGCGCGCG CCCGTCCTCG ACCACGACGC

9251  CGCGTAGGTT GCTGGCGAAC GCGACGACGC GGCGGTTGAT CTCCTGAATC
      GCGCATCCAA CGACCGCTTG CGCTGCTGCG CCGCCAACTA GAGGACTTAG

9301  TGGCGCCTCT GCGTGAAGAC GACGGGCCCG GTGAGCTTGA ACCTGAAAGA
      ACCGCGGAGA CGCACTTCTG CTGCCCGGGC CACTCGAACT TGGACTTTCT
```

FIG. 26A-11

```
9351   GAGTTCGACA GAATCAATTT CGGTGTCGTT GACGGCGGCC TGGCGCAAAA
       CTCAAGCTGT CTTAGTTAAA GCCACAGCAA CTGCCGCCGG ACCGCGTTTT

9401   TCTCCTGCAC GTCTCCTGAG TTGTCTTGAT AGGCGATCTC GGCCATGAAC
       AGAGGACGTG CAGAGGACTC AACAGAACTA TCCGCTAGAG CCGGTACTTG

9451   TGCTCGATCT CTTCCTCCTG GAGATCTCCG CGTCCGGCTC GCTCCACGGT
       ACGAGCTAGA GAAGGAGGAC CTCTAGAGGC GCAGGCCGAG CGAGGTGCCA

9501   GGCGGCGAGG TCGTTGGAAA TGCGGGCCAT GAGCTGCGAG AAGGCGTTGA
       CCGCCGCTCC AGCAACCTTT ACGCCCGGTA CTCGACGCTC TTCCGCAACT

9551   GGCCTCCCTC GTTCCAGACG CGGCTGTAGA CCACGCCCCC TTCGGCATCG
       CCGGAGGGAG CAAGGTCTGC GCCGACATCT GGTGCGGGGG AAGCCGTAGC

9601   CGGGCGCGCA TGACCACCTG CGCGAGATTG AGCTCCACGT GCCGGGCGAA
       GCCCGCGCGT ACTGGTGGAC GCGCTCTAAC TCGAGGTGCA CGGCCCGCTT

9651   GACGGCGTAG TTTCGCAGGC GCTGAAAGAG GTAGTTGAGG GTGGTGGCGG
       CTGCCGCATC AAAGCGTCCG CGACTTTCTC CATCAACTCC CACCACCGCC

9701   TGTGTTCTGC CACGAAGAAG TACATAACCC AGCGTCGCAA CGTGGATTCG
       ACACAAGACG GTGCTTCTTC ATGTATTGGG TCGCAGCGTT GCACCTAAGC

9751   TTGATATCCC CCAAGGCCTC AAGGCGCTCC ATGGCCTCGT AGAAGTCCAC
       AACTATAGGG GGTTCCGGAG TTCCGCGAGG TACCGGAGCA TCTTCAGGTG

9801   GGCGAAGTTG AAAAACTGGG AGTTGCGCGC CGACACGGTT AACTCCTCCT
       CCGCTTCAAC TTTTTGACCC TCAACGCGCG GCTGTGCCAA TTGAGGAGGA

9851   CCAGAAGACG GATGAGCTCG GCGACAGTGT CGCGCACCTC GCGCTCAAAG
       GGTCTTCTGC CTACTCGAGC CGCTGTCACA GCGCGTGGAG CGCGAGTTTC

9901   GCTACAGGGG CCTCTTCTTC TTCTTCAATC TCCTCTTCCA TAAGGGCCTC
       CGATGTCCCC GGAGAAGAAG AAGAAGTTAG AGGAGAAGGT ATTCCCGGAG

9951   CCCTTCTTCT TCTTCTGGCG GCGGTGGGGG AGGGGGGACA CGGCGGCGAC
       GGGAAGAAGA AGAAGACCGC CGCCACCCCC TCCCCCCTGT GCCGCCGCTG

10001  GACGGCGCAC CGGGAGGCGG TCGACAAAGC GCTCGATCAT CTCCCCGCGG
       CTGCCGCGTG GCCCTCCGCC AGCTGTTTCG CGAGCTAGTA GAGGGGCGCC

10051  CGACGGCGCA TGGTCTCGGT GACGGCGCGG CCGTTCTCGC GGGGGCGCAG
       GCTGCCGCGT ACCAGAGCCA CTGCCGCGCC GGCAAGAGCG CCCCCGCGTC

10101  TTGGAAGACG CCGCCCGTCA TGTCCCGGTT ATGGGTTGGC GGGGGGCTGC
       AACCTTCTGC GGCGGGCAGT ACAGGGCCAA TACCCAACCG CCCCCCGACG

10151  CATGCGGCAG GGATACGGCG CTAACGATGC ATCTCAACAA TTGTTGTGTA
       GTACGCCGTC CCTATGCCGC GATTGCTACG TAGAGTTGTT AACAACACAT
```

FIG. 26A-12

```
10201  GGTACTCCGC CGCCGAGGGA CCTGAGCGAG TCCGCATCGA CCGGATCGGA
       CCATGAGGCG GCGGCTCCCT GGACTCGCTC AGGCGTAGCT GGCCTAGCCT

10251  AAACCTCTCG AGAAAGGCGT CTAACCAGTC ACAGTCGCAA GGTAGGCTGA
       TTTGGAGAGC TCTTTCCGCA GATTGGTCAG TGTCAGCGTT CCATCCGACT

10301  GCACCGTGGC GGGCGGCAGC GGGCGGCGGT CGGGGTTGTT TCTGGCGGAG
       CGTGGCACCG CCCGCCGTCG CCCGCCGCCA GCCCCAACAA AGACCGCCTC

10351  GTGCTGCTGA TGATGTAATT AAAGTAGGCG GTCTTGAGAC GGCGGATGGT
       CACGACGACT ACTACATTAA TTTCATCCGC CAGAACTCTG CCGCCTACCA

10401  CGACAGAAGC ACCATGTCCT TGGGTCCGGC CTGCTGAATG CGCAGGCGGT
       GCTGTCTTCG TGGTACAGGA ACCCAGGCCG GACGACTTAC GCGTCCGCCA

10451  CGGCCATGCC CCAGGCTTCG TTTTGACATC GGCGCAGGTC TTTGTAGTAG
       GCCGGTACGG GGTCCGAAGC AAAACTGTAG CCGCGTCCAG AAACATCATC

10501  TCTTGCATGA GCCTTTCTAC CGGCACTTCT TCTTCTCCTT CCTCTTGTCC
       AGAACGTACT CGGAAAGATG GCCGTGAAGA AGAAGAGGAA GGAGAACAGG

10551  TGCATCTCTT GCATCTATCG CTGCGGCGGC GGCGGAGTTT GGCCGTAGGT
       ACGTAGAGAA CGTAGATAGC GACGCCGCCG CCGCCTCAAA CCGGCATCCA

10601  GGCGCCCTCT TCCTCCCATG CGTGTGACCC CGAAGCCCCT CATCGGCTGA
       CCGCGGGAGA AGGAGGGTAC GCACACTGGG GCTTCGGGGA GTAGCCGACT

10651  AGCAGGGCTA GGTCGGCGAC AACGCGCTCG GCTAATATGG CCTGCTGCAC
       TCGTCCCGAT CCAGCCGCTG TTGCGCGAGC CGATTATACC GGACGACGTG

10701  CTGCGTGAGG GTAGACTGGA AGTCATCCAT GTCCACAAAG CGGTGGTATG
       GACGCACTCC CATCTGACCT TCAGTAGGTA CAGGTGTTTC GCCACCATAC

10751  CGCCCGTGTT GATGGTGTAA GTGCAGTTGG CCATAACGGA CCAGTTAACG
       GCGGGCACAA CTACCACATT CACGTCAACC GGTATTGCCT GGTCAATTGC

10801  GTCTGGTGAC CCGGCTGCGA GAGCTCGGTG TACCTGAGAC GCGAGTAAGC
       CAGACCACTG GGCCGACGCT CTCGAGCCAC ATGGACTCTG CGCTCATTCG

10851  CCTCGAGTCA AATACGTAGT CGTTGCAAGT CCGCACCAGG TACTGGTATC
       GGAGCTCAGT TTATGCATCA GCAACGTTCA GGCGTGGTCC ATGACCATAG

10901  CCACCAAAAA GTGCGGCGGC GGCTGGCGGT AGAGGGGCCA GCGTAGGGTG
       GGTGGTTTTT CACGCCGCCG CCGACCGCCA TCTCCCCGGT CGCATCCCAC

10951  GCCGGGGCTC CGGGGGCGAG ATCTTCCAAC ATAAGGCGAT GATATCCGTA
       CGGCCCCGAG GCCCCCGCTC TAGAAGGTTG TATTCCGCTA CTATAGGCAT

11001  GATGTACCTG GACATCCAGG TGATGCCGGC GGCGGTGGTG GAGGCGCGCG
       CTACATGGAC CTGTAGGTCC ACTACGGCCG CCGCCACCAC CTCCGCGCGC
```

FIG. 26A-13

```
11051  GAAAGTCGCG GACGCGGTTC CAGATGTTGC GCAGCGGCAA AAAGTGCTCC
       CTTTCAGCGC CTGCGCCAAG GTCTACAACG CGTCGCCGTT TTTCACGAGG

11101  ATGGTCGGGA CGCTCTGGCC GGTCAGGCGC GCGCAATCGT TGACGCTCTA
       TACCAGCCCT GCGAGACCGG CCAGTCCGCG CGCGTTAGCA ACTGCGAGAT

11151  GACCGTGCAA AAGGAGAGCC TGTAAGCGGG CACTCTTCCG TGGTCTGGTG
       CTGGCACGTT TTCCTCTCGG ACATTCGCCC GTGAGAAGGC ACCAGACCAC

11201  GATAAATTCG CAAGGGTATC ATGGCGGACG ACCGGGGTTC GAGCCCCGTA
       CTATTTAAGC GTTCCCATAG TACCGCCTGC TGGCCCCAAG CTCGGGGCAT

11251  TCCGGCCGTC CGCCGTGATC CATGCGGTTA CCGCCCGCGT GTCGAACCCA
       AGGCCGGCAG GCGGCACTAG GTACGCCAAT GGCGGGCGCA CAGCTTGGGT

11301  GGTGTGCGAC GTCAGACAAC GGGGGAGTGC TCCTTTTGGC TTCCTTCCAG
       CCACACGCTG CAGTCTGTTG CCCCCTCACG AGGAAAACCG AAGGAAGGTC

11351  GCGCGGCGGC TGCTGCGCTA GCTTTTTTGG CCACTGGCCG CGCGCAGCGT
       CGCGCCGCCG ACGACGCGAT CGAAAAAACC GGTGACCGGC GCGCGTCGCA

11401  AAGCGGTTAG GCTGGAAAGC GAAAGCATTA AGTGGCTCGC TCCCTGTAGC
       TTCGCCAATC CGACCTTTCG CTTTCGTAAT TCACCGAGCG AGGGACATCG

11451  CGGAGGGTTA TTTTCCAAGG GTTGAGTCGC GGGACCCCCG GTTCGAGTCT
       GCCTCCCAAT AAAAGGTTCC CAACTCAGCG CCCTGGGGGC CAAGCTCAGA

11501  CGGACCGGCC GGACTGCGGC GAACGGGGGT TTGCCTCCCC GTCATGCAAG
       GCCTGGCCGG CCTGACGCCG CTTGCCCCCA AACGGAGGGG CAGTACGTTC

11551  ACCCCGCTTG CAAATTCCTC CGGAAACAGG GACGAGCCCC TTTTTTGCTT
       TGGGGCGAAC GTTTAAGGAG GCCTTTGTCC CTGCTCGGGG AAAAAACGAA

11601  TTCCCAGATG CATCCGGTGC TGCGGCAGAT GCGCCCCCCT CCTCAGCAGC
       AAGGGTCTAC GTAGGCCACG ACGCCGTCTA CGCGGGGGGA GGAGTCGTCG

11651  GGCAAGAGCA AGAGCAGCGG CAGACATGCA GGGCACCCTC CCCTCCTCCT
       CCGTTCTCGT TCTCGTCGCC GTCTGTACGT CCCGTGGGAG GGGAGGAGGA

11701  ACCGCGTCAG GAGGGGCGAC ATCCGCGGTT GACGCGGCAG CAGATGGTGA
       TGGCGCAGTC CTCCCCGCTG TAGGCGCCAA CTGCGCCGTC GTCTACCACT

11751  TTACGAACCC CCGCGGCGCC GGGCCCGGCA CTACCTGGAC TTGGAGGAGG
       AATGCTTGGG GGCGCCGCGG CCCGGGCCGT GATGGACCTG AACCTCCTCC

11801  GCGAGGGCCT GGCGCGGCTA GGAGCGCCCT CTCCTGAGCG GCACCCAAGG
       CGCTCCCGGA CCGCGCCGAT CCTCGCGGGA GAGGACTCGC CGTGGGTTCC

11851  GTGCAGCTGA AGCGTGATAC GCGTGAGGCG TACGTGCCGC GGCAGAACCT
       CACGTCGACT TCGCACTATG CGCACTCCGC ATGCACGGCG CCGTCTTGGA
```

FIG. 26A-14

```
11901 GTTTCGCGAC CGCGAGGGAG AGGAGCCCGA GGAGATGCGG GATCGAAAGT
      CAAAGCGCTG GCGCTCCCTC TCCTCGGGCT CCTCTACGCC CTAGCTTTCA

11951 TCCACGCAGG GCGCGAGCTG CGGCATGGCC TGAATCGCGA GCGGTTGCTG
      AGGTGCGTCC CGCGCTCGAC GCCGTACCGG ACTTAGCGCT CGCCAACGAC

12001 CGCGAGGAGG ACTTTGAGCC CGACGCGCGA ACCGGGATTA GTCCCGCGCG
      GCGCTCCTCC TGAAACTCGG GCTGCGCGCT TGGCCCTAAT CAGGGCGCGC

12051 CGCACACGTG GCGGCCGCCG ACCTGGTAAC CGCATACGAG CAGACGGTGA
      GCGTGTGCAC CGCCGGCGGC TGGACCATTG GCGTATGCTC GTCTGCCACT

12101 ACCAGGAGAT TAACTTTCAA AAAAGCTTTA ACAACCACGT GCGTACGCTT
      TGGTCCTCTA ATTGAAAGTT TTTTCGAAAT TGTTGGTGCA CGCATGCGAA

12151 GTGGCGCGCG AGGAGGTGGC TATAGGACTG ATGCATCTGT GGGACTTTGT
      CACCGCGCGC TCCTCCACCG ATATCCTGAC TACGTAGACA CCCTGAAACA

12201 AAGCGCGCTG GAGCAAAACC CAAATAGCAA GCCGCTCATG GCGCAGCTGT
      TTCGCGCGAC CTCGTTTTGG GTTTATCGTT CGGCGAGTAC CGCGTCGACA

12251 TCCTTATAGT GCAGCACAGC AGGGACAACG AGGCATTCAG GGATGCGCTG
      AGGAATATCA CGTCGTGTCG TCCCTGTTGC TCCGTAAGTC CCTACGCGAC

12301 CTAAACATAG TAGAGCCCGA GGGCCGCTGG CTGCTCGATT TGATAAACAT
      GATTTGTATC ATCTCGGGCT CCCGGCGACC GACGAGCTAA ACTATTTGTA

12351 CCTGCAGAGC ATAGTGGTGC AGGAGCGCAG CTTGAGCCTG GCTGACAAGG
      GGACGTCTCG TATCACCACG TCCTCGCGTC GAACTCGGAC CGACTGTTCC

12401 TGGCCGCCAT CAACTATTCC ATGCTTAGCC TGGGCAAGTT TTACGCCCGC
      ACCGGCGGTA GTTGATAAGG TACGAATCGG ACCCGTTCAA AATGCGGGCG

12451 AAGATATACC ATACCCCTTA CGTTCCCATA GACAAGGAGG TAAAGATCGA
      TTCTATATGG TATGGGGAAT GCAAGGGTAT CTGTTCCTCC ATTTCTAGCT

12501 GGGGTTCTAC ATGCGCATGG CGCTGAAGGT GCTTACCTTG AGCGACGACC
      CCCCAAGATG TACGCGTACC GCGACTTCCA CGAATGGAAC TCGCTGCTGG

12551 TGGGCGTTTA TCGCAACGAG CGCATCCACA AGGCCGTGAG CGTGAGCCGG
      ACCCGCAAAT AGCGTTGCTC GCGTAGGTGT TCCGGCACTC GCACTCGGCC

12601 CGGCGCGAGC TCAGCGACCG CGAGCTGATG CACAGCCTGC AAAGGGCCCT
      GCCGCGCTCG AGTCGCTGGC GCTCGACTAC GTGTCGGACG TTTCCCGGGA

12651 GGCTGGCACG GGCAGCGGCG ATAGAGAGGC CGAGTCCTAC TTTGACGCGG
      CCGACCGTGC CCGTCGCCGC TATCTCTCCG GCTCAGGATG AAACTGCGCC

12701 GCGCTGACCT GCGCTGGGCC CCAAGCCGAC GCGCCCTGGA GGCAGCTGGG
      CGCGACTGGA CGCGACCCGG GGTTCGGCTG CGCGGGACCT CCGTCGACCC
```

FIG. 26A-15

```
12751  GCCGGACCTG GGCTGGCGGT GGCACCCGCG CGCGCTGGCA ACGTCGGCGG
       CGGCCTGGAC CCGACCGCCA CCGTGGGCGC GCGCGACCGT TGCAGCCGCC

12801  CGTGGAGGAA TATGACGAGG ACGATGAGTA CGAGCCAGAG GACGGCGAGT
       GCACCTCCTT ATACTGCTCC TGCTACTCAT GCTCGGTCTC CTGCCGCTCA

12851  ACTAAGCGGT GATGTTTCTG ATCAGATGAT GCAAGACGCA ACGGACCCGG
       TGATTCGCCA CTACAAAGAC TAGTCTACTA CGTTCTGCGT TGCCTGGGCC

12901  CGGTGCGGGC GGCGCTGCAG AGCCAGCCGT CCGGCCTTAA CTCCACGGAC
       GCCACGCCCG CCGCGACGTC TCGGTCGGCA GGCCGGAATT GAGGTGCCTG

12951  GACTGGCGCC AGGTCATGGA CCGCATCATG TCGCTGACTG CGCGCAATCC
       CTGACCGCGG TCCAGTACCT GGCGTAGTAC AGCGACTGAC GCGCGTTAGG

13001  TGACGCGTTC CGGCAGCAGC CGCAGGCCAA CCGGCTCTCC GCAATTCTGG
       ACTGCGCAAG GCCGTCGTCG GCGTCCGGTT GGCCGAGAGG CGTTAAGACC

13051  AAGCGGTGGT CCCGGCGCGC GCAAACCCCA CGCACGAGAA GGTGCTGGCG
       TTCGCCACCA GGGCCGCGCG CGTTTGGGGT GCGTGCTCTT CCACGACCGC

13101  ATCGTAAACG CGCTGGCCGA AAACAGGGCC ATCCGGCCCG ACGAGGCCGG
       TAGCATTTGC GCGACCGGCT TTTGTCCCGG TAGGCCGGGC TGCTCCGGCC

13151  CCTGGTCTAC GACGCGCTGC TTCAGCGCGT GGCTCGTTAC AACAGCGGCA
       GGACCAGATG CTGCGCGACG AAGTCGCGCA CCGAGCAATG TTGTCGCCGT

13201  ACGTGCAGAC CAACCTGGAC CGGCTGGTGG GGGATGTGCG CGAGGCCGTG
       TGCACGTCTG GTTGGACCTG GCCGACCACC CCCTACACGC GCTCCGGCAC

13251  GCGCAGCGTG AGCGCGCGCA GCAGCAGGGC AACCTGGGCT CCATGGTTGC
       CGCGTCGCAC TCGCGCGCGT CGTCGTCCCG TTGGACCCGA GGTACCAACG

13301  ACTAAACGCC TTCCTGAGTA CACAGCCCGC CAACGTGCCG CGGGGACAGG
       TGATTTGCGG AAGGACTCAT GTGTCGGGCG GTTGCACGGC GCCCCTGTCC

13351  AGGACTACAC CAACTTTGTG AGCGCACTGC GGCTAATGGT GACTGAGACA
       TCCTGATGTG GTTGAAACAC TCGCGTGACG CCGATTACCA CTGACTCTGT

13401  CCGCAAAGTG AGGTGTACCA GTCTGGGCCA GACTATTTTT TCCAGACCAG
       GGCGTTTCAC TCCACATGGT CAGACCCGGT CTGATAAAAA AGGTCTGGTC

13451  TAGACAAGGC CTGCAGACCG TAAACCTGAG CCAGGCTTTC AAAAACTTGC
       ATCTGTTCCG GACGTCTGGC ATTTGGACTC GGTCCGAAAG TTTTTGAACG

13501  AGGGGCTGTG GGGGGTGCGG GCTCCCACAG GCGACCGCGC GACCGTGTCT
       TCCCCGACAC CCCCCACGCC CGAGGGTGTC CGCTGGCGCG CTGGCACAGA

13551  AGCTTGCTGA CGCCCAACTC GCGCCTGTTG CTGCTGCTAA TAGCGCCCTT
       TCGAACGACT GCGGGTTGAG CGCGGACAAC GACGACGATT ATCGCGGGAA
```

FIG. 26A-16

```
13601  CACGGACAGT GGCAGCGTGT CCCGGGACAC ATACCTAGGT CACTTGCTGA
       GTGCCTGTCA CCGTCGCACA GGGCCCTGTG TATGGATCCA GTGAACGACT

13651  CACTGTACCG CGAGGCCATA GGTCAGGCGC ATGTGGACGA GCATACTTTC
       GTGACATGGC GCTCCGGTAT CCAGTCCGCG TACACCTGCT CGTATGAAAG

13701  CAGGAGATTA CAAGTGTCAG CCGCGCGCTG GGGCAGGAGG ACACGGGCAG
       GTCCTCTAAT GTTCACAGTC GGCGCGCGAC CCCGTCCTCC TGTGCCCGTC

13751  CCTGGAGGCA ACCCTAAACT ACCTGCTGAC CAACCGGCGG CAGAAGATCC
       GGACCTCCGT TGGGATTTGA TGGACGACTG GTTGGCCGCC GTCTTCTAGG

13801  CCTCGTTGCA CAGTTTAAAC AGCGAGGAGG AGCGCATTTT GCGCTACGTG
       GGAGCAACGT GTCAAATTTG TCGCTCCTCC TCGCGTAAAA CGCGATGCAC

13851  CAGCAGAGCG TGAGCCTTAA CCTGATGCGC GACGGGGTAA CGCCCAGCGT
       GTCGTCTCGC ACTCGGAATT GGACTACGCG CTGCCCCATT GCGGGTCGCA

13901  GGCGCTGGAC ATGACCGCGC GCAACATGGA ACCGGGCATG TATGCCTCAA
       CCGCGACCTG TACTGGCGCG CGTTGTACCT TGGCCCGTAC ATACGGAGTT

13951  ACCGGCCGTT TATCAACCGC CTAATGGACT ACTTGCATCG CGCGGCCGCC
       TGGCCGGCAA ATAGTTGGCG GATTACCTGA TGAACGTAGC GCGCCGGCGG

14001  GTGAACCCCG AGTATTTCAC CAATGCCATC TTGAACCCGC ACTGGCTACC
       CACTTGGGGC TCATAAAGTG GTTACGGTAG AACTTGGGCG TGACCGATGG

14051  GCCCCCTGGT TTCTACACCG GGGGATTCGA GGTGCCCGAG GGTAACGATG
       CGGGGGACCA AAGATGTGGC CCCCTAAGCT CCACGGGCTC CCATTGCTAC

14101  GATTCCTCTG GGACGACATA GACGACAGCG TGTTTTCCCC GCAACCGCAG
       CTAAGGAGAC CCTGCTGTAT CTGCTGTCGC ACAAAAGGGG CGTTGGCGTC

14151  ACCCTGCTAG AGTTGCAACA GCGCGAGCAG GCAGAGGCGG CGCTGCGAAA
       TGGGACGATC TCAACGTTGT CGCGCTCGTC CGTCTCCGCC GCGACGCTTT

14201  GGAAAGCTTC CGCAGGCCAA GCAGCTTGTC CGATCTAGGC GCTGCGGCCC
       CCTTTCGAAG GCGTCCGGTT CGTCGAACAG GCTAGATCCG CGACGCCGGG

14251  CGCGGTCAGA TGCTAGTAGC CCATTTCCAA GCTTGATAGG GTCTCTTACC
       GCGCCAGTCT ACGATCATCG GGTAAAGGTT CGAACTATCC CAGAGAATGG

14301  AGCACTCGCA CCACCCGCCC GCGCCTGCTG GGCGAGGAGG AGTACCTAAA
       TCGTGAGCGT GGTGGGCGGG CGCGGACGAC CCGCTCCTCC TCATGGATTT

14351  CAACTCGCTG CTGCAGCCGC AGCGCGAAAA AAACCTGCCT CCGGCATTTC
       GTTGAGCGAC GACGTCGGCG TCGCGCTTTT TTTGGACGGA GGCCGTAAAG

14401  CCAACAACGG GATAGAGAGC CTAGTGGACA AGATGAGTAG ATGGAAGACG
       GGTTGTTGCC CTATCTCTCG GATCACCTGT TCTACTCATC TACCTTCTGC
```

FIG. 26A-17

```
14451  TACGCGCAGG AGCACAGGGA CGTGCCAGGC CCGCGCCCGC CCACCCGTCG
       ATGCGCGTCC TCGTGTCCCT GCACGGTCCG GGCGCGGGCG GGTGGGCAGC

14501  TCAAAGGCAC GACCGTCAGC GGGGTCTGGT GTGGGAGGAC GATGACTCGG
       AGTTTCCGTG CTGGCAGTCG CCCCAGACCA CACCCTCCTG CTACTGAGCC

14551  CAGACGACAG CAGCGTCCTG GATTTGGGAG GGAGTGGCAA CCCGTTTGCG
       GTCTGCTGTC GTCGCAGGAC CTAAACCCTC CCTCACCGTT GGGCAAACGC

14601  CACCTTCGCC CCAGGCTGGG GAGAATGTTT TAAAAAAAAA AAAAGCATGA
       GTGGAAGCGG GGTCCGACCC CTCTTACAAA ATTTTTTTTT TTTTCGTACT

14651  TGCAAAATAA AAAACTCACC AAGGCCATGG CACCGAGCGT TGGTTTTCTT
       ACGTTTTATT TTTTGAGTGG TTCCGGTACC GTGGCTCGCA ACCAAAAGAA

14701  GTATTCCCCT TAGTATGCGG CGCGCGGCGA TGTATGAGGA AGGTCCTCCT
       CATAAGGGGA ATCATACGCC GCGCGCCGCT ACATACTCCT TCCAGGAGGA

14751  CCCTCCTACG AGAGTGTGGT GAGCGCGGCG CCAGTGGCGG CGGCGCTGGG
       GGGAGGATGC TCTCACACCA CTCGCGCCGC GGTCACCGCC GCCGCGACCC

14801  TTCTCCCTTC GATGCTCCCC TGGACCCGCC GTTTGTGCCT CCGCGGTACC
       AAGAGGGAAG CTACGAGGGG ACCTGGGCGG CAAACACGGA GGCGCCATGG

14851  TGCGGCCTAC CGGGGGGAGA AACAGCATCC GTTACTCTGA GTTGGCACCC
       ACGCCGGATG GCCCCCCTCT TTGTCGTAGG CAATGAGACT CAACCGTGGG

14901  CTATTCGACA CCACCCGTGT GTACCTGGTG GACAACAAGT CAACGGATGT
       GATAAGCTGT GGTGGGCACA CATGGACCAC CTGTTGTTCA GTTGCCTACA

14951  GGCATCCCTG AACTACCAGA ACGACCACAG CAACTTTCTG ACCACGGTCA
       CCGTAGGGAC TTGATGGTCT TGCTGGTGTC GTTGAAAGAC TGGTGCCAGT

15001  TTCAAAACAA TGACTACAGC CCGGGGGAGG CAAGCACACA GACCATCAAT
       AAGTTTTGTT ACTGATGTCG GGCCCCCTCC GTTCGTGTGT CTGGTAGTTA

15051  CTTGACGACC GGTCGCACTG GGGCGGCGAC CTGAAAACCA TCCTGCATAC
       GAACTGCTGG CCAGCGTGAC CCCGCCGCTG GACTTTTGGT AGGACGTATG

15101  CAACATGCCA AATGTGAACG AGTTCATGTT TACCAATAAG TTTAAGGCGC
       GTTGTACGGT TTACACTTGC TCAAGTACAA ATGGTTATTC AAATTCCGCG

15151  GGGTGATGGT GTCGCGCTTG CCTACTAAGG ACAATCAGGT GGAGCTGAAA
       CCCACTACCA CAGCGCGAAC GGATGATTCC TGTTAGTCCA CCTCGACTTT

15201  TACGAGTGGG TGGAGTTCAC GCTGCCCGAG GGCAACTACT CCGAGACCAT
       ATGCTCACCC ACCTCAAGTG CGACGGGCTC CCGTTGATGA GGCTCTGGTA

15251  GACCATAGAC CTTATGAACA ACGCGATCGT GGAGCACTAC TTGAAAGTGG
       CTGGTATCTG GAATACTTGT TGCGCTAGCA CCTCGTGATG AACTTTCACC
```

FIG. 26A-18

15301 GCAGACAGAA CGGGGTTCTG GAAAGCGACA TCGGGGTAAA GTTTGACACC
CGTCTGTCTT GCCCCAAGAC CTTTCGCTGT AGCCCCATTT CAAACTGTGG

15351 CGCAACTTCA GACTGGGGTT TGACCCCGTC ACTGGTCTTG TCATGCCTGG
GCGTTGAAGT CTGACCCCAA ACTGGGGCAG TGACCAGAAC AGTACGGACC

15401 GGTATATACA AACGAAGCCT TCCATCCAGA CATCATTTTG CTGCCAGGAT
CCATATATGT TTGCTTCGGA AGGTAGGTCT GTAGTAAAAC GACGGTCCTA

15451 GCGGGGTGGA CTTCACCCAC AGCCGCCTGA GCAACTTGTT GGGCATCCGC
CGCCCCACCT GAAGTGGGTG TCGGCGGACT CGTTGAACAA CCCGTAGGCG

15501 AAGCGGCAAC CCTTCCAGGA GGGCTTTAGG ATCACCTACG ATGATCTGGA
TTCGCCGTTG GGAAGGTCCT CCCGAAATCC TAGTGGATGC TACTAGACCT

15551 GGGTGGTAAC ATTCCCGCAC TGTTGGATGT GGACGCCTAC CAGGCGAGCT
CCCACCATTG TAAGGGCGTG ACAACCTACA CCTGCGGATG GTCCGCTCGA

15601 TGAAAGATGA CACCGAACAG GGCGGGGGTG GCGCAGGCGG CAGCAACAGC
ACTTTCTACT GTGGCTTGTC CCGCCCCCAC CGCGTCCGCC GTCGTTGTCG

15651 AGTGGCAGCG GCGCGGAAGA GAACTCCAAC GCGGCAGCCG CGGCAATGCA
TCACCGTCGC CGCGCCTTCT CTTGAGGTTG CGCCGTCGGC GCCGTTACGT

15701 GCCGGTGGAG GACATGAACG ATCATGCCAT TCGCGGCGAC ACCTTTGCCA
CGGCCACCTC CTGTACTTGC TAGTACGGTA AGCGCCGCTG TGGAAACGGT

15751 CACGGGCTGA GGAGAAGCGC GCTGAGGCCG AAGCAGCGGC CGAAGCTGCC
GTGCCCGACT CCTCTTCGCG CGACTCCGGC TTCGTCGCCG GCTTCGACGG

15801 GCCCCCGCTG CGCAACCCGA GGTCGAGAAG CCTCAGAAGA AACCGGTGAT
CGGGGGCGAC GCGTTGGGCT CCAGCTCTTC GGAGTCTTCT TTGGCCACTA

15851 CAAACCCCTG ACAGAGGACA GCAAGAAACG CAGTTACAAC CTAATAAGCA
GTTTGGGGAC TGTCTCCTGT CGTTCTTTGC GTCAATGTTG GATTATTCGT

15901 ATGACAGCAC CTTCACCCAG TACCGCAGCT GGTACCTTGC ATACAACTAC
TACTGTCGTG GAAGTGGGTC ATGGCGTCGA CCATGGAACG TATGTTGATG

15951 GGCGACCCTC AGACCGGAAT CCGCTCATGG ACCCTGCTTT GCACTCCTGA
CCGCTGGGAG TCTGGCCTTA GGCGAGTACC TGGGACGAAA CGTGAGGACT

16001 CGTAACCTGC GGCTCGGAGC AGGTCTACTG GTCGTTGCCA GACATGATGC
GCATTGGACG CCGAGCCTCG TCCAGATGAC CAGCAACGGT CTGTACTACG

16051 AAGACCCCGT GACCTTCCGC TCCACGCGCC AGATCAGCAA CTTTCCGGTG
TTCTGGGGCA CTGGAAGGCG AGGTGCGCGG TCTAGTCGTT GAAAGGCCAC

16101 GTGGGCGCCG AGCTGTTGCC CGTGCACTCC AAGAGCTTCT ACAACGACCA
CACCCGCGGC TCGACAACGG GCACGTGAGG TTCTCGAAGA TGTTGCTGGT

FIG. 26A-19

16151 GGCCGTCTAC TCCCAACTCA TCCGCCAGTT TACCTCTCTG ACCCACGTGT
CCGGCAGATG AGGGTTGAGT AGGCGGTCAA ATGGAGAGAC TGGGTGCACA

16201 TCAATCGCTT TCCCGAGAAC CAGATTTTGG CGCGCCCGCC AGCCCCCACC
AGTTAGCGAA AGGGCTCTTG GTCTAAAACC GCGCGGGCGG TCGGGGGTGG

16251 ATCACCACCG TCAGTGAAAA CGTTCCTGCT CTCACAGATC ACGGGACGCT
TAGTGGTGGC AGTCACTTTT GCAAGGACGA GAGTGTCTAG TGCCCTGCGA

16301 ACCGCTGCGC AACAGCATCG GAGGAGTCCA GCGAGTGACC ATTACTGACG
TGGCGACGCG TTGTCGTAGC CTCCTCAGGT CGCTCACTGG TAATGACTGC

16351 CCAGACGCCG CACCTGCCCC TACGTTTACA AGGCCCTGGG CATAGTCTCG
GGTCTGCGGC GTGGACGGGG ATGCAAATGT TCCGGGACCC GTATCAGAGC

16401 CCGCGCGTCC TATCGAGCCG CACTTTTTGA GCAAGCATGT CCATCCTTAT
GGCGCGCAGG ATAGCTCGGC GTGAAAAACT CGTTCGTACA GGTAGGAATA

16451 ATCGCCCAGC AATAACACAG GCTGGGGCCT GCGCTTCCCA AGCAAGATGT
TAGCGGGTCG TTATTGTGTC CGACCCCGGA CGCGAAGGGT TCGTTCTACA

16501 TTGGCGGGGC CAAGAAGCGC TCCGACCAAC ACCCAGTGCG CGTGCGCGGG
AACCGCCCCG GTTCTTCGCG AGGCTGGTTG TGGGTCACGC GCACGCGCCC

16551 CACTACCGCG CGCCCTGGGG CGCGCACAAA CGCGGCCGCA CTGGGCGCAC
GTGATGGCGC GCGGGACCCC GCGCGTGTTT GCGCCGGCGT GACCCGCGTG

16601 CACCGTCGAT GACGCCATCG ACGCGGTGGT GGAGGAGGCG CGCAACTACA
GTGGCAGCTA CTGCGGTAGC TGCGCCACCA CCTCCTCCGC GCGTTGATGT

16651 CGCCCACGCC GCCACCAGTG TCCACAGTGG ACGCGGCCAT TCAGACCGTG
GCGGGTGCGG CGGTGGTCAC AGGTGTCACC TGCGCCGGTA AGTCTGGCAC

16701 GTGCGCGGAG CCCGGCGCTA TGCTAAAATG AAGAGACGGC GGAGGCGCGT
CACGCGCCTC GGGCCGCGAT ACGATTTTAC TTCTCTGCCG CCTCCGCGCA

16751 AGCACGTCGC CACCGCCGCC GACCCGGCAC TGCCGCCCAA CGCGCGGCGG
TCGTGCAGCG GTGGCGGCGG CTGGGCCGTG ACGGCGGGTT GCGCGCCGCC

16801 CGGCCCTGCT TAACCGCGCA CGTCGCACCG GCCGACGGGC GGCCATGCGG
GCCGGGACGA ATTGGCGCGT GCAGCGTGGC CGGCTGCCCG CCGGTACGCC

16851 GCCGCTCGAA GGCTGGCCGC GGGTATTGTC ACTGTGCCCC CCAGGTCCAG
CGGCGAGCTT CCGACCGGCG CCCATAACAG TGACACGGGG GGTCCAGGTC

16901 GCGACGAGCG GCCGCCGCAG CAGCCGCGGC CATTAGTGCT ATGACTCAGG
CGCTGCTCGC CGGCGGCGTC GTCGGCGCCG GTAATCACGA TACTGAGTCC

16951 GTCGCAGGGG CAACGTGTAT TGGGTGCGCG ACTCGGTTAG CGGCCTGCGC
CAGCGTCCCC GTTGCACATA ACCCACGCGC TGAGCCAATC GCCGGACGCG

FIG. 26A-20

```
17001  GTGCCCGTGC GCACCCGCCC CCCGCGCAAC TAGATTGCAA GAAAAAACTA
       CACGGGCACG CGTGGGCGGG GGGCGCGTTG ATCTAACGTT CTTTTTTGAT

17051  CTTAGACTCG TACTGTTGTA TGTATCCAGC GGCGGCGGCG CGCAACGAAG
       GAATCTGAGC ATGACAACAT ACATAGGTCG CCGCCGCCGC GCGTTGCTTC

17101  CTATGTCCAA GCGCAAAATC AAAGAAGAGA TGCTCCAGGT CATCGCGCCG
       GATACAGGTT CGCGTTTTAG TTTCTTCTCT ACGAGGTCCA GTAGCGCGGC

17151  GAGATCTATG GCCCCCCGAA GAAGGAAGAG CAGGATTACA AGCCCCGAAA
       CTCTAGATAC CGGGGGGCTT CTTCCTTCTC GTCCTAATGT TCGGGGCTTT

17201  GCTAAAGCGG GTCAAAAAGA AAAAGAAAGA TGATGATGAT GAACTTGACG
       CGATTTCGCC CAGTTTTTCT TTTTCTTTCT ACTACTACTA CTTGAACTGC

17251  ACGAGGTGGA ACTGCTGCAC GCTACCGCGC CCAGGCGACG GGTACAGTGG
       TGCTCCACCT TGACGACGTG CGATGGCGCG GGTCCGCTGC CCATGTCACC

17301  AAAGGTCGAC GCGTAAAACG TGTTTTGCGA CCCGGCACCA CCGTAGTCTT
       TTTCCAGCTG CGCATTTTGC ACAAAACGCT GGGCCGTGGT GGCATCAGAA

17351  TACGCCCGGT GAGCGCTCCA CCCGCACCTA CAAGCGCGTG TATGATGAGG
       ATGCGGGCCA CTCGCGAGGT GGGCGTGGAT GTTCGCGCAC ATACTACTCC

17401  TGTACGGCGA CGAGGACCTG CTTGAGCAGG CCAACGAGCG CCTCGGGGAG
       ACATGCCGCT GCTCCTGGAC GAACTCGTCC GGTTGCTCGC GGAGCCCCTC

17451  TTTGCCTACG GAAAGCGGCA TAAGGACATG CTGGCGTTGC CGCTGGACGA
       AAACGGATGC CTTTCGCCGT ATTCCTGTAC GACCGCAACG GCGACCTGCT

17501  GGGCAACCCA ACACCTAGCC TAAAGCCCGT AACACTGCAG CAGGTGCTGC
       CCCGTTGGGT TGTGGATCGG ATTTCGGGCA TTGTGACGTC GTCCACGACG

17551  CCGCGCTTGC ACCGTCCGAA GAAAAGCGCG GCCTAAAGCG CGAGTCTGGT
       GGCGCGAACG TGGCAGGCTT CTTTTCGCGC CGGATTTCGC GCTCAGACCA

17601  GACTTGGCAC CCACCGTGCA GCTGATGGTA CCCAAGCGCC AGCGACTGGA
       CTGAACCGTG GGTGGCACGT CGACTACCAT GGGTTCGCGG TCGCTGACCT

17651  AGATGTCTTG GAAAAAATGA CCGTGGAACC TGGGCTGGAG CCCGAGGTCC
       TCTACAGAAC CTTTTTTACT GGCACCTTGG ACCCGACCTC GGGCTCCAGG

17701  GCGTGCGGCC AATCAAGCAG GTGGCGCCGG GACTGGGCGT GCAGACCGTG
       CGCACGCCGG TTAGTTCGTC CACCGCGGCC CTGACCCGCA CGTCTGGCAC

17751  GACGTTCAGA TACCCACTAC CAGTAGCACC AGTATTGCCA CCGCCACAGA
       CTGCAAGTCT ATGGGTGATG GTCATCGTGG TCATAACGGT GGCGGTGTCT

17801  GGGCATGGAG ACACAAACGT CCCCGGTTGC CTCAGCGGTG GCGGATGCCG
       CCCGTACCTC TGTGTTTGCA GGGGCCAACG GAGTCGCCAC CGCCTACGGC
```

FIG. 26A-21

```
17851  CGGTGCAGGC GGTCGCTGCG GCCGCGTCCA AGACCTCTAC GGAGGTGCAA
       GCCACGTCCG CCAGCGACGC CGGCGCAGGT TCTGGAGATG CCTCCACGTT

17901  ACGGACCCGT GGATGTTTCG CGTTTCAGCC CCCCGGCGCC CGCGCCGTTC
       TGCCTGGGCA CCTACAAAGC GCAAAGTCGG GGGGCCGCGG GCGCGGCAAG

17951  GAGGAAGTAC GGCGCCGCCA GCGCGCTACT GCCCGAATAT GCCCTACATC
       CTCCTTCATG CCGCGGCGGT CGCGCGATGA CGGGCTTATA CGGGATGTAG

18001  CTTCCATTGC GCCTACCCCC GGCTATCGTG GCTACACCTA CCGCCCCAGA
       GAAGGTAACG CGGATGGGGG CCGATAGCAC CGATGTGGAT GGCGGGGTCT

18051  AGACGAGCAA CTACCCGACG CCGAACCACC ACTGGAACCC GCCGCCGCCG
       TCTGCTCGTT GATGGGCTGC GGCTTGGTGG TGACCTTGGG CGGCGGCGGC

18101  TCGCCGTCGC CAGCCCGTGC TGGCCCCGAT TTCCGTGCGC AGGGTGGCTC
       AGCGGCAGCG GTCGGGCACG ACCGGGGCTA AAGGCACGCG TCCCACCGAG

18151  GCGAAGGAGG CAGGACCCTG GTGCTGCCAA CAGCGCGCTA CCACCCCAGC
       CGCTTCCTCC GTCCTGGGAC CACGACGGTT GTCGCGCGAT GGTGGGGTCG

18201  ATCGTTTAAA AGCCGGTCTT TGTGGTTCTT GCAGATATGG CCCTCACCTG
       TAGCAAATTT TCGGCCAGAA ACACCAAGAA CGTCTATACC GGGAGTGGAC

18251  CCGCCTCCGT TTCCCGGTGC CGGGATTCCG AGGAAGAATG CACCGTAGGA
       GGCGGAGGCA AAGGGCCACG GCCCTAAGGC TCCTTCTTAC GTGGCATCCT

18301  GGGGCATGGC CGGCCACGGC CTGACGGGCG GCATGCGTCG TGCGCACCAC
       CCCCGTACCG GCCGGTGCCG GACTGCCCGC CGTACGCAGC ACGCGTGGTG

18351  CGGCGGCGGC GCGCGTCGCA CCGTCGCATG CGCGGCGGTA TCCTGCCCCT
       GCCGCCGCCG CGCGCAGCGT GGCAGCGTAC GCGCCGCCAT AGGACGGGGA

18401  CCTTATTCCA CTGATCGCCG CGGCGATTGG CGCCGTGCCC GGAATTGCAT
       GGAATAAGGT GACTAGCGGC GCCGCTAACC GCGGCACGGG CCTTAACGTA

18451  CCGTGGCCTT GCAGGCGCAG AGACACTGAT TAAAAACAAG TTGCATGTGG
       GGCACCGGAA CGTCCGCGTC TCTGTGACTA ATTTTTGTTC AACGTACACC

18501  AAAAATCAAA ATAAAAAGTC TGGACTCTCA CGCTCGCTTG GTCCTGTAAC
       TTTTTAGTTT TATTTTTCAG ACCTGAGAGT GCGAGCGAAC CAGGACATTG

18551  TATTTTGTAG AATGGAAGAC ATCAACTTTG CGTCTCTGGC CCCGCGACAC
       ATAAAACATC TTACCTTCTG TAGTTGAAAC GCAGAGACCG GGGCGCTGTG

18601  GGCTCGCGCC CGTTCATGGG AAACTGGCAA GATATCGGCA CCAGCAATAT
       CCGAGCGCGG GCAAGTACCC TTTGACCGTT CTATAGCCGT GGTCGTTATA

18651  GAGCGGTGGC GCCTTCAGCT GGGGCTCGCT GTGGAGCGGC ATTAAAAATT
       CTCGCCACCG CGGAAGTCGA CCCCGAGCGA CACCTCGCCG TAATTTTTAA
```

FIG. 26A-22

```
18701  TCGGTTCCAC CGTTAAGAAC TATGGCAGCA AGGCCTGGAA CAGCAGCACA
       AGCCAAGGTG GCAATTCTTG ATACCGTCGT TCCGGACCTT GTCGTCGTGT

18751  GGCCAGATGC TGAGGGATAA GTTGAAAGAG CAAAATTTCC AACAAAAGGT
       CCGGTCTACG ACTCCCTATT CAACTTTCTC GTTTTAAAGG TTGTTTTCCA

18801  GGTAGATGGC CTGGCCTCTG GCATTAGCGG GGTGGTGGAC CTGGCCAACC
       CCATCTACCG GACCGGAGAC CGTAATCGCC CCACCACCTG GACCGGTTGG

18851  AGGCAGTGCA AAATAAGATT AACAGTAAGC TTGATCCCCG CCCTCCCGTA
       TCCGTCACGT TTTATTCTAA TTGTCATTCG AACTAGGGGC GGGAGGGCAT

18901  GAGGAGCCTC CACCGGCCGT GGAGACAGTG TCTCCAGAGG GGCGTGGCGA
       CTCCTCGGAG GTGGCCGGCA CCTCTGTCAC AGAGGTCTCC CCGCACCGCT

18951  AAAGCGTCCG CGCCCCGACA GGGAAGAAAC TCTGGTGACG CAAATAGACG
       TTTCGCAGGC GCGGGGCTGT CCCTTCTTTG AGACCACTGC GTTTATCTGC

19001  AGCCTCCCTC GTACGAGGAG GCACTAAAGC AAGGCCTGCC CACCACCCGT
       TCGGAGGGAG CATGCTCCTC CGTGATTTCG TTCCGGACGG GTGGTGGGCA

19051  CCCATCGCGC CCATGGCTAC CGGAGTGCTG GGCCAGCACA CACCCGTAAC
       GGGTAGCGCG GGTACCGATG GCCTCACGAC CCGGTCGTGT GTGGGCATTG

19101  GCTGGACCTG CCTCCCCCCG CCGACACCCA GCAGAAACCT GTGCTGCCAG
       CGACCTGGAC GGAGGGGGGC GGCTGTGGGT CGTCTTTGGA CACGACGGTC

19151  GCCCGACCGC CGTTGTTGTA ACCCGTCCTA GCCGCGCGTC CCTGCGCCGC
       CGGGCTGGCG GCAACAACAT TGGGCAGGAT CGGCGCGCAG GGACGCGGCG

19201  GCCGCCAGCG GTCCGCGATC GTTGCGGCCC GTAGCCAGTG GCAACTGGCA
       CGGCGGTCGC CAGGCGCTAG CAACGCCGGG CATCGGTCAC CGTTGACCGT

19251  AAGCACACTG AACAGCATCG TGGGTCTGGG GGTGCAATCC CTGAAGCGCC
       TTCGTGTGAC TTGTCGTAGC ACCCAGACCC CCACGTTAGG GACTTCGCGG

19301  GACGATGCTT CTGATAGCTA ACGTGTCGTA TGTGTGTCAT GTATGCGTCC
       CTGCTACGAA GACTATCGAT TGCACAGCAT ACACACAGTA CATACGCAGG

19351  ATGTCGCCGC CAGAGGAGCT GCTGAGCCGC CGCGCGCCCG CTTTCCAAGA
       TACAGCGGCG GTCTCCTCGA CGACTCGGCG GCGCGCGGGC GAAAGGTTCT

19401  TGGCTACCCC TTCGATGATG CCGCAGTGGT CTTACATGCA CATCTCGGGC
       ACCGATGGGG AAGCTACTAC GGCGTCACCA GAATGTACGT GTAGAGCCCG

19451  CAGGACGCCT CGGAGTACCT GAGCCCCGGG CTGGTGCAGT TTGCCCGCGC
       GTCCTGCGGA GCCTCATGGA CTCGGGGCCC GACCACGTCA AACGGGCGCG

19501  CACCGAGACG TACTTCAGCC TGAATAACAA GTTTAGAAAC CCCACGGTGG
       GTGGCTCTGC ATGAAGTCGG ACTTATTGTT CAAATCTTTG GGGTGCCACC
```

FIG. 26A-23

```
19551  CGCCTACGCA CGACGTGACC ACAGACCGGT CCCAGCGTTT GACGCTGCGG
       GCGGATGCGT GCTGCACTGG TGTCTGGCCA GGGTCGCAAA CTGCGACGCC

19601  TTCATCCCTG TGGACCGTGA GGATACTGCG TACTCGTACA AGGCGCGGTT
       AAGTAGGGAC ACCTGGCACT CCTATGACGC ATGAGCATGT TCCGCGCCAA

19651  CACCCTAGCT GTGGGTGATA ACCGTGTGCT GGACATGGCT TCCACGTACT
       GTGGGATCGA CACCCACTAT TGGCACACGA CCTGTACCGA AGGTGCATGA

19701  TTGACATCCG CGGCGTGCTG GACAGGGGCC CTACTTTTAA GCCCTACTCT
       AACTGTAGGC GCCGCACGAC CTGTCCCCGG GATGAAAATT CGGGATGAGA

19751  GGCACTGCCT ACAACGCCCT GGCTCCCAAG GGTGCCCCAA ATCCTTGCGA
       CCGTGACGGA TGTTGCGGGA CCGAGGGTTC CCACGGGGTT TAGGAACGCT

19801  ATGGGATGAA GCTGCTACTG CTCTTGAAAT AAACCTAGAA GAAGAGGACG
       TACCCTACTT CGACGATGAC GAGAACTTTA TTTGGATCTT CTTCTCCTGC

19851  ATGACAACGA AGACGAAGTA GACGAGCAAG CTGAGCAGCA AAAAACTCAC
       TACTGTTGCT TCTGCTTCAT CTGCTCGTTC GACTCGTCGT TTTTTGAGTG

19901  GTATTTGGGC AGGCGCCTTA TTCTGGTATA AATATTACAA AGGAGGGTAT
       CATAAACCCG TCCGCGGAAT AAGACCATAT TTATAATGTT TCCTCCCATA

19951  TCAAATAGGT GTCGAAGGTC AAACACCTAA ATATGCCGAT AAAACATTTC
       AGTTTATCCA CAGCTTCCAG TTTGTGGATT TATACGGCTA TTTTGTAAAG

20001  AACCTGAACC TCAAATAGGA GAATCTCAGT GGTACGAAAC AGAAATTAAT
       TTGGACTTGG AGTTTATCCT CTTAGAGTCA CCATGCTTTG TCTTTAATTA

20051  CATGCAGCTG GGAGAGTCCT AAAAAAGACT ACCCCAATGA AACCATGTTA
       GTACGTCGAC CCTCTCAGGA TTTTTTCTGA TGGGGTTACT TTGGTACAAT

20101  CGGTTCATAT GCAAAACCCA CAAATGAAAA TGGAGGGCAA GGCATTCTTG
       GCCAAGTATA CGTTTTGGGT GTTTACTTTT ACCTCCCGTT CCGTAAGAAC

20151  TAAAGCAACA AAATGGAAAG CTAGAAAGTC AAGTGGAAAT GCAATTTTTC
       ATTTCGTTGT TTTACCTTTC GATCTTTCAG TTCACCTTTA CGTTAAAAAG

20201  TCAACTACTG AGGCAGCCGC AGGCAATGGT GATAACTTGA CTCCTAAAGT
       AGTTGATGAC TCCGTCGGCG TCCGTTACCA CTATTGAACT GAGGATTTCA

20251  GGTATTGTAC AGTGAAGATG TAGATATAGA AACCCCAGAC ACTCATATTT
       CCATAACATG TCACTTCTAC ATCTATATCT TTGGGGTCTG TGAGTATAAA

20301  CTTACATGCC CACTATTAAG GAAGGTAACT CACGAGAACT AATGGGCCAA
       GAATGTACGG GTGATAATTC CTTCCATTGA GTGCTCTTGA TTACCCGGTT

20351  CAATCTATGC CCAACAGGCC TAATTACATT GCTTTTAGGG ACAATTTTAT
       GTTAGATACG GGTTGTCCGG ATTAATGTAA CGAAAATCCC TGTTAAAATA
```

FIG. 26A-24

```
20401  TGGTCTAATG TATTACAACA GCACGGGTAA TATGGGTGTT CTGGCGGGCC
       ACCAGATTAC ATAATGTTGT CGTGCCCATT ATACCCACAA GACCGCCCGG

20451  AAGCATCGCA GTTGAATGCT GTTGTAGATT TGCAAGACAG AAACACAGAG
       TTCGTAGCGT CAACTTACGA CAACATCTAA ACGTTCTGTC TTTGTGTCTC

20501  CTTTCATACC AGCTTTTGCT TGATTCCATT GGTGATAGAA CCAGGTACTT
       GAAAGTATGG TCGAAAACGA ACTAAGGTAA CCACTATCTT GGTCCATGAA

20551  TTCTATGTGG AATCAGGCTG TTGACAGCTA TGATCCAGAT GTTAGAATTA
       AAGATACACC TTAGTCCGAC AACTGTCGAT ACTAGGTCTA CAATCTTAAT

20601  TTGAAAATCA TGGAACTGAA GATGAACTTC CAAATTACTG CTTTCCACTG
       AACTTTTAGT ACCTTGACTT CTACTTGAAG GTTTAATGAC GAAAGGTGAC

20651  GGAGGTGTGA TTAATACAGA GACTCTTACC AAGGTAAAAC CTAAAACAGG
       CCTCCACACT AATTATGTCT CTGAGAATGG TTCCATTTTG GATTTTGTCC

20701  TCAGGAAAAT GGATGGGAAA AAGATGCTAC AGAATTTTCA GATAAAAATG
       AGTCCTTTTA CCTACCCTTT TTCTACGATG TCTTAAAAGT CTATTTTTAC

20751  AAATAAGAGT TGGAAATAAT TTTGCCATGG AAATCAATCT AAATGCCAAC
       TTTATTCTCA ACCTTTATTA AAACGGTACC TTTAGTTAGA TTTACGGTTG

20801  CTGTGGAGAA ATTTCCTGTA CTCCAACATA GCGCTGTATT TGCCCGACAA
       GACACCTCTT TAAAGGACAT GAGGTTGTAT CGCGACATAA ACGGGCTGTT

20851  GCTAAAGTAC AGTCCTTCCA ACGTAAAAAT TTCTGATAAC CCAAACACCT
       CGATTTCATG TCAGGAAGGT TGCATTTTTA AAGACTATTG GGTTTGTGGA

20901  ACGACTACAT GAACAAGCGA GTGGTGGCTC CCGGGCTAGT GGACTGCTAC
       TGCTGATGTA CTTGTTCGCT CACCACCGAG GGCCCGATCA CCTGACGATG

20951  ATTAACCTTG GAGCACGCTG GTCCCTTGAC TATATGGACA ACGTCAACCC
       TAATTGGAAC CTCGTGCGAC CAGGGAACTG ATATACCTGT TGCAGTTGGG

21001  ATTTAACCAC CACCGCAATG CTGGCCTGCG CTACCGCTCA ATGTTGCTGG
       TAAATTGGTG GTGGCGTTAC GACCGGACGC GATGGCGAGT TACAACGACC

21051  GCAATGGTCG CTATGTGCCC TTCCACATCC AGGTGCCTCA GAAGTTCTTT
       CGTTACCAGC GATACACGGG AAGGTGTAGG TCCACGGAGT CTTCAAGAAA

21101  GCCATTAAAA ACCTCCTTCT CCTGCCGGGC TCATACACCT ACGAGTGGAA
       CGGTAATTTT TGGAGGAAGA GGACGGCCCG AGTATGTGGA TGCTCACCTT

21151  CTTCAGGAAG GATGTTAACA TGGTTCTGCA GAGCTCCCTA GGAAATGACC
       GAAGTCCTTC CTACAATTGT ACCAAGACGT CTCGAGGGAT CCTTTACTGG

21201  TAAGGGTTGA CGGAGCCAGC ATTAAGTTTG ATAGCATTTG CCTTTACGCC
       ATTCCCAACT GCCTCGGTCG TAATTCAAAC TATCGTAAAC GGAAATGCGG
```

FIG. 26A-25

```
21251  ACCTTCTTCC CCATGGCCCA CAACACCGCC TCCACGCTTG AGGCCATGCT
       TGGAAGAAGG GGTACCGGGT GTTGTGGCGG AGGTGCGAAC TCCGGTACGA

21301  TAGAAACGAC ACCAACGACC AGTCCTTTAA CGACTATCTC TCCGCCGCCA
       ATCTTTGCTG TGGTTGCTGG TCAGGAAATT GCTGATAGAG AGGCGGCGGT

21351  ACATGCTCTA CCCTATACCC GCCAACGCTA CCAACGTGCC CATATCCATC
       TGTACGAGAT GGGATATGGG CGGTTGCGAT GGTTGCACGG GTATAGGTAG

21401  CCCTCCCGCA ACTGGGCGGC TTTCCGCGGC TGGGCCTTCA CGCGCCTTAA
       GGGAGGGCGT TGACCCGCCG AAAGGCGCCG ACCCGGAAGT GCGCGGAATT

21451  GACTAAGGAA ACCCCATCAC TGGGCTCGGG CTACGACCCT TATTACACCT
       CTGATTCCTT TGGGGTAGTG ACCCGAGCCC GATGCTGGGA ATAATGTGGA

21501  ACTCTGGCTC TATACCCTAC CTAGATGGAA CCTTTTACCT CAACCACACC
       TGAGACCGAG ATATGGGATG GATCTACCTT GGAAAATGGA GTTGGTGTGG

21551  TTTAAGAAGG TGGCCATTAC CTTTGACTCT TCTGTCAGCT GGCCTGGCAA
       AAATTCTTCC ACCGGTAATG GAAACTGAGA AGACAGTCGA CCGGACCGTT

21601  TGACCGCCTG CTTACCCCCA ACGAGTTTGA AATTAAGCGC TCAGTTGACG
       ACTGGCGGAC GAATGGGGGT TGCTCAAACT TTAATTCGCG AGTCAACTGC

21651  GGGAGGGTTA CAACGTTGCC CAGTGTAACA TGACCAAAGA CTGGTTCCTG
       CCCTCCCAAT GTTGCAACGG GTCACATTGT ACTGGTTTCT GACCAAGGAC

21701  GTACAAATGC TAGCTAACTA TAACATTGGC TACCAGGGCT TCTATATCCC
       CATGTTTACG ATCGATTGAT ATTGTAACCG ATGGTCCCGA AGATATAGGG

21751  AGAGAGCTAC AAGGACCGCA TGTACTCCTT CTTTAGAAAC TTCCAGCCCA
       TCTCTCGATG TTCCTGGCGT ACATGAGGAA GAAATCTTTG AAGGTCGGGT

21801  TGAGCCGTCA GGTGGTGGAT GATACTAAAT ACAAGGACTA CCAACAGGTG
       ACTCGGCAGT CCACCACCTA CTATGATTTA TGTTCCTGAT GGTTGTCCAC

21851  GGCATCCTAC ACCAACACAA CAACTCTGGA TTTGTTGGCT ACCTTGCCCC
       CCGTAGGATG TGGTTGTGTT GTTGAGACCT AAACAACCGA TGGAACGGGG

21901  CACCATGCGC GAAGGACAGG CCTACCCTGC TAACTTCCCC TATCCGCTTA
       GTGGTACGCG CTTCCTGTCC GGATGGGACG ATTGAAGGGG ATAGGCGAAT

21951  TAGGCAAGAC CGCAGTTGAC AGCATTACCC AGAAAAAGTT TCTTTGCGAT
       ATCCGTTCTG GCGTCAACTG TCGTAATGGG TCTTTTTCAA AGAAACGCTA

22001  CGCACCCTTT GGCGCATCCC ATTCTCCAGT AACTTTATGT CCATGGGCGC
       GCGTGGGAAA CCGCGTAGGG TAAGAGGTCA TTGAAATACA GGTACCCGCG

22051  ACTCACAGAC CTGGGCCAAA ACCTTCTCTA CGCCAACTCC GCCCACGCGC
       TGAGTGTCTG GACCCGGTTT TGGAAGAGAT GCGGTTGAGG CGGGTGCGCG
```

FIG. 26A-26

22101 TAGACATGAC TTTTGAGGTG GATCCCATGG ACGAGCCCAC CCTTCTTTAT
ATCTGTACTG AAAACTCCAC CTAGGGTACC TGCTCGGGTG GGAAGAAATA

22151 GTTTTGTTTG AAGTCTTTGA CGTGGTCCGT GTGCACCAGC CGCACCGCGG
CAAAACAAAC TTCAGAAACT GCACCAGGCA CACGTGGTCG GCGTGGCGCC

22201 CGTCATCGAA ACCGTGTACC TGCGCACGCC CTTCTCGGCC GGCAACGCCA
GCAGTAGCTT TGGCACATGG ACGCGTGCGG GAAGAGCCGG CCGTTGCGGT

22251 CAACATAAAG AAGCAAGCAA CATCAACAAC AGCTGCCGCC ATGGGCTCCA
GTTGTATTTC TTCGTTCGTT GTAGTTGTTG TCGACGGCGG TACCCGAGGT

22301 GTGAGCAGGA ACTGAAAGCC ATTGTCAAAG ATCTTGGTTG TGGGCCATAT
CACTCGTCCT TGACTTTCGG TAACAGTTTC TAGAACCAAC ACCCGGTATA

22351 TTTTTGGGCA CCTATGACAA GCGCTTTCCA GGCTTTGTTT CTCCACACAA
AAAAACCCGT GGATACTGTT CGCGAAAGGT CCGAAACAAA GAGGTGTGTT

22401 GCTCGCCTGC GCCATAGTCA ATACGGCCGG TCGCGAGACT GGGGGCGTAC
CGAGCGGACG CGGTATCAGT TATGCCGGCC AGCGCTCTGA CCCCCGCATG

22451 ACTGGATGGC CTTTGCCTGG AACCCGCACT CAAAAACATG CTACCTCTTT
TGACCTACCG GAAACGGACC TTGGGCGTGA GTTTTTGTAC GATGGAGAAA

22501 GAGCCCTTTG GCTTTTCTGA CCAGCGACTC AAGCAGGTTT ACCAGTTTGA
CTCGGGAAAC CGAAAAGACT GGTCGCTGAG TTCGTCCAAA TGGTCAAACT

22551 GTACGAGTCA CTCCTGCGCC GTAGCGCCAT TGCTTCTTCC CCCGACCGCT
CATGCTCAGT GAGGACGCGG CATCGCGGTA ACGAAGAAGG GGGCTGGCGA

22601 GTATAACGCT GGAAAAGTCC ACCCAAAGCG TACAGGGGCC CAACTCGGCC
CATATTGCGA CCTTTTCAGG TGGGTTTCGC ATGTCCCCGG GTTGAGCCGG

22651 GCCTGTGGAC TATTCTGCTG CATGTTTCTC CACGCCTTTG CCAACTGGCC
CGGACACCTG ATAAGACGAC GTACAAAGAG GTGCGGAAAC GGTTGACCGG

22701 CCAAACTCCC ATGGATCACA ACCCCACCAT GAACCTTATT ACCGGGGTAC
GGTTTGAGGG TACCTAGTGT TGGGGTGGTA CTTGGAATAA TGGCCCCATG

22751 CCAACTCCAT GCTCAACAGT CCCCAGGTAC AGCCCACCCT GCGTCGCAAC
GGTTGAGGTA CGAGTTGTCA GGGGTCCATG TCGGGTGGGA CGCAGCGTTG

22801 CAGGAACAGC TCTACAGCTT CCTGGAGCGC CACTCGCCCT ACTTCCGCAG
GTCCTTGTCG AGATGTCGAA GGACCTCGCG GTGAGCGGGA TGAAGGCGTC

22851 CCACAGTGCG CAGATTAGGA GCGCCACTTC TTTTTGTCAC TTGAAAAACA
GGTGTCACGC GTCTAATCCT CGCGGTGAAG AAAAACAGTG AACTTTTTGT

22901 TGTAAAAATA ATGTACTAGA GACACTTTCA ATAAAGGCAA ATGCTTTTAT
ACATTTTTAT TACATGATCT CTGTGAAAGT TATTTCCGTT TACGAAAATA

FIG. 26A-27

```
22951  TTGTACACTC TCGGGTGATT ATTTACCCCC ACCCTTGCCG TCTGCGCCGT
       AACATGTGAG AGCCCACTAA TAAATGGGGG TGGGAACGGC AGACGCGGCA

23001  TTAAAAATCA AAGGGGTTCT GCCGCGCATC GCTATGCGCC ACTGGCAGGG
       AATTTTTAGT TTCCCCAAGA CGGCGCGTAG CGATACGCGG TGACCGTCCC

23051  ACACGTTGCG ATACTGGTGT TTAGTGCTCC ACTTAAACTC AGGCACAACC
       TGTGCAACGC TATGACCACA AATCACGAGG TGAATTTGAG TCCGTGTTGG

23101  ATCCGCGGCA GCTCGGTGAA GTTTTCACTC CACAGGCTGC GCACCATCAC
       TAGGCGCCGT CGAGCCACTT CAAAAGTGAG GTGTCCGACG CGTGGTAGTG

23151  CAACGCGTTT AGCAGGTCGG GCGCCGATAT CTTGAAGTCG CAGTTGGGGC
       GTTGCGCAAA TCGTCCAGCC CGCGGCTATA GAACTTCAGC GTCAACCCCG

23201  CTCCGCCCTG CGCGCGCGAG TTGCGATACA CAGGGTTGCA GCACTGGAAC
       GAGGCGGGAC GCGCGCGCTC AACGCTATGT GTCCCAACGT CGTGACCTTG

23251  ACTATCAGCG CCGGGTGGTG CACGCTGGCC AGCACGCTCT TGTCGGAGAT
       TGATAGTCGC GGCCCACCAC GTGCGACCGG TCGTGCGAGA ACAGCCTCTA

23301  CAGATCCGCG TCCAGGTCCT CCGCGTTGCT CAGGGCGAAC GGAGTCAACT
       GTCTAGGCGC AGGTCCAGGA GGCGCAACGA GTCCCGCTTG CCTCAGTTGA

23351  TTGGTAGCTG CCTTCCCAAA AAGGGCGCGT GCCCAGGCTT TGAGTTGCAC
       AACCATCGAC GGAAGGGTTT TTCCCGCGCA CGGGTCCGAA ACTCAACGTG

23401  TCGCACCGTA GTGGCATCAA AAGGTGACCG TGCCCGGTCT GGGCGTTAGG
       AGCGTGGCAT CACCGTAGTT TTCCACTGGC ACGGGCCAGA CCCGCAATCC

23451  ATACAGCGCC TGCATAAAAG CCTTGATCTG CTTAAAAGCC ACCTGAGCCT
       TATGTCGCGG ACGTATTTTC GGAACTAGAC GAATTTTCGG TGGACTCGGA

23501  TTGCGCCTTC AGAGAAGAAC ATGCCGCAAG ACTTGCCGGA AAACTGATTG
       AACGCGGAAG TCTCTTCTTG TACGGCGTTC TGAACGGCCT TTTGACTAAC

23551  GCCGGACAGG CCGCGTCGTG CACGCAGCAC CTTGCGTCGG TGTTGGAGAT
       CGGCCTGTCC GGCGCAGCAC GTGCGTCGTG GAACGCAGCC ACAACCTCTA

23601  CTGCACCACA TTTCGGCCCC ACCGGTTCTT CACGATCTTG GCCTTGCTAG
       GACGTGGTGT AAAGCCGGGG TGGCCAAGAA GTGCTAGAAC CGGAACGATC

23651  ACTGCTCCTT CAGCGCGCGC TGCCCGTTTT CGCTCGTCAC ATCCATTTCA
       TGACGAGGAA GTCGCGCGCG ACGGGCAAAA GCGAGCAGTG TAGGTAAAGT

23701  ATCACGTGCT CCTTATTTAT CATAATGCTT CCGTGTAGAC ACTTAAGCTC
       TAGTGCACGA GGAATAAATA GTATTACGAA GGCACATCTG TGAATTCGAG

23751  GCCTTCGATC TCAGCGCAGC GGTGCAGCCA CAACGCGCAG CCCGTGGGCT
       CGGAAGCTAG AGTCGCGTCG CCACGTCGGT GTTGCGCGTC GGGCACCCGA
```

FIG. 26A-28

```
23801  CGTGATGCTT GTAGGTCACC TCTGCAAACG ACTGCAGGTA CGCCTGCAGG
       GCACTACGAA CATCCAGTGG AGACGTTTGC TGACGTCCAT GCGGACGTCC

23851  AATCGCCCCA TCATCGTCAC AAAGGTCTTG TTGCTGGTGA AGGTCAGCTG
       TTAGCGGGGT AGTAGCAGTG TTTCCAGAAC AACGACCACT TCCAGTCGAC

23901  CAACCCGCGG TGCTCCTCGT TCAGCCAGGT CTTGCATACG GCCGCCAGAG
       GTTGGGCGCC ACGAGGAGCA AGTCGGTCCA GAACGTATGC CGGCGGTCTC

23951  CTTCCACTTG GTCAGGCAGT AGTTTGAAGT TCGCCTTTAG ATCGTTATCC
       GAAGGTGAAC CAGTCCGTCA TCAAACTTCA AGCGGAAATC TAGCAATAGG

24001  ACGTGGTACT TGTCCATCAG CGCGCGCGCA GCCTCCATGC CCTTCTCCCA
       TGCACCATGA ACAGGTAGTC GCGCGCGCGT CGGAGGTACG GGAAGAGGGT

24051  CGCAGACACG ATCGGCACAC TCAGCGGGTT CATCACCGTA ATTTCACTTT
       GCGTCTGTGC TAGCCGTGTG AGTCGCCCAA GTAGTGGCAT TAAAGTGAAA

24101  CCGCTTCGCT GGGCTCTTCC TCTTCCTCTT GCGTCCGCAT ACCACGCGCC
       GGCGAAGCGA CCCGAGAAGG AGAAGGAGAA CGCAGGCGTA TGGTGCGCGG

24151  ACTGGGTCGT CTTCATTCAG CCGCCGCACT GTGCGCTTAC CTCCTTTGCC
       TGACCCAGCA GAAGTAAGTC GGCGGCGTGA CACGCGAATG GAGGAAACGG

24201  ATGCTTGATT AGCACCGGTG GGTTGCTGAA ACCCACCATT TGTAGCGCCA
       TACGAACTAA TCGTGGCCAC CCAACGACTT TGGGTGGTAA ACATCGCGGT

24251  CATCTTCTCT TTCTTCCTCG CTGTCCACGA TTACCTCTGG TGATGGCGGG
       GTAGAAGAGA AAGAAGGAGC GACAGGTGCT AATGGAGACC ACTACCGCCC

24301  CGCTCGGGCT TGGGAGAAGG GCGCTTCTTT TTCTTCTTGG GCGCAATGGC
       GCGAGCCCGA ACCCTCTTCC CGCGAAGAAA AAGAAGAACC CGCGTTACCG

24351  CAAATCCGCC GCCGAGGTCG ATGGCCGCGG GCTGGGTGTG CGCGGCACCA
       GTTTAGGCGG CGGCTCCAGC TACCGGCGCC CGACCCACAC GCGCCGTGGT

24401  GCGCGTCTTG TGATGAGTCT TCCTCGTCCT CGGACTCGAT ACGCCGCCTC
       CGCGCAGAAC ACTACTCAGA AGGAGCAGGA GCCTGAGCTA TGCGGCGGAG

24451  ATCCGCTTTT TTGGGGGCGC CCGGGGAGGC GGCGGCGACG GGGACGGGGA
       TAGGCGAAAA AACCCCCGCG GGCCCCTCCG CCGCCGCTGC CCCTGCCCCT

24501  CGACACGTCC TCCATGGTTG GGGGACGTCG CGCCGCACCG CGTCCGCGCT
       GCTGTGCAGG AGGTACCAAC CCCCTGCAGC GCGGCGTGGC GCAGGCGCGA

24551  CGGGGGTGGT TTCGCGCTGC TCCTCTTCCC GACTGGCCAT TTCCTTCTCC
       GCCCCCACCA AAGCGCGACG AGGAGAAGGG CTGACCGGTA AAGGAAGAGG

24601  TATAGGCAGA AAAAGATCAT GGAGTCAGTC GAGAAGAAGG ACAGCCTAAC
       ATATCCGTCT TTTTCTAGTA CCTCAGTCAG CTCTTCTTCC TGTCGGATTG
```

FIG. 26A-29

```
24651  CGCCCCCTCT GAGTTCGCCA CCACCGCCTC CACCGATGCC GCCAACGCGC
       GCGGGGGAGA CTCAAGCGGT GGTGGCGGAG GTGGCTACGG CGGTTGCGCG

24701  CTACCACCTT CCCCGTCGAG GCACCCCCGC TTGAGGAGGA GGAAGTGATT
       GATGGTGGAA GGGGCAGCTC CGTGGGGGCG AACTCCTCCT CCTTCACTAA

24751  ATCGAGCAGG ACCCAGGTTT TGTAAGCGAA GACGACGAGG ACCGCTCAGT
       TAGCTCGTCC TGGGTCCAAA ACATTCGCTT CTGCTGCTCC TGGCGAGTCA

24801  ACCAACAGAG GATAAAAAGC AAGACCAGGA CAACGCAGAG GCAAACGAGG
       TGGTTGTCTC CTATTTTTCG TTCTGGTCCT GTTGCGTCTC CGTTTGCTCC

24851  AACAAGTCGG GCGGGGGGAC GAAAGGCATG GCGACTACCT AGATGTGGGA
       TTGTTCAGCC CGCCCCCCTG CTTTCCGTAC CGCTGATGGA TCTACACCCT

24901  GACGACGTGC TGTTGAAGCA TCTGCAGCGC CAGTGCGCCA TTATCTGCGA
       CTGCTGCACG ACAACTTCGT AGACGTCGCG GTCACGCGGT AATAGACGCT

24951  CGCGTTGCAA GAGCGCAGCG ATGTGCCCCT CGCCATAGCG GATGTCAGCC
       GCGCAACGTT CTCGCGTCGC TACACGGGGA GCGGTATCGC CTACAGTCGG

25001  TTGCCTACGA ACGCCACCTA TTCTCACCGC GCGTACCCCC CAAACGCCAA
       AACGGATGCT TGCGGTGGAT AAGAGTGGCG CGCATGGGGG GTTTGCGGTT

25051  GAAAACGGCA CATGCGAGCC CAACCCGCGC CTCAACTTCT ACCCCGTATT
       CTTTTGCCGT GTACGCTCGG GTTGGGCGCG GAGTTGAAGA TGGGGCATAA

25101  TGCCGTGCCA GAGGTGCTTG CCACCTATCA CATCTTTTTC CAAAACTGCA
       ACGGCACGGT CTCCACGAAC GGTGGATAGT GTAGAAAAAG GTTTTGACGT

25151  AGATACCCCT ATCCTGCCGT GCCAACCGCA GCCGAGCGGA CAAGCAGCTG
       TCTATGGGGA TAGGACGGCA CGGTTGGCGT CGGCTCGCCT GTTCGTCGAC

25201  GCCTTGCGGC AGGGCGCTGT CATACCTGAT ATCGCCTCGC TCAACGAAGT
       CGGAACGCCG TCCCGCGACA GTATGGACTA TAGCGGAGCG AGTTGCTTCA

25251  GCCAAAAATC TTTGAGGGTC TTGGACGCGA CGAGAAGCGC GCGGCAAACG
       CGGTTTTTAG AAACTCCCAG AACCTGCGCT GCTCTTCGCG CGCCGTTTGC

25301  CTCTGCAACA GGAAAACAGC GAAAATGAAA GTCACTCTGG AGTGTTGGTG
       GAGACGTTGT CCTTTTGTCG CTTTTACTTT CAGTGAGACC TCACAACCAC

25351  GAACTCGAGG GTGACAACGC GCGCCTAGCC GTACTAAAAC GCAGCATCGA
       CTTGAGCTCC CACTGTTGCG CGCGGATCGG CATGATTTTG CGTCGTAGCT

25401  GGTCACCCAC TTTGCCTACC CGGCACTTAA CCTACCCCCC AAGGTCATGA
       CCAGTGGGTG AAACGGATGG GCCGTGAATT GGATGGGGGG TTCCAGTACT

25451  GCACAGTCAT GAGTGAGCTG ATCGTGCGCC GTGCGCAGCC CCTGGAGAGG
       CGTGTCAGTA CTCACTCGAC TAGCACGCGG CACGCGTCGG GGACCTCTCC
```

FIG. 26A-30

```
25501  GATGCAAATT TGCAAGAACA AACAGAGGAG GGCCTACCCG CAGTTGGCGA
       CTACGTTTAA ACGTTCTTGT TTGTCTCCTC CCGGATGGGC GTCAACCGCT

25551  CGAGCAGCTA GCGCGCTGGC TTCAAACGCG CGAGCCTGCC GACTTGGAGG
       GCTCGTCGAT CGCGCGACCG AAGTTTGCGC GCTCGGACGG CTGAACCTCC

25601  AGCGACGCAA ACTAATGATG GCCGCAGTGC TCGTTACCGT GGAGCTTGAG
       TCGCTGCGTT TGATTACTAC CGGCGTCACG AGCAATGGCA CCTCGAACTC

25651  TGCATGCAGC GGTTCTTTGC TGACCCGGAG ATGCAGCGCA AGCTAGAGGA
       ACGTACGTCG CCAAGAAACG ACTGGGCCTC TACGTCGCGT TCGATCTCCT

25701  AACATTGCAC TACACCTTTC GACAGGGCTA CGTACGCCAG GCCTGCAAGA
       TTGTAACGTG ATGTGGAAAG CTGTCCCGAT GCATGCGGTC CGGACGTTCT

25751  TCTCCAACGT GGAGCTCTGC AACCTGGTCT CCTACCTTGG AATTTTGCAC
       AGAGGTTGCA CCTCGAGACG TTGGACCAGA GGATGGAACC TTAAAACGTG

25801  GAAAACCGCC TTGGGCAAAA CGTGCTTCAT TCCACGCTCA AGGGCGAGGC
       CTTTTGGCGG AACCCGTTTT GCACGAAGTA AGGTGCGAGT TCCCGCTCCG

25851  GCGCCGCGAC TACGTCCGCG ACTGCGTTTA CTTATTTCTA TGCTACACCT
       CGCGGCGCTG ATGCAGGCGC TGACGCAAAT GAATAAAGAT ACGATGTGGA

25901  GGCAGACGGC CATGGGCGTT TGGCAGCAGT GCTTGGAGGA GTGCAACCTC
       CCGTCTGCCG GTACCCGCAA ACCGTCGTCA CGAACCTCCT CACGTTGGAG

25951  AAGGAGCTGC AGAAACTGCT AAAGCAAAAC TTGAAGGACC TATGGACGGC
       TTCCTCGACG TCTTTGACGA TTTCGTTTTG AACTTCCTGG ATACCTGCCG

26001  CTTCAACGAG CGCTCCGTGG CCGCGCACCT GGCGGACATC ATTTTCCCCG
       GAAGTTGCTC GCGAGGCACC GGCGCGTGGA CCGCCTGTAG TAAAAGGGGC

26051  AACGCCTGCT TAAAACCCTG CAACAGGGTC TGCCAGACTT CACCAGTCAA
       TTGCGGACGA ATTTTGGGAC GTTGTCCCAG ACGGTCTGAA GTGGTCAGTT

26101  AGCATGTTGC AGAACTTTAG GAACTTTATC CTAGAGCGCT CAGGAATCTT
       TCGTACAACG TCTTGAAATC CTTGAAATAG GATCTCGCGA GTCCTTAGAA

26151  GCCCGCCACC TGCTGTGCAC TTCCTAGCGA CTTTGTGCCC ATTAAGTACC
       CGGGCGGTGG ACGACACGTG AAGGATCGCT GAAACACGGG TAATTCATGG

26201  GCGAATGCCC TCCGCCGCTT TGGGGCCACT GCTACCTTCT GCAGCTAGCC
       CGCTTACGGG AGGCGGCGAA ACCCCGGTGA CGATGGAAGA CGTCGATCGG

26251  AACTACCTTG CCTACCACTC TGACATAATG GAAGACGTGA GCGGTGACGG
       TTGATGGAAC GGATGGTGAG ACTGTATTAC CTTCTGCACT CGCCACTGCC

26301  TCTACTGGAG TGTCACTGTC GCTGCAACCT ATGCACCCCG CACCGCTCCC
       AGATGACCTC ACAGTGACAG CGACGTTGGA TACGTGGGGC GTGGCGAGGG
```

FIG. 26A-31

26351 TGGTTTGCAA TTCGCAGCTG CTTAACGAAA GTCAAATTAT CGGTACCTTT
ACCAAACGTT AAGCGTCGAC GAATTGCTTT CAGTTTAATA GCCATGGAAA

26401 GAGCTGCAGG GTCCCTCGCC TGACGAAAAG TCCGCGGCTC CGGGGTTGAA
CTCGACGTCC CAGGGAGCGG ACTGCTTTTC AGGCGCCGAG GCCCCAACTT

26451 ACTCACTCCG GGGCTGTGGA CGTCGGCTTA CCTTCGCAAA TTTGTACCTG
TGAGTGAGGC CCCGACACCT GCAGCCGAAT GGAAGCGTTT AAACATGGAC

26501 AGGACTACCA CGCCCACGAG ATTAGGTTCT ACGAAGACCA ATCCCGCCCG
TCCTGATGGT GCGGGTGCTC TAATCCAAGA TGCTTCTGGT TAGGGCGGGC

26551 CCTAATGCGG AGCTTACCGC CTGCGTCATT ACCCAGGGCC ACATTCTTGG
GGATTACGCC TCGAATGGCG GACGCAGTAA TGGGTCCCGG TGTAAGAACC

26601 CCAATTGCAA GCCATCAACA AAGCCCGCCA AGAGTTTCTG CTACGAAAGG
GGTTAACGTT CGGTAGTTGT TTCGGGCGGT TCTCAAAGAC GATGCTTTCC

26651 GACGGGGGGT TTACTTGGAC CCCCAGTCCG GCGAGGAGCT CAACCCAATC
CTGCCCCCCA AATGAACCTG GGGGTCAGGC CGCTCCTCGA GTTGGGTTAG

26701 CCCCCGCCGC CGCAGCCCTA TCAGCAGCAG CCGCGGGCCC TTGCTTCCCA
GGGGGCGGCG GCGTCGGGAT AGTCGTCGTC GGCGCCCGGG AACGAAGGGT

26751 GGATGGCACC CAAAAAGAAG CTGCAGCTGC CGCCGCCACC CACGGACGAG
CCTACCGTGG GTTTTTCTTC GACGTCGACG GCGGCGGTGG GTGCCTGCTC

26801 GAGGAATACT GGGACAGTCA GGCAGAGGAG GTTTTGGACG AGGAGGAGGA
CTCCTTATGA CCCTGTCAGT CCGTCTCCTC CAAAACCTGC TCCTCCTCCT

26851 GGACATGATG GAAGACTGGG AGAGCCTAGA CGAGGAAGCT TCCGAGGTCG
CCTGTACTAC CTTCTGACCC TCTCGGATCT GCTCCTTCGA AGGCTCCAGC

26901 AAGAGGTGTC AGACGAAACA CCGTCACCCT CGGTCGCATT CCCCTCGCCG
TTCTCCACAG TCTGCTTTGT GGCAGTGGGA GCCAGCGTAA GGGGAGCGGC

26951 GCGCCCCAGA AATCGGCAAC CGGTTCCAGC ATGGCTACAA CCTCCGCTCC
CGCGGGGTCT TTAGCCGTTG GCCAAGGTCG TACCGATGTT GGAGGCGAGG

27001 TCAGGCGCCG CCGGCACTGC CCGTTCGCCG ACCCAACCGT AGATGGGACA
AGTCCGCGGC GGCCGTGACG GGCAAGCGGC TGGGTTGGCA TCTACCCTGT

27051 CCACTGGAAC CAGGGCCGGT AAGTCCAAGC AGCCGCCGCC GTTAGCCCAA
GGTGACCTTG GTCCCGGCCA TTCAGGTTCG TCGGCGGCGG CAATCGGGTT

27101 GAGCAACAAC AGCGCCAAGG CTACCGCTCA TGGCGCGGGC ACAAGAACGC
CTCGTTGTTG TCGCGGTTCC GATGGCGAGT ACCGCGCCCG TGTTCTTGCG

27151 CATAGTTGCT TGCTTGCAAG ACTGTGGGGG CAACATCTCC TTCGCCCGCC
GTATCAACGA ACGAACGTTC TGACACCCCC GTTGTAGAGG AAGCGGGCGG

FIG. 26A-32

```
27201  GCTTTCTTCT CTACCATCAC GGCGTGGCCT TCCCCCGTAA CATCCTGCAT
       CGAAAGAAGA GATGGTAGTG CCGCACCGGA AGGGGGCATT GTAGGACGTA

27251  TACTACCGTC ATCTCTACAG CCCATACTGC ACCGGCGGCA GCGGCAGCAA
       ATGATGGCAG TAGAGATGTC GGGTATGACG TGGCCGCCGT CGCCGTCGTT

27301  CAGCAGCGGC CACACAGAAG CAAAGGCGAC CGGATAGCAA GACTCTGACA
       GTCGTCGCCG GTGTGTCTTC GTTTCCGCTG GCCTATCGTT CTGAGACTGT

27351  AAGCCCAAGA AATCCACAGC GGCGGCAGCA GCAGGAGGAG GAGCGCTGCG
       TTCGGGTTCT TTAGGTGTCG CCGCCGTCGT CGTCCTCCTC CTCGCGACGC

27401  TCTGGCGCCC AACGAACCCG TATCGACCCG CGAGCTTAGA AACAGGATTT
       AGACCGCGGG TTGCTTGGGC ATAGCTGGGC GCTCGAATCT TTGTCCTAAA

27451  TTCCCACTCT GTATGCTATA TTTCAACAGA GCAGGGGCCA AGAACAAGAG
       AAGGGTGAGA CATACGATAT AAAGTTGTCT CGTCCCCGGT TCTTGTTCTC

27501  CTGAAAATAA AAAACAGGTC TCTGCGATCC CTCACCCGCA GCTGCCTGTA
       GACTTTTATT TTTTGTCCAG AGACGCTAGG GAGTGGGCGT CGACGGACAT

27551  TCACAAAAGC GAAGATCAGC TTCGGCGCAC GCTGGAAGAC GCGGAGGCTC
       AGTGTTTTCG CTTCTAGTCG AAGCCGCGTG CGACCTTCTG CGCCTCCGAG

27601  TCTTCAGTAA ATACTGCGCG CTGACTCTTA AGGACTAGTT TCGCGCCCTT
       AGAAGTCATT TATGACGCGC GACTGAGAAT TCCTGATCAA AGCGCGGGAA

27651  TCTCAAATTT AAGCGCGAAA ACTACGTCAT CTCCAGCGGC CACACCCGGC
       AGAGTTTAAA TTCGCGCTTT TGATGCAGTA GAGGTCGCCG GTGTGGGCCG

27701  GCCAGCACCT GTTGTCAGCG CCATTATGAG CAAGGAAATT CCCACGCCCT
       CGGTCGTGGA CAACAGTCGC GGTAATACTC GTTCCTTTAA GGGTGCGGGA

27751  ACATGTGGAG TTACCAGCCA CAAATGGGAC TTGCGGCTGG AGCTGCCCAA
       TGTACACCTC AATGGTCGGT GTTTACCCTG AACGCCGACC TCGACGGGTT

27801  GACTACTCAA CCCGAATAAA CTACATGAGC GCGGGACCCC ACATGATATC
       CTGATGAGTT GGGCTTATTT GATGTACTCG CGCCCTGGGG TGTACTATAG

27851  CCGGGTCAAC GGAATACGCG CCCACCGAAA CCGAATTCTC CTGGAACAGG
       GGCCCAGTTG CCTTATGCGC GGGTGGCTTT GGCTTAAGAG GACCTTGTCC

27901  CGGCTATTAC CACCACACCT CGTAATAACC TTAATCCCCG TAGTTGGCCC
       GCCGATAATG GTGGTGTGGA GCATTATTGG AATTAGGGGC ATCAACCGGG

27951  GCTGCCCTGG TGTACCAGGA AAGTCCCGCT CCCACCACTG TGGTACTTCC
       CGACGGGACC ACATGGTCCT TTCAGGGCGA GGGTGGTGAC ACCATGAAGG

28001  CAGAGACGCC CAGGCCGAAG TTCAGATGAC TAACTCAGGG GCGCAGCTTG
       GTCTCTGCGG GTCCGGCTTC AAGTCTACTG ATTGAGTCCC CGCGTCGAAC
```

FIG. 26A-33

```
28051  CGGGCGGCTT TCGTCACAGG GTGCGGTCGC CCGGGCAGGG TATAACTCAC
       GCCCGCCGAA AGCAGTGTCC CACGCCAGCG GGCCCGTCCC ATATTGAGTG

28101  CTGACAATCA GAGGGCGAGG TATTCAGCTC AACGACGAGT CGGTGAGCTC
       GACTGTTAGT CTCCCGCTCC ATAAGTCGAG TTGCTGCTCA GCCACTCGAG

28151  CTCGCTTGGT CTCCGTCCGG ACGGGACATT TCAGATCGGC GGCGCCGGCC
       GAGCGAACCA GAGGCAGGCC TGCCCTGTAA AGTCTAGCCG CCGCGGCCGG

28201  GCTCTTCATT CACGCCTCGT CAGGCAATCC TAACTCTGCA GACCTCGTCC
       CGAGAAGTAA GTGCGGAGCA GTCCGTTAGG ATTGAGACGT CTGGAGCAGG

28251  TCTGAGCCGC GCTCTGGAGG CATTGGAACT CTGCAATTTA TTGAGGAGTT
       AGACTCGGCG CGAGACCTCC GTAACCTTGA GACGTTAAAT AACTCCTCAA

28301  TGTGCCATCG GTCTACTTTA ACCCCTTCTC GGGACCTCCC GGCCACTATC
       ACACGGTAGC CAGATGAAAT TGGGGAAGAG CCCTGGAGGG CCGGTGATAG

28351  CGGATCAATT TATTCCTAAC TTTGACGCGG TAAAGGACTC GGCGGACGGC
       GCCTAGTTAA ATAAGGATTG AAACTGCGCC ATTTCCTGAG CCGCCTGCCG

28401  TACGACTGAA TGTTAAGTGG AGAGGCAGAG CAACTGCGCC TGAAACACCT
       ATGCTGACTT ACAATTCACC TCTCCGTCTC GTTGACGCGG ACTTTGTGGA

28451  GGTCCACTGT CGCCGCCACA AGTGCTTTGC CCGCGACTCC GGTGAGTTTT
       CCAGGTGACA GCGGCGGTGT TCACGAAACG GGCGCTGAGG CCACTCAAAA

28501  GCTACTTTGA ATTGCCCGAG GATCATATCG AGGGCCCGGC GCACGGCGTC
       CGATGAAACT TAACGGGCTC CTAGTATAGC TCCCGGGCCG CGTGCCGCAG

28551  CGGCTTACCG CCCAGGGAGA GCTTGCCCGT AGCCTGATTC GGGAGTTTAC
       GCCGAATGGC GGGTCCCTCT CGAACGGGCA TCGGACTAAG CCCTCAAATG

28601  CCAGCGCCCC CTGCTAGTTG AGCGGGACAG GGGACCCTGT GTTCTCACTG
       GGTCGCGGGG GACGATCAAC TCGCCCTGTC CCCTGGGACA CAAGAGTGAC

28651  TGATTTGCAA CTGTCCTAAC CCTGGATTAC ATCAAGATCT TTGTTGCCAT
       ACTAAACGTT GACAGGATTG GGACCTAATG TAGTTCTAGA AACAACGGTA

28701  CTCTGTGCTG AGTATAATAA ATACAGAAAT TAAAATATAC TGGGGCTCCT
       GAGACACGAC TCATATTATT TATGTCTTTA ATTTTATATG ACCCCGAGGA

28751  ATCGCCATCC TGTAAACGCC ACCGTCTTCA CCCGCCCAAG CAAACCAAGG
       TAGCGGTAGG ACATTTGCGG TGGCAGAAGT GGGCGGGTTC GTTTGGTTCC

28801  CGAACCTTAC CTGGTACTTT TAACATCTCT CCCTCTGTGA TTTACAACAG
       GCTTGGAATG GACCATGAAA ATTGTAGAGA GGGAGACACT AAATGTTGTC

28851  TTTCAACCCA GACGGAGTGA GTCTACGAGA GAACCTCTCC GAGCTCAGCT
       AAAGTTGGGT CTGCCTCACT CAGATGCTCT CTTGGAGAGG CTCGAGTCGA
```

FIG. 26A-34

28901 ACTCCATCAG AAAAAACACC ACCCTCCTTA CCTGCCGGGA ACGTACGAGT
TGAGGTAGTC TTTTTTGTGG TGGGAGGAAT GGACGGCCCT TGCATGCTCA

28951 GCGTCACCGG CCGCTGCACC ACACCTACCG CCTGACCGTA AACCAGACTT
CGCAGTGGCC GGCGACGTGG TGTGGATGGC GGACTGGCAT TTGGTCTGAA

29001 TTTCCGGACA GACCTCAATA ACTCTGTTTA CCAGAACAGG AGGTGAGCTT
AAAGGCCTGT CTGGAGTTAT TGAGACAAAT GGTCTTGTCC TCCACTCGAA

29051 AGAAAACCCT TAGGGTATTA GGCCAAAGGC GCAGCTACTG TGGGGTTTAT
TCTTTTGGGA ATCCCATAAT CCGGTTTCCG CGTCGATGAC ACCCCAAATA

29101 GAACAATTCA AGCAACTCTA CGGGCTATTC TAATTCAGGT TTCTCTAGAA
CTTGTTAAGT TCGTTGAGAT GCCCGATAAG ATTAAGTCCA AAGAGATCTT

29151 TCGGGGTTGG GGTTATTCTC TGTCTTGTGA TTCTCTTTAT TCTTATACTA
AGCCCCAACC CCAATAAGAG ACAGAACACT AAGAGAAATA AGAATATGAT

29201 ACGCTTCTCT GCCTAAGGCT CGCCGCCTGC TGTGTGCACA TTTGCATTTA
TGCGAAGAGA CGGATTCCGA GCGGCGGACG ACACACGTGT AAACGTAAAT

29251 TTGTCAGCTT TTTAAACGCT GGGGTCGCCA CCCAAGATGA TTAGGTACAT
AACAGTCGAA AAATTTGCGA CCCCAGCGGT GGGTTCTACT AATCCATGTA

29301 AATCCTAGGT TTACTCACCC TTGCGTCAGC CCACGGTACC ACCCAAAAGG
TTAGGATCCA AATGAGTGGG AACGCAGTCG GGTGCCATGG TGGGTTTTCC

29351 TGGATTTTAA GGAGCCAGCC TGTAATGTTA CATTCGCAGC TGAAGCTAAT
ACCTAAAATT CCTCGGTCGG ACATTACAAT GTAAGCGTCG ACTTCGATTA

29401 GAGTGCACCA CTCTTATAAA ATGCACCACA GAACATGAAA AGCTGCTTAT
CTCACGTGGT GAGAATATTT TACGTGGTGT CTTGTACTTT TCGACGAATA

29451 TCGCCACAAA AACAAAATTG GCAAGTATGC TGTTTATGCT ATTTGGCAGC
AGCGGTGTTT TTGTTTTAAC CGTTCATACG ACAAATACGA TAAACCGTCG

29501 CAGGTGACAC TACAGAGTAT AATGTTACAG TTTTCCAGGG TAAAAGTCAT
GTCCACTGTG ATGTCTCATA TTACAATGTC AAAAGGTCCC ATTTTCAGTA

29551 AAAACTTTTA TGTATACTTT TCCATTTTAT GAAATGTGCG ACATTACCAT
TTTTGAAAAT ACATATGAAA AGGTAAAATA CTTTACACGC TGTAATGGTA

29601 GTACATGAGC AAACAGTATA AGTTGTGGCC CCCACAAAAT TGTGTGGAAA
CATGTACTCG TTTGTCATAT TCAACACCGG GGGTGTTTTA ACACACCTTT

29651 ACACTGGCAC TTTCTGCTGC ACTGCTATGC TAATTACAGT GCTCGCTTTG
TGTGACCGTG AAAGACGACG TGACGATACG ATTAATGTCA CGAGCGAAAC

29701 GTCTGTACCC TACTCTATAT TAAATACAAA AGCAGACGCA GCTTTATTGA
CAGACATGGG ATGAGATATA ATTTATGTTT TCGTCTGCGT CGAAATAACT

FIG. 26A-35

```
29751  GGAAAAGAAA ATGCCTTAAT TTACTAAGTT ACAAAGCTAA TGTCACCACT
       CCTTTTCTTT TACGGAATTA AATGATTCAA TGTTTCGATT ACAGTGGTGA

29801  AACTGCTTTA CTCGCTGCTT GCAAAACAAA TTCAAAAAGT TAGCATTATA
       TTGACGAAAT GAGCGACGAA CGTTTTGTTT AAGTTTTTCA ATCGTAATAT

29851  ATTAGAATAG GATTTAAACC CCCCGGTCAT TTCCTGCTCA ATACCATTCC
       TAATCTTATC CTAAATTTGG GGGGCCAGTA AAGGACGAGT TATGGTAAGG

29901  CCTGAACAAT TGACTCTATG TGGGATATGC TCCAGCGCTA CAACCTTGAA
       GGACTTGTTA ACTGAGATAC ACCCTATACG AGGTCGCGAT GTTGGAACTT

29951  GTCAGGCTTC CTGGATGTCA GCATCTGACT TTGGCCAGCA CCTGTCCCGC
       CAGTCCGAAG GACCTACAGT CGTAGACTGA AACCGGTCGT GGACAGGGCG

30001  GGATTTGTTC CAGTCCAACT ACAGCGACCC ACCCTAACAG AGATGACCAA
       CCTAAACAAG GTCAGGTTGA TGTCGCTGGG TGGGATTGTC TCTACTGGTT

30051  CACAACCAAC GCGGCCGCCG CTACCGGACT TACATCTACC ACAAATACAC
       GTGTTGGTTG CGCCGGCGGC GATGGCCTGA ATGTAGATGG TGTTTATGTG

30101  CCCAAGTTTC TGCCTTTGTC AATAACTGGG ATAACTTGGG CATGTGGTGG
       GGGTTCAAAG ACGGAAACAG TTATTGACCC TATTGAACCC GTACACCACC

30151  TTCTCCATAG CGCTTATGTT TGTATGCCTT ATTATTATGT GGCTCATCTG
       AAGAGGTATC GCGAATACAA ACATACGGAA TAATAATACA CCGAGTAGAC

30201  CTGCCTAAAG CGCAAACGCG CCCGACCACC CATCTATAGT CCCATCATTG
       GACGGATTTC GCGTTTGCGC GGGCTGGTGG GTAGATATCA GGGTAGTAAC

30251  TGCTACACCC AAACAATGAT GGAATCCATA GATTGGACGG ACTGAAACAC
       ACGATGTGGG TTTGTTACTA CCTTAGGTAT CTAACCTGCC TGACTTTGTG

30301  ATGTTCTTTT CTCTTACAGT ATGATTAAAT GAGACATGAT TCCTCGAGTT
       TACAAGAAAA GAGAATGTCA TACTAATTTA CTCTGTACTA AGGAGCTCAA

30351  TTTATATTAC TGACCCTTGT TGCGCTTTTT TGTGCGTGCT CCACATTGGC
       AAATATAATG ACTGGGAACA ACGCGAAAAA ACACGCACGA GGTGTAACCG

30401  TGCGGTTTCT CACATCGAAG TAGACTGCAT TCCAGCCTTC ACAGTCTATT
       ACGCCAAAGA GTGTAGCTTC ATCTGACGTA AGGTCGGAAG TGTCAGATAA

30451  TGCTTTACGG ATTTGTCACC CTCACGCTCA TCTGCAGCCT CATCACTGTG
       ACGAAATGCC TAAACAGTGG GAGTGCGAGT AGACGTCGGA GTAGTGACAC

30501  GTCATCGCCT TTATCCAGTG CATTGACTGG GTCTGTGTGC GCTTTGCATA
       CAGTAGCGGA AATAGGTCAC GTAACTGACC CAGACACACG CGAAACGTAT

30551  TCTCAGACAC CATCCCCAGT ACAGGGACAG GACTATAGCT GAGCTTCTTA
       AGAGTCTGTG GTAGGGGTCA TGTCCCTGTC CTGATATCGA CTCGAAGAAT
```

FIG. 26A-36

```
30601  GAATTCTTTA ATTATGAAAT TTACTGTGAC TTTTCTGCTG ATTATTTGCA
       CTTAAGAAAT TAATACTTTA AATGACACTG AAAAGACGAC TAATAAACGT

30651  CCCTATCTGC GTTTTGTTCC CCGACCTCCA AGCCTCAAAG ACATATATCA
       GGGATAGACG CAAAACAAGG GGCTGGAGGT TCGGAGTTTC TGTATATAGT

30701  TGCAGATTCA CTCGTATATG GAATATTCCA AGTTGCTACA ATGAAAAAAG
       ACGTCTAAGT GAGCATATAC CTTATAAGGT TCAACGATGT TACTTTTTTC

30751  CGATCTTTCC GAAGCCTGGT TATATGCAAT CATCTCTGTT ATGGTGTTCT
       GCTAGAAAGG CTTCGGACCA ATATACGTTA GTAGAGACAA TACCACAAGA

30801  GCAGTACCAT CTTAGCCCTA GCTATATATC CCTACCTTGA CATTGGCTGG
       CGTCATGGTA GAATCGGGAT CGATATATAG GGATGGAACT GTAACCGACC

30851  AACGCAATAG ATGCCATGAA CCACCCAACT TTCCCCGCGC CCGCTATGCT
       TTGCGTTATC TACGGTACTT GGTGGGTTGA AAGGGGCGCG GGCGATACGA

30901  TCCACTGCAA CAAGTTGTTG CCGGCGGCTT TGTCCCAGCC AATCAGCCTC
       AGGTGACGTT GTTCAACAAC GGCCGCCGAA ACAGGGTCGG TTAGTCGGAG

30951  GCCCACCTTC TCCCACCCCC ACTGAAATCA GCTACTTTAA TCTAACAGGA
       CGGGTGGAAG AGGGTGGGGG TGACTTTAGT CGATGAAATT AGATTGTCCT

31001  GGAGATGACT GACACCCTAG ATCTAGAAAT GGACGGAATT ATTACAGAGC
       CCTCTACTGA CTGTGGGATC TAGATCTTTA CCTGCCTTAA TAATGTCTCG

31051  AGCGCCTGCT AGAAAGACGC AGGGCAGCGG CCGAGCAACA GCGCATGAAT
       TCGCGGACGA TCTTTCTGCG TCCCGTCGCC GGCTCGTTGT CGCGTACTTA

31101  CAAGAGCTCC AAGACATGGT TAACTTGCAC CAGTGCAAAA GGGGTATCTT
       GTTCTCGAGG TTCTGTACCA ATTGAACGTG GTCACGTTTT CCCCATAGAA

31151  TTGTCTCGTA AAGCAGGCCA AAGTCACCTA CGACAGTAAT ACCACCGGAC
       AACAGAGCAT TTCGTCCGGT TTCAGTGGAT GCTGTCATTA TGGTGGCCTG

31201  ACCGCCTTAG CTACAAGTTG CCAACCAAGC GTCAGAAATT GGTGGTCATG
       TGGCGGAATC GATGTTCAAC GGTTGGTTCG CAGTCTTTAA CCACCAGTAC

31251  GTGGGAGAAA AGCCCATTAC CATAACTCAG CACTCGGTAG AAACCGAAGG
       CACCCTCTTT TCGGGTAATG GTATTGAGTC GTGAGCCATC TTTGGCTTCC

31301  CTGCATTCAC TCACCTTGTC AAGGACCTGA GGATCTCTGC ACCCTTATTA
       GACGTAAGTG AGTGGAACAG TTCCTGGACT CCTAGAGACG TGGGAATAAT

31351  AGACCCTGTG CGGTCTCAAA GATCTTATTC CCTTTAACTA ATAAAAAAAA
       TCTGGGACAC GCCAGAGTTT CTAGAATAAG GGAAATTGAT TATTTTTTTT

31401  ATAATAAAGC ATCACTTACT TAAAATCAGT TAGCAAATTT CTGTCCAGTT
       TATTATTTCG TAGTGAATGA ATTTTAGTCA ATCGTTTAAA GACAGGTCAA
```

FIG. 26A-37

31451 TATTCAGCAG CACCTCCTTG CCCTCCTCCC AGCTCTGGTA TTGCAGCTTC
ATAAGTCGTC GTGGAGGAAC GGGAGGAGGG TCGAGACCAT AACGTCGAAG

31501 CTCCTGGCTG CAAACTTTCT CCACAATCTA AATGGAATGT CAGTTTCCTC
GAGGACCGAC GTTTGAAAGA GGTGTTAGAT TTACCTTACA GTCAAAGGAG

31551 CTGTTCCTGT CCATCCGCAC CCACTATCTT CATGTTGTTG CAGATGAAGC
GACAAGGACA GGTAGGCGTG GGTGATAGAA GTACAACAAC GTCTACTTCG

31601 GCGCAAGACC GTCTGAAGAT ACCTTCAACC CCGTGTATCC ATATGACACG
CGCGTTCTGG CAGACTTCTA TGGAAGTTGG GGCACATAGG TATACTGTGC

31651 GAAACCGGTC CTCCAACTGT GCCTTTTCTT ACTCCTCCCT TTGTATCCCC
CTTTGGCCAG GAGGTTGACA CGGAAAAGAA TGAGGAGGGA AACATAGGGG

31701 CAATGGGTTT CAAGAGAGTC CCCCTGGGGT ACTCTCTTTG CGCCTATCCG
GTTACCCAAA GTTCTCTCAG GGGGACCCCA TGAGAGAAAC GCGGATAGGC

31751 AACCTCTAGT TACCTCCAAT GGCATGCTTG CGCTCAAAAT GGGCAACGGC
TTGGAGATCA ATGGAGGTTA CCGTACGAAC GCGAGTTTTA CCCGTTGCCG

31801 CTCTCTCTGG ACGAGGCCGG CAACCTTACC TCCCAAAATG TAACCACTGT
GAGAGAGACC TGCTCCGGCC GTTGGAATGG AGGGTTTTAC ATTGGTGACA

31851 GAGCCCACCT CTCAAAAAAA CCAAGTCAAA CATAAACCTG GAAATATCTG
CTCGGGTGGA GAGTTTTTTT GGTTCAGTTT GTATTTGGAC CTTTATAGAC

31901 CACCCCTCAC AGTTACCTCA GAAGCCCTAA CTGTGGCTGC CGCCGCACCT
GTGGGGAGTG TCAATGGAGT CTTCGGGATT GACACCGACG GCGGCGTGGA

31951 CTAATGGTCG CGGGCAACAC ACTCACCATG CAATCACAGG CCCCGCTAAC
GATTACCAGC GCCCGTTGTG TGAGTGGTAC GTTAGTGTCC GGGGCGATTG

32001 CGTGCACGAC TCCAAACTTA GCATTGCCAC CCAAGGACCC CTCACAGTGT
GCACGTGCTG AGGTTTGAAT CGTAACGGTG GGTTCCTGGG GAGTGTCACA

32051 CAGAAGGAAA GCTAGCCCTG CAAACATCAG GCCCCCTCAC CACCACCGAT
GTCTTCCTTT CGATCGGGAC GTTTGTAGTC CGGGGGAGTG GTGGTGGCTA

32101 AGCAGTACCC TTACTATCAC TGCCTCACCC CCTCTAACTA CTGCCACTGG
TCGTCATGGG AATGATAGTG ACGGAGTGGG GGAGATTGAT GACGGTGACC

32151 TAGCTTGGGC ATTGACTTGA AAGAGCCCAT TTATACACAA AATGGAAAAC
ATCGAACCCG TAACTGAACT TTCTCGGGTA AATATGTGTT TTACCTTTTG

32201 TAGGACTAAA GTACGGGGCT CCTTTGCATG TAACAGACGA CCTAAACACT
ATCCTGATTT CATGCCCCGA GGAAACGTAC ATTGTCTGCT GGATTTGTGA

32251 TTGACCGTAG CAACTGGTCC AGGTGTGACT ATTAATAATA CTTCCTTGCA
AACTGGCATC GTTGACCAGG TCCACACTGA TAATTATTAT GAAGGAACGT

FIG. 26A-38

```
32301  AACTAAAGTT ACTGGAGCCT TGGGTTTTGA TTCACAAGGC AATATGCAAC
       TTGATTTCAA TGACCTCGGA ACCCAAAACT AAGTGTTCCG TTATACGTTG

32351  TTAATGTAGC AGGAGGACTA AGGATTGATT CTCAAAACAG ACGCCTTATA
       AATTACATCG TCCTCCTGAT TCCTAACTAA GAGTTTTGTC TGCGGAATAT

32401  CTTGATGTTA GTTATCCGTT TGATGCTCAA AACCAACTAA ATCTAAGACT
       GAACTACAAT CAATAGGCAA ACTACGAGTT TTGGTTGATT TAGATTCTGA

32451  AGGACAGGGC CCTCTTTTTA TAAACTCAGC CCACAACTTG GATATTAACT
       TCCTGTCCCG GGAGAAAAAT ATTTGAGTCG GGTGTTGAAC CTATAATTGA

32501  ACAACAAAGG CCTTTACTTG TTTACAGCTT CAAACAATTC CAAAAAGCTT
       TGTTGTTTCC GGAAATGAAC AAATGTCGAA GTTTGTTAAG GTTTTTCGAA

32551  GAGGTTAACC TAAGCACTGC CAAGGGGTTG ATGTTTGACG CTACAGCCAT
       CTCCAATTGG ATTCGTGACG GTTCCCCAAC TACAAACTGC GATGTCGGTA

32601  AGCCATTAAT GCAGGAGATG GGCTTGAATT TGGTTCACCT AATGCACCAA
       TCGGTAATTA CGTCCTCTAC CCGAACTTAA ACCAAGTGGA TTACGTGGTT

32651  ACACAAATCC CCTCAAAACA AAAATTGGCC ATGGCCTAGA ATTTGATTCA
       TGTGTTTAGG GGAGTTTTGT TTTTAACCGG TACCGGATCT TAAACTAAGT

32701  AACAAGGCTA TGGTTCCTAA ACTAGGAACT GGCCTTAGTT TTGACAGCAC
       TTGTTCCGAT ACCAAGGATT TGATCCTTGA CCGGAATCAA AACTGTCGTG

32751  AGGTGCCATT ACAGTAGGAA ACAAAAATAA TGATAAGCTA ACTTTGTGGA
       TCCACGGTAA TGTCATCCTT TGTTTTTATT ACTATTCGAT TGAAACACCT

32801  CCACACCAGC TCCATCTCCT AACTGTAGAC TAAATGCAGA GAAAGATGCT
       GGTGTGGTCG AGGTAGAGGA TTGACATCTG ATTTACGTCT CTTTCTACGA

32851  AAACTCACTT TGGTCTTAAC AAAATGTGGC AGTCAAATAC TTGCTACAGT
       TTTGAGTGAA ACCAGAATTG TTTTACACCG TCAGTTTATG AACGATGTCA

32901  TTCAGTTTTG GCTGTTAAAG GCAGTTTGGC TCCAATATCT GGAACAGTTC
       AAGTCAAAAC CGACAATTTC CGTCAAACCG AGGTTATAGA CCTTGTCAAG

32951  AAAGTGCTCA TCTTATTATA AGATTTGACG AAAATGGAGT GCTACTAAAC
       TTTCACGAGT AGAATAATAT TCTAAACTGC TTTTACCTCA CGATGATTTG

33001  AATTCCTTCC TGGACCCAGA ATATTGGAAC TTTAGAAATG GAGATCTTAC
       TTAAGGAAGG ACCTGGGTCT TATAACCTTG AAATCTTTAC CTCTAGAATG

33051  TGAAGGCACA GCCTATACAA ACGCTGTTGG ATTTATGCCT AACCTATCAG
       ACTTCCGTGT CGGATATGTT TGCGACAACC TAAATACGGA TTGGATAGTC

33101  CTTATCCAAA ATCTCACGGT AAAACTGCCA AAAGTAACAT TGTCAGTCAA
       GAATAGGTTT TAGAGTGCCA TTTTGACGGT TTTCATTGTA ACAGTCAGTT
```

FIG. 26A-39

```
33151  GTTTACTTAA ACGGAGACAA AACTAAACCT GTAACACTAA CCATTACACT
       CAAATGAATT TGCCTCTGTT TTGATTTGGA CATTGTGATT GGTAATGTGA

33201  AAACGGTACA CAGGAAACAG GAGACACAAC TCCAAGTGCA TACTCTATGT
       TTTGCCATGT GTCCTTTGTC CTCTGTGTTG AGGTTCACGT ATGAGATACA

33251  CATTTTCATG GGACTGGTCT GGCCACAACT ACATTAATGA AATATTTGCC
       GTAAAAGTAC CCTGACCAGA CCGGTGTTGA TGTAATTACT TTATAAACGG

33301  ACATCCTCTT ACACTTTTTC ATACATTGCC CAAGAATAAA GAATCGTTTG
       TGTAGGAGAA TGTGAAAAAG TATGTAACGG GTTCTTATTT CTTAGCAAAC

33351  TGTTATGTTT CAACGTGTTT ATTTTTCAAT TGCAGAAAAT TTCAAGTCAT
       ACAATACAAA GTTGCACAAA TAAAAAGTTA ACGTCTTTTA AAGTTCAGTA

33401  TTTTCATTCA GTAGTATAGC CCCACCACCA CATAGCTTAT ACAGATCACC
       AAAAGTAAGT CATCATATCG GGGTGGTGGT GTATCGAATA TGTCTAGTGG

33451  GTACCTTAAT CAAACTCACA GAACCCTAGT ATTCAACCTG CCACCTCCCT
       CATGGAATTA GTTTGAGTGT CTTGGGATCA TAAGTTGGAC GGTGGAGGGA

33501  CCCAACACAC AGAGTACACA GTCCTTTCTC CCCGGCTGGC CTTAAAAAGC
       GGGTTGTGTG TCTCATGTGT CAGGAAAGAG GGGCCGACCG GAATTTTTCG

33551  ATCATATCAT GGGTAACAGA CATATTCTTA GGTGTTATAT TCCACACGGT
       TAGTATAGTA CCCATTGTCT GTATAAGAAT CCACAATATA AGGTGTGCCA

33601  TTCCTGTCGA GCCAAACGCT CATCAGTGAT ATTAATAAAC TCCCCGGGCA
       AAGGACAGCT CGGTTTGCGA GTAGTCACTA TAATTATTTG AGGGGCCCGT

33651  GCTCACTTAA GTTCATGTCG CTGTCCAGCT GCTGAGCCAC AGGCTGCTGT
       CGAGTGAATT CAAGTACAGC GACAGGTCGA CGACTCGGTG TCCGACGACA

33701  CCAACTTGCG GTTGCTTAAC GGGCGGCGAA GGAGAAGTCC ACGCCTACAT
       GGTTGAACGC CAACGAATTG CCCGCCGCTT CCTCTTCAGG TGCGGATGTA

33751  GGGGGTAGAG TCATAATCGT GCATCAGGAT AGGGCGGTGG TGCTGCAGCA
       CCCCCATCTC AGTATTAGCA CGTAGTCCTA TCCCGCCACC ACGACGTCGT

33801  GCGCGCGAAT AAACTGCTGC CGCCGCCGCT CCGTCCTGCA GGAATACAAC
       CGCGCGCTTA TTTGACGACG GCGGCGGCGA GGCAGGACGT CCTTATGTTG

33851  ATGGCAGTGG TCTCCTCAGC GATGATTCGC ACCGCCCGCA GCATAAGGCG
       TACCGTCACC AGAGGAGTCG CTACTAAGCG TGGCGGGCGT CGTATTCCGC

33901  CCTTGTCCTC CGGGCACAGC AGCGCACCCT GATCTCACTT AAATCAGCAC
       GGAACAGGAG GCCCGTGTCG TCGCGTGGGA CTAGAGTGAA TTTAGTCGTG

33951  AGTAACTGCA GCACAGCACC ACAATATTGT TCAAAATCCC ACAGTGCAAG
       TCATTGACGT CGTGTCGTGG TGTTATAACA AGTTTTAGGG TGTCACGTTC
```

FIG. 26A-40

```
34001  GCGCTGTATC CAAAGCTCAT GGCGGGGACC ACAGAACCCA CGTGGCCATC
       CGCGACATAG GTTTCGAGTA CCGCCCCTGG TGTCTTGGGT GCACCGGTAG

34051  ATACCACAAG CGCAGGTAGA TTAAGTGGCG ACCCCTCATA AACACGCTGG
       TATGGTGTTC GCGTCCATCT AATTCACCGC TGGGGAGTAT TTGTGCGACC

34101  ACATAAACAT TACCTCTTTT GGCATGTTGT AATTCACCAC CTCCCGGTAC
       TGTATTTGTA ATGGAGAAAA CCGTACAACA TTAAGTGGTG GAGGGCCATG

34151  CATATAAACC TCTGATTAAA CATGGCGCCA TCCACCACCA TCCTAAACCA
       GTATATTTGG AGACTAATTT GTACCGCGGT AGGTGGTGGT AGGATTTGGT

34201  GCTGGCCAAA ACCTGCCCGC CGGCTATACA CTGCAGGGAA CCGGGACTGG
       CGACCGGTTT TGGACGGGCG GCCGATATGT GACGTCCCTT GGCCCTGACC

34251  AACAATGACA GTGGAGAGCC CAGGACTCGT AACCATGGAT CATCATGCTC
       TTGTTACTGT CACCTCTCGG GTCCTGAGCA TTGGTACCTA GTAGTACGAG

34301  GTCATGATAT CAATGTTGGC ACAACACAGG CACACGTGCA TACACTTCCT
       CAGTACTATA GTTACAACCG TGTTGTGTCC GTGTGCACGT ATGTGAAGGA

34351  CAGGATTACA AGCTCCTCCC GCGTTAGAAC CATATCCCAG GGAACAACCC
       GTCCTAATGT TCGAGGAGGG CGCAATCTTG GTATAGGGTC CCTTGTTGGG

34401  ATTCCTGAAT CAGCGTAAAT CCCACACTGC AGGGAAGACC TCGCACGTAA
       TAAGGACTTA GTCGCATTTA GGGTGTGACG TCCCTTCTGG AGCGTGCATT

34451  CTCACGTTGT GCATTGTCAA AGTGTTACAT TCGGGCAGCA GCGGATGATC
       GAGTGCAACA CGTAACAGTT TCACAATGTA AGCCCGTCGT CGCCTACTAG

34501  CTCCAGTATG GTAGCGCGGG TTTCTGTCTC AAAAGGAGGT AGACGATCCC
       GAGGTCATAC CATCGCGCCC AAAGACAGAG TTTTCCTCCA TCTGCTAGGG

34551  TACTGTACGG AGTGCGCCGA GACAACCGAG ATCGTGTTGG TCGTAGTGTC
       ATGACATGCC TCACGCGGCT CTGTTGGCTC TAGCACAACC AGCATCACAG

34601  ATGCCAAATG GAACGCCGGA CGTAGTCATA TTTCCTGAAG CAAAACCAGG
       TACGGTTTAC CTTGCGGCCT GCATCAGTAT AAAGGACTTC GTTTTGGTCC

34651  TGCGGGCGTG ACAAACAGAT CTGCGTCTCC GGTCTCGCCG CTTAGATCGC
       ACGCCCGCAC TGTTTGTCTA GACGCAGAGG CCAGAGCGGC GAATCTAGCG

34701  TCTGTGTAGT AGTTGTAGTA TATCCACTCT CTCAAAGCAT CCAGGCGCCC
       AGACACATCA TCAACATCAT ATAGGTGAGA GAGTTTCGTA GGTCCGCGGG

34751  CCTGGCTTCG GGTTCTATGT AAACTCCTTC ATGCGCCGCT GCCCTGATAA
       GGACCGAAGC CCAAGATACA TTTGAGGAAG TACGCGGCGA CGGGACTATT

34801  CATCCACCAC CGCAGAATAA GCCACACCCA GCCAACCTAC ACATTCGTTC
       GTAGGTGGTG GCGTCTTATT CGGTGTGGGT CGGTTGGATG TGTAAGCAAG
```

FIG. 26A-41

```
34851  TGCGAGTCAC ACACGGGAGG AGCGGGAAGA GCTGGAAGAA CCATGTTTTT
       ACGCTCAGTG TGTGCCCTCC TCGCCCTTCT CGACCTTCTT GGTACAAAAA

34901  TTTTTTATTC CAAAAGATTA TCCAAAACCT CAAAATGAAG ATCTATTAAG
       AAAAAATAAG GTTTTCTAAT AGGTTTTGGA GTTTTACTTC TAGATAATTC

34951  TGAACGCGCT CCCCTCCGGT GGCGTGGTCA AACTCTACAG CCAAAGAACA
       ACTTGCGCGA GGGGAGGCCA CCGCACCAGT TTGAGATGTC GGTTTCTTGT

35001  GATAATGGCA TTTGTAAGAT GTTGCACAAT GGCTTCCAAA AGGCAAACGG
       CTATTACCGT AAACATTCTA CAACGTGTTA CCGAAGGTTT TCCGTTTGCC

35051  CCCTCACGTC CAAGTGGACG TAAAGGCTAA ACCCTTCAGG GTGAATCTCC
       GGGAGTGCAG GTTCACCTGC ATTTCCGATT TGGGAAGTCC CACTTAGAGG

35101  TCTATAAACA TTCCAGCACC TTCAACCATG CCCAAATAAT TCTCATCTCG
       AGATATTTGT AAGGTCGTGG AAGTTGGTAC GGGTTTATTA AGAGTAGAGC

35151  CCACCTTCTC AATATATCTC TAAGCAAATC CCGAATATTA AGTCCGGCCA
       GGTGGAAGAG TTATATAGAG ATTCGTTTAG GGCTTATAAT TCAGGCCGGT

35201  TTGTAAAAAT CTGCTCCAGA GCGCCCTCCA CCTTCAGCCT CAAGCAGCGA
       AACATTTTTA GACGAGGTCT CGCGGGAGGT GGAAGTCGGA GTTCGTCGCT

35251  ATCATGATTG CAAAAATTCA GGTTCCTCAC AGACCTGTAT AAGATTCAAA
       TAGTACTAAC GTTTTTAAGT CCAAGGAGTG TCTGGACATA TTCTAAGTTT

35301  AGCGGAACAT TAACAAAAAT ACCGCGATCC CGTAGGTCCC TTCGCAGGGC
       TCGCCTTGTA ATTGTTTTTA TGGCGCTAGG GCATCCAGGG AAGCGTCCCG

35351  CAGCTGAACA TAATCGTGCA GGTCTGCACG GACCAGCGCG GCCACTTCCC
       GTCGACTTGT ATTAGCACGT CCAGACGTGC CTGGTCGCGC CGGTGAAGGG

35401  CGCCAGGAAC CATGACAAAA GAACCCACAC TGATTATGAC ACGCATACTC
       GCGGTCCTTG GTACTGTTTT CTTGGGTGTG ACTAATACTG TGCGTATGAG

35451  GGAGCTATGC TAACCAGCGT AGCCCCGATG TAAGCTTGTT GCATGGGCGG
       CCTCGATACG ATTGGTCGCA TCGGGGCTAC ATTCGAACAA CGTACCCGCC

35501  CGATATAAAA TGCAAGGTGC TGCTCAAAAA ATCAGGCAAA GCCTCGCGCA
       GCTATATTTT ACGTTCCACG ACGAGTTTTT TAGTCCGTTT CGGAGCGCGT

35551  AAAAAGAAAG CACATCGTAG TCATGCTCAT GCAGATAAAG GCAGGTAAGC
       TTTTTCTTTC GTGTAGCATC AGTACGAGTA CGTCTATTTC CGTCCATTCG

35601  TCCGGAACCA CCACAGAAAA AGACACCATT TTTCTCTCAA ACATGTCTGC
       AGGCCTTGGT GGTGTCTTTT TCTGTGGTAA AAAGAGAGTT TGTACAGACG

35651  GGGTTTCTGC ATAAACACAA AATAAAATAA CAAAAAAACA TTTAAACATT
       CCCAAAGACG TATTTGTGTT TTATTTTATT GTTTTTTTGT AAATTTGTAA
```

FIG. 26A-42

```
35701  AGAAGCCTGT CTTACAACAG GAAAAACAAC CCTTATAAGC ATAAGACGGA
       TCTTCGGACA GAATGTTGTC CTTTTTGTTG GGAATATTCG TATTCTGCCT

35751  CTACGGCCAT GCCGGCGTGA CCGTAAAAAA ACTGGTCACC GTGATTAAAA
       GATGCCGGTA CGGCCGCACT GGCATTTTTT TGACCAGTGG CACTAATTTT

35801  AGCACCACCG ACAGCTCCTC GGTCATGTCC GGAGTCATAA TGTAAGACTC
       TCGTGGTGGC TGTCGAGGAG CCAGTACAGG CCTCAGTATT ACATTCTGAG

35851  GGTAAACACA TCAGGTTGAT TCACATCGGT CAGTGCTAAA AAGCGACCGA
       CCATTTGTGT AGTCCAACTA AGTGTAGCCA GTCACGATTT TTCGCTGGCT

35901  AATAGCCCGG GGGAATACAT ACCCGCAGGC GTAGAGACAA CATTACAGCC
       TTATCGGGCC CCCTTATGTA TGGGCGTCCG CATCTCTGTT GTAATGTCGG

35951  CCCATAGGAG GTATAACAAA ATTAATAGGA GAGAAAAACA CATAAACACC
       GGGTATCCTC CATATTGTTT TAATTATCCT CTCTTTTTGT GTATTTGTGG

36001  TGAAAAACCC TCCTGCCTAG GCAAAATAGC ACCCTCCCGC TCCAGAACAA
       ACTTTTTGGG AGGACGGATC CGTTTTATCG TGGGAGGGCG AGGTCTTGTT

36051  CATACAGCGC TTCCACAGCG GCAGCCATAA CAGTCAGCCT TACCAGTAAA
       GTATGTCGCG AAGGTGTCGC CGTCGGTATT GTCAGTCGGA ATGGTCATTT

36101  AAAGAAAACC TATTAAAAAA ACACCACTCG ACACGGCACC AGCTCAATCA
       TTTCTTTTGG ATAATTTTTT TGTGGTGAGC TGTGCCGTGG TCGAGTTAGT

36151  GTCACAGTGT AAAAAAGGGC CAAGTGCAGA GCGAGTATAT ATAGGACTAA
       CAGTGTCACA TTTTTTCCCG GTTCACGTCT CGCTCATATA TATCCTGATT

36201  AAAATGACGT AACGGTTAAA GTCCACAAAA AACACCCAGA AAACCGCACG
       TTTTACTGCA TTGCCAATTT CAGGTGTTTT TTGTGGGTCT TTTGGCGTGC

36251  CGAACCTACG CCCAGAAACG AAAGCCAAAA AACCCACAAC TTCCTCAAAT
       GCTTGGATGC GGGTCTTTGC TTTCGGTTTT TTGGGTGTTG AAGGAGTTTA

36301  CGTCACTTCC GTTTTCCCAC GTTACGTCAC TTCCCATTTT AAGAAAACTA
       GCAGTGAAGG CAAAAGGGTG CAATGCAGTG AAGGGTAAAA TTCTTTTGAT

36351  CAATTCCCAA CACATACAAG TTACTCCGCC CTAAAACCTA CGTCACCCGC
       GTTAAGGGTT GTGTATGTTC AATGAGGCGG GATTTTGGAT GCAGTGGGCG

36401  CCCGTTCCCA CGCCCCGCGC CACGTCACAA ACTCCACCCC CTCATTATCA
       GGGCAAGGGT GCGGGGCGCG GTGCAGTGTT TGAGGTGGGG GAGTAATAGT

                                                    PacI
                                                  ~~~~~~~~
36451  TATTGGCTTC AATCCAAAAT AAGGTATATT ATTGATGATG TTAATTAAGA
       ATAACCGAAG TTAGGTTTTA TTCCATATAA TAACTACTAC AATTAATTCT
```

FIG. 26A-43

```
36501  ATTCGGATCT GCGACGCGAG GCTGGATGGC CTTCCCCATT ATGATTCTTC
       TAAGCCTAGA CGCTGCGCTC CGACCTACCG GAAGGGGTAA TACTAAGAAG

36551  TCGCTTCCGG CGGCATCGGG ATGCCCGCGT TGCAGGCCAT GCTGTCCAGG
       AGCGAAGGCC GCCGTAGCCC TACGGGCGCA ACGTCCGGTA CGACAGGTCC

36601  CAGGTAGATG ACGACCATCA GGGACAGCTT CAAGGCCAGC AAAAGGCCAG
       GTCCATCTAC TGCTGGTAGT CCCTGTCGAA GTTCCGGTCG TTTTCCGGTC

36651  GAACCGTAAA AAGGCCGCGT TGCTGGCGTT TTTCCATAGG CTCCGCCCCC
       CTTGGCATTT TTCCGGCGCA ACGACCGCAA AAAGGTATCC GAGGCGGGGG

36701  CTGACGAGCA TCACAAAAAT CGACGCTCAA GTCAGAGGTG GCGAAACCCG
       GACTGCTCGT AGTGTTTTTA GCTGCGAGTT CAGTCTCCAC CGCTTTGGGC

36751  ACAGGACTAT AAAGATACCA GGCGTTTCCC CCTGGAAGCT CCCTCGTGCG
       TGTCCTGATA TTTCTATGGT CCGCAAAGGG GGACCTTCGA GGGAGCACGC

36801  CTCTCCTGTT CCGACCCTGC CGCTTACCGG ATACCTGTCC GCCTTTCTCC
       GAGAGGACAA GGCTGGGACG GCGAATGGCC TATGGACAGG CGGAAAGAGG

36851  CTTCGGGAAG CGTGGCGCTT TCTCATAGCT CACGCTGTAG GTATCTCAGT
       GAAGCCCTTC GCACCGCGAA AGAGTATCGA GTGCGACATC CATAGAGTCA

36901  TCGGTGTAGG TCGTTCGCTC CAAGCTGGGC TGTGTGCACG AACCCCCCGT
       AGCCACATCC AGCAAGCGAG GTTCGACCCG ACACACGTGC TTGGGGGGCA

36951  TCAGCCCGAC CGCTGCGCCT TATCCGGTAA CTATCGTCTT GAGTCCAACC
       AGTCGGGCTG GCGACGCGGA ATAGGCCATT GATAGCAGAA CTCAGGTTGG

37001  CGGTAAGACA CGACTTATCG CCACTGGCAG CAGCCACTGG TAACAGGATT
       GCCATTCTGT GCTGAATAGC GGTGACCGTC GTCGGTGACC ATTGTCCTAA

37051  AGCAGAGCGA GGTATGTAGG CGGTGCTACA GAGTTCTTGA AGTGGTGGCC
       TCGTCTCGCT CCATACATCC GCCACGATGT CTCAAGAACT TCACCACCGG

37101  TAACTACGGC TACACTAGAA GGACAGTATT TGGTATCTGC GCTCTGCTGA
       ATTGATGCCG ATGTGATCTT CCTGTCATAA ACCATAGACG CGAGACGACT

37151  AGCCAGTTAC CTTCGGAAAA AGAGTTGGTA GCTCTTGATC CGGCAAACAA
       TCGGTCAATG GAAGCCTTTT TCTCAACCAT CGAGAACTAG GCCGTTTGTT

37201  ACCACCGCTG GTAGCGGTGG TTTTTTTGTT TGCAAGCAGC AGATTACGCG
       TGGTGGCGAC CATCGCCACC AAAAAAACAA ACGTTCGTCG TCTAATGCGC

37251  CAGAAAAAAA GGATCTCAAG AAGATCCTTT GATCTTTTCT ACGGGGTCTG
       GTCTTTTTTT CCTAGAGTTC TTCTAGGAAA CTAGAAAAGA TGCCCCAGAC

37301  ACGCTCAGTG GAACGAAAAC TCACGTTAAG GGATTTTGGT CATGAGATTA
       TGCGAGTCAC CTTGCTTTTG AGTGCAATTC CCTAAAACCA GTACTCTAAT
```

FIG. 26A-44

```
37351  TCAAAAAGGA TCTTCACCTA GATCCTTTTA AATCAATCTA AAGTATATAT
       AGTTTTTCCT AGAAGTGGAT CTAGGAAAAT TTAGTTAGAT TTCATATATA

37401  GAGTAAACTT GGTCTGACAG TTACCAATGC TTAATCAGTG AGGCACCTAT
       CTCATTTGAA CCAGACTGTC AATGGTTACG AATTAGTCAC TCCGTGGATA

37451  CTCAGCGATC TGTCTATTTC GTTCATCCAT AGTTGCCTGA CTCCCCGTCG
       GAGTCGCTAG ACAGATAAAG CAAGTAGGTA TCAACGGACT GAGGGGCAGC

37501  TGTAGATAAC TACGATACGG GAGGGCTTAC CATCTGGCCC CAGTGCTGCA
       ACATCTATTG ATGCTATGCC CTCCCGAATG GTAGACCGGG GTCACGACGT

37551  ATGATACCGC GAGACCCACG CTCACCGGCT CCAGATTTAT CAGCAATAAA
       TACTATGGCG CTCTGGGTGC GAGTGGCCGA GGTCTAAATA GTCGTTATTT

37601  CCAGCCAGCC GGAAGGGCCG AGCGCAGAAG TGGTCCTGCA ACTTTATCCG
       GGTCGGTCGG CCTTCCCGGC TCGCGTCTTC ACCAGGACGT TGAAATAGGC

37651  CCTCCATCCA GTCTATTAAT TGTTGCCGGG AAGCTAGAGT AAGTAGTTCG
       GGAGGTAGGT CAGATAATTA ACAACGGCCC TTCGATCTCA TTCATCAAGC

37701  CCAGTTAATA GTTTGCGCAA CGTTGTTGCC ATTGCTACAG GCATCGTGGT
       GGTCAATTAT CAAACGCGTT GCAACAACGG TAACGATGTC CGTAGCACCA

37751  GTCACGCTCG TCGTTTGGTA TGGCTTCATT CAGCTCCGGT TCCCAACGAT
       CAGTGCGAGC AGCAAACCAT ACCGAAGTAA GTCGAGGCCA AGGGTTGCTA

37801  CAAGGCGAGT TACATGATCC CCCATGTTGT GCAAAAAAGC GGTTAGCTCC
       GTTCCGCTCA ATGTACTAGG GGGTACAACA CGTTTTTTCG CCAATCGAGG

37851  TTCGGTCCTC CGATCGTTGT CAGAAGTAAG TTGGCCGCAG TGTTATCACT
       AAGCCAGGAG GCTAGCAACA GTCTTCATTC AACCGGCGTC ACAATAGTGA

37901  CATGGTTATG GCAGCACTGC ATAATTCTCT TACTGTCATG CCATCCGTAA
       GTACCAATAC CGTCGTGACG TATTAAGAGA ATGACAGTAC GGTAGGCATT

37951  GATGCTTTTC TGTGACTGGT GAGTACTCAA CCAAGTCATT CTGAGAATAG
       CTACGAAAAG ACACTGACCA CTCATGAGTT GGTTCAGTAA GACTCTTATC

38001  TGTATGCGGC GACCGAGTTG CTCTTGCCCG GCGTCAACAC GGGATAATAC
       ACATACGCCG CTGGCTCAAC GAGAACGGGC CGCAGTTGTG CCCTATTATG

38051  CGCGCCACAT AGCAGAACTT TAAAAGTGCT CATCATTGGA AAACGTTCTT
       GCGCGGTGTA TCGTCTTGAA ATTTTCACGA GTAGTAACCT TTTGCAAGAA

38101  CGGGGCGAAA ACTCTCAAGG ATCTTACCGC TGTTGAGATC CAGTTCGATG
       GCCCCGCTTT TGAGAGTTCC TAGAATGGCG ACAACTCTAG GTCAAGCTAC

38151  TAACCCACTC GTGCACCCAA CTGATCTTCA GCATCTTTTA CTTTCACCAG
       ATTGGGTGAG CACGTGGGTT GACTAGAAGT CGTAGAAAAT GAAAGTGGTC
```

FIG. 26A-45

```
38201  CGTTTCTGGG TGAGCAAAAA CAGGAAGGCA AAATGCCGCA AAAAAGGGAA
       GCAAAGACCC ACTCGTTTTT GTCCTTCCGT TTTACGGCGT TTTTTCCCTT

38251  TAAGGGCGAC ACGGAAATGT TGAATACTCA TACTCTTCCT TTTTCAATAT
       ATTCCCGCTG TGCCTTTACA ACTTATGAGT ATGAGAAGGA AAAAGTTATA

38301  TATTGAAGCA TTTATCAGGG TTATTGTCTC ATGAGCGGAT ACATATTTGA
       ATAACTTCGT AAATAGTCCC AATAACAGAG TACTCGCCTA TGTATAAACT

38351  ATGTATTTAG AAAAATAAAC AAATAGGGGT TCCGCGCACA TTTCCCCGAA
       TACATAAATC TTTTTATTTG TTTATCCCCA AGGCGCGTGT AAAGGGGCTT

38401  AAGTGCCACC TGACGTCTAA GAAACCATTA TTATCATGAC ATTAACCTAT
       TTCACGGTGG ACTGCAGATT CTTTGGTAAT AATAGTACTG TAATTGGATA

38451  AAAAATAGGC GTATCACGAG GCCCTTTCGT CTTCAAGAAT TGGATCCGAA
       TTTTTATCCG CATAGTGCTC CGGGAAAGCA GAAGTTCTTA ACCTAGGCTT

                        PacI
                      ~~~~~~~
38501  TTCTTAATTT CTTAATTAA   (SEQ ID NO: 28)
       AAGAATTAAA GAATTAATT   (SEQ ID NO: 29)
```

FIG. 26A-46

```
1    CATCATCAAT AATATACCTT ATTTTGGATT GAAGCCAATA TGATAATGAG
     GTAGTAGTTA TTATATGGAA TAAAACCTAA CTTCGGTTAT ACTATTACTC

51   GGGGTGGAGT TTGTGACGTG GCGCGGGGCG TGGGAACGGG GCGGGTGACG
     CCCCACCTCA AACACTGCAC CGCGCCCCGC ACCCTTGCCC CGCCCACTGC

101  TAGTAGTGTG GCGGAAGTGT GATGTTGCAA GTGTGGCGGA ACACATGTAA
     ATCATCACAC CGCCTTCACA CTACAACGTT CACACCGCCT TGTGTACATT

151  GCGACGGATG TGGCAAAAGT GACGTTTTTG GTGTGCGCCG GTGTACACAG
     CGCTGCCTAC ACCGTTTTCA CTGCAAAAAC CACACGCGGC CACATGTGTC

201  GAAGTGACAA TTTTCGCGCG GTTTTAGGCG GATGTTGTAG TAAATTTGGG
     CTTCACTGTT AAAAGCGCGC CAAAATCCGC CTACAACATC ATTTAAACCC

251  CGTAACCGAG TAAGATTTGG CCATTTTCGC GGGAAAACTG AATAAGAGGA
     GCATTGGCTC ATTCTAAACC GGTAAAAGCG CCCTTTTGAC TTATTCTCCT

301  AGTGAAATCT GAATAATTTT GTGTTACTCA TAGCGCGTAA TATTTGTCTA
     TCACTTTAGA CTTATTAAAA CACAATGAGT ATCGCGCATT ATAAACAGAT

351  GGGCCGCGGG GACTTTGACC GTTTACGTGG AGACTCGCCC AGGTGTTTTT
     CCCGGCGCCC CTGAAACTGG CAAATGCACC TCTGAGCGGG TCCACAAAAA

401  CTCAGGTGTT TTCCGCGTTC CGGGTCAAAG TTGGCGTTTT ATTATTATAG
     GAGTCCACAA AAGGCGCAAG GCCCAGTTTC AACCGCAAAA TAATAATATC

451  GCGGCCGCGA TCCATTGCAT ACGTTGTATC CATATCATAA TATGTACATT
     CGCCGGCGCT AGGTAACGTA TGCAACATAG GTATAGTATT ATACATGTAA

501  TATATTGGCT CATGTCCAAC ATTACCGCCA TGTTGACATT GATTATTGAC
     ATATAACCGA GTACAGGTTG TAATGGCGGT ACAACTGTAA CTAATAACTG

551  TAGTTATTAA TAGTAATCAA TTACGGGGTC ATTAGTTCAT AGCCCATATA
     ATCAATAATT ATCATTAGTT AATGCCCCAG TAATCAAGTA TCGGGTATAT

601  TGGAGTTCCG CGTTACATAA CTTACGGTAA ATGGCCCGCC TGGCTGACCG
     ACCTCAAGGC GCAATGTATT GAATGCCATT TACCGGGCGG ACCGACTGGC

651  CCCAACGACC CCCGCCCATT GACGTCAATA ATGACGTATG TTCCCATAGT
     GGGTTGCTGG GGGCGGGTAA CTGCAGTTAT TACTGCATAC AAGGGTATCA

701  AACGCCAATA GGGACTTTCC ATTGACGTCA ATGGGTGGAG TATTTACGGT
     TTGCGGTTAT CCCTGAAAGG TAACTGCAGT TACCCACCTC ATAAATGCCA

751  AAACTGCCCA CTTGGCAGTA CATCAAGTGT ATCATATGCC AAGTACGCCC
     TTTGACGGGT GAACCGTCAT GTAGTTCACA TAGTATACGG TTCATGCGGG

801  CCTATTGACG TCAATGACGG TAAATGGCCC GCCTGGCATT ATGCCCAGTA
     GGATAACTGC AGTTACTGCC ATTTACCGGG CGGACCGTAA TACGGGTCAT
```

FIG. 27A-1

```
 851  CATGACCTTA TGGGACTTTC CTACTTGGCA GTACATCTAC GTATTAGTCA
      GTACTGGAAT ACCCTGAAAG GATGAACCGT CATGTAGATG CATAATCAGT

 901  TCGCTATTAC CATGGTGATG CGGTTTTGGC AGTACATCAA TGGGCGTGGA
      AGCGATAATG GTACCACTAC GCCAAAACCG TCATGTAGTT ACCCGCACCT

 951  TAGCGGTTTG ACTCACGGGG ATTTCCAAGT CTCCACCCCA TTGACGTCAA
      ATCGCCAAAC TGAGTGCCCC TAAAGGTTCA GAGGTGGGGT AACTGCAGTT

1001  TGGGAGTTTG TTTTGGCACC AAAATCAACG GGACTTTCCA AAATGTCGTA
      ACCCTCAAAC AAAACCGTGG TTTTAGTTGC CCTGAAAGGT TTTACAGCAT

1051  ACAACTCCGC CCCATTGACG CAAATGGGCG GTAGGCGTGT ACGGTGGGAG
      TGTTGAGGCG GGGTAACTGC GTTTACCCGC CATCCGCACA TGCCACCCTC

1101  GTCTATATAA GCAGAGCTCG TTTAGTGAAC CGTCAGATCG CCTGGAGACG
      CAGATATATT CGTCTCGAGC AAATCACTTG GCAGTCTAGC GGACCTCTGC

1151  CCATCCACGC TGTTTTGACC TCCATAGAAG ACACCGGGAC CGATCCAGCC
      GGTAGGTGCG ACAAAACTGG AGGTATCTTC TGTGGCCCTG GCTAGGTCGG

1201  TCCGCGGCCG GGAACGGTGC ATTGGAACGC GGATTCCCCG TGCCAAGAGT
      AGGCGCCGGC CCTTGCCACG TAACCTTGCG CCTAAGGGGC ACGGTTCTCA

1251  GAGATCTGCC ACCATGGCCG GCAAGTGGTC CAAGAGGTCC GTGCCCGGCT
      CTCTAGACGG TGGTACCGGC CGTTCACCAG GTTCTCCAGG CACGGGCCGA

1301  GGTCCACCGT GAGGGAGAGG ATGAGGAGGG CCGAGCCCGC CGCCGACAGG
      CCAGGTGGCA CTCCCTCTCC TACTCCTCCC GGCTCGGGCG GCGGCTGTCC

1351  GTGAGGAGGA CCGAGCCCGC CGCAGTGGGC GTGGGCGCCG TGTCCAGGGA
      CACTCCTCCT GGCTCGGGCG GCGTCACCCG CACCCGCGGC ACAGGTCCCT

1401  CCTGGAGAAG CACGGCGCCA TCACCTCCTC CAACACCGCC GCCACCAACG
      GGACCTCTTC GTGCCGCGGT AGTGGAGGAG GTTGTGGCGG CGGTGGTTGC

1451  CCGACTGCGC CTGGCTGGAG GCCCAGGAGG ACGAGGAGGT GGGCTTCCCC
      GGCTGACGCG GACCGACCTC CGGGTCCTCC TGCTCCTCCA CCCGAAGGGG

1501  GTGAGGCCCC AGGTGCCCCT GAGGCCCATG ACCTACAAGG GCGCCGTGGA
      CACTCCGGGG TCCACGGGGA CTCCGGGTAC TGGATGTTCC CGCGGCACCT

1551  CCTGTCCCAC TTCCTGAAGG AGAAGGGCGG CCTGGAGGGC CTGATCCACT
      GGACAGGGTG AAGGACTTCC TCTTCCCGCC GGACCTCCCG GACTAGGTGA

1601  CCCAGAAGAG GCAGGACATC CTGGACCTGT GGGTGTACCA CACCCAGGGC
      GGGTCTTCTC CGTCCTGTAG GACCTGGACA CCCACATGGT GTGGGTCCCG

1651  TACTTCCCCG ACTGGCAGAA CTACACCCCC GGCCCCGGCA TCAGGTTCCC
      ATGAAGGGGC TGACCGTCTT GATGTGGGGG CCGGGGCCGT AGTCCAAGGG
```

FIG. 27A-2

```
1701  CCTGACCTTC GGCTGGTGCT TCAAGCTGGT GCCCGTGGAG CCCGAGAAGG
      GGACTGGAAG CCGACCACGA AGTTCGACCA CGGGCACCTC GGGCTCTTCC

1751  TGGAGGAGGC CAACGAGGGC GAGAACAACT GCGCCGCCCA CCCCATGTCC
      ACCTCCTCCG GTTGCTCCCG CTCTTGTTGA CGCGGCGGGT GGGGTACAGG

1801  CAGCACGGCA TCGAGGACCC CGAGAAGGAG GTGCTGGAGT GGAGGTTCGA
      GTCGTGCCGT AGCTCCTGGG GCTCTTCCTC CACGACCTCA CCTCCAAGCT

1851  CTCCAAGCTG GCCTTCCACC ACGTGGCCAG GGAGCTGCAC CCCGAGTACT
      GAGGTTCGAC CGGAAGGTGG TGCACCGGTC CCTCGACGTG GGGCTCATGA

1901  ACAAGGACTG CTAAAGCCCG GGCAGATCTG CTGTGCCTTC TAGTTGCCAG
      TGTTCCTGAC GATTTCGGGC CCGTCTAGAC GACACGGAAG ATCAACGGTC

1951  CCATCTGTTG TTTGCCCCTC CCCCGTGCCT TCCTTGACCC TGGAAGGTGC
      GGTAGACAAC AAACGGGGAG GGGGCACGGA AGGAACTGGG ACCTTCCACG

2001  CACTCCCACT GTCCTTTCCT AATAAAATGA GGAAATTGCA TCGCATTGTC
      GTGAGGGTGA CAGGAAAGGA TTATTTTACT CCTTTAACGT AGCGTAACAG

2051  TGAGTAGGTG TCATTCTATT CTGGGGGGTG GGGTGGGGCA GGACAGCAAG
      ACTCATCCAC AGTAAGATAA GACCCCCCAC CCCACCCCGT CCTGTCGTTC

2101  GGGGAGGATT GGGAAGACAA TAGCAGGCAT GCTGGGGATG CGGTGGGCTC
      CCCCTCCTAA CCCTTCTGTT ATCGTCCGTA CGACCCCTAC GCCACCCGAG

2151  TATGGCCGAT CGGCGCGCCG TACTGAAATG TGTGGGCGTG GCTTAAGGGT
      ATACCGGCTA GCCGCGCGGC ATGACTTTAC ACACCCGCAC CGAATTCCCA

2201  GGGAAAGAAT ATATAAGGTG GGGGTCTTAT GTAGTTTTGT ATCTGTTTTG
      CCCTTTCTTA TATATTCCAC CCCCAGAATA CATCAAAACA TAGACAAAAC

2251  CAGCAGCCGC CGCCGCCATG AGCACCAACT CGTTTGATGG AAGCATTGTG
      GTCGTCGGCG GCGGCGGTAC TCGTGGTTGA GCAAACTACC TTCGTAACAC

2301  AGCTCATATT TGACAACGCG CATGCCCCCA TGGGCCGGGG TGCGTCAGAA
      TCGAGTATAA ACTGTTGCGC GTACGGGGGT ACCCGGCCCC ACGCAGTCTT

2351  TGTGATGGGC TCCAGCATTG ATGGTCGCCC CGTCCTGCCC GCAAACTCTA
      ACACTACCCG AGGTCGTAAC TACCAGCGGG GCAGGACGGG CGTTTGAGAT

2401  CTACCTTGAC CTACGAGACC GTGTCTGGAA CGCCGTTGGA GACTGCAGCC
      GATGGAACTG GATGCTCTGG CACAGACCTT GCGGCAACCT CTGACGTCGG

2451  TCCGCCGCCG CTTCAGCCGC TGCAGCCACC GCCCGCGGGA TTGTGACTGA
      AGGCGGCGGC GAAGTCGGCG ACGTCGGTGG CGGGCGCCCT AACACTGACT

2501  CTTTGCTTTC CTGAGCCCGC TTGCAAACAG TGCAGCTTCC CGTTCATCCG
      GAAACGAAAG GACTCGGGCG AACGTTTGTC ACGTCGAAGG GCAAGTAGGC
```

FIG. 27A-3

```
2551  CCCGCGATGA CAAGTTGACG GCTCTTTTGG CACAATTGGA TTCTTTGACC
      GGGCGCTACT GTTCAACTGC CGAGAAAACC GTGTTAACCT AAGAAACTGG

2601  CGGGAACTTA ATGTCGTTTC TCAGCAGCTG TTGGATCTGC GCCAGCAGGT
      GCCCTTGAAT TACAGCAAAG AGTCGTCGAC AACCTAGACG CGGTCGTCCA

2651  TTCTGCCCTG AAGGCTTCCT CCCCTCCCAA TGCGGTTTAA AACATAAATA
      AAGACGGGAC TTCCGAAGGA GGGGAGGGTT ACGCCAAATT TTGTATTTAT

2701  AAAAACCAGA CTCTGTTTGG ATTTGGATCA AGCAAGTGTC TTGCTGTCTT
      TTTTTGGTCT GAGACAAACC TAAACCTAGT TCGTTCACAG AACGACAGAA

2751  TATTTAGGGG TTTTGCGCGC GCGGTAGGCC CGGGACCAGC GGTCTCGGTC
      ATAAATCCCC AAAACGCGCG CGCCATCCGG GCCCTGGTCG CCAGAGCCAG

2801  GTTGAGGGTC CTGTGTATTT TTTCCAGGAC GTGGTAAAGG TGACTCTGGA
      CAACTCCCAG GACACATAAA AAAGGTCCTG CACCATTTCC ACTGAGACCT

2851  TGTTCAGATA CATGGGCATA AGCCCGTCTC TGGGGTGGAG GTAGCACCAC
      ACAAGTCTAT GTACCCGTAT TCGGGCAGAG ACCCCACCTC CATCGTGGTG

2901  TGCAGAGCTT CATGCTGCGG GGTGGTGTTG TAGATGATCC AGTCGTAGCA
      ACGTCTCGAA GTACGACGCC CCACCACAAC ATCTACTAGG TCAGCATCGT

2951  GGAGCGCTGG GCGTGGTGCC TAAAAATGTC TTTCAGTAGC AAGCTGATTG
      CCTCGCGACC CGCACCACGG ATTTTTACAG AAAGTCATCG TTCGACTAAC

3001  CCAGGGGCAG GCCCTTGGTG TAAGTGTTTA CAAAGCGGTT AAGCTGGGAT
      GGTCCCCGTC CGGGAACCAC ATTCACAAAT GTTTCGCCAA TTCGACCCTA

3051  GGGTGCATAC GTGGGGATAT GAGATGCATC TTGGACTGTA TTTTTAGGTT
      CCCACGTATG CACCCCTATA CTCTACGTAG AACCTGACAT AAAAATCCAA

3101  GGCTATGTTC CCAGCCATAT CCCTCCGGGG ATTCATGTTG TGCAGAACCA
      CCGATACAAG GGTCGGTATA GGGAGGCCCC TAAGTACAAC ACGTCTTGGT

3151  CCAGCACAGT GTATCCGGTG CACTTGGGAA ATTTGTCATG TAGCTTAGAA
      GGTCGTGTCA CATAGGCCAC GTGAACCCTT TAAACAGTAC ATCGAATCTT

3201  GGAAATGCGT GGAAGAACTT GGAGACGCCC TTGTGACCTC CAAGATTTTC
      CCTTTACGCA CCTTCTTGAA CCTCTGCGGG AACACTGGAG GTTCTAAAAG

3251  CATGCATTCG TCCATAATGA TGGCAATGGG CCCACGGGCG GCGGCCTGGG
      GTACGTAAGC AGGTATTACT ACCGTTACCC GGGTGCCCGC CGCCGGACCC

3301  CGAAGATATT TCTGGGATCA CTAACGTCAT AGTTGTGTTC CAGGATGAGA
      GCTTCTATAA AGACCCTAGT GATTGCAGTA TCAACACAAG GTCCTACTCT

3351  TCGTCATAGG CCATTTTTAC AAAGCGCGGG CGGAGGGTGC CAGACTGCGG
      AGCAGTATCC GGTAAAAATG TTTCGCGCCC GCCTCCCACG GTCTGACGCC
```

FIG. 27A-4

```
3401  TATAATGGTT CCATCCGGCC CAGGGGCGTA GTTACCCTCA CAGATTTGCA
      ATATTACCAA GGTAGGCCGG GTCCCCGCAT CAATGGGAGT GTCTAAACGT

3451  TTTCCCACGC TTTGAGTTCA GATGGGGGGA TCATGTCTAC CTGCGGGGCG
      AAAGGGTGCG AAACTCAAGT CTACCCCCCT AGTACAGATG GACGCCCCGC

3501  ATGAAGAAAA CGGTTTCCGG GGTAGGGGAG ATCAGCTGGG AAGAAAGCAG
      TACTTCTTTT GCCAAAGGCC CCATCCCCTC TAGTCGACCC TTCTTTCGTC

3551  GTTCCTGAGC AGCTGCGACT TACCGCAGCC GGTGGGCCCG TAAATCACAC
      CAAGGACTCG TCGACGCTGA ATGGCGTCGG CCACCCGGGC ATTTAGTGTG

3601  CTATTACCGG CTGCAACTGG TAGTTAAGAG AGCTGCAGCT GCCGTCATCC
      GATAATGGCC GACGTTGACC ATCAATTCTC TCGACGTCGA CGGCAGTAGG

3651  CTGAGCAGGG GGGCCACTTC GTTAAGCATG TCCCTGACTC GCATGTTTTC
      GACTCGTCCC CCCGGTGAAG CAATTCGTAC AGGGACTGAG CGTACAAAAG

3701  CCTGACCAAA TCCGCCAGAA GGCGCTCGCC GCCCAGCGAT AGCAGTTCTT
      GGACTGGTTT AGGCGGTCTT CCGCGAGCGG CGGGTCGCTA TCGTCAAGAA

3751  GCAAGGAAGC AAAGTTTTTC AACGGTTTGA GACCGTCCGC CGTAGGCATG
      CGTTCCTTCG TTTCAAAAAG TTGCCAAACT CTGGCAGGCG GCATCCGTAC

3801  CTTTTGAGCG TTTGACCAAG CAGTTCCAGG CGGTCCCACA GCTCGGTCAC
      GAAAACTCGC AAACTGGTTC GTCAAGGTCC GCCAGGGTGT CGAGCCAGTG

3851  CTGCTCTACG GCATCTCGAT CCAGCATATC TCCTCGTTTC GCGGGTTGGG
      GACGAGATGC CGTAGAGCTA GGTCGTATAG AGGAGCAAAG CGCCCAACCC

3901  GCGGCTTTCG CTGTACGGCA GTAGTCGGTG CTCGTCCAGA CGGGCCAGGG
      CGCCGAAAGC GACATGCCGT CATCAGCCAC GAGCAGGTCT GCCCGGTCCC

3951  TCATGTCTTT CCACGGGCGC AGGGTCCTCG TCAGCGTAGT CTGGGTCACG
      AGTACAGAAA GGTGCCCGCG TCCCAGGAGC AGTCGCATCA GACCCAGTGC

4001  GTGAAGGGGT GCGCTCCGGG CTGCGCGCTG GCCAGGGTGC GCTTGAGGCT
      CACTTCCCCA CGCGAGGCCC GACGCGCGAC CGGTCCCACG CGAACTCCGA

4051  GGTCCTGCTG GTGCTGAAGC GCTGCCGGTC TTCGCCCTGC GCGTCGGCCA
      CCAGGACGAC CACGACTTCG CGACGGCCAG AAGCGGGACG CGCAGCCGGT

4101  GGTAGCATTT GACCATGGTG TCATAGTCCA GCCCCTCCGC GGCGTGGCCC
      CCATCGTAAA CTGGTACCAC AGTATCAGGT CGGGGAGGCG CCGCACCGGG

4151  TTGGCGCGCA GCTTGCCCTT GGAGGAGGCG CCGCACGAGG GGCAGTGCAG
      AACCGCGCGT CGAACGGGAA CCTCCTCCGC GGCGTGCTCC CCGTCACGTC

4201  ACTTTTGAGG GCGTAGAGCT TGGGCGCGAG AAATACCGAT TCCGGGGAGT
      TGAAAACTCC CGCATCTCGA ACCCGCGCTC TTTATGGCTA AGGCCCCTCA
```

FIG. 27A-5

```
4251  AGGCATCCGC GCCGCAGGCC CCGCAGACGG TCTCGCATTC CACGAGCCAG
      TCCGTAGGCG CGGCGTCCGG GGCGTCTGCC AGAGCGTAAG GTGCTCGGTC

4301  GTGAGCTCTG GCCGTTCGGG GTCAAAAACC AGGTTTCCCC CATGCTTTTT
      CACTCGAGAC CGGCAAGCCC CAGTTTTTGG TCCAAAGGGG GTACGAAAAA

4351  GATGCGTTTC TTACCTCTGG TTTCCATGAG CCGGTGTCCA CGCTCGGTGA
      CTACGCAAAG AATGGAGACC AAAGGTACTC GGCCACAGGT GCGAGCCACT

4401  CGAAAAGGCT GTCCGTGTCC CCGTATACAG ACTTGAGAGG CCTGTCCTCG
      GCTTTTCCGA CAGGCACAGG GGCATATGTC TGAACTCTCC GGACAGGAGC

4451  AGCGGTGTTC CGCGGTCCTC CTCGTATAGA AACTCGGACC ACTCTGAGAC
      TCGCCACAAG GCGCCAGGAG GAGCATATCT TTGAGCCTGG TGAGACTCTG

4501  AAAGGCTCGC GTCCAGGCCA GCACGAAGGA GGCTAAGTGG GAGGGGTAGC
      TTTCCGAGCG CAGGTCCGGT CGTGCTTCCT CCGATTCACC CTCCCCATCG

4551  GGTCGTTGTC CACTAGGGGG TCCACTCGCT CCAGGGTGTG AAGACACATG
      CCAGCAACAG GTGATCCCCC AGGTGAGCGA GGTCCCACAC TTCTGTGTAC

4601  TCGCCCTCTT CGGCATCAAG GAAGGTGATT GGTTTGTAGG TGTAGGCCAC
      AGCGGGAGAA GCCGTAGTTC CTTCCACTAA CCAAACATCC ACATCCGGTG

4651  GTGACCGGGT GTTCCTGAAG GGGGGCTATA AAAGGGGGTG GGGGCGCGTT
      CACTGGCCCA CAAGGACTTC CCCCCGATAT TTTCCCCCAC CCCCGCGCAA

4701  CGTCCTCACT CTCTTCCGCA TCGCTGTCTG CGAGGGCCAG CTGTTGGGGT
      GCAGGAGTGA GAGAAGGCGT AGCGACAGAC GCTCCCGGTC GACAACCCCA

4751  GAGTACTCCC TCTGAAAAGC GGGCATGACT TCTGCGCTAA GATTGTCAGT
      CTCATGAGGG AGACTTTTCG CCCGTACTGA AGACGCGATT CTAACAGTCA

4801  TTCCAAAAAC GAGGAGGATT TGATATTCAC CTGGCCCGCG GTGATGCCTT
      AAGGTTTTTG CTCCTCCTAA ACTATAAGTG GACCGGGCGC CACTACGGAA

4851  TGAGGGTGGC CGCATCCATC TGGTCAGAAA AGACAATCTT TTTGTTGTCA
      ACTCCCACCG GCGTAGGTAG ACCAGTCTTT TCTGTTAGAA AAACAACAGT

4901  AGCTTGGTGG CAAACGACCC GTAGAGGGCG TTGGACAGCA ACTTGGCGAT
      TCGAACCACC GTTTGCTGGG CATCTCCCGC AACCTGTCGT TGAACCGCTA

4951  GGAGCGCAGG GTTTGGTTTT TGTCGCGATC GGCGCGCTCC TTGGCCGCGA
      CCTCGCGTCC CAAACCAAAA ACAGCGCTAG CCGCGCGAGG AACCGGCGCT

5001  TGTTTAGCTG CACGTATTCG CGCGCAACGC ACCGCCATTC GGGAAAGACG
      ACAAATCGAC GTGCATAAGC GCGCGTTGCG TGGCGGTAAG CCCTTTCTGC

5051  GTGGTGCGCT CGTCGGGCAC CAGGTGCACG CGCCAACCGC GGTTGTGCAG
      CACCACGCGA GCAGCCCGTG GTCCACGTGC GCGGTTGGCG CCAACACGTC
```

FIG. 27A-6

```
5101  GGTGACAAGG TCAACGCTGG TGGCTACCTC TCCGCGTAGG CGCTCGTTGG
      CCACTGTTCC AGTTGCGACC ACCGATGGAG AGGCGCATCC GCGAGCAACC

5151  TCCAGCAGAG GCGGCCGCCC TTGCGCGAGC AGAATGGCGG TAGGGGGTCT
      AGGTCGTCTC CGCCGGCGGG AACGCGCTCG TCTTACCGCC ATCCCCCAGA

5201  AGCTGCGTCT CGTCCGGGGG GTCTGCGTCC ACGGTAAAGA CCCCGGGCAG
      TCGACGCAGA GCAGGCCCCC CAGACGCAGG TGCCATTTCT GGGGCCCGTC

5251  CAGGCGCGCG TCGAAGTAGT CTATCTTGCA TCCTTGCAAG TCTAGCGCCT
      GTCCGCGCGC AGCTTCATCA GATAGAACGT AGGAACGTTC AGATCGCGGA

5301  GCTGCCATGC GCGGGCGGCA AGCGCGCGCT CGTATGGGTT GAGTGGGGGA
      CGACGGTACG CGCCCGCCGT TCGCGCGCGA GCATACCCAA CTCACCCCCT

5351  CCCCATGGCA TGGGGTGGGT GAGCGCGGAG GCGTACATGC CGCAAATGTC
      GGGGTACCGT ACCCCACCCA CTCGCGCCTC CGCATGTACG GCGTTTACAG

5401  GTAAACGTAG AGGGGCTCTC TGAGTATTCC AAGATATGTA GGGTAGCATC
      CATTTGCATC TCCCCGAGAG ACTCATAAGG TTCTATACAT CCCATCGTAG

5451  TTCCACCGCG GATGCTGGCG CGCACGTAAT CGTATAGTTC GTGCGAGGGA
      AAGGTGGCGC CTACGACCGC GCGTGCATTA GCATATCAAG CACGCTCCCT

5501  GCGAGGAGGT CGGGACCGAG GTTGCTACGG GCGGGCTGCT CTGCTCGGAA
      CGCTCCTCCA GCCCTGGCTC CAACGATGCC CGCCCGACGA GACGAGCCTT

5551  GACTATCTGC CTGAAGATGG CATGTGAGTT GGATGATATG GTTGGACGCT
      CTGATAGACG GACTTCTACC GTACACTCAA CCTACTATAC CAACCTGCGA

5601  GGAAGACGTT GAAGCTGGCG TCTGTGAGAC CTACCGCGTC ACGCACGAAG
      CCTTCTGCAA CTTCGACCGC AGACACTCTG GATGGCGCAG TGCGTGCTTC

5651  GAGGCGTAGG AGTCGCGCAG CTTGTTGACC AGCTCGGCGG TGACCTGCAC
      CTCCGCATCC TCAGCGCGTC GAACAACTGG TCGAGCCGCC ACTGGACGTG

5701  GTCTAGGGCG CAGTAGTCCA GGGTTTCCTT GATGATGTCA TACTTATCCT
      CAGATCCCGC GTCATCAGGT CCCAAAGGAA CTACTACAGT ATGAATAGGA

5751  GTCCCTTTTT TTTCCACAGC TCGCGGTTGA GGACAAACTC TTCGCGGTCT
      CAGGGAAAAA AAAGGTGTCG AGCGCCAACT CCTGTTTGAG AAGCGCCAGA

5801  TTCCAGTACT CTTGGATCGG AAACCCGTCG GCCTCCGAAC GGTAAGAGCC
      AAGGTCATGA GAACCTAGCC TTTGGGCAGC CGGAGGCTTG CCATTCTCGG

5851  TAGCATGTAG AACTGGTTGA CGGCCTGGTA GGCGCAGCAT CCCTTTTCTA
      ATCGTACATC TTGACCAACT GCCGGACCAT CCGCGTCGTA GGGAAAAGAT

5901  CGGGTAGCGC GTATGCCTGC GCGGCCTTCC GGAGCGAGGT GTGGGTGAGC
      GCCCATCGCG CATACGGACG CGCCGGAAGG CCTCGCTCCA CACCCACTCG
```

FIG. 27A-7

```
5951  GCAAAGGTGT CCCTGACCAT GACTTTGAGG TACTGGTATT TGAAGTCAGT
      CGTTTCCACA GGGACTGGTA CTGAAACTCC ATGACCATAA ACTTCAGTCA

6001  GTCGTCGCAT CCGCCCTGCT CCCAGAGCAA AAAGTCCGTG CGCTTTTTGG
      CAGCAGCGTA GGCGGGACGA GGGTCTCGTT TTTCAGGCAC GCGAAAAACC

6051  AACGCGGATT TGGCAGGGCG AAGGTGACAT CGTTGAAGAG TATCTTTCCC
      TTGCGCCTAA ACCGTCCCGC TTCCACTGTA GCAACTTCTC ATAGAAAGGG

6101  GCGCGAGGCA TAAAGTTGCG TGTGATGCGG AAGGGTCCCG GCACCTCGGA
      CGCGCTCCGT ATTTCAACGC ACACTACGCC TTCCCAGGGC CGTGGAGCCT

6151  ACGGTTGTTA ATTACCTGGG CGGCGAGCAC GATCTCGTCA AAGCCGTTGA
      TGCCAACAAT TAATGGACCC GCCGCTCGTG CTAGAGCAGT TTCGGCAACT

6201  TGTTGTGGCC CACAATGTAA AGTTCCAAGA AGCGCGGGAT GCCCTTGATG
      ACAACACCGG GTGTTACATT TCAAGGTTCT TCGCGCCCTA CGGGAACTAC

6251  GAAGGCAATT TTTTAAGTTC CTCGTAGGTG AGCTCTTCAG GGGAGCTGAG
      CTTCCGTTAA AAAATTCAAG GAGCATCCAC TCGAGAAGTC CCCTCGACTC

6301  CCCGTGCTCT GAAAGGGCCC AGTCTGCAAG ATGAGGGTTG GAAGCGACGA
      GGGCACGAGA CTTTCCCGGG TCAGACGTTC TACTCCCAAC CTTCGCTGCT

6351  ATGAGCTCCA CAGGTCACGG GCCATTAGCA TTTGCAGGTG GTCGCGAAAG
      TACTCGAGGT GTCCAGTGCC CGGTAATCGT AAACGTCCAC CAGCGCTTTC

6401  GTCCTAAACT GGCGACCTAT GGCCATTTTT TCTGGGGTGA TGCAGTAGAA
      CAGGATTTGA CCGCTGGATA CCGGTAAAAA AGACCCCACT ACGTCATCTT

6451  GGTAAGCGGG TCTTGTTCCC AGCGGTCCCA TCCAAGGTTC GCGGCTAGGT
      CCATTCGCCC AGAACAAGGG TCGCCAGGGT AGGTTCCAAG CGCCGATCCA

6501  CTCGCGCGGC AGTCACTAGA GGCTCATCTC CGCCGAACTT CATGACCAGC
      GAGCGCGCCG TCAGTGATCT CCGAGTAGAG GCGGCTTGAA GTACTGGTCG

6551  ATGAAGGGCA CGAGCTGCTT CCCAAAGGCC CCCATCCAAG TATAGGTCTC
      TACTTCCCGT GCTCGACGAA GGGTTTCCGG GGGTAGGTTC ATATCCAGAG

6601  TACATCGTAG GTGACAAAGA GACGCTCGGT GCGAGGATGC GAGCCGATCG
      ATGTAGCATC CACTGTTTCT CTGCGAGCCA CGCTCCTACG CTCGGCTAGC

6651  GGAAGAACTG GATCTCCCGC CACCAATTGG AGGAGTGGCT ATTGATGTGG
      CCTTCTTGAC CTAGAGGGCG GTGGTTAACC TCCTCACCGA TAACTACACC

6701  TGAAAGTAGA AGTCCCTGCG ACGGGCCGAA CACTCGTGCT GGCTTTTGTA
      ACTTTCATCT TCAGGGACGC TGCCCGGCTT GTGAGCACGA CCGAAAACAT

6751  AAAACGTGCG CAGTACTGGC AGCGGTGCAC GGGCTGTACA TCCTGCACGA
      TTTTGCACGC GTCATGACCG TCGCCACGTG CCCGACATGT AGGACGTGCT
```

FIG. 27A-8

```
6801  GGTTGACCTG ACGACCGCGC ACAAGGAAGC AGAGTGGGAA TTTGAGCCCC
      CCAACTGGAC TGCTGGCGCG TGTTCCTTCG TCTCACCCTT AAACTCGGGG

6851  TCGCCTGGCG GGTTTGGCTG GTGGTCTTCT ACTTCGGCTG CTTGTCCTTG
      AGCGGACCGC CCAAACCGAC CACCAGAAGA TGAAGCCGAC GAACAGGAAC

6901  ACCGTCTGGC TGCTCGAGGG GAGTTACGGT GGATCGGACC ACCACGCCGC
      TGGCAGACCG ACGAGCTCCC CTCAATGCCA CCTAGCCTGG TGGTGCGGCG

6951  GCGAGCCCAA AGTCCAGATG TCCGCGCGCG GCGGTCGGAG CTTGATGACA
      CGCTCGGGTT TCAGGTCTAC AGGCGCGCGC CGCCAGCCTC GAACTACTGT

7001  ACATCGCGCA GATGGGAGCT GTCCATGGTC TGGAGCTCCC GCGGCGTCAG
      TGTAGCGCGT CTACCCTCGA CAGGTACCAG ACCTCGAGGG CGCCGCAGTC

7051  GTCAGGCGGG AGCTCCTGCA GGTTTACCTC GCATAGACGG GTCAGGGCGC
      CAGTCCGCCC TCGAGGACGT CCAAATGGAG CGTATCTGCC CAGTCCCGCG

7101  GGGCTAGATC CAGGTGATAC CTAATTTCCA GGGGCTGGTT GGTGGCGGCG
      CCCGATCTAG GTCCACTATG GATTAAAGGT CCCCGACCAA CCACCGCCGC

7151  TCGATGGCTT GCAAGAGGCC GCATCCCCGC GGCGCGACTA CGGTACCGCG
      AGCTACCGAA CGTTCTCCGG CGTAGGGGCG CCGCGCTGAT GCCATGGCGC

7201  CGGCGGGCGG TGGGCCGCGG GGGTGTCCTT GGATGATGCA TCTAAAAGCG
      GCCGCCCGCC ACCCGGCGCC CCCACAGGAA CCTACTACGT AGATTTTCGC

7251  GTGACGCGGG CGAGCCCCCG GAGGTAGGGG GGGCTCCGGA CCCGCCGGGA
      CACTGCGCCC GCTCGGGGGC CTCCATCCCC CCCGAGGCCT GGGCGGCCCT

7301  GAGGGGGCAG GGGCACGTCG GCGCCGCGCG CGGGCAGGAG CTGGTGCTGC
      CTCCCCCGTC CCCGTGCAGC CGCGGCGCGC GCCCGTCCTC GACCACGACG

7351  GCGCGTAGGT TGCTGGCGAA CGCGACGACG CGGCGGTTGA TCTCCTGAAT
      CGCGCATCCA ACGACCGCTT GCGCTGCTGC GCCGCCAACT AGAGGACTTA

7401  CTGGCGCCTC TGCGTGAAGA CGACGGGCCC GGTGAGCTTG AACCTGAAAG
      GACCGCGGAG ACGCACTTCT GCTGCCCGGG CCACTCGAAC TTGGACTTTC

7451  AGAGTTCGAC AGAATCAATT TCGGTGTCGT TGACGGCGGC CTGGCGCAAA
      TCTCAAGCTG TCTTAGTTAA AGCCACAGCA ACTGCCGCCG GACCGCGTTT

7501  ATCTCCTGCA CGTCTCCTGA GTTGTCTTGA TAGGCGATCT CGGCCATGAA
      TAGAGGACGT GCAGAGGACT CAACAGAACT ATCCGCTAGA GCCGGTACTT

7551  CTGCTCGATC TCTTCCTCCT GGAGATCTCC GCGTCCGGCT CGCTCCACGG
      GACGAGCTAG AGAAGGAGGA CCTCTAGAGG CGCAGGCCGA GCGAGGTGCC

7601  TGGCGGCGAG GTCGTTGGAA ATGCGGGCCA TGAGCTGCGA GAAGGCGTTG
      ACCGCCGCTC CAGCAACCTT TACGCCCGGT ACTCGACGCT CTTCCGCAAC
```

FIG. 27A-9

```
7651 AGGCCTCCCT CGTTCCAGAC GCGGCTGTAG ACCACGCCCC CTTCGGCATC
     TCCGGAGGGA GCAAGGTCTG CGCCGACATC TGGTGCGGGG GAAGCCGTAG

7701 GCGGGCGCGC ATGACCACCT GCGCGAGATT GAGCTCCACG TGCCGGGCGA
     CGCCCGCGCG TACTGGTGGA CGCGCTCTAA CTCGAGGTGC ACGGCCCGCT

7751 AGACGGCGTA GTTTCGCAGG CGCTGAAAGA GGTAGTTGAG GGTGGTGGCG
     TCTGCCGCAT CAAAGCGTCC GCGACTTTCT CCATCAACTC CCACCACCGC

7801 GTGTGTTCTG CCACGAAGAA GTACATAACC CAGCGTCGCA ACGTGGATTC
     CACACAAGAC GGTGCTTCTT CATGTATTGG GTCGCAGCGT TGCACCTAAG

7851 GTTGATATCC CCCAAGGCCT CAAGGCGCTC CATGGCCTCG TAGAAGTCCA
     CAACTATAGG GGGTTCCGGA GTTCCGCGAG GTACCGGAGC ATCTTCAGGT

7901 CGGCGAAGTT GAAAAACTGG GAGTTGCGCG CCGACACGGT TAACTCCTCC
     GCCGCTTCAA CTTTTTGACC CTCAACGCGC GGCTGTGCCA ATTGAGGAGG

7951 TCCAGAAGAC GGATGAGCTC GGCGACAGTG TCGCGCACCT CGCGCTCAAA
     AGGTCTTCTG CCTACTCGAG CCGCTGTCAC AGCGCGTGGA GCGCGAGTTT

8001 GGCTACAGGG GCCTCTTCTT CTTCTTCAAT CTCCTCTTCC ATAAGGGCCT
     CCGATGTCCC CGGAGAAGAA GAAGAAGTTA GAGGAGAAGG TATTCCCGGA

8051 CCCCTTCTTC TTCTTCTGGC GGCGGTGGGG GAGGGGGGAC ACGGCGGCGA
     GGGGAAGAAG AAGAAGACCG CCGCCACCCC CTCCCCCCTG TGCCGCCGCT

8101 CGACGGCGCA CCGGGAGGCG GTCGACAAAG CGCTCGATCA TCTCCCCGCG
     GCTGCCGCGT GGCCCTCCGC CAGCTGTTTC GCGAGCTAGT AGAGGGGCGC

8151 GCGACGGCGC ATGGTCTCGG TGACGGCGCG GCCGTTCTCG CGGGGGCGCA
     CGCTGCCGCG TACCAGAGCC ACTGCCGCGC CGGCAAGAGC GCCCCCGCGT

8201 GTTGGAAGAC GCCGCCCGTC ATGTCCCGGT TATGGGTTGG CGGGGGGCTG
     CAACCTTCTG CGGCGGGCAG TACAGGGCCA ATACCCAACC GCCCCCCGAC

8251 CCATGCGGCA GGGATACGGC GCTAACGATG CATCTCAACA ATTGTTGTGT
     GGTACGCCGT CCCTATGCCG CGATTGCTAC GTAGAGTTGT TAACAACACA

8301 AGGTACTCCG CCGCCGAGGG ACCTGAGCGA GTCCGCATCG ACCGGATCGG
     TCCATGAGGC GGCGGCTCCC TGGACTCGCT CAGGCGTAGC TGGCCTAGCC

8351 AAAACCTCTC GAGAAAGGCG TCTAACCAGT CACAGTCGCA AGGTAGGCTG
     TTTTGGAGAG CTCTTTCCGC AGATTGGTCA GTGTCAGCGT TCCATCCGAC

8401 AGCACCGTGG CGGGCGGCAG CGGGCGGCGG TCGGGGTTGT TTCTGGCGGA
     TCGTGGCACC GCCCGCCGTC GCCCGCCGCC AGCCCCAACA AAGACCGCCT

8451 GGTGCTGCTG ATGATGTAAT TAAAGTAGGC GGTCTTGAGA CGGCGGATGG
     CCACGACGAC TACTACATTA ATTTCATCCG CCAGAACTCT GCCGCCTACC
```

FIG. 27A-10

```
8501  TCGACAGAAG CACCATGTCC TTGGGTCCGG CCTGCTGAAT GCGCAGGCGG
      AGCTGTCTTC GTGGTACAGG AACCCAGGCC GGACGACTTA CGCGTCCGCC

8551  TCGGCCATGC CCCAGGCTTC GTTTTGACAT CGGCGCAGGT CTTTGTAGTA
      AGCCGGTACG GGGTCCGAAG CAAAACTGTA GCCGCGTCCA GAAACATCAT

8601  GTCTTGCATG AGCCTTTCTA CCGGCACTTC TTCTTCTCCT TCCTCTTGTC
      CAGAACGTAC TCGGAAAGAT GGCCGTGAAG AAGAAGAGGA AGGAGAACAG

8651  CTGCATCTCT TGCATCTATC GCTGCGGCGG CGGCGGAGTT TGGCCGTAGG
      GACGTAGAGA ACGTAGATAG CGACGCCGCC GCCGCCTCAA ACCGGCATCC

8701  TGGCGCCCTC TTCCTCCCAT GCGTGTGACC CCGAAGCCCC TCATCGGCTG
      ACCGCGGGAG AAGGAGGGTA CGCACACTGG GGCTTCGGGG AGTAGCCGAC

8751  AAGCAGGGCT AGGTCGGCGA CAACGCGCTC GGCTAATATG GCCTGCTGCA
      TTCGTCCCGA TCCAGCCGCT GTTGCGCGAG CCGATTATAC CGGACGACGT

8801  CCTGCGTGAG GGTAGACTGG AAGTCATCCA TGTCCACAAA GCGGTGGTAT
      GGACGCACTC CCATCTGACC TTCAGTAGGT ACAGGTGTTT CGCCACCATA

8851  GCGCCCGTGT TGATGGTGTA AGTGCAGTTG GCCATAACGG ACCAGTTAAC
      CGCGGGCACA ACTACCACAT TCACGTCAAC CGGTATTGCC TGGTCAATTG

8901  GGTCTGGTGA CCCGGCTGCG AGAGCTCGGT GTACCTGAGA CGCGAGTAAG
      CCAGACCACT GGGCCGACGC TCTCGAGCCA CATGGACTCT GCGCTCATTC

8951  CCCTCGAGTC AAATACGTAG TCGTTGCAAG TCCGCACCAG GTACTGGTAT
      GGGAGCTCAG TTTATGCATC AGCAACGTTC AGGCGTGGTC CATGACCATA

9001  CCCACCAAAA AGTGCGGCGG CGGCTGGCGG TAGAGGGGCC AGCGTAGGGT
      GGGTGGTTTT TCACGCCGCC GCCGACCGCC ATCTCCCCGG TCGCATCCCA

9051  GGCCGGGGCT CCGGGGGCGA GATCTTCCAA CATAAGGCGA TGATATCCGT
      CCGGCCCCGA GGCCCCCGCT CTAGAAGGTT GTATTCCGCT ACTATAGGCA

9101  AGATGTACCT GGACATCCAG GTGATGCCGG CGGCGGTGGT GGAGGCGCGC
      TCTACATGGA CCTGTAGGTC CACTACGGCC GCCGCCACCA CCTCCGCGCG

9151  GGAAAGTCGC GGACGCGGTT CCAGATGTTG CGCAGCGGCA AAAAGTGCTC
      CCTTTCAGCG CCTGCGCCAA GGTCTACAAC GCGTCGCCGT TTTTCACGAG

9201  CATGGTCGGG ACGCTCTGGC CGGTCAGGCG CGCGCAATCG TTGACGCTCT
      GTACCAGCCC TGCGAGACCG GCCAGTCCGC GCGCGTTAGC AACTGCGAGA

9251  AGACCGTGCA AAAGGAGAGC CTGTAAGCGG GCACTCTTCC GTGGTCTGGT
      TCTGGCACGT TTTCCTCTCG GACATTCGCC CGTGAGAAGG CACCAGACCA

9301  GGATAAATTC GCAAGGGTAT CATGGCGGAC GACCGGGGTT CGAGCCCCGT
      CCTATTTAAG CGTTCCCATA GTACCGCCTG CTGGCCCCAA GCTCGGGGCA
```

FIG. 27A-11

```
9351  ATCCGGCCGT CCGCCGTGAT CCATGCGGTT ACCGCCCGCG TGTCGAACCC
      TAGGCCGGCA GGCGGCACTA GGTACGCCAA TGGCGGGCGC ACAGCTTGGG

9401  AGGTGTGCGA CGTCAGACAA CGGGGGAGTG CTCCTTTTGG CTTCCTTCCA
      TCCACACGCT GCAGTCTGTT GCCCCCTCAC GAGGAAAACC GAAGGAAGGT

9451  GGCGCGGCGG CTGCTGCGCT AGCTTTTTTG GCCACTGGCC GCGCGCAGCG
      CCGCGCCGCC GACGACGCGA TCGAAAAAAC CGGTGACCGG CGCGCGTCGC

9501  TAAGCGGTTA GGCTGGAAAG CGAAAGCATT AAGTGGCTCG CTCCCTGTAG
      ATTCGCCAAT CCGACCTTTC GCTTTCGTAA TTCACCGAGC GAGGGACATC

9551  CCGGAGGGTT ATTTTCCAAG GGTTGAGTCG CGGGACCCCC GGTTCGAGTC
      GGCCTCCCAA TAAAAGGTTC CCAACTCAGC GCCCTGGGGG CCAAGCTCAG

9601  TCGGACCGGC CGGACTGCGG CGAACGGGGG TTTGCCTCCC CGTCATGCAA
      AGCCTGGCCG GCCTGACGCC GCTTGCCCCC AAACGGAGGG GCAGTACGTT

9651  GACCCCGCTT GCAAATTCCT CCGGAAACAG GGACGAGCCC CTTTTTTGCT
      CTGGGGCGAA CGTTTAAGGA GGCCTTTGTC CCTGCTCGGG GAAAAAACGA

9701  TTTCCCAGAT GCATCCGGTG CTGCGGCAGA TGCGCCCCCC TCCTCAGCAG
      AAAGGGTCTA CGTAGGCCAC GACGCCGTCT ACGCGGGGGG AGGAGTCGTC

9751  CGGCAAGAGC AAGAGCAGCG GCAGACATGC AGGGCACCCT CCCCTCCTCC
      GCCGTTCTCG TTCTCGTCGC CGTCTGTACG TCCCGTGGGA GGGGAGGAGG

9801  TACCGCGTCA GGAGGGGCGA CATCCGCGGT TGACGCGGCA GCAGATGGTG
      ATGGCGCAGT CCTCCCCGCT GTAGGCGCCA ACTGCGCCGT CGTCTACCAC

9851  ATTACGAACC CCCGCGGCGC CGGGCCCGGC ACTACCTGGA CTTGGAGGAG
      TAATGCTTGG GGGCGCCGCG GCCCGGGCCG TGATGGACCT GAACCTCCTC

9901  GGCGAGGGCC TGGCGCGGCT AGGAGCGCCC TCTCCTGAGC GGCACCCAAG
      CCGCTCCCGG ACCGCGCCGA TCCTCGCGGG AGAGGACTCG CCGTGGGTTC

9951  GGTGCAGCTG AAGCGTGATA CGCGTGAGGC GTACGTGCCG CGGCAGAACC
      CCACGTCGAC TTCGCACTAT GCGCACTCCG CATGCACGGC GCCGTCTTGG

10001 TGTTTCGCGA CCGCGAGGGA GAGGAGCCCG AGGAGATGCG GGATCGAAAG
      ACAAAGCGCT GGCGCTCCCT CTCCTCGGGC TCCTCTACGC CCTAGCTTTC

10051 TTCCACGCAG GGCGCGAGCT GCGGCATGGC CTGAATCGCG AGCGGTTGCT
      AAGGTGCGTC CCGCGCTCGA CGCCGTACCG GACTTAGCGC TCGCCAACGA

10101 GCGCGAGGAG GACTTTGAGC CCGACGCGCG AACCGGGATT AGTCCCGCGC
      CGCGCTCCTC CTGAAACTCG GGCTGCGCGC TTGGCCCTAA TCAGGGCGCG

10151 GCGCACACGT GGCGGCCGCC GACCTGGTAA CCGCATACGA GCAGACGGTG
      CGCGTGTGCA CCGCCGGCGG CTGGACCATT GGCGTATGCT CGTCTGCCAC
```

FIG. 27A-12

```
10201  AACCAGGAGA TTAACTTTCA AAAAAGCTTT AACAACCACG TGCGTACGCT
       TTGGTCCTCT AATTGAAAGT TTTTTCGAAA TTGTTGGTGC ACGCATGCGA

10251  TGTGGCGCGC GAGGAGGTGG CTATAGGACT GATGCATCTG TGGGACTTTG
       ACACCGCGCG CTCCTCCACC GATATCCTGA CTACGTAGAC ACCCTGAAAC

10301  TAAGCGCGCT GGAGCAAAAC CCAAATAGCA AGCCGCTCAT GGCGCAGCTG
       ATTCGCGCGA CCTCGTTTTG GGTTTATCGT TCGGCGAGTA CCGCGTCGAC

10351  TTCCTTATAG TGCAGCACAG CAGGGACAAC GAGGCATTCA GGGATGCGCT
       AAGGAATATC ACGTCGTGTC GTCCCTGTTG CTCCGTAAGT CCCTACGCGA

10401  GCTAAACATA GTAGAGCCCG AGGGCCGCTG GCTGCTCGAT TTGATAAACA
       CGATTTGTAT CATCTCGGGC TCCCGGCGAC CGACGAGCTA AACTATTTGT

10451  TCCTGCAGAG CATAGTGGTG CAGGAGCGCA GCTTGAGCCT GGCTGACAAG
       AGGACGTCTC GTATCACCAC GTCCTCGCGT CGAACTCGGA CCGACTGTTC

10501  GTGGCCGCCA TCAACTATTC CATGCTTAGC CTGGGCAAGT TTTACGCCCG
       CACCGGCGGT AGTTGATAAG GTACGAATCG GACCCGTTCA AAATGCGGGC

10551  CAAGATATAC CATACCCCTT ACGTTCCCAT AGACAAGGAG GTAAAGATCG
       GTTCTATATG GTATGGGGAA TGCAAGGGTA TCTGTTCCTC CATTTCTAGC

10601  AGGGGTTCTA CATGCGCATG GCGCTGAAGG TGCTTACCTT GAGCGACGAC
       TCCCCAAGAT GTACGCGTAC CGCGACTTCC ACGAATGGAA CTCGCTGCTG

10651  CTGGGCGTTT ATCGCAACGA GCGCATCCAC AAGGCCGTGA GCGTGAGCCG
       GACCCGCAAA TAGCGTTGCT CGCGTAGGTG TTCCGGCACT CGCACTCGGC

10701  GCGGCGCGAG CTCAGCGACC GCGAGCTGAT GCACAGCCTG CAAAGGGCCC
       CGCCGCGCTC GAGTCGCTGG CGCTCGACTA CGTGTCGGAC GTTTCCCGGG

10751  TGGCTGGCAC GGGCAGCGGC GATAGAGAGG CCGAGTCCTA CTTTGACGCG
       ACCGACCGTG CCCGTCGCCG CTATCTCTCC GGCTCAGGAT GAAACTGCGC

10801  GGCGCTGACC TGCGCTGGGC CCCAAGCCGA CGCGCCCTGG AGGCAGCTGG
       CCGCGACTGG ACGCGACCCG GGGTTCGGCT GCGCGGGACC TCCGTCGACC

10851  GGCCGGACCT GGGCTGGCGG TGGCACCCGC GCGCGCTGGC AACGTCGGCG
       CCGGCCTGGA CCCGACCGCC ACCGTGGGCG CGCGCGACCG TTGCAGCCGC

10901  GCGTGGAGGA ATATGACGAG GACGATGAGT ACGAGCCAGA GGACGGCGAG
       CGCACCTCCT TATACTGCTC CTGCTACTCA TGCTCGGTCT CCTGCCGCTC

10951  TACTAAGCGG TGATGTTTCT GATCAGATGA TGCAAGACGC AACGGACCCG
       ATGATTCGCC ACTACAAAGA CTAGTCTACT ACGTTCTGCG TTGCCTGGGC

11001  GCGGTGCGGG CGGCGCTGCA GAGCCAGCCG TCCGGCCTTA ACTCCACGGA
       CGCCACGCCC GCCGCGACGT CTCGGTCGGC AGGCCGGAAT TGAGGTGCCT
```

FIG. 27A-13

```
11051  CGACTGGCGC CAGGTCATGG ACCGCATCAT GTCGCTGACT GCGCGCAATC
       GCTGACCGCG GTCCAGTACC TGGCGTAGTA CAGCGACTGA CGCGCGTTAG

11101  CTGACGCGTT CCGGCAGCAG CCGCAGGCCA ACCGGCTCTC CGCAATTCTG
       GACTGCGCAA GGCCGTCGTC GGCGTCCGGT TGGCCGAGAG GCGTTAAGAC

11151  GAAGCGGTGG TCCCGGCGCG CGCAAACCCC ACGCACGAGA AGGTGCTGGC
       CTTCGCCACC AGGGCCGCGC GCGTTTGGGG TGCGTGCTCT TCCACGACCG

11201  GATCGTAAAC GCGCTGGCCG AAAACAGGGC CATCCGGCCC GACGAGGCCG
       CTAGCATTTG CGCGACCGGC TTTTGTCCCG GTAGGCCGGG CTGCTCCGGC

11251  GCCTGGTCTA CGACGCGCTG CTTCAGCGCG TGGCTCGTTA CAACAGCGGC
       CGGACCAGAT GCTGCGCGAC GAAGTCGCGC ACCGAGCAAT GTTGTCGCCG

11301  AACGTGCAGA CCAACCTGGA CCGGCTGGTG GGGGATGTGC GCGAGGCCGT
       TTGCACGTCT GGTTGGACCT GGCCGACCAC CCCCTACACG CGCTCCGGCA

11351  GGCGCAGCGT GAGCGCGCGC AGCAGCAGGG CAACCTGGGC TCCATGGTTG
       CCGCGTCGCA CTCGCGCGCG TCGTCGTCCC GTTGGACCCG AGGTACCAAC

11401  CACTAAACGC CTTCCTGAGT ACACAGCCCG CCAACGTGCC GCGGGGACAG
       GTGATTTGCG GAAGGACTCA TGTGTCGGGC GGTTGCACGG CGCCCCTGTC

11451  GAGGACTACA CCAACTTTGT GAGCGCACTG CGGCTAATGG TGACTGAGAC
       CTCCTGATGT GGTTGAAACA CTCGCGTGAC GCCGATTACC ACTGACTCTG

11501  ACCGCAAAGT GAGGTGTACC AGTCTGGGCC AGACTATTTT TTCCAGACCA
       TGGCGTTTCA CTCCACATGG TCAGACCCGG TCTGATAAAA AAGGTCTGGT

11551  GTAGACAAGG CCTGCAGACC GTAAACCTGA GCCAGGCTTT CAAAAACTTG
       CATCTGTTCC GGACGTCTGG CATTTGGACT CGGTCCGAAA GTTTTTGAAC

11601  CAGGGGCTGT GGGGGGTGCG GGCTCCCACA GGCGACCGCG CGACCGTGTC
       GTCCCCGACA CCCCCCACGC CCGAGGGTGT CCGCTGGCGC GCTGGCACAG

11651  TAGCTTGCTG ACGCCCAACT CGCGCCTGTT GCTGCTGCTA ATAGCGCCCT
       ATCGAACGAC TGCGGGTTGA GCGCGGACAA CGACGACGAT TATCGCGGGA

11701  TCACGGACAG TGGCAGCGTG TCCCGGGACA CATACCTAGG TCACTTGCTG
       AGTGCCTGTC ACCGTCGCAC AGGGCCCTGT GTATGGATCC AGTGAACGAC

11751  ACACTGTACC GCGAGGCCAT AGGTCAGGCG CATGTGGACG AGCATACTTT
       TGTGACATGG CGCTCCGGTA TCCAGTCCGC GTACACCTGC TCGTATGAAA

11801  CCAGGAGATT ACAAGTGTCA GCCGCGCGCT GGGGCAGGAG GACACGGGCA
       GGTCCTCTAA TGTTCACAGT CGGCGCGCGA CCCCGTCCTC CTGTGCCCGT

11851  GCCTGGAGGC AACCCTAAAC TACCTGCTGA CCAACCGGCG GCAGAAGATC
       CGGACCTCCG TTGGGATTTG ATGGACGACT GGTTGGCCGC CGTCTTCTAG
```

FIG. 27A-14

```
11901  CCCTCGTTGC ACAGTTTAAA CAGCGAGGAG GAGCGCATTT TGCGCTACGT
       GGGAGCAACG TGTCAAATTT GTCGCTCCTC CTCGCGTAAA ACGCGATGCA

11951  GCAGCAGAGC GTGAGCCTTA ACCTGATGCG CGACGGGGTA ACGCCCAGCG
       CGTCGTCTCG CACTCGGAAT TGGACTACGC GCTGCCCCAT TGCGGGTCGC

12001  TGGCGCTGGA CATGACCGCG CGCAACATGG AACCGGGCAT GTATGCCTCA
       ACCGCGACCT GTACTGGCGC GCGTTGTACC TTGGCCCGTA CATACGGAGT

12051  AACCGGCCGT TTATCAACCG CCTAATGGAC TACTTGCATC GCGCGGCCGC
       TTGGCCGGCA AATAGTTGGC GGATTACCTG ATGAACGTAG CGCGCCGGCG

12101  CGTGAACCCC GAGTATTTCA CCAATGCCAT CTTGAACCCG CACTGGCTAC
       GCACTTGGGG CTCATAAAGT GGTTACGGTA GAACTTGGGC GTGACCGATG

12151  CGCCCCCTGG TTTCTACACC GGGGGATTCG AGGTGCCCGA GGGTAACGAT
       GCGGGGGACC AAAGATGTGG CCCCCTAAGC TCCACGGGCT CCCATTGCTA

12201  GGATTCCTCT GGGACGACAT AGACGACAGC GTGTTTTCCC CGCAACCGCA
       CCTAAGGAGA CCCTGCTGTA TCTGCTGTCG CACAAAAGGG GCGTTGGCGT

12251  GACCCTGCTA GAGTTGCAAC AGCGCGAGCA GGCAGAGGCG GCGCTGCGAA
       CTGGGACGAT CTCAACGTTG TCGCGCTCGT CCGTCTCCGC CGCGACGCTT

12301  AGGAAAGCTT CCGCAGGCCA AGCAGCTTGT CCGATCTAGG CGCTGCGGCC
       TCCTTTCGAA GGCGTCCGGT TCGTCGAACA GGCTAGATCC GCGACGCCGG

12351  CCGCGGTCAG ATGCTAGTAG CCCATTTCCA AGCTTGATAG GGTCTCTTAC
       GGCGCCAGTC TACGATCATC GGGTAAAGGT TCGAACTATC CCAGAGAATG

12401  CAGCACTCGC ACCACCCGCC CGCGCCTGCT GGGCGAGGAG GAGTACCTAA
       GTCGTGAGCG TGGTGGGCGG GCGCGGACGA CCCGCTCCTC CTCATGGATT

12451  ACAACTCGCT GCTGCAGCCG CAGCGCGAAA AAAACCTGCC TCCGGCATTT
       TGTTGAGCGA CGACGTCGGC GTCGCGCTTT TTTTGGACGG AGGCCGTAAA

12501  CCCAACAACG GGATAGAGAG CCTAGTGGAC AAGATGAGTA GATGGAAGAC
       GGGTTGTTGC CCTATCTCTC GGATCACCTG TTCTACTCAT CTACCTTCTG

12551  GTACGCGCAG GAGCACAGGG ACGTGCCAGG CCCGCGCCCG CCCACCCGTC
       CATGCGCGTC CTCGTGTCCC TGCACGGTCC GGGCGCGGGC GGGTGGGCAG

12601  GTCAAAGGCA CGACCGTCAG CGGGGTCTGG TGTGGGAGGA CGATGACTCG
       CAGTTTCCGT GCTGGCAGTC GCCCCAGACC ACACCCTCCT GCTACTGAGC

12651  GCAGACGACA GCAGCGTCCT GGATTTGGGA GGGAGTGGCA ACCCGTTTGC
       CGTCTGCTGT CGTCGCAGGA CCTAAACCCT CCCTCACCGT TGGGCAAACG

12701  GCACCTTCGC CCCAGGCTGG GGAGAATGTT TTAAAAAAAA AAAAAGCATG
       CGTGGAAGCG GGGTCCGACC CCTCTTACAA AATTTTTTTT TTTTTCGTAC
```

FIG. 27A-15

```
12751  ATGCAAAATA AAAAACTCAC CAAGGCCATG GCACCGAGCG TTGGTTTTCT
       TACGTTTTAT TTTTTGAGTG GTTCCGGTAC CGTGGCTCGC AACCAAAAGA

12801  TGTATTCCCC TTAGTATGCG GCGCGCGGCG ATGTATGAGG AAGGTCCTCC
       ACATAAGGGG AATCATACGC CGCGCGCCGC TACATACTCC TTCCAGGAGG

12851  TCCCTCCTAC GAGAGTGTGG TGAGCGCGGC GCCAGTGGCG GCGGCGCTGG
       AGGGAGGATG CTCTCACACC ACTCGCGCCG CGGTCACCGC CGCCGCGACC

12901  GTTCTCCCTT CGATGCTCCC CTGGACCCGC CGTTTGTGCC TCCGCGGTAC
       CAAGAGGGAA GCTACGAGGG GACCTGGGCG GCAAACACGG AGGCGCCATG

12951  CTGCGGCCTA CCGGGGGGAG AAACAGCATC CGTTACTCTG AGTTGGCACC
       GACGCCGGAT GGCCCCCCTC TTTGTCGTAG GCAATGAGAC TCAACCGTGG

13001  CCTATTCGAC ACCACCCGTG TGTACCTGGT GGACAACAAG TCAACGGATG
       GGATAAGCTG TGGTGGGCAC ACATGGACCA CCTGTTGTTC AGTTGCCTAC

13051  TGGCATCCCT GAACTACCAG AACGACCACA GCAACTTTCT GACCACGGTC
       ACCGTAGGGA CTTGATGGTC TTGCTGGTGT CGTTGAAAGA CTGGTGCCAG

13101  ATTCAAAACA ATGACTACAG CCCGGGGGAG GCAAGCACAC AGACCATCAA
       TAAGTTTTGT TACTGATGTC GGGCCCCCTC CGTTCGTGTG TCTGGTAGTT

13151  TCTTGACGAC CGGTCGCACT GGGGCGGCGA CCTGAAAACC ATCCTGCATA
       AGAACTGCTG GCCAGCGTGA CCCCGCCGCT GGACTTTTGG TAGGACGTAT

13201  CCAACATGCC AAATGTGAAC GAGTTCATGT TTACCAATAA GTTTAAGGCG
       GGTTGTACGG TTTACACTTG CTCAAGTACA AATGGTTATT CAAATTCCGC

13251  CGGGTGATGG TGTCGCGCTT GCCTACTAAG GACAATCAGG TGGAGCTGAA
       GCCCACTACC ACAGCGCGAA CGGATGATTC CTGTTAGTCC ACCTCGACTT

13301  ATACGAGTGG GTGGAGTTCA CGCTGCCCGA GGGCAACTAC TCCGAGACCA
       TATGCTCACC CACCTCAAGT GCGACGGGCT CCCGTTGATG AGGCTCTGGT

13351  TGACCATAGA CCTTATGAAC AACGCGATCG TGGAGCACTA CTTGAAAGTG
       ACTGGTATCT GGAATACTTG TTGCGCTAGC ACCTCGTGAT GAACTTTCAC

13401  GGCAGACAGA ACGGGGTTCT GGAAAGCGAC ATCGGGGTAA AGTTTGACAC
       CCGTCTGTCT TGCCCCAAGA CCTTTCGCTG TAGCCCCATT TCAAACTGTG

13451  CCGCAACTTC AGACTGGGGT TTGACCCCGT CACTGGTCTT GTCATGCCTG
       GGCGTTGAAG TCTGACCCCA AACTGGGGCA GTGACCAGAA CAGTACGGAC

13501  GGGTATATAC AAACGAAGCC TTCCATCCAG ACATCATTTT GCTGCCAGGA
       CCCATATATG TTTGCTTCGG AAGGTAGGTC TGTAGTAAAA CGACGGTCCT

13551  TGCGGGGTGG ACTTCACCCA CAGCCGCCTG AGCAACTTGT TGGGCATCCG
       ACGCCCCACC TGAAGTGGGT GTCGGCGGAC TCGTTGAACA ACCCGTAGGC
```

FIG. 27A-16

```
13601  CAAGCGGCAA CCCTTCCAGG AGGGCTTTAG GATCACCTAC GATGATCTGG
       GTTCGCCGTT GGGAAGGTCC TCCCGAAATC CTAGTGGATG CTACTAGACC

13651  AGGGTGGTAA CATTCCCGCA CTGTTGGATG TGGACGCCTA CCAGGCGAGC
       TCCCACCATT GTAAGGGCGT GACAACCTAC ACCTGCGGAT GGTCCGCTCG

13701  TTGAAAGATG ACACCGAACA GGGCGGGGGT GGCGCAGGCG GCAGCAACAG
       AACTTTCTAC TGTGGCTTGT CCCGCCCCCA CCGCGTCCGC CGTCGTTGTC

13751  CAGTGGCAGC GGCGCGGAAG AGAACTCCAA CGCGGCAGCC GCGGCAATGC
       GTCACCGTCG CCGCGCCTTC TCTTGAGGTT GCGCCGTCGG CGCCGTTACG

13801  AGCCGGTGGA GGACATGAAC GATCATGCCA TTCGCGGCGA CACCTTTGCC
       TCGGCCACCT CCTGTACTTG CTAGTACGGT AAGCGCCGCT GTGGAAACGG

13851  ACACGGGCTG AGGAGAAGCG CGCTGAGGCC GAAGCAGCGG CCGAAGCTGC
       TGTGCCCGAC TCCTCTTCGC GCGACTCCGG CTTCGTCGCC GGCTTCGACG

13901  CGCCCCCGCT GCGCAACCCG AGGTCGAGAA GCCTCAGAAG AAACCGGTGA
       GCGGGGGCGA CGCGTTGGGC TCCAGCTCTT CGGAGTCTTC TTTGGCCACT

13951  TCAAACCCCT GACAGAGGAC AGCAAGAAAC GCAGTTACAA CCTAATAAGC
       AGTTTGGGGA CTGTCTCCTG TCGTTCTTTG CGTCAATGTT GGATTATTCG

14001  AATGACAGCA CCTTCACCCA GTACCGCAGC TGGTACCTTG CATACAACTA
       TTACTGTCGT GGAAGTGGGT CATGGCGTCG ACCATGGAAC GTATGTTGAT

14051  CGGCGACCCT CAGACCGGAA TCCGCTCATG GACCCTGCTT TGCACTCCTG
       GCCGCTGGGA GTCTGGCCTT AGGCGAGTAC CTGGGACGAA ACGTGAGGAC

14101  ACGTAACCTG CGGCTCGGAG CAGGTCTACT GGTCGTTGCC AGACATGATG
       TGCATTGGAC GCCGAGCCTC GTCCAGATGA CCAGCAACGG TCTGTACTAC

14151  CAAGACCCCG TGACCTTCCG CTCCACGCGC CAGATCAGCA ACTTTCCGGT
       GTTCTGGGGC ACTGGAAGGC GAGGTGCGCG GTCTAGTCGT TGAAAGGCCA

14201  GGTGGGCGCC GAGCTGTTGC CCGTGCACTC CAAGAGCTTC TACAACGACC
       CCACCCGCGG CTCGACAACG GGCACGTGAG GTTCTCGAAG ATGTTGCTGG

14251  AGGCCGTCTA CTCCCAACTC ATCCGCCAGT TTACCTCTCT GACCCACGTG
       TCCGGCAGAT GAGGGTTGAG TAGGCGGTCA AATGGAGAGA CTGGGTGCAC

14301  TTCAATCGCT TTCCCGAGAA CCAGATTTTG GCGCGCCCGC CAGCCCCCAC
       AAGTTAGCGA AAGGGCTCTT GGTCTAAAAC CGCGCGGGCG GTCGGGGGTG

14351  CATCACCACC GTCAGTGAAA ACGTTCCTGC TCTCACAGAT CACGGGACGC
       GTAGTGGTGG CAGTCACTTT TGCAAGGACG AGAGTGTCTA GTGCCCTGCG

14401  TACCGCTGCG CAACAGCATC GGAGGAGTCC AGCGAGTGAC CATTACTGAC
       ATGGCGACGC GTTGTCGTAG CCTCCTCAGG TCGCTCACTG GTAATGACTG
```

FIG. 27A-17

```
14451  GCCAGACGCC GCACCTGCCC CTACGTTTAC AAGGCCCTGG GCATAGTCTC
       CGGTCTGCGG CGTGGACGGG GATGCAAATG TTCCGGGACC CGTATCAGAG

14501  GCCGCGCGTC CTATCGAGCC GCACTTTTTG AGCAAGCATG TCCATCCTTA
       CGGCGCGCAG GATAGCTCGG CGTGAAAAAC TCGTTCGTAC AGGTAGGAAT

14551  TATCGCCCAG CAATAACACA GGCTGGGGCC TGCGCTTCCC AAGCAAGATG
       ATAGCGGGTC GTTATTGTGT CCGACCCCGG ACGCGAAGGG TTCGTTCTAC

14601  TTTGGCGGGG CCAAGAAGCG CTCCGACCAA CACCCAGTGC GCGTGCGCGG
       AAACCGCCCC GGTTCTTCGC GAGGCTGGTT GTGGGTCACG CGCACGCGCC

14651  GCACTACCGC GCGCCCTGGG GCGCGCACAA ACGCGGCCGC ACTGGGCGCA
       CGTGATGGCG CGCGGGACCC CGCGCGTGTT TGCGCCGGCG TGACCCGCGT

14701  CCACCGTCGA TGACGCCATC GACGCGGTGG TGGAGGAGGC GCGCAACTAC
       GGTGGCAGCT ACTGCGGTAG CTGCGCCACC ACCTCCTCCG CGCGTTGATG

14751  ACGCCCACGC CGCCACCAGT GTCCACAGTG GACGCGGCCA TTCAGACCGT
       TGCGGGTGCG GCGGTGGTCA CAGGTGTCAC CTGCGCCGGT AAGTCTGGCA

14801  GGTGCGCGGA GCCCGGCGCT ATGCTAAAAT GAAGAGACGG CGGAGGCGCG
       CCACGCGCCT CGGGCCGCGA TACGATTTTA CTTCTCTGCC GCCTCCGCGC

14851  TAGCACGTCG CCACCGCCGC CGACCCGGCA CTGCCGCCCA ACGCGCGGCG
       ATCGTGCAGC GGTGGCGGCG GCTGGGCCGT GACGGCGGGT TGCGCGCCGC

14901  GCGGCCCTGC TTAACCGCGC ACGTCGCACC GGCCGACGGG CGGCCATGCG
       CGCCGGGACG AATTGGCGCG TGCAGCGTGG CCGGCTGCCC GCCGGTACGC

14951  GGCCGCTCGA AGGCTGGCCG CGGGTATTGT CACTGTGCCC CCCAGGTCCA
       CCGGCGAGCT TCCGACCGGC GCCCATAACA GTGACACGGG GGGTCCAGGT

15001  GGCGACGAGC GGCCGCCGCA GCAGCCGCGG CCATTAGTGC TATGACTCAG
       CCGCTGCTCG CCGGCGGCGT CGTCGGCGCC GGTAATCACG ATACTGAGTC

15051  GGTCGCAGGG GCAACGTGTA TTGGGTGCGC GACTCGGTTA GCGGCCTGCG
       CCAGCGTCCC CGTTGCACAT AACCCACGCG CTGAGCCAAT CGCCGGACGC

15101  CGTGCCCGTG CGCACCCGCC CCCCGCGCAA CTAGATTGCA AGAAAAAACT
       GCACGGGCAC GCGTGGGCGG GGGGCGCGTT GATCTAACGT TCTTTTTTGA

15151  ACTTAGACTC GTACTGTTGT ATGTATCCAG CGGCGGCGGC GCGCAACGAA
       TGAATCTGAG CATGACAACA TACATAGGTC GCCGCCGCCG CGCGTTGCTT

15201  GCTATGTCCA AGCGCAAAAT CAAAGAAGAG ATGCTCCAGG TCATCGCGCC
       CGATACAGGT TCGCGTTTTA GTTTCTTCTC TACGAGGTCC AGTAGCGCGG

15251  GGAGATCTAT GGCCCCCCGA AGAAGGAAGA GCAGGATTAC AAGCCCCGAA
       CCTCTAGATA CCGGGGGGCT TCTTCCTTCT CGTCCTAATG TTCGGGGCTT
```

FIG. 27A-18

```
15301  AGCTAAAGCG GGTCAAAAAG AAAAAGAAAG ATGATGATGA TGAACTTGAC
       TCGATTTCGC CCAGTTTTTC TTTTTCTTTC TACTACTACT ACTTGAACTG

15351  GACGAGGTGG AACTGCTGCA CGCTACCGCG CCCAGGCGAC GGGTACAGTG
       CTGCTCCACC TTGACGACGT GCGATGGCGC GGGTCCGCTG CCCATGTCAC

15401  GAAAGGTCGA CGCGTAAAAC GTGTTTTGCG ACCCGGCACC ACCGTAGTCT
       CTTTCCAGCT GCGCATTTTG CACAAAACGC TGGGCCGTGG TGGCATCAGA

15451  TTACGCCCGG TGAGCGCTCC ACCCGCACCT ACAAGCGCGT GTATGATGAG
       AATGCGGGCC ACTCGCGAGG TGGGCGTGGA TGTTCGCGCA CATACTACTC

15501  GTGTACGGCG ACGAGGACCT GCTTGAGCAG GCCAACGAGC GCCTCGGGGA
       CACATGCCGC TGCTCCTGGA CGAACTCGTC CGGTTGCTCG CGGAGCCCCT

15551  GTTTGCCTAC GGAAAGCGGC ATAAGGACAT GCTGGCGTTG CCGCTGGACG
       CAAACGGATG CCTTTCGCCG TATTCCTGTA CGACCGCAAC GGCGACCTGC

15601  AGGGCAACCC AACACCTAGC CTAAAGCCCG TAACACTGCA GCAGGTGCTG
       TCCCGTTGGG TTGTGGATCG GATTTCGGGC ATTGTGACGT CGTCCACGAC

15651  CCCGCGCTTG CACCGTCCGA AGAAAAGCGC GGCCTAAAGC GCGAGTCTGG
       GGGCGCGAAC GTGGCAGGCT TCTTTTCGCG CCGGATTTCG CGCTCAGACC

15701  TGACTTGGCA CCCACCGTGC AGCTGATGGT ACCCAAGCGC CAGCGACTGG
       ACTGAACCGT GGGTGGCACG TCGACTACCA TGGGTTCGCG GTCGCTGACC

15751  AAGATGTCTT GGAAAAAATG ACCGTGGAAC CTGGGCTGGA GCCCGAGGTC
       TTCTACAGAA CCTTTTTTAC TGGCACCTTG GACCCGACCT CGGGCTCCAG

15801  CGCGTGCGGC CAATCAAGCA GGTGGCGCCG GGACTGGGCG TGCAGACCGT
       GCGCACGCCG GTTAGTTCGT CCACCGCGGC CCTGACCCGC ACGTCTGGCA

15851  GGACGTTCAG ATACCCACTA CCAGTAGCAC CAGTATTGCC ACCGCCACAG
       CCTGCAAGTC TATGGGTGAT GGTCATCGTG GTCATAACGG TGGCGGTGTC

15901  AGGGCATGGA GACACAAACG TCCCCGGTTG CCTCAGCGGT GGCGGATGCC
       TCCCGTACCT CTGTGTTTGC AGGGGCCAAC GGAGTCGCCA CCGCCTACGG

15951  GCGGTGCAGG CGGTCGCTGC GGCCGCGTCC AAGACCTCTA CGGAGGTGCA
       CGCCACGTCC GCCAGCGACG CCGGCGCAGG TTCTGGAGAT GCCTCCACGT

16001  AACGGACCCG TGGATGTTTC GCGTTTCAGC CCCCCGGCGC CCGCGCCGTT
       TTGCCTGGGC ACCTACAAAG CGCAAAGTCG GGGGGCCGCG GGCGCGGCAA

16051  CGAGGAAGTA CGGCGCCGCC AGCGCGCTAC TGCCCGAATA TGCCCTACAT
       GCTCCTTCAT GCCGCGGCGG TCGCGCGATG ACGGGCTTAT ACGGGATGTA

16101  CCTTCCATTG CGCCTACCCC CGGCTATCGT GGCTACACCT ACCGCCCCAG
       GGAAGGTAAC GCGGATGGGG GCCGATAGCA CCGATGTGGA TGGCGGGGTC
```

FIG. 27A-19

```
16151  AAGACGAGCA ACTACCCGAC GCCGAACCAC CACTGGAACC CGCCGCCGCC
       TTCTGCTCGT TGATGGGCTG CGGCTTGGTG GTGACCTTGG GCGGCGGCGG

16201  GTCGCCGTCG CCAGCCCGTG CTGGCCCCGA TTTCCGTGCG CAGGGTGGCT
       CAGCGGCAGC GGTCGGGCAC GACCGGGGCT AAAGGCACGC GTCCCACCGA

16251  CGCGAAGGAG GCAGGACCCT GGTGCTGCCA ACAGCGCGCT ACCACCCCAG
       GCGCTTCCTC CGTCCTGGGA CCACGACGGT TGTCGCGCGA TGGTGGGGTC

16301  CATCGTTTAA AAGCCGGTCT TTGTGGTTCT TGCAGATATG GCCCTCACCT
       GTAGCAAATT TTCGGCCAGA AACACCAAGA ACGTCTATAC CGGGAGTGGA

16351  GCCGCCTCCG TTTCCCGGTG CCGGGATTCC GAGGAAGAAT GCACCGTAGG
       CGGCGGAGGC AAAGGGCCAC GGCCCTAAGG CTCCTTCTTA CGTGGCATCC

16401  AGGGGCATGG CCGGCCACGG CCTGACGGGC GGCATGCGTC GTGCGCACCA
       TCCCCGTACC GGCCGGTGCC GGACTGCCCG CCGTACGCAG CACGCGTGGT

16451  CCGGCGGCGG CGCGCGTCGC ACCGTCGCAT GCGCGGCGGT ATCCTGCCCC
       GGCCGCCGCC GCGCGCAGCG TGGCAGCGTA CGCGCCGCCA TAGGACGGGG

16501  TCCTTATTCC ACTGATCGCC GCGGCGATTG GCGCCGTGCC CGGAATTGCA
       AGGAATAAGG TGACTAGCGG CGCCGCTAAC CGCGGCACGG GCCTTAACGT

16551  TCCGTGGCCT TGCAGGCGCA GAGACACTGA TTAAAAACAA GTTGCATGTG
       AGGCACCGGA ACGTCCGCGT CTCTGTGACT AATTTTTGTT CAACGTACAC

16601  GAAAAATCAA AATAAAAAGT CTGGACTCTC ACGCTCGCTT GGTCCTGTAA
       CTTTTTAGTT TTATTTTTCA GACCTGAGAG TGCGAGCGAA CCAGGACATT

16651  CTATTTTGTA GAATGGAAGA CATCAACTTT GCGTCTCTGG CCCCGCGACA
       GATAAAACAT CTTACCTTCT GTAGTTGAAA CGCAGAGACC GGGGCGCTGT

16701  CGGCTCGCGC CCGTTCATGG GAAACTGGCA AGATATCGGC ACCAGCAATA
       GCCGAGCGCG GGCAAGTACC CTTTGACCGT TCTATAGCCG TGGTCGTTAT

16751  TGAGCGGTGG CGCCTTCAGC TGGGGCTCGC TGTGGAGCGG CATTAAAAAT
       ACTCGCCACC GCGGAAGTCG ACCCCGAGCG ACACCTCGCC GTAATTTTTA

16801  TTCGGTTCCA CCGTTAAGAA CTATGGCAGC AAGGCCTGGA ACAGCAGCAC
       AAGCCAAGGT GGCAATTCTT GATACCGTCG TTCCGGACCT TGTCGTCGTG

16851  AGGCCAGATG CTGAGGGATA AGTTGAAAGA GCAAAATTTC CAACAAAAGG
       TCCGGTCTAC GACTCCCTAT TCAACTTTCT CGTTTTAAAG GTTGTTTTCC

16901  TGGTAGATGG CCTGGCCTCT GGCATTAGCG GGGTGGTGGA CCTGGCCAAC
       ACCATCTACC GGACCGGAGA CCGTAATCGC CCCACCACCT GGACCGGTTG

16951  CAGGCAGTGC AAAATAAGAT TAACAGTAAG CTTGATCCCC GCCCTCCCGT
       GTCCGTCACG TTTTATTCTA ATTGTCATTC GAACTAGGGG CGGGAGGGCA
```

FIG. 27A-20

```
17001  AGAGGAGCCT CCACCGGCCG TGGAGACAGT GTCTCCAGAG GGGCGTGGCG
       TCTCCTCGGA GGTGGCCGGC ACCTCTGTCA CAGAGGTCTC CCCGCACCGC

17051  AAAAGCGTCC GCGCCCCGAC AGGGAAGAAA CTCTGGTGAC GCAAATAGAC
       TTTTCGCAGG CGCGGGGCTG TCCCTTCTTT GAGACCACTG CGTTTATCTG

17101  GAGCCTCCCT CGTACGAGGA GGCACTAAAG CAAGGCCTGC CCACCACCCG
       CTCGGAGGGA GCATGCTCCT CCGTGATTTC GTTCCGGACG GGTGGTGGGC

17151  TCCCATCGCG CCCATGGCTA CCGGAGTGCT GGGCCAGCAC ACACCCGTAA
       AGGGTAGCGC GGGTACCGAT GGCCTCACGA CCCGGTCGTG TGTGGGCATT

17201  CGCTGGACCT GCCTCCCCCC GCCGACACCC AGCAGAAACC TGTGCTGCCA
       GCGACCTGGA CGGAGGGGGG CGGCTGTGGG TCGTCTTTGG ACACGACGGT

17251  GGCCCGACCG CCGTTGTTGT AACCCGTCCT AGCCGCGCGT CCCTGCGCCG
       CCGGGCTGGC GGCAACAACA TTGGGCAGGA TCGGCGCGCA GGGACGCGGC

17301  CGCCGCCAGC GGTCCGCGAT CGTTGCGGCC CGTAGCCAGT GGCAACTGGC
       GCGGCGGTCG CCAGGCGCTA GCAACGCCGG GCATCGGTCA CCGTTGACCG

17351  AAAGCACACT GAACAGCATC GTGGGTCTGG GGGTGCAATC CCTGAAGCGC
       TTTCGTGTGA CTTGTCGTAG CACCCAGACC CCCACGTTAG GGACTTCGCG

17401  CGACGATGCT TCTGATAGCT AACGTGTCGT ATGTGTGTCA TGTATGCGTC
       GCTGCTACGA AGACTATCGA TTGCACAGCA TACACACAGT ACATACGCAG

17451  CATGTCGCCG CCAGAGGAGC TGCTGAGCCG CCGCGCGCCC GCTTTCCAAG
       GTACAGCGGC GGTCTCCTCG ACGACTCGGC GGCGCGCGGG CGAAAGGTTC

17501  ATGGCTACCC CTTCGATGAT GCCGCAGTGG TCTTACATGC ACATCTCGGG
       TACCGATGGG GAAGCTACTA CGGCGTCACC AGAATGTACG TGTAGAGCCC

17551  CCAGGACGCC TCGGAGTACC TGAGCCCCGG GCTGGTGCAG TTTGCCCGCG
       GGTCCTGCGG AGCCTCATGG ACTCGGGGCC CGACCACGTC AAACGGGCGC

17601  CCACCGAGAC GTACTTCAGC CTGAATAACA AGTTTAGAAA CCCCACGGTG
       GGTGGCTCTG CATGAAGTCG GACTTATTGT TCAAATCTTT GGGGTGCCAC

17651  GCGCCTACGC ACGACGTGAC CACAGACCGG TCCCAGCGTT TGACGCTGCG
       CGCGGATGCG TGCTGCACTG GTGTCTGGCC AGGGTCGCAA ACTGCGACGC

17701  GTTCATCCCT GTGGACCGTG AGGATACTGC GTACTCGTAC AAGGCGCGGT
       CAAGTAGGGA CACCTGGCAC TCCTATGACG CATGAGCATG TTCCGCGCCA

17751  TCACCCTAGC TGTGGGTGAT AACCGTGTGC TGGACATGGC TTCCACGTAC
       AGTGGGATCG ACACCCACTA TTGGCACACG ACCTGTACCG AAGGTGCATG

17801  TTTGACATCC GCGGCGTGCT GGACAGGGGC CCTACTTTTA AGCCCTACTC
       AAACTGTAGG CGCCGCACGA CCTGTCCCCG GGATGAAAAT TCGGGATGAG
```

FIG. 27A-21

```
17851  TGGCACTGCC TACAACGCCC TGGCTCCCAA GGGTGCCCCA AATCCTTGCG
       ACCGTGACGG ATGTTGCGGG ACCGAGGGTT CCCACGGGGT TTAGGAACGC

17901  AATGGGATGA AGCTGCTACT GCTCTTGAAA TAAACCTAGA AGAAGAGGAC
       TTACCCTACT TCGACGATGA CGAGAACTTT ATTTGGATCT TCTTCTCCTG

17951  GATGACAACG AAGACGAAGT AGACGAGCAA GCTGAGCAGC AAAAAACTCA
       CTACTGTTGC TTCTGCTTCA TCTGCTCGTT CGACTCGTCG TTTTTTGAGT

18001  CGTATTTGGG CAGGCGCCTT ATTCTGGTAT AAATATTACA AAGGAGGGTA
       GCATAAACCC GTCCGCGGAA TAAGACCATA TTTATAATGT TTCCTCCCAT

18051  TTCAAATAGG TGTCGAAGGT CAAACACCTA AATATGCCGA TAAAACATTT
       AAGTTTATCC ACAGCTTCCA GTTTGTGGAT TTATACGGCT ATTTTGTAAA

18101  CAACCTGAAC CTCAAATAGG AGAATCTCAG TGGTACGAAA CAGAAATTAA
       GTTGGACTTG GAGTTTATCC TCTTAGAGTC ACCATGCTTT GTCTTTAATT

18151  TCATGCAGCT GGGAGAGTCC TAAAAAAGAC TACCCCAATG AAACCATGTT
       AGTACGTCGA CCCTCTCAGG ATTTTTTCTG ATGGGGTTAC TTTGGTACAA

18201  ACGGTTCATA TGCAAAACCC ACAAATGAAA ATGGAGGGCA AGGCATTCTT
       TGCCAAGTAT ACGTTTTGGG TGTTTACTTT TACCTCCCGT TCCGTAAGAA

18251  GTAAAGCAAC AAAATGGAAA GCTAGAAAGT CAAGTGGAAA TGCAATTTTT
       CATTTCGTTG TTTTACCTTT CGATCTTTCA GTTCACCTTT ACGTTAAAAA

18301  CTCAACTACT GAGGCAGCCG CAGGCAATGG TGATAACTTG ACTCCTAAAG
       GAGTTGATGA CTCCGTCGGC GTCCGTTACC ACTATTGAAC TGAGGATTTC

18351  TGGTATTGTA CAGTGAAGAT GTAGATATAG AAACCCCAGA CACTCATATT
       ACCATAACAT GTCACTTCTA CATCTATATC TTTGGGGTCT GTGAGTATAA

18401  TCTTACATGC CCACTATTAA GGAAGGTAAC TCACGAGAAC TAATGGGCCA
       AGAATGTACG GGTGATAATT CCTTCCATTG AGTGCTCTTG ATTACCCGGT

18451  ACAATCTATG CCCAACAGGC CTAATTACAT TGCTTTTAGG GACAATTTTA
       TGTTAGATAC GGGTTGTCCG GATTAATGTA ACGAAAATCC CTGTTAAAAT

18501  TTGGTCTAAT GTATTACAAC AGCACGGGTA ATATGGGTGT TCTGGCGGGC
       AACCAGATTA CATAATGTTG TCGTGCCCAT TATACCCACA AGACCGCCCG

18551  CAAGCATCGC AGTTGAATGC TGTTGTAGAT TTGCAAGACA GAAACACAGA
       GTTCGTAGCG TCAACTTACG ACAACATCTA AACGTTCTGT CTTTGTGTCT

18601  GCTTTCATAC CAGCTTTTGC TTGATTCCAT TGGTGATAGA ACCAGGTACT
       CGAAAGTATG GTCGAAAACG AACTAAGGTA ACCACTATCT TGGTCCATGA

18651  TTTCTATGTG GAATCAGGCT GTTGACAGCT ATGATCCAGA TGTTAGAATT
       AAAGATACAC CTTAGTCCGA CAACTGTCGA TACTAGGTCT ACAATCTTAA
```

FIG. 27A-22

```
18701 ATTGAAAATC ATGGAACTGA AGATGAACTT CCAAATTACT GCTTTCCACT
      TAACTTTTAG TACCTTGACT TCTACTTGAA GGTTTAATGA CGAAAGGTGA

18751 GGGAGGTGTG ATTAATACAG AGACTCTTAC CAAGGTAAAA CCTAAAACAG
      CCCTCCACAC TAATTATGTC TCTGAGAATG GTTCCATTTT GGATTTTGTC

18801 GTCAGGAAAA TGGATGGGAA AAAGATGCTA CAGAATTTTC AGATAAAAAT
      CAGTCCTTTT ACCTACCCTT TTTCTACGAT GTCTTAAAAG TCTATTTTTA

18851 GAAATAAGAG TTGGAAATAA TTTTGCCATG GAAATCAATC TAAATGCCAA
      CTTTATTCTC AACCTTTATT AAAACGGTAC CTTTAGTTAG ATTTACGGTT

18901 CCTGTGGAGA AATTTCCTGT ACTCCAACAT AGCGCTGTAT TTGCCCGACA
      GGACACCTCT TTAAAGGACA TGAGGTTGTA TCGCGACATA AACGGGCTGT

18951 AGCTAAAGTA CAGTCCTTCC AACGTAAAAA TTTCTGATAA CCCAAACACC
      TCGATTTCAT GTCAGGAAGG TTGCATTTTT AAAGACTATT GGGTTTGTGG

19001 TACGACTACA TGAACAAGCG AGTGGTGGCT CCCGGGCTAG TGGACTGCTA
      ATGCTGATGT ACTTGTTCGC TCACCACCGA GGGCCCGATC ACCTGACGAT

19051 CATTAACCTT GGAGCACGCT GGTCCCTTGA CTATATGGAC AACGTCAACC
      GTAATTGGAA CCTCGTGCGA CCAGGGAACT GATATACCTG TTGCAGTTGG

19101 CATTTAACCA CCACCGCAAT GCTGGCCTGC GCTACCGCTC AATGTTGCTG
      GTAAATTGGT GGTGGCGTTA CGACCGGACG CGATGGCGAG TTACAACGAC

19151 GGCAATGGTC GCTATGTGCC CTTCCACATC CAGGTGCCTC AGAAGTTCTT
      CCGTTACCAG CGATACACGG GAAGGTGTAG GTCCACGGAG TCTTCAAGAA

19201 TGCCATTAAA AACCTCCTTC TCCTGCCGGG CTCATACACC TACGAGTGGA
      ACGGTAATTT TTGGAGGAAG AGGACGGCCC GAGTATGTGG ATGCTCACCT

19251 ACTTCAGGAA GGATGTTAAC ATGGTTCTGC AGAGCTCCCT AGGAAATGAC
      TGAAGTCCTT CCTACAATTG TACCAAGACG TCTCGAGGGA TCCTTTACTG

19301 CTAAGGGTTG ACGGAGCCAG CATTAAGTTT GATAGCATTT GCCTTTACGC
      GATTCCCAAC TGCCTCGGTC GTAATTCAAA CTATCGTAAA CGGAAATGCG

19351 CACCTTCTTC CCCATGGCCC ACAACACCGC CTCCACGCTT GAGGCCATGC
      GTGGAAGAAG GGGTACCGGG TGTTGTGGCG GAGGTGCGAA CTCCGGTACG

19401 TTAGAAACGA CACCAACGAC CAGTCCTTTA ACGACTATCT CTCCGCCGCC
      AATCTTTGCT GTGGTTGCTG GTCAGGAAAT TGCTGATAGA GAGGCGGCGG

19451 AACATGCTCT ACCCTATACC CGCCAACGCT ACCAACGTGC CCATATCCAT
      TTGTACGAGA TGGGATATGG GCGGTTGCGA TGGTTGCACG GGTATAGGTA

19501 CCCCTCCCGC AACTGGGCGG CTTTCCGCGG CTGGGCCTTC ACGCGCCTTA
      GGGGAGGGCG TTGACCCGCC GAAAGGCGCC GACCCGGAAG TGCGCGGAAT
```

FIG. 27A-23

```
19551  AGACTAAGGA AACCCCATCA CTGGGCTCGG GCTACGACCC TTATTACACC
       TCTGATTCCT TTGGGGTAGT GACCCGAGCC CGATGCTGGG AATAATGTGG

19601  TACTCTGGCT CTATACCCTA CCTAGATGGA ACCTTTTACC TCAACCACAC
       ATGAGACCGA GATATGGGAT GGATCTACCT TGGAAAATGG AGTTGGTGTG

19651  CTTTAAGAAG GTGGCCATTA CCTTTGACTC TTCTGTCAGC TGGCCTGGCA
       GAAATTCTTC CACCGGTAAT GGAAACTGAG AAGACAGTCG ACCGGACCGT

19701  ATGACCGCCT GCTTACCCCC AACGAGTTTG AAATTAAGCG CTCAGTTGAC
       TACTGGCGGA CGAATGGGGG TTGCTCAAAC TTTAATTCGC GAGTCAACTG

19751  GGGGAGGGTT ACAACGTTGC CCAGTGTAAC ATGACCAAAG ACTGGTTCCT
       CCCCTCCCAA TGTTGCAACG GGTCACATTG TACTGGTTTC TGACCAAGGA

19801  GGTACAAATG CTAGCTAACT ATAACATTGG CTACCAGGGC TTCTATATCC
       CCATGTTTAC GATCGATTGA TATTGTAACC GATGGTCCCG AAGATATAGG

19851  CAGAGAGCTA CAAGGACCGC ATGTACTCCT TCTTTAGAAA CTTCCAGCCC
       GTCTCTCGAT GTTCCTGGCG TACATGAGGA AGAAATCTTT GAAGGTCGGG

19901  ATGAGCCGTC AGGTGGTGGA TGATACTAAA TACAAGGACT ACCAACAGGT
       TACTCGGCAG TCCACCACCT ACTATGATTT ATGTTCCTGA TGGTTGTCCA

19951  GGGCATCCTA CACCAACACA ACAACTCTGG ATTTGTTGGC TACCTTGCCC
       CCCGTAGGAT GTGGTTGTGT TGTTGAGACC TAAACAACCG ATGGAACGGG

20001  CCACCATGCG CGAAGGACAG GCCTACCCTG CTAACTTCCC CTATCCGCTT
       GGTGGTACGC GCTTCCTGTC CGGATGGGAC GATTGAAGGG GATAGGCGAA

20051  ATAGGCAAGA CCGCAGTTGA CAGCATTACC CAGAAAAAGT TTCTTTGCGA
       TATCCGTTCT GGCGTCAACT GTCGTAATGG GTCTTTTTCA AAGAAACGCT

20101  TCGCACCCTT TGGCGCATCC CATTCTCCAG TAACTTTATG TCCATGGGCG
       AGCGTGGGAA ACCGCGTAGG GTAAGAGGTC ATTGAAATAC AGGTACCCGC

20151  CACTCACAGA CCTGGGCCAA AACCTTCTCT ACGCCAACTC CGCCCACGCG
       GTGAGTGTCT GGACCCGGTT TTGGAAGAGA TGCGGTTGAG GCGGGTGCGC

20201  CTAGACATGA CTTTTGAGGT GGATCCCATG GACGAGCCCA CCCTTCTTTA
       GATCTGTACT GAAAACTCCA CCTAGGGTAC CTGCTCGGGT GGGAAGAAAT

20251  TGTTTTGTTT GAAGTCTTTG ACGTGGTCCG TGTGCACCAG CCGCACCGCG
       ACAAAACAAA CTTCAGAAAC TGCACCAGGC ACACGTGGTC GGCGTGGCGC

20301  GCGTCATCGA AACCGTGTAC CTGCGCACGC CCTTCTCGGC CGGCAACGCC
       CGCAGTAGCT TTGGCACATG GACGCGTGCG GGAAGAGCCG GCCGTTGCGG

20351  ACAACATAAA GAAGCAAGCA ACATCAACAA CAGCTGCCGC CATGGGCTCC
       TGTTGTATTT CTTCGTTCGT TGTAGTTGTT GTCGACGGCG GTACCCGAGG
```

FIG. 27A-24

```
20401  AGTGAGCAGG AACTGAAAGC CATTGTCAAA GATCTTGGTT GTGGGCCATA
       TCACTCGTCC TTGACTTTCG GTAACAGTTT CTAGAACCAA CACCCGGTAT

20451  TTTTTTGGGC ACCTATGACA AGCGCTTTCC AGGCTTTGTT TCTCCACACA
       AAAAAACCCG TGGATACTGT TCGCGAAAGG TCCGAAACAA AGAGGTGTGT

20501  AGCTCGCCTG CGCCATAGTC AATACGGCCG GTCGCGAGAC TGGGGGCGTA
       TCGAGCGGAC GCGGTATCAG TTATGCCGGC CAGCGCTCTG ACCCCCGCAT

20551  CACTGGATGG CCTTTGCCTG GAACCCGCAC TCAAAAACAT GCTACCTCTT
       GTGACCTACC GGAAACGGAC CTTGGGCGTG AGTTTTTGTA CGATGGAGAA

20601  TGAGCCCTTT GGCTTTTCTG ACCAGCGACT CAAGCAGGTT TACCAGTTTG
       ACTCGGGAAA CCGAAAAGAC TGGTCGCTGA GTTCGTCCAA ATGGTCAAAC

20651  AGTACGAGTC ACTCCTGCGC CGTAGCGCCA TTGCTTCTTC CCCCGACCGC
       TCATGCTCAG TGAGGACGCG GCATCGCGGT AACGAAGAAG GGGGCTGGCG

20701  TGTATAACGC TGGAAAAGTC CACCCAAAGC GTACAGGGGC CCAACTCGGC
       ACATATTGCG ACCTTTTCAG GTGGGTTTCG CATGTCCCCG GGTTGAGCCG

20751  CGCCTGTGGA CTATTCTGCT GCATGTTTCT CCACGCCTTT GCCAACTGGC
       GCGGACACCT GATAAGACGA CGTACAAAGA GGTGCGGAAA CGGTTGACCG

20801  CCCAAACTCC CATGGATCAC AACCCCACCA TGAACCTTAT TACCGGGGTA
       GGGTTTGAGG GTACCTAGTG TTGGGGTGGT ACTTGGAATA ATGGCCCCAT

20851  CCCAACTCCA TGCTCAACAG TCCCCAGGTA CAGCCCACCC TGCGTCGCAA
       GGGTTGAGGT ACGAGTTGTC AGGGGTCCAT GTCGGGTGGG ACGCAGCGTT

20901  CCAGGAACAG CTCTACAGCT TCCTGGAGCG CCACTCGCCC TACTTCCGCA
       GGTCCTTGTC GAGATGTCGA AGGACCTCGC GGTGAGCGGG ATGAAGGCGT

20951  GCCACAGTGC GCAGATTAGG AGCGCCACTT CTTTTTGTCA CTTGAAAAAC
       CGGTGTCACG CGTCTAATCC TCGCGGTGAA GAAAAACAGT GAACTTTTTG

21001  ATGTAAAAAT AATGTACTAG AGACACTTTC AATAAAGGCA AATGCTTTTA
       TACATTTTTA TTACATGATC TCTGTGAAAG TTATTTCCGT TTACGAAAAT

21051  TTTGTACACT CTCGGGTGAT TATTTACCCC CACCCTTGCC GTCTGCGCCG
       AAACATGTGA GAGCCCACTA ATAAATGGGG GTGGGAACGG CAGACGCGGC

21101  TTTAAAAATC AAAGGGGTTC TGCCGCGCAT CGCTATGCGC CACTGGCAGG
       AAATTTTTAG TTTCCCCAAG ACGGCGCGTA GCGATACGCG GTGACCGTCC

21151  GACACGTTGC GATACTGGTG TTTAGTGCTC CACTTAAACT CAGGCACAAC
       CTGTGCAACG CTATGACCAC AAATCACGAG GTGAATTTGA GTCCGTGTTG

21201  CATCCGCGGC AGCTCGGTGA AGTTTTCACT CCACAGGCTG CGCACCATCA
       GTAGGCGCCG TCGAGCCACT TCAAAAGTGA GGTGTCCGAC GCGTGGTAGT
```

FIG. 27A-25

```
21251  CCAACGCGTT TAGCAGGTCG GGCGCCGATA TCTTGAAGTC GCAGTTGGGG
       GGTTGCGCAA ATCGTCCAGC CCGCGGCTAT AGAACTTCAG CGTCAACCCC

21301  CCTCCGCCCT GCGCGCGCGA GTTGCGATAC ACAGGGTTGC AGCACTGGAA
       GGAGGCGGGA CGCGCGCGCT CAACGCTATG TGTCCCAACG TCGTGACCTT

21351  CACTATCAGC GCCGGGTGGT GCACGCTGGC CAGCACGCTC TTGTCGGAGA
       GTGATAGTCG CGGCCCACCA CGTGCGACCG GTCGTGCGAG AACAGCCTCT

21401  TCAGATCCGC GTCCAGGTCC TCCGCGTTGC TCAGGGCGAA CGGAGTCAAC
       AGTCTAGGCG CAGGTCCAGG AGGCGCAACG AGTCCCGCTT GCCTCAGTTG

21451  TTTGGTAGCT GCCTTCCCAA AAAGGGCGCG TGCCCAGGCT TTGAGTTGCA
       AAACCATCGA CGGAAGGGTT TTTCCCGCGC ACGGGTCCGA AACTCAACGT

21501  CTCGCACCGT AGTGGCATCA AAAGGTGACC GTGCCCGGTC TGGGCGTTAG
       GAGCGTGGCA TCACCGTAGT TTTCCACTGG CACGGGCCAG ACCCGCAATC

21551  GATACAGCGC CTGCATAAAA GCCTTGATCT GCTTAAAAGC CACCTGAGCC
       CTATGTCGCG GACGTATTTT CGGAACTAGA CGAATTTTCG GTGGACTCGG

21601  TTTGCGCCTT CAGAGAAGAA CATGCCGCAA GACTTGCCGG AAAACTGATT
       AAACGCGGAA GTCTCTTCTT GTACGGCGTT CTGAACGGCC TTTTGACTAA

21651  GGCCGGACAG GCCGCGTCGT GCACGCAGCA CCTTGCGTCG GTGTTGGAGA
       CCGGCCTGTC CGGCGCAGCA CGTGCGTCGT GGAACGCAGC CACAACCTCT

21701  TCTGCACCAC ATTTCGGCCC CACCGGTTCT TCACGATCTT GGCCTTGCTA
       AGACGTGGTG TAAAGCCGGG GTGGCCAAGA AGTGCTAGAA CCGGAACGAT

21751  GACTGCTCCT TCAGCGCGCG CTGCCCGTTT TCGCTCGTCA CATCCATTTC
       CTGACGAGGA AGTCGCGCGC GACGGGCAAA AGCGAGCAGT GTAGGTAAAG

21801  AATCACGTGC TCCTTATTTA TCATAATGCT TCCGTGTAGA CACTTAAGCT
       TTAGTGCACG AGGAATAAAT AGTATTACGA AGGCACATCT GTGAATTCGA

21851  CGCCTTCGAT CTCAGCGCAG CGGTGCAGCC ACAACGCGCA GCCCGTGGGC
       GCGGAAGCTA GAGTCGCGTC GCCACGTCGG TGTTGCGCGT CGGGCACCCG

21901  TCGTGATGCT TGTAGGTCAC CTCTGCAAAC GACTGCAGGT ACGCCTGCAG
       AGCACTACGA ACATCCAGTG GAGACGTTTG CTGACGTCCA TGCGGACGTC

21951  GAATCGCCCC ATCATCGTCA CAAAGGTCTT GTTGCTGGTG AAGGTCAGCT
       CTTAGCGGGG TAGTAGCAGT GTTTCCAGAA CAACGACCAC TTCCAGTCGA

22001  GCAACCCGCG GTGCTCCTCG TTCAGCCAGG TCTTGCATAC GGCCGCCAGA
       CGTTGGGCGC CACGAGGAGC AAGTCGGTCC AGAACGTATG CCGGCGGTCT

22051  GCTTCCACTT GGTCAGGCAG TAGTTTGAAG TTCGCCTTTA GATCGTTATC
       CGAAGGTGAA CCAGTCCGTC ATCAAACTTC AAGCGGAAAT CTAGCAATAG
```

FIG. 27A-26

```
22101  CACGTGGTAC TTGTCCATCA GCGCGCGCGC AGCCTCCATG CCCTTCTCCC
       GTGCACCATG AACAGGTAGT CGCGCGCGCG TCGGAGGTAC GGGAAGAGGG

22151  ACGCAGACAC GATCGGCACA CTCAGCGGGT TCATCACCGT AATTTCACTT
       TGCGTCTGTG CTAGCCGTGT GAGTCGCCCA AGTAGTGGCA TTAAAGTGAA

22201  TCCGCTTCGC TGGGCTCTTC CTCTTCCTCT TGCGTCCGCA TACCACGCGC
       AGGCGAAGCG ACCCGAGAAG GAGAAGGAGA ACGCAGGCGT ATGGTGCGCG

22251  CACTGGGTCG TCTTCATTCA GCCGCCGCAC TGTGCGCTTA CCTCCTTTGC
       GTGACCCAGC AGAAGTAAGT CGGCGGCGTG ACACGCGAAT GGAGGAAACG

22301  CATGCTTGAT TAGCACCGGT GGGTTGCTGA AACCCACCAT TTGTAGCGCC
       GTACGAACTA ATCGTGGCCA CCCAACGACT TTGGGTGGTA AACATCGCGG

22351  ACATCTTCTC TTTCTTCCTC GCTGTCCACG ATTACCTCTG GTGATGGCGG
       TGTAGAAGAG AAAGAAGGAG CGACAGGTGC TAATGGAGAC CACTACCGCC

22401  GCGCTCGGGC TTGGGAGAAG GGCGCTTCTT TTTCTTCTTG GGCGCAATGG
       CGCGAGCCCG AACCCTCTTC CCGCGAAGAA AAAGAAGAAC CCGCGTTACC

22451  CCAAATCCGC CGCCGAGGTC GATGGCCGCG GGCTGGGTGT GCGCGGCACC
       GGTTTAGGCG GCGGCTCCAG CTACCGGCGC CCGACCCACA CGCGCCGTGG

22501  AGCGCGTCTT GTGATGAGTC TTCCTCGTCC TCGGACTCGA TACGCCGCCT
       TCGCGCAGAA CACTACTCAG AAGGAGCAGG AGCCTGAGCT ATGCGGCGGA

22551  CATCCGCTTT TTTGGGGGCG CCCGGGGAGG CGGCGGCGAC GGGGACGGGG
       GTAGGCGAAA AAACCCCCGC GGGCCCCTCC GCCGCCGCTG CCCCTGCCCC

22601  ACGACACGTC CTCCATGGTT GGGGGACGTC GCGCCGCACC GCGTCCGCGC
       TGCTGTGCAG GAGGTACCAA CCCCCTGCAG CGCGGCGTGG CGCAGGCGCG

22651  TCGGGGGTGG TTTCGCGCTG CTCCTCTTCC CGACTGGCCA TTTCCTTCTC
       AGCCCCCACC AAAGCGCGAC GAGGAGAAGG GCTGACCGGT AAAGGAAGAG

22701  CTATAGGCAG AAAAAGATCA TGGAGTCAGT CGAGAAGAAG GACAGCCTAA
       GATATCCGTC TTTTTCTAGT ACCTCAGTCA GCTCTTCTTC CTGTCGGATT

22751  CCGCCCCCTC TGAGTTCGCC ACCACCGCCT CCACCGATGC CGCCAACGCG
       GGCGGGGGAG ACTCAAGCGG TGGTGGCGGA GGTGGCTACG GCGGTTGCGC

22801  CCTACCACCT TCCCCGTCGA GGCACCCCCG CTTGAGGAGG AGGAAGTGAT
       GGATGGTGGA AGGGGCAGCT CCGTGGGGGC GAACTCCTCC TCCTTCACTA

22851  TATCGAGCAG GACCCAGGTT TTGTAAGCGA AGACGACGAG GACCGCTCAG
       ATAGCTCGTC CTGGGTCCAA AACATTCGCT TCTGCTGCTC CTGGCGAGTC

22901  TACCAACAGA GGATAAAAAG CAAGACCAGG ACAACGCAGA GGCAAACGAG
       ATGGTTGTCT CCTATTTTTC GTTCTGGTCC TGTTGCGTCT CCGTTTGCTC
```

FIG. 27A-27

```
22951  GAACAAGTCG GGCGGGGGGA CGAAAGGCAT GGCGACTACC TAGATGTGGG
       CTTGTTCAGC CCGCCCCCCT GCTTTCCGTA CCGCTGATGG ATCTACACCC

23001  AGACGACGTG CTGTTGAAGC ATCTGCAGCG CCAGTGCGCC ATTATCTGCG
       TCTGCTGCAC GACAACTTCG TAGACGTCGC GGTCACGCGG TAATAGACGC

23051  ACGCGTTGCA AGAGCGCAGC GATGTGCCCC TCGCCATAGC GGATGTCAGC
       TGCGCAACGT TCTCGCGTCG CTACACGGGG AGCGGTATCG CCTACAGTCG

23101  CTTGCCTACG AACGCCACCT ATTCTCACCG CGCGTACCCC CCAAACGCCA
       GAACGGATGC TTGCGGTGGA TAAGAGTGGC GCGCATGGGG GGTTTGCGGT

23151  AGAAAACGGC ACATGCGAGC CCAACCCGCG CCTCAACTTC TACCCCGTAT
       TCTTTTGCCG TGTACGCTCG GGTTGGGCGC GGAGTTGAAG ATGGGGCATA

23201  TTGCCGTGCC AGAGGTGCTT GCCACCTATC ACATCTTTTT CCAAAACTGC
       AACGGCACGG TCTCCACGAA CGGTGGATAG TGTAGAAAAA GGTTTTGACG

23251  AAGATACCCC TATCCTGCCG TGCCAACCGC AGCCGAGCGG ACAAGCAGCT
       TTCTATGGGG ATAGGACGGC ACGGTTGGCG TCGGCTCGCC TGTTCGTCGA

23301  GGCCTTGCGG CAGGGCGCTG TCATACCTGA TATCGCCTCG CTCAACGAAG
       CCGGAACGCC GTCCCGCGAC AGTATGGACT ATAGCGGAGC GAGTTGCTTC

23351  TGCCAAAAAT CTTTGAGGGT CTTGGACGCG ACGAGAAGCG CGCGGCAAAC
       ACGGTTTTTA GAAACTCCCA GAACCTGCGC TGCTCTTCGC GCGCCGTTTG

23401  GCTCTGCAAC AGGAAAACAG CGAAAATGAA AGTCACTCTG GAGTGTTGGT
       CGAGACGTTG TCCTTTTGTC GCTTTTACTT TCAGTGAGAC CTCACAACCA

23451  GGAACTCGAG GGTGACAACG CGCGCCTAGC CGTACTAAAA CGCAGCATCG
       CCTTGAGCTC CCACTGTTGC GCGCGGATCG GCATGATTTT GCGTCGTAGC

23501  AGGTCACCCA CTTTGCCTAC CCGGCACTTA ACCTACCCCC CAAGGTCATG
       TCCAGTGGGT GAAACGGATG GGCCGTGAAT TGGATGGGGG GTTCCAGTAC

23551  AGCACAGTCA TGAGTGAGCT GATCGTGCGC CGTGCGCAGC CCCTGGAGAG
       TCGTGTCAGT ACTCACTCGA CTAGCACGCG GCACGCGTCG GGGACCTCTC

23601  GGATGCAAAT TTGCAAGAAC AAACAGAGGA GGGCCTACCC GCAGTTGGCG
       CCTACGTTTA AACGTTCTTG TTTGTCTCCT CCCGGATGGG CGTCAACCGC

23651  ACGAGCAGCT AGCGCGCTGG CTTCAAACGC GCGAGCCTGC CGACTTGGAG
       TGCTCGTCGA TCGCGCGACC GAAGTTTGCG CGCTCGGACG GCTGAACCTC

23701  GAGCGACGCA AACTAATGAT GGCCGCAGTG CTCGTTACCG TGGAGCTTGA
       CTCGCTGCGT TTGATTACTA CCGGCGTCAC GAGCAATGGC ACCTCGAACT

23751  GTGCATGCAG CGGTTCTTTG CTGACCCGGA GATGCAGCGC AAGCTAGAGG
       CACGTACGTC GCCAAGAAAC GACTGGGCCT CTACGTCGCG TTCGATCTCC
```

FIG. 27A-28

```
23801  AAACATTGCA CTACACCTTT CGACAGGGCT ACGTACGCCA GGCCTGCAAG
       TTTGTAACGT GATGTGGAAA GCTGTCCCGA TGCATGCGGT CCGGACGTTC

23851  ATCTCCAACG TGGAGCTCTG CAACCTGGTC TCCTACCTTG GAATTTTGCA
       TAGAGGTTGC ACCTCGAGAC GTTGGACCAG AGGATGGAAC CTTAAAACGT

23901  CGAAAACCGC CTTGGGCAAA ACGTGCTTCA TTCCACGCTC AAGGGCGAGG
       GCTTTTGGCG GAACCCGTTT TGCACGAAGT AAGGTGCGAG TTCCCGCTCC

23951  CGCGCCGCGA CTACGTCCGC GACTGCGTTT ACTTATTTCT ATGCTACACC
       GCGCGGCGCT GATGCAGGCG CTGACGCAAA TGAATAAAGA TACGATGTGG

24001  TGGCAGACGG CCATGGGCGT TTGGCAGCAG TGCTTGGAGG AGTGCAACCT
       ACCGTCTGCC GGTACCCGCA AACCGTCGTC ACGAACCTCC TCACGTTGGA

24051  CAAGGAGCTG CAGAAACTGC TAAAGCAAAA CTTGAAGGAC CTATGGACGG
       GTTCCTCGAC GTCTTTGACG ATTTCGTTTT GAACTTCCTG GATACCTGCC

24101  CCTTCAACGA GCGCTCCGTG GCCGCGCACC TGGCGGACAT CATTTTCCCC
       GGAAGTTGCT CGCGAGGCAC CGGCGCGTGG ACCGCCTGTA GTAAAAGGGG

24151  GAACGCCTGC TTAAAACCCT GCAACAGGGT CTGCCAGACT TCACCAGTCA
       CTTGCGGACG AATTTTGGGA CGTTGTCCCA GACGGTCTGA AGTGGTCAGT

24201  AAGCATGTTG CAGAACTTTA GGAACTTTAT CCTAGAGCGC TCAGGAATCT
       TTCGTACAAC GTCTTGAAAT CCTTGAAATA GGATCTCGCG AGTCCTTAGA

24251  TGCCCGCCAC CTGCTGTGCA CTTCCTAGCG ACTTTGTGCC CATTAAGTAC
       ACGGGCGGTG GACGACACGT GAAGGATCGC TGAAACACGG GTAATTCATG

24301  CGCGAATGCC CTCCGCCGCT TTGGGGCCAC TGCTACCTTC TGCAGCTAGC
       GCGCTTACGG GAGGCGGCGA AACCCCGGTG ACGATGGAAG ACGTCGATCG

24351  CAACTACCTT GCCTACCACT CTGACATAAT GGAAGACGTG AGCGGTGACG
       GTTGATGGAA CGGATGGTGA GACTGTATTA CCTTCTGCAC TCGCCACTGC

24401  GTCTACTGGA GTGTCACTGT CGCTGCAACC TATGCACCCC GCACCGCTCC
       CAGATGACCT CACAGTGACA GCGACGTTGG ATACGTGGGG CGTGGCGAGG

24451  CTGGTTTGCA ATTCGCAGCT GCTTAACGAA AGTCAAATTA TCGGTACCTT
       GACCAAACGT TAAGCGTCGA CGAATTGCTT TCAGTTTAAT AGCCATGGAA

24501  TGAGCTGCAG GGTCCCTCGC CTGACGAAAA GTCCGCGGCT CCGGGGTTGA
       ACTCGACGTC CCAGGGAGCG GACTGCTTTT CAGGCGCCGA GGCCCCAACT

24551  AACTCACTCC GGGGCTGTGG ACGTCGGCTT ACCTTCGCAA ATTTGTACCT
       TTGAGTGAGG CCCCGACACC TGCAGCCGAA TGGAAGCGTT TAAACATGGA

24601  GAGGACTACC ACGCCCACGA GATTAGGTTC TACGAAGACC AATCCCGCCC
       CTCCTGATGG TGCGGGTGCT CTAATCCAAG ATGCTTCTGG TTAGGGCGGG
```

FIG. 27A-29

```
24651  GCCTAATGCG GAGCTTACCG CCTGCGTCAT TACCCAGGGC CACATTCTTG
       CGGATTACGC CTCGAATGGC GGACGCAGTA ATGGGTCCCG GTGTAAGAAC

24701  GCCAATTGCA AGCCATCAAC AAAGCCCGCC AAGAGTTTCT GCTACGAAAG
       CGGTTAACGT TCGGTAGTTG TTTCGGGCGG TTCTCAAAGA CGATGCTTTC

24751  GGACGGGGGG TTTACTTGGA CCCCCAGTCC GGCGAGGAGC TCAACCCAAT
       CCTGCCCCCC AAATGAACCT GGGGGTCAGG CCGCTCCTCG AGTTGGGTTA

24801  CCCCCCGCCG CCGCAGCCCT ATCAGCAGCA GCCGCGGGCC CTTGCTTCCC
       GGGGGGCGGC GGCGTCGGGA TAGTCGTCGT CGGCGCCCGG GAACGAAGGG

24851  AGGATGGCAC CCAAAAAGAA GCTGCAGCTG CCGCCGCCAC CCACGGACGA
       TCCTACCGTG GGTTTTTCTT CGACGTCGAC GGCGGCGGTG GGTGCCTGCT

24901  GGAGGAATAC TGGGACAGTC AGGCAGAGGA GGTTTTGGAC GAGGAGGAGG
       CCTCCTTATG ACCCTGTCAG TCCGTCTCCT CCAAAACCTG CTCCTCCTCC

24951  AGGACATGAT GGAAGACTGG GAGAGCCTAG ACGAGGAAGC TTCCGAGGTC
       TCCTGTACTA CCTTCTGACC CTCTCGGATC TGCTCCTTCG AAGGCTCCAG

25001  GAAGAGGTGT CAGACGAAAC ACCGTCACCC TCGGTCGCAT TCCCCTCGCC
       CTTCTCCACA GTCTGCTTTG TGGCAGTGGG AGCCAGCGTA AGGGGAGCGG

25051  GGCGCCCCAG AAATCGGCAA CCGGTTCCAG CATGGCTACA ACCTCCGCTC
       CCGCGGGGTC TTTAGCCGTT GGCCAAGGTC GTACCGATGT TGGAGGCGAG

25101  CTCAGGCGCC GCCGGCACTG CCCGTTCGCC GACCCAACCG TAGATGGGAC
       GAGTCCGCGG CGGCCGTGAC GGGCAAGCGG CTGGGTTGGC ATCTACCCTG

25151  ACCACTGGAA CCAGGGCCGG TAAGTCCAAG CAGCCGCCGC CGTTAGCCCA
       TGGTGACCTT GGTCCCGGCC ATTCAGGTTC GTCGGCGGCG GCAATCGGGT

25201  AGAGCAACAA CAGCGCCAAG GCTACCGCTC ATGGCGCGGG CACAAGAACG
       TCTCGTTGTT GTCGCGGTTC CGATGGCGAG TACCGCGCCC GTGTTCTTGC

25251  CCATAGTTGC TTGCTTGCAA GACTGTGGGG GCAACATCTC CTTCGCCCGC
       GGTATCAACG AACGAACGTT CTGACACCCC CGTTGTAGAG GAAGCGGGCG

25301  CGCTTTCTTC TCTACCATCA CGGCGTGGCC TTCCCCCGTA ACATCCTGCA
       GCGAAAGAAG AGATGGTAGT GCCGCACCGG AAGGGGGCAT TGTAGGACGT

25351  TTACTACCGT CATCTCTACA GCCCATACTG CACCGGCGGC AGCGGCAGCA
       AATGATGGCA GTAGAGATGT CGGGTATGAC GTGGCCGCCG TCGCCGTCGT

25401  ACAGCAGCGG CCACACAGAA GCAAAGGCGA CCGGATAGCA AGACTCTGAC
       TGTCGTCGCC GGTGTGTCTT CGTTTCCGCT GGCCTATCGT TCTGAGACTG

25451  AAAGCCCAAG AAATCCACAG CGGCGGCAGC AGCAGGAGGA GGAGCGCTGC
       TTTCGGGTTC TTTAGGTGTC GCCGCCGTCG TCGTCCTCCT CCTCGCGACG
```

FIG. 27A-30

```
25501  GTCTGGCGCC CAACGAACCC GTATCGACCC GCGAGCTTAG AAACAGGATT
       CAGACCGCGG GTTGCTTGGG CATAGCTGGG CGCTCGAATC TTTGTCCTAA

25551  TTTCCCACTC TGTATGCTAT ATTTCAACAG AGCAGGGGCC AAGAACAAGA
       AAAGGGTGAG ACATACGATA TAAAGTTGTC TCGTCCCCGG TTCTTGTTCT

25601  GCTGAAAATA AAAAACAGGT CTCTGCGATC CCTCACCCGC AGCTGCCTGT
       CGACTTTTAT TTTTTGTCCA GAGACGCTAG GGAGTGGGCG TCGACGGACA

25651  ATCACAAAAG CGAAGATCAG CTTCGGCGCA CGCTGGAAGA CGCGGAGGCT
       TAGTGTTTTC GCTTCTAGTC GAAGCCGCGT GCGACCTTCT GCGCCTCCGA

25701  CTCTTCAGTA AATACTGCGC GCTGACTCTT AAGGACTAGT TTCGCGCCCT
       GAGAAGTCAT TTATGACGCG CGACTGAGAA TTCCTGATCA AAGCGCGGGA

25751  TTCTCAAATT TAAGCGCGAA AACTACGTCA TCTCCAGCGG CCACACCCGG
       AAGAGTTTAA ATTCGCGCTT TTGATGCAGT AGAGGTCGCC GGTGTGGGCC

25801  CGCCAGCACC TGTTGTCAGC GCCATTATGA GCAAGGAAAT TCCCACGCCC
       GCGGTCGTGG ACAACAGTCG CGGTAATACT CGTTCCTTTA AGGGTGCGGG

25851  TACATGTGGA GTTACCAGCC ACAAATGGGA CTTGCGGCTG GAGCTGCCCA
       ATGTACACCT CAATGGTCGG TGTTTACCCT GAACGCCGAC CTCGACGGGT

25901  AGACTACTCA ACCCGAATAA ACTACATGAG CGCGGGACCC CACATGATAT
       TCTGATGAGT TGGGCTTATT TGATGTACTC GCGCCCTGGG GTGTACTATA

25951  CCCGGGTCAA CGGAATACGC GCCCACCGAA ACCGAATTCT CCTGGAACAG
       GGGCCCAGTT GCCTTATGCG CGGGTGGCTT TGGCTTAAGA GGACCTTGTC

26001  GCGGCTATTA CCACCACACC TCGTAATAAC CTTAATCCCC GTAGTTGGCC
       CGCCGATAAT GGTGGTGTGG AGCATTATTG GAATTAGGGG CATCAACCGG

26051  CGCTGCCCTG GTGTACCAGG AAAGTCCCGC TCCCACCACT GTGGTACTTC
       GCGACGGGAC CACATGGTCC TTTCAGGGCG AGGGTGGTGA CACCATGAAG

26101  CCAGAGACGC CCAGGCCGAA GTTCAGATGA CTAACTCAGG GGCGCAGCTT
       GGTCTCTGCG GGTCCGGCTT CAAGTCTACT GATTGAGTCC CCGCGTCGAA

26151  GCGGGCGGCT TTCGTCACAG GGTGCGGTCG CCCGGGCAGG GTATAACTCA
       CGCCCGCCGA AAGCAGTGTC CCACGCCAGC GGGCCCGTCC CATATTGAGT

26201  CCTGACAATC AGAGGGCGAG GTATTCAGCT CAACGACGAG TCGGTGAGCT
       GGACTGTTAG TCTCCCGCTC CATAAGTCGA GTTGCTGCTC AGCCACTCGA

26251  CCTCGCTTGG TCTCCGTCCG GACGGGACAT TTCAGATCGG CGGCGCCGGC
       GGAGCGAACC AGAGGCAGGC CTGCCCTGTA AAGTCTAGCC GCCGCGGCCG

26301  CGCTCTTCAT TCACGCCTCG TCAGGCAATC CTAACTCTGC AGACCTCGTC
       GCGAGAAGTA AGTGCGGAGC AGTCCGTTAG GATTGAGACG TCTGGAGCAG
```

FIG. 27A-31

```
26351  CTCTGAGCCG CGCTCTGGAG GCATTGGAAC TCTGCAATTT ATTGAGGAGT
       GAGACTCGGC GCGAGACCTC CGTAACCTTG AGACGTTAAA TAACTCCTCA

26401  TTGTGCCATC GGTCTACTTT AACCCCTTCT CGGGACCTCC CGGCCACTAT
       AACACGGTAG CCAGATGAAA TTGGGGAAGA GCCCTGGAGG GCCGGTGATA

26451  CCGGATCAAT TTATTCCTAA CTTTGACGCG GTAAAGGACT CGGCGGACGG
       GGCCTAGTTA AATAAGGATT GAAACTGCGC CATTTCCTGA GCCGCCTGCC

26501  CTACGACTGA ATGTTAAGTG GAGAGGCAGA GCAACTGCGC CTGAAACACC
       GATGCTGACT TACAATTCAC CTCTCCGTCT CGTTGACGCG GACTTTGTGG

26551  TGGTCCACTG TCGCCGCCAC AAGTGCTTTG CCCGCGACTC CGGTGAGTTT
       ACCAGGTGAC AGCGGCGGTG TTCACGAAAC GGGCGCTGAG GCCACTCAAA

26601  TGCTACTTTG AATTGCCCGA GGATCATATC GAGGGCCCGG CGCACGGCGT
       ACGATGAAAC TTAACGGGCT CCTAGTATAG CTCCCGGGCC GCGTGCCGCA

26651  CCGGCTTACC GCCCAGGGAG AGCTTGCCCG TAGCCTGATT CGGGAGTTTA
       GGCCGAATGG CGGGTCCCTC TCGAACGGGC ATCGGACTAA GCCCTCAAAT

26701  CCCAGCGCCC CCTGCTAGTT GAGCGGGACA GGGGACCCTG TGTTCTCACT
       GGGTCGCGGG GGACGATCAA CTCGCCCTGT CCCCTGGGAC ACAAGAGTGA

26751  GTGATTTGCA ACTGTCCTAA CCCTGGATTA CATCAAGATC TTTGTTGCCA
       CACTAAACGT TGACAGGATT GGGACCTAAT GTAGTTCTAG AAACAACGGT

26801  TCTCTGTGCT GAGTATAATA AATACAGAAA TTAAAATATA CTGGGGCTCC
       AGAGACACGA CTCATATTAT TTATGTCTTT AATTTTATAT GACCCCGAGG

26851  TATCGCCATC CTGTAAACGC CACCGTCTTC ACCCGCCCAA GCAAACCAAG
       ATAGCGGTAG GACATTTGCG GTGGCAGAAG TGGGCGGGTT CGTTTGGTTC

26901  GCGAACCTTA CCTGGTACTT TTAACATCTC TCCCTCTGTG ATTTACAACA
       CGCTTGGAAT GGACCATGAA AATTGTAGAG AGGGAGACAC TAAATGTTGT

26951  GTTTCAACCC AGACGGAGTG AGTCTACGAG AGAACCTCTC CGAGCTCAGC
       CAAAGTTGGG TCTGCCTCAC TCAGATGCTC TCTTGGAGAG GCTCGAGTCG

27001  TACTCCATCA GAAAAAACAC CACCCTCCTT ACCTGCCGGG AACGTACGAG
       ATGAGGTAGT CTTTTTTGTG GTGGGAGGAA TGGACGGCCC TTGCATGCTC

27051  TGCGTCACCG GCCGCTGCAC CACACCTACC GCCTGACCGT AAACCAGACT
       ACGCAGTGGC CGGCGACGTG GTGTGGATGG CGGACTGGCA TTTGGTCTGA

27101  TTTTCCGGAC AGACCTCAAT AACTCTGTTT ACCAGAACAG GAGGTGAGCT
       AAAAGGCCTG TCTGGAGTTA TTGAGACAAA TGGTCTTGTC CTCCACTCGA

27151  TAGAAAACCC TTAGGGTATT AGGCCAAAGG CGCAGCTACT GTGGGGTTTA
       ATCTTTTGGG AATCCCATAA TCCGGTTTCC GCGTCGATGA CACCCCAAAT
```

FIG. 27A-32

| | | | | | |
|---|---|---|---|---|---|
| 27201 | TGAACAATTC | AAGCAACTCT | ACGGGCTATT | CTAATTCAGG | TTTCTCTAGA |
| | ACTTGTTAAG | TTCGTTGAGA | TGCCCGATAA | GATTAAGTCC | AAAGAGATCT |
| 27251 | ATCGGGGTTG | GGGTTATTCT | CTGTCTTGTG | ATTCTCTTTA | TTCTTATACT |
| | TAGCCCCAAC | CCCAATAAGA | GACAGAACAC | TAAGAGAAAT | AAGAATATGA |
| 27301 | AACGCTTCTC | TGCCTAAGGC | TCGCCGCCTG | CTGTGTGCAC | ATTTGCATTT |
| | TTGCGAAGAG | ACGGATTCCG | AGCGGCGGAC | GACACACGTG | TAAACGTAAA |
| 27351 | ATTGTCAGCT | TTTTAAACGC | TGGGGTCGCC | ACCCAAGATG | ATTAGGTACA |
| | TAACAGTCGA | AAAATTTGCG | ACCCCAGCGG | TGGGTTCTAC | TAATCCATGT |
| 27401 | TAATCCTAGG | TTTACTCACC | CTTGCGTCAG | CCCACGGTAC | CACCCAAAAG |
| | ATTAGGATCC | AAATGAGTGG | GAACGCAGTC | GGGTGCCATG | GTGGGTTTTC |
| 27451 | GTGGATTTTA | AGGAGCCAGC | CTGTAATGTT | ACATTCGCAG | CTGAAGCTAA |
| | CACCTAAAAT | TCCTCGGTCG | GACATTACAA | TGTAAGCGTC | GACTTCGATT |
| 27501 | TGAGTGCACC | ACTCTTATAA | AATGCACCAC | AGAACATGAA | AAGCTGCTTA |
| | ACTCACGTGG | TGAGAATATT | TTACGTGGTG | TCTTGTACTT | TTCGACGAAT |
| 27551 | TTCGCCACAA | AAACAAAATT | GGCAAGTATG | CTGTTTATGC | TATTTGGCAG |
| | AAGCGGTGTT | TTTGTTTTAA | CCGTTCATAC | GACAAATACG | ATAAACCGTC |
| 27601 | CCAGGTGACA | CTACAGAGTA | TAATGTTACA | GTTTTCCAGG | GTAAAAGTCA |
| | GGTCCACTGT | GATGTCTCAT | ATTACAATGT | CAAAAGGTCC | CATTTTCAGT |
| 27651 | TAAAACTTTT | ATGTATACTT | TTCCATTTTA | TGAAATGTGC | GACATTACCA |
| | ATTTTGAAAA | TACATATGAA | AAGGTAAAAT | ACTTTACACG | CTGTAATGGT |
| 27701 | TGTACATGAG | CAAACAGTAT | AAGTTGTGGC | CCCCACAAAA | TTGTGTGGAA |
| | ACATGTACTC | GTTTGTCATA | TTCAACACCG | GGGGTGTTTT | AACACACCTT |
| 27751 | AACACTGGCA | CTTTCTGCTG | CACTGCTATG | CTAATTACAG | TGCTCGCTTT |
| | TTGTGACCGT | GAAAGACGAC | GTGACGATAC | GATTAATGTC | ACGAGCGAAA |
| 27801 | GGTCTGTACC | CTACTCTATA | TTAAATACAA | AAGCAGACGC | AGCTTTATTG |
| | CCAGACATGG | GATGAGATAT | AATTTATGTT | TTCGTCTGCG | TCGAAATAAC |
| 27851 | AGGAAAAGAA | AATGCCTTAA | TTTACTAAGT | TACAAAGCTA | ATGTCACCAC |
| | TCCTTTTCTT | TTACGGAATT | AAATGATTCA | ATGTTTCGAT | TACAGTGGTG |
| 27901 | TAACTGCTTT | ACTCGCTGCT | TGCAAAACAA | ATTCAAAAAG | TTAGCATTAT |
| | ATTGACGAAA | TGAGCGACGA | ACGTTTTGTT | TAAGTTTTTC | AATCGTAATA |
| 27951 | AATTAGAATA | GGATTTAAAC | CCCCCGGTCA | TTTCCTGCTC | AATACCATTC |
| | TTAATCTTAT | CCTAAATTTG | GGGGGCCAGT | AAAGGACGAG | TTATGGTAAG |
| 28001 | CCCTGAACAA | TTGACTCTAT | GTGGGATATG | CTCCAGCGCT | ACAACCTTGA |
| | GGGACTTGTT | AACTGAGATA | CACCCTATAC | GAGGTCGCGA | TGTTGGAACT |

FIG. 27A-33

```
28051  AGTCAGGCTT CCTGGATGTC AGCATCTGAC TTTGGCCAGC ACCTGTCCCG
       TCAGTCCGAA GGACCTACAG TCGTAGACTG AAACCGGTCG TGGACAGGGC

28101  CGGATTTGTT CCAGTCCAAC TACAGCGACC CACCCTAACA GAGATGACCA
       GCCTAAACAA GGTCAGGTTG ATGTCGCTGG GTGGGATTGT CTCTACTGGT

28151  ACACAACCAA CGCGGCCGCC GCTACCGGAC TTACATCTAC CACAAATACA
       TGTGTTGGTT GCGCCGGCGG CGATGGCCTG AATGTAGATG GTGTTTATGT

28201  CCCCAAGTTT CTGCCTTTGT CAATAACTGG GATAACTTGG GCATGTGGTG
       GGGGTTCAAA GACGGAAACA GTTATTGACC CTATTGAACC CGTACACCAC

28251  GTTCTCCATA GCGCTTATGT TTGTATGCCT TATTATTATG TGGCTCATCT
       CAAGAGGTAT CGCGAATACA AACATACGGA ATAATAATAC ACCGAGTAGA

28301  GCTGCCTAAA GCGCAAACGC GCCCGACCAC CCATCTATAG TCCCATCATT
       CGACGGATTT CGCGTTTGCG CGGGCTGGTG GGTAGATATC AGGGTAGTAA

28351  GTGCTACACC CAAACAATGA TGGAATCCAT AGATTGGACG GACTGAAACA
       CACGATGTGG GTTTGTTACT ACCTTAGGTA TCTAACCTGC CTGACTTTGT

28401  CATGTTCTTT TCTCTTACAG TATGATTAAA TGAGACATGA TTCCTCGAGT
       GTACAAGAAA AGAGAATGTC ATACTAATTT ACTCTGTACT AAGGAGCTCA

28451  TTTTATATTA CTGACCCTTG TTGCGCTTTT TTGTGCGTGC TCCACATTGG
       AAAATATAAT GACTGGGAAC AACGCGAAAA AACACGCACG AGGTGTAACC

28501  CTGCGGTTTC TCACATCGAA GTAGACTGCA TTCCAGCCTT CACAGTCTAT
       GACGCCAAAG AGTGTAGCTT CATCTGACGT AAGGTCGGAA GTGTCAGATA

28551  TTGCTTTACG GATTTGTCAC CCTCACGCTC ATCTGCAGCC TCATCACTGT
       AACGAAATGC CTAAACAGTG GGAGTGCGAG TAGACGTCGG AGTAGTGACA

28601  GGTCATCGCC TTTATCCAGT GCATTGACTG GGTCTGTGTG CGCTTTGCAT
       CCAGTAGCGG AAATAGGTCA CGTAACTGAC CCAGACACAC GCGAAACGTA

28651  ATCTCAGACA CCATCCCCAG TACAGGGACA GGACTATAGC TGAGCTTCTT
       TAGAGTCTGT GGTAGGGGTC ATGTCCCTGT CCTGATATCG ACTCGAAGAA

28701  AGAATTCTTT AATTATGAAA TTTACTGTGA CTTTTCTGCT GATTATTTGC
       TCTTAAGAAA TTAATACTTT AAATGACACT GAAAAGACGA CTAATAAACG

28751  ACCCTATCTG CGTTTTGTTC CCCGACCTCC AAGCCTCAAA GACATATATC
       TGGGATAGAC GCAAAACAAG GGGCTGGAGG TTCGGAGTTT CTGTATATAG

28801  ATGCAGATTC ACTCGTATAT GGAATATTCC AAGTTGCTAC AATGAAAAAA
       TACGTCTAAG TGAGCATATA CCTTATAAGG TTCAACGATG TTACTTTTTT

28851  GCGATCTTTC CGAAGCCTGG TTATATGCAA TCATCTCTGT TATGGTGTTC
       CGCTAGAAAG GCTTCGGACC AATATACGTT AGTAGAGACA ATACCACAAG
```

FIG. 27A-34

```
28901  TGCAGTACCA TCTTAGCCCT AGCTATATAT CCCTACCTTG ACATTGGCTG
       ACGTCATGGT AGAATCGGGA TCGATATATA GGGATGGAAC TGTAACCGAC

28951  GAACGCAATA GATGCCATGA ACCACCCAAC TTTCCCCGCG CCCGCTATGC
       CTTGCGTTAT CTACGGTACT TGGTGGGTTG AAAGGGGCGC GGGCGATACG

29001  TTCCACTGCA ACAAGTTGTT GCCGGCGGCT TTGTCCCAGC CAATCAGCCT
       AAGGTGACGT TGTTCAACAA CGGCCGCCGA AACAGGGTCG GTTAGTCGGA

29051  CGCCCACCTT CTCCCACCCC CACTGAAATC AGCTACTTTA ATCTAACAGG
       GCGGGTGGAA GAGGGTGGGG GTGACTTTAG TCGATGAAAT TAGATTGTCC

29101  AGGAGATGAC TGACACCCTA GATCTAGAAA TGGACGGAAT TATTACAGAG
       TCCTCTACTG ACTGTGGGAT CTAGATCTTT ACCTGCCTTA ATAATGTCTC

29151  CAGCGCCTGC TAGAAAGACG CAGGGCAGCG GCCGAGCAAC AGCGCATGAA
       GTCGCGGACG ATCTTTCTGC GTCCCGTCGC CGGCTCGTTG TCGCGTACTT

29201  TCAAGAGCTC CAAGACATGG TTAACTTGCA CCAGTGCAAA AGGGGTATCT
       AGTTCTCGAG GTTCTGTACC AATTGAACGT GGTCACGTTT TCCCCATAGA

29251  TTTGTCTCGT AAAGCAGGCC AAAGTCACCT ACGACAGTAA TACCACCGGA
       AAACAGAGCA TTTCGTCCGG TTTCAGTGGA TGCTGTCATT ATGGTGGCCT

29301  CACCGCCTTA GCTACAAGTT GCCAACCAAG CGTCAGAAAT TGGTGGTCAT
       GTGGCGGAAT CGATGTTCAA CGGTTGGTTC GCAGTCTTTA ACCACCAGTA

29351  GGTGGGAGAA AAGCCCATTA CCATAACTCA GCACTCGGTA GAAACCGAAG
       CCACCCTCTT TTCGGGTAAT GGTATTGAGT CGTGAGCCAT CTTTGGCTTC

29401  GCTGCATTCA CTCACCTTGT CAAGGACCTG AGGATCTCTG CACCCTTATT
       CGACGTAAGT GAGTGGAACA GTTCCTGGAC TCCTAGAGAC GTGGGAATAA

29451  AAGACCCTGT GCGGTCTCAA AGATCTTATT CCCTTTAACT AATAAAAAAA
       TTCTGGGACA CGCCAGAGTT TCTAGAATAA GGGAAATTGA TTATTTTTTT

29501  AATAATAAAG CATCACTTAC TTAAAATCAG TTAGCAAATT TCTGTCCAGT
       TTATTATTTC GTAGTGAATG AATTTTAGTC AATCGTTTAA AGACAGGTCA

29551  TTATTCAGCA GCACCTCCTT GCCCTCCTCC CAGCTCTGGT ATTGCAGCTT
       AATAAGTCGT CGTGGAGGAA CGGGAGGAGG GTCGAGACCA TAACGTCGAA

29601  CCTCCTGGCT GCAAACTTTC TCCACAATCT AAATGGAATG TCAGTTTCCT
       GGAGGACCGA CGTTTGAAAG AGGTGTTAGA TTTACCTTAC AGTCAAAGGA

29651  CCTGTTCCTG TCCATCCGCA CCCACTATCT TCATGTTGTT GCAGATGAAG
       GGACAAGGAC AGGTAGGCGT GGGTGATAGA AGTACAACAA CGTCTACTTC

29701  CGCGCAAGAC CGTCTGAAGA TACCTTCAAC CCCGTGTATC CATATGACAC
       GCGCGTTCTG GCAGACTTCT ATGGAAGTTG GGGCACATAG GTATACTGTG
```

FIG. 27A-35

```
29751  GGAAACCGGT CCTCCAACTG TGCCTTTTCT TACTCCTCCC TTTGTATCCC
       CCTTTGGCCA GGAGGTTGAC ACGGAAAAGA ATGAGGAGGG AAACATAGGG

29801  CCAATGGGTT TCAAGAGAGT CCCCCTGGGG TACTCTCTTT GCGCCTATCC
       GGTTACCCAA AGTTCTCTCA GGGGGACCCC ATGAGAGAAA CGCGGATAGG

29851  GAACCTCTAG TTACCTCCAA TGGCATGCTT GCGCTCAAAA TGGGCAACGG
       CTTGGAGATC AATGGAGGTT ACCGTACGAA CGCGAGTTTT ACCCGTTGCC

29901  CCTCTCTCTG GACGAGGCCG GCAACCTTAC CTCCCAAAAT GTAACCACTG
       GGAGAGAGAC CTGCTCCGGC CGTTGGAATG GAGGGTTTTA CATTGGTGAC

29951  TGAGCCCACC TCTCAAAAAA ACCAAGTCAA ACATAAACCT GGAAATATCT
       ACTCGGGTGG AGAGTTTTTT TGGTTCAGTT TGTATTTGGA CCTTTATAGA

30001  GCACCCCTCA CAGTTACCTC AGAAGCCCTA ACTGTGGCTG CCGCCGCACC
       CGTGGGGAGT GTCAATGGAG TCTTCGGGAT TGACACCGAC GGCGGCGTGG

30051  TCTAATGGTC GCGGGCAACA CACTCACCAT GCAATCACAG GCCCCGCTAA
       AGATTACCAG CGCCCGTTGT GTGAGTGGTA CGTTAGTGTC CGGGGCGATT

30101  CCGTGCACGA CTCCAAACTT AGCATTGCCA CCCAAGGACC CCTCACAGTG
       GGCACGTGCT GAGGTTTGAA TCGTAACGGT GGGTTCCTGG GGAGTGTCAC

30151  TCAGAAGGAA AGCTAGCCCT GCAAACATCA GGCCCCCTCA CCACCACCGA
       AGTCTTCCTT TCGATCGGGA CGTTTGTAGT CCGGGGGAGT GGTGGTGGCT

30201  TAGCAGTACC CTTACTATCA CTGCCTCACC CCCTCTAACT ACTGCCACTG
       ATCGTCATGG GAATGATAGT GACGGAGTGG GGGAGATTGA TGACGGTGAC

30251  GTAGCTTGGG CATTGACTTG AAAGAGCCCA TTTATACACA AAATGGAAAA
       CATCGAACCC GTAACTGAAC TTTCTCGGGT AAATATGTGT TTTACCTTTT

30301  CTAGGACTAA AGTACGGGGC TCCTTTGCAT GTAACAGACG ACCTAAACAC
       GATCCTGATT TCATGCCCCG AGGAAACGTA CATTGTCTGC TGGATTTGTG

30351  TTTGACCGTA GCAACTGGTC CAGGTGTGAC TATTAATAAT ACTTCCTTGC
       AAACTGGCAT CGTTGACCAG GTCCACACTG ATAATTATTA TGAAGGAACG

30401  AAACTAAAGT TACTGGAGCC TTGGGTTTTG ATTCACAAGG CAATATGCAA
       TTTGATTTCA ATGACCTCGG AACCCAAAAC TAAGTGTTCC GTTATACGTT

30451  CTTAATGTAG CAGGAGGACT AAGGATTGAT TCTCAAAACA GACGCCTTAT
       GAATTACATC GTCCTCCTGA TTCCTAACTA AGAGTTTTGT CTGCGGAATA

30501  ACTTGATGTT AGTTATCCGT TTGATGCTCA AAACCAACTA AATCTAAGAC
       TGAACTACAA TCAATAGGCA AACTACGAGT TTTGGTTGAT TTAGATTCTG

30551  TAGGACAGGG CCCTCTTTTT ATAAACTCAG CCCACAACTT GGATATTAAC
       ATCCTGTCCC GGGAGAAAAA TATTTGAGTC GGGTGTTGAA CCTATAATTG
```

FIG. 27A-36

30601 TACAACAAAG GCCTTTACTT GTTTACAGCT TCAAACAATT CCAAAAAGCT
ATGTTGTTTC CGGAAATGAA CAAATGTCGA AGTTTGTTAA GGTTTTTCGA

30651 TGAGGTTAAC CTAAGCACTG CCAAGGGGTT GATGTTTGAC GCTACAGCCA
ACTCCAATTG GATTCGTGAC GGTTCCCCAA CTACAAACTG CGATGTCGGT

30701 TAGCCATTAA TGCAGGAGAT GGGCTTGAAT TTGGTTCACC TAATGCACCA
ATCGGTAATT ACGTCCTCTA CCCGAACTTA AACCAAGTGG ATTACGTGGT

30751 AACACAAATC CCCTCAAAAC AAAAATTGGC CATGGCCTAG AATTTGATTC
TTGTGTTTAG GGGAGTTTTG TTTTTAACCG GTACCGGATC TTAAACTAAG

30801 AAACAAGGCT ATGGTTCCTA AACTAGGAAC TGGCCTTAGT TTTGACAGCA
TTTGTTCCGA TACCAAGGAT TTGATCCTTG ACCGGAATCA AAACTGTCGT

30851 CAGGTGCCAT TACAGTAGGA AACAAAAATA ATGATAAGCT AACTTTGTGG
GTCCACGGTA ATGTCATCCT TTGTTTTTAT TACTATTCGA TTGAAACACC

30901 ACCACACCAG CTCCATCTCC TAACTGTAGA CTAAATGCAG AGAAAGATGC
TGGTGTGGTC GAGGTAGAGG ATTGACATCT GATTTACGTC TCTTTCTACG

30951 TAAACTCACT TTGGTCTTAA CAAAATGTGG CAGTCAAATA CTTGCTACAG
ATTTGAGTGA AACCAGAATT GTTTTACACC GTCAGTTTAT GAACGATGTC

31001 TTTCAGTTTT GGCTGTTAAA GGCAGTTTGG CTCCAATATC TGGAACAGTT
AAAGTCAAAA CCGACAATTT CCGTCAAACC GAGGTTATAG ACCTTGTCAA

31051 CAAAGTGCTC ATCTTATTAT AAGATTTGAC GAAAATGGAG TGCTACTAAA
GTTTCACGAG TAGAATAATA TTCTAAACTG CTTTTACCTC ACGATGATTT

31101 CAATTCCTTC CTGGACCCAG AATATTGGAA CTTTAGAAAT GGAGATCTTA
GTTAAGGAAG GACCTGGGTC TTATAACCTT GAAATCTTTA CCTCTAGAAT

31151 CTGAAGGCAC AGCCTATACA AACGCTGTTG GATTTATGCC TAACCTATCA
GACTTCCGTG TCGGATATGT TTGCGACAAC CTAAATACGG ATTGGATAGT

31201 GCTTATCCAA AATCTCACGG TAAAACTGCC AAAAGTAACA TTGTCAGTCA
CGAATAGGTT TTAGAGTGCC ATTTTGACGG TTTTCATTGT AACAGTCAGT

31251 AGTTTACTTA AACGGAGACA AAACTAAACC TGTAACACTA ACCATTACAC
TCAAATGAAT TTGCCTCTGT TTTGATTTGG ACATTGTGAT TGGTAATGTG

31301 TAAACGGTAC ACAGGAAACA GGAGACACAA CTCCAAGTGC ATACTCTATG
ATTTGCCATG TGTCCTTTGT CCTCTGTGTT GAGGTTCACG TATGAGATAC

31351 TCATTTTCAT GGGACTGGTC TGGCCACAAC TACATTAATG AAATATTTGC
AGTAAAAGTA CCCTGACCAG ACCGGTGTTG ATGTAATTAC TTTATAAACG

31401 CACATCCTCT TACACTTTTT CATACATTGC CCAAGAATAA AGAATCGTTT
GTGTAGGAGA ATGTGAAAAA GTATGTAACG GGTTCTTATT TCTTAGCAAA

FIG. 27A-37

31451 GTGTTATGTT TCAACGTGTT TATTTTTCAA TTGCAGAAAA TTTCAAGTCA
CACAATACAA AGTTGCACAA ATAAAAAGTT AACGTCTTTT AAAGTTCAGT

31501 TTTTTCATTC AGTAGTATAG CCCCACCACC ACATAGCTTA TACAGATCAC
AAAAAGTAAG TCATCATATC GGGGTGGTGG TGTATCGAAT ATGTCTAGTG

31551 CGTACCTTAA TCAAACTCAC AGAACCCTAG TATTCAACCT GCCACCTCCC
GCATGGAATT AGTTTGAGTG TCTTGGGATC ATAAGTTGGA CGGTGGAGGG

31601 TCCCAACACA CAGAGTACAC AGTCCTTTCT CCCCGGCTGG CCTTAAAAAG
AGGGTTGTGT GTCTCATGTG TCAGGAAAGA GGGGCCGACC GGAATTTTTC

31651 CATCATATCA TGGGTAACAG ACATATTCTT AGGTGTTATA TTCCACACGG
GTAGTATAGT ACCCATTGTC TGTATAAGAA TCCACAATAT AAGGTGTGCC

31701 TTTCCTGTCG AGCCAAACGC TCATCAGTGA TATTAATAAA CTCCCCGGGC
AAAGGACAGC TCGGTTTGCG AGTAGTCACT ATAATTATTT GAGGGGCCCG

31751 AGCTCACTTA AGTTCATGTC GCTGTCCAGC TGCTGAGCCA CAGGCTGCTG
TCGAGTGAAT TCAAGTACAG CGACAGGTCG ACGACTCGGT GTCCGACGAC

31801 TCCAACTTGC GGTTGCTTAA CGGGCGGCGA AGGAGAAGTC CACGCCTACA
AGGTTGAACG CCAACGAATT GCCCGCCGCT TCCTCTTCAG GTGCGGATGT

31851 TGGGGGTAGA GTCATAATCG TGCATCAGGA TAGGGCGGTG GTGCTGCAGC
ACCCCCATCT CAGTATTAGC ACGTAGTCCT ATCCCGCCAC CACGACGTCG

31901 AGCGCGCGAA TAAACTGCTG CCGCCGCCGC TCCGTCCTGC AGGAATACAA
TCGCGCGCTT ATTTGACGAC GGCGGCGGCG AGGCAGGACG TCCTTATGTT

31951 CATGGCAGTG GTCTCCTCAG CGATGATTCG CACCGCCCGC AGCATAAGGC
GTACCGTCAC CAGAGGAGTC GCTACTAAGC GTGGCGGGCG TCGTATTCCG

32001 GCCTTGTCCT CCGGGCACAG CAGCGCACCC TGATCTCACT TAAATCAGCA
CGGAACAGGA GGCCCGTGTC GTCGCGTGGG ACTAGAGTGA ATTTAGTCGT

32051 CAGTAACTGC AGCACAGCAC CACAATATTG TTCAAAATCC CACAGTGCAA
GTCATTGACG TCGTGTCGTG GTGTTATAAC AAGTTTTAGG GTGTCACGTT

32101 GGCGCTGTAT CCAAAGCTCA TGGCGGGGAC CACAGAACCC ACGTGGCCAT
CCGCGACATA GGTTTCGAGT ACCGCCCCTG GTGTCTTGGG TGCACCGGTA

32151 CATACCACAA GCGCAGGTAG ATTAAGTGGC GACCCCTCAT AAACACGCTG
GTATGGTGTT CGCGTCCATC TAATTCACCG CTGGGGAGTA TTTGTGCGAC

32201 GACATAAACA TTACCTCTTT TGGCATGTTG TAATTCACCA CCTCCCGGTA
CTGTATTTGT AATGGAGAAA ACCGTACAAC ATTAAGTGGT GGAGGGCCAT

32251 CCATATAAAC CTCTGATTAA ACATGGCGCC ATCCACCACC ATCCTAAACC
GGTATATTTG GAGACTAATT TGTACCGCGG TAGGTGGTGG TAGGATTTGG

FIG. 27A-38

```
32301  AGCTGGCCAA AACCTGCCCG CCGGCTATAC ACTGCAGGGA ACCGGGACTG
       TCGACCGGTT TTGGACGGGC GGCCGATATG TGACGTCCCT TGGCCCTGAC

32351  GAACAATGAC AGTGGAGAGC CCAGGACTCG TAACCATGGA TCATCATGCT
       CTTGTTACTG TCACCTCTCG GGTCCTGAGC ATTGGTACCT AGTAGTACGA

32401  CGTCATGATA TCAATGTTGG CACAACACAG GCACACGTGC ATACACTTCC
       GCAGTACTAT AGTTACAACC GTGTTGTGTC CGTGTGCACG TATGTGAAGG

32451  TCAGGATTAC AAGCTCCTCC CGCGTTAGAA CCATATCCCA GGGAACAACC
       AGTCCTAATG TTCGAGGAGG GCGCAATCTT GGTATAGGGT CCCTTGTTGG

32501  CATTCCTGAA TCAGCGTAAA TCCCACACTG CAGGGAAGAC CTCGCACGTA
       GTAAGGACTT AGTCGCATTT AGGGTGTGAC GTCCCTTCTG GAGCGTGCAT

32551  ACTCACGTTG TGCATTGTCA AAGTGTTACA TTCGGGCAGC AGCGGATGAT
       TGAGTGCAAC ACGTAACAGT TTCACAATGT AAGCCCGTCG TCGCCTACTA

32601  CCTCCAGTAT GGTAGCGCGG GTTTCTGTCT CAAAAGGAGG TAGACGATCC
       GGAGGTCATA CCATCGCGCC CAAAGACAGA GTTTTCCTCC ATCTGCTAGG

32651  CTACTGTACG GAGTGCGCCG AGACAACCGA GATCGTGTTG GTCGTAGTGT
       GATGACATGC CTCACGCGGC TCTGTTGGCT CTAGCACAAC CAGCATCACA

32701  CATGCCAAAT GGAACGCCGG ACGTAGTCAT ATTTCCTGAA GCAAAACCAG
       GTACGGTTTA CCTTGCGGCC TGCATCAGTA TAAAGGACTT CGTTTTGGTC

32751  GTGCGGGCGT GACAAACAGA TCTGCGTCTC CGGTCTCGCC GCTTAGATCG
       CACGCCCGCA CTGTTTGTCT AGACGCAGAG GCCAGAGCGG CGAATCTAGC

32801  CTCTGTGTAG TAGTTGTAGT ATATCCACTC TCTCAAAGCA TCCAGGCGCC
       GAGACACATC ATCAACATCA TATAGGTGAG AGAGTTTCGT AGGTCCGCGG

32851  CCCTGGCTTC GGGTTCTATG TAAACTCCTT CATGCGCCGC TGCCCTGATA
       GGGACCGAAG CCCAAGATAC ATTTGAGGAA GTACGCGGCG ACGGGACTAT

32901  ACATCCACCA CCGCAGAATA AGCCACACCC AGCCAACCTA CACATTCGTT
       TGTAGGTGGT GGCGTCTTAT TCGGTGTGGG TCGGTTGGAT GTGTAAGCAA

32951  CTGCGAGTCA CACACGGGAG GAGCGGGAAG AGCTGGAAGA ACCATGTTTT
       GACGCTCAGT GTGTGCCCTC CTCGCCCTTC TCGACCTTCT TGGTACAAAA

33001  TTTTTTTATT CCAAAAGATT ATCCAAAACC TCAAAATGAA GATCTATTAA
       AAAAAAATAA GGTTTTCTAA TAGGTTTTGG AGTTTTACTT CTAGATAATT

33051  GTGAACGCGC TCCCCTCCGG TGGCGTGGTC AAACTCTACA GCCAAAGAAC
       CACTTGCGCG AGGGGAGGCC ACCGCACCAG TTTGAGATGT CGGTTTCTTG

33101  AGATAATGGC ATTTGTAAGA TGTTGCACAA TGGCTTCCAA AAGGCAAACG
       TCTATTACCG TAAACATTCT ACAACGTGTT ACCGAAGGTT TTCCGTTTGC
```

FIG. 27A-39

```
33151  GCCCTCACGT CCAAGTGGAC GTAAAGGCTA AACCCTTCAG GGTGAATCTC
       CGGGAGTGCA GGTTCACCTG CATTTCCGAT TTGGGAAGTC CCACTTAGAG

33201  CTCTATAAAC ATTCCAGCAC CTTCAACCAT GCCCAAATAA TTCTCATCTC
       GAGATATTTG TAAGGTCGTG GAAGTTGGTA CGGGTTTATT AAGAGTAGAG

33251  GCCACCTTCT CAATATATCT CTAAGCAAAT CCCGAATATT AAGTCCGGCC
       CGGTGGAAGA GTTATATAGA GATTCGTTTA GGGCTTATAA TTCAGGCCGG

33301  ATTGTAAAAA TCTGCTCCAG AGCGCCCTCC ACCTTCAGCC TCAAGCAGCG
       TAACATTTTT AGACGAGGTC TCGCGGGAGG TGGAAGTCGG AGTTCGTCGC

33351  AATCATGATT GCAAAAATTC AGGTTCCTCA CAGACCTGTA TAAGATTCAA
       TTAGTACTAA CGTTTTTAAG TCCAAGGAGT GTCTGGACAT ATTCTAAGTT

33401  AAGCGGAACA TTAACAAAAA TACCGCGATC CCGTAGGTCC CTTCGCAGGG
       TTCGCCTTGT AATTGTTTTT ATGGCGCTAG GGCATCCAGG GAAGCGTCCC

33451  CCAGCTGAAC ATAATCGTGC AGGTCTGCAC GGACCAGCGC GGCCACTTCC
       GGTCGACTTG TATTAGCACG TCCAGACGTG CCTGGTCGCG CCGGTGAAGG

33501  CCGCCAGGAA CCATGACAAA AGAACCCACA CTGATTATGA CACGCATACT
       GGCGGTCCTT GGTACTGTTT TCTTGGGTGT GACTAATACT GTGCGTATGA

33551  CGGAGCTATG CTAACCAGCG TAGCCCCGAT GTAAGCTTGT TGCATGGGCG
       GCCTCGATAC GATTGGTCGC ATCGGGGCTA CATTCGAACA ACGTACCCGC

33601  GCGATATAAA ATGCAAGGTG CTGCTCAAAA AATCAGGCAA AGCCTCGCGC
       CGCTATATTT TACGTTCCAC GACGAGTTTT TTAGTCCGTT TCGGAGCGCG

33651  AAAAAAGAAA GCACATCGTA GTCATGCTCA TGCAGATAAA GGCAGGTAAG
       TTTTTTCTTT CGTGTAGCAT CAGTACGAGT ACGTCTATTT CCGTCCATTC

33701  CTCCGGAACC ACCACAGAAA AAGACACCAT TTTTCTCTCA AACATGTCTG
       GAGGCCTTGG TGGTGTCTTT TTCTGTGGTA AAAAGAGAGT TTGTACAGAC

33751  CGGGTTTCTG CATAAACACA AAATAAAATA ACAAAAAAAC ATTTAAACAT
       GCCCAAAGAC GTATTTGTGT TTTATTTTAT TGTTTTTTTG TAAATTTGTA

33801  TAGAAGCCTG TCTTACAACA GGAAAAACAA CCCTTATAAG CATAAGACGG
       ATCTTCGGAC AGAATGTTGT CCTTTTTGTT GGGAATATTC GTATTCTGCC

33851  ACTACGGCCA TGCCGGCGTG ACCGTAAAAA AACTGGTCAC CGTGATTAAA
       TGATGCCGGT ACGGCCGCAC TGGCATTTTT TTGACCAGTG GCACTAATTT

33901  AAGCACCACC GACAGCTCCT CGGTCATGTC CGGAGTCATA ATGTAAGACT
       TTCGTGGTGG CTGTCGAGGA GCCAGTACAG GCCTCAGTAT TACATTCTGA

33951  CGGTAAACAC ATCAGGTTGA TTCACATCGG TCAGTGCTAA AAAGCGACCG
       GCCATTTGTG TAGTCCAACT AAGTGTAGCC AGTCACGATT TTTCGCTGGC
```

FIG. 27A-40

```
34001  AAATAGCCCG GGGGAATACA TACCCGCAGG CGTAGAGACA ACATTACAGC
       TTTATCGGGC CCCCTTATGT ATGGGCGTCC GCATCTCTGT TGTAATGTCG

34051  CCCCATAGGA GGTATAACAA AATTAATAGG AGAGAAAAAC ACATAAACAC
       GGGGTATCCT CCATATTGTT TTAATTATCC TCTCTTTTTG TGTATTTGTG

34101  CTGAAAAACC CTCCTGCCTA GGCAAAATAG CACCCTCCCG CTCCAGAACA
       GACTTTTTGG GAGGACGGAT CCGTTTTATC GTGGGAGGGC GAGGTCTTGT

34151  ACATACAGCG CTTCCACAGC GGCAGCCATA ACAGTCAGCC TTACCAGTAA
       TGTATGTCGC GAAGGTGTCG CCGTCGGTAT TGTCAGTCGG AATGGTCATT

34201  AAAAGAAAAC CTATTAAAAA AACACCACTC GACACGGCAC CAGCTCAATC
       TTTTCTTTTG GATAATTTTT TTGTGGTGAG CTGTGCCGTG GTCGAGTTAG

34251  AGTCACAGTG TAAAAAAGGG CCAAGTGCAG AGCGAGTATA TATAGGACTA
       TCAGTGTCAC ATTTTTTCCC GGTTCACGTC TCGCTCATAT ATATCCTGAT

34301  AAAAATGACG TAACGGTTAA AGTCCACAAA AAACACCCAG AAAACCGCAC
       TTTTTACTGC ATTGCCAATT TCAGGTGTTT TTTGTGGGTC TTTTGGCGTG

34351  GCGAACCTAC GCCCAGAAAC GAAAGCCAAA AAACCCACAA CTTCCTCAAA
       CGCTTGGATG CGGGTCTTTG CTTTCGGTTT TTTGGGTGTT GAAGGAGTTT

34401  TCGTCACTTC CGTTTTCCCA CGTTACGTCA CTTCCCATTT TAAGAAAACT
       AGCAGTGAAG GCAAAAGGGT GCAATGCAGT GAAGGGTAAA ATTCTTTTGA

34451  ACAATTCCCA ACACATACAA GTTACTCCGC CCTAAAACCT ACGTCACCCG
       TGTTAAGGGT TGTGTATGTT CAATGAGGCG GGATTTTGGA TGCAGTGGGC

34501  CCCCGTTCCC ACGCCCCGCG CCACGTCACA AACTCCACCC CCTCATTATC
       GGGGCAAGGG TGCGGGGCGC GGTGCAGTGT TTGAGGTGGG GGAGTAATAG

                                                    PacI
                                                  ~~~~~~~~
34551  ATATTGGCTT CAATCCAAAA TAAGGTATAT TATTGATGAT GTTAATTAAG
       TATAACCGAA GTTAGGTTTT ATTCCATATA ATAACTACTA CAATTAATTC

34601  AATTCGGATC TGCGACGCGA GGCTGGATGG CCTTCCCCAT TATGATTCTT
       TTAAGCCTAG ACGCTGCGCT CCGACCTACC GGAAGGGGTA ATACTAAGAA

34651  CTCGCTTCCG GCGGCATCGG GATGCCCGCG TTGCAGGCCA TGCTGTCCAG
       GAGCGAAGGC CGCCGTAGCC CTACGGGCGC AACGTCCGGT ACGACAGGTC

34701  GCAGGTAGAT GACGACCATC AGGGACAGCT TCAAGGCCAG CAAAAGGCCA
       CGTCCATCTA CTGCTGGTAG TCCCTGTCGA AGTTCCGGTC GTTTTCCGGT

34751  GGAACCGTAA AAAGGCCGCG TTGCTGGCGT TTTTCCATAG GCTCCGCCCC
       CCTTGGCATT TTTCCGGCGC AACGACCGCA AAAAGGTATC CGAGGCGGGG
```

FIG. 27A-41

```
34801  CCTGACGAGC ATCACAAAAA TCGACGCTCA AGTCAGAGGT GGCGAAACCC
       GGACTGCTCG TAGTGTTTTT AGCTGCGAGT TCAGTCTCCA CCGCTTTGGG

34851  GACAGGACTA TAAAGATACC AGGCGTTTCC CCCTGGAAGC TCCCTCGTGC
       CTGTCCTGAT ATTTCTATGG TCCGCAAAGG GGGACCTTCG AGGGAGCACG

34901  GCTCTCCTGT TCCGACCCTG CCGCTTACCG GATACCTGTC CGCCTTTCTC
       CGAGAGGACA AGGCTGGGAC GGCGAATGGC CTATGGACAG GCGGAAAGAG

34951  CCTTCGGGAA GCGTGGCGCT TTCTCATAGC TCACGCTGTA GGTATCTCAG
       GGAAGCCCTT CGCACCGCGA AAGAGTATCG AGTGCGACAT CCATAGAGTC

35001  TTCGGTGTAG GTCGTTCGCT CCAAGCTGGG CTGTGTGCAC GAACCCCCCG
       AAGCCACATC CAGCAAGCGA GGTTCGACCC GACACACGTG CTTGGGGGGC

35051  TTCAGCCCGA CCGCTGCGCC TTATCCGGTA ACTATCGTCT TGAGTCCAAC
       AAGTCGGGCT GGCGACGCGG AATAGGCCAT TGATAGCAGA ACTCAGGTTG

35101  CCGGTAAGAC ACGACTTATC GCCACTGGCA GCAGCCACTG GTAACAGGAT
       GGCCATTCTG TGCTGAATAG CGGTGACCGT CGTCGGTGAC CATTGTCCTA

35151  TAGCAGAGCG AGGTATGTAG GCGGTGCTAC AGAGTTCTTG AAGTGGTGGC
       ATCGTCTCGC TCCATACATC CGCCACGATG TCTCAAGAAC TTCACCACCG

35201  CTAACTACGG CTACACTAGA AGGACAGTAT TTGGTATCTG CGCTCTGCTG
       GATTGATGCC GATGTGATCT TCCTGTCATA AACCATAGAC GCGAGACGAC

35251  AAGCCAGTTA CCTTCGGAAA AAGAGTTGGT AGCTCTTGAT CCGGCAAACA
       TTCGGTCAAT GGAAGCCTTT TTCTCAACCA TCGAGAACTA GGCCGTTTGT

35301  AACCACCGCT GGTAGCGGTG GTTTTTTTGT TTGCAAGCAG CAGATTACGC
       TTGGTGGCGA CCATCGCCAC CAAAAAAACA AACGTTCGTC GTCTAATGCG

35351  GCAGAAAAAA AGGATCTCAA GAAGATCCTT TGATCTTTTC TACGGGGTCT
       CGTCTTTTTT TCCTAGAGTT CTTCTAGGAA ACTAGAAAAG ATGCCCCAGA

35401  GACGCTCAGT GGAACGAAAA CTCACGTTAA GGGATTTTGG TCATGAGATT
       CTGCGAGTCA CCTTGCTTTT GAGTGCAATT CCCTAAAACC AGTACTCTAA

35451  ATCAAAAAGG ATCTTCACCT AGATCCTTTT AAATCAATCT AAAGTATATA
       TAGTTTTTCC TAGAAGTGGA TCTAGGAAAA TTTAGTTAGA TTTCATATAT

35501  TGAGTAAACT TGGTCTGACA GTTACCAATG CTTAATCAGT GAGGCACCTA
       ACTCATTTGA ACCAGACTGT CAATGGTTAC GAATTAGTCA CTCCGTGGAT

35551  TCTCAGCGAT CTGTCTATTT CGTTCATCCA TAGTTGCCTG ACTCCCCGTC
       AGAGTCGCTA GACAGATAAA GCAAGTAGGT ATCAACGGAC TGAGGGGCAG

35601  GTGTAGATAA CTACGATACG GGAGGGCTTA CCATCTGGCC CCAGTGCTGC
       CACATCTATT GATGCTATGC CCTCCCGAAT GGTAGACCGG GGTCACGACG
```

FIG. 27A-42

```
35651  AATGATACCG CGAGACCCAC GCTCACCGGC TCCAGATTTA TCAGCAATAA
       TTACTATGGC GCTCTGGGTG CGAGTGGCCG AGGTCTAAAT AGTCGTTATT

35701  ACCAGCCAGC CGGAAGGGCC GAGCGCAGAA GTGGTCCTGC AACTTTATCC
       TGGTCGGTCG GCCTTCCCGG CTCGCGTCTT CACCAGGACG TTGAAATAGG

35751  GCCTCCATCC AGTCTATTAA TTGTTGCCGG GAAGCTAGAG TAAGTAGTTC
       CGGAGGTAGG TCAGATAATT AACAACGGCC CTTCGATCTC ATTCATCAAG

35801  GCCAGTTAAT AGTTTGCGCA ACGTTGTTGC CATTGCTACA GGCATCGTGG
       CGGTCAATTA TCAAACGCGT TGCAACAACG GTAACGATGT CCGTAGCACC

35851  TGTCACGCTC GTCGTTTGGT ATGGCTTCAT TCAGCTCCGG TTCCCAACGA
       ACAGTGCGAG CAGCAAACCA TACCGAAGTA AGTCGAGGCC AAGGGTTGCT

35901  TCAAGGCGAG TTACATGATC CCCCATGTTG TGCAAAAAAG CGGTTAGCTC
       AGTTCCGCTC AATGTACTAG GGGGTACAAC ACGTTTTTTC GCCAATCGAG

35951  CTTCGGTCCT CCGATCGTTG TCAGAAGTAA GTTGGCCGCA GTGTTATCAC
       GAAGCCAGGA GGCTAGCAAC AGTCTTCATT CAACCGGCGT CACAATAGTG

36001  TCATGGTTAT GGCAGCACTG CATAATTCTC TTACTGTCAT GCCATCCGTA
       AGTACCAATA CCGTCGTGAC GTATTAAGAG AATGACAGTA CGGTAGGCAT

36051  AGATGCTTTT CTGTGACTGG TGAGTACTCA ACCAAGTCAT TCTGAGAATA
       TCTACGAAAA GACACTGACC ACTCATGAGT TGGTTCAGTA AGACTCTTAT

36101  GTGTATGCGG CGACCGAGTT GCTCTTGCCC GGCGTCAACA CGGGATAATA
       CACATACGCC GCTGGCTCAA CGAGAACGGG CCGCAGTTGT GCCCTATTAT

36151  CCGCGCCACA TAGCAGAACT TTAAAAGTGC TCATCATTGG AAAACGTTCT
       GGCGCGGTGT ATCGTCTTGA AATTTTCACG AGTAGTAACC TTTTGCAAGA

36201  TCGGGGCGAA AACTCTCAAG GATCTTACCG CTGTTGAGAT CCAGTTCGAT
       AGCCCCGCTT TTGAGAGTTC CTAGAATGGC GACAACTCTA GGTCAAGCTA

36251  GTAACCCACT CGTGCACCCA ACTGATCTTC AGCATCTTTT ACTTTCACCA
       CATTGGGTGA GCACGTGGGT TGACTAGAAG TCGTAGAAAA TGAAAGTGGT

36301  GCGTTTCTGG GTGAGCAAAA ACAGGAAGGC AAAATGCCGC AAAAAAGGGA
       CGCAAAGACC CACTCGTTTT TGTCCTTCCG TTTTACGGCG TTTTTTCCCT

36351  ATAAGGGCGA CACGGAAATG TTGAATACTC ATACTCTTCC TTTTTCAATA
       TATTCCCGCT GTGCCTTTAC AACTTATGAG TATGAGAAGG AAAAAGTTAT

36401  TTATTGAAGC ATTTATCAGG GTTATTGTCT CATGAGCGGA TACATATTTG
       AATAACTTCG TAAATAGTCC CAATAACAGA GTACTCGCCT ATGTATAAAC

36451  AATGTATTTA GAAAAATAAA CAAATAGGGG TTCCGCGCAC ATTTCCCCGA
       TTACATAAAT CTTTTTATTT GTTTATCCCC AAGGCGCGTG TAAAGGGGCT
```

FIG. 27A-43

```
36501  AAAGTGCCAC CTGACGTCTA AGAAACCATT ATTATCATGA CATTAACCTA
       TTTCACGGTG GACTGCAGAT TCTTTGGTAA TAATAGTACT GTAATTGGAT

36551  TAAAAATAGG CGTATCACGA GGCCCTTTCG TCTTCAAGAA TTGGATCCGA
       ATTTTTATCC GCATAGTGCT CCGGGAAAGC AGAAGTTCTT AACCTAGGCT

                          PacI
                        ~~~~~~~~
36601  ATTCTTAATT TCTTAATTAA   (SEQ ID NO: 30)
       TAAGAATTAA AGAATTAATT   (SEQ ID NO: 31)
```

FIG. 27A-44

```
atg gat gca atg aag aga ggg ctc tgc tgt gtg ctg ctg ctg tgt gga      48
Met Asp Ala Met Lys Arg Gly Leu Cys Cys Val Leu Leu Leu Cys Gly
 1               5                  10                  15

gca gtc ttc gtt tcg ccc agc gag atc tcc att gtg tgg gcc tcc agg      96
Ala Val Phe Val Ser Pro Ser Glu Ile Ser Ile Val Trp Ala Ser Arg
            20                  25                  30

gag ctg gag agg ttt gct gtg aac cct ggc ctg ctg gag acc tct gag     144
Glu Leu Glu Arg Phe Ala Val Asn Pro Gly Leu Leu Glu Thr Ser Glu
        35                  40                  45

ggg tgc agg cag atc ctg ggc cag ctc cag ccc tcc ctg caa aca ggc     192
Gly Cys Arg Gln Ile Leu Gly Gln Leu Gln Pro Ser Leu Gln Thr Gly
    50                  55                  60

tct gag gag ctg agg tcc ctg tac aac aca gtg gct acc ctg tac tgt     240
Ser Glu Glu Leu Arg Ser Leu Tyr Asn Thr Val Ala Thr Leu Tyr Cys
65                  70                  75                  80

gtg cac cag aag att gat gtg aag gac acc aag gag gcc ctg gag aag     288
Val His Gln Lys Ile Asp Val Lys Asp Thr Lys Glu Ala Leu Glu Lys
                85                  90                  95

att gag gag gag cag aac aag tcc aag aag aag gcc cag cag gct gct     336
Ile Glu Glu Glu Gln Asn Lys Ser Lys Lys Lys Ala Gln Gln Ala Ala
            100                 105                 110

gct ggc aca ggc aac tcc agc cag gtg tcc cag aac tac ccc att gtg     384
Ala Gly Thr Gly Asn Ser Ser Gln Val Ser Gln Asn Tyr Pro Ile Val
        115                 120                 125

cag aac ctc cag ggc cag atg gtg cac cag gcc atc tcc ccc cgg acc     432
Gln Asn Leu Gln Gly Gln Met Val His Gln Ala Ile Ser Pro Arg Thr
    130                 135                 140

ctg aat gcc tgg gtg aag gtg gtg gag gag aag gcc ttc tcc cct gag     480
Leu Asn Ala Trp Val Lys Val Val Glu Glu Lys Ala Phe Ser Pro Glu
145                 150                 155                 160

gtg atc ccc atg ttc tct gcc ctg tct gag ggt gcc acc ccc cag gac     528
Val Ile Pro Met Phe Ser Ala Leu Ser Glu Gly Ala Thr Pro Gln Asp
                165                 170                 175

ctg aac acc atg ctg aac aca gtg ggg ggc cat cag gct gcc atg cag     576
Leu Asn Thr Met Leu Asn Thr Val Gly Gly His Gln Ala Ala Met Gln
            180                 185                 190

atg ctg aag gag acc atc aat gag gag gct gct gag tgg gac agg ctg     624
Met Leu Lys Glu Thr Ile Asn Glu Glu Ala Ala Glu Trp Asp Arg Leu
        195                 200                 205

cat cct gtg cac gct ggc ccc att gcc ccc ggc cag atg agg gag ccc     672
His Pro Val His Ala Gly Pro Ile Ala Pro Gly Gln Met Arg Glu Pro
    210                 215                 220

agg ggc tct gac att gct ggc acc acc tcc acc ctc cag gag cag att     720
Arg Gly Ser Asp Ile Ala Gly Thr Thr Ser Thr Leu Gln Glu Gln Ile
225                 230                 235                 240

ggc tgg atg acc aac aac ccc ccc atc cct gtg ggg gaa atc tac aag     768
Gly Trp Met Thr Asn Asn Pro Pro Ile Pro Val Gly Glu Ile Tyr Lys
                245                 250                 255
```

FIG. 30A-1

```
agg tgg atc atc ctg ggc ctg aac aag att gtg agg atg tac tcc ccc       816
Arg Trp Ile Ile Leu Gly Leu Asn Lys Ile Val Arg Met Tyr Ser Pro
            260                 265                 270

acc tcc atc ctg gac atc agg cag ggc ccc aag gag ccc ttc agg gac       864
Thr Ser Ile Leu Asp Ile Arg Gln Gly Pro Lys Glu Pro Phe Arg Asp
        275                 280                 285

tat gtg gac agg ttc tac aag acc ctg agg gct gag cag gcc tcc cag       912
Tyr Val Asp Arg Phe Tyr Lys Thr Leu Arg Ala Glu Gln Ala Ser Gln
    290                 295                 300

gag gtg aag aac tgg atg aca gag acc ctg ctg gtg cag aat gcc aac       960
Glu Val Lys Asn Trp Met Thr Glu Thr Leu Leu Val Gln Asn Ala Asn
305                 310                 315                 320

cct gac tgc aag acc atc ctg aag gcc ctg ggc cct gct gcc acc ctg      1008
Pro Asp Cys Lys Thr Ile Leu Lys Ala Leu Gly Pro Ala Ala Thr Leu
                325                 330                 335

gag gag atg atg aca gcc tgc cag ggg gtg ggg ggc cct ggt cac aag      1056
Glu Glu Met Met Thr Ala Cys Gln Gly Val Gly Gly Pro Gly His Lys
            340                 345                 350

gcc agg gtg ctg gct gag gcc atg tcc cag gtg acc aac tcc gcc acc      1104
Ala Arg Val Leu Ala Glu Ala Met Ser Gln Val Thr Asn Ser Ala Thr
        355                 360                 365

atc atg atg cag agg ggc aac ttc agg aac cag agg aag aca gtg aag      1152
Ile Met Met Gln Arg Gly Asn Phe Arg Asn Gln Arg Lys Thr Val Lys
    370                 375                 380

tgc ttc aac tgt ggc aag gtg ggc cac att gcc aag aac tgt agg gcc      1200
Cys Phe Asn Cys Gly Lys Val Gly His Ile Ala Lys Asn Cys Arg Ala
385                 390                 395                 400

ccc agg aag aag ggc tgc tgg aag tgt ggc aag gag ggc cac cag atg      1248
Pro Arg Lys Lys Gly Cys Trp Lys Cys Gly Lys Glu Gly His Gln Met
                405                 410                 415

aag gac tgc aat gag agg cag gcc aac ttc ctg ggc aaa atc tgg ccc      1296
Lys Asp Cys Asn Glu Arg Gln Ala Asn Phe Leu Gly Lys Ile Trp Pro
            420                 425                 430

tcc cac aag ggc agg cct ggc aac ttc ctc cag tcc agg cct gag ccc      1344
Ser His Lys Gly Arg Pro Gly Asn Phe Leu Gln Ser Arg Pro Glu Pro
        435                 440                 445

aca gcc cct ccc gag gag tcc ttc agg ttt ggg gag gag aag acc acc      1392
Thr Ala Pro Pro Glu Glu Ser Phe Arg Phe Gly Glu Glu Lys Thr Thr
    450                 455                 460

ccc agc cag aag cag gag ccc att gac aag gag ctg tac ccc ctg gcc      1440
Pro Ser Gln Lys Gln Glu Pro Ile Asp Lys Glu Leu Tyr Pro Leu Ala
465                 470                 475                 480

tcc ctg agg tcc ctg ttt ggc aac gac ccc tcc tcc cag taa (SID NO:32) 1482
Ser Leu Arg Ser Leu Phe Gly Asn Asp Pro Ser Ser Gln  *  (SID NO:33)
                485                 490
```

FIG. 30A-2

ATGGGTGCTA GGGCTTCTGT GCTGTCTGGT GGTGAGCTGG ACAAGTGGGA GAAGATCAGG
CTGAGGCCTG GTGGCAAGAA GAAGTACAAG CTAAAGCACA TTGTGTGGGC CTCCAGGGAG
CTGGAGAGGT TTGCTGTGAA CCCTGGCCTG CTGGAGACCT CTGAGGGGTG CAGGCAGATC
CTGGGCCAGC TCCAGCCCTC CCTGCAAACA GGCTCTGAGG AGCTGAGGTC CCTGTACAAC
ACAGTGGCTA CCCTGTACTG TGTGCACCAG AAGATTGATG TGAAGGACAC CAAGGAGGCC
CTGGAGAAGA TTGAGGAGGA GCAGAACAAG TCCAAGAAGA AGGCCCAGCA GGCTGCTGCT
GGCACAGGCA ACTCCAGCCA GGTGTCCCAG AACTACCCCA TTGTGCAGAA CCTCCAGGGC
CAGATGGTGC ACCAGGCCAT CTCCCCCCGG ACCCTGAATG CCTGGGTGAA GGTGGTGGAG
GAGAAGGCCT TCTCCCCTGA GGTGATCCCC ATGTTCTCTG CCCTGTCTGA GGGTGCCACC
CCCCAGGACC TGAACACCAT GCTGAACACA GTGGGGGGCC ATCAGGCTGC CATGCAGATG
CTGAAGGAGA CCATCAATGA GGAGGCTGCT GAGTGGGACA GGCTGCATCC TGTGCACGCT
GGCCCCATTG CCCCCGGCCA GATGAGGGAG CCCAGGGGCT CTGACATTGC TGGCACCACC
TCCACCCTCC AGGAGCAGAT TGGCTGGATG ACCAACAACC CCCCCATCCC TGTGGGGGAA
ATCTACAAGA GGTGGATCAT CCTGGGCCTG AACAAGATTG TGAGGATGTA CTCCCCCACC
TCCATCCTGG ACATCAGGCA GGGCCCCAAG GAGCCCTTCA GGGACTATGT GGACAGGTTC
TACAAGACCC TGAGGGCTGA GCAGGCCTCC CAGGAGGTGA AGAACTGGAT GACAGAGACC
CTGCTGGTGC AGAATGCCAA CCCTGACTGC AAGACCATCC TGAAGGCCCT GGGCCCTGCT
GCCACCCTGG AGGAGATGAT GACAGCCTGC CAGGGGGTGG GGGGCCCTGG TCACAAGGCC
AGGGTGCTGG CTGAGGCCAT GTCCCAGGTG ACCAACTCCG CCACCATCAT GATGCAGAGG
GGCAACTTCA GGAACCAGAG GAAGACAGTG AAGTGCTTCA ACTGTGGCAA GGTGGGCCAC
ATTGCCAAGA ACTGTAGGGC CCCCAGGAAG AAGGGCTGCT GGAAGTGTGG CAAGGAGGGC
CACCAGATGA AGGACTGCAA TGAGAGGCAG GCCAACTTCC TGGGCAAAAT CTGGCCCTCC
CACAAGGGCA GGCCTGGCAA CTTCCTCCAG TCCAGGCCTG AGCCCACAGC CCCTCCCGAG
GAGTCCTTCA GGTTTGGGGA GGAGAAGACC ACCCCCAGCC AGAAGCAGGA GCCCATTGAC
AAGGAGCTGT ACCCCCTGGC CTCCCTGAGG TCCCTGTTTG GCAACGACCC CTCCTCCCAG
ATGGCTCCCA TCTCCCCCAT TGAGACTGTG CCTGTGAAGC TGAAGCCTGG CATGGATGGC
CCCAAGGTGA AGCAGTGGCC CCTGACTGAG GAGAAGATCA AGGCCCTGGT GGAAATCTGC
ACTGAGATGG AGAAGGAGGG CAAAATCTCC AAGATTGGCC CCGAGAACCC CTACAACACC
CCTGTGTTTG CCATCAAGAA GAAGGACTCC ACCAAGTGGA GGAAGCTGGT GGACTTCAGG
GAGCTGAACA AGAGGACCCA GGACTTCTGG GAGGTGCAGC TGGGCATCCC CCACCCCGCT
GGCCTGAAGA AGAAGAAGTC TGTGACTGTG CTGGCTGTGG GGGATGCCTA CTTCTCTGTG
CCCCTGGATG AGGACTTCAG GAAGTACACT GCCTTCACCA TCCCCTCCAT CAACAATGAG
ACCCCTGGCA TCAGGTACCA GTACAATGTG CTGCCCCAGG GCTGGAAGGG CTCCCCTGCC
ATCTTCCAGT CCTCCATGAC CAAGATCCTG GAGCCCTTCA GGAAGCAGAA CCCTGACATT
GTGATCTACC AGTACATGGC TGCCCTGTAT GTGGGCTCTG ACCTGGAGAT TGGGCAGCAC
AGGACCAAGA TTGAGGAGCT GAGGCAGCAC CTGCTGAGGT GGGGCCTGAC CACCCCTGAC
AAGAAGCACC AGAAGGAGCC CCCCTTCCTG TGGATGGGCT ATGAGCTGCA CCCCGACAAG
TGGACTGTGC AGCCCATTGT GCTGCCTGAG AAGGACTCCT GGACTGTGAA TGACATCCAG
AAGCTGGTGG GCAAGCTGAA CTGGGCCTCC CAAATCTACC CTGGCATCAA GGTGAGGCAG
CTGTGCAAGC TGCTGAGGGG CACCAAGGCC CTGACTGAGG TGATCCCCCT GACTGAGGAG
GCTGAGCTGG AGCTGGCTGA GAACAGGGAG ATCCTGAAGG AGCCTGTGCA TGGGGTGTAC
TATGACCCCT CCAAGGACCT GATTGCTGAG ATCCAGAAGC AGGGCCAGGG CCAGTGGACC

FIG. 33A-1

```
TACCAAATCT ACCAGGAGCC CTTCAAGAAC CTGAAGACTG GCAAGTATGC CAGGATGAGG
GGGGCCCACA CCAATGATGT GAAGCAGCTG ACTGAGGCTG TGCAGAAGAT CACCACTGAG
TCCATTGTGA TCTGGGGCAA GACCCCCAAG TTCAAGCTGC CCATCCAGAA GGAGACCTGG
GAGACCTGGT GGACTGAGTA CTGGCAGGCC ACCTGGATCC CTGAGTGGGA GTTTGTGAAC
ACCCCCCCCC TGGTGAAGCT GTGGTACCAG CTGGAGAAGG AGCCCATTGT GGGGGCTGAG
ACCTTCTATG TGGCTGGGGC TGCCAACAGG GAGACCAAGC TGGGCAAGGC TGGCTATGTG
ACCAACAGGG GCAGGCAGAA GGTGGTGACC CTGACTGACA CCACCAACCA GAAGACTGCC
CTCCAGGCCA TCTACCTGGC CCTCCAGGAC TCTGGCCTGG AGGTGAACAT TGTGACTGCC
TCCCAGTATG CCCTGGGCAT CATCCAGGCC CAGCCTGATC AGTCTGAGTC TGAGCTGGTG
AACCAGATCA TTGAGCAGCT GATCAAGAAG GAGAAGGTGT ACCTGGCCTG GGTGCCTGCC
CACAAGGGCA TTGGGGGCAA TGAGCAGGTG GACAAGCTGG TGTCTGCTGG CATCAGGAAG
GTGCTGTTCC TGGATGGCAT TGACAAGGCC CAGGATGAGC ATGAGAAGTA CCACTCCAAC
TGGAGGGCTA TGGCCTCTGA CTTCAACCTG CCCCCTGTGG TGGCTAAGGA GATTGTGGCC
TCCTGTGACA AGTGCCAGCT GAAGGGGGAG GCCATGCATG GGCAGGTGGA CTGCTCCCCT
GGCATCTGGC AGCTGGCCTG CACCCACCTG GAGGGCAAGG TGATCCTGGT GGCTGTGCAT
GTGGCCTCCG GCTACATTGA GGCTGAGGTG ATCCCTGCTG AGACAGGCCA GGAGACTGCC
TACTTCCTGC TGAAGCTGGC TGGCAGGTGG CCTGTGAAGA CCATCCACAC TGCCAATGGC
TCCAACTTCA CTGGGGCCAC AGTGAGGGCT GCCTGCTGGT GGGCTGGCAT CAAGCAGGAG
TTTGGCATCC CCTACAACCC CCAGTCCCAG GGGGTGGTGG CCTCCATGAA CAAGGAGCTG
AAGAAGATCA TTGGGCAGGT GAGGGACCAG GCTGAGCACC TGAAGACAGC TGTGCAGATG
GCTGTGTTCA TCCACAACTT CAAGAGGAAG GGGGGCATCG GGGGCTACTC CGCTGGGGAG
AGGATTGTGG ACATCATTGC CACAGACATC CAGACCAAGG AGCTCCAGAA GCAGATCACC
AAGATCCAGA ACTTCAGGGT GTACTACAGG GACTCCAGGA ACCCCCTGTG GAAGGGCCCT
GCCAAGCTGC TGTGGAAGGG GGAGGGGGCT GTGGTGATCC AGGACAACTC TGACATCAAG
GTGGTGCCCA GGAGGAAGGC CAAGATCATC AGGGACTATG GCAAGCAGAT GGCTGGGGAT
GACTGTGTGG CCTCCAGGCA GGATGAGGAC TAA
(SEQ ID NO: 34)
```

FIG. 33A-2

Met Gly Ala Arg Ala Ser Val Leu Ser Gly Gly Glu Leu Asp Lys Trp Glu Lys
Ile Arg Leu Arg Pro Gly Gly Lys Lys Lys Tyr Lys Leu Lys His Ile Val Trp
Ala Ser Arg Glu Leu Glu Arg Phe Ala Val Asn Pro Gly Leu Leu Glu Thr Ser
Glu Gly Cys Arg Gln Ile Leu Gly Gln Leu Gln Pro Ser Leu Gln Thr Gly Ser
Glu Glu Leu Arg Ser Leu Tyr Asn Thr Val Ala Thr Leu Tyr Cys Val His Gln
Lys Ile Asp Val Lys Asp Thr Lys Glu Ala Leu Glu Lys Ile Glu Glu Glu Gln
Asn Lys Ser Lys Lys Lys Ala Gln Gln Ala Ala Ala Gly Thr Gly Asn Ser Ser
Gln Val Ser Gln Asn Tyr Pro Ile Val Gln Asn Leu Gln Gly Gln Met Val His
Gln Ala Ile Ser Pro Arg Thr Leu Asn Ala Trp Val Lys Val Val Glu Glu Lys
Ala Phe Ser Pro Glu Val Ile Pro Met Phe Ser Ala Leu Ser Glu Gly Ala Thr
Pro Gln Asp Leu Asn Thr Met Leu Asn Thr Val Gly Gly His Gln Ala Ala Met
Gln Met Leu Lys Glu Thr Ile Asn Glu Glu Ala Ala Glu Trp Asp Arg Leu His
Pro Val His Ala Gly Pro Ile Ala Pro Gly Gln Met Arg Glu Pro Arg Gly Ser
Asp Ile Ala Gly Thr Thr Ser Thr Leu Gln Glu Gln Ile Gly Trp Met Thr Asn
Asn Pro Pro Ile Pro Val Gly Glu Ile Tyr Lys Arg Trp Ile Ile Leu Gly Leu
Asn Lys Ile Val Arg Met Tyr Ser Pro Thr Ser Ile Leu Asp Ile Arg Gln Gly
Pro Lys Glu Pro Phe Arg Asp Tyr Val Asp Arg Phe Tyr Lys Thr Leu Arg Ala
Glu Gln Ala Ser Gln Glu Val Lys Asn Trp Met Thr Glu Thr Leu Leu Val Gln
Asn Ala Asn Pro Asp Cys Lys Thr Ile Leu Lys Ala Leu Gly Pro Ala Ala Thr
Leu Glu Glu Met Met Thr Ala Cys Gln Gly Val Gly Gly Pro Gly His Lys Ala
Arg Val Leu Ala Glu Ala Met Ser Gln Val Thr Asn Ser Ala Thr Ile Met Met
Gln Arg Gly Asn Phe Arg Asn Gln Arg Lys Thr Val Lys Cys Phe Asn Cys Gly
Lys Val Gly His Ile Ala Lys Asn Cys Arg Ala Pro Arg Lys Lys Gly Cys Trp
Lys Cys Gly Lys Glu Gly His Gln Met Lys Asp Cys Asn Glu Arg Gln Ala Asn
Phe Leu Gly Lys Ile Trp Pro Ser His Lys Gly Arg Pro Gly Asn Phe Leu Gln
Ser Arg Pro Glu Pro Thr Ala Pro Pro Glu Glu Ser Phe Arg Phe Gly Glu Glu
Lys Thr Thr Pro Ser Gln Lys Gln Glu Pro Ile Asp Lys Glu Leu Tyr Pro Leu
Ala Ser Leu Arg Ser Leu Phe Gly Asn Asp Pro Ser Ser Gln Met Ala Pro Ile
Ser Pro Ile Glu Thr Val Pro Val Lys Leu Lys Pro Gly Met Asp Gly Pro Lys
Val Lys Gln Trp Pro Leu Thr Glu Glu Lys Ile Lys Ala Leu Val Glu Ile Cys
Thr Glu Met Glu Lys Glu Gly Lys Ile Ser Lys Ile Gly Pro Glu Asn Pro Tyr
Asn Thr Pro Val Phe Ala Ile Lys Lys Lys Asp Ser Thr Lys Trp Arg Lys Leu
Val Asp Phe Arg Glu Leu Asn Lys Arg Thr Gln Asp Phe Trp Glu Val Gln Leu
Gly Ile Pro His Pro Ala Gly Leu Lys Lys Lys Lys Ser Val Thr Val Leu Ala
Val Gly Asp Ala Tyr Phe Ser Val Pro Leu Asp Glu Asp Phe Arg Lys Tyr Thr
Ala Phe Thr Ile Pro Ser Ile Asn Asn Glu Thr Pro Gly Ile Arg Tyr Gln Tyr
Asn Val Leu Pro Gln Gly Trp Lys Gly Ser Pro Ala Ile Phe Gln Ser Ser Met
Thr Lys Ile Leu Glu Pro Phe Arg Lys Gln Asn Pro Asp Ile Val Ile Tyr Gln
Tyr Met Ala Ala Leu Tyr Val Gly Ser Asp Leu Glu Ile Gly Gln His Arg Thr
Lys Ile Glu Glu Leu Arg Gln His Leu Leu Arg Trp Gly Leu Thr Thr Pro Asp
Lys Lys His Gln Lys Glu Pro Pro Phe Leu Trp Met Gly Tyr Glu Leu His Pro
Asp Lys Trp Thr Val Gln Pro Ile Val Leu Pro Glu Lys Asp Ser Trp Thr Val

FIG. 34A-1

Asn Asp Ile Gln Lys Leu Val Gly Lys Leu Asn Trp Ala Ser Gln Ile Tyr Pro
Gly Ile Lys Val Arg Gln Leu Cys Lys Leu Leu Arg Gly Thr Lys Ala Leu Thr
Glu Val Ile Pro Leu Thr Glu Glu Ala Glu Leu Glu Leu Ala Glu Asn Arg Glu
Ile Leu Lys Glu Pro Val His Gly Val Tyr Tyr Asp Pro Ser Lys Asp Leu Ile
Ala Glu Ile Gln Lys Gln Gly Gln Gly Gln Trp Thr Tyr Gln Ile Tyr Gln Glu
Pro Phe Lys Asn Leu Lys Thr Gly Lys Tyr Ala Arg Met Arg Gly Ala His Thr
Asn Asp Val Lys Gln Leu Thr Glu Ala Val Gln Lys Ile Thr Thr Glu Ser Ile
Val Ile Trp Gly Lys Thr Pro Lys Phe Lys Leu Pro Ile Gln Lys Glu Thr Trp
Glu Thr Trp Trp Thr Glu Tyr Trp Gln Ala Thr Trp Ile Pro Glu Trp Glu Phe
Val Asn Thr Pro Pro Leu Val Lys Leu Trp Tyr Gln Leu Glu Lys Glu Pro Ile
Val Gly Ala Glu Thr Phe Tyr Val Ala Gly Ala Ala Asn Arg Glu Thr Lys Leu
Gly Lys Ala Gly Tyr Val Thr Asn Arg Gly Arg Gln Lys Val Val Thr Leu Thr
Asp Thr Thr Asn Gln Lys Thr Ala Leu Gln Ala Ile Tyr Leu Ala Leu Gln Asp
Ser Gly Leu Glu Val Asn Ile Val Thr Ala Ser Gln Tyr Ala Leu Gly Ile Ile
Gln Ala Gln Pro Asp Gln Ser Glu Ser Glu Leu Val Asn Gln Ile Ile Glu Gln
Leu Ile Lys Lys Glu Lys Val Tyr Leu Ala Trp Val Pro Ala His Lys Gly Ile
Gly Gly Asn Glu Gln Val Asp Lys Leu Val Ser Ala Gly Ile Arg Lys Val Leu
Phe Leu Asp Gly Ile Asp Lys Ala Gln Asp Glu His Glu Lys Tyr His Ser Asn
Trp Arg Ala Met Ala Ser Asp Phe Asn Leu Pro Pro Val Val Ala Lys Glu Ile
Val Ala Ser Cys Asp Lys Cys Gln Leu Lys Gly Glu Ala Met His Gly Gln Val
Asp Cys Ser Pro Gly Ile Trp Gln Leu Ala Cys Thr His Leu Glu Gly Lys Val
Ile Leu Val Ala Val His Val Ala Ser Gly Tyr Ile Glu Ala Glu Val Ile Pro
Ala Glu Thr Gly Gln Glu Thr Ala Tyr Phe Leu Leu Lys Leu Ala Gly Arg Trp
Pro Val Lys Thr Ile His Thr Ala Asn Gly Ser Asn Phe Thr Gly Ala Thr Val
Arg Ala Ala Cys Trp Trp Ala Gly Ile Lys Gln Glu Phe Gly Ile Pro Tyr Asn
Pro Gln Ser Gln Gly Val Val Ala Ser Met Asn Lys Glu Leu Lys Lys Ile Ile
Gly Gln Val Arg Asp Gln Ala Glu His Leu Lys Thr Ala Val Gln Met Ala Val
Phe Ile His Asn Phe Lys Arg Lys Gly Gly Ile Gly Gly Tyr Ser Ala Gly Glu
Arg Ile Val Asp Ile Ile Ala Thr Asp Ile Gln Thr Lys Glu Leu Gln Lys Gln
Ile Thr Lys Ile Gln Asn Phe Arg Val Tyr Tyr Arg Asp Ser Arg Asn Pro Leu
Trp Lys Gly Pro Ala Lys Leu Leu Trp Lys Gly Glu Gly Ala Val Val Ile Gln
Asp Asn Ser Asp Ile Lys Val Val Pro Arg Arg Lys Ala Lys Ile Ile Arg Asp
Tyr Gly Lys Gln Met Ala Gly Asp Asp Cys Val Ala Ser Arg Gln Asp Glu Asp
(SEQ ID NO: 35)

FIG. 34A-2

ENHANCED FIRST GENERATION ADENOVIRUS VACCINES EXPRESSING CODON OPTIMIZED HIV1-GAG, POL, NEF AND MODIFICATIONS

CROSS-REFERENCE TO RELATED APPLICATIONS

This application claims the benefit, under 35 U.S.C. §119(e), of U.S. provisional applications Nos. 60/233,180, 60/279,056, and 60/317,814, filed Sep. 15, 2000, Mar. 27, 2001, and Sep. 7, 2001, respectively.

STATEMENT REGARDING FEDERALLY-SPONSORED R&D

Not Applicable

REFERENCE TO MICROFICHE APPENDIX

Not Applicable

FIELD OF THE INVENTION

The present invention relates to recombinant, replication-deficient first generation adenovirus vaccines found to exhibit enhanced growth properties and greater cellular-mediated immunity as compared to other replication-deficient vectors. The invention also relates to the associated first generation adenoviral vectors described herein, which, through the incorporation of additional 5' adenovirus sequence, enhance large scale production efficiency of the recombinant, replication-defective adenovirus described herein. Another aspect of the instant invention is the surprising discovery that the intron A portion of the human cytomegalovirus (hCMV) promoter constitutes a region of instability in adenoviral vector constructs. Removal of this region from adenoviral expression constructs results in greatly improved vector stability. Therefore, improved vectors expressing a transgene under the control of an intron A-deleted CMV promoter constitute a further aspect of this invention. These adenoviral vectors are useful for generating recombinant adenovirus vaccines against human immunodeficiency virus (HIV). In particular, the first generation adenovirus vectors disclosed herein are utilized to construct and generate adenovirus-based HIV-1 vaccines which contain HIV-1 Gag, HIV-1 Pol and/or HIV-1 Nef polynucleotide pharmaceutical products, and biologically active modifications thereof. Host administration of the recombinant, replication-deficient adenovirus vaccines described herein results in expression of HIV-1 Gag, HIV-1-Pol and/or Nef protein or immunologically relevant modifications thereof, inducing a cellular immune response which specifically recognizes HIV-1. The exemplified polynucleotides of the present invention are synthetic DNA molecules encoding codon optimized HIV-1 Gag, HIV-1 Pol, derivatives of optimized HIV-1 Pol (including constructs wherein protease, reverse transcriptase, RNAse H and integrase activity of HIV-1 Pol is inactivated), HIV-1 Nef, and derivatives of optimized HIV-1 Nef, including nef mutants which effect wild type characteristics of Nef, such as myristylation and down regulation of host CD4. The HIV adenovirus vaccines of the present invention, when administered alone or in a combined modality and/or prime/boost regimen, will offer a prophylactic advantage to previously uninfected individuals and/or provide a therapeutic effect by reducing viral load levels within an infected individual, thus prolonging the asymptomatic phase of HIV-1 infection.

BACKGROUND OF THE INVENTION

Human Immunodeficiency Virus-1 (HIV-1) is the etiological agent of acquired human immune deficiency syndrome (AIDS) and related disorders. HIV-1 is an RNA virus of the Retroviridae family and exhibits the 5' LTR-gag-pol-env-LTR 3' organization of all retroviruses. The integrated form of HIV-1, known as the provirus, is approximately 9.8 Kb in length. Each end of the viral genome contains flanking sequences known as long terminal repeats (LTRs). The HIV genes encode at least nine proteins and are divided into three classes; the major structural proteins (Gag, Pol, and Env), the regulatory proteins (Tat and Rev); and the accessory proteins (Vpu, Vpr, Vif and Nef).

The gag gene encodes a 55-kilodalton (kDa) precursor protein (p55) which is expressed from the unspliced viral mRNA and is proteolytically processed by the HIV protease, a product of the pol gene. The mature p55 protein products are p17 (matrix), p24 (capsid), p9 (nucleocapsid) and p6.

The pol gene encodes proteins necessary for virus replication; a reverse transcriptase, a protease, integrase and RNAse H. These viral proteins are expressed as a Gag-Pol fusion protein, a 160 kDa precursor protein which is generated via a ribosomal frame shifting. The viral encoded protease proteolytically cleaves the Pol polypeptide away from the Gag-Pol fusion and further cleaves the Pol polypeptide to the mature proteins which provide protease (Pro, P10), reverse transcriptase (RT, P50), integrase (IN, p31) and RNAse H (RNAse, p15) activities.

The nef gene encodes an early accessory HIV protein (Nef) which has been shown to possess several activities such as down regulating CD4 expression, disturbing T-cell activation and stimulating HIV infectivity.

The env gene encodes the viral envelope glycoprotein that is translated as a 160-kilodalton (kDa) precursor (gp160) and then cleaved by a cellular protease to yield the external 120-kDa envelope glycoprotein (gp120) and the transmembrane 41-kDa envelope glycoprotein (gp41). Gp120 and gp41 remain associated and are displayed on the viral particles and the surface of HIV-infected cells.

The tat gene encodes a long form and a short form of the Tat protein, a RNA binding protein which is a transcriptional transactivator essential for HIV-1 replication.

The rev gene encodes the 13 kDa Rev protein, a RNA binding protein. The Rev protein binds to a region of the viral RNA termed the Rev response element (RRE). The Rev protein promotes transfer of unspliced viral RNA from the nucleus to the cytoplasm. The Rev protein is required for HIV late gene expression and in turn, HIV replication.

Gp120 binds to the CD4/chemokine receptor present on the surface of helper T-lymphocytes, macrophages and other target cells in addition to other co-receptor molecules. X4 (macrophage tropic) virus show tropism for CD4/CXCR4 complexes while a R5 (T-cell line tropic) virus interacts with a CD4/CCR5 receptor complex. After gp120 binds to CD4, gp41 mediates the fusion event responsible for virus entry. The virus fuses with and enters the target cell, followed by reverse transcription of its single stranded RNA genome into the double-stranded DNA via a RNA dependent DNA polymerase. The viral DNA, known as provirus, enters the cell nucleus, where the viral DNA directs the production of new viral RNA within the nucleus, expression of early and late HIV viral proteins, and subsequently the production and cellular release of new virus particles. Recent advances in the ability to detect viral load within the host shows that the primary infection results in an extremely high generation and tissue distribution of the virus, followed by a steady state level of virus (albeit through a continual viral production and turnover during this phase), leading ultimately to another burst of virus load which leads to the onset of clinical AIDS. Productively infected cells have a half life of several days, whereas chronically or latently infected cells have a 3-week half life, followed by non-productively infected cells which have a long half life (over 100 days) but do not significantly contribute to day to day viral loads seen throughout the course of disease.

Destruction of CD4 helper T lymphocytes, which are critical to immune defense, is a major cause of the progressive immune dysfunction that is the hallmark of HIV infection. The loss of CD4 T-cells seriously impairs the body's ability to fight most invaders, but it has a particularly severe impact on the defenses against viruses, fungi, parasites and certain bacteria, including mycobacteria.

Effective treatment regimens for HIV-1 infected individuals have become available recently. However, these drugs will not have a significant impact on the disease in many parts of the world and they will have a minimal impact in halting the spread of infection within the human population. As is true of many other infectious diseases, a significant epidemiologic impact on the spread of HIV-1 infection will only occur subsequent to the development and introduction of an effective vaccine. There are a number of factors that have contributed to the lack of successful vaccine development to date. As noted above, it is now apparent that in a chronically infected person there exists constant virus production in spite of the presence of anti-HIV-1 humoral and cellular immune responses and destruction of virally infected cells. As in the case of other infectious diseases, the outcome of disease is the result of a balance between the kinetics and the magnitude of the immune response and the pathogen replicative rate and accessibility to the immune response. Pre-existing immunity may be more successful with an acute infection than an evolving immune response can be with an established infection. A second factor is the considerable genetic variability of the virus. Although anti-HIV-1 antibodies exist that can neutralize HIV-1 infectivity in cell culture, these antibodies are generally virus isolate-specific in their activity. It has proven impossible to define serological groupings of HIV-1 using traditional methods. Rather, the virus seems to define a serological "continuum" so that individual neutralizing antibody responses, at best, are effective against only a handful of viral variants. Given this latter observation, it would be useful to identify immunogens and related delivery technologies that are likely to elicit anti-HIV-1 cellular immune responses. It is known that in order to generate CTL responses antigen must be synthesized within or introduced into cells, subsequently processed into small peptides by the proteasome complex, and translocated into the endoplasmic reticulum/Golgi complex secretory pathway for eventual association with major histocompatibility complex (MHC) class I proteins. $CD8^+$ T lymphocytes recognize antigen in association with class I MHC via the T cell receptor (TCR) and the CD8 cell surface protein. Activation of naive $CD8^+$ T cells into activated effector or memory cells generally requires both TCR engagement of antigen as described above as well as engagement of costimulatory proteins. Optimal induction of CTL responses usually requires "help" in the form of cytokines from $CD4^+$ T lymphocytes which recognize antigen associated with MHC class II molecules via TCR and CD4 engagement.

European Patent Applications 0 638 316 (Published Feb. 15, 1995) and 0 586 076 (Published Mar. 9, 1994), (both assigned to American Home Products Corporation) describe replicating adenovirus vectors carrying an HIV gene, including env or gag. Various treatment regimens were used with chimpanzees and dogs, some of which included booster adenovirus or protein plus alum treatments.

Replication-defective adenoviral vectors harboring deletions in the E1 region are known, and recent adenoviral vectors have incorporated the known packaging repeats into these vectors; e.g., see EP 0 707 071, disclosing, inter alia, an adenoviral vector deleted of E1 sequences from base pairs 459 to 3328; and U.S. Pat. No. 6,033,908, disclosing, inter alia, an adenoviral vector deleted of base pairs 459–3510. The packaging efficiency of adenovirus has been taught to depend on the number of incorporated individual A (packaging) repeats; see, e.g., Gräble and Hearing, 1990 *J. Virol.* 64(5):2047–2056; Gräble and Hearing, 1992 *J. Virol.* 66(2):723–731.

Larder, et al., (1987*, Nature* 327: 716–717) and Larder, et al., (1989*, Proc. Natl. Acad. Sci.* 86: 4803–4807) disclose site specific mutagenesis of HIV-1 RT and the effect such changes have on in vitro activity and infectivity related to interaction with known inhibitors of RT.

Davies, et al. (1991*, Science* 252:, 88–95) disclose the crystal structure of the RNase H domain of HIV-1 Pol.

Schatz, et al. (1989*, FEBS Lett.* 257: 311–314) disclose that mutations Glu478Gln and His539Phe in a complete HIV-1 RT/RNase H DNA fragment results in defective RNase activity without effecting RT activity.

Mizrahi, et al. (1990*, Nucl. Acids. Res.* 18: pp. 5359–5353) disclose additional mutations Asp443Asn and Asp498Asn in the RNase region of the pol gene which also results in defective RNase activity. The authors note that the Asp498Asn mutant was difficult to characterize due to instability of this mutant protein.

Leavitt, et al. (1993*, J. Biol. Chem.* 268: 2113–2119) disclose several mutations, including a Asp64Val mutation, which show differing effect on HIV-1 integrase (IN) activity.

Wiskerchen, et al. (1995*, J. Virol.* 69: 376–386) disclose singe and double mutants, including mutation of aspartic acid residues which effect HIV-1 IN and viral replication functions.

It would be of great import in the battle against AIDS to produce a prophylactic- and/or therapeutic-based HIV vaccine which generates a strong cellular immune response against an HIV infection. The present invention addresses and meets these needs by disclosing a class of adenovirus vaccines which, upon host administration, express codon optimized and modified versions of the HIV-1 genes, gag, pol and nef. These recombinant, replication-defective adenovirus vaccines may be administered to a host, such as a human, alone or as part of a combined modality regimen and/or prime-boost vaccination regimen with components of the present invention and/or a distinct viral HIV DNA vaccine, non-viral HIV DNA vaccine, HIV subunit vaccine, an HIV whole killed vaccine and/or a live attenuated HIV vaccine.

SUMMARY OF THE INVENTION

The present invention relates to enhanced replication-defective recombinant adenovirus vaccine vectors and associated recombinant, replication-deficient adenovirus vaccines which encode various forms of HIV-1 Gag, HIV-1 Pol, and/or HIV-1 Nef, including immunologically relevant modifications of HIV-1 Gag, HIV-1 Pol and HIV-1 Nef. The adenovirus vaccines of the present invention express HIV antigens and provide for improved cellular-mediated immune responses upon host administration. Potential vaccinees include but are not limited to primates and especially humans and non-human primates, and also include any non-human mammal of commercial or domestic veterinary importance. An effect of the improved recombinant adenovirus-based vaccines of the present invention should be a lower transmission rate to previously uninfected individuals (i.e., prophylactic applications) and/or reduction in the levels of the viral loads within an infected individual (i.e., therapeutic applications), so as to prolong the asymptomatic phase of HIV-1 infection. In particular, the present invention relates to adenoviral-based vaccines which encode various forms of codon optimized HIV-1 Gag (including but in no way limited to p55 versions of codon optimized full length (FL) Gag and tPA-Gag fusion proteins), HIV-1 Pol, HIV-1 Nef, and selected modifications of immunological relevance. The administration, intracellular delivery and expression of these adenovirus vaccines elicit a host CTL and Th response. The preferred replication-defective recombinant adenoviral vaccine vectors include but are not limited to synthetic DNA molecules which (1) encode codon optimized versions of wild type HIV-1 Gag; (2) encode codon optimized versions of HIV-1 Pol; (3) encode codon optimized versions of HIV-1 Pol fusion proteins; (4) encode codon optimized versions of modified HIV-1 Pol proteins and fusion proteins, including but not limited to pol modifications involving residues within the catalytic regions responsible for RT, RNase and IN activity within the host cell; (5) encode codon optimized versions of wild type HIV-1 Nef; (6) codon optimized versions of HIV-1 Nef fusion proteins; and/or (7) codon optimized versions of HIV-1 Nef derivatives, including but not limited to nef modifications involving introduction of an amino-terminal leader sequence, removal of an amino-terminal myristylation site and/or introduction of dileucine motif mutations. The Nef-based fusion and modified proteins, disclosed within this specification and expressed from an adenoviral-based vector vaccine this specification, may possess altered trafficking and/or host cell function while retaining the ability to be properly presented to the host MHC I complex and in turn elicit a host CTL and Th response. Examples of HIV-1 Gag, Pol and/or Nef fusion proteins include but are not limited to fusion of a leader or signal peptide at the $NH_2$-teriminal portion of the viral antigen coding region. Such a leader peptide includes but is not limited to a tPA leader peptide.

The adenoviral vector utilized in construction of the HIV-1 Gag-, HIV-1 Pol- and/or HIV-1 Nef-based vaccines of the present invention may comprise any replication-defective adenoviral vector which provides for enhanced genetic stability of the recombinant adenoviral genome through large scale production and purification of the recombinant virus. In other words, an HIV-1 Gag-, Pol- or Nef-based adenovirus vaccine of the present invention is a purified recombinant, replication-defective adenovirus which is shown to be genetically stable through multiple passages in cell culture and remains so during large scale production and purification procedures. Such a recombinant adenovirus vector and harvested adenovirus vaccine lends itself to large scale dose filling and subsequent worldwide distribution procedures which will be demanded of an efficacious monovalent or multivalent HIV vaccine. The present invention meets this basic requirement with description of a replication-defective adenoviral vector and vectors derived therefrom, at least partially deleted in E1, comprising a wildtype adenovirus cis-acting packaging region from about base pair 1 to between from about base pair 342 (more preferably, 400) to about base pair 458 of the wildtype adenovirus genome. A preferred embodiment of the instant invention comprises base pairs 1–450 of a wildtype adenovirus. In other preferred embodiments, the replication-defective adenoviral vector has, in addition thereto, a region 3' to the E1-deleted region comprising base pairs 3511–3523. Basepairs 342–450 (more particularly, 400–450) constitute an extension of the 5' region of previously disclosed vectors carrying viral antigens, particularly HIV antigens (see, e.g., PCT International Application PCT/US00/18332, published Jan. 11, 2001 (WO 01/02067), which claims priority to U.S. Provisional Application Serial Nos. 60/142,631 and 60/148,981, filed Jul. 6, 1999 and Aug. 13, 1999, respectively; these documents herein incorporated by reference. Applicants have found that extending the 5' region further into the E1 gene into the disclosed vaccine vectors incorporated elements found to be important in optimizing the packaging of the virus.

As compared to previous vectors not comprising basepairs from about 1 to between from about base pair 342 (more preferably, 400) to about base pair 458 of the wildtype adenovirus genome, vectors comprising the above region exhibited enhanced growth characteristics, with approximately 5–10 fold greater amplification rates, a more potent virus effect, allowing lower doses of virus to be used to generate equivalent immunity; and a greater cellular-mediated immune response than replication-deficient vectors not comprising this region (basepairs 1–450). Even more important, adenoviral constructs derived therefrom are very stable genetically in large-scale production, particularly those comprising an expression cassette under the control of a hCMV promoter devoid of intron A. This is because Applicants have surprisingly found that the intron A portion of the hCMV promoter constituted a region of instability when employed in adenoviral vectors. Applicants have, therefore, identified an enhanced adenoviral vector which is particularly suited for use in gene therapy and nucleotide-based vaccine vectors which, favorably, lends itself to large scale propagation.

A preferred embodiment of this invention is a replication-defective adenoviral vector in accordance with the above description wherein the gene is inserted in the form of a gene expression cassette comprising (a) a nucleic acid encoding a protein or biologically active and/or immunologically relevant portion thereof; (b) a heterologous promoter operatively linked to the nucleic acid of part a); and, (c) a transcription terminator.

In preferred embodiments, the E1 gene, other than that contained within basepairs 1–450 or, alternatively, that contained within base pairs 1–450 and 3511–3523 has been deleted from the adenoviral vector, and the gene expression cassette has replaced the deleted E1 gene. In other preferred embodiments, the replication defective adenovirus genome does not have a functional E3 gene, or the E3 gene has been deleted. Most preferably, the E3 region is present within the adenoviral genome. Further preferred embodiments are wherein the gene expression cassette is in an E1 anti-parallel (transcribed in a 3' to 5' direction relative to the vector backbone) orientation or, more preferably, an E1 parallel (transcribed in a 5' to 3' direction relative to the vector backbone) orientation.

Further embodiments relate to a shuttle plasmid vector comprising: an adenoviral portion and a plasmid portion, wherein said adenovirus portion comprises: a) a replication defective adenovirus genome, at least partially deleted in E1, comprising a wildtype adenovirus cis-acting packaging region from about base pair 1 to between from about base pair 342 (more preferably, 400) to about base pair 458 (preferably, 1–450) of the wildtype adenovirus genome and, preferably, in addition thereto, basepairs 3511–3523 of a wildtype adenovirus sequence; and b) a gene expression cassette comprising: (a) a nucleic acid encoding a protein or biologically active and/or immunologically relevant portion thereof; (b) a heterologous promoter operatively linked to the nucleic acid of part a);and (c) a transcription terminator and/or a polyadenylation site.

Other aspects of this invention include a host cell comprising said adenoviral vectors and/or said shuttle plasmid vectors; vaccine compositions comprising said vectors; and methods of producing the vectors comprising (a) introducing the adenoviral vector into a host cell which expresses adenoviral E1 protein, and (b) harvesting the resultant adenoviral vectors.

To this end, the present invention particularly relates to harvested recombinant, replication defective virus derived from a host cell, such as but not limited to 293 cells or PER.C6® cells, including but not limited to harvested virus related to any of the MRKAd5 vector backbones, with or without an accompanying transgene, including but not limited to the HIV-1 antigens described herein. An HIV-1 vaccine is represented by any harvested, recombinant adenovirus material which expresses any one or more of the HIV-1 antigens disclosed herein. This harvested material may then be purified, formulated and stored prior to host administration.

Another aspect of this invention is a method of generating a cellular immune response against a protein in an individual comprising administering to the individual an adenovirus vaccine vector comprising:

a) a recombinant, replication defective adenoviral vector, at least partially deleted in E1, comprising a wildtype adenovirus cis-acting adenovirus packaging region from about base pair 1 to between from about base pair 342 (more preferably, 400) to about base pair 458 (preferably, 1–450) and, preferably in addition thereto, base pairs 3511–3523 of a wildtype adenovirus sequence, and, b) a gene expression cassette comprising:(i) a nucleic acid encoding a protein or biologically active and/or immunologically relevant portion thereof; (ii) a heterologous promoter operatively linked to the nucleic acid of part a); and (iii) a transcription terminator and/or a polyadenylation site.

In view of the efficacious nature of the adenoviral and/or DNA plasmid vaccines described herein, the present invention relates to all methodology regarding administration of one or more of these adenoviral and/or DNA plasmid vaccines to provide effective immunoprophylaxis, to prevent establishment of an HIV-1 infection following exposure to this virus, or as a post-HIV infection therapeutic vaccine to mitigate the acute HIV-1 infection so as to result in the establishment of a lower virus load with beneficial long term consequences. As discussed herein, such a treatment regimen may include a monovalent or multivalent composition, various combined modality applications, and/or a prime/boost regimen to as to optimize antigen expression and a concomitant cellular-mediated and/or humoral immune response upon inoculation into a living vertebrate tissue. Therefore, the present invention provides for methods of using the adenoviral and/or DNA plasmid vaccines disclosed herein within the various parameters disclosed herein as well as any additional parameters known in the art, which, upon introduction into mammalian tissue induces intracellular expression of the gag, pol and/or nef-based vaccines.

To this end, the present invention relates in part to methods of generating a cellular immune response in a vaccinee, preferably a human vaccinee, wherein the individual is given more than one administration of adenovirus vaccine vector, and it may be given in a regimen accompanied by the administration of a plasmid vaccine. The plasmid vaccine (also referred to herein as a "DNA plasmid vaccine" or "vaccine plasmid" comprises a nucleic acid encoding a protein or an immunologically relevant portion thereof, a heterologous promoter operably linked to the nucleic acid sequence, and a transcription terminator or a polyadenylation signal (such as bGH or SPA, respectively). There may be a predetermined minimum amount of time separating the administrations. The individual can be given a first dose of plasmid vaccine, and then a second dose of plasmid vaccine. Alternatively, the individual may be given a first dose of adenovirus vaccine, and then a second dose of adenovirus vaccine. In other embodiments, the plasmid vaccine is administered first, followed after a time by administration of the adenovirus vaccine. Conversely, the adenovirus vaccine may be administered first, followed by administration of plasmid vaccine after a time. In these embodiments, an individual may be given multiple doses of the same adenovirus serotype in either viral vector or plasmid form, or the virus may be of differing serotypes. In the alternative, a viral antigen of interest can be first delivered via a viral vaccine other than an adenovirus-based vaccine, and then followed with the adenoviral vaccine disclosed. Alternative viral vaccines include but are not limited to pox virus and Venezuelan equine encephilitis virus.

The present invention also relates to multivalent adenovirus vaccine compositions which comprise Gag, Pol and Nef components described herein; see, e.g., Example 29 and Table 25. Such compositions will provide for an enhanced cellular immune response subsequent to host administration, particularly given the genetic diversity of human MHCs and of circulating virus. Examples, but not limitations, include MRKAd5-vector based multivalent vaccine compositions which provide for a divalent (i.e., gag and nef, gag and pol, or pol and nef components) or a trivalent vaccine (i.e., gag, pol and nef components) composition. Such a mutlivalent vaccine may be filled for a single dose or may consist of multiple inoculations of each individually filled component; and may in addition be part of a prime/boost regimen with viral or non-viral vector vaccines as introduced in the previous paragraph. To this end, preferred compositions are MRKAd5 adenovirus used in combination with multiple, distinct HIV antigen classes. Each HIV antigen class is subject to sequence manipulation, thus providing for a multitude of potential vaccine combinations; and such combinations are within the scope of the present invention. The utilization of such combined modalities vaccine formulation and administration increase the probability of eliciting an even more potent cellular immune response when compared to inoculation with a single modality regimen.

The concept of a "combined modality" as disclosed herein also covers the alternative mode of administration whereby multiple HIV-1 viral antigens may be ligated into a proper shuttle plasmid for generation of a pre-adenoviral plasmid comprising multiple open reading frames. For example, a trivalent vector may comprise a gag-pol-nef fusion, in either a E3(−) or E3(+) background, preferably a E3 deleted backbone, or possibly a "2+1" divalent vaccine, such as a gag-pol fusion (i.e., codon optimized p55 gag and inactivated optimized pol; Example 29 and Table 25) within the same MRKAd5 backbone, with each open reading frame being operatively linked to a distinct promoter and transcription termination sequence. Alternatively, the two open reading frames may be operatively linked to a single promoter, with the open reading frames operatively linked by an internal ribosome entry sequence (IRES). Therefore, a multivalent vaccine delivered as a single, or possibly a second harvested recombinant, replication-deficient adenovirus is contemplated as part of the present invention.

Therefore, the adenoviral vaccines and plasmid DNA vaccines of this invention may be administered alone, or may be part of a prime and boost administration regimen. A mixed modality priming and booster inoculation scheme will result in an enhanced immune response, particularly if pre-existing anti-vector immune responses are present. This one aspect of this invention is a method of priming a subject with the plasmid vaccine by administering the plasmid vaccine at least one time, allowing a predetermined length of time to pass, and then boosting by administering the adenoviral vaccine. Multiple primings typically, 1–4, are usually employed, although more may be used. The length of time between priming and boost may typically vary from about four months to a year, but other time frames may be used. In experiments with rhesus monkeys, the animals were primed four times with plasmid vaccines, then were boosted 4 months later with the adenoviral vaccine. Their cellular immune response was notably higher than that of animals which had only received adenoviral vaccine. The use of a priming regimen may be particularly preferred in situations where a person has a pre-existing anti-adenovirus immune response.

It is an object of the present invention to provide for enhanced replication-defective recombinant adenoviral vaccine vector backbones. These recombinant adenoviral backbones may accept one or more transgenes, which may be passaged through cell culture for growth, amplification and harvest.

It is a further object to provide for enhanced replication-defective recombinant adenoviral vaccine vectors which encode various transgenes.

It is also an object of the present invention to provide for a harvested recombinant, replication-deficient adenovirus which shows enhanced growth and amplification rates while in combination with increased virus stability after continuous passage in cell culture. Such a recombinant adenovirus is particularly suited for use in gene therapy and nucleotide-based vaccine vectors which, favorably, lends itself to large scale propagation.

To this end, it is an object of the present invention to provide for (1) enhanced replication-defective recombinant adenoviral vaccine vectors as described herein which encode various forms of HIV-1 Gag, HIV-1 Pol, and/or HIV-1 Nef, including immunologically relevant modifications of HIV-1 Gag, HIV-1 Pol and HIV-1 Nef, and (2) harvested, purified recombinant replication-deficient adenovirus generated by passage of the adenoviral vectors of (1) through one or multiple passages through cell culture, including but not limited to passage through 293 cells or PER.C6® cells.

It is also an object of the present invention to provide for recombinant adenovirus harvested by one or multiple passages through cell culture. As relating to recombinant adenoviral vaccine vector, this recombinant virus is harvested and formulated for subsequent host administration.

It is also an object of the present invention to provide for replication-defective adenoviral vectors wherein at least one gene is inserted in the form of a gene expression cassette comprising (a) a nucleic acid encoding a protein or biologically active and/or immunologically relevant portion thereof; (b) a heterologous promoter operatively linked to the nucleic acid of part a); and, (c) a transcription terminator.

It is also an object of the present invention to provide for a host cell comprising said adenoviral vectors and/or said shuttle plasmid vectors; vaccine compositions comprising said vectors; and methods of producing the vectors comprising (a) introducing the adenoviral vector into a host cell which expresses adenoviral E1 protein, and (b) harvesting the resultant adenoviral vectors. It is a further object of the present invention to provide for methods of generating a cellular immune response against a protein in an individual comprising administering to the individual an adenovirus vaccine vector comprising a) a replication defective adenoviral vector, at least partially deleted in E1, comprising a wildtype adenovirus cis-acting packaging region from about base pair 1 to between from about base pair 342 (more preferably, 400) to about 450 (preferably, 1–450) and, preferably, 3511–3523 of a wildtype adenovirus sequence, and, b) a gene expression cassette comprising:(i) a nucleic acid encoding a protein or biologically active and/or immunologically relevant portion thereof; (ii) a heterologous promoter operatively linked to the nucleic acid of part a); and (iii) a transcription terminator and/or a polyadenylation site.

It is also an objet of the present invention to provide various alternatives for vaccine administration regimes, namely administration of one or more adenoviral and/or DNA plasmid vaccines described herein to provide effective immunoprophylaxis for uninfected individuals or a therapeutic treatment for HIV infected patients. Such processes include but are not limited to multivalent HIV-1 vaccine compositions, various combined modality regimes as well as various prime/boost alternatives. These methods of administration, relating to vaccine composition and/or scheduled administration, will increase the probability of eliciting an even more potent cellular immune response when compared to inoculation with a single modality regimen.

As used throughout the specification and claims, the following definitions and abbreviations are used:

"HAART" refers to—highly active antiretroviral therapy—.

"first generation" vectors are characterized as being replication-defective. They typically have a deleted or inactivated E1 gene region, and preferably have a deleted or inactivated E3 gene region as well.

"AEX" refers to Anion Exchange chromatography.

"QPA" refers to Quick PCR-based Potency Assay.

"bps" refers to basepairs.

"s" or "str" denotes that the transgene is in the E1 parallel or "straight" orientation.

"PBMCs" refers to peripheral blood monocyte cells.

"FL" refers to full length.

"FLgag" refers to a full-length optimized gag gene, as shown in FIG. 2.

"Ad5-Flgag" refers to an adenovirus serotype 5 replication deficient virus which carries an expression cassette which comprises a full length optimized gag gene under the control of a CMV promoter.

"Promoter" means a recognition site on a DNA strand to which an RNA polymerase binds. The promoter forms an initiation complex with RNA polymerase to initiate and drive transcriptional activity. The complex can be modified by activating sequences such as enhancers or inhibiting sequences such as silencers.

"Leader" means a DNA sequence at the 5' end of a structural gene which is transcribed along with the gene. This usually results a protein having an N-terminal peptide extension, often referred to as a pro-sequences.

"Intron" means a section of DNA occurring in the middle of a gene which does not code for an amino acid in the gene product. The precursor RNA of the intron is excised and is therefore not transcribed into mRNA not translated into protein.

"Immunologically relevant" or "biologically active" means (1) with regards to a viral protein, that the protein is capable, upon administration, of eliciting a measurable immune response within an individual sufficient to retard the propagation and/or spread of the virus and/or to reduce the viral load present within the individual; or (2) with regards to a nucleotide sequence, that the sequence is capable of encoding for a protein capable of the above.

"Cassette" refers to a nucleic acid sequence which is to be expressed, along with its transcription and translational control sequences. By changing the cassette, a vector can express a different sequence.

"bGHpA" refers to the bovine growth hormone transcription terminator/polyadenylation sequence.

"tPAgag" refers to a fusion between the leader sequence of the tissue plasminogen activator leader sequence and an optimized HIV gag gene, as exemplified in FIGS. 30A–B, whether in a DNA or adenovirus-based vaccine vector.

Where utilized, "IA" or "inact" refers to an inactivated version of a gene (e.g. IApol).

"MCS" is "multiple cloning site".

In general, adenoviral constructs, gene constructs are named by reference to the genes contained therein. For example:

"Ad5 HIV-1 gag", also referred to as the original HIV-1 gag adenoviral vector, is a vector containing a transgene cassette composed of a hCMV intron A promoter, the full length version of the human codon-optimized HIV-1 gag gene, and the bovine growth hormone polyadenylation signal. The transgene was inserted in the E1 antiparallel orientation in an E1 and E3 deleted adenovector.

"MRK Ad5 HIV-1 gag" also referred to as "MRKAd5gag" or "Ad5gag2" is an adenoviral vector taught herein which is deleted of E1, comprises basepairs 1–450 and 3511–3523, and has a human codon-optimized HIV-1 gene in an E1 parallel orientation under the control of a CMV promoter without intron A. The construct also comprises a bovine growth hormone polyadenylation signal.

"pV1JnsHIVgag", also referred to as "HIVFLgagPR9901", is a plasmid comprising the CMV immediate-early (IE) promoter and intron A, a full-length codon-optimized HIV gag gene, a bovine growth hormone-derived polyadenylation and transcriptional termination sequence, and a minimal pUC backbone.

"pV1JnsCMV(no intron)-FLgag-bGHpA" is a plasmid derived from pV1JnsHIVgag which is deleted of the intron A portion of CMV and which comprises the full length HIV gag gene. This plasmid is also referred to as "pV1JnsHIVgag-bGHpA", pV1Jns-hCMV-FL-gag-bGHpA" and "pV1JnsCMV(no intron)+FLgag+bGHpA".

"pV1JnsCMV(no intron)-FLgag-SPA" is a plasmid of the same composition as pV1JnsCMV(no intron)-FLgag-bGHpA except that the SPA termination sequence replaces that of bGHpA. This plasmid is also referred to as "pV1Jns-HIVgag-SPA" and pV1Jns-hCMV-FLgag-SPA".

"pdelE1sp1A" is a universal shuttle vector with no expression cassette (i.e., no promoter or polyA). The vector comprises wildtype adenovirus serotype 5 (Ad5) sequences from bp 1 to bp 341 and bp 3524 to bp 5798, and has a multiple cloning site between the Ad5 sequences ending 341 bp and beginning 3524 bp. This plasmid is also referred to as the original Ad 5 shuttle vector.

"MRKpdelE1 sp1A" or "MRKpdelE1 (Pac/pIX/pack450)" or

"MRKpdelE1(Pac/pIX/pack450)Cla1" is a universal shuttle vector with no expression cassette (i.e. no promoter or polyA) comprising wildtype adenovirus serotype 5 (Ad5) sequences from bp1 to bp450 and bp 3511 to bp 5798. The vector has a multiple cloning site between the Ad5 sequence ending 450 bp and beginning 3511 bp. This shuttle vector may be used to insert the CMV promoter and the bGHpA fragments in both the straight ("str". or E1 parallel) orientation or in the opposite (opp. or E1 antiparallel) orientation)

"MRKpdelE1(Pac/pIX/pack450)+CMVmin+BGHpA (str.)" is still another shuttle vector which is the modified vector that contains the CMV promoter (no intronA) and the bGHpA fragments. The expression unit containing the hCMV promoter (no intron A) and the bovine growth hormone polyadenylation signal has been inserted into the shuttle vector such that insertion of the gene of choice at a unique BglII site will ensure the direction of transcription of the transgene will be Ad5 E1 parallel when inserted into the MRKpAd5(E1/E3+)Cla1 pre-plasmid. This shuttle vector, as shown in FIGS. 22 and 23, was used to insert the respective IApol and G2A,LLAA nef genes directly into.

"MRKpdelE1-CMV(no intron)-FLgag-bGHpA" is a shuttle comprising Ad5 sequences from basepairs 1–450 and 3511–5798, with an expression cassette containing human CMV without intron A, the full-length human codon-optimized HIV gag gene and bovine growth hormone polyadenylation signal. This plasmid is also referred to as "MRKpdelE1 shuttle +hCMV-FL-gag-BGHpA"

"MRKpAdHVE3+CMV(no intron)-FLgag-bGHpA" is an adenoviral vector comprising all Ad5 sequences except those nucleotides encompassing the E1 region (from 451–3510), a human CMV promoter without intron A, a full-length human codon-optimized HIV gag gene, and a bovine growth hormone polyadenylation signal. This vector is also referred to as "MRKpAdHVE3+hCMV-FL-gag-BGHpA", "MRKpAd5HIV-1gag", "MRKpAd5gag", "pMRKAd5gag" or "pAd5gag2".

"pV1Jns-HIV-pol inact(opt)" or "pV1Jns-HIV IA pol (opt) is the inactivated Pol gene (contained within SEQ ID NO:3) cloned into the BglII site of V1Jns (FIGS. 17A–C). As noted herein, various derivatives of HIV-1 pol may be cloned into a plasmid expression vector such as V1Jns or V1Jns-tPA, thus serving directly as DNA vaccine candidates or as a source for subcloning into an appropriate adenoviral vector.

"MRKpdel+hCMVmin+FL-pol+bGHpA(s)" is the "MRKpdelE1(Pac/pIX/pack450)+CMVmin+BGHpA (str.)" shuttle mentioned above which contains the IA pol gene is the proper orientation. This shuttle vector is used in a bacterial recombination with MRKpAd(E1−/E3+)Cla1.

"MRKpAd+hCMVmin+FL-pol+bGHpA(S)E3+", also referred to herein as "pMRKAd5pol", is the pre-adenovirus plasmid which comprises a CMV-pol inact (opt)-pGHpA construct. The construction of this pre-adenovirus plasmid is shown in FIG. 22.

"pV1Jns/nef (G2A,LLAA)" or "V1Jns/opt nef (G2A, LLAA)" comprises codon optimized HIV-1 Nef wherein the open reading frame codes for modifications at the amino terminal myristylation site (Gly-2 to Ala-2) and substitution of the Leu-174-Leu-175 dileucine motif to Ala-174-Ala-175 (SEQ ID NO:13; which comprises an initiating methionine residue at nucleotides 12–14 and a "TAA" stop codon from nucleotides 660–662). This fragment is subcloned into the Bgl II site of V1Jns and/or V1Jns-tPA (FIGS. 16A–B). As noted above for HIV-1 pol, HIV-1 nef constructs may be cloned into a plasmid expression vector such as V1Jns or V1Jns-tPA, thus serving directly as DNA vaccine candidates or as a source for subcloning into an appropriate adenoviral vector.

"MRKpdelE1hCMVminFL-nefBGHpA(s)", also referred to herein as "pMRKAd5nef", is the pre-adenovirus plasmid which comprises a CMV-nef (G2A,LLAA) codon optimized sequence. The construction of this pre-adenovirus plasmid is shown in FIG. 23.

BRIEF DESCRIPTION OF THE FIGURES

FIG. 2 shows the nucleic acid sequence (SEQ ID NO: 27) of the optimized human HIV-1 gag open reading frame.

FIG. 7A shows the hCMV-Flgag-bGHpA adenovectors constructed within the MRKpAdHVE3 and MRKpAdHVO adenovector backbones. Both E1 parallel and E1 antiparallel transgene orientation are represented. FIG. 7B shows the hCMV-Flgag-SPA adenovectors constructed within the MRKpAdHVE3 and MRKpAdHVO adenovector backbones. Again, both E1 parallel and E1 antiparallel transgene orientation are represented. FIG. 7C shows the mCMV-Flgag-bGHpA adenovectors constructed within the MRKpAdHVE3 and MRK-pAdHVO adenovector backbones. Once again, both E1 parallel and E1 antiparallel transgene orientation are represented.

FIGS. 15A-1 to 15A-45 illustrate the nucleotide sequence of the pMRKAd5HIV-1gag vector (SEQ ID NO:25 and SEQ ID NO:26.

FIGS. 17A-1 to 17A-3 show the nucleotide (SEQ ID NO:3) and amino acid sequence (SEQ ID NO:4) of IA-Pol. Underlined codons and amino acids denote mutations, as listed in Table 1.

FIG. 18 shows codon optimized nucleotide and amino acid sequences through the fusion junction of tPA-pol inact (opt) (contained within SEQ ID NOs: 7 and 8, respectively). The underlined portion represents the $NH_2$-terminal region of IA-Pol.

FIGS. 19A-1 to 19A-2 show a nucleotide sequence comparison between wild type nef(jrfl) and codon optimized nef. The wild type nef gene from the jrfl isolate consists of 648 nucleotides capable of encoding a 216 amino acid polypeptide. WT, wild type sequence (SEQ ID NO: 19); opt, codon-optimized sequence (contained within SEQ ID NO:9). The Nef amino acid sequence is shown in one-letter code (SEQ ID NO: 10).

FIGS. 20A–C show nucleotide sequences at junctions between nef coding sequence and plasmid backbone of nef expression vectors V1Jns/nef (FIG. 20A), V1Jns/nef(G2A, LLAA) (FIG. 20B), V1Jns/tpanef (FIG. 20C) and V1Jns/tpanef(LLAA) (FIG. 20C, also). 5' and 3' flanking sequences of codon optimized nef or codon optimized nef mutant genes are indicated by bold/italic letters; nef and nef mutant coding sequences are indicated by plain letters. Also indicated (as underlined) are the restriction endonuclease sites involved in construction of respective nef expression vectors. V1Jns/tpanef and V1Jns/tpanef(LLAA) have identical sequences at the junctions.

FIG. 21 shows a schematic presentation of nef and nef derivatives. Amino acid residues involved in Nef derivatives are presented. Glycine 2 and Leucine174 and 175 are the sites involved in myristylation and dileucine motif, respectively. For both versions of the tpanef fusion genes, the putative leader peptide cleavage sites are indicated with "*", and a exogenous serine residue introduced during the construction of the mutants is underlined.

FIG. 22 shows diagrammatically the construction of the pre-adenovirus plasmid construct, MRKAd5Pol.

FIG. 23 shows diagrammatically the construction of the pre-adenovirus plasmid construct, MRKAd5Nef.

FIG. 24 shows a comparison of clade B vs. lade C anti-gag T cell responses in lade B HIV-infected subjects.

FIG. 25 shows a comparison of clade B vs. clade C anti-nef T cell responses in clade B HIV-infected subjects.

FIGS. 26A-1 to 26A-46 illustrate the nucleotide sequence of the pMRKAd5HIV-1pol adenoviral vector (SEQ ID NO:28 and SEQ ID NO:29), comprising the coding region of the inactivated pol gene (SEQ ID NO:3).

FIGS. 27A-1 to 27A-44 illustrate the nucleotide sequence of the pMRKAd5HIV-1 nef adenoviral vector (SEQ ID NO:30 and SEQ ID NO:31), comprising the coding region of the inactivated nef gene (SEQ ID NO: 13).

FIG. 28 shows the stability of MRKAd5 vectors comprising various promoter fragments (hCMV or mCMV) and terminations signals (bGH or SPA) in E3(+) or E3(–) backbones.

FIGS. 30A-1 to 30A-2 show the nucleotide sequence (SEQ ID NO:32) and amino acid sequence (SEQ ID NO:33) comprising the open reading frame of a representative tPA-gag fusion for use in the DNA and/or adenoviral vaccine disclosed herein.

FIG. 31 shows the intracellular γIFN staining of PBMCs collected at week 10 (post DNA prime) and week 30 (post Ad boost). The cells were stimulated overnight in the presence or absence of the gag peptide pool. They were subsequently stained using fluorescence-tagged anti-CD3, anti-CD8, anti-CD4, and anti-γIFN monoclonal antibodies. Each plot shows all CD3+ T cells which were segregated in terms of positive staining for surface CD8 and γIFN production. The numbers in the upper right and lower right quadrants of each plot are the percentages of $CD3^+$ cells that were $CD8^+γIFN^+$ and $CD4^+γIFN^+$, respectively.

FIG. 32 shows a comparison of single-modality adenovirus immunization with DNA+adjuvant prime/adenovirus boost immunization.

FIGS. 33A-1 to 33A-2 show the nucleotide sequence (SEQ ID NO: 34) of the open reading frame for the gag-IApol fusion of Example 29.

FIGS. 34A-1 to 34A-2 show the protein sequence (SEQ ID NO:35) of the gag-IApol fusion frame.

DETAILED DESCRIPTION OF THE INVENTION

Figure 1:
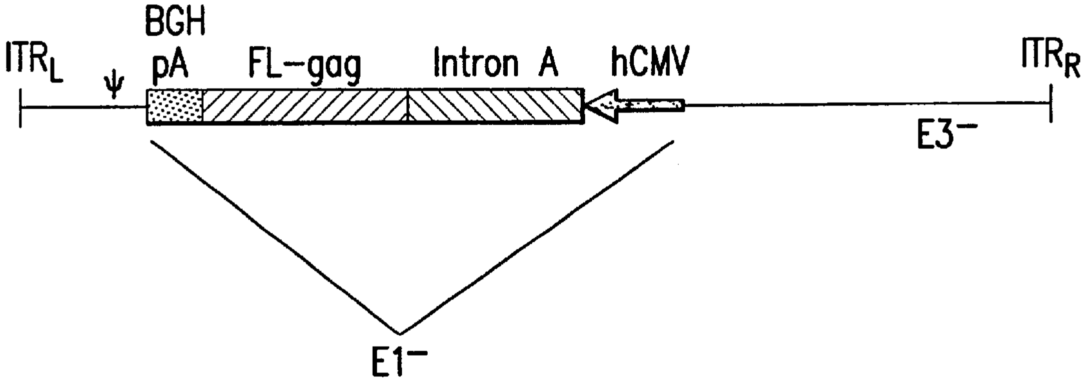
FIG. 1 shows the original HIV-1 gag adenovector (Ad5HIV-1gag). This vector is disclosed in PCT International Application No. PCT/US00/18332 (WO 01/02607) filed Jul. 3, 2000, claiming priority to U.S. Provisional Application Serial No. 60/142,631, filed Jul. 6, 1999 and U.S. application Ser. No. 60/148,981, filed Aug. 13, 1999, all three applications which are hereby incorporated by reference.

A novel replication-defective, or "first generation," adenoviral vector suitable for use in gene therapy or nucleotide-based vaccine vectors is described. This vector is at least partially deleted in E1 and comprises a wildtype adenovirus cis-acting packaging region from about base pair 1 to between about base pair 342 (more preferably, 400) to about 458 (preferably, 1–450) and, preferably, 3511–3523 of a wild-type adenovirus sequence. It has been found that a vector of this description possesses enhanced growth characteristics, with approximately 5–10 fold greater amplification rates, and is more potent allowing lower doses of virus to be used to generate equivalent immunity. The vector, furthermore, generates a harvested recombinant adenovirus which shows greater cellular-mediated immune responses than replication-deficient vectors not comprising this region (basepairs 342–450). Adenoviral constructs derived from these vectors are, further, very stable genetically, particularly those comprising a transgene under the control of a hCMV promoter devoid of intron A. Viruses in accordance with this description were passaged continually and analyzed; see Example 12. Each virus analyzed maintained it correct genetic structure. Analysis was also carried out under propagation conditions similar to that performed in large scale production. Again, the vectors were found to possess enhanced genetic stability; see FIG. 12. Following 21 passages, the viral DNA showed no evidence of rearrangement, and was highly reproducible from one production lot to the next. The outcome of all relevant tests indicate that the adenoviral vector is extremely well suited for large-scale production of recombinant, replication-deficient adenovirus, as shown herein with the data associated with FIG. 28.

A preferred adenoviral vector in accordance with this description is a vector comprising basepairs 1–450, which is deleted in E3. This vector can accommodate up to approximately 7,500 base pairs of foreign DNA inserts (or exogenous genetic material). Another preferred vector is one retaining E3 which comprises basepairs 1–450. A preferred vector of this description is an E3+vector comprising basepairs 1–450 and 3511–3523. This vector, when deleted of the region spanning basepairs 451–3510, can accommodate up to approximately, 4,850 base pairs of foreign DNA inserts (or exogenous genetic material). The cloning capacities of the above vectors have been determined using 105% of the wildtype Ad5 sequence as the upper genome size limit.

Wildtype adenovirus serotype 5 is used as the basis for the specific basepair numbers provided throughout the specification. The wildtype adenovirus serotype 5 sequence is known and described in the art; see, Chroboczek et al., 1992 *J. Virology* 186:280, which is hereby incorporated by reference. Accordingly, a particular embodiment of the instant invention is a vector based on the adenovirus serotype 5 sequence. One of skill in the art can readily identify the above regions in other adenovirus serotypes (e.g., serotypes 2, 4, 6, 12, 16, 17, 24, 31, 33, and 42), regions defined by basepairs corresponding to the above basepair positions given for adenovirus serotype 5. Accordingly, the instant invention encompasses all adenoviral vectors partially deleted in E1 comprising basepairs corresponding to 1–450 (particularly, 342–450) and, preferably, 3511–3523 of a wild-type adenovirus serotype 5 (Ad5) nucleic acid sequence. Particularly preferred embodiments of the instant invention are those derived from adenoviruses like Ad5 which are classified in subgroup C (e.g., Ad2).

Vectors in accordance with the instant invention are at least partially deleted in E1. Preferably the E1 region is completely deleted or inactivated. Most preferably, the region deleted of E1 is within basepairs 451–3510. It is to be noted that the extended 5' and 3' regions of the disclosed vectors are believed to effectively reduce the size of the E1 deletion of previous constructs without overlapping any part of the E1A/E1B gene present in the cell line used, i.e., the PER.C6® cell line transefected with base pairs 459–3510. Overlap of adenoviral sequences is avoided because of the possibility of recombination. One of ordinary skill in the art can certainly appreciate that the instant invention can, therefore, be modified if a different cell line transfected with a different segment of adenovirus DNA is utilized. For purposes of exemplification, a 5' region of base pairs 1 to up to 449 is more appropriate if a cell line is transfected with adenoviral sequence from base pairs 450–3510. This holds true as well in the consideration of segments 3' to the E1 deletion.

Preferred embodiments of the instant invention possess an intact E3 region (i.e., an E3 gene capable of encoding a functional E3). Alternate embodiments have a partially deleted E3, an inactivated E3 region, or a sequence completely deleted of E3. Applicants have found, in accordance with the instant invention, that virus comprising the E3 gene were able to amplify more rapidly compared with virus not comprising an E3 gene; see FIG. 6 wherein a diagnostic CsCl band corresponding to the E3+virus tested (5,665 bp) was present in greater amount compared with the diagnostic band of 3,010 bp corresponding to the E3-virus. These results were obtained following a virus competition study involving mixing equal MOI ratio (1:1) of adenovectors both comprising the E3 gene and not comprising the E3 gene. This increased amplification capacity of the E3+ adenovectors was subsequently confirmed with growth studies; see Table 4A, wherein the E3+ virus exhibit amplification ratios of 470, 420 and 320 as compared with the 115 and 40–50 of the E3-constructs.

As stated above, vectors in accordance with the instant invention can accommodate up to approximately 4,850 base pairs of exogenous genetic material for an E3+ vector and approximately 7,500 base pairs for an E3-vector. Preferably, the insert brings the adenoviral vector as close as possible to a wild-type genomic size (e.g., for Ad5, 35,935 basepairs). It is well known that adenovirus amplifies best when they are close to their wild-type genomic size.

The genetic material can be inserted in an E1-parallel or an E1 anti-parallel orientation, as such is illustrated in FIGS. 7A, 7B, 7C and FIG. 8A. Particularly preferred embodiments of the instant invention, have the insert in an E1-parallel orientation. Applicants have found, via competition experiments with plasmids containing transgenes in differing orientation (FIG. 8A), that vector constructs with the foreign DNA insert in an E1-parallel orientation amplify better and actually out-compete E1-antiparallel-oriented transgenes. Viral DNA analysis of the mixtures at passage 3 and certainly at passage 6, showed a greater ratio of the virus carrying the transgene in the E1 parallel orientation as compared with the E1 anti-parallel version. By passage 10, the only viral species observed was the adenovector with the transgene in the E1 parallel orientation for both transgenes tested.

Adenoviral vectors in accordance with the instant invention are particularly well suited to effectuate expression of desired proteins, one example of which is an HIV protein, particularly an HIV full length gag protein. Exogenous genetic material encoding a protein of interest can exist in the form of an expression cassette. A gene expression cassette preferably comprises (a) a nucleic acid encoding a protein of interest; (b) a heterologous promoter operatively linked to the nucleic acid encoding the protein; and (c) a transcription terminator.

The transcriptional promoter is preferably recognized by an eukaryotic RNA polymerase. In a preferred embodiment, the promoter is a "strong" or "efficient" promoter. An example of a strong promoter is the immediate early human cytomegalovirus promoter (Chapman et al, 1991 *Nucl. Acids Res* 19:3979–3986, which is incorporated by reference), preferably without intronic sequences. Most preferred for use within the instant adenoviral vector is a human CMV promoter without intronic seqeunces, like intron A. Applicants have found that intron A, a portion of the human cytomegalovirus promoter (hCMV), constitutes a region of instability for adenoviral vectors. CMV without intron A has been found to effectuate (Examples 1–3) comparable expression capabilities in vitro when driving HIV gag expression and, furthermore, behaved equivalently to intron A-containing constructs in Balb/c mice in vivo with respect to their antibody and T-cell responses at both dosages of plasmid DNA tested (20 $\mu$g and 200 $\mu$g). Those skilled in the art will appreciate that any of a number of other known promoters, such as the strong immunoglobulin, or other eukaryotic gene promoters may also be used, including the EF1 alpha promoter, the murine CMV promoter, Rous sarcoma virus (RSV) promoter, SV40 early/late promoters and the beta-actin promoter.

In preferred embodiments, the promoter may also comprise a regulatable sequence such as the Tet operator sequence. This would be extremely useful, for example, in cases where the gene products are effecting a result other than that desired and repression is sought.

Preferred transcription termination sequences present within the gene expression cassette are the bovine growth hormone terminator/polyadenylation signal (bGHpA) and the short synthetic polyA signal (SPA) of 50 nucleotides in length, defined as follows: AATAAAA GATCTTTATTTTCATTAGATCTGTGTGTTGGT-TTTTTGTGTG (SEQ ID NO:26).

The combination of the CMV promoter (devoid of the intron A region) with the BGH terminator is particularly preferred although other promoter/terminator combinations in the context of FG adenovirus may also be used.

Other embodiments incorporate a leader or signal peptide into the transgene. A preferred leader is that from the tissue-specific plasminogen activator protein, tPA. Examples include but are not limited to the various tPA-gag, tPA-pol and tPA-nef adenovirus-based vaccines disclosed throughout this specification.

In view of the improved adenovirus vectors described herein, an essential portion of the present invention are adenoviral-based HIV vaccines comprising said adenovirus backbones which may be administered to a mammalian host, preferably a human host, in either a prophylactic or therapeutic setting. The HIV vaccines of the present invention, whether administered alone or in combination regimens with other viral- or non-viral-based DNA vaccines, should elicit potent and broad cellular immune responses against HIV that will either lessen the likelihood of persistent virus infection and/or lead to the establishment of a clinically significant lowered virus load subject to HIV infection or in combination with HAART therapy, mitigate the effects of previously established HIV infection (antiviral immunotherapy(ARI)). While any HIV antigen (e.g., gag, pol, nef, gp160, gp41, gp120, tat, rev, etc.) may be utilized in the herein described recombinant adenoviral vectors, preferred embodiments include the codon optimized p55 gag antigen (herein exemplified as MRKAd5gag), pol and nef. Sequences based on different Clades of HIV-1 are suitable for use in the instant invention, most preferred of which are Clade B and Clade C. Particularly preferred embodiments are those sequences (especially, codon-optimized sequences) based on concensus Clade B sequences. Preferred versions of the MRKAd5pol and MRKAd5nef series of adenoviral vaccines will encode modified versions of pol or nef, as discussed herein. Preferred embodiments of the MRKAd5HIV-1 vectors carrying HIV envelope genes and modifications thereof comprise the HIV codon-optimized env sequences of PCT International Applications PCT/US97/02294 and PCT/US97/10517, published Aug. 28, 1997 (WO 97/31115) and Dec. 24, 1997, respectively; both documents of which are hereby incorporated by reference.

A most preferred aspect of the instant invention is the disclosed use of the adenoviral vector described above to effectuate expression of HIV gag. Sequences for many genes of many HIV strains are publicly available in GENBANK and primary, field isolates of HIV are available from the National Institute of Allergy and Infectious Diseases (NIAID) which has contracted with Quality Biological (Gaithersburg, Md.) to make these strains available. Strains are also available from the World Health Organization (WHO), Geneva Switzerland. It is preferred that the gag gene be from an HIV-1 strain (CAM-1; Myers et al, eds. "Human Retroviruses and AIDS: 1995, IIA3-IIA19, which is hereby incorporated by reference). This gene closely resembles the consensus amino acid sequence for the clade B (North American/European) sequence. Therefore, it is within the purview of the skilled artisan to choose an appropriate nucleotide sequence which encodes a specific HIV gag antigen, or immunologically relevant portion thereof. As shown in Example 25, a clade B or lade C based p55 gag antigen will potentially be useful on a global scale. As noted herein, the transgene of choice for insertion in to a DNA or MRKAd-based adenoviral vector of the present invention is a codon optimized version of p55 gag. Such a MRKAd5gag adenoviral vector is documented in Example 11 and is at least referred to herein as MRKAd5HIV-1gag. Of course, additional versions are contemplated, including but not limited to modifications such as promoter (e.g., mCMV for hCMV) and/or pA-terminations signal (SPA for bGH) switching, as well as generating MRK Ad5 backbones with or without deletion of the Ad5 E3 gene.

The present invention also relates a series of MRKAd5pol-based adenoviral vaccines which are shown herein to generate cellular immune responses subsequent to administration in mice and non-human primate studies. Several of the MRKAd5pol series are exemplified herein. One such adenoviral vector is referred to as MRKAd5hCMV-inact opt pol(E3+), which comprises the MRKAd5 backbone, the hCMV promoter (no intron A), an inactivated pol transgene, and contains the Ad5 E3 gene in the adenoviral backbone. A second exemplified pre-adenovirus plasmid and concomitant virus is referred to as MRKAd5hCMV-inact opt pol(E3−), which is identical to the former adenoviral vector except that the E3 is deleted. Both constructions contain a codon optimized, inactivated version of HIV-1 Pol, wherein at least the entire coding region is disclosed herein as SEQ ID NO:3 and the expressed protein is shown as SEQ ID NO:4 (see also FIGS. 17A–C and Table 1, which show targeted deletion for inactivated pol. This and other preferred codon optimized versions of HIV Pol as disclosed herein are essentially as described in U.S. application Ser. No. 09/745,221, filed Dec. 21, 2000 and PCT International Application PCT/US00/34724, also filed Dec. 21, 2000, both documents which are hereby incorporated by reference. As disclosed in the above-mentioned documents, the open reading frame for these codon-optimized HIV-1 Pol-based DNA vaccines are represented by codon optimized DNA molecules encoding codon optimized HIV-1 Pol (e.g. SEQ ID NO:2), codon optimized HIV-1 Pol fused to an amino terminal localized leader sequence (e.g. SEQ ID NO:6), and especially preferable, and exemplified by the MRKAd5-Pol construct in e.g., Example 19, biologically inactivated pol ("inact opt Pol"; e.g., SEQ ID NO:4) which is devoid of significant PR, RT, RNase or IN activity associated with wild type Pol. In addition, a construct related to SEQ ID NO:4 is contemplated which contains a leader peptide at the amino terminal region of the IA Pol protein. A specific construct is ligated within an appropriate DNA plasmid vector containing regulatory regions operatively linked to the respective HIV-1 Pol coding region, with or without a nucleotide sequence encoding a functional leader peptide. To this end, various HIV-1 Pol constructs disclosed herein relate to open reading frames for cloning to the enhanced first generation Ad vectors of the present invention (such a series of MRKAd5pol adenoviral vaccine vectors), including but not limited to wild type Pol (comprising the DNA molecule encoding WT opt Pol, as set forth in SEQ ID NO:2), tPA-opt WTPol, (comprising the DNA molecule encoding tPA Pol, as set forth in SEQ ID NO:6), inact opt Pol (comprising the DNA molecule encoding IA Pol, as set forth in SEQ ID NO:4), and tPA-inact opt Pol, (comprising the DNA molecule encoding tPA-inact opt Pol, as set forth in SEQ ID NO:8). The pol-based versions of enhanced first generation adenovirus vaccines elicit CTL and Th cellular immune responses upon administration to the host, including primates and especially humans. As noted in the above, an effect of the cellular immune-directed vaccines of the present invention should be a lower transmission rate to previously uninfected individuals and/or reduction in the levels of the viral loads within an infected individual, so as to prolong the asymptomatic phase of HIV-1 infection.

The present invention further relates to a series of MRKAd5nef-based adenoviral vaccines which, similar to HIV gag and pol antigens, generate cellular immune responses subsequent to administration in mice and non-human primate studies. The MRKAd5nef series are exemplified herein by utilizing the improved MRK adenoviral backbone in combination with modified versions of HIV nef. These exemplified MRKAd5nef vectors are as follows: (1) MRKAd5hCMV-nef(G2A,LLAA) (E3+), which comprises the improved MRKAd5 backbone, a human CMV promoter an intact Ad5 E3 gene and a modified nef gene: (2) MRKAd5mCMV-nef(G2A,LLAA) (E3+), which is the same as (1) above but substituting a murine CMV promoter for a human CMV promoter; and (3) MRKAd5mCMV-tpanef(LLAA) (E3+), which is the same as (2) except that the nef transgene is tpanef(LLAA). Codon optimized versions of HIV-1 Nef and HIV-1 Nef modifications are essentially as described in U.S. application Ser. No. 09/738,782, filed Dec. 15, 2000 and PCT International Application PCT/US00/34162, also filed Dec. 15, 2000, both documents which are hereby incorporated by reference. Particular embodiments of codon optimized Nef and Nef modifications relate to a DNA molecule encoding HIV-1 Nef from the HIV-1 jfrl isolate wherein the codons are optimized for expression in a mammalian system such as a human. The DNA molecule which encodes this protein is disclosed herein as SEQ ID NO:9, while the expressed open reading frame is disclosed herein as SEQ ID NO:10. Another embodiment of Nef-based coding regions for use in the adenoviral vectors of the present invention comprise a codon optimized DNA molecule encoding a protein containing the human plasminogen activator (tpa) leader peptide fused with the $NH_2$-terminus of the HIV-1 Nef polypeptide. The DNA molecule which encodes this protein is disclosed herein as SEQ ID NO:11, while the expressed open reading frame is disclosed herein as SEQ ID NO:12. Another modified Nef optimized coding region relates to a DNA molecule encoding optimized HIV-1 Nef wherein the open reading frame codes for modifications at the amino terminal myristylation site (Gly-2 to Ala-2) and substitution of the Leu-174-Leu-175 dileucine motif to Ala-174-Ala-175, herein described as opt nef (G2A, LLAA). The DNA molecule which encodes this protein is disclosed herein as SEQ ID NO:13, while the expressed open reading frame is disclosed herein as SEQ ID NO:14. MRKAd5nef vectors (1) MRKAd5hCMV-nef(G2A, LLAA) (E3+) and (2) MRKAd5mCMV-nef(G2A,LLAA) (E3+) contain this transgene. An additional embodiment relates to a DNA molecule encoding optimized HIV-1 Nef wherein the amino terminal myristylation site and dileucine motif have been deleted, as well as comprising a tPA leader peptide. This DNA molecule, opt tpanef (LLAA), comprises an open reading frame which encodes a Nef protein containing a tPA leader sequence fused to amino acid residue 6–216 of HIV-1 Nef (jfrl), wherein Leu-174 and Leu-175 are substituted with Ala-174 and Ala-175, herein referred to as opt tpanef (LLAA) is disclosed herein as SEQ ID NO:15, while the expressed open reading frame is disclosed herein as SEQ ID NO:16. The MRKAd5nef vector "MRKAd5mCMV-tpanef(LLAA) (E3+)" contains this transgene.

Along with the improved MRKAd5gag adenovirus vaccine vector described herein, generation of a MRKAd5pol and MRKAd5nef adenovirus vector provide for enhanced HIV vaccine capabilities. Namely, the generation of this trio of adenoviral vaccine vectors, all shown to generate effective cellular immune responses subsequent to host administration, provide for the ability to administer these vaccine candidates not only alone, but preferably as part of a divalent (i.e., gag and nef, gag and pol, or pol and nef components) or a trivalent vaccine (i.e., gag, pol and nef components). Therefore, a preferred aspect of the present invention are vaccine formulations and associated methods of administration and concomitant generation of host cellular immune responses associated with formulating three separate series of MRKAd5-based adenoviral vector vaccines. Of course, this MRKAd5 vaccine series based on distinct HIV antigens promotes expanded opportunities for formulation of a divalent or trivalent vaccine, or possibly administration of separate formulations of one or more monovalent or divalent formulations within a reasonable window of time. It is also within the scope of the present invention to embark on combined modality regimes which include multiple but distinct components from a specific antigen. An example, but certainly not a limitation, would be separate MRKAd5pol vectors, with one vaccine vector expressing wild type Pol (SEQ ID NO:2) and another MRKAd5pol vector expressing inactivated Pol (SEQ ID NO:6). Another example might be separate MRKAd5nef vectors, with one vaccine vector expressing the tPA/LLAA version of Nef (SEQ ID NO:16) and another MRKAd5nef vector expressing the G2A,LLAA modified version of Nef (SEQ ID NO:14). Therefore, the MRKAd5 adenoviral vectors of the present invention may be used in combination with multiple, distinct HIV antigen classes. Each HIV antigen class is subject to sequence manipulation, thus providing for a multitude of potential vaccine combinations; and such combinations are within the scope of the present invention. The utilization of such combined modalities vaccine formulation and administration increase the probability of eliciting an even more potent cellular immune response when compared to inoculation with a single modality regimen.

The present invention also relates to application of a mono-, dual-, or tri-modality administration regime of the MRKAd5gag, pol and nef adenoviral vaccine series in a prime/boost vaccination schedule. This prime/boost schedule may include any reasonable combination of the MRKAd5gag, pol and nef adenoviral vaccine series disclosed herein. In addition, a prime/boost regime may also involve other viral and/or non-viral DNA vaccines. A preferable addition to an adenoviral vaccine vector regime includes but is not limited to plasmid DNA vaccines, especially DNA plasmid vaccines that contain at least one of the codon optimized gag, pol and nef constructions, as disclosed herein.

Therefore, one aspect of this invention is the administration of the adenoviral vector containing the optimized gag gene in a prime/boost regiment in conjunction with a plasmid DNA encoding gag. To distinguish this plasmid from the adenoviral-containing shuttle plasmids used in the construction of an adenovirus vector, this plasmid will be referred to as a "vaccine plasmid" or "DNA plasmid vaccine". Preferred vaccine plasmids for use in this administration protocol are disclosed in pending U.S. patent application Ser. No. 09/017,981, filed Feb. 3, 1998 and WO98/34640, published Aug. 13, 1998, both of which are hereby incorporated by reference. Briefly, the preferred vaccine plasmid is designated V1Jns-FLgag, which expresses the same codon-optimized gag gene as the adenoviral vectors of this invention (see FIG. 2 for the nucleotide sequence of the exemplified optimized codon version of full length p55 gag). The vaccine plasmid backbone, designated V1Jns contains the CMV immediate-early (IE) promoter and intron A, a bovine growth hormone-derived polyadenylation and transcription termination sequence as the gene expression regulatory elements, and a minimal pUC backbone; see Montgomery et al., 1993, *DNA Cell Biol.* 12:777–783. The pUC sequence permits high levels of plasmid production in *E. coli* and has a neomycin resistance gene in place of an ampicillin resistance gene to provide selected growth in the presence of kanamycin. Alternatively, a vaccine plasmid which has the CMV promoter deleted of intron A can be used. Those of skill in the art will recognize that alternative vaccine plasmid vectors may be easily substituted for these specific constructs, and this invention specifically envisions use of such alternative plasmid DNA vaccine vectors.

Another aspect of the present invention is a prime/boost regimen which includes a vaccine plasmid which encodes an HIV pol antigen, preferably a codon optimized form of pol and also preferably a vaccine plasmid which comprises a nucleotide sequence which encodes a Pol antigen selected from the group of Pol antigens as shown in SEQ ID NOs: 2, 4, 6 and 8. The variety of potential DNA plasmid vaccines which encode various biologically active forms of HIV-1 Pol, wherein administration, intracellular delivery and expression of the HIV-1 Pol gene of interest elicits a host CTL and Th response. The preferred synthetic DNA molecules of the present invention encode codon optimized wild type Pol (without Pro activity) and various codon optimized inactivated HIV-1 Pol proteins. The HIV-1 pol open reading disclosed herein are especially preferred for pharmaceutical uses, especially for human administration as delivered via a recombinant adenoviral vaccine, especially an enhanced first generation recombinant adenoviral vaccine as described herein. Several embodiments of this portion of the invention are provided in detail below, namely DNA molecules which comprise a HIV-1 pol open reading frame, whether encoding full length pol or a modification or fusion as described herein, wherein the codon usage has been optimized for expression in a mammal, especially a human. Again, these DNA sequences are positioned appropriately within a recombinant adenoviral vector, such as the exemplified recombinant adenoviral vector described herein, so as to promote expression of the respective HIV-1 Pol gene of interest, and subsequent to administration, elicit a host CTL and Th response. Again, these preferred, but in no way limiting, pol genes are as disclosed herein and essentially as described in U.S. application Ser. No. 09/745,221, filed Dec. 21, 2000 and PCT International Application PCT/US00/34724, also filed Dec. 21, 2000, both documents which are hereby incorporated by reference.

A third series of vaccine plasmids which are useful in a combined modality and/or prime/boost regimen are vaccine plasmids which encode an HIV nef antigen or biologically and/or immunologically relevant modification thereof. As noted elsewhere, preferred vaccine plasmids contain a codon optimized form of nef and also preferably comprise a nucleotide sequence which encodes a Nef antigen selected from the group of Nef antigens as shown in SEQ ID NOs: 10, 12, 14 and 16. These preferred nef coding regions are disclosed herein, as well as being described in U.S. application Ser. No. 09/738,782, filed Dec. 15, 2000 and PCT International Application PCT/US00/34162, also filed Dec. 15, 2000, both documents which are hereby incorporated by reference.

Therefore, the adenoviral vaccines and plasmid DNA vaccines of this invention may be administered alone, or may be part of a prime and boost administration regimen. A mixed modality priming and booster inoculation scheme will result in an enhanced immune response, particularly is pre-existing anti-vector immune responses are present. This one aspect of this invention is a method of priming a subject with the plasmid vaccine by administering the plasmid vaccine at least one time, allowing a predetermined length of time to pass, and then boosting by administering the adenoviral vaccine. Multiple primings typically, 1–4, are usually employed, although more may be used. The length of time between priming and boost may typically vary from about four months to a year, but other time frames may be used. In experiments with rhesus monkeys, the animals were primed four times with plasmid vaccines, then were boosted 4 months later with the adenoviral vaccine. Their cellular immune response was notably higher than that of animals which had only received adenoviral vaccine. The use of a priming regimen may be particularly preferred in situations where a person has a pre-existing anti-adenovirus immune response.

Figure 9:
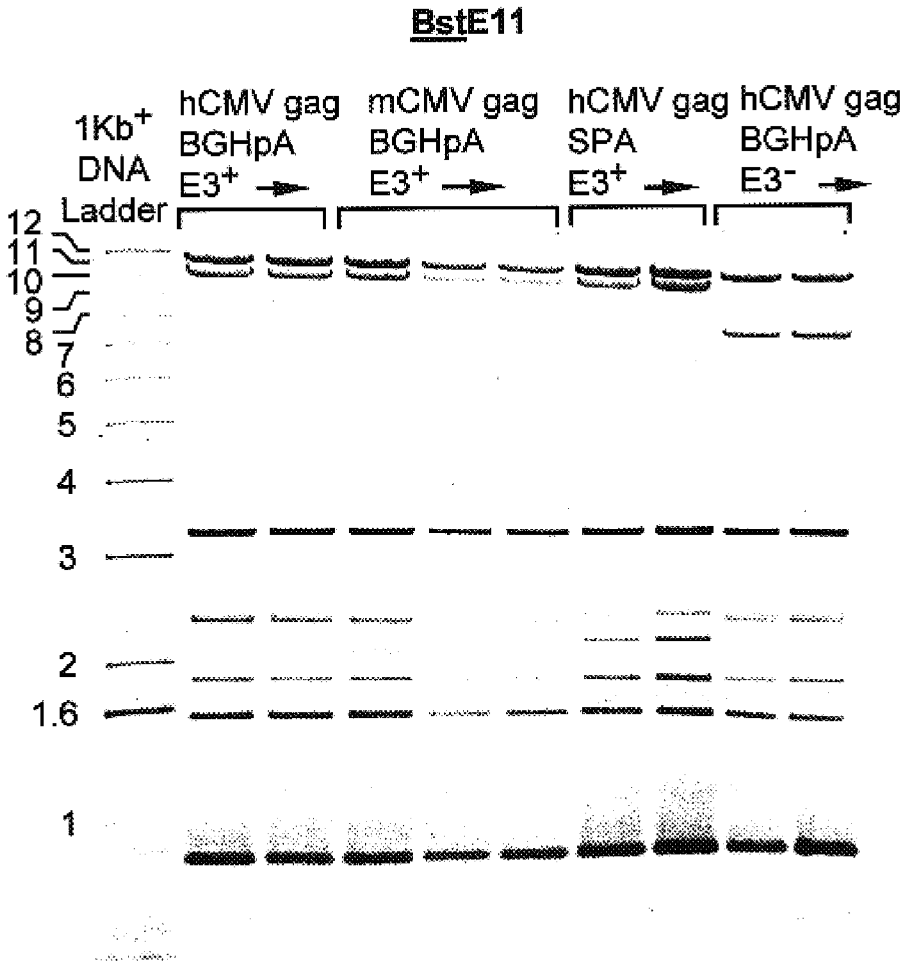
FIG. 9 shows viral DNA from the four adenoviral vectors tested (Example 12) at P5, following BstE11 digestion.
Figure 28:
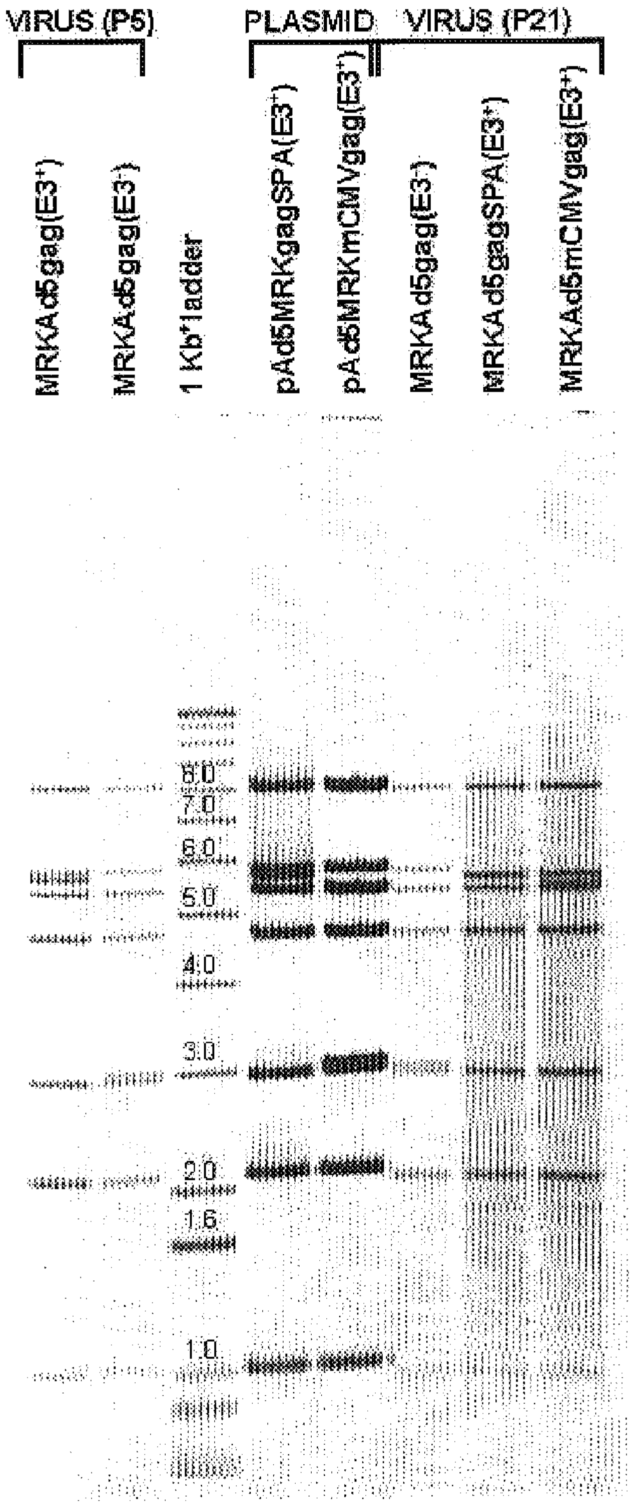

Furthermore and in the alternative, multiple HIV-1 viral antigens, such as the MRKAd5 adenoviral vaccines disclosed herein, may be ligated into a proper shuttle plasmid for generation of a pre-adenoviral plasmid comprising multiple open reading frames. For example a trivalent vector may comprise a gag-pol-nef fusion, in either a E3(−) or E3(+) background, preferably a E3 deleted backbone, or possible a "2+1" divalent vaccine, such as a gag-pol fusion (i.e., codon optimized p55 gag and inactivated optimized pol; Example 29 and Table 25) within the same MRKAd5 backbone, with each open reading frame being operatively linked to a distinct promoter and transcription termination sequence. Alternatively, the two open reading frames may be operatively linked to a single promoter, with the open reading frames operatively linked by an internal ribosome entry sequence (IRES), as disclosed in International Publication No. WO 95/24485, which is hereby incorporated by reference. FIG. 9 shows that the use of multiple promoters and termination sequences provide for similar growth properties, while FIG. 28 shows that these MRKAd5gag-based vectors are also stable at least through passage 21. In the absence of the use of IRES-based technology, it is preferred that a distinct promoter be used to support each respective open reading frame, so as to best preserve vector stability. As examples, and certainly not as limitations, potential multiple transgene vaccines may include a three transgene vector such as hCMV-gagpol-bGHpA+mCMV-nef-SPA in an E3 deleted backbone or hCMV-gagpol-bGHpA+mCMV-nef-SPA(E3+). Potential "2+1" divalent vaccines of the present invention might be a hCMV-gag-bGHpA +mCMV-nef-SPA in an E3+backbone (vector #1) in combination with hCMV-pol-bGHpA in an E3+backbone (vector #2), with all transgenes in the E1 parallel orientation. Fusion constructs other than the gag-pol fusion described above are also suitable for use in various divalent vaccine strategies and can be composed of any two HIV antigens fused to one another (e.g., nef-pol and gag-nef). These adenoviral compositions are, as above, preferably delivered along with an adenoviral composition comprising an additional HIV antigen in order to diversify the immune response generated upon administration. Therefore, a multivalent vaccine delivered in a single, or possible second, adenoviral vector is certainly contemplated as part of the present invention. Again, this mode of administration is another example of whereby an efficaceous adenovirus-based HIV-1 vaccine may be administered via a combined modality regime. It is important to note, however, that in terms of deciding on an insert for the disclosed adenoviral vectors, due consideration must be dedicated to the effective packaging limitations of the adenovirus vehicle. Adenovirus has been shown to exhibit an upper cloning capacity limit of approximately 105% of the wildtype Ad5 sequence.

Regardless of the gene chosen for expression, it is preferred that the sequence be "optimized" for expression in a human cellular environment. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist variable natural hierarchy or "preference" for certain codons in certain types of cells. As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an *E. coli* host will depend to some extent on the frequency of codon use. For example, a gene rich in TTA codons will in all probability be poorly expressed in *E. coli*, whereas a CTG rich gene will probably highly express the polypeptide. Similarly, when yeast cells are the projected transformation host cells for expression of a leucine-rich polypeptide, a preferred codon for use in an inserted DNA would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide a preferred form of foreign genetic material for practice of recombinant DNA techniques. Thus, one aspect of this invention is an adenovirus vector or adenovirus vector in some combination with a vaccine plasmid where both specifically include a gene which is codon optimized for expression in a human cellular environment. As noted herein, a preferred gene for use in the instant invention is a codon-optimized HIV gene and, particularly, HIV gag, pol or nef.

Adenoviral vectors in accordance with the instant invention can be constructed using known techniques, such as those reviewed in Hitt et al, 1997"Human Adenovirus Vectors for Gene Transfer into Mammalian Cells" *Advances in Pharmacology* 40:137–206, which is hereby incorporated by reference.

In constructing the adenoviral vectors of this invention, it is often convenient to insert them into a plasmid or shuttle vector. These techniques are known and described in Hitt et al., supra. This invention specifically includes both the adenovirus and the adenovirus when inserted into a shuttle plasmid.

Preferred shuttle vectors contain an adenoviral portion and a plasmid portion. The adenoviral portion is essentially the same as the adenovirus vector discussed supra, containing adenoviral sequences (with non-functional or deleted E1 and E3 regions) and the gene expression cassette, flanked by convenient restriction sites. The plasmid portion of the shuttle vector often contains an antibiotic resistance marker under transcriptional control of a prokaryotic promoter so that expression of the antibiotic does not occur in eukaryotic cells. Ampicillin resistance genes, neomycin resistance genes and other pharmaceutically acceptable antibiotic resistance markers may be used. To aid in the high level production of the polynucleotide by fermentation in prokaryotic organisms, it is advantageous for the shuttle vector to contain a prokaryotic origin of replication and be of high copy number. A number of commercially available prokaryotic cloning vectors provide these benefits. It is desirable to remove non-essential DNA sequences. It is also desirable that the vectors not be able to replicate in eukaryotic cells. This minimizes the risk of integration of polynucleotide vaccine sequences into the recipients' genome. Tissue-specific promoters or enhancers may be used whenever it is desirable to limit expression of the polynucleotide to a particular tissue type.

Figure 22:
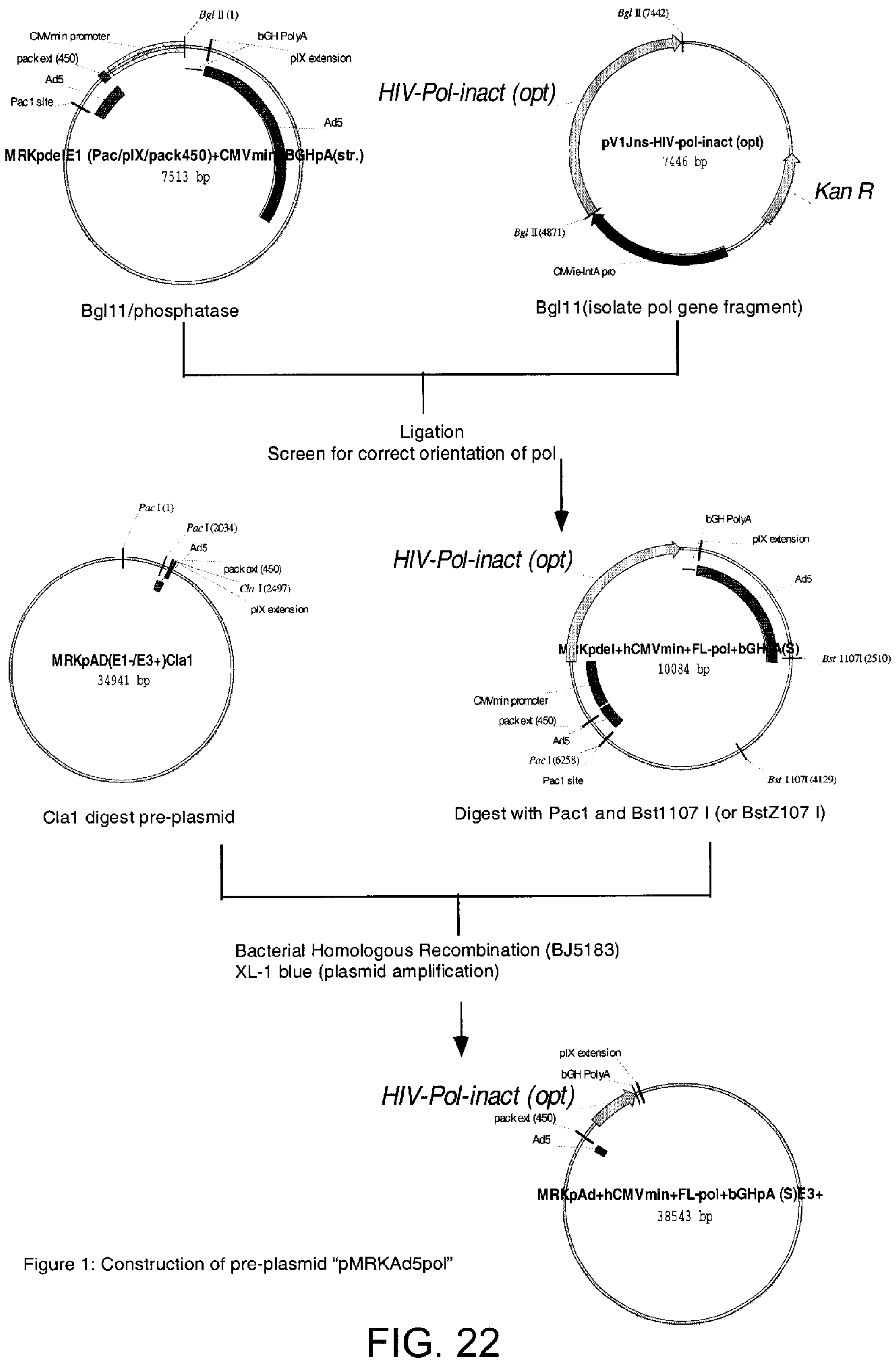
Figure 23:
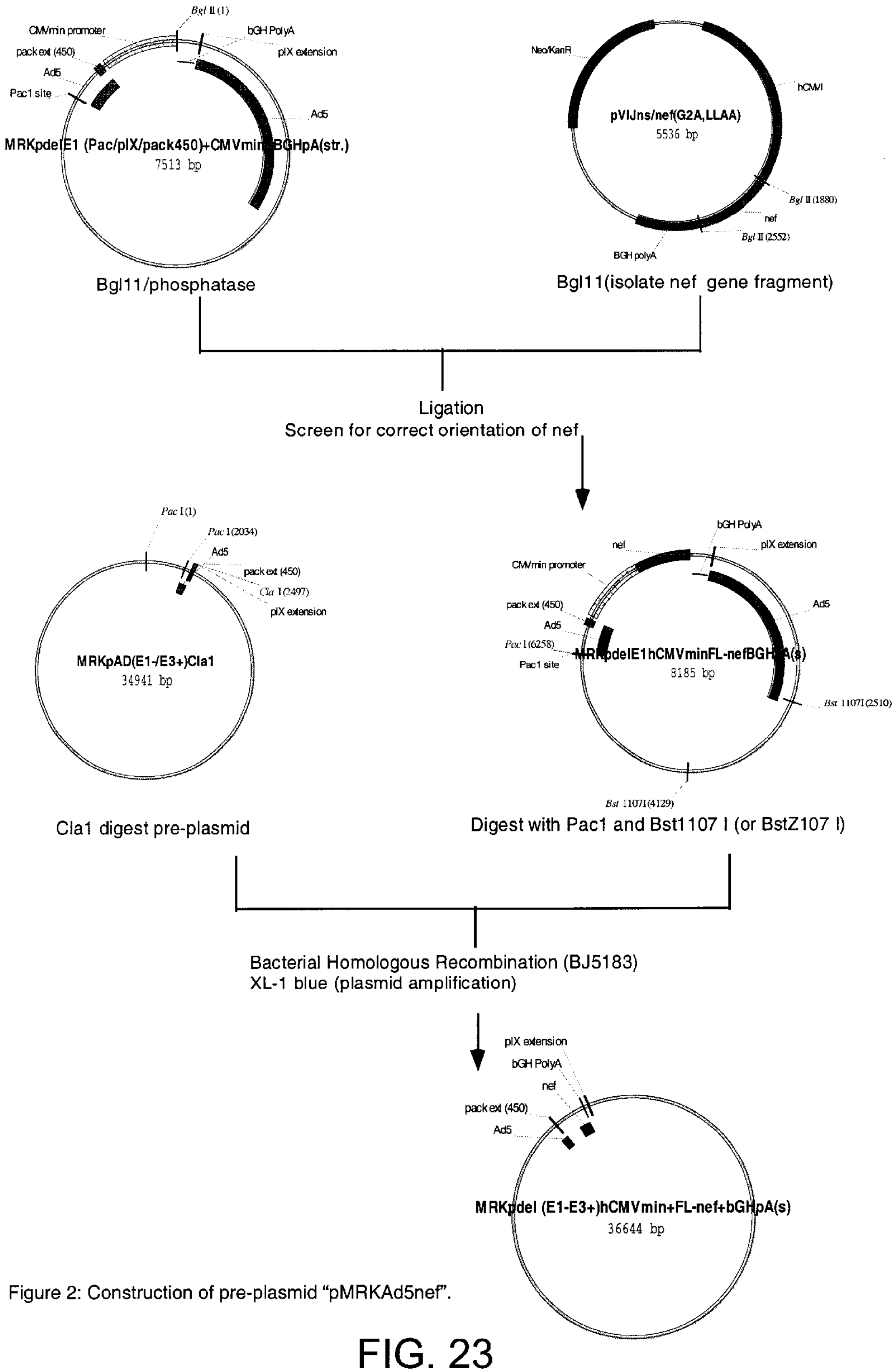

In one embodiment of this invention, the pre-plasmids (e.g., pMRKAd5pol, pMRKAd5nef and pMRKAd5gag were generated by homologous recombination using the MRKHVE3 (and MRKHVO for the E3-version) backbones and the appropriate shuttle vector, as shown for pMRKAd5pol in FIG. 22 and for pMRKAd5nef in FIG. 23. The plasmid in linear form is capable of replication after entering the PER.C6® cells and virus is produced. The infected cells and media were harvested after viral replication was complete.

Viral vectors can be propagated in various E1 complementing cell lines, including the known cell lines 293 and PER.C6®. Both these cell lines express the adenoviral E1 gene product. PER.C6® is described in WO 97/00326 (published Jan. 3, 1997) and issued U.S. Pat. No. 6,033,908, both of which are hereby incorporated by reference. It is a primary human retinoblast cell line transduced with an E1 gene segment that complements the production of replication deficient (FG) adenovirus, but is designed to prevent generation of replication competent adenovirus by homologous recombination. Cells of particular interest have been stably transformed with a transgene that encodes the AD5E1A and E1B gene, like PER.C6®, from 459 bp to 3510 bp inclusive. 293 cells are described in Graham et al., 1977 *J. Gen. Virol* 36:59–72, which is hereby incorporated by reference. As stated above, consideration must be given to the adenoviral sequences present in the complementing cell line used. It is important that the sequences not overlap with that present in the vector if the possibility of recombination is to be minimized.

It has been found that vectors generated in accordance with the above description are more effective in inducing an immune response and, thus, constitute very promising vaccine candidates. More particularly, it has been found that first generation adenoviral vectors in accordance with the above description carrying a codon-optimized HIV gag gene, regulated with a strong heterologous promoter can be used as human anti-HIV vaccines, and are capable of inducing immune responses.

Standard techniques of molecular biology for preparing and purifying DNA constructs enable the preparation of the DNA immunogens of this invention.

A vaccine composition comprising an adenoviral vector in accordance with the instant invention may contain physiologically acceptable components, such as buffer, normal saline or phosphate buffered saline, sucrose, other salts and polysorbate. One preferred formulation has: 2.5–10 mM TRIS buffer, preferably about 5 mM TRIS buffer; 25–100 mM NaCl, preferably about 75 mM NaCl; 2.5–10% sucrose, preferably about 5% sucrose; 0.01–2 mM $MgCl_2$; and 0.001%–0.01% polysorbate 80 (plant derived). The pH should range from about 7.0–9.0, preferably about 8.0. One skilled in the art will appreciate that other conventional vaccine excipients may also be used it make the formulation. The preferred formulation contains 5 mM TRIS, 75 mM NaCl, 5% sucrose, 1 mM $MgCl_2$, 0.005% polysorbate 80 at pH 8.0 This has a pH and divalent cation composition which is near the optimum for Ad5 stability and minimizes the potential for adsorption of virus to a glass surface. It does not cause tissue irritation upon intramuscular injection. It is preferably frozen until use.

The amount of adenoviral particles in the vaccine composition to be introduced into a vaccine recipient will depend on the strength of the transcriptional and translational promoters used and on the immunogenicity of the expressed gene product. In general, an immunologically or prophylactically effective dose of $1\times10^7$ to $1\times10^{12}$ particles and preferably about $1\times10^{10}$ to $1\times10^{11}$ particles is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided. Following vaccination with HIV adenoviral vector, boosting with a subsequent HIV adenoviral vector and/or plasmid may be desirable. Parenteral administration, such as intravenous, intramuscular, subcutaneous or other means of administration of interleukin-12 protein, concurrently with or subsequent to parenteral introduction of the vaccine compositions of this invention is also advantageous.

The adenoviral vector and/or vaccine plasmids of this invention polynucleotide may be unassociated with any proteins, adjuvants or other agents which impact on the recipients' immune system. In this case, it is desirable for the vector to be in a physiologically acceptable solution, such as, but not limited to, sterile saline or sterile buffered saline. Alternatively, the vector may be associated with an adjuvant known in the art to boost immune responses (i.e., a "biologically effective" adjuvant), such as a protein or other carrier. Vaccine plasmids of this invention may, for instance, be delivered in saline (e.g., PBS) with or without an adjuvant. Preferred adjuvants are Alum or CRL1005 Block Copolymer. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

This invention also includes a prime and boost regimen wherein a first adenoviral vector is administered, then a booster dose is given. The booster dose may be repeated at selected time intervals. Alternatively, a preferred inoculation scheme comprises priming with a first adenovirus serotype and then boosting with a second adenovirus serotype. More preferably, the inoculation scheme comprises priming with a first adenovirus serotype and then boosting with a second adenovirus serotype, wherein the first and second adenovirus serotypes are classified within separate subgroups of adenoviruses. The above prime/boost schemes are particularly preferred in those situations where a preexisting immunity is identified to the adenoviral vector of choice. In this type of scheme, the individual or population of individuals is primed with an adenovirus of a serotype other than that to which the preexisting immunity is identified. This enables the first adenovirus to effectuate sufficient expression of the transgene while evading existing immunity to the second adenovirus (the boosting adenovirus) and, further, allows for the subsequent delivery of the transgene via the boosting adenovirus to be more effective. Adenovirus serotype 5 is one example of a virus to which such a scheme might be desirable. In accordance with this invention, therefore, one might decide to prime with a non-group C adenovirus (e.g., Ad12, a group A adenovirus, Ad24, a group D adenovirus, or Ad35, a group B adenovirus) to evade anti-Ad5 immunity and then boost with Ad5, a group C adenovirus. Another preferred embodiment involves administration of a different adenovirus (including non-human adenovirus) vaccine followed by administration of the adenoviral vaccines disclosed. In the alternative, a viral antigen of interest can be first delivered via a viral vaccine other than an adenovirus-based vaccine, and then followed with the adenoviral vaccine disclosed. Alternative viral vaccines include but are not limited to pox virus and venezuelan equine encephilitis virus.

A large body of human and animal data supports the importance of cellular immune responses, especially CTL in controlling (or eliminating) HIV infection. In humans, very high levels of CTL develop following primary infection and correlate with the control of viremia. Several small groups of individuals have been described who are repeatedly exposed to HIV by remain uninfected; CTL has been noted in several of these cohorts. In the SIV model of HIV infection, CTL similarly develops following primary infection, and it has been demonstrated that addition of anti-CD8 monoclonal antibody abrogated this control of infection and leads to disease progression. This invention uses adenoviral vaccines alone or in combination with plasmid vaccines to induce CTL.

The following non-limiting Examples are presented to better illustrate the invention.

EXAMPLE 1

Removal of the Intron A Portion of the hCMV Promoter

GMP grade pVIJnsHIVgag was used as the starting material to amplify the hCMV promoter. PVIJnsHIVgag is a plasmid comprising the CMV immediate-early (IE) promoter and intron A, a full-length codon-optimized HIV gag gene, a bovine growth hormone-derived polyadenylation and transcriptional termination sequence, and a minimal pUC backbone; see Montgomery et al., supra for a description of the plasmid backbone. The amplification was performed with primers suitably positioned to flank the hCMV promoter. A 5' primer was placed upstream of the Msc1 site of the hCMV promoter and a 3' primer (designed to contain the BglII recognition sequence) was placed 3' of the hCMV promoter. The resulting PCR product (using high fidelity Taq polymerase) which encompassed the entire hCMV promoter (minus intron A) was cloned into TOPO PCR blunt vector and then removed by double digestion with Msc1 and BglII. This fragment was then cloned back into the original GMP grade pV1JnsHIVgag plasmid from which the original promoter, intron A, and the gag gene were removed following Msc1 and BglII digestion. This ligation reaction resulted in the construction of a hCMV promoter (minus intron A)+bGHpA expression cassette within the original pV1JnsHIVgag vector backbone. This vector is designated pVIJnsCMV(no intron).

The FLgag gene was excised from pV1JnsHIVgag using BglII digestion and the 1,526 bp gene was gel purified and cloned into pV1JnsCMV(no intron) at the BglII site. Colonies were screened using Sma1 restriction enzymes to identify clones that carried the Flgag gene in the correct orientation. This plasmid, designated pV1JnsCMV(no intron)-FLgag-bGHpA, was fully sequenced to confirm sequence integrity.

Two additional transgenes were also constructed. The plasmid, pV1JnsCMV(no intron)-FLgag-SPA, is identical to pV1JnsCMV(no intron)-FLgag-bGHpA except that the bovine growth hormone polyadenylation signal has been replaced with a short synthetic polyA signal (SPA) of 50 nucleotides in length. The sequence of the SPA is as shown, with the essential components (poly(A) site, $(GT)_n$, and $(T)_n$; respectively) underlined:

AATAAAAGATCTTTATTTTCATTAGATCTGTGTGTTGGTTTTTTGTGTG (SEQ ID NO:18).

The plasmid, pV1Jns-mCMV-FLgag-bGHpA, is identical to the pV1JnsCMV(no intron)-FLgag-bGHpA except that the hCMV promoter has been removed and replaced with the murine CMV (mCMV) promoter.

Figure 3:
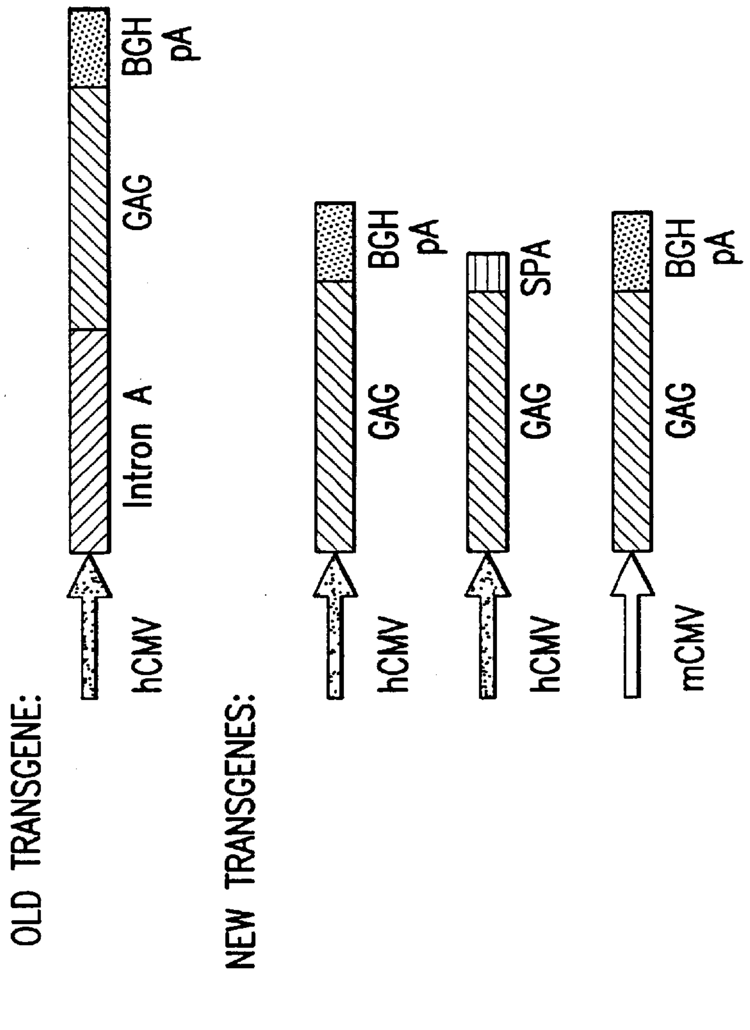
FIG. 3 shows diagrammatically the new transgene constructs in comparison with the original gag transgene.

FIG. 3 diagrammatically shows the new transgene constructs in comparison with the original transgene.

EXAMPLE 2

Gag Expression Assay for Modified Gag Transgenes

Gag Elisa was performed on culture supernatants obtained from transient tissue culture transfection experiments in which the two new hCMV-containing plasmid constructs, pV1JnsCMV(no intron)-FLgag-bGHpA and pV1JnsCMV (no intron)-FLgag-SPA, both devoid of intron A, were compared to pV1JnsHIVgag which, as noted above possesses the intron A as part of the hCMV promoter. Table 2 below shows the in vitro gag expression data of the new gag plasmids compared with the GMP grade original plasmid. The results displayed in Table 2 show that both of the new hCMV gag plasmid constructs have expression capacities comparable to the original plasmid construct which contains the intron A portion of the hCMV promoter.

TABLE 2

In vitro DNA transfection of original and new plasmid HIV-1 gag constructs.

| Plasmid | μg gag/10e6 COS cells/5 μg DNA/48 hr |
|---|---|
| HIVFL-gagPR9901[a] | 10.8 |
| PVIJns.hCMV-FLgag-bGHpA[b] | 16.6 |
| pV1Jns-hCMV-FLgag-SPA[b,c] | 12.0 |

[a]GMP grade pV1Jns-hCMVintronA-FLgag-bGHpA.
[b]New plasmid constructions that have the intron A portion removed from the hCMV promoter.
[c]In this construct the bGH terminator has been replaced with the short synthetic polyadenylation signal (SPA)

EXAMPLE 3

Rodent (Balb/c) Study for Modified Gag Transgenes

A rodent study was performed on the two new plasmid constructs described above—pV1JnsCMV(no intron)-FLgag-bGHpA and pV1JnsCMV(no intron)-FLgag-SPA—in order to compare them with the construct described above possessing the intron A portion of the CMV promoter, pV1JnsHIVgag. Gag antibody and Elispot responses (described in PCT International Application No. PCT/US00/18332 (WO 01/02607) filed Jul. 3, 2000, claiming priority to U.S. Provisional Application Serial No. 60/142,631, filed Jul. 6, 1999 and U.S. application Ser. No. 60/148,981, filed Aug. 13, 1999, all three applications which are hereby incorporated by reference) were measured. The results displayed in Table 3 below, show that the new plasmid constructs behaved equivalently to the original construct in Balb/c mice with respect to their antibody and T-cell responses at both dosages of plasmid DNA tested, 20 μg and 200 μg.

EXAMPLE 4

TABLE 3

HIV191: Immunogenicity of V1Jns-gag under different promoter and termination control elements.

| DNA[a] Promoter/ terminator | Dose, ug[b] | Anti-p24 Titers (3 Wk PD1)[c] GMT | +SE | −SE | Media | SFC/10^6 Cells (4 Wk PD1)[d] gag197–205 | p24 |
|---|---|---|---|---|---|---|---|
| HIVFL-gag PR9901 (GMP grade) | 200 | 12800 | 4652 | 3412 | 2(2) | 129(19) | 30(11) |
| | 20 | 5572 | 1574 | 1227 | 0 | 56(9) | 25(6) |
| pV1Jns-hCMV-FL-gag-bGHpA | 200 | 11143 | 2831 | 2257 | 0 | 98(5) | 12(6) |
| | 20 | 7352 | 2808 | 2032 | 0 | 73(9) | 11(6) |
| pV1Jns-hCMV-FL-gag-SPA | 200 | 16890 | 5815 | 4326 | 1(1) | 94(4) | 26(7) |
| | 20 | 5971 | 5361 | 2825 | 0 | 85(17) | 38(10) |
| Naïve | 0 | 123 | 50 | 36 | 0 | 0 | 0 |

[a]in PBS
[b]i.m. Injections into both quads, 50 μL per quad
[c]n = 10; GMT, geometric mean titer; SE, standard. error
[d]n = 5, pooled spleens; mean of triplicate wells and standard. deviation. in parentheses;

Construction of the Modified Shuttle Vector-"MRKpdelE1 Shuttle"

The modifications to the original Ad5 shuttle vector (pdelE1sp1A; a vector comprising Ad5 sequences from basepairs 1–341 and 3524–5798, with a multiple cloning region between nucleotides 341 and 3524 of Ad5, included the following three manipulations carried out in sequential cloning steps as follows:

(1) The left ITR region was extended to include the Pac1 site at the junction between the vector backbone and the adenovirus left ITR sequences. This allow for easier manipulations using the bacterial homologous recombination system.

(2) The packaging region was extended to include sequences of the wild-type (WT) adenovirus from 342 bp to 450 bp inclusive.

(3) The area downstream of pIX was extended 13 nucleotides (i.e., nucleotides 3511–3523 inclusive).

Figure 4:
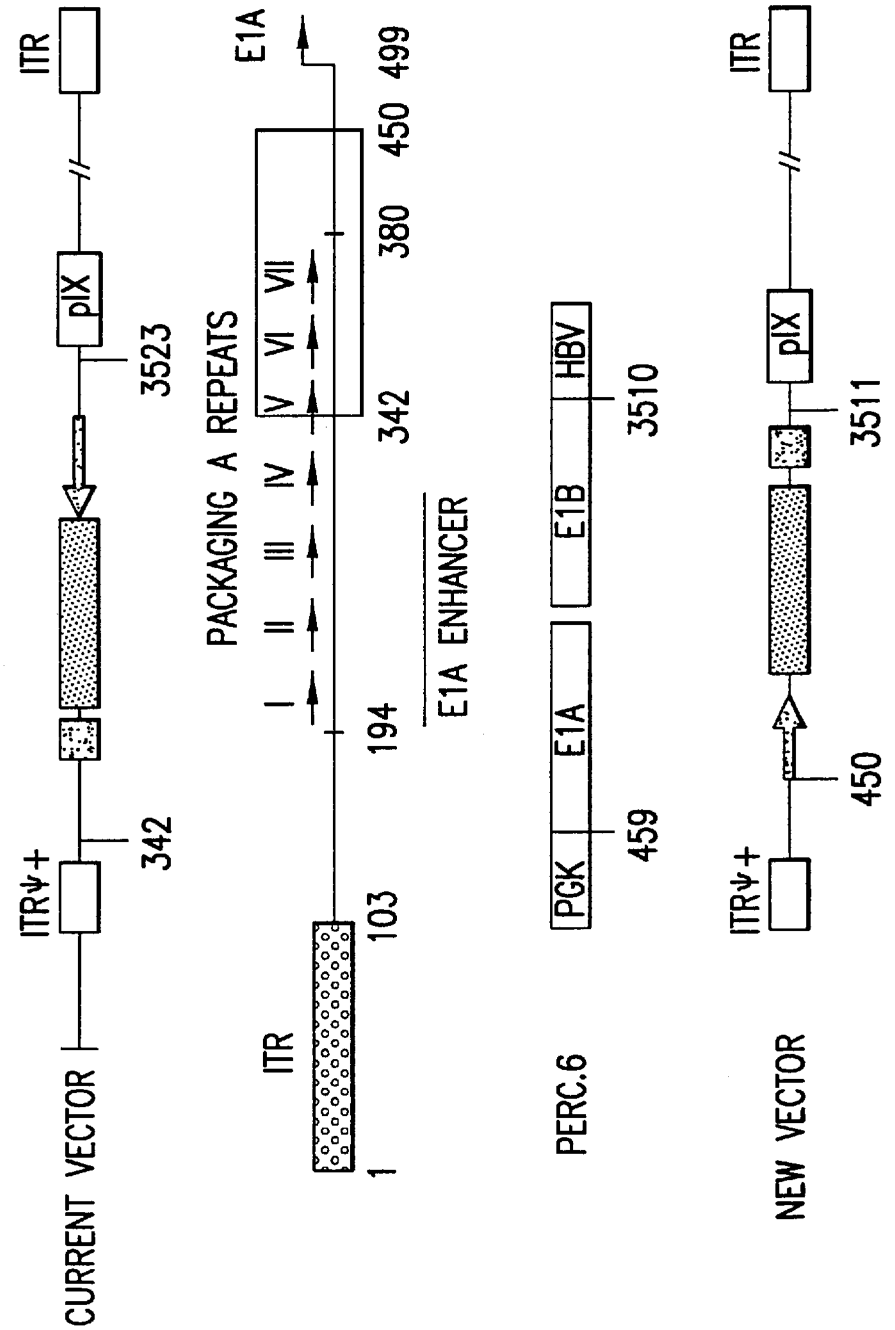
FIG. 4 shows the modifications made to the original adenovector backbone in the generation of the novel vectors of the instant invention.

These modifications (FIG. 4) effectively reduced the size of the E1 deletion without overlapping with any part of the E1A/E1B gene present in the transformed PER.C6® cell line. All manipulations were performed by modifying the Ad shuttle vector pdelE1sp1A.

Once the modifications were made to the shuttle vector, the changes were incorporated into the original Ad5 adenovector backbones (pAdHVO and pAdHVE3) by bacterial homologous recombination using *E. coli* BJ5183 chemically competent cells.

EXAMPLE 5

Construction of Modified Adenovector Backbones (E3+ and E3−)

The original adenovectors pAdHVO (comprising all Ad5 sequences except those nucleotides encompassing the E1 and E3 regions) and pADHVE3 (comprising all Ad5 sequences except those nucleotides encompassing the E1 region), were each reconstructed so that they contained the modifications to the E1 region. This was accomplished by digesting the newly modified shuttle vector (MRKpdelE1 shuttle) with Pac1 and BstZ1101 and isolating the 2,734 bp fragment which corresponds to the adenovirus sequence. This fragment was co-transformed with DNA from either Cla1 linearized pAdHVO (E3− adenovector) or Cla1 linearized pAdHVE3 (E3+adenovector) into *E. coli* BJ5183 competent cells. At least two colonies from each transformation were selected and grown in Terrific™ broth for 6–8 hours until turbidity was reached. DNA was extracted from each cell pellet and then transformed into *E. coli* XL1 competent cells. One colony from each transformation was selected and grown for plasmid DNA purification. The plasmid was analyzed by restriction digestions to identify correct clones. The modified adenovectors were designated MRKpAdHVO (E3− plasmid) and MRKpAdHVE3 (E3+ plasmid). Virus from these new adenovectors (MRKHVO and MRKHVE3, respectively) as well as the old version of the adenovectors were generated in the PER.C6® cell lines to accommodate the following series of viral competition experiments. In addition, the multiple cloning site of the original shuttle vector contained Cla1, BamHI, Xho I, EcoRV, HindIII, Sal I, and Bgl II sites. This MCS was replaced with a new MCS containing Not I, CIa I, EcoRV and Asc I sites. This new MCS has been transferred to the MRKpAdHVO and MRKpAdHVE3 pre-plasmids along with the modification made to the packaging region and pIX gene.

EXAMPLE 6

Analysis of the Effect of the Packaging Signal Extension

Figure 5:
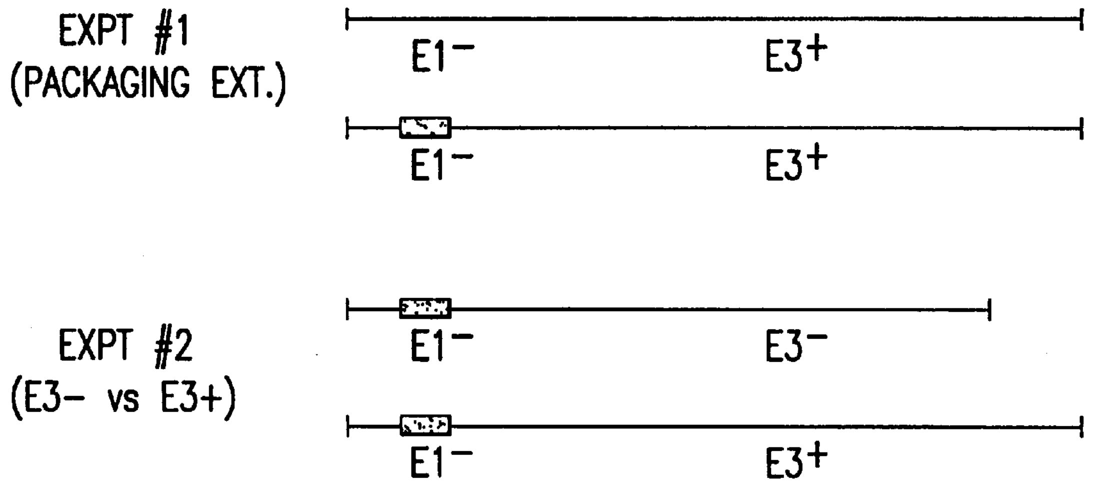
FIG. 5 shows the virus mixing experiments that were carried out to determine the effects of the addition made to the packaging signal region (Expt. #1) and the E3 gene on viral growth (Expt. #2). The bars denote the region of modifications made to the E1 deletion.
Figure 6A:
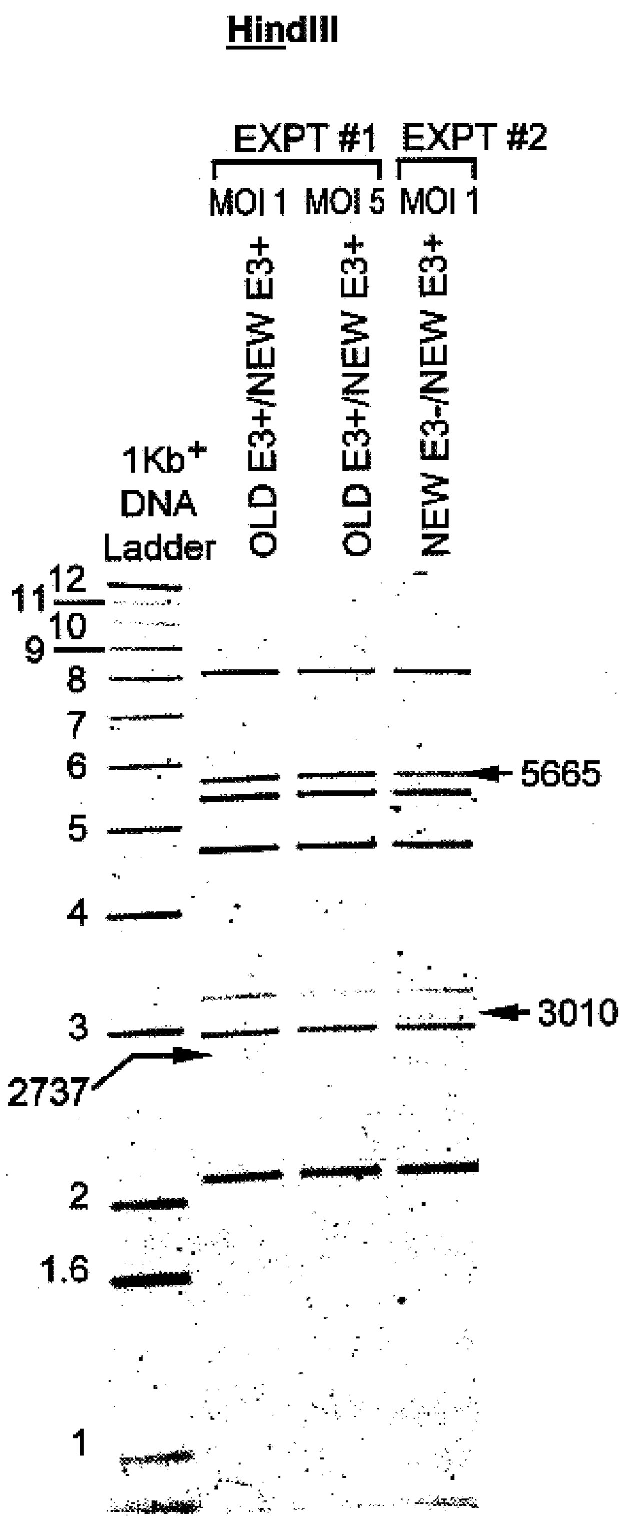
FIGS. 6A–6B show an autoradiograph of viral DNA analysis following the viral mixing experiments described in Examples 6 and 7.
Figure 6B:
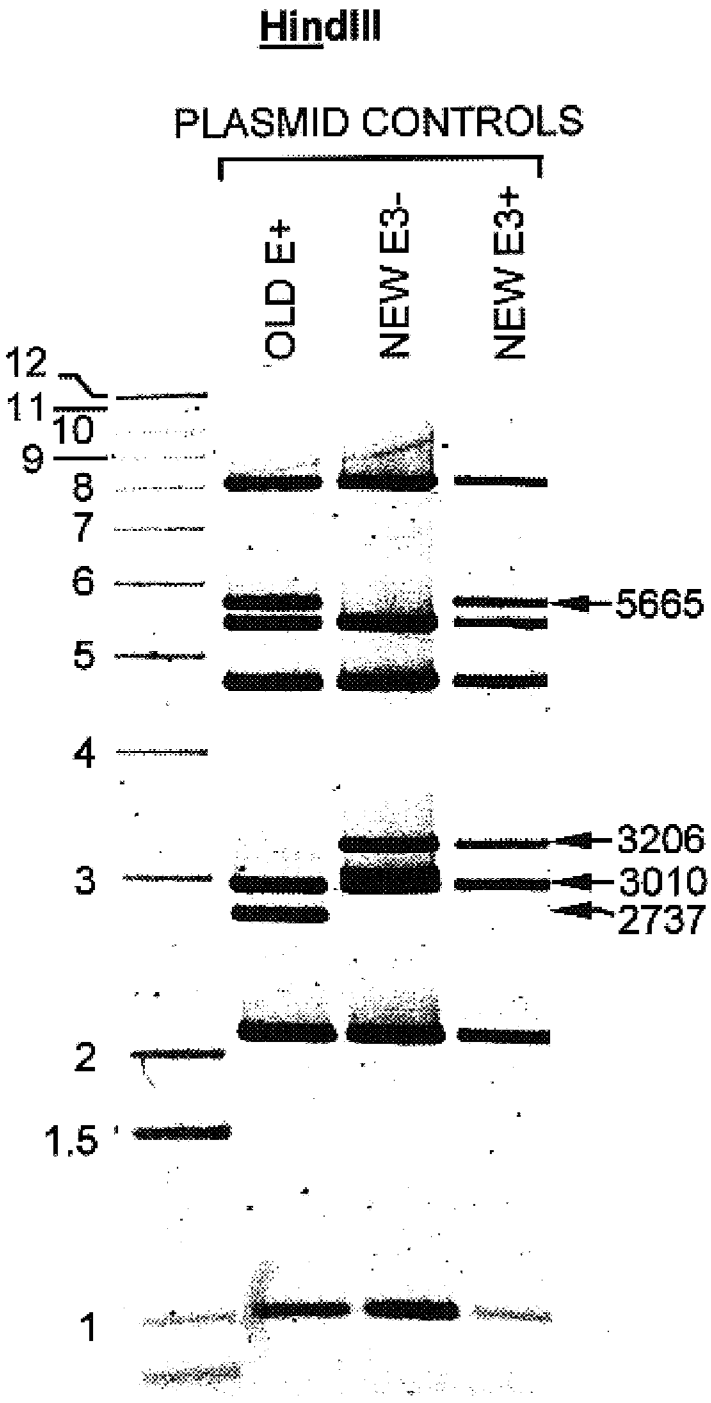

To study the effects of the modifications made to the E1 deletion region, the viruses obtained from the original backbone (pAdHVE3) and the new backbone (MRKpAdHVE3) were mixed together in equal MOI ratios (1:1 and 5:5) and passaged through several rounds; see FIG. 5, Expt.#1. Both of the viruses in the experiment contained the E3 gene intact and did not contain a transgene. The only difference between the two viruses was within the region of the E1 deletion. Following the coinfection of the viruses at P1 (passage 1), the mixtures were propagated through an additional 4 passages at which time the cells were harvested and the virus extracted and purified by CsCl banding. The viral DNA was extracted and digested with HindIII and the digestion products were then radioactively labeled. For the controls, the respective pre-plasmids (pAdHVE3 ("OLD E3+"); MRKpAdHVE3 ("NEW E3+")) were also digested with HindIII (and Pac1 to remove the vector backbone) and subsequently labeled with [$^{33}$P]dATP. The radioactively labeled digestion products were subjected to gel electrophoresis and the gel was dried down onto Whatman paper before being exposed to autoradiographic film. FIG. 6 clearly shows that the new adenovirus which has the addition made to the packaging signal region has a growth advantage compared with the original adenovirus. In the experiments performed (at either ratio tested), only the digestion bands pertaining to the newly modified virus were present. The diagnostic band of size 3,206 (from the new virus) was clearly present. However, there was no evidence of the diagnostic band of size 2,737 bp expected from the original virus.

EXAMPLE 7

Analysis of the Effect of the E3 Gene

The second set of the virus competition study involved mixing equal MOI ratio (1:1) of the newly modified viruses, that obtained from MRKpAdHVO and MRKpAdHVE3 (FIG. 5, Expt. #2). In this set, both viruses had the new modifications made to the E1 deletion. The first virus (that from MRKpAdHVO) does not contain an E3 gene. The second virus (that from MKpAdHVE3) does contain the E3 gene. Neither of the viruses contain a transgene. Following co-infection of the viruses, the mixtures were propagated through an additional 4 passages at which time the cells were harvested and the total virus extracted and purified by CsCl banding. The viral DNA was extracted and digested with HindIII and the digestion products were then radioactively labeled. For the controls, the respective pre-plasmids MRKpAdHVO ("NEW E3−"); MRKpAdHVE3 ("NEW E3+") were also digested with HindIII (and Pac1 to remove the vector backbone) and then labeled with [$^{33}$P]dATP. The radioactively labeled digestion products were subjected to gel electrophoresis and the gel was dried down onto Whatman paper before being exposed to autoradiographic film. FIG. 6 shows the results of the viral DNA analysis of the E3+ virus and E3− virus mixing experiment. The diagnostic band corresponding to the E3+ virus (5,665 bp) was present in greater amount compared with the diagnostic band of 3,010 bp corresponding to the E3− virus. This indicates that the virus that contains the E3 gene is able to amplify more rapidly compared with the virus that does not contain an E3 gene. This increased amplification capacity has been confirmed by growth studies; see Table 4 below.

EXAMPLE 8

Construction of the New Shuttle Vector Containing Modified Gag Transgene—"MRKpdelE1-CMV(No Intron)-FLgag-bGHpA"

The modified plasmid pV1JnsCMV(no intron)-FLgag-bGHpA was digested with Msc1 overnight and then digested with Sfi1 for 2 hours at 50° C. The DNA was then treated with Mungbean nuclease for 30 mins at 30° C. The DNA mixture was desalted using the Qiaex II kit and then Klenow treated for 30 mins at 37° C. to fully blunt the ends of the transgene fragment. The 2,559 bp transgene fragment was then gel purified. The modified shuttle vector (MRKpdelE1 shuttle) was linearized by digestion with EcoRV, treated with calf intestinal phosphatase and the resulting 6,479 bp fragment was then gel purified. The two purified fragments were then ligated together and several dozen clones were screened to check for insertion of the transgene within the shuttle vector. Diagnostic restriction digestion was performed to identify those clones carrying the transgene in the E1 parallel and E1 anti-parallel orientation. This strategy was followed to clone in the other gag transgenes in the MRKpdelE1 shuttle vector.

EXAMPLE 9

Construction of the MRK FG Adenovectors

Figure 7A:
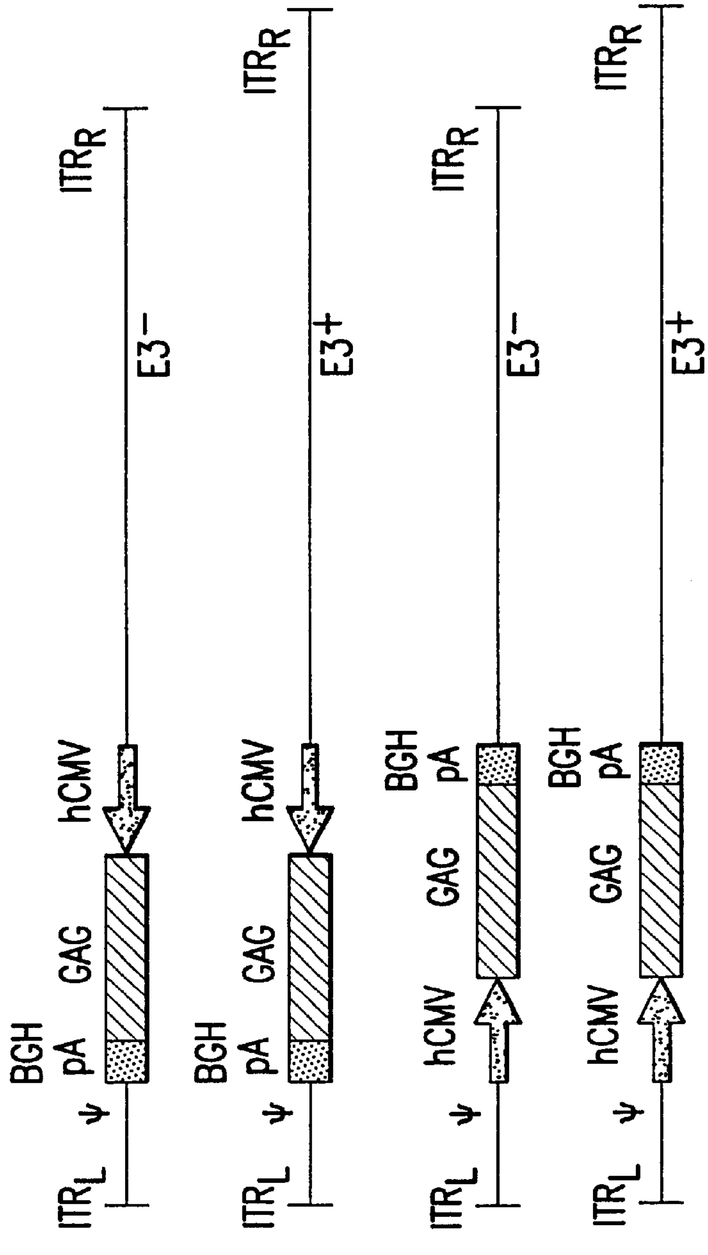
FIGS. 7A, 7B and 7C are as follows.
Figure 7B:
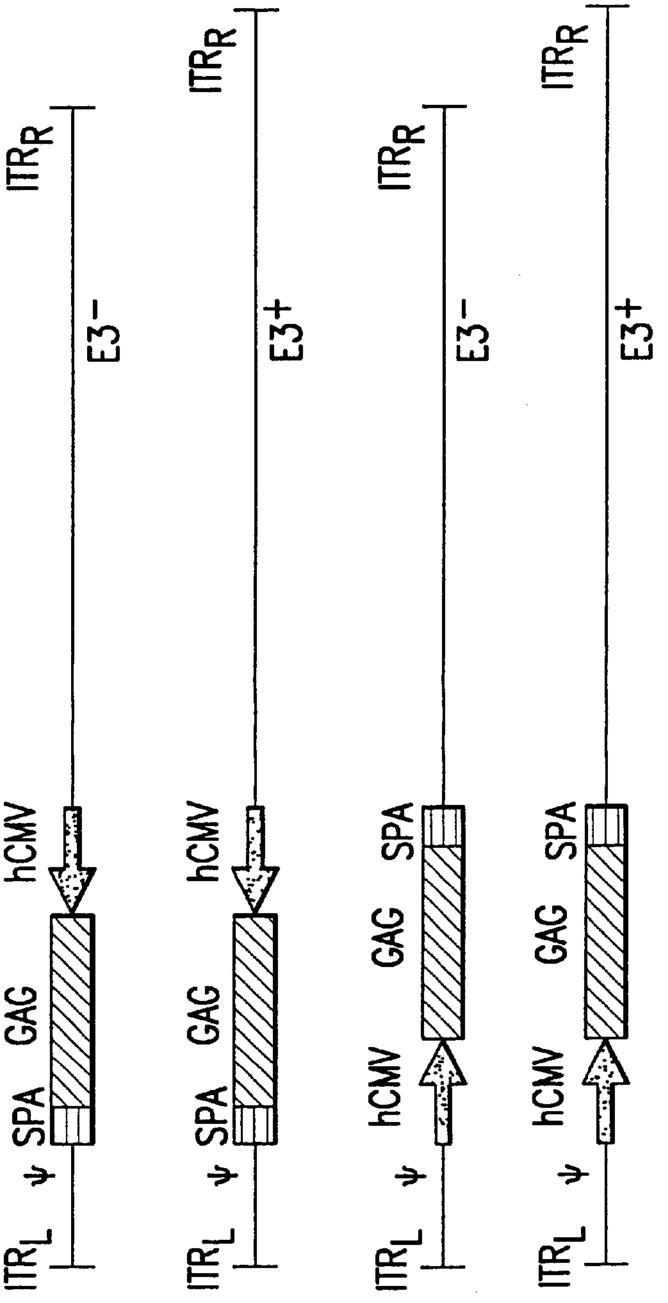
Figure 7C:
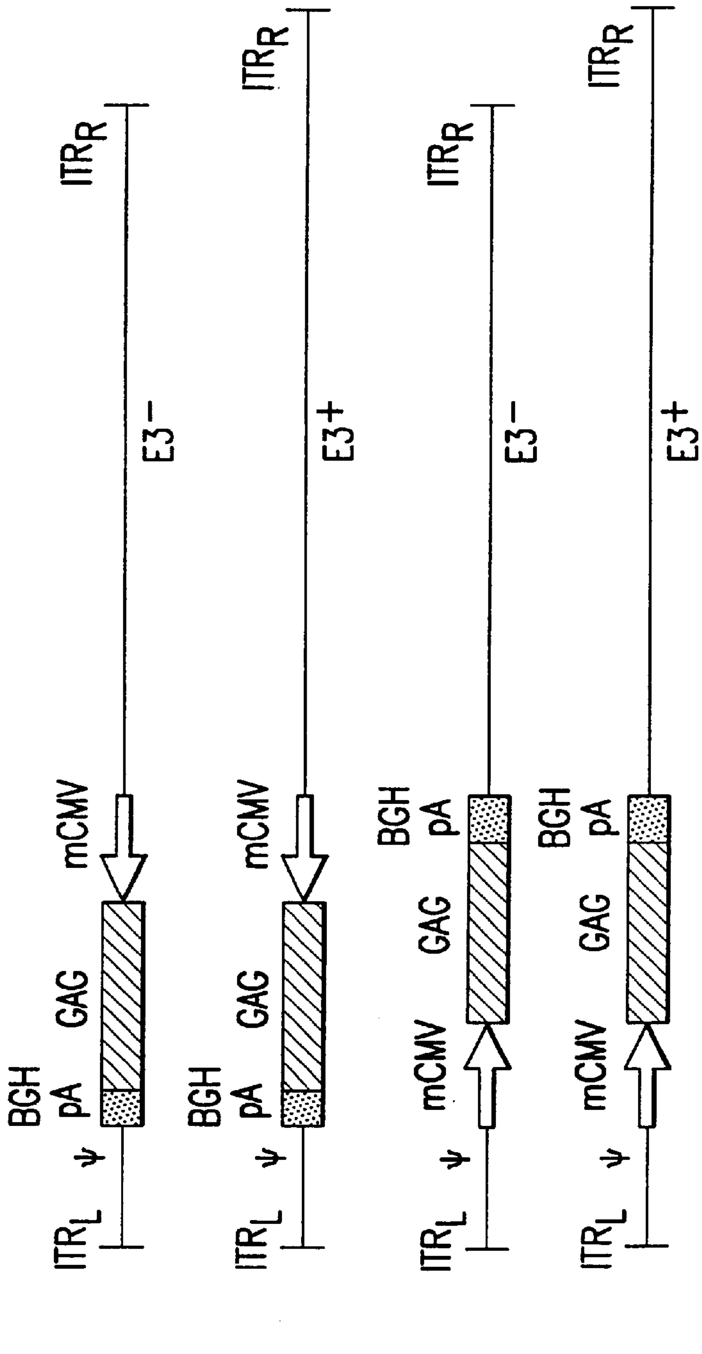

The shuttle vector containing the HIV-1 gag transgene in the E1 parallel orientation, MRKpdelE1-CMV(no intron)-FLgag-bGHpA, was digested with Pac1. The reaction mixture was digested with BsfZ171. The 5,291 bp fragment was purified by gel extraction. The MRKpAdHVE3 plasmid was digested with Cla1 overnight at 37° C. and gel purified. About 100 ng of the 5,290 bp shuttle +transgene fragment and ~100 ng of linearized MRKpAdHVE3 DNA were co-transformed into *E. coli* BJ5183 chemically competent cells. Several clones were selected and grown in 2 ml Terrific™ broth for 6–8 hours, until turbidity was reached. The total DNA from the cell pellet was purified using Qiagen alkaline lysis and phenol chloroform method. The DNA was precipitated with isopropanol and resuspended in 20 μl dH$_2$O. A 2 μl aliquot of this DNA was transformed into *E. coli* XL-1 competent cells. A single colony from each separate transformation was selected and grown overnight in 3 ml LB+100 μg/ml ampicillin. The DNA was isolated using Qiagen columns. A positive clone was identified by digestion with the restriction enzyme BstEII which cleaves within the gag gene as well as the plasmid backbone. The pre-plasmid clone is designated MRKpAdHVE3+CMV(no intron)-FLgag-bGHpA and is 37,498 bp in size. This strategy was followed to generate E3− and E3+ versions of each of the other gag transgene constructions in both E1 parallel and E1 anti-parallel versions. FIGS. 7A, 7B and 7C show the various combinations of adenovectors constructed.

EXAMPLE 10

Plasmid Competition Studies

Figure 8A:
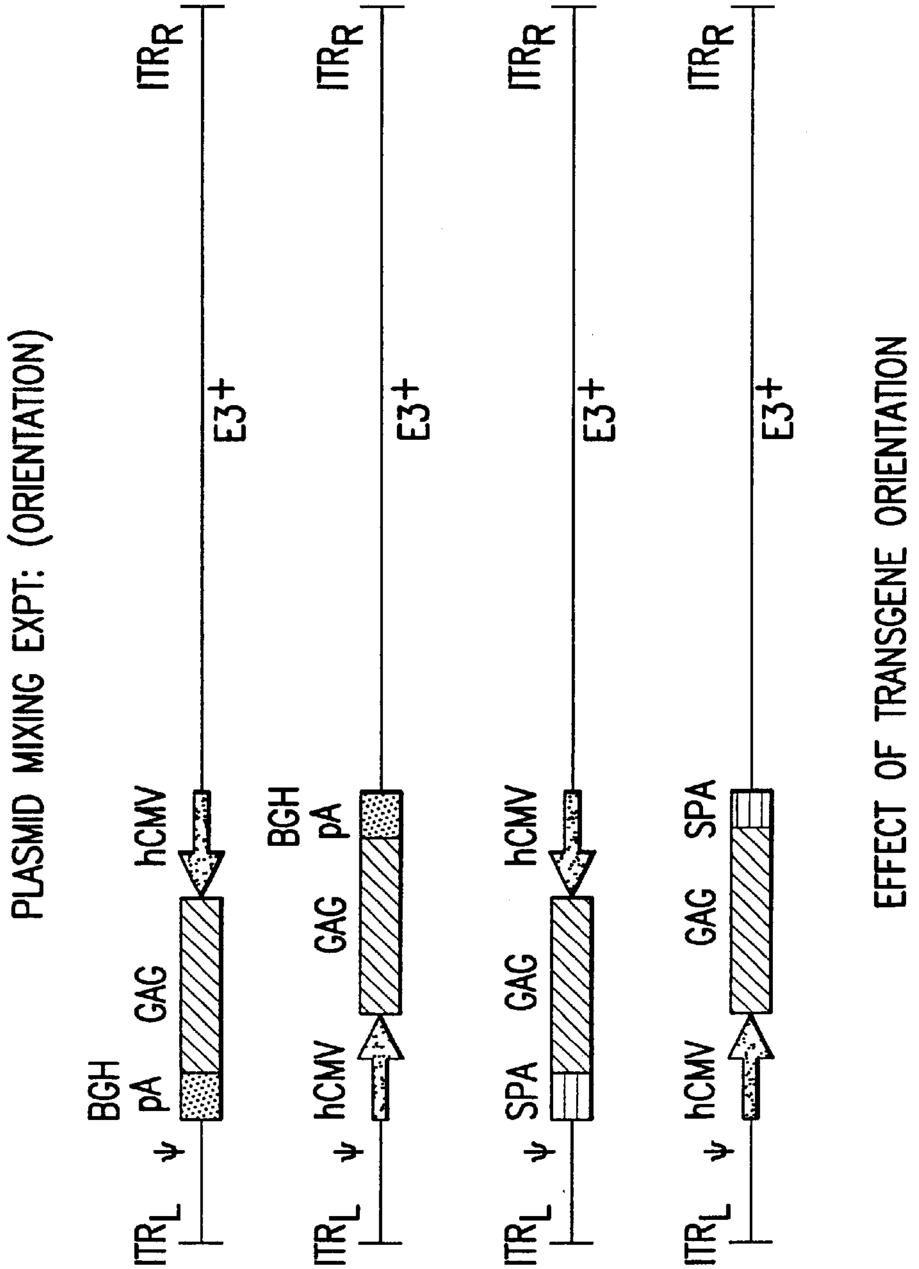
FIG. 8A shows the experiment designed to test the effect of transgene orientation.
Figure 8B:
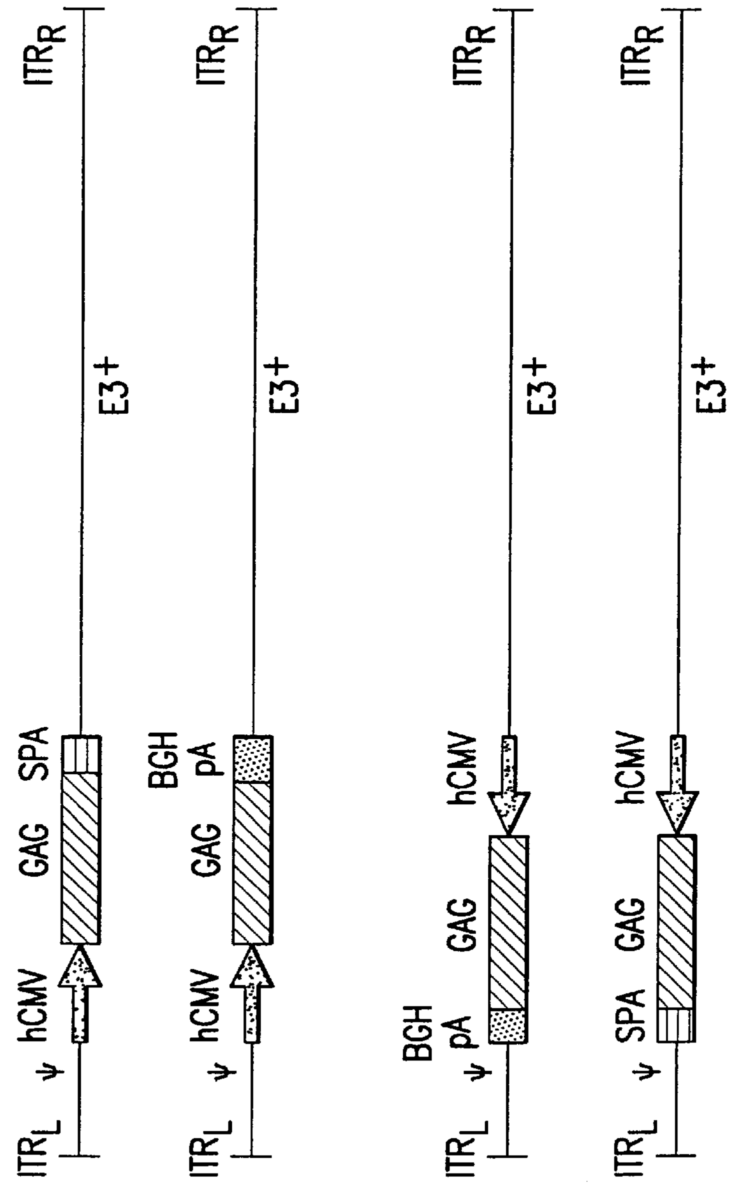
FIG. 8B shows the experiments designed to test the effect of polyadenylation signal.

A series of plasmid competition studies was carried out. Briefly, the screening of the various combinations of new constructs was performed by mixing equal amounts of each of two competing plasmids. In the experiment shown in FIG. 8A, plasmids containing the same transgene but in different orientations were mixed together to create a "competition" between the two plasmids. The aim was to look at the effects of transgene orientation. In the experiment shown in FIG. 8B, plasmids containing different polyadenylation signals (but in the same orientation) were mixed together in equal amounts. The aim was to assess effects of polyA signals. Following the initial transfection, the virus was passaged through ten rounds and the viral DNA analyzed by radioactive restriction analysis.

Analysis of the viral species from the plasmid mixing experiment (FIG. 8A) showed that adenovectors which had the transgene inserted in the E1 parallel orientation amplified better and were able to out-compete the adenovirus which had the transgene inserted in the E1 anti-parallel orientation. Viral DNA analysis of the mixtures at passage 3 and certainly at passage 6, showed a greater ratio of the virus carrying the transgene in the E1 parallel orientation compared with the E1 antiparallel version. By passage 10, the only viral species observed was the adenovector with the transgene in the E1 parallel orientation for both transgenes tested (hCMV(no intron)-FLgag-bGHpA and hCMV(no intron)-FLgag-SPA).

Analysis of the viral species from the plasmid mixing experiment #2 (FIG. 8B) at passages 3 and 6 showed that the polyadenylation signals tested (bGHpA and SPA) did not have an effect on the growth of the virus. Even at passage 10 the two viral species in the mixture were still present in equal amounts.

EXAMPLE 11

Virus Generation of an Enhanced Adenoviral Construct—"MRK Ad5 HIV-1gag"

The results obtained from the competition study allowed us to make the following conclusions: (1) The packaging signal extension is beneficial; (2) Presence of E3 does enhance viral growth; (3) E1 parallel orientation is recommended; and (4) PolyA signals have no effect on the growth of the adenovirus.

MRK Ad5 HIV-1 gag exhibited the most desirable results. This construct contains the hCMV(no intron)-FLgag-bGHpA transgene inserted into the new E3+ adenovector backbone, MRKpAdHVE3, in the E1 parallel orientation. We have designated this adenovector MRK Ad5 HIV-1 gag. This construct was prepared as outlined below:

The pre-plasmid MRKpAdHVE3+CMV(no intron)-FLgag-bGHpA was digested was Pac1 to release the vector backbone and 3.3 μg was transfected by calcium phosphate method (Amersham Pharmacia Biotech.) in a 6 cm dish containing PER.C6® cells at ~60% confluence. Once CPE was reached (7–10 days), the culture was freeze/thawed three times and the cell debris pelleted. 1 ml of this cell lysate was used to infect into a 6 cm dish containing PER.C6® cells at 80–90% confluence. Once CPE was reached, the culture was freeze/thawed three times and the cell debris pelleted. The cell lysate was then used to infect a 15 cm dish containing PER.C6® cells at 80–90% confluence. This infection procedure was continued and expanded at passage 6. The virus was then extracted from the cell pellet by CsCl method. Two bandings were performed (3-gradient CsCl followed by a continuous CsCl gradient). Following the second banding, the virus was dialyzed in A105 buffer. Viral DNA was extracted using pronase treatment followed by phenol chloroform. The viral DNA was then digested with HindIII and radioactively labeled with [$^{33}$P]dATP. Following gel electrophoresis to separate the digestion products the gel was dried down on Whatman paper and then subjected to autoradiography. The digestion products were compared with the digestion products from the pre-plasmid (that had been digested with Pac1/HindIII prior to labeling). The expected sizes were observed, indicating that the virus had been successfully rescued. This strategy was used to rescue virus from each of the various adenovector plasmid constructs prepared.

EXAMPLE 12

Stability Analyses

To determine whether the various adenovector constructs (e.g., MRK Ad5 HIV-1 gag) show genetic stability, the viruses were each passaged continually. The viral DNA was analyzed at passages 3, 6 and 10. Each virus maintained its correct genetic structure. In addition, the stability of the MRK Ad5 HIV-1 gag was analyzed under propagation conditions similar to that performed in large scale production. For this analysis, the transfections of MRK Ad5 HIV-1 gag as well as three other adenoviral vectors were repeated and the virus was purified at P3. The three other adenovectors were as follows: (1) that comprising hCMV(no intron)-Flgag with a bGHpA terminator in an E3− adenovector backbone; (2) that comprising hCMV(no intron)-Flgag with a SPA termination signal in an E3+ adenovector backbone, and that comprising a mCMV-Flgag with a bGHpA terminator in an E3+ adenovector backbone. All of the vectors have the transgene inserted in the E1 parallel orientation. Viral DNA was analyzed by radioactive restriction analysis to confirm that it was correct before being delivered to fermentation cell culture for continued passaging in serum-free media. At P5 each of the four viruses were purified and the viral DNA extracted for analysis by the restriction digestion and radiolabeling procedure. This virus has subsequently been used in a series of studies (in vitro gag expression in COS cells, rodent study and rhesus monkey study) as will be described below. The viruses from P5 are shown in FIG. 9.

Figure 10:
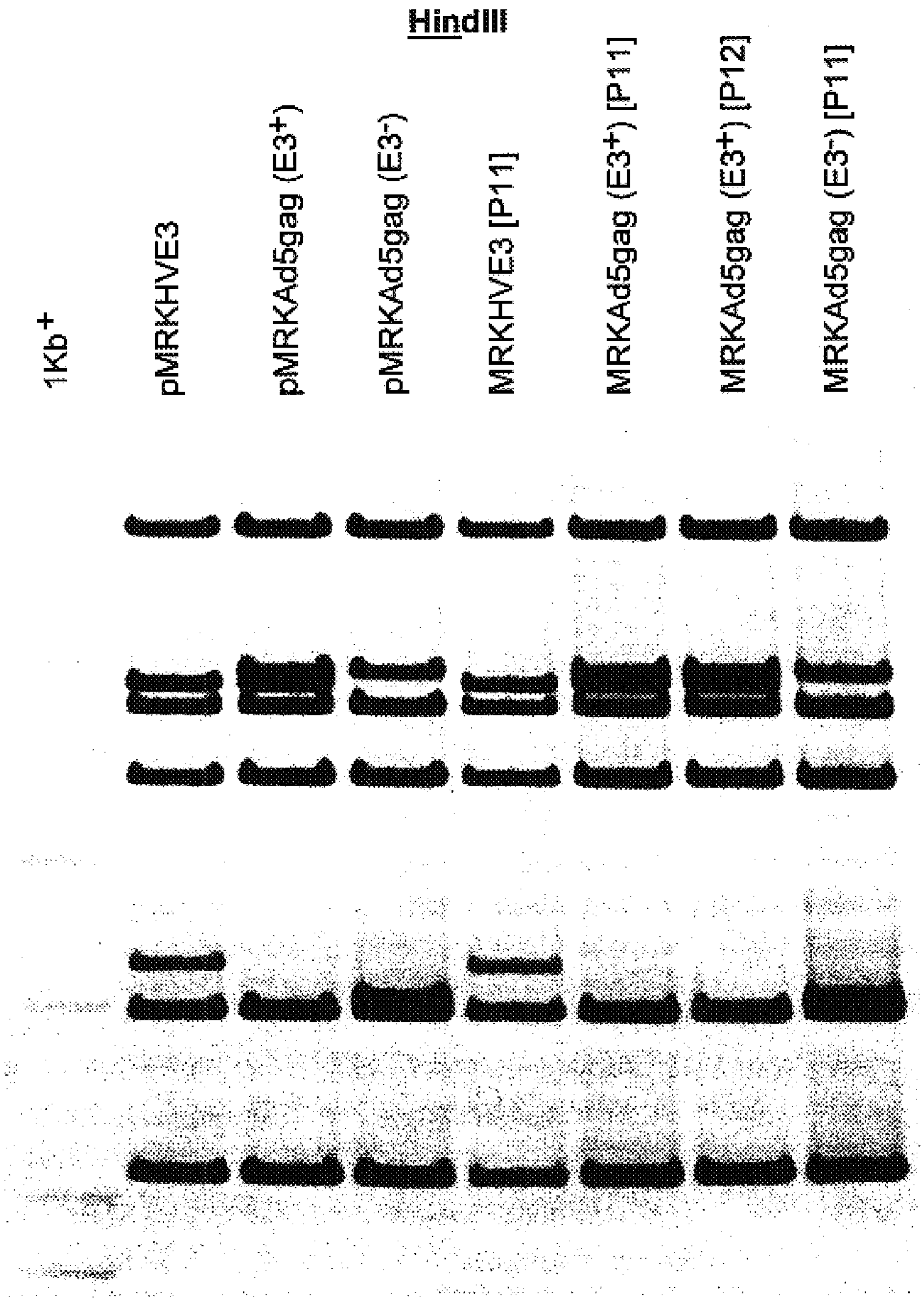
FIG. 10 shows viral DNA analysis of passages 11 and 12 of MRKpAdHVE3, MRKAd5HIV-1gag, and MRKAd5HIV-1gagE3–.

The passaging under serum-free conditions was continued for the MRKHVE3 (transgene-less, obtained from MRK-pAdHVE3 pre-plasmid) and the MRKAd5HIV-1gag (obtained from MRKpAdHVE3+CMV(no intron)-FLgag-bGHpA pre-plasmid) viruses. FIG. 10 shows viral DNA analysis by radioactive restriction digestion at passage 11 for MRKHVE3, MRKAd5HIV-1gagE3–, and passage 11 and 12 for MRKAd5HIV-1gag. Aside from the first lane which is the DNA marker lane, the next three lanes are virus from the pre-plasmid controls (controls based on the original virus)-MRKpAdHVE3 (also referred to as "pMRKHVE3" ), MRKpAdHVE3+CMV(no intron)-FLgag-bGHpA, and pMRKAd5gag(E3–), respectively. As seen in FIG. 10, each of the viral DNA samples show the expected bands with no extraneous bands showing. This signifies that there are no major variant adenovirus species present that can be detected by autoradiography.

Figure 11:
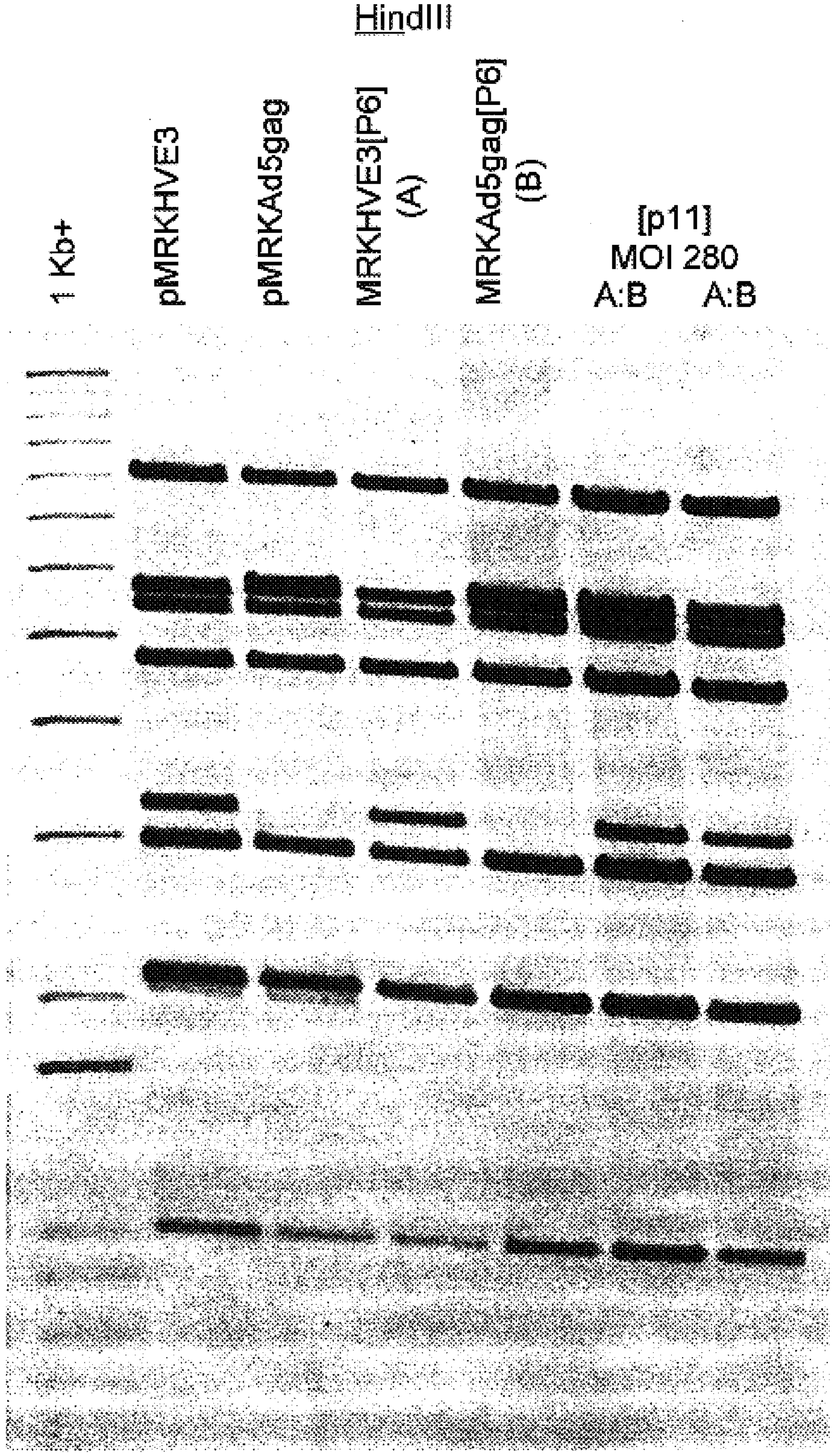
FIG. 11 shows viral DNA analysis (HindIII digestion) of passage 6 MRKpAdHVE3 and MRKAd5HIV-1gag used to initiate the viral competition study. The last two lanes are passage 11 analysis of duplicate passages of the competition study (each virus at MOI of 280 viral particles).

FIG. 11 shows the results of viral competition study between MRKHVE3 and MRKAd5HIV-1gag. These viruses were mixed together at equal MOI (140 viral particles each; 280 vp total) at passage 6 and continued to be passaged until P11. Aside from the first lane which is the DNA marker lane, the next two lanes are the pre-plasmid controls obtained from MRKpAdHVE3 and MRKpAdHVE3+CMV(no intron)-FLgag-bGHpA. The next two lanes are the viral DNA from the starting viral material at passage six. The last two lanes are the competition studies performed in duplicate. The data in FIG. 11 shows the effect the gag transgene in culture. Growth of a MRKAd5gag virus was compared with growth of a "transgene-less" MRKHVE3. These two viruses were infected at the same MOI (i.e. 140 vp each) at passage 6 and then passaged through to passage 11 and the viral pool was analyzed by radioactive restriction analysis. The data shows that one virus did not out compete the other. Therefore, the gag transgene did not show obvious signs of toxicity to the adenovirus.

Figure 12:
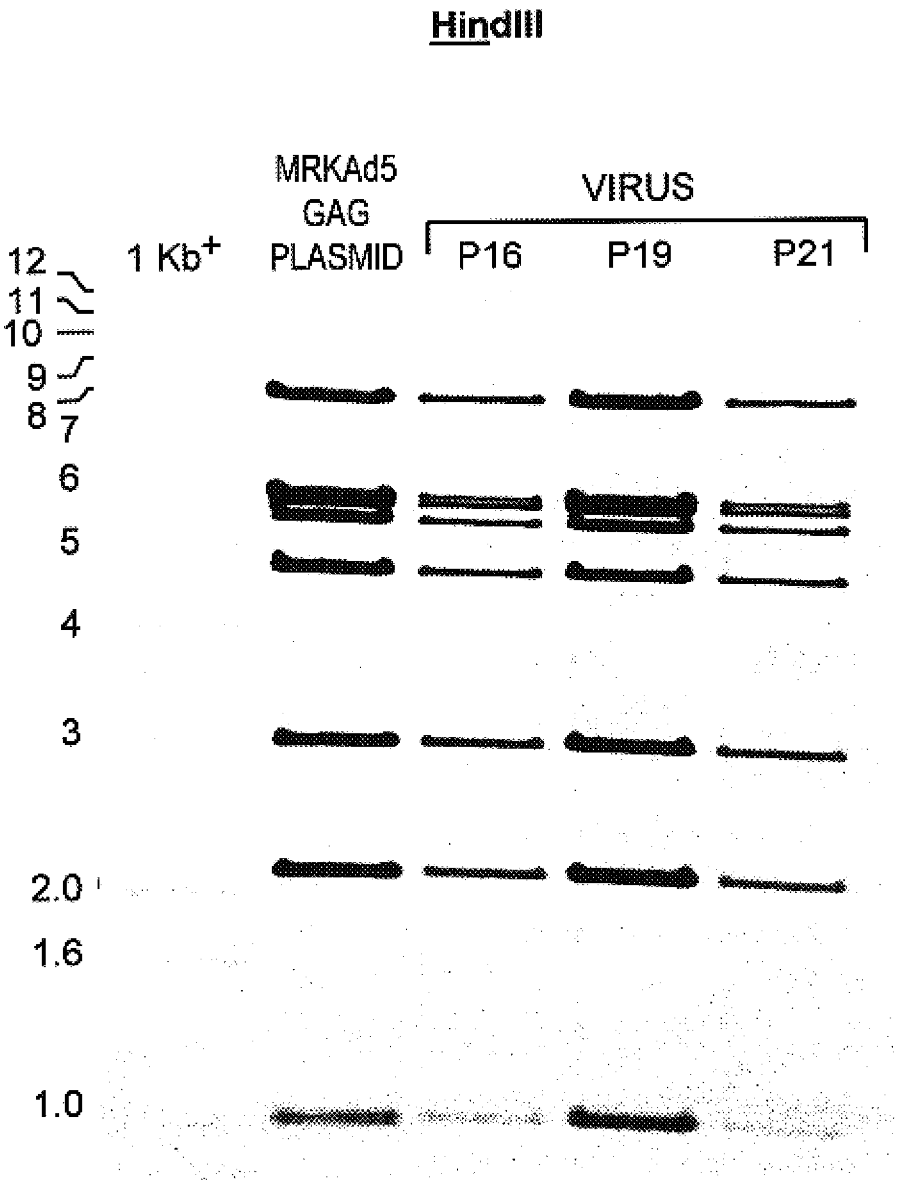
FIG. 12 shows viral DNA analysis by HindIII digestion on high passage numbers for MRKAd5HIV-1gag in serum-containing media with collections made at specified times. The first lane shows the 1 kb DNA size marker. The other lanes represent pre-plasmid control (digested with Pac1 and HindIII), MRKAd5HIV-1gag at P16, P19, and P21.

Analysis by HindIII digestion shows that each virus specie is present in approximately equal amounts. As above, there does not appear to be signs of any extraneous bands. FIG. 12 shows higher passage numbers for MRKAd5HIV-1gag grown under serum-containing conditions. The genome integrity again has been maintained and there is no evidence of rearrangements, even at the highest passage level (P21).

Each of the four vectors shown in FIG. 9 were analyzed for amplification capacity. Table 4 below shows the QPA analysis used in the estimation of viral amplification ratios at P4. The determination of the amplification ratio for the original HIV-1 gag construct is based on the clinical lot at P12. It has been shown that amplification rates increases with higher passage number for the original virus. The reason for this observation is due to the emergence of variants which exhibit increased growth rates compared to the intact adenovector. With continued passaging of the original Ad gag vector, the level of variants increases and hence amplification rates increase also.

The MRK Ad5 HIV-1 gag virus has also been continually passaged under process conditions (i.e., serum-free media). Viral DNA extracted from passages 11 and 12 show no evidence of rearrangement.

TABLE 4

Amplification Ratios Based on AEX and QPA Analysis of Virus Amplification from Passage 3 to Passage 4.

| Ad gag construct | Amplification Ratio |
|---|---|
| MRKAd5gag | 470 |
| HCMV-Flgag-bGHpA [E3–] | 115 |
| HCMV-Flgag-SPA [E3+] | 320 |
| mCMV-FLgag-bGHpA [E3+] | 420 |
| Original construct* | 40–50 |

*This estimation is based on the clinical lot growth characteristics at Passage 12.

EXAMPLE 13

Analytical Evaluation of the Enhanced Ad5 Constructs

To study the effects of the transgene and the E3 gene on virus amplification, the enhanced adenoviral vector, MRK Ad5 HIV-1 gag, along with its transgene-less version (MRKpAdHVE3) and its E3– version (MRK Ad5 HIV-1 gag E3–), was studied for several passages under serum-free conditions. Table 5A shows the amplification ratios determined for passages P3 to P8 for MRK Ad5 HIV-1 gag. Within a certain MOI range, it has been determined that the virus output is directly proportional to the virus input. Therefore, the greater the number of virus particles per cell at infection, the greater the virus amount produced. Viral amplification ratios, on the other hand, are inversely proportional to the virus input. The lower the virus input, the greater the amplification ratio.

Figure 14:
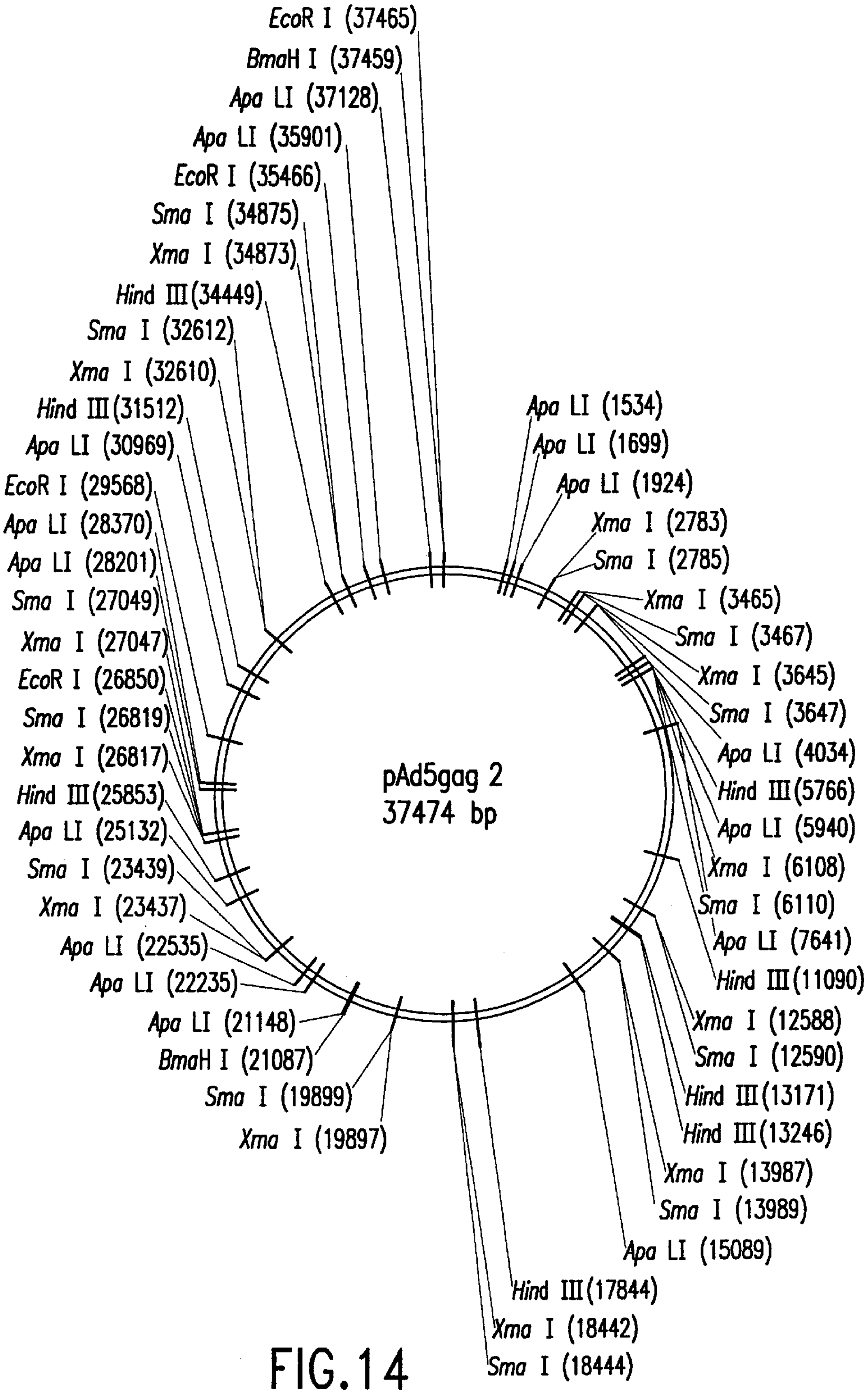
FIG. 14 shows a restriction map of the pMRKAd5HIV-1gag vector.

Table 5B shows the amplification rates of the new E3+ vector backbone MRKpAdHVE3. It has a significantly lower rate of amplification compared with the gag transgene containing version. This may be contributed to the larger size MRK Ad5 HIV-1 gag since it contains the transgene. This inclusion of the transgene brings the size of the adenovirus closer to the size of a wild type Ad5 virus. It is well known that adenoviruses amplify best when they are at close to their wild type genomic size. Wild type Ad5 is 35,935 bp. The MRKpAdHVE3 is 32, 905 bp in length. The enhanced adenovector MRK Ad5 HIV-1 gag is 35,453bp (See FIG. 14 for vector map; see also FIGS. 15A–X show the complete pre-adenoviral vector sequence, which includes an additional 2,021 bp of the vector backbone).

Table 5C shows the amplification rates of the new E3– gag containing virus MRK Ad5 HIV-1 gag E3–. Once again, this virus shows lower growth rate than the enhanced adenoviral vector. This may be attributed to the decreased sized of this virus (due to the E3 gene deletion) compared with wild type Ad5. The MRK Ad5 HIV-1 gag E3– virus is 32,810 bp in length. This can be compared with the wild type Ad5 which is 35,935 bp and MRK Ad5 HIV-1 gag which is 35,453 bp in length.

TABLE 5A

Amplification ratios determined by AEX and QPA for MRKAd5gag over several continuous passaging in serum free media. Following P5, two replicate samples were taken (rep-1 and rep-2) and analyzed.

MRKAd5gag rep1

| | Xv ($10^6$ cells/ml), Viability (%) | | Harvest Time | Cell Passage | Titer $10^{10}$ vp/ | Titer $10^4$ | QPA | Ratio | Amplification | AEX Internal |
|---|---|---|---|---|---|---|---|---|---|---|
| | Infection | Harvest | h.p.l. | Number | ml culture | vp/cell | $10^9$ $TCID_{50}$/ml | AEX:QPA | Ratio | Control |
| P4 | 1.49, 81% | 0.58, 50% | 44 | 46 | 8.7 | 5.9 | 1.72 | 50 | 470 (MOI = 125) | |
| P5 | 1.38, 93% | 0.66, 47% | 48 | 49 | 6.7 | 4.9 | 1.38 | 49 | 170 | |
| P6 | 1.04, 94% | 0.68, 77% | 47 | 48 | 5.8 | 5.6 | 1.42 | 41 | 200 | |
| P7 | 1.50, 84% | 0.96, 61% | 49.5 | 50 | 3.9 | 1.4 | 0.97 | 40 | 50 | |
| P7 | 1.09, 97% | 0.76, 59% | 50 | 52 | 5.2 | 4.7 | 1.70 | 31 | 170 | |
| P8 | 1.03, 94% | 0.86, 64% | 47.5 | 54 | 9.0 | 8.7 | 1.10 | 82 | 310 | |
| P9 | 0.89, 95% | 0.99, 73% | 47.5 | 56 | 4.4 | 4.9 | 1.03 | 43 | 175 | 3.12<br>2.84 |
| P10 | 1.09, 91% | 1.06, 66% | 47.5 | 58 | 3.0 | 2.8 | 1.16 | 26 | 100 | 2.70<br>2.60 |
| P11 | 1.19, 88% | 0.98, 65% | 47 | 60 | 3.6 | 3.0 | 1.15 | 31 | 110 | 2.70<br>2.70 |
| P12 | 0.98, 91% | 0.85, 63% | 47.5 | 47 | 5.4 | 5.5 | 1.20 | 45 | 200 | 2.86<br>2.60 |
| P13 | 1.00, 88% | 0.70, 67% | 49 | 49 | 5.8 | 5.8 | 1.11 | 52 | 210 | 3.18<br>3.18 |
| P14 | 1.94, 92% | 0.88, 67% | 46 | 53 | 8.6 | 4.4 | | | 160 | 3.28<br>3.27 |
| P15 | 0.97, 96% | 0.64, 66% | 47 | 47 | 6.9 | 7.1 | | | 250 | 3.12<br>2.91 |

TABLE 5B

Amplification ratios determined by AEX and QPA for MRKHVE3 over several continuous passaging in serum free media. MRKHVE3 is the new vector backbone which does NOT carry a transgene.

MRKHVE3

| | Xv ($10^6$ cells/ml), Viability (%) | | Harvest Time | Cell Passage | Titer $10^{10}$ vp/ | Titer | QPA | Ratio | Amplification | AEX Internal |
|---|---|---|---|---|---|---|---|---|---|---|
| | Infection | Harvest | h.p.l. | Number | ml culture | $10^4$ vp/cell | $10^9$ $TCID_{50}$/ml | AEX:QPA | Ratio | Control |
| P4 | 1.10, 97% | 1.28, 79% | 49 | 54 | 4.1 | 3.8 | 1.70 | 25 | 300 (MOI = 125) | |
| P5 | 0.92, 89% | 1.18, 77% | 47 | 48 | 4.3 | 4.7 | 1.24 | 35 | 170 | |
| P6 | 1.55, 86% | 1.26, 76% | 49.5 | 50 | 1.2 | 0.8 | 0.56 | 21 | 30 | |
| P6 | 1.09, 97% | 1.11, 81% | 49 | 52 | 4.0 | 3.6 | 1.16 | 34 | 130 | |
| P7 | 1.17, 91% | 1.22, 91% | 47.5 | 54 | 3.7 | 3.2 | 0.50 | 74 | 110 | |
| P8 | 0.98, 88% | 1.41, 83% | 48 | 56 | 2.1 | 2.1 | 0.47 | 45 | 75 | 3.12<br>2.84 |
| P9 | 1.20, 89% | 1.26, 81% | 47.5 | 58 | 0.8 | 0.7 | 0.29 | 28 | 25 | 2.70<br>2.60 |
| P10 | 0.99, 82% | 1.55, 86% | 47 | 60 | 2.3 | 2.3 | 0.43 | 53 | 80 | 2.70<br>2.70 |
| P11 | 1.07, 96% | 1.25, 83% | 48 | 47 | 2.7 | 2.5 | 0.41 | 66 | 90 | 2.86<br>2.60 |
| P12 | 0.80, 91% | 1.14, 80% | 49.5 | 49 | 5.9 | 7.4 | 0.48 | 123 | 260 | 3.18<br>3.18 |
| P13 | 1.96, 95% | 1.14, 85% | 45.5 | 53 | 5.8 | 3.0 | | | 110 | 3.28<br>3.27 |
| P14 | 0.97, 96% | 1.03, 98% | 48.5 | 47 | 9.4 | 9.7 | | | 350 | 3.12<br>2.91 |
| P15 | 0.87, 99% | 0.97, 59% | 49.5 | 49 | 5.3 | 6.1 | | | 218 | 2.78<br>2.52 |

TABLE 5C

Amplification ratios determined by AEX and QPA for MRKAd5gag(E3−) over several continuous passaging in serum free media. This construct is identical to the MRKAd5gag construct except that this version is DELETED of the E3 gene.

MRKAd5gag(E3−)

| | Xv ($10^6$ cells/ml), Viability (%) | | Harvest Time | Cell Passage | Titer $10^{10}$ vp/ | Titer | QPA | Ratio | Amplification | AEX Internal |
|---|---|---|---|---|---|---|---|---|---|---|
| | Infection | Harvest | h.p.l. | Number | ml culture | $10^4$ vp/cell | $10^9$ $TCID_{50}$/ml | AEX:QPA | Ratio | Control |
| P4 | 1.62, 77% | 1.12, 62% | 47.5 | 46 | 2.0 | 1.2 | 0.92 | 20 | 100 | |
| | | | | | | | | | (MOI = 125) | |
| P5 | 1.16, 92% | 0.62, 43% | 49 | 49 | 3.3 | 2.9 | 0.99 | 34 | 100 | |
| P6 | 1.71, 86% | 0.20, 10% | 49 | 50 | 4.7 | 2.7 | 1.70 | 28 | 100 | |
| P6 | 1.09, 97% | 0.63, 54% | 49.5 | 52 | 5.4 | 5.0 | 1.76 | 31 | 180 | |
| P7 | 1.17, 91% | 0.98, 72% | 47.50 | 54 | 7.1 | 6.1 | 0.67 | 106 | 220 | |
| P8 | 0.98, 88% | 0.77, 48% | 48 | 56 | 3.1 | 3.2 | 0.66 | 47 | 115 | 3.12 |
| | | | | | | | | | | 2.84 |
| P9 | 1.20, 89% | 1.03, 72% | 48 | 58 | 1.8 | 1.5 | 0.57 | 32 | 55 | 2.70 |
| | | | | | | | | | | 2.60 |
| P10 | 0.99, 82% | 0.80, 62% | 46.5 | 60 | 3.2 | 3.2 | 0.68 | 47 | 115 | 2.70 |
| | | | | | | | | | | 2.70 |
| P11 | 1.07, 96% | 0.98, 70% | 48.5 | 47 | 5.9 | 5.5 | 0.68 | 87 | 200 | 2.86 |
| | | | | | | | | | | 2.60 |
| P12 | 0.80, 91% | 0.67, 59% | 50 | 49 | 5.1 | 6.4 | 0.72 | 71 | 230 | 3.18 |
| | | | | | | | | | | 3.18 |
| P13 | 1.96, 95% | 0.91, 59% | 45.5 | 53 | 7.4 | 3.8 | | | 135 | 3.28 |
| | | | | | | | | | | 3.27 |
| P14 | 0.97, 96% | 0.81, 74% | 48 | 47 | 6.8 | 7.0 | | | 250 | 3.12 |
| | | | | | | | | | | 2.91 |
| P15 | 0.87, 99% | 0.84, 56% | 49 | 49 | 4.8 | 5.5 | | | 196 | 2.78 |
| | | | | | | | | | | 2.52 |

EXAMPLE 14

Gag Expression Analysis of the Novel Constructs

In vitro gag analysis of the MRK Ad5 HIV-1 gag and the original HIV-gag vectors (research and clinical lot) show comparable gag expression. The clinical lot shows only a slightly reduced gag expression level. The most noticeable difference is with the mCMV vector. This vector shows roughly 3 fold lower expression levels compared with the other vectors tested (which all contain hCMV promoters). The mCMV-FLgag with bGHpA assay was performed three times using different propagation and purification lots and it consistently exhibited weaker gag expression.

EXAMPLE 15

Evaluation of MRK Ad5 HIV-1 gag and Other gag-Containing Adenovectors in Balb/c Mice Cohorts of 10 balb/c mice were vaccinated intramuscularly with escalating doses of MRK Ad5 HIV-1 gag, and the research and clinical lots of original Ad5HIV-1gag. Serum samples were collected 3 weeks post dose 1 and analyzed by anti-p24 sandwich ELISA.

Figure 13:
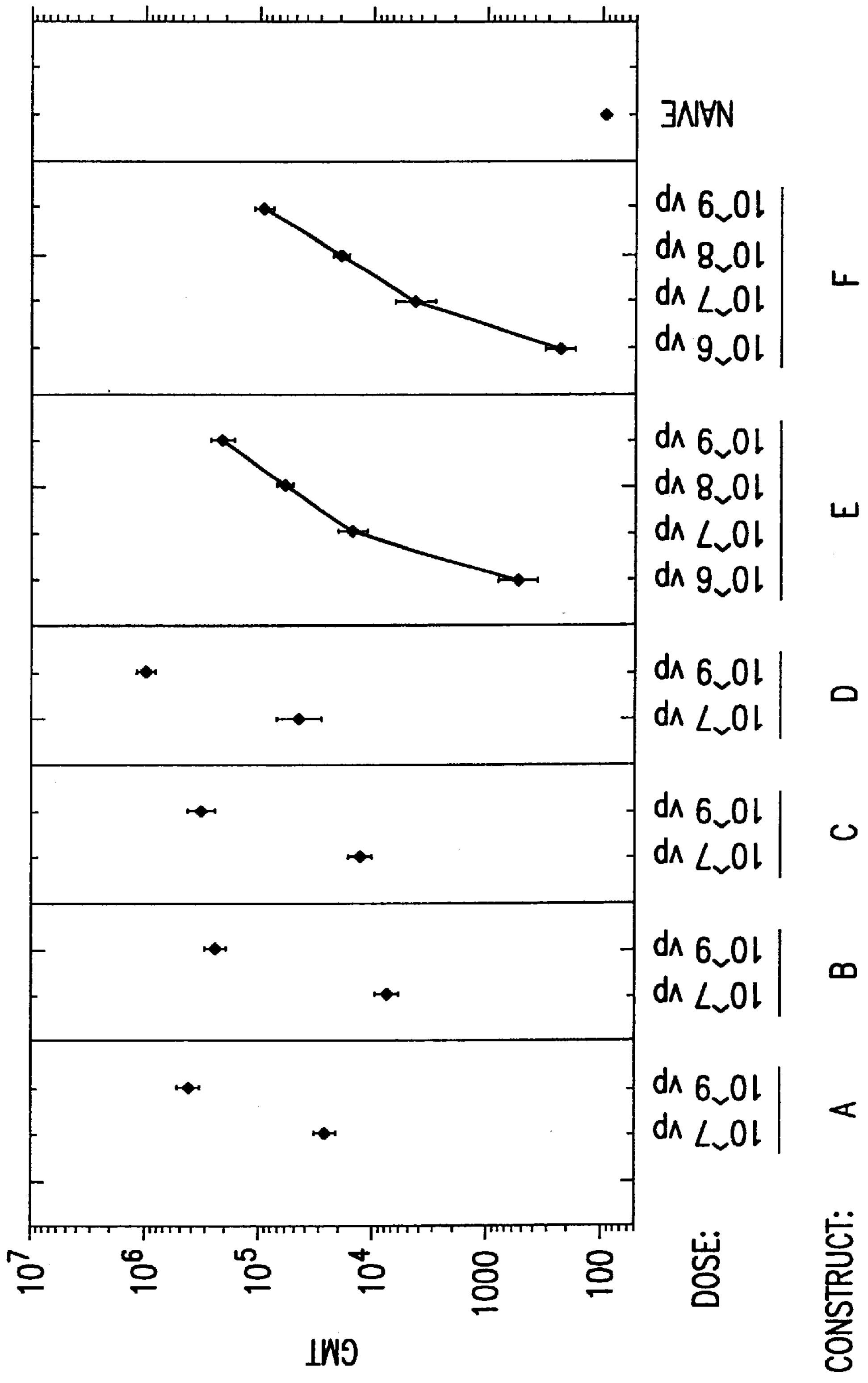
FIG. 13 shows serum anti-p24 levels at 3 wks post i.m. immunization of balb/c mice (n=10) with varying doses of several Adgag constructs: (A) MRK Ad5 HIV-1 gag (through passage 5); (B) MRKAd5 hCMV-FLgag-bGHpA (E3–); (C) MRKAd5 hCMV-FLgag-SPA (E3+); (D) MRKAd5 mCMV-FLgag-bGHpA (E3+); (E) research lot (293 cell-derived) of Ad5HIV-1 gag; and (F) clinical lot (Ad5gagFN0001) of Ad5HIV-1 gag. Reported are the geometric mean titers (GMT) for each cohort along with the standard error bars.

Anti-p24 titers in mice that received MRK Ad5 HIV-1 gag (107 and 109 vp(viral particle) doses) were comparable (FIG. 13) to those of the research lot of Ad5HIV-1 gag, for which much of the early rhesus data were generated on. These titers were also comparable when E3 is deleted (MRKAd5hCMVgagbGHpA(E3−)) or SPA is substituted for bGHpA terminator (MRKAd5 hCMV-gag-SPA (E3+)) or murine CMV promoter is used in place of hCMV (MRKAd5 mCMV-gag-bGHpA (E3+)) in the MRKAd5 backbone.

The results shown in Table 7 indicate that the three other vectors (in addition to the preferred vector, MRK Ad5 HIV-1 gag, are also capable of inducing strong anti-gag antibody responses in mice. Interestingly enough, while the mCMV-FLgag construct containing bGHpA and E3+ in an E1 parallel orientation showed lowest gag expression in the COS cell in vitro infection (Table 6) in comparison with the other vectors tested, it generated the greatest anti-gag antibody response this in vivo Balb/c study. Table 7 also shows a dose response in anti-gag antibody production in both the research and the clinical lot. As expected, the clinical lot shows reduced anti-gag antibody induction at each dosage level compared to the same dosage used for the research lot.

TABLE 6

In vitro analysis for gag expression in COS cells by Elisa assay.

| Viral Vectors[a] | μg gag/4.8 × 10e5 COS/10e8 parts/48 hr |
|---|---|
| MRKAd5gag[b] | 1.40 |
| Clinical lot Ad5gag[c] | 1.28 |
| Research lot Ad5gag[d] | 1.32 |
| MCMVFL-gagbGHpA[e] | 0.42 |

[a]$A_{260nm}$ absorbance readings taken for viral particle determinations.

[b]MRKAd5gag was produced in serum free conditions and purified at P5.

[c]Clinical lot# Ad5gagFN0001

[d]Research Ad5FLgag lot# 6399

[e]mCMVFL-gagbGHpA was produced in serum free conditions and purified at P5.

TABLE 7 mHIV020 Anti-p24 Ab Titers in Balb/c mice (n = 10) vaccinated with various Adgag constructs and lots (3 week post dose1).

| Group ID | Vaccine | Dose (vp) | GMT | SE upper | SE lower |
|---|---|---|---|---|---|
| 1 | [a]MRKAd5gag | 10^7 | 25600 | 5877 | 4780 |
| 2 | " | 10^9 | 409600 | 94028 | 76473 |
| 3 | hCMV FL-gag bGHpA [E3−] → | 10^7 | 7352 | 2077 | 1620 |
| 4 | " | 10^9 | 235253 | 59767 | 47659 |
| 5 | hCMV FL-gag SPA [E3+] → | 10^7 | 12800 | 9905 | 236 |
| 6 | " | 10^9 | 310419 | 99181 | 75165 |
| 7 | [b]mCMV FL-gag bGHpA [E3+] → | 10^7 | 44572 | 23504 | 15389 |
| 8 | " | 10^9 | 941014 | 239068 | 190636 |
| 9 | [c]hCMV FL-gag bGHpA [E3−] ← | 10^7 | 3676 | 934 | 745 |
| 10 | " | 10^9 | 117627 | 17491 | 15227 |
| 11 | research lot hCMV intronA FL-gag bGHpA [E3−] <− | 10^6 | 528 | 262 | 175 |
| 12 | " | 10^7 | 14703 | 5274 | 3882 |
| 13 | " | 10^8 | 58813 | 14942 | 11915 |
| 14 | " | 10^9 | 204800 | 53232 | 42250 |
| 15 | clinical lot hCMVintronA FL-gag bGHpA [E3−] <− | 10^6 | 230 | 82 | 61 |
| 16 | " | 10^7 | 4222 | 3405 | 1138 |
| 17 | " | 10^8 | 19401 | 3939 | 3274 |
| 18 | " | 10^9 | 89144 | 25187 | 19639 |
| 19 | Naïve | none | 93 | 7 | 6 |

*2 × 50 $\mu$L i.m. (quad) injections/animal
P.l.s: Youil, Chen, Casimiro
Vaccination: T. Toner, Q. Su
Assay: M. Chen
[a]The structure of MRKAd5gag is: hCMVFL-gagbGHpA [E3+] → The same lot of MRKAd5gag used in this rodent study was used in the Rhesus monkey study (Tables 7 and 8).
[b]The same lot of mCMVFL-gagbGHpA[E3+] used in the in vitro study (Table 6) ws used here.
[c]This construct was designed by Volker Sandig. It contains a shorter version of the hCMV promoter than that used in the MRK constructs. The adenovector backbone is identical to the original backbone used in the original Adgag vector. Expression at 10e7 dose from this vector is 7 fold lower then the same dose of the MRKAd5gag and 4 fold lower than the research lot.

EXAMPLE 16

Comparison of Humoral and Cellular Responses Towards the Original Ad-gag Construct with the New MRK Ad5 HIV-1 gag in Rhesus Monkeys Cohorts of 3 rhesus monkeys were vaccinated intramuscularly with MRK Ad5 HIV-1 gag or the clinical Ad5gag bulk at two doses, $10^{11}$ vp and $10^9$ vp. Immunizations were conducted at week 0, 4, and 25. Serum and PBMC samples were collected at selected time points. The serum sample were assayed for anti-p24 Ab titers (using competitive based assay) and the PBMCs for antigen-specific IFN-gamma secretion following overnight stimulation with gag 20-mer peptide pool (via ELISpot assay).

The results shown in Table 8 indicate comparable responses with respect to the generation of anti-gag antibodies. The frequencies of gag-specific T cells in peripheral blood assummarized in Table 9 demonstrate a strong cellular immune response generated after a single dose with the new construct MRK Ad5 HIV-1 gag. The responses are also boostable with second dose of the same vector. The vector is also able to induce CD8+ T cell responses (as evident by remaining spot counts after CD4+ depletion of PBMCs) which are responsible for cytotoxic activity.

TABLE 8

Anti-p24 antibody titers (in mMU/mL) in rhesus macaques immunized with gag-expressing adenovectors (Protocol HIV203).

| Vaccine | Pre | Wk 4 | Wk 8 | Wk 12 | Wk 16 | Wk 20 | Wk 25 | Wk 28 |
|---|---|---|---|---|---|---|---|---|
| MRKAd5gag[a], 10^11 vp | | | | | | | | |
| 97N010 | <10 | 118 | 5528 | 11523 | 7062 | 21997 | ND | 51593 |
| 97N116 | <10 | 62 | 772 | 1447 | 1562 | 2174 | ND | 20029 |
| 98X007 | <10 | 66 | 3353 | 6156 | 6845 | 3719 | ND | 24031 |
| MRKAd5gag, 10^9 vp | | | | | | | | |
| 97N120 | <10 | 51 | 204 | 318 | 366 | 482 | ND | 6550 |
| 97N144 | <10 | 18 | 118 | 274 | 706 | 888 | ND | 7136 |

TABLE 8-continued

Anti-p24 antibody titers (in mMU/mL) in rhesus macaques immunized with gag-expressing adenovectors (Protocol HIV203).

| Vaccine | Pre | Wk 4 | Wk 8 | Wk 12 | Wk 16 | Wk 20 | Wk 25 | Wk 28 |
|---|---|---|---|---|---|---|---|---|
| 98X008 | <10 | 15 | 444 | 386 | 996 | 1072 | ND | 12851 |
| Ad5 gag[b], Clinical Lot, 10^11 vp | | | | | | | | |
| 97X001 | <10 | 87 | 2579 | 4718 | 7174 | 7250 | ND | 69226 |
| 97N146 | <10 | 72 | 3604 | 7380 | 7526 | 18906 | ND | 60283 |
| 98X009 | <10 | 78 | 4183 | 3946 | 3124 | 6956 | ND | 26226 |
| Ad5 gag, Clinical Lot, 10^9 vp | | | | | | | | |
| 97N020 | <10 | <10 | 143 | 371 | 390 | 1821 | ND | 17177 |
| 97X003 | <10 | <10 | 39 | 93 | 156 | 596 | ND | 2053 |
| 98X012 | <10 | 81 | 342 | 717 | 956 | 1558 | ND | 11861 |

[a]MRKAd5gag (hCMV, bGHpA, E3+)
[b]original Ad5gag vector (hCMV/Intron A, bGHpA, E3−), lot#F N0001
ND, not determined

TABLE 9

Number of gag-specific T cells per million peripheral blood mononuclear cells (PBMCs) in rhesus monkeys immunized with gag-expressing adenovectors. Also included are those frequencies in PBMCs depleted of $CD4^+$ T cells.

| | Vaccination | Monkey | T = 4 Wk | | T = 6 Wk | | T = 11 Wk | | T = 16 Wk | | T = 25 Wk | | T = 28 Wk | |
|---|---|---|---|---|---|---|---|---|---|---|---|---|---|---|
| Grp# | T = 0, 4, 25 wks | ID | Media[a] | Gag H[b] | Media | Gag H | Media | Gag H | Media | Gag H | Media | Gag H | Media | Gag H |
| 1 | MRKAd5gag 10^11 vp | 97N010 | 6 | 89 | 0 | 395 | 0 | 1058 | 0 | 1174 | 3 | 775 | 4 | 1074 |
| | | 97N010 (CD4−) | 4 | 38 | | | 3 | 993 | | | 0 | 76 | 0 | 594 |
| | | 97N116 | 1 | 396 | 1 | 609 | 0 | 534 | 4 | 395 | 1 | 261 | 0 | 408 |
| | | 97N116 (CD4−) | 11 | 676 | | | 0 | 593 | | | 0 | 184 | 0 | 666 |
| | | 98X007 | 10 | 579 | 0 | 1304 | 3 | 2193 | 1 | 2118 | 3 | 1588 | 0 | 2113 |
| | | 98X007 (CD4−) | 20 | 965 | | | 0 | 2675 | | | 0 | 1656 | 0 | 1278 |
| 2 | MRKAd5gag 10^9 vp | 97N120 | 5 | 275 | 1 | 249 | 4 | 141 | 4 | 119 | 9 | 206 | 4 | 219 |
| | | 97N120 (CD4−) | 11 | 170 | | | 0 | 85 | | | 0 | 75 | 1 | 219 |
| | | 97N144 | 3 | 236 | 6 | 438 | 1 | 318 | 3 | 256 | 1 | 98 | 5 | 373 |
| | | 97N144 (CD4−) | 6 | 148 | | | 0 | 285 | | | ND | ND | 0 | 625 |
| | | 98X008 | 4 | 368 | 1 | 1090 | 3 | 891 | 4 | 673 | 3 | 473 | 5 | 735 |
| | | 98X008 (CD4−) | 14 | 696 | | | 0 | 1175 | | | 0 | 391 | 4 | 848 |
| 3 | Ad5gag clinical lot 10^11 vp | 97X001 | 0 | 261 | 1 | 485 | 0 | 817 | 0 | 1220b | 1 | 894 | 0 | 1858 |
| | | 97X001 (CD4−) | 10 | 283 | | | 3 | 996 | | | 0 | 1010 | 0 | 1123 |
| | | 97N146 | 3 | 150 | 1 | 465 | 0 | 339 | 1 | 1272 | 3 | 1238 | 3 | 1785 |
| | | 97N146 (CD4−) | 6 | 133 | | | 0 | 370 | | | 0 | 654 | 0 | 971 |
| | | 98X009 | 0 | 93 | 3 | 339 | 3 | 559 | 0 | 896 | 1 | 384 | 0 | 1748 |
| | | 98X009 (CD4−) | 0 | 73 | | | 0 | 333 | | | 0 | 225 | 0 | 644 |
| 4 | Ad5gag clinical lot 10^9 vp | 97N020 | 3 | 30 | 1 | 101 | 0 | 66 | 0 | 36 | 0 | 26 | 0 | 41 |
| | | 97N020 (CD4−) | 10 | 29 | | | 0 | 15 | | | 0 | 1 | 0 | 16 |
| | | 97X003 | 4 | 68 | 5 | 134 | 0 | 18 | 1 | 38 | 4 | 38 | 6 | 81 |
| | | 97X003 (CD4−) | 9 | 40 | | | 0 | 6 | | | 0 | 4 | 0 | 19 |
| | | 98X012 | 5 | 95 | 3 | 54 | 1 | 34 | 0 | 18 | 0 | 20 | 1 | 121 |
| | | 98X012 (CD4−) | 11 | 70 | | | 0 | 11 | | | 0 | 8 | 0 | 41 |

TABLE 9-continued

Number of gag-specific T cells per million peripheral blood mononuclear cells (PBMCs) in rhesus monkeys immunized with gag-expressing adenovectors. Also included are those frequencies in PBMCs depleted of $CD4^+$ T cells.

| | Vaccination | Monkey | T = 4 Wk | | T = 6 Wk | | T = 11 Wk | | T = 16 Wk | | T = 25 Wk | | T = 28 Wk | |
|---|---|---|---|---|---|---|---|---|---|---|---|---|---|---|
| Grp# | T = 0, 4, 25 wks | ID | Media[a] | Gag H[b] | Media | Gag H | Media | Gag H | Media | Gag H | Media | Gag H | Media | Gag H |
| 5 | Naïve | 96R041 | 6 | 8 | 1 | 1 | 0 | 0 | 0 | 0 | 0 | 0 | 1 | 0 |
| | | 053F | 14 | 18 | 5 | 16 | 20 | 14 | 19 | 15 | 10 | 15 | 24 | 9 |

Based on either 4 × 10^5 or 2 × 10^5 cells per well (depending on spot density)
ND, not determined
[a]mock or no peptide control
[b]Pool of 20-aa peptides overlapping by 10 aa and encompassing the gag sequence The adenovectors described herein and, particularly, MRK Ad5 HIV-1 gag, represent very promising HIV-gag adenovectors with respect to their enhanced growth characteristics in both serum and, more importantly, in serum-free media conditions. In comparison with the current HIV-1 gag adenovector construct, MRK Ad5 HIV-1 gag shows a 5–10 fold increased amplification rate. We have shown that it is genetically stable at passage 21. This construct is able to generate significant cellular immune responses in vivo even at a relatively low dose of 10^9 vp. The potency of the MRKAd5gag construct is comparable to, if not better than the original HIV-1gag vector as shown in this rhesus monkey study.

EXAMPLE 17

Codon Optimized HIV-1 pol and Codon Optimzed HIV-1 pol Modifications

The open reading frames for the various synthetic pol genes disclosed herein comprise coding sequences for the reverse transcriptase (or RT which consists of a polymerase and RNase H activity) and integrase (IN). The protein sequence is based on that of Hxb2r, a clonal isolate of IIIB; this sequence has been shown to be closest to the consensus clade B sequence with only 16 nonidentical residues out of 848 (Korber, et al., 1998, Human retroviruses and AIDS, Los Alamos National Laboratory, Los Alamos, New Mexico). The skilled artisan will understand after review of this specification that any available HIV-1 or HIV-2 strain provides a potential template for the generation of HIV pol DNA vaccine constructs disclosed herein. It is further noted that the protease gene is excluded from the DNA vaccine constructs of the present invention to insure safety from any residual protease activity in spite of mutational inactivation. The design of the gene sequences for both wild-type (wt-pol) and inactivated pol (IA-pol) incorporates the use of human preferred ("humanized") codons for each amino acid residue in the sequence in order to maximize in vivo mammalian expression (Lathe, 1985*, J. Mol. Biol.* 183:1–12). As can be discerned by inspecting the codon usage in SEQ ID NOs: 1, 3, 5 and 7, the following codon usage for mammalian optimization is preferred: Met (ATG), Gly (GGC), Lys (AAG), Trp (TGG), Ser (TCC), Arg (AGG), Val (GTG), Pro (CCC), Thr (ACC), Glu (GAG); Leu (CTG), His (CAC), Ile (ATC), Asn (AAC), Cys (TGC), Ala (GCC), Gln (CAG), Phe (TTC) and Tyr (TAC). For an additional discussion relating to mammalian (human) codon optimization, see WO 97/31115 (PCT/US97/02294), which, as noted elsewhere in this specification, is hereby incorporated by reference. It is intended that the skilled artisan may use alternative versions of codon optimization or may omit this step when generating HIV pol vaccine constructs within the scope of the present invention. Therefore, the present invention also relates to non-codon optimized versions of DNA molecules and associated recombinant adenoviral HIV vaccines which encode the various wild type and modified forms of the HIV Pol protein disclosed herein. However, codon optimization of these constructs is a preferred embodiment of this invention.

A particular embodiment of this portion of the invention comprisies codon optimized nucleotide sequences which encode wt-pol DNA constructs (herein, "wt-pol" or "wt-pol (codon optimized))" wherein DNA sequences encoding the protease (PR) activity are deleted, leaving codon optimized "wild type" sequences which encode RT (reverse transcriptase and RNase H activity) and IN integrase activity. A DNA molecule which encodes this protein is disclosed herein as SEQ ID NO:1, the open reading frame being contained from an initiating Met residue at nucleotides 10–12 to a termination codon from nucleotides 2560–2562. SEQ ID NO:1 is as follows:

```
AGATCTACCA TGGCCCCCAT CTCCCCCATT GAGACTGTGC CTGTGAAGCT GAAGCCTGGC  (SEQ ID NO:1)

ATGGATGGCC CCAAGGTGAA GCAGTGGCCC CTGACTGAGG AGAAGATCAA GGCCCTGGTG

GAAATCTGCA CTGAGATGGA GAAGGAGGGC AAAATCTCCA AGATTGGCCC CGAGAACCCC

TACAACACCC CTGTGTTTGC CATCAAGAAG AAGGACTCCA CCAAGTGGAG GAAGCTGGTG

GACTTCAGGG AGCTGAACAA GAGGACCCAG GACTTCTGGG AGGTGCAGCT GGGCATCCCC

CACCCCGCTG GCCTGAAGAA GAAGAAGTCT GTGACTGTGC TGGATGTGGG GGATGCCTAC
```

-continued

TTCTCTGTGC CCCTGGATGA GGACTTCAGG AAGTACACTG CCTTCACCAT CCCCTCCATC

AACAATGAGA CCCCTGGCAT CAGGTACCAG TACAATGTGC TGCCCCAGGG CTGGAAGGGC

TCCCCTGCCA TCTTCCAGTC CTCCATGACC AAGATCCTGG AGCCCTTCAG GAAGCAGAAC

CCTGACATTG TGATCTACCA GTACATGGAT GACCTGTATG TGGGCTCTGA CCTGGAGATT

GGGCAGCACA GGACCAAGAT TGAGGAGCTG AGGCAGCACC TGCTGAGGTG GGGCCTGACC

ACCCCTGACA AGAAGCACCA GAAGGAGCCC CCCTTCCTGT GGATGGGCTA TGAGCTGCAC

CCCGACAAGT GGACTGTGCA GCCCATTGTG CTGCCTGAGA AGGACTCCTG GACTGTGAAT

GACATCCAGA AGCTGGTGGG CAAGCTGAAC TGGGCCTCCC AAATCTACCC TGGCATCAAG

GTGAGGCAGC TGTGCAAGCT GCTGAGGGGC ACCAAGGCCC TGACTGAGGT GATCCCCCTG

ACTGAGGAGG CTGAGCTGGA GCTGGCTGAG AACAGGGAGA TCCTGAAGGA GCCTGTGCAT

GGGGTGTACT ATGACCCCTC CAAGGACCTG ATTGCTGAGA TCCAGAAGCA GGGCCAGGGC

CAGTGGACCT ACCAAATCTA CCAGGAGCCC TTCAAGAACC TGAAGACTGG CAAGTATGCC

AGGATGAGGG GGGCCCACAC CAATGATGTG AAGCAGCTGA CTGAGGCTGT GCAGAAGATC

ACCACTGAGT CCATTGTGAT CTGGGGCAAG ACCCCCAAGT TCAAGCTGCC CATCCAGAAG

GAGACCTGGG AGACCTGGTG GACTGAGTAC TGGCAGGCCA CCTGGATCCC TGAGTGGGAG

TTTGTGAACA CCCCCCCCCT GGTGAAGCTG TGGTACCAGC TGGAGAAGGA GCCCATTGTG

GGGGCTGAGA CCTTCTATGT GGATGGGGCT GCCAACAGGG AGACCAAGCT GGGCAAGGCT

GGCTATGTGA CCAACAGGGG CAGGCAGAAG GTGGTGACCC TGACTGACAC CACCAACCAG

AAGACTGAGC TCCAGGCCAT CTACCTGGCC CTCCAGGACT CTGGCCTGGA GGTGAACATT

GTGACTGACT CCCAGTATGC CCTGGGCATC ATCCAGGCCC AGCCTGATCA GTCTGAGTCT

GAGCTGGTGA ACCAGATCAT TGAGCAGCTG ATCAAGAAGG AGAAGGTGTA CCTGGCCTGG

GTGCCTGCCC ACAAGGGCAT TGGGGGCAAT GAGCAGGTGG ACAAGCTGGT GTCTGCTGGC

ATCAGGAAGG TGCTGTTCCT GGATGGCATT GACAAGGCCC AGGATGAGCA TGAGAAGTAC

CACTCCAACT GGAGGGCTAT GGCCTCTGAC TTCAACCTGC CCCCTGTGGT GGCTAAGGAG

ATTGTGGCCT CCTGTGACAA GTGCCAGCTG AAGGGGGAGG CCATGCATGG GCAGGTGGAC

TGCTCCCCTG GCATCTGGCA GCTGGACTGC ACCCACCTGG AGGGCAAGGT GATCCTGGTG

GCTGTGCATG TGGCCTCCGG CTACATTGAG GCTGAGGTGA TCCCTGCTGA GACAGGCCAG

GAGACTGCCT ACTTCCTGCT GAAGCTGGCT GGCAGGTGGC CTGTGAAGAC CATCCACACT

GACAATGGCT CCAACTTCAC TGGGGCCACA GTGAGGGCTG CCTGCTGGTG GGCTGGCATC

AAGCAGGAGT TTGGCATCCC CTACAACCCC CAGTCCCAGG GGGTGGTGGA GTCCATGAAC

AAGGAGCTGA AGAAGATCAT TGGGCAGGTG AGGGACCAGG CTGAGCACCT GAAGACAGCT

GTGCAGATGG CTGTGTTCAT CCACAACTTC AAGAGGAAGG GGGGCATCGG GGGCTACTCC

GCTGGGGAGA GGATTGTGGA CATCATTGCC ACAGACATCC AGACCAAGGA GCTCCAGAAG

CAGATCACCA AGATCCAGAA CTTCAGGGTG TACTACAGGG ACTCCAGGAA CCCCCTGTGG

AAGGGCCCTG CCAAGCTGCT GTGGAAGGGG GAGGGGGCTG TGGTGATCCA GGACAACTCT

GACATCAAGG TGGTGCCCAG GAGGAAGGCC AAGATCATCA GGGACTATGG CAAGCAGATG

GCTGGGGATG ACTGTGTGGC CTCCAGGCAG GATGAGGACT AAAGCCCGGG CAGATCT.

The open reading frame of the wild type pol construct disclosed as SEQ ID NO:1 contains 850 amino acids, disclosed herein as SEQ ID NO:2, as follows:

Met Ala Pro Ile Ser Pro Ile Glu Thr Val Pro Val Lys Leu Lys Pro (SEQ ID NO:2)

Gly Met Asp Gly Pro Lys Val Lys Gln Trp Pro Leu Thr Glu Glu Lys

Ile Lys Ala Leu Val Glu Ile Cys Thr Glu Met Glu Lys Glu Gly Lys

Ile Ser Lys Ile Gly Pro Glu Asn Pro Tyr Asn Thr Pro Val Phe Ala

Ile Lys Lys Lys Asp Ser Thr Lys Trp Arg Lys Leu Val Asp Phe Arg

Glu Leu Asn Lys Arg Thr Gln Asp Phe Trp Glu Val Gln Leu Gly Ile

Pro His Pro Ala Gly Leu Lys Lys Lys Lys Ser Val Thr Val Leu Asp

Val Gly Asp Ala Tyr Phe Ser Val Pro Leu Asp Glu Asp Phe Arg Lys

Tyr Thr Ala Phe Thr Ile Pro Ser Ile Asn Asn Glu Thr Pro Gly Ile

Arg Tyr Gln Tyr Asn Val Leu Pro Gln Gly Trp Lys Gly Ser Pro Ala

Ile Phe Gln Ser Ser Met Thr Lys Ile Leu Glu Pro Phe Arg Lys Gln

Asn Pro Asp Ile Val Ile Tyr Gln Tyr Met Asp Asp Leu Tyr Val Gly

Ser Asp Leu Glu Ile Gly Gln His Arg Thr Lys Ile Glu Glu Leu Arg

Gln His Leu Leu Arg Trp Gly Leu Thr Thr Pro Asp Lys Lys His Gln

Lys Glu Pro Pro Phe Leu Trp Met Gly Tyr Glu Leu His Pro Asp Lys

Trp Thr Val Gln Pro Ile Val Leu Pro Glu Lys Asp Ser Trp Thr Val

Asn Asp Ile Gln Lys Leu Val Gly Lys Leu Asn Trp Ala Ser Gln Ile

Tyr Pro Gly Ile Lys Val Arg Gln Leu Cys Lys Leu Leu Arg Gly Thr

Lys Ala Leu Thr Glu Val Ile Pro Leu Thr Glu Glu Ala Glu Leu Glu

Leu Ala Glu Asn Arg Glu Ile Leu Lys Glu Pro Val His Gly Val Tyr

Tyr Asp Pro Ser Lys Asp Leu Ile Ala Glu Ile Gln Lys Gln Gly Gln

Gly Gln Trp Thr Tyr Gln Ile Tyr Gln Glu Pro Phe Lys Asn Leu Lys

Thr Gly Lys Tyr Ala Arg Met Arg Gly Ala His Thr Asn Asp Val Lys

Gln Leu Thr Glu Ala Val Gln Lys Ile Thr Thr Glu Ser Ile Val Ile

Trp Gly Lys Thr Pro Lys Phe Lys Leu Pro Ile Gln Lys Glu Thr Trp

Glu Thr Trp Trp Thr Glu Tyr Trp Gln Ala Thr Trp Ile Pro Glu Trp

Glu Phe Val Asn Thr Pro Pro Leu Val Lys Leu Trp Tyr Gln Leu Glu

Lys Glu Pro Ile Val Gly Ala Glu Thr Phe Tyr Val Asp Gly Ala Ala

Asn Arg Glu Thr Lys Leu Gly Lys Ala Gly Tyr Val Thr Asn Arg Gly

Arg Gln Lys Val Val Thr Leu Thr Asp Thr Thr Asn Gln Lys Thr Glu

Leu Gln Ala Ile Tyr Leu Ala Leu Gln Asp Ser Gly Leu Glu Val Asn

Ile Val Thr Asp Ser Gln Tyr Ala Leu Gly Ile Ile Gln Ala Gln Pro

Asp Gln Ser Glu Ser Glu Leu Val Asn Gln Ile Ile Glu Gln Leu Ile

Lys Lys Glu Lys Val Tyr Leu Ala Trp Val Pro Ala His Lys Gly Ile

Gly Gly Asn Glu Gln Val Asp Lys Leu Val Ser Ala Gly Ile Arg Lys

Val Leu Phe Leu Asp Gly Ile Asp Lys Ala Gln Asp Glu His Glu Lys

Tyr His Ser Asn Trp Arg Ala Met Ala Ser Asp Phe Asn Leu Pro Pro

Val Val Ala Lys Glu Ile Val Ala Ser Cys Asp Lys Cys Gln Leu Lys

Gly Glu Ala Met His Gly Gln Val Asp Cys Ser Pro Gly Ile Trp Gln

Leu Asp Cys Thr His Leu Glu Gly Lys Val Ile Leu Val Ala Val His

-continued

Val Ala Ser Gly Tyr Ile Glu Ala Glu Val Ile Pro Ala Glu Thr Gly

Gln Glu Thr Ala Tyr Phe Leu Leu Lys Leu Ala Gly Arg Trp Pro Val

Lys Thr Ile His Thr Asp Asn Gly Ser Asn Phe Thr Gly Ala Thr Val

Arg Ala Ala Cys Trp Trp Ala Gly Ile Lys Gln Glu Phe Gly Ile Pro

Tyr Asn Pro Gln Ser Gln Gly Val Val Glu Ser Met Asn Lys Glu Leu

Lys Lys Ile Ile Gly Gln Val Arg Asp Gln Ala Glu His Leu Lys Thr

Ala Val Gln Met Ala Val Phe Ile His Asn Phe Lys Arg Lys Gly Gly

Ile Gly Gly Tyr Ser Ala Gly Glu Arg Ile Val Asp Ile Ile Ala Thr

Asp Ile Gln Thr Lys Glu Leu Gln Lys Gln Ile Thr Lys Ile Gln Asn

Phe Arg Val Tyr Tyr Arg Asp Ser Arg Asn Pro Leu Trp Lys Gly Pro

Ala Lys Leu Leu Trp Lys Gly Glu Gly Ala Val Val Ile Gln Asp Asn

Ser Asp Ile Lys Val Val Pro Arg Arg Lys Ala Lys Ile Ile Arg Asp

Tyr Gly Lys Gln Met Ala Gly Asp Asp Cys Val Ala Ser Arg Gln Asp

Glu Asp.

The present invention especially relates to an adenoviral vector vaccine which comprises a codon optimized HIV-1 DNA pol construct wherein, in addition to deletion of the portion of the wild type sequence encoding the protease activity, a combination of active site residue mutations are introduced which are deleterious to HIV-1 pol (RT-RH-IN) activity of the expressed protein. Therefore, the present invention preferably relates to an adenoviral HIV-1 DNA pol-based vaccine wherein the construct is devoid of DNA sequences encoding any PR activity, as well as containing a mutation(s) which at least partially, and preferably substantially, abolishes RT, RNase and/or IN activity. One type of HIV-1 pol mutant which is part and parcel of an adenoviral vector vaccine may include but is not limited to a mutated DNA molecule comprising at least one nucleotide substitution which results in a point mutation which effectively alters an active site within the RT, RNase and/or IN regions of the expressed protein, resulting in at least substantially decreased enzymatic activity for the RT, RNase H and/or IN functions of HIV-1 Pol. In a preferred embodiment of this portion of the invention, a HIV-1 DNA pol construct contains a mutation or mutations within the Pol coding region which effectively abolishes RT, RNase H and IN activity. An especially preferable HIV-1 DNA pol construct in a DNA molecule which contains at least one point mutation which alters the active site of the RT, RNase H and IN domains of Pol, such that each activity is at least substantially abolished. Such a HIV-1 Pol mutant will most likely comprise at least one point mutation in or around each catalytic domain responsible for RT, RNase H and IN activity, respectfully. To this end, an especially preferred HIV-1 DNA pol construct is exemplified herein and contains nine codon substitution mutations which results in an inactivated Pol protein (IA Pol: SEQ ID NO:4, FIGS. 17A–C) which has no PR, RT, RNase or IN activity, wherein three such point mutations reside within each of the RT, RNase and IN catalytic domains. Therefore, an especially preferred exemplification is an adenoviral vaccine which comprises, in an appropriate fashion, a DNA molecule which encodes IA-pol, which contains all nine mutations as shown below in Table 1. An additional preferred amino acid residue for substitution is Asp551, localized within the RNase domain of Pol. Any combination of the mutations disclosed herein may suitable and therefore may be utilized as an IA-Pol-based vaccine of the present invention. While addition and deletion mutations are contemplated and within the scope of the invention, the preferred mutation is a point mutation resulting in a substitution of the wild type amino acid with an alternative amino acid residue.

TABLE 1

| wt aa | aa residue | mutant aa | enzyme function |
|---|---|---|---|
| Asp | 112 | Ala | RT |
| Asp | 187 | Ala | RT |
| Asp | 188 | Ala | RT |
| Asp | 445 | Ala | RNase H |
| Glu | 480 | Ala | RNase H |
| Asp | 500 | Ala | RNase H |
| Asp | 626 | Ala | IN |
| Asp | 678 | Ala | IN |
| Glu | 714 | Ala | IN |

It is preferred that point mutations be incorporated into the IApol mutant adenoviral vaccines of the present invention so as to lessen the possibility of altering epitopes in and around the active site(s) of HIV-1 Pol.

To this end, SEQ ID NO:3 discloses the nucleotide sequence which codes for a codon optimized pol in addition to the nine mutations shown in Table 1, disclosed as follows, and referred to herein as "IApol":

AGATCTACCA TGGCCCCCAT CTCCCCCATT GAGACTGTGC CTGTGAAGCT GAAGCCTGGC (SEQ ID NO:3)

ATGGATGGCC CCAAGGTGAA GCAGTGGCCC CTGACTGAGG AGAAGATCAA GGCCCTGGTG

GAAATCTGCA CTGAGATGGA GAAGGAGGGC AAAATCTCCA AGATTGGCCC CGAGAACCCC

-continued

TACAACACCC CTGTGTTTGC CATCAAGAAG AAGGACTCCA CCAAGTGGAG GAAGCTGGTG

GACTTCAGGG AGCTGAACAA GAGGACCCAG GACTTCTGGG AGGTGCAGCT GGGCATCCCC

CACCCCGCTG GCCTGAAGAA GAAGAAGTCT GTGACTGTGC TGGCTGTGGG GGATGCCTAC

TTCTCTGTGC CCCTGGATGA GGACTTCAGG AAGTACACTG CCTTCACCAT CCCCTCCATC

AACAATGAGA CCCCTGGCAT CAGGTACCAG TACAATGTGC TGCCCCAGGG CTGGAAGGGC

TCCCCTGCCA TCTTCCAGTC CTCCATGACC AAGATCCTGG AGCCCTTCAG GAAGCAGAAC

CCTGACATTG TGATCTACCA GTACATGGCT GCCCTGTATG TGGGCTCTGA CCTGGAGATT

GGGCAGCACA GGACCAAGAT TGAGGAGCTG AGGCAGCACC TGCTGAGGTG GGGCCTGACC

ACCCCTGACA AGAAGCACCA GAAGGAGCCC CCCTTCCTGT GGATGGGCTA TGAGCTGCAC

CCCGACAAGT GGACTGTGCA GCCCATTGTG CTGCCTGAGA AGGACTCCTG GACTGTGAAT

GACATCCAGA AGCTGGTGGG CAAGCTGAAC TGGGCCTCCC AAATCTACCC TGGCATCAAG

GTGAGGCAGC TGTGCAAGCT GCTGAGGGGC ACCAAGGCCC TGACTGAGGT GATCCCCCTG

ACTGAGGAGG CTGAGCTGGA GCTGGCTGAG AACAGGGAGA TCCTGAAGGA GCCTGTGCAT

GGGGTGTACT ATGACCCCTC CAAGGACCTG ATTGCTGAGA TCCAGAAGCA GGGCCAGGGC

CAGTGGACCT ACCAAATCTA CCAGGAGCCC TTCAAGAACC TGAAGACTGG CAAGTATGCC

AGGATGAGGG GGGCCCACAC CAATGATGTG AAGCAGCTGA CTGAGGCTGT GCAGAAGATC

ACCACTGAGT CCATTGTGAT CTGGGGCAAG ACCCCCAAGT TCAAGCTGCC CATCCAGAAG

GAGACCTGGG AGACCTGGTG GACTGAGTAC TGGCAGGCCA CCTGGATCCC TGAGTGGGAG

TTTGTGAACA CCCCCCCCCT GGTGAAGCTG TGGTACCAGC TGGAGAAGGA GCCCATTGTG

GGGGCTGAGA CCTTCTATGT GGCTGGGGCT GCCAACAGGG AGACCAAGCT GGGCAAGGCT

GGCTATGTGA CCAACAGGGG CAGGCAGAAG GTGGTGACCC TGACTGACAC CACCAACCAG

AAGACTGCCC TCCAGGCCAT CTACCTGGCC CTCCAGGACT CTGGCCTGGA GGTGAACATT

GTGACTGCCT CCCAGTATGC CCTGGGCATC ATCCAGGCCC AGCCTGATCA GTCTGAGTCT

GAGCTGGTGA ACCAGATCAT TGAGCAGCTG ATCAAGAAGG AGAAGGTGTA CCTGGCCTGG

GTGCCTGCCC ACAAGGGCAT TGGGGGCAAT GAGCAGGTGG ACAAGCTGGT GTCTGCTGGC

ATCAGGAAGG TGCTGTTCCT GGATGGCATT GACAAGGCCC AGGATGAGCA TGAGAAGTAC

CACTCCAACT GGAGGGCTAT GGCCTCTGAC TTCAACCTGC CCCCTGTGGT GGCTAAGGAG

ATTGTGGCCT CCTGTGACAA GTGCCAGCTG AAGGGGGAGG CCATGCATGG GCAGGTGGAC

TGCTCCCCTG GCATCTGGCA GCTGGCCTGC ACCCACCTGG AGGGCAAGGT GATCCTGGTG

GCTGTGCATG TGGCCTCCGG CTACATTGAG GCTGAGGTGA TCCCTGCTGA GACAGGCCAG

GAGACTGCCT ACTTCCTGCT GAAGCTGGCT GGCAGGTGGC CTGTGAAGAC CATCCACACT

GCCAATGGCT CCAACTTCAC TGGGGCCACA GTGAGGGCTG CCTGCTGGTG GGCTGGCATC

AAGCAGGAGT TTGGCATCCC CTACAACCCC CAGTCCCAGG GGGTGGTGGC CTCCATGAAC

AAGGAGCTGA AGAAGATCAT TGGGCAGGTG AGGGACCAGG CTGAGCACCT GAAGACAGCT

GTGCAGATGG CTGTGTTCAT CCACAACTTC AAGAGGAAGG GGGGCATCGG GGGCTACTCC

GCTGGGGAGA GGATTGTGGA CATCATTGCC ACAGACATCC AGACCAAGGA GCTCCAGAAG

CAGATCACCA AGATCCAGAA CTTCAGGGTG TACTACAGGG ACTCCAGGAA CCCCCTGTGG

AAGGGCCCTG CCAAGCTGCT GTGGAAGGGG GAGGGGGCTG TGGTGATCCA GGACAACTCT

GACATCAAGG TGGTGCCCAG GAGGAAGGCC AAGATCATCA GGGACTATGG CAAGCAGATG

GCTGGGGATG ACTGTGTGGC CTCCAGGCAG GATGAGGACT AAAGCCCGGG CAGATCT.

In order to produce the IA-pol-based adenoviral vaccines of the present invention, inactivation of the enzymatic functions was achieved by replacing a total of nine active site residues from the enzyme subunits with alanine side-chains. As shown in Table 1, all residues that comprise the catalytic triad of the polymerase, namely Asp112, Asp187, and Asp188, were substituted with alanine (Ala) residues (Larder, et al., *Nature* 1987, 327: 716–717; Larder, et al., 1989*, Proc. Natl. Acad. Sci.* 1989, 86: 4803–4807). Three additional mutations were introduced at Asp445, Glu480 and Asp500 to abolish RNase H activity (Asp551 was left unchanged in this IA Pol construct), with each residue being substituted for an Ala residue, respectively (Davies, et al., 1991, Science 252:, 88–95; Schatz, et al., 1989*, FEBS Lett.* 257: 311–314; Mizrahi, et al., 1990, Nucl. Acids. Res. 18: pp. 5359–5353). HIV pol integrase function was abolished through three mutations at Asp626, Asp678 and Glu714. Again, each of these residues has been substituted with an Ala residue (Wiskerchen, et al., 1995, J. Virol. 69: 376–386; Leavitt, et al., 1993, J. Biol. Chem. 268: 2113–2119). Amino acid residue Pro3 of SEQ ID NO:4 marks the start of the RT gene. The complete amino acid sequence of IA-Pol is disclosed herein as SEQ ID NO:4 and FIGS. 17A–C, as follows:

```
Met Ala Pro Ile Ser Pro Ile Glu Thr Val Pro Val Lys Leu Lys Pro  (SEQ ID NO:4)

Gly Met Asp Gly Pro Lys Val Lys Gln Trp Pro Leu Thr Glu Glu Lys

Ile Lys Ala Leu Val Glu Ile Cys Thr Glu Met Glu Lys Gly Gly Lys

Ile Ser Lys Ile Gly Pro Glu Asn Pro Tyr Asn Thr Pro Val Phe Ala

Ile Lys Lys Lys Asp Ser Thr Lys Trp Arg Lys Leu Val Asp Phe Arg

Glu Leu Asn Lys Arg Thr Gln Asp Phe Trp Glu Val Gln Leu Gly Ile

Pro His Pro Ala Gly Leu Lys Lys Lys Lys Ser Val Thr Val Leu Ala

Val Gly Asp Ala Tyr Phe Ser Val Pro Leu Asp Glu Asp Phe Arg Lys

Tyr Thr Ala Phe Thr Ile Pro Ser Ile Asn Asn Glu Thr Pro Gly Ile

Arg Tyr Gln Tyr Asn Val Leu Pro Gln Gly Trp Lys Gly Ser Pro Ala

Ile Phe Gln Ser Ser Met Thr Lys Ile Leu Glu Pro Phe Arg Lys Gln

Asn Pro Asp Ile Val Ile Tyr Gln Tyr Met Ala Ala Leu Tyr Val Gly

Ser Asp Leu Glu Ile Gly Gln His Arg Thr Lys Ile Glu Glu Leu Arg

Gln His Leu Leu Arg Trp Gly Leu Thr Thr Pro Asp Lys Lys His Gln

Lys Glu Pro Pro Phe Leu Trp Met Gly Tyr Glu Leu His Pro Asp Lys

Trp Thr Val Gln Pro Ile Val Leu Pro Glu Lys Asp Ser Trp Thr Val

Asn Asp Ile Gln Lys Leu Val Gly Lys Leu Asn Trp Ala Ser Gln Ile

Tyr Pro Gly Ile Lys Val Arg Gln Leu Cys Lys Leu Leu Arg Gly Thr

Lys Ala Leu Thr Glu Val Ile Pro Leu Thr Glu Glu Ala Glu Leu Glu

Leu Ala Glu Asn Arg Glu Ile Leu Lys Glu Pro Val His Gly Val Tyr

Tyr Asp Pro Ser Lys Asp Leu Ile Ala Glu Ile Gln Lys Gln Gly Gln

Gly Gln Trp Thr Tyr Gln Ile Tyr Gln Glu Pro Phe Lys Asn Leu Lys

Thr Gly Lys Tyr Ala Arg Met Arg Gly Ala His Thr Asn Asp Val Lys

Gln Leu Thr Glu Ala Val Gln Lys Ile Thr Thr Glu Ser Ile Val Ile

Trp Gly Lys Thr Pro Lys Phe Lys Leu Pro Ile Gln Lys Glu Thr Trp

Glu Thr Trp Trp Thr Glu Tyr Trp Gln Ala Thr Trp Ile Pro Glu Trp

Glu Phe Val Asn Thr Pro Pro Leu Val Lys Leu Trp Tyr Gln Leu Glu

Lys Glu Pro Ile Val Gly Ala Glu Thr Phe Tyr Val Ala Gly Ala Ala

Asn Arg Glu Thr Lys Leu Gly Lys Ala Gly Tyr Val Thr Asn Arg Gly

Arg Gln Lys Val Val Thr Leu Thr Asp Thr Thr Asn Gln Lys Thr Ala

Leu Gln Ala Ile Tyr Leu Ala Leu Gln Asp Ser Gly Leu Glu Val Asn

Ile Val Thr Ala Ser Gln Tyr Ala Leu Gly Ile Ile Gln Ala Gln Pro
```

-continued

Asp Gln Ser Glu Ser Glu Leu Val Asn Gln Ile Ile Glu Gln Leu Ile

Lys Lys Glu Lys Val Tyr Leu Ala Trp Val Pro Ala His Lys Gly Ile

Gly Gly Asn Glu Gln Val Asp Lys Leu Val Ser Ala Gly Ile Arg Lys

Val Leu Phe Leu Asp Gly Ile Asp Lys Ala Gln Asp Glu His Glu Lys

Tyr His Ser Asn Trp Arg Ala Met Ala Ser Asp Phe Asn Leu Pro Pro

Val Val Ala Lys Glu Ile Val Ala Ser Cys Asp Lys Cys Gln Leu Lys

Gly Glu Ala Met His Gly Gln Val Asp Cys Ser Pro Gly Ile Trp Gln

Leu Ala Cys Thr His Leu Glu Gly Lys Val Ile Leu Val Ala Val His

Val Ala Ser Gly Tyr Ile Glu Ala Glu Val Ile Pro Ala Glu Thr Gly

Gln Glu Thr Ala Tyr Phe Leu Leu Lys Leu Ala Gly Arg Trp Pro Val

Lys Thr Ile His Thr Ala Asn Gly Ser Asn Phe Thr Gly Ala Thr Val

Arg Ala Ala Cys Trp Trp Ala Gly Ile Lys Gln Glu Phe Gly Ile Pro

Tyr Asn Pro Gln Ser Gln Gly Val Val Ala Ser Met Asn Lys Glu Leu

Lys Lys Ile Ile Gly Gln Val Arg Asp Gln Ala Glu His Leu Lys Thr

Ala Val Gln Met Ala Val Phe Ile His Asn Phe Lys Arg Lys Gly Gly

Ile Gly Gly Tyr Ser Ala Gly Glu Arg Ile Val Asp Ile Ile Ala Thr

Asp Ile Gln Thr Lys Glu Leu Gln Lys Gln Ile Thr Lys Ile Gln Asn

Phe Arg Val Tyr Tyr Arg Asp Ser Arg Asn Pro Leu Trp Lys Gly Pro

Ala Lys Leu Leu Trp Lys Gly Glu Gly Ala Val Val Ile Gln Asp Asn

Ser Asp Ile Lys Val Val Pro Arg Arg Lys Ala Lys Ile Ile Arg Asp

Tyr Gly Lys Gln Met Ala Gly Asp Asp Cys Val Ala Ser Arg Gln Asp

Glu Asp.

As noted above, it will be understood that any combination of the mutations disclosed above may be suitable and therefore be utilized as an IA-pol-based adenoviral HIV vaccine of the present invention, either when administered alone or in a combined modality regime and/or a prime-boost regimen. For example, it may be possible to mutate only 2 of the 3 residues within the respective reverse transcriptase, RNase H, and integrase coding regions while still abolishing these enzymatic activities. However, the IA-pol construct described above and disclosed as SEQ ID NO:3, as well as the expressed protein (SEQ ID NO:4;) is preferred. It is also preferred that at least one mutation be present in each of the three catalytic domains.

Another aspect of this portion of the invention are codon optimized HIV-1 Pol-based vaccine constructions which comprise a eukaryotic trafficking signal peptide such as from tPA (tissue-type plasminogen activator) or by a leader peptide such as is found in highly expressed mammalian proteins such as immunoglobulin leader peptides. Any functional leader peptide may be tested for efficacy. However, a preferred embodiment of the present invention, as with HIV-1 Nef constructs shown herein, is to provide for a HIV-1 Pol mutant adenoviral vaccine construction wherein the pol coding region or a portion thereof is operatively linked to a leader peptide, preferably a leader peptide from human tPA. In other words, a codon optimized HIV-1 Pol mutant such as IA-Pol (SEQ ID NO:4) may also comprise a leader peptide at the amino terminal portion of the protein, which may effect cellular trafficking and hence, immunogenicity of the expressed protein within the host cell. As noted in FIGS. 16A–B, a DNA vector which may be utilized to practice the present invention may be modified by known recombinant DNA methodology to contain a leader signal peptide of interest, such that downstream cloning of the modified HIV-1 protein of interest results in a nucleotide sequence which encodes a modified HIV-1 tPA/Pol protein. In the alternative, as noted above, insertion of a nucleotide sequence which encodes a leader peptide may be inserted into a DNA vector housing the open reading frame for the Pol protein of interest. Regardless of the cloning strategy, the end result is a polynucleotide vaccine which comprises vector components for effective gene expression in conjunction with nucleotide sequences which encode a modified HIV-1 Pol protein of interest, including but not limited to a HIV-1 Pol protein which contains a leader peptide. The amino acid sequence of the human tPA leader utilized herein is as follows: MDAMKRGLCCVLLLCGAVFVSPSEISS (SEQ ID NO:17). Therefore, another aspect of the present invention is to generate HIV-1 Pol-based vaccine constructions which comprise a eukaryotic trafficking signal peptide such as from tPA. To this end, the present invention relates to a DNA molecule which encodes a codon optimized wt-pol DNA construct wherein the protease (PR) activity is deleted and a human tPA leader sequence is fused to the 5' end of the coding region. A DNA molecule which encodes this protein is disclosed herein as SEQ ID NO:5, the open reading frame disclosed herein as SEQ ID NO:6.

To this end, the present invention relates to a DNA molecule which encodes a codon optimized wt-pol DNA construct wherein the protease (PR) activity is deleted and a human tPA leader sequence is fused to the 5' end of the coding region (herein, "tPA-wt-pol"). A DNA molecule which encodes this protein is disclosed herein as SEQ ID NO:5, the open reading frame being contained from an initiating Met residue at nucleotides 8–10 to a termination codon from nucleotides 2633–2635. SEQ ID NO:5 is as follows:

```
GATCACCATG GATGCAATGA AGAGAGGGCT CTGCTGTGTG CTGCTGCTGT GTGGAGCAGT  (SEQ ID NO:5)
CTTCGTTTCG CCCAGCGAGA TCTCCGCCCC CATCTCCCCC ATTGAGACTG TGCCTGTGAA
GCTGAAGCCT GGCATGGATC GCCCCAAGGT GAAGCAGTGG CCCCTGACTG AGGAGAAGAT
CAAGGCCCTG GTGGAAATCT GCACTGAGAT GGAGAAGGAG GGCAAAATCT CCAAGATTGG
CCCCGAGAAC CCCTACAACA CCCCTGTGTT TGCCATCAAG AAGAAGGACT CCACCAAGTG
GAGGAAGCTG GTGGACTTCA GGGAGCTGAA CAAGAGGACC CAGGACTTCT GGGAGGTGCA
GCTGGGCATC CCCCACCCCG CTGGCCTGAA GAAGAAGAAG TCTGTGACTG TGCTGGATGT
GGGGGATGCC TACTTCTCTG TGCCCCTGGA TGAGGACTTC AGGAAGTACA CTGCCTTCAC
CATCCCCTCC ATCAACAATG AGACCCCTGG CATCAGGTAC CAGTACAATG TGCTGCCCCA
GGGCTGGAAG GGCTCCCCTG CCATCTTCCA GTCCTCCATG ACCAAGATCC TGGAGCCCTT
CAGGAAGCAG AACCCTGACA TTGTGATCTA CCAGTACATG GATGACCTGT ATGTGGGCTC
TGACCTGGAG ATTGGGCAGC ACAGGACCAA GATTGAGGAG CTGAGGCAGC ACCTGCTGAG
GTGGGGCCTG ACCACCCCTG ACAAGAAGCA CCAGAAGGAG CCCCCCTTCC TGTGGATGGG
CTATGAGCTG CACCCCGACA AGTGGACTGT GCAGCCCATT GTGCTGCCTG AGAAGGACTC
CTGGACTGTG AATGACATCC AGAAGCTGGT GGGCAAGCTG AACTGGGCCT CCCAAATCTA
CCCTGGCATC AAGGTGAGGC AGCTGTGCAA GCTGCTGAGG GGCACCAAGG CCCTGACTGA
GGTGATCCCC CTGACTGAGG AGGCTGAGCT GGAGCTGGCT GAGAACAGGG AGATCCTGAA
GGAGCCTGTG CATGGGGTGT ACTATGACCC CTCCAAGGAC CTGATTGCTG AGATCCAGAA
GCAGGGCCAG GGCCAGTGGA CCTACCAAAT CTACCAGGAG CCCTTCAAGA ACCTGAAGAC
TGGCAAGTAT GCCAGGATGA GGGGGGCCCA CACCAATGAT GTGAAGCAGC TGACTGAGGC
TGTGCAGAAG ATCACCACTG AGTCCATTGT GATCTGGGGC AAGACCCCCA AGTTCAAGCT
GCCCATCCAG AAGGAGACCT GGGAGACCTG GTGGACTGAG TACTGGCAGG CCACCTGGAT
CCCTGAGTGG GAGTTTGTGA ACACCCCCCC CCTGGTGAAG CTGTGGTACC AGCTGGAGAA
GGAGCCCATT GTGGGGGCTG AGACCTTCTA TGTGGATGGG GCTGCCAACA GGGAGACCAA
GCTGGGCAAG GCTGGCTATG TGACCAACAG GGGCAGGCAG AAGGTGGTGA CCCTGACTGA
CACCACCAAC CAGAAGACTG AGCTCCAGGC CATCTACCTG GCCCTCCAGG ACTCTGGCCT
GGAGGTGAAC ATTGTGACTG ACTCCCAGTA TGCCCTGGGC ATCATCCAGG CCCAGCCTGA
TCAGTCTGAG TCTGAGCTGG TGAACCAGAT CATTGAGCAG CTGATCAAGA AGGAGAAGGT
GTACCTGGCC TGGGTGCCTG CCCACAAGGG CATTGGGGGC AATGAGCAGG TGGACAAGCT
GGTGTCTGCT GGCATCAGGA AGGTGCTGTT CCTGGATGGC ATTGACAAGG CCCAGGATGA
GCATGAGAAG TACCACTCCA ACTGGAGGGC TATGGCCTCT GACTTCAACC TGCCCCCTGT
GGTGGCTAAG GAGATTGTGG CCTCCTGTGA CAAGTGCCAG CTGAAGGGGG AGGCCATGCA
TGGGCAGGTG GACTGCTCCC CTGGCATCTG GCAGCTGGAC TGCACCCACC TGGAGGGCAA
GGTGATCCTG GTGGCTGTGC ATGTGGCCTC CGGCTACATT GAGGCTGAGG TGATCCCTGC
TGAGACAGGC CAGGAGACTG CCTACTTCCT GCTGAAGCTG GCTGGCAGGT GGCCTGTGAA
GACCATCCAC ACTGACAATG GCTCCAACTT CACTGGGGCC ACAGTGAGGG CTGCCTGCTG
GTGGGCTGGC ATCAAGCAGG AGTTTGGCAT CCCCTACAAC CCCCAGTCCC AGGGGGTGGT
```

-continued

GGAGTCCATG AACAAGGAGC TGAAGAAGAT CATTGGGCAG GTGAGGGACC AGGCTGAGCA

CCTGAAGACA GCTGTGCAGA TGGCTGTGTT CATCCACAAC TTCAAGAGGA AGGGGGGCAT

CGGGGGCTAC TCCGCTGGGG AGAGGATTGT GGACATCATT GCCACAGACA TCCAGACCAA

GGAGCTCCAG AAGCAGATCA CCAAGATCCA GAACTTCAGG GTGTACTACA GGGACTCCAG

GAACCCCCTG TGGAAGGGCC CTGCCAAGCT GCTGTGGAAG GGGGAGGGGG CTGTGGTGAT

CCAGGACAAC TCTGACATCA AGGTGGTGCC CAGGAGGAAG GCCAAGATCA TCAGGGACTA

TGGCAAGCAG ATGGCTGGGG ATGACTGTGT GGCCTCCAGG CAGGATGAGG ACTAAAGCCC

GGGCAGATCT.

The open reading frame of the wild type tPA-pol construct disclosed as SEQ ID NO:5 contains 875 amino acids, disclosed herein as SEQ ID NO:6, as follows:

Met Asp Ala Met Lys Arg Gly Leu Cys Cys Val Leu Leu Leu Cys Gly (SEQ ID NO:6)

Ala Val Phe Val Ser Pro Ser Glu Ile Ser Ala Pro Ile Ser Pro Ile

Glu Thr Val Pro Val Lys Leu Lys Pro Gly Met Asp Gly Pro Lys Val

Lys Gln Trp Pro Leu Thr Glu Glu Lys Ile Lys Ala Leu Val Glu Ile

Cys Thr Glu Met Glu Lys Glu Gly Lys Ile Ser Lys Ile Gly Pro Glu

Asn Pro Tyr Asn Thr Pro Val Phe Ala Ile Lys Lys Lys Asp Ser Thr

Lys Trp Arg Lys Leu Val Asp Phe Arg Glu Leu Asn Lys Arg Thr Gln

Asp Phe Trp Glu Val Gln Leu Gly Ile Pro His Pro Ala Gly Leu Lys

Lys Lys Lys Ser Val Thr Val Leu Asp Val Gly Asp Ala Tyr Phe Ser

Val Pro Leu Asp Glu Asp Phe Arg Lys Tyr Thr Ala Phe Thr Ile Pro

Ser Ile Asn Asn Glu Thr Pro Gly Ile Arg Tyr Gln Tyr Asn Val Leu

Pro Gln Gly Trp Lys Gly Ser Pro Ala Ile Phe Gln Ser Ser Met Thr

Lys Ile Leu Glu Pro Phe Arg Lys Gln Asn Pro Asp Ile Val Ile Tyr

Gln Tyr Met Asp Asp Leu Tyr Val Gly Ser Asp Leu Glu Ile Gly Gln

His Arg Thr Lys Ile Glu Glu Leu Arg Gln His Leu Leu Arg Trp Gly

Leu Thr Thr Pro Asp Lys Lys His Gln Lys Glu Pro Pro Phe Leu Trp

Met Gly Tyr Glu Leu His Pro Asp Lys Trp Thr Val Gln Pro Ile Val

Leu Pro Glu Lys Asp Ser Trp Thr Val Asn Asp Ile Gln Lys Leu Val

Gly Lys Leu Asn Trp Ala Ser Gln Ile Tyr Pro Gly Ile Lys Val Arg

Gln Leu Cys Lys Leu Leu Arg Gly Thr Lys Ala Leu Thr Glu Val Ile

Pro Leu Thr Glu Glu Ala Glu Leu Glu Leu Ala 0Th Asn Arg Glu Ile

Leu Lys Glu Pro Val His Gly Val Tyr Tyr Asp Pro Ser Lys Asp Leu

Ile Ala Glu Ile Gln Lys Gln Gly Gln Gly Gln Trp Thr Tyr Gln Ile

Tyr Gln Glu Pro Phe Lys Asn Leu Lys Thr Gly Lys Tyr Ala Arg Met

Arg Gly Ala His Thr Asn Asp Val Lys Gln Leu Thr Glu Ala Val Gln

Lys Ile Thr Thr Glu Ser Ile Val Ile Trp Gly Lys Thr Pro Lys Phe

Lys Leu Pro Ile Gln Lys Glu Thr Trp Glu Thr Trp Trp Thr Glu Tyr

Trp Gln Ala Thr Trp Ile Pro Glu Trp Glu Phe Val Asn Thr Pro Pro

-continued

Leu Val Lys Leu Trp Tyr Gln Leu Glu Lys Glu Pro Ile Val Gly Ala

Glu Thr Phe Tyr Val Asp Gly Ala Ala Asn Arg Glu Thr Lys Leu Gly

Lys Ala Gly Tyr Val Thr Asn Arg Gly Arg Gln Lys Val Val Thr Leu

Thr Asp Thr Thr Asn Gln Lys Thr Glu Leu Gln Ala Ile Tyr Leu Ala

Leu Gln Asp Ser Gly Leu Glu Val Asn Ile Val Thr Asp Ser Gln Tyr

Ala Leu Gly Ile Ile Gln Ala Gln Pro Asp Gln Ser Glu Ser Glu Leu

Val Asn Gln Ile Ile Glu Gln Leu Ile Lys Lys Glu Lys Val Tyr Leu

Ala Trp Val Pro Ala His Lys Gly Ile Gly Gly Asn Glu Gln Val Asp

Lys Leu Val Ser Ala Gly Ile Arg Lys Val Leu Phe Leu Asp Gly Ile

Asp Lys Ala Gln Asp Glu His Glu Lys Tyr His Ser Asn Trp Arg Ala

Met Ala Ser Asp Phe Asn Leu Pro Pro Val Val Ala Lys Glu Ile Val

Ala Ser Cys Asp Lys Cys Gln Leu Lys Gly Glu Ala Met His Gly Gln

Val Asp Cys Ser Pro Gly Ile Trp Gln Leu Asp Cys Thr His Leu Glu

Gly Lys Val Ile Leu Val Ala Val His Val Ala Ser Gly Tyr Ile Glu

Ala Glu Val Ile Pro Ala Glu Thr Gly Gln Glu Thr Ala Tyr Phe Leu

Leu Lys Leu Ala Gly Arg Trp Pro Val Lys Thr Ile His Thr Asp Asn

Gly Ser Asn Phe Thr Gly Ala Thr Val Arg Ala Ala Cys Trp Trp Ala

Gly Ile Lys Gln Glu Phe Gly Ile Pro Tyr Asn Pro Gln Ser Gln Gly

Val Val Glu Ser Met Asn Lys Glu Leu Lys Lys Ile Ile Gly Gln Val

Arg Asp Gln Ala Glu His Leu Lys Thr Ala Val Gln Met Ala Val Phe

Ile His Asn Phe Lys Arg Lys Gly Gly Ile Gly Gly Tyr Ser Ala Gly

Glu Arg Ile Val Asp Ile Ile Ala Thr Asp Ile Gln Thr Lys Glu Leu

Gln Lys Gln Ile Thr Lys Ile Gln Asn Phe Arg Val Tyr Tyr Arg Asp

Ser Arg Asn Pro Leu Trp Lys Gly Pro Ala Lys Leu Leu Trp Lys Gly

Glu Gly Ala Val Val Ile Gln Asp Asn Ser Asp Ile Lys Val Val Pro

Arg Arg Lys Ala Lys Ile Ile Arg Asp Tyr Gly Lys Gln Met Ala Gly

Asp Asp Cys Val Ala Ser Arg Gln Asp Glu Asp.

The present invention also relates to a codon optimized HIV-1 Pol mutant contained within a recombinant adenoviral vector such as IA-Pol (SEQ ID NO:4) which comprises a leader peptide at the amino terminal portion of the protein, which may effect cellular trafficking and hence, immunogenicity of the expressed protein within the host cell. Any such adenoviral-based HIV-1 DNA pol mutant disclosed in the above paragraphs is suitable for fusion downstream of a leader peptide, such as a leader peptide including but not limited to the human tPA leader sequence. Therefore, any such leader peptide-based HIV-1 pol mutant construct may include but is not limited to a mutated DNA molecule which effectively alters the catalytic activity of the RT, RNase and/or IN region of the expressed protein, resulting in at least substantially decreased enzymatic activity one or more of the RT, RNase H and/or IN functions of HIV-1 Pol. In a preferred embodiment of this portion of the invention, a leader peptide/HIV-1 DNA pol construct contains a mutation or mutations within the Pol coding region which effectively abolishes RT, RNase H and IN activity. An especially preferable HIV-1 DNA pol construct is a DNA molecule which contains at least one point mutation which alters the active site and catalytic activity within the RT, RNase H and IN domains of Pol, such that each activity is at least substantially abolished, and preferably totally abolished. Such a HIV-1 Pol mutant will most likely comprise at least one point mutation in or around each catalytic domain responsible for RT, RNase H and IN activity, respectfully. An especially preferred embodiment of this portion of the invention relates to a human tPA leader fused to the IA-Pol protein comprising the nine mutations shown in Table 1. The DNA molecule is disclosed herein as SEQ ID NO:7 and the expressed tPA-IA Pol protein comprises a fusion junction as shown in FIG. 18. The complete amino acid sequence of the expressed protein is set forth in SEQ ID NO:8. To this end, SEQ ID NO:7 discloses the nucleotide sequence which codes for a human tPA leader fused to the IA Pol protein comprising the nine mutations shown in Table 1 (herein, “tPA-opt-IApol”). The open reading frame begins with the initiating Met (nucleotides 8–10) and terminates with a “TAA” codon at nucleotides 2633–2635. The nucleotide sequence encoding tPA-IAPol is also disclosed as follows:

GATCACCATG GATGCAATGA AGAGAGGGCT CTGCTGTGTG CTGCTGCTGT GTGGAGCAGT (SEQ ID NO:7)
CTTCGTTTCG CCCAGCGAGA TCTCCGCCCC CATCTCCCCC ATTGAGACTG TGCCTGTGAA
GCTGAAGCCT GGCATGGATG GCCCCAAGGT GAAGCAGTGG CCCCTGACTG AGGAGAAGAT
CAAGGCCCTG GTGGAAATCT GCACTGAGAT GGAGAAGGAG GGCAAAATCT CCAAGATTGG
CCCCGAGAAC CCCTACAACA CCCCTGTGTT TGCCATCAAG AAGAAGGACT CCACCAAGTG
GAGGAAGCTG GTGGACTTCA GGGAGCTGAA CAAGAGGACC CAGGACTTCT GGGAGGTGCA
GCTGGGCATC CCCCACCCCG CTGGCCTGAA GAAGAAGAAG TCTGTGACTG TGCTGGCTGT
GGGGGATGCC TACTTCTCTG TGCCCCTGGA TGAGGACTTC AGGAAGTACA CTGCCTTCAC
CATCCCCTCC ATCAACAATG AGACCCCTGG CATCAGGTAC CAGTACAATG TGCTGCCCCA
GGGCTGGAAG GGCTCCCCTG CCATCTTCCA GTCCTCCATG ACCAAGATCC TGGAGCCCTT
CAGGAAGCAG AACCCTGACA TTGTGATCTA CCAGTACATG GCTGCCCTGT ATGTGGGCTC
TGACCTGGAG ATTGGGCAGC ACAGGACCAA GATTGAGGAG CTGAGGCAGC ACCTGCTGAG
GTGGGGCCTG ACCACCCCTG ACAAGAAGCA CCAGAAGGAG CCCCCCTTCC TGTGGATGGG
CTATGAGCTG CACCCCGACA AGTGGACTGT GCAGCCCATT GTGCTGCCTG AGAAGGACTC
CTGGACTGTG AATGACATCC AGAAGCTGGT GGGCAAGCTG AACTGGGCCT CCCAAATCTA
CCCTGGCATC AAGGTGAGGC AGCTGTGCAA GCTGCTGAGG GGCACCAAGG CCCTGACTGA
GGTGATCCCC CTGACTGAGG AGGCTGAGCT GGAGCTGGCT GAGAACAGGG AGATCCTGAA
GGAGCCTGTG CATGGGGTGT ACTATGACCC CTCCAAGGAC CTGATTGCTG AGATCCAGAA
GCAGGGCCAG GGCCAGTGGA CCTACCAAAT CTACCAGGAG CCCTTCAAGA ACCTGAAGAC
TGGCAAGTAT GCCAGGATGA GGGGGGCCCA CACCAATGAT GTGAAGCAGC TGACTGAGGC
TGTGCAGAAG ATCACCACTG AGTCCATTGT GATCTGGGGC AAGACCCCCA AGTTCAAGCT
GCCCATCCAG AAGGAGACCT GGGAGACCTG GTGGACTGAG TACTGGCAGG CCACCTGGAT
CCCTGAGTGG GAGTTTGTGA ACACCCCCCC CCTGGTGAAG CTGTGGTACC AGCTGGAGAA
GGAGCCCATT GTGGGGGCTG AGACCTTCTA TGTGGCTGGG GCTGCCAACA GGGAGACCAA
GCTGGGCAAG GCTGGCTATG TGACCAACAG GGGCAGGCAG AAGGTGGTGA CCCTGACTGA
CACCACCAAC CAGAAGACTG CCCTCCAGGC CATCTACCTG GCCCTCCAGG ACTCTGGCCT
GGAGGTGAAC ATTGTGACTG CCTCCCAGTA TGCCCTGGGC ATCATCCAGG CCCAGCCTGA
TCAGTCTGAG TCTGAGCTGG TGAACCAGAT CATTGAGCAG CTGATCAAGA AGGAGAAGGT
GTACCTGGCC TGGGTGCCTG CCCACAAGGG CATTGGGGGC AATGAGCAGG TGGACAAGCT
GGTGTCTGCT GGCATCAGGA AGGTGCTGTT CCTGGATGGC ATTGACAAGG CCCAGGATGA
GCATGAGAAG TACCACTCCA ACTGGAGGGC TATGGCCTCT GACTTCAACC TGCCCCCTGT
GGTGGCTAAG GAGATTGTGG CCTCCTGTGA CAAGTGCCAG CTGAAGGGGG AGGCCATGCA
TGGGCAGGTG GACTGCTCCC CTGGCATCTG GCAGCTGGCC TGCACCCACC TGGAGGGCAA
GGTGATCCTG GTGGCTGTGC ATGTGGCCTC CGGCTACATT GAGGCTGAGG TGATCCCTGC
TGAGACAGGC CAGGAGACTG CCTACTTCCT GCTGAAGCTG GCTGGCAGGT GGCCTGTGAA
GACCATCCAC ACTGCCAATG GCTCCAACTT CACTGGGGCC ACAGTGAGGG CTGCCTGCTG
GTGGGCTGGC ATCAAGCAGG AGTTTGGCAT CCCCTACAAC CCCCAGTCCC AGGGGGTGGT
GGCCTCCATG AACAAGGAGC TGAAGAAGAT CATTGGGCAG GTGAGGGACC AGGCTGAGCA
CCTGAAGACA GCTGTGCAGA TGGCTGTGTT CATCCACAAC TTCAAGAGGA AGGGGGGCAT
CGGGGGCTAC TCCGCTGGGG AGAGGATTGT GGACATCATT GCCACAGACA TCCAGACCAA

-continued

```
GGAGCTCCAG AAGCAGATCA CCAAGATCCA GAACTTCAGG GTGTACTACA GGGACTCCAG

GAACCCCCTG TGGAAGGGCC CTGCCAAGCT GCTGTGGAAG GGGGAGGGGG CTGTGGTGAT

CCAGGACAAC TCTGACATCA AGGTGGTGCC CAGGAGGAAG GCCAAGATCA TCAGGGACTA

TGGCAAGCAG ATGGCTGGGG ATGACTGTGT GGCCTCCAGG CAGGATGAGG ACTAAAGCCC

GGGCAGATCT.
```

The open reading frame of the tPA-IA-pol construct disclosed as SEQ ID NO:7 contains 875 amino acids, disclosed herein as tPA-IA-Pol and SEQ ID NO:8, as follows:

```
Met Asp Ala Met Lys Arg Gly Leu Cys Cys Val Leu Leu Leu Cys Gly  (SEQ ID NO:8)

Ala Val Phe Val Ser Pro Ser Glu Ile Ser Ala Pro Ile Ser Pro Ile

Glu Thr Val Pro Val Lys Leu Lys Pro Gly Met Asp Gly Pro Lys Val

Lys Gln Trp Pro Leu Thr Glu Glu Lys Ile Lys Ala Leu Val Glu Ile

Cys Thr Glu Met Glu Lys Glu Gly Lys Ile Ser Lys Ile Gly Pro Glu

Asn Pro Tyr Asn Thr Pro Val Phe Ala Ile Lys Lys Lys Asp Ser Thr

Lys Trp Arg Lys Leu Val Asp Phe Arg Glu Leu Asn Lys Arg Thr Gln

Asp Phe Trp Glu Val Gln Leu Gly Ile Pro His Pro Ala Gly Leu Lys

Lys Lys Lys Ser Val Thr Val Leu Ala Val Gly Asp Ala Tyr Phe Ser

Val Pro Leu Asp Glu Asp Phe Arg Lys Tyr Thr Ala Phe Thr Ile Pro

Ser Ile Asn Asn Glu Thr Pro Gly Ile Arg Tyr Gln Tyr Asn Val Leu

Pro Gln Gly Trp Lys Gly Ser Pro Ala Ile Phe Gln Ser Ser Met Thr

Lys Ile Leu Glu Pro Phe Arg Lys Gln Asn Pro Asp Ile Val Ile Tyr

Gln Tyr Met Ala Ala Leu Tyr Val Gly Ser Asp Leu GTh Ile Gly Gln

His Arg Thr Lys Ile Ghl Glu Leu Arg Gln His Leu Leu Arg Trp Gly

Leu Thr Thr Pro Asp Lys Lys His Gln Lys Glu Pro Pro Phe Leu Trp

Met Gly Tyr Glu Leu His Pro Asp Lys Trp Thr Val Gln Pro Ile Val

Leu Pro Glu Lys Asp Ser Trp Thr Val Asn Asp Ile Gln Lys Leu Val

Gly Lys Leu Asn Trp Ala Ser Gln Ile Tyr Pro Gly Ile Lys Val Arg

Gln Leu Cys Lys Leu Leu Arg Gly Thr Lys Ala Leu Thr Glu Val Ile

Pro Leu Thr Glu Glu Ala Glu Leu Glu Leu Ala Glu Asn Arg Glu Ile

Leu Lys Glu Pro Val His Gly Val Tyr Tyr Asp Pro Ser Lys Asp Leu

Ile Ala Glu Ile Gln Lys Gln Gly Gln Gly Gln Trp Thr Tyr Gln Ile

Tyr Gln Glu Pro Phe Lys Asn Leu Lys Thr Gly Lys Tyr Ala Arg Met

Arg Gly Ala His Thr Asn Asp Val Lys Gln Leu Thr Glu Ala Val Gln

Lys Ile Thr Thr Glu Ser Ile Val Ile Trp Gly Lys Thr Pro Lys Phe

Lys Leu Pro Ile Gln Lys Glu Thr Trp Glu Thr Trp Trp Thr Glu Tyr

Trp Gln Ala Thr Trp Ile Pro Glu Trp Glu Phe Val Asn Thr Pro Pro

Leu Val Lys Leu Trp Tyr Gln Leu Glu Lys Glu Pro Ile Val Gly Ala

Glu Thr Phe Tyr Val Ala Gly Ala Ala Asn Arg Glu Thr Lys Leu Gly

Lys Ala Gly Tyr Val Thr Asn Arg Gly Arg Gln Lys Val Val Thr Leu
```

-continued

Thr Asp Thr Thr Asn Gln Lys Thr Ala Leu Gln Ala Ile Tyr Leu Ala

Leu Gln Asp Ser Gly Leu Glu Val Asn Ile Val Thr Ala Ser Gln Tyr

Ala Leu Gly Ile Ile Gln Ala Gln Pro Asp Gln Ser Glu Ser Glu Leu

Val Asn Gln Ile Ile Glu Gln Leu Ile Lys Lys Glu Lys Val Tyr Leu

Ala Trp Val Pro Ala His Lys Gly Ile Gly Gly Asn Glu Gln Val Asp

Lys Leu Val Ser Ala Gly Ile Arg Lys Val Leu Phe Leu Asp Gly Ile

Asp Lys Ala Gln Asp Glu His Glu Lys Tyr His Ser Asn Trp Arg Ala

Met Ala Ser Asp Phe Asn Leu Pro Pro Val Val Ala Lys Glu Ile Val

Ala Ser Cys Asp Lys Cys Gln Leu Lys Gly Glu Ala Met His Gly Gln

Val Asp Cys Ser Pro Gly Ile Trp Gln Leu Ala Cys Thr His Leu Glu

Gly Lys Val Ile Leu Val Ala Val His Val Ala Ser Gly Tyr Ile Glu

Ala Glu Val Ile Pro Ala Glu Thr Gly Gln Glu Thr Ala Tyr Phe Leu

Leu Lys Leu Ala Gly Arg Trp Pro Val Lys Thr Ile His Thr Ala Asn

Gly Ser Asn Phe Thr Gly Ala Thr Val Arg Ala Ala Cys Trp Trp Ala

Gly Ile Lys Gln Glu Phe Gly Ile Pro Tyr Asn Pro Gln Ser Gln Gly

Val Val Ala Ser Met Asn Lys Glu Leu Lys Lys Ile Ile Gly Gln Val

Arg Asp Gln Ala Glu His Leu Lys Thr Ala Val Gln Met Ala Val Phe

Ile His Asn Phe Lys Arg Lys Gly Gly Ile Gly Gly Tyr Ser Ala Gly

Glu Arg Ile Val Asp Ile Ile Ala Thr Asp Ile Gln Thr Lys Glu Leu

Gln Lys Gln Ile Thr Lys Ile Gln Asn Phe Arg Val Tyr Tyr Arg Asp

Ser Arg Asn Pro Leu Trp Lys Gly Pro Ala Lys Leu Leu Trp Lys Gly

Glu Gly Ala Val Val Ile Gln Asp Asn Ser Asp Ile Lys Val Val Pro

Arg Arg Lys Ala Lys Ile Ile Arg Asp Tyr Gly Lys Gln Met Ala Gly

Asp Asp Cys Val Ala Ser Arg Gln Asp Glu Asp.

EXAMPLE 18

Codon Optimized HIV-1 Nef and Codon Optimzed HIV-1 Nef Modifications

Codon optimized version of HIV-1 Nef and HIV-1 Nef modifications are essentially as described in U.S. application Ser. No. 09/738,782, filed Dec. 15, 2000 and PCT International Application PCT/US00/34162, also filed Dec. 15, 2000, both documents which are hereby incorporated by reference. As disclosed within the above-mentioned documents, particular embodiments of codon optimized Nef and Nef modifications relate to a DNA molecule encoding HIV-1 Nef from the HIV-1 jfrl isolate wherein the codons are optimized for expression in a mammalian system such as a human. The DNA molecule which encodes this protein is disclosed herein as SEQ ID NO:9, while the expressed open reading frame is disclosed herein as SEQ ID NO:10. Another embodiment of Nef-based coding regions for use in the adenoviral vectors of the present invention comprise a codon optimized DNA molecule encoding a protein containing the human plasminogen activator (tpa) leader peptide fused with the $NH_2$-terminus of the HIV-1 Nef polypeptide. The DNA molecule which encodes this protein is disclosed herein as SEQ ID NO:11, while the expressed open reading frame is disclosed herein as SEQ ID NO:12. Another modified Nef optimized coding region relates to a DNA molecule encoding optimized HIV-1 Nef wherein the open reading frame codes for modifications at the amino terminal myristylation site (Gly-2 to Ala-2) and substitution of the Leu-174-Leu-175 dileucine motif to Ala-174-Ala-175, herein described as opt nef (G2A, LLAA). The DNA molecule which encodes this protein is disclosed herein as SEQ ID NO:13, while the expressed open reading frame is disclosed herein as SEQ ID NO:14. An additional embodiment relates to a DNA molecule encoding optimized HIV-1 Nef wherein the amino terminal myristylation site and dileucine motif have been deleted, as well as comprising a tPA leader peptide. This DNA molecule, opt tpanef (LLAA), comprises an open reading frame which encodes a Nef protein containing a tPA leader sequence fused to amino acid residue 6–216 of HIV-1 Nef (jfrl), wherein Leu-174 and Leu-175 are substituted with Ala-174 and Ala-175, herein referred to as opt tpanef (LLAA) is disclosed herein as SEQ ID NO:15, while the expressed open reading frame is disclosed herein as SEQ ID NO:16.

As disclosed in the above-identified documents (U.S. application Ser. No. 09/738,782 and PCT International Application PCT/US00/34162) and reiterated herein, the following nef-based nucleotide and amino acid sequences which comprise the respective open reading frame are as follows:

1. The nucleotide sequence of the codon optimized version of HIV-1 jrfl nef gene is disclosed herein as SEQ ID NO:9, as shown herein:

```
GATCTGCCAC CATGGGCGGC AAGTGGTCCA AGAGGTCCGT GCCCGGCTGG TCCACCGTGA  (SEQ ID NO:9)
GGGAGAGGAT GAGGAGGGCC GAGCCCGCCG CCGACAGGGT GAGGAGGACC GAGCCCGCCG
CCGTGGGCGT GGGCGCCGTG TCCAGGGACC TGGAGAAGCA CGGCGCCATC ACCTCCTCCA
ACACCGCCGC CACCAACGCC GACTGCGCCT GGCTGGAGGC CCAGGAGGAC GAGGAGGTGG
GCTTCCCCGT GAGGCCCCAG GTGCCCCTGA GGCCCATGAC CTACAAGGGC GCCGTGGACC
TGTCCCACTT CCTGAAGGAG AAGGGCGGCC TGGAGGGCCT GATCCACTCC CAGAAGAGGC
AGGACATCCT GGACCTGTGG GTGTACCACA CCCAGGGCTA CTTCCCCGAC TGGCAGAACT
ACACCCCCGG CCCCGGCATC AGGTTCCCCC TGACCTTCGG CTGGTGCTTC AAGCTGGTGC
CCGTGGAGCC CGAGAAGGTG GAGGAGGCCA ACGAGGGCGA GAACAACTGC CTGCTGCACC
CCATGTCCCA GCACGGCATC GAGGACCCCG AGAAGGAGGT GCTGGAGTGG AGGTTCGACT
CCAAGCTGGC CTTCCACCAC GTGGCCAGGG AGCTGCACCC CGAGTACTAC AAGGACTGCT
AAAGCCCGGG C.
```

Preferred codon usage is as follows: Met (ATG), Gly (GGC), Lys (AAG), Trp (TGG), Ser (TCC), Arg (AGG), Val (GTG), Pro (CCC), Thr (ACC), Glu (GAG); Leu (CTG), His (CAC), Ile (ATC), Asn (AAC), Cys (TGC), Ala (GCC), Gln (CAG), Phe (TTC) and Tyr (TAC). For an additional discussion relating to mammalian (human) codon optimization, see WO 97/31115 (PCT/US97/02294), which is hereby incorporated by reference. See also FIGS. 19A–B for a comparion of wild type vs. codon optimized nucleotides comprising the open reading frame of HIV-Nef.

The open reading frame for SEQ ID NO:9 above comprises an initiating methionine residue at nucleotides 12–14 and a "TAA" stop codon from nucleotides 660–662. The open reading frame of SEQ ID NO:9 provides for a 216 amino acid HIV-1 Nef protein expressed through utilization of a codon optimized DNA vaccine vector. The 216 amino acid HIV-1 Nef (jfrl) protein is disclosed herein as SEQ ID NO:10, and as follows:

HIV-1 Nef is a 216 amino acid cytosolic protein which associates with the inner surface of the host cell plasma membrane through myristylation of Gly-2 (Franchini et al., 1986, *Virology* 155: 593–599). While not all possible Nef functions have been elucidated, it has become clear that correct trafficking of Nef to the inner plasma membrane promotes viral replication by altering the host intracellular environment to facilitate the early phase of the HIV-1 life cycle and by increasing the infectivity of progeny viral particles. In one aspect of the invention regarding codon-optimized, protein-modified polypeptides, the nef-encoding region of the adenovirus vector of the present invention is modified to contain a nucleotide sequence which encodes a heterologous leader peptide such that the amino terminal region of the expressed protein will contain the leader peptide. The diversity of function that typifies eukaryotic cells depends upon the structural differentiation of their membrane boundaries. To generate and maintain these structures, proteins must be transported from their site of

```
Met Gly Gly Lys Trp Ser Lys Arg Ser Val Pro Gly Trp Ser Thr Val  (SEQ ID NO:10)
Arg Clu Arg Met Arg Arg Ala Glu Pro Ala Ala Asp Arg Val Arg Arg
Thr Glu Pro Ala Ala Val Gly Val Gly Ala Val Ser Arg Asp Leu Glu
Lys His Gly Ala Ile Thr Ser Ser Asn Thr Ala Ala Thr Asn Ala Asp
Cys Ala Trp Leu Glu Ala Gln Glu Asp Glu Glu Val Gly Phe Pro Val
Arg Pro Gln Val Pro Leu Arg Pro Met Thr Tyr Lys Gly Ala Val Asp
Leu Ser His Phe Leu Lys Glu Lys Gly Gly Leu Glu Gly Leu Ile His
Ser Gln Lys Arg Gln Asp Ile Leu Asp Leu Trp Val Tyr His Thr Gln
Gly Tyr Phe Pro Asp Trp Gln Asn Tyr Thr Pro Gly Pro Gly Ile Arg
Phe Pro Leu Thr Phe Gly Trp Cys Phe Lys Leu Val Pro Val Glu Pro
Glu Lys Val Glu Glu Ala Asn Glu Gly Glu Asn Asn Cys Leu Leu His
Pro Met Ser Gln His Gly Ile Glu Asp Pro Glu Lys Glu Val Leu Glu
Trp Arg Phe Asp Ser Lys Leu Ala Phe His His Val Ala Arg Glu Leu
His Pro Glu Tyr Tyr Lys Asp Cys.
```

synthesis in the endoplasmic reticulum to predetermined destinations throughout the cell. This requires that the trafficking proteins display sorting signals that are recognized by the molecular machinery responsible for route selection located at the access points to the main trafficking pathways. Sorting decisions for most proteins need to be made only once as they traverse their biosynthetic pathways since their final destination, the cellular location at which they perform their function, becomes their permanent residence. Maintenance of intracellular integrity depends in part on the selective sorting and accurate transport of proteins to their correct destinations. Defined sequence motifs exist in proteins which can act as 'address labels'. A number of sorting signals have been found associated with the cytoplasmic domains of membrane proteins. An effective induction of CTL responses often required sustained, high level endogenous expression of an antigen. As membrane-association via myristylation is an essential requirement for most of Nef's function, mutants lacking myristylation, by glycine-to-alanine change, change of the dileucine motif and/or by substitution with a tpa leader sequence as described herein, will be functionally defective, and therefore will have improved safety profile compared to wild-type Nef for use as an HIV-1 vaccine component.

Figure 16A:
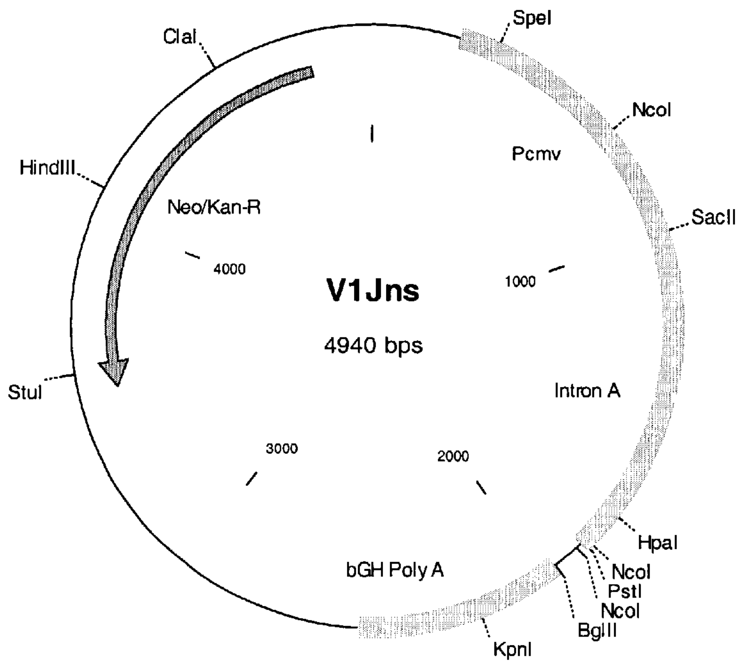
FIGS. 16A–B shows a schematic representation of DNA vaccine expression vectors V1Jns (A) and V1Jns-tPA (B), which are utilized for HIV-1 gag, pol and nef constructs in various DNA/viral vector combined modality regimens as disclosed herein.
Figure 16B:
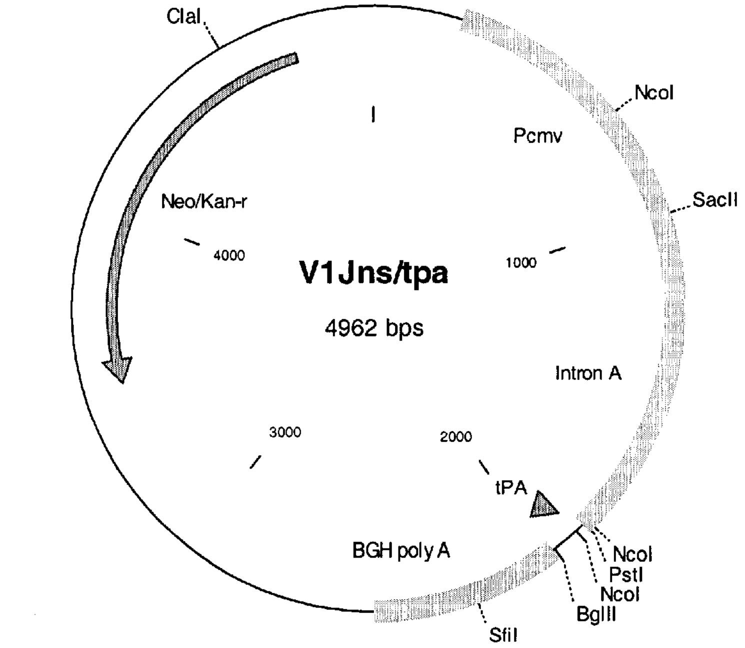

In another embodiment of this portion of the invention, either the DNA vector or the HIV-1 nef nucleotide sequence is modified to include the human tissue-specific plasminogen activator (tPA) leader. As shown in FIGS. 16A–B, a DNA vector may be modified by known recombinant DNA methodology to contain a leader signal peptide of interest, such that downstream cloning of the modified HIV-1 protein of interest results in a nucleotide sequence which encodes a modified HIV-1 tPA/Nef protein. In the alternative, as noted above, insertion of a nucleotide sequence which encodes a leader peptide may be inserted into a DNA vector housing the open reading frame for the Nef protein of interest. Regardless of the cloning strategy, the end result is a polynucleotide vaccine which comprises vector components for effective gene expression in conjunction with nucleotide sequences which encode a modified HIV-1 Nef protein of interest, including but not limited to a HIV-1 Nef protein which contains a leader peptide. The amino acid sequence of the human tPA leader utilized herein is as follows: MDAMKRGLCCVLLLCGAVFVSPSEISS (SEQ ID NO:17).

It has been shown that myristylation of Gly-2 in conjunction with a dileucine motif in the carboxy region of the protein is essential for Nef-induced down regulation of CD4 (Aiken et al., 1994, *Cell* 76: 853–864) via endocytosis. It has also been shown that Nef expression promotes down regulation of MHCI (Schwartz et al., 1996, *Nature Medicine* 2(3): 338–342) via endocytosis. The present invention relates in part to DNA vaccines which encode modified Nef proteins altered in trafficking and/or functional properties. The modifications introduced into the adenoviral vector HIV vaccines of the present invention include but are not limited to additions, deletions or substitutions to the nef open reading frame which results in the expression of a modified Nef protein which includes an amino terminal leader peptide, modification or deletion of the amino terminal myristylation site, and modification or deletion of the dileucine motif within the Nef protein and which alter function within the infected host cell. Therefore, a central theme of the DNA molecules and recombinant adenoviral HIV vaccines of the present invention is (1) host administration and intracellular delivery of a codon optimized nef-based adenoviral HIV vaccine; (2) expression of a modified Nef protein which is immunogenic in terms of eliciting both CTL and Th responses; and, (3) inhibiting or at least altering known early viral functions of Nef which have been shown to promote HIV-1 replication and load within an infected host. Therefore, the nef coding region may be altered, resulting in a DNA vaccine which expresses a modified Nef protein wherein the amino terminal Gly-2 myristylation residue is either deleted or modified to express alternate amino acid residues. Also, the nef coding region may be altered so as to result in a DNA vaccine which expresses a modified Nef protein wherein the dileucine motif is either deleted or modified to express alternate amino acid residues. In addition, the adenoviral vector HIV vaccines of the present invention also relate to an isolated DNA molecule, regardless of codon usage, which expresses a wild type or modified Nef protein as described herein, including but not limited to modified Nef proteins which comprise a deletion or substitution of Gly 2, a deletion or substitution of Leu 174 and Leu 175 and/or inclusion of a leader sequence.

Therefore, specific Nef-based constructs further include the following, as exemplification's and not limitations. For example, the present invention relates to an adenoviral vector vaccine which encodes modified forms of HIV-1, an open reading frame which encodes a Nef protein which comprises a tPA leader sequence fused to amino acid residue 6–216 of HIV-1 Nef (jfrl) is referred to herein as opt tpanef. The nucleotide sequence comprising the open reading frame of opt tpanef is disclosed herein as SEQ ID NO:11, as shown below:

```
CATGGATGCA ATGAAGAGAG GGCTCTGCTG TGTGCTGCTG CTGTCTGGAG CAGTCTTCGT  (SEQ ID NO:11)
TTCGCCCAGC GAGATCTCCT CCAAGAGGTC CGTGCCCGGC TGGTCCACCG TGAGGGAGAG
GATGAGGAGG GCCGAGCCCG CCGCCGACAG GGTGAGGAGG ACCGAGCCCG CCGCCGTGGG
CGTGGGCGCC GTGTCCAGGG ACCTGGAGAA GCACGGCGCC ATCACCTCCT CCAACACCGC
CGCCACCAAC GCCGACTGCG CCTGGCTGGA GGCCCAGGAG GACGAGGAGG TGGGCTTCCC
CGTGAGGCCC CAGGTGCCCC TGAGGCCCAT GACCTACAAG GGCGCCGTGG ACCTGTCCCA
CTTCCTGAAG GAGAAGGGCG GCCTGGAGGG CCTGATCCAC TCCCAGAAGA GGCAGGACAT
```

-continued

```
CCTGGACCTG TGGGTGTACC ACACCCAGGG CTACTTCCCC GACTGGCAGA ACTACACCCC

CGGCCCCGGC ATCAGGTTCC CCCTGACCTT CGGCTGGTGC TTCAAGCTGG TGCCCGTGGA

GCCCGAGAAG GTGGAGGAGG CCAACGAGGG CGAGAACAAC TGCCTGCTGC ACCCCATGTC

CCAGCACGGC ATCGAGGACC CCGAGAAGGA GGTGCTGGAG TGGAGGTTCG ACTCCAAGCT

GGCCTTCCAC CACGTGGCCA GGGAGCTGCA CCCCGAGTAC TACAAGGACT GCTAAAGCC
```

The open reading frame of SEQ ID NO:11 provides for a 237 amino acid HIV-1 Nef protein which comprises a tPA leader sequence fused to amino acids 6–216 of HIV-1 Nef, including the dileucine motif at amino acid residues 174 and 175. This 237 amino acid tPA/Nef (jfrl) fusion protein is disclosed herein as SEQ ID NO:12, and is shown as follows:

```
Met Asp Ala Met Lys Arg Gly Leu Cys Cys Val Leu Leu Leu Cys Gly  (SEQ ID NO:12)

Ala Val Phe Val Ser Pro Ser Glu Ile Ser Ser Lys Arg Ser Val Pro

Gly Trp Ser Thr Val Arg Glu Arg Met Arg Arg Ala Glu Pro Ala Ala

Asp Arg Val Arg Arg Thr Glu Pro Ala Ala Val Gly Val Gly Ala Val

Ser Arg Asp Leu Glu Lys His Gly Ala Ile Thr Ser Ser Asn Thr Ala

Ala Thr Asn Ala Asp Cys Ala Trp Leu Glu Ala Gln Glu Asp Glu Glu

Val Gly Phe Pro Val Arg Pro Gln Val Pro Leu Arg Pro Met Thr Tyr

Lys Gly Ala Val Asp Leu Ser His Phe Leu Lys Glu Lys Gly Gly Leu

Glu Gly Leu Ile His Ser Gln Lys Arg Gln Asp Ile Leu Asp Leu Trp

Val Tyr His Thr Gln Gly Tyr Phe Pro Asp Trp Gln Asn Tyr Thr Pro

Gly Pro Gly Ile Arg Phe Pro Leu Thr Phe Gly Trp Cys Phe Lys Leu

Val Pro Val Glu Pro Glu Lys Val Glu Glu Ala Asn Glu Gly Glu Asn

Asn Cys Leu Leu His Pro Met Ser Gln His Gly Ile Glu Asp Pro Glu

Lys Glu Val Leu Glu Trp Arg Phe Asp Ser Lys Leu Ala Phe His His

Val Ala Arg Glu Leu His Pro Glu Tyr Tyr Lys Asp Cys.
```

Therefore, this exemplified Nef protein, Opt tPA-Nef, contains both a tPA leader sequence as well as deleting the myristylation site of Gly-2A DNA molecule encoding HIV-1 Nef from the HIV-1 jfrl isolate wherein the codons are optimized for expression in a mammalian system such as a human.

In another specific embodiment of the present invention, a DNA molecule is disclosed which encodes optimized HIV-1 Nef wherein the open reading frame of a recombinant adenoviral HIV vaccine encodes for modifications at the amino terminal myristylation site (Gly-2 to Ala-2) and substitution of the Leu-174-Leu-175 dileucine motif to Ala-174-Ala-175. This open reading frame is herein described as opt nef (G2A,LLAA) and is disclosed as SEQ ID NO:13, which comprises an initiating methionine residue at nucleotides 12–14 and a "TAA" stop codon from nucleotides 660–662. The nucleotide sequence of this codon optimized version of HIV-1 jrfl nef gene with the above mentioned modifications is disclosed herein as SEQ ID NO:13, as follows:

```
GATCTGCCAC CATGGCCGGC AAGTGGTCCA AGAGGTCCGT GCCCGGCTGG TCCACCGTGA  (SEQ ID NO:13)

GGGAGAGGAT GAGGAGGGCC GAGCCCGCCG CCGACAGGGT GAGGAGGACC GAGCCCGCCG

CCGTGGGCGT GGGCGCCGTG TCCAGGGACC TGGAGAAGCA CGGCGCCATC ACCTCCTCCA

ACACCGCCGC CACCAACGCC GACTGCGCCT GGCTGGAGGC CCAGGAGGAC GAGGAGGTGG

GCTTCCCCGT GAGGCCCCAG GTGCCCCTGA GGCCCATGAC CTACAAGGGC GCCGTGGACC

TGTCCCACTT CCTGAAGGAG AAGGGCGGCC TGGAGGGCCT GATCCACTCC CAGAAGAGGC
```

-continued

```
AGGACATCCT GGACCTGTGG GTGTACCACA CCCAGGGCTA CTTCCCCGAC TGGCAGAACT
ACACCCCCGG CCCCGGCATC AGGTTCCCCC TGACCTTCGG CTGGTGCTTC AAGCTGGTGC
CCGTGGAGCC CGAGAAGGTG GAGGAGGCCA ACGAGGGCGA GAACAACTGC GCCGCCCACC
CCATGTCCCA GCACGGCATC GAGGACCCCG AGAAGGAGGT GCTGGAGTGG AGGTTCGACT
CCAAGCTGGC CTTCCACCAC GTGGCCAGGG AGCTGCACCC CGAGTACTAC AAGGACTGCT
AAAGCCCGGG C.
```

The open reading frame of SEQ ID NO:13 encodes Nef (G2A,LLAA), disclosed herein as SEQ ID NO:14, as follows:

```
Met Ala Gly Lys Trp Ser Lys Arg Ser Val Pro Gly Trp Ser Thr Val  (SEQ ID NO:14).
Arg Glu Arg Met Arg Arg Ala Glu Pro Ala Ala Asp Arg Val Arg Arg
Thr Glu Pro Ala Ala Val Gly Val Gly Ala Val Ser Arg Asp Leu Glu
Lys His Gly Ala Ile Thr Ser Ser Asn Thr Ala Ala Thr Asn Ala Asp
Cys Ala Trp Leu Glu Ala Gln Glu Asp Glu Glu Val Gly Phe Pro Val
Arg Pro Gln Val Pro Leu Arg Pro Met Thr Tyr Lys Gly Ala Val Asp
Leu Ser His Phe Leu Lys Glu Lys Gly Gly Leu Glu Gly Leu Ile His
Ser Gln Lys Arg Gln Asp Ile Leu Asp Leu Trp Val Tyr His Thr Gln
Gly Tyr Phe Pro Asp Trp Gln Asn Tyr Thr Pro Gly Pro Gly Ile Arg
Phe Pro Leu Thr Phe Gly Trp Cys Phe Lys Leu Val Pro Val Glu Pro
Glu Lys Val Glu Glu Ala Asn Glu Gly Glu Asn Asn Cys Ala Ala His
Pro Met Ser Gln His Gly Ile Glu Asp Pro Glu Lys Glu Val Leu Glu
Trp Arg Phe Asp Ser Lys Leu Ala Phe His His Val Ala Arg Glu Leu
His Pro Glu Tyr Tyr Lys Asp Cys Ser
```

An additional embodiment of the present invention relates to another DNA molecule encoding optimized HIV-1 Nef wherein the amino terminal myristylation site and dileucine motif have been deleted, as well as comprising a tPA leader peptide. This DNA molecule, opt tpanef (LLAA) comprises an open reading frame which encodes a Nef protein containing a tPA leader sequence fused to amino acid residue 6–216 of HIV-1 Nef (jfrl), wherein Leu-174 and Leu-175 are substituted with Ala-174 and Ala-175 (Ala-195 and Ala-196 in this tPA-based fusion protein). The nucleotide sequence comprising the open reading frame of opt tpanef (LLAA) is disclosed herein as SEQ ID NO:15, as shown below:

```
CATGGATGCA ATGAAGAGAG GGCTCTGCTG TGTGCTGCTG CTGTGTGGAG CAGTCTTCGT  (SEQ ID NO:15)
TTCGCCCAGC GAGATCTCCT CCAAGAGGTC CGTGCCCGGC TGGTCCACCG TGAGGGAGAG
GATGAGGAGG GCCGAGCCCG CCGCCGACAG GGTGAGGAGG ACCGAGCCCG CCGCCGTGGG
CGTGGGCGCC GTGTCCAGGG ACCTGGAGAA GCACGGCGCC ATCACCTCCT CCAACACCGC
CGCCACCAAC GCCGACTGCG CCTGGCTGGA GGCCCAGGAG GACGAGGAGG TGGGCTTCCC
CGTGAGGCCC CAGGTGCCCC TGAGGCCCAT GACCTACAAG GGCGCCGTGG ACCTGTCCCA
CTTCCTGAAG GAGAAGGGCG GCCTGGAGGG CCTGATCCAC TCCCAGAAGA GGCAGGACAT
CCTGGACCTG TGGGTGTACC ACACCCAGGG CTACTTCCCC GACTGGCAGA ACTACACCCC
CGGCCCCGGC ATCAGGTTCC CCCTGACCTT CGGCTGGTGC TTCAAGCTGG TGCCCGTGGA
GCCCGAGAAG GTGGAGGAGG CCAACGAGGG CGAGAACAAC TGCGCCGCCC ACCCCATGTC
```

-continued

```
CCAGCACGGC ATCGAGGACC CCGAGAAGGA GGTGCTGGAG TGGAGGTTCG ACTCCAAGCT

GGCCTTCCAC CACGTGGCCA GGGAGCTGCA CCCCGAGTAC TACAAGGACT GCTAAAGCCC
```

The open reading frame of SEQ ID NO:15 encoding tPA-Nef (LLAA), disclosed herein as SEQ ID NO:16, is as follows:

```
Met Asp Ala Met Lys Arg Gly Leu Cys Cys Val Leu Leu Leu Cys Gly  (SEQ ID NO:16)

Ala Val Phe Val Ser Pro Ser Glu Ile Ser Ser Lys Arg Ser Val Pro

Gly Trp Ser Thr Val Arg Glu Arg Met Arg Arg Ala Glu Pro Ala Ala

Asp Arg Val Arg Arg Thr Glu Pro Ala Ala Val Gly Val Gly Ala Val

Ser Arg Asp Leu Glu Lys His Gly Ala Ile Thr Ser Ser Asn Thr Ala

Ala Thr Asn Ala Asp Cys Ala Trp Leu Glu Ala Gln Glu Asp Glu Glu

Val Gly Phe Pro Val Arg Pro Gln Val Pro Leu Arg Pro Met Thr Tyr

Lys Gly Ala Val Asp Leu Ser His Phe Leu Lys Glu Lys Gly Gly Leu

Glu Gly Leu Ile His Ser Gln Lys Arg Gln Asp Ile Leu Asp Leu Trp

Val Tyr His Thr Gln Gly Tyr Phe Pro Asp Trp Gln Asn Tyr Thr Pro

Gly Pro Gly Ile Arg Phe Pro Leu Thr Phe Gly Trp Cys Phe Lys Leu

Val Pro Val Glu Pro Glu Lys Val Glu Glu Ala Asn Glu Gly Glu Asn

Asn Cys Ala Ala His Pro Met Ser Gln His Gly Ile Glu Asp Pro Glu

Lys Glu Val Leu Glu Trp Arg Phe Asp Ser Lys Leu Ala Phe His His

Val Ala Arg Glu Leu His Pro Glu Tyr Tyr Lys Asp Cys.
```

An adenoviral vector of the present invention may comprise a DNA sequence, regardless of codon usage, which expresses a wild type or modified Nef protein as described herein, including but not limited to modified Nef proteins which comprise a deletion or substitution of Gly 2, a deletion of substitution of Leu 174 and Leu 175 and/or inclusion of a leader sequence. Therefore, partial or fully codon optimized DNA vaccine expression vector constructs are preferred since such constructs should result in increased host expression. However, it is within the scope of the present invention to utilize "non-codon optimized" versions of the constructs disclosed herein, especially modified versions of HIV Nef which are shown to promote a substantial cellular immune response subsequent to host administration.

FIGS. 20A–C show nucleotide sequences at junctions between nef coding sequence and plasmid backbone of nef expression vectors V1Jns/nef (FIG. 20A), V1Jns/nef(G2A, LLAA) (FIG. 20B), V1Jns/tpanef (FIG. 20C) and V1Jns/tpanef(LLAA) (FIG. 20C, also). 5' and 3' flanking sequences of codon optimized nef or codon optimized nef mutant genes are indicated by bold/italic letters; nef and nef mutant coding sequences are indicated by plain letters. Also indicated (as underlined) are the restriction endonuclease sites involved in construction of respective nef expression vectors. V1Jns/tpanef and V1Jns/tpanef(LLAA) have identical sequences at the junctions.

Figure 21:
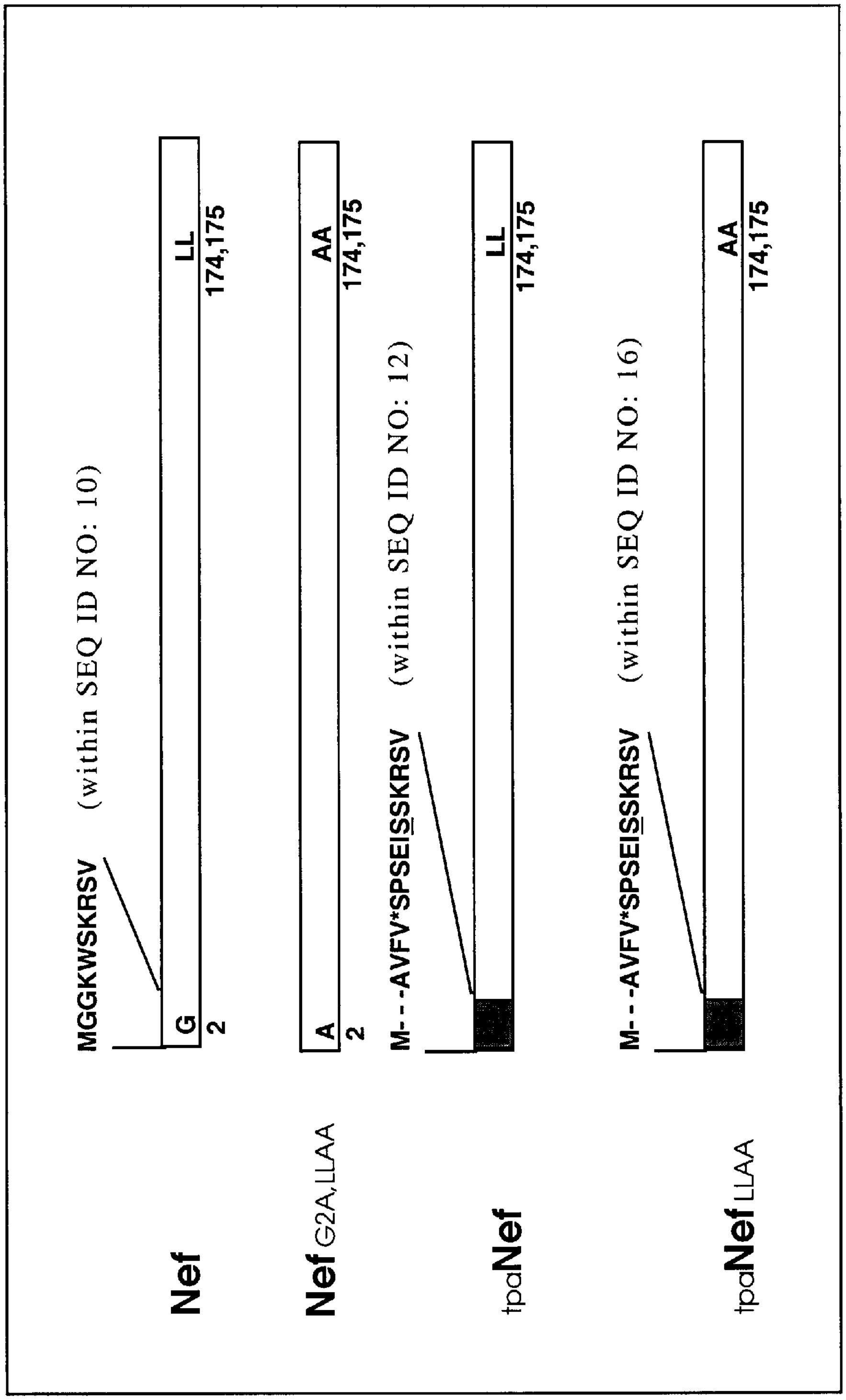

FIG. 21 shows a schematic presentation of nef and nef derivatives. Amino acid residues involved in Nef derivatives are presented. Glycine 2 and Leucine174 and 175 are the sites involved in myristylation and dileucine motif, respectively.

EXAMPLE 19

MRKAd5Pol Construction and Virus Rescue

Construction of Vector: Shuttle Plasmid and Pre-Adenovirus Plasmid—Key steps performed in the construction of the vectors, including the pre-adenovirus plasmid denoted MRKAd5pol, is depicted in FIG. 22. Briefly, the adenoviral shuttle vector for the full-length inactivated HIV-1 pol gene is as follows. The vector MRKpdelE1(Pac/pIX/pack450)+CMVmin+BGHpA(str.) is a derivative of the shuttle vector used in the construction of the MRKAd5gag adenoviral pre-plasmid. The vector contains an expression cassette with the hCMV promoter (no intronA) and the bovine growth hormone polyadenylation signal. The expression unit has been inserted into the shuttle vector such that insertion of the gene of choice at a unique BglII site will ensure the direction of transcription of the transgene will be Ad5 E1 parallel when inserted into the MRKpAd5(E1−/E3+)Cla1 (or MRKpAdHVE3) pre-plasmid. The vector, similar to the original shuttle vector contains the Pac1 site, extension to the packaging signal region, and extension to the pIX gene. The synthetic full-length codon-optimized HIV-1 pol gene was isolated directly from the plasmid pV1Jns-HIV-pol-inact(opt). Digestion of this plasmid with Bgl II releases the pol gene intact (comprising a codon optimized IA pol sequence as disclosed in SEQ ID NO:3). The pol fragment was gel purified and ligated into the MRKpdelE1(Pac/pIX/pack450)+CMVmin+BGHpA(str.) shuttle vector at the BglII site. The clones were checked for the correct orientation of the gene by using restriction enzymes DraIII/Not1. A positive clone was isolated and named MRKpdel+hCMVmin+FL-pol+bGHpA(s). The genetic structure of this plasmid was verified by PCR, restriction enzyme and DNA sequencing. The pre-adenovirus plasmid was constructed as follows. Shuttle plasmid MRKpdel+hCMVmin+FL-pol+bGHpA(S) was digested with restriction enzymes Pac1 and Bst1107 I (or its isoschizomer, BstZ107 I) and then co-transformed into *E. coli* strain BJ5183 with linearized (Cla1 digested) adenoviral backbone plasmid, MRKpAd(E1−/E3+)Cla1. The resulting pre-plasmid originally named MRKpAd+hCMVmin+FL-pol+bGHpA(S)E3+ is now referred to as "pMRKAd5pol". The genetic structure of the resulting pMRKAd5pol was verified by PCR, restriction enzyme and DNA sequence analysis. The vectors were transformed into competent *E. coli* XL-1 Blue for preparative production. The recovered plasmid was verified by restriction enzyme digestion and DNA sequence analysis, and by expression of the pol transgene in transient transfection cell culture. The complete nucleotide sequence of this pMRKAd5HIV-1pol adenoviral vector is shown in FIGS. 26A–AO.

Generation of Research-Grade Recombinant Adenovirus—The pre-adenovirus plasmid, pMRKAd5pol, was rescued as infectious virions in PER.C6® adherent monolayer cell culture. To rescue infectious virus, 12 $\mu$g of pMRKAd5pol was digested with restriction enzyme PacI (New England Biolabs) and 3.3 $\mu$g was transfected per 6 cm dish of PER.C6® cells using the calcium phosphate co-precipitation technique (Cell Phect Transfection Kit, Amersham Pharmacia Biotech Inc.). PacI digestion releases the viral genome from plasmid sequences allowing viral replication to occur after entry into PER.C6®cells. Infected cells and media were harvested 6–10 days post-transfection, after complete viral cytopathic effect (CPE) was observed. Infected cells and media were stored at ≦−60° C. This pol containing recombinant adenovirus is referred to herein as "MRKAd5pol". This recombinant adenovirus expresses an inactivated HIV-1 Pol protein as shown in SEQ ID NO:6.

EXAMPLE 20

MRKAd5Nef Construction and Virus Rescue

Construction of Vector: Shuttle Plasmid and Pre-Adenovirus Plasmid—Key steps performed in the construction of the vectors, including the pre-adenovirus plasmid denoted MRKAd5nef, is depicted in FIG. 23. Briefly, as shown in Example 19 above, the vector MRKpdelE1(Pac/pIX/pack450)+CMVmin+BGHpA(str.) is the shuttle vector used in the construction of the MRKAd5gag adenoviral pre-plasmid. It has been modified to contain the Pac1 site, extension to the packaging signal region, and extension to the pIX gene. It contains an expression cassette with the hCMV promoter (no intronA) and the bovine growth hormone polyadenylation signal. The expression unit has been inserted into the shuttle vector such that insertion of the gene of choice at a unique Bgl11 site will ensure the direction of transcription of the transgene will be Ad5 E1 parallel when inserted into the MRKpAd5(E1−/E3+)Cla1 pre-plasmid. The synthetic full-length codon-optimized HIV-1 nef gene was isolated directly from the plasmid pV1Jns/nef (G2A, LLAA). Digestion of this plasmid with Bgl11 releases the nef gene intact, which comprises the nucleotide sequence as disclosed in SEQ ID NO:13. The nef fragment was gel purified and ligated into the MRKpdelE1+CMVmin+BGHpA(str.) shuttle vector at the Bgl11 site. The clones were checked for correction orientation of the gene by using restriction enzyme Sca1. A positive clone was isolated and named MRKpdelE1hCMVminFL-nefBGHpA(s). The genetic structure of this plasmid was verified by PCR, restriction enzyme and DNA sequencing. The pre-adenovirus plasmid was constructed as follows. Shuttle plasmid MRKpdelE1hCMVminFL-nefBGHpA(s) was digested with restriction enzymes Pac1 and Bst1107 I (or its isoschizomer, BstZ107 I) and then co-transformed into *E. coli* strain BJ5183 with linearized (Cla1 digested) adenoviral backbone plasmid, MRKpAd(E1/E3+)Cla1. The resulting pre-plasmid originally named MRKpdelE1hCMVminFL-nefBGHpA(s) is now referred to as "pMRKAd5nef". The genetic structure of the resulting pMRKAd5nef was verified by PCR, restriction enzyme and DNA sequence analysis. The vectors were transformed into competent *E. coli* XL-1 Blue for preparative production. The recovered plasmid was verified by restriction enzyme digestion and DNA sequence analysis, and by expression of the nef transgene in transient transfection cell culture. The complete nucleotide sequence of this pMRKAd5HIV-1nef adenoviral vector is shown in FIGS. 27A–AM.

Generation of Research-Grade Recombinant Adenovirus—The pre-adenovirus plasmid, pMRKAd5nef, was rescued as infectious virions in PER.C6® adherent monolayer cell culture. To rescue infectious virus, 12 $\mu$g of pMRKAdnef was digested with restriction enzyme Pac1 (New England Biolabs) and 3.3 $\mu$g was transfected per 6 cm dish of PER.C6® cells using the calcium phosphate co-precipitation technique (Cell Phect Transfection Kit, Amersham Pharmacia Biotech Inc.). Pac1 digestion releases the viral genome from plasmid sequences allowing viral replication to occur after entry into PER.C6® cells. Infected cells and media were harvested 6–10 days post-transfection, after complete viral cytopathic effect (CPE) was observed. Infected cells and media were stored at ≦−60° C. This nef containing recombinant adenovirus is now referred to as "MRKAd5nef".

EXAMPLE 21

Construction of Murine CMV Promoter Containing Shuttle Vectors for Inactivated Pol and Nef/G2A, LLAA The murine CMV (mCMV) was amplified from the plasmid pMH4 (supplied by Frank Graham, McMaster University) using the primer set: mCMV (Not I) Forward: 5'-ATA AGA AT<u>G CGG CCG C</u>CA TAT ACT GAG TCA TTA GG-3' (SEQ ID NO:20); mCMV (Bgl II)Reverse: 5'-AAG GA<u>A GAT CT</u>A CCG ACG CTG GTC GCG CCT C-3' (SEQ ID NO:21). The underlined nucleotides represent the Not I and the Bgl II sites respectively for each primer. This PCR amplicon was used for the construction of the mCMV shuttle vector containing the transgene in the E1 parallel orientation. The hCMV promoter was removed from the original shuttle vector (containing the hCMV-gag-bGHpA transgene in the E1 parallel orientation) by digestion with Not I and Bgl II. The mCMV promoter (Not I/Bgl II digested PCR product) was inserted into the shuttle vector in a directional manner. The shuttle vector was then digested with Bgl II and the gag reporter gene (Bgl II fragment) was re-inserted back into the shuttle vector. Several clones were screened for correct orientation of the reporter gene. For the construction of the mCMV-gag in the E1 antiparallel orientation, the mCMV promoter was amplified from the plasmid pMH4 using the following primer set: mCMV (Asc I) Forward: 5'-ATA AGA AT<u>G GCGCGC C</u>AT ATA CTG AGT CAT TAG G (SEQ ID NO:22); mCMV (Bgl II) Reverse: 5' AAG GA<u>A GAT CT</u>A CCG ACG CTG GTC GCG CCT C (SEQ ID NO:21). The underlined nucleotides represent the Asc I and Bgl II sites, respectively for each primer. The shuttle vector containing the hCMV-gag transgene in the E1 antiparallel orientation was digested with Asc1 and Bgl11 to remove the hCMV-gag portion of the transgene. The mCMV promoter (Asc1/Bgl11 digested PCR product) was inserted into the shuttle vector in a directional manner. The vector was then digested with Bgl11 and the gag reporter gene (Bgl11 fragment) was re-inserted. Several clones were screened for correct orientation of the reporter gene. For each of the full length IA pol and full length nef/G2A,LLAA genes, cloning was performed using the unique Bgl II site within the mCMV-bGHpA shuttle vector. The pol and nef genes were excised from their respective pV1Jns plasmids by Bgl II digestion.

EXAMPLE 22

Construction of mCMV Full Length Inactivated Pol and Full Length nef/G2A.LLAA Adenovectors Each of these transgenes of Example 21 were inserted into the modified shuttle vector in both the E1 parallel and E1 anti-parallel orientations. Pac1 and BstZ110I digestion of each shuttle vector was performed and each specific transgene fragment containing the flanking Ad5 sequences was isolated and co-transformed with Cla I digested MRKpAd5 (E3+) or MRKpAd5(E3−) adenovector plasmids via bacterial homologous recombination in BJ5183 *E. coli* cells. Recombinant pre-plasmid adenovectors containing the various transgenes in both the E3− and E3+ versions (and in the E1 parallel and E1 antiparallel orientations) were subsequently prepared in large scale following transformation into XL-1 Blue *E. coli* cells and analyzed by restriction analysis and sequencing.

EXAMPLE 23

Construction of hCMV-tpa-nef (LLAA) Adenovector

The tpa-nef gene was amplified out from GMP grade pV1Jns-tpanef (LLAA) vector using the primer sets: Tpanef (BamHI) F 5'-ATT <u>GGA TCC</u> ATG GAT GCA ATG AAG AGA GGG (SEQ ID 23); Tpanef (BamHI) R 5'-ATA <u>GGA TCC</u> TTA GCA GTC CTT GTA GTA CTC G (SEQ ID NO:24). The resulting PCR product was digested with BamHI, gel purified and cloned into the Bgl II site of MRKAd5CMV-bGHpA shuttle vector (Bgl II digested and calf intestinal phosphatase treated). Clones containing the tpanef (LLAA) gene (see SEQ ID NO:15 for complet coding region) in the correct orientation with respect to the hCMV promoter were selected following Sca I digestion. The resulting MRKAd5tpanef shuttle vector was digested with Pac I and Bst Z1101 and cloned into the E3+ MRKAd5 adenovector via bacterial homologous recombination techniques.

EXAMPLE 24

Immunogenicity of MRKAd5pol and MRKAd5nef Vaccine

Materials and Methods—Rodent Immunization—Groups of N=10 BALB/c mice were immunized i.m. with the following vectors: (1) MRKAd5hCMV-IApol (E3+) at either 10^7 vp and 10^9 vp; and (2) MRKAd5hCMV-IApol (E3−) at either 10^7 vp and 10^9 vp. At 7 weeks post dose, 5 of the 10 mice per cohort were boosted with the same vector and dose they initially received. At 3 weeks post the second does, sera and spleens were collected from all the animals for RT ELISA and IFNg ELIspot analyses, respectively. For all rodent immunizations, the Ad5 vectors were diluted in 5 mM Tris, 5% sucrose, 75 mM NaCl, 1 mM MgCl2, 0.005% polysorbate 80, pH 8.0. The total dose was injected to both quadricep muscles in 50 $\mu$L aliquots using a 0.3-mL insulin syringe with 28½ G needles (Becton-Dickinson, Franklin Lakes, N.J.).

Groups of N=10 C57/BL6 mice were immunized i.m. with the following vectors: (1) MRKAd5hCMV-nef(G2A, LLAA) (E3+) at either 10^7 vp and 10^9 vp; (2) MRKAd5mCMV-nef(G2A,LLAA) (E3+) at either 10^7 vp and 10^9 vp; and (3) MRKAd5mCMV-tpanef(LLAA) (E3+) at either 10^7 vp and 10^9 vp. At 7 weeks post dose, 5 of the 10 mice per cohort were boosted with the same vector and dose they initially received. At 3 weeks post the second does, sera and spleens were collected from all the animals for RT ELISA and IFNg ELIspot analyses, respectively.

Non-Human Primate Immunization—Cohorts of 3 rhesus macaques (2–3 kg) were vaccinated with the following Ad vectors: (1) MRKAd5hCMV-IApol (E3+) at either 10^9 vp and 10^11 vp dose; and (2) MRKAd5hCMV-IApol (E3−) at either 10^9 vp and 10^11 vp; (3) MRKAd5hCMV-nef(G2A, LLAA) (E3+) at either 10^9 vp and 10^11 vp; and (4) MRKAd5mCMV-nef(G2A,LLAA) (E3+) at either 10^9 vp and 10^11 vp. The vaccine was administered to chemically restrained monkeys (10 mg/kg ketamine) by needle injection of two 0.5 mL aliquots of the Ad vectors (in 5 mM Tris, 5% sucrose, 75 mM NaCl, 1 mM $MgCl_2$, 0.005% polysorbate 80, pH 8.0) into both deltoid muscles. The animals were immunized twice at a 4 week interval (T=0, 4 weeks).

Murine Anti-RT and Anti-Nef ELISA—Anti-RT titers were obtained following standard secondary antibody-based ELISA. Maxisorp plates (NUNC, Rochester, N.Y.) were coated by overnight incubation with 100 $\mu$L of 1 $\mu$g/mL HIV-1 RT protein (Advanced Biotechnologies, Columbia, Md.) in PBS. For anti-nef ELISA, 100 uL of 1 ug/mL HIV-1 nef (Advanced Biotechnologies, Columbia, Md.) was used to coat the plates. The plates were washed with PBS/0.05% Tween 20 using Titertek MAP instrument (Hunstville, Ala.) and incubated for 2 h with 200 $\mu$L/well of blocking solution (PBS/0.05% tween/1% BSA). An initial serum dilution of 100-fold was performed followed by 4-fold serial dilution. 100-$\mu$L aliquots of serially diluted samples were added per well and incubated for 2 h at room temperature. The plates were washed and 100 $\mu$L of 1/1000-diluted HRP-rabbit anti-mouse IgG (ZYMED, San Francisco, Calif.) were added with 1 h incubation. The plates were washed thoroughly and soaked with 100 $\mu$L 1,2-phenylenediamine dihydrochloride/hydrogen peroxide (DAKO, Norway) solution for 15 min. The reaction was quenched by adding 100 $\mu$L of 0.5M $H_2SO4$ per well. $OD_{492}$ readings were recorded using Titertek Multiskan MCC/340 with S20 stacker. End-point titers were defined as the highest serum dilution that resulted in an absorbance value of greater than or equal to 0.1 $OD_{492}$ (2.5 times the background value).

Non-Human Primate and Murine ELIspot Assays—The enzyme-linked immuno-spot (ELISpot) assay was utilized to enumerate antigen-specific INFγ-secreting cells from mouse spleens (Miyahira, et al.1995*, J. Immunol. Methods* 181:45–54) or macaque PBMCs. Mouse spleens were pooled from 5 mice/cohort and single cell suspensions were prepared at $5\times10^6$/mL in complete RPMI media (RPMI1640, 10% FBS, 2 mM L-glutamine, 100 U/mL Penicillin, 100 u/mL streptomycin, 10 mM Hepes, 50 uM β-ME). Rhesus PBMCs were prepared from 8-15 mL of heparinized blood following standard Ficoll gradient separation (Coligan, et al, 1998, *Current Protocols in Immunology.* John Wiley & Sons, Inc.). Multiscreen opaque plates (Millipore, France) were coated with 100 μl/well of either 5 μg/mL purified rat anti-mouse IFN-γ IgG1, clone R4-6A2 (Pharmingen, San Diego, Calif.), or 15 ug/mL mouse anti-human IFN-γ $IgG_{2a}$ (Cat. No. 1598-00, R&D Systems, Minneapolis, Minn.) in PBS at 4° C. overnight for murine or monkey assays, respectively. The plates were washed with PBS/penicillin/streptomycin and blocked with 200 μL/well of complete RPMI media for 37° C. for at least 2 h.

To each well, 50 μL of cell samples (4–5×$10^5$ cells per well) and 50 μL of the antigen solution were added. To the control well, 50 μL of the media containing DMSO were added; for specific responses, either selected peptides or peptide pools (4 ug/mL per peptide final concentration) were added. For BALB/c mice immunized with the pol constructs, stimulation was conducted using a pool of $CD4^+$-epitope containing 20-mer peptides (aa21–40, aa411–430, aa641–660, aa731–750, aa771–790 or a pool of $CD8^+$-epitope containing peptides (aa201–220, aa311–330, aa781–800). For C57/BL6 mice immunized with the nef construct, either aa51–70 ($CD8^+$ T cell epitope) or aa81–100 ($CD4^+$) peptide derived from the nef sequence was added for specific stimulation. In monkeys, the responses against pol were evaluated using two pools (L and R) of 20-aa peptides that encompass the entire pol sequence and overlap by 10 amino acids. In monkeys vaccinated with the nef constructs, a single pool containing 20-mer peptides covering the entire HIV-1 nef sequence and overlapping by 10 aa was used. Each sample/antigen mixture was performed in triplicate wells for murine samples or in duplicate wells for rhesus PBMCs. Plates were incubated at 37° C., 5% $CO_2$, 90% humidity for 20–24 h. The plates were washed with PBS/0.05% Tween 20 and incubated with 100 μL/well of either 1.25 μg/mL biotin-conjugated rat anti-mouse IFN-γ mAb, clone XMG1.2 (Pharmingen) or of 0.1 ug/mL biotinylated anti-human IFN-gamma goat polyclonal antibody (R&D Systems) at 4° C. overnight. The plates were washed and incubated with 100 μL/well 1/2500 dilution of strepavidin-alkaline phosphatase conjugate (Pharmingen) in PBS/0.005% Tween/5% FBS for 30 min at 37° C. Spots were developed by incubating with 100 μL/well 1-step NBT/BCIP (Pierce Chemicals) for 6–10 min. The plates were washed with water and allowed to air dry. The number of spots in each well was determined using a dissecting microscope and the data normalized to $10^6$ cell input.

Non-Human Primate Anti-RT ELISA—The pol-specific antibodies in the monkeys were measured in a competitive RT EIA assay, wherein sample activity is determined by the ability to block RT antigen from binding to coating antibody on the plate well. Briefly, Maxisorp plates were coated with saturating amounts of pol positive human serum (#97111234). 250 uL of each sample is incubated with 15 uL of 266 ng/mL RT recombinant protein (in RCM 563, 1% BSA, 0.1% tween, 0.1% $NaN_3$) and 20 uL of lysis buffer (Coulter p24 antigen assay kit) for 15 min at room temperature. Similar mixtures are prepared using serially diluted samples of a standard and a negative control which defines maximum RT binding. 200 uL/well of each sample and standard were added to the washed plate and the plate incubated 16–24 h at room temperature. Bound RT is quantified following the procedures described in Coulter p24 assay kit and reported in milliMerck units per mL arbitrarily defined by the chosen standard.

Results—Rodent Studies—BALB/c mice (n=5 mice/cohort) were immunized once or twice with varying doses of MRKAd5hCMV-IApol(E3+) and MRKAd5hCMV-IApol (E3−). At 3 weeks after the second dose, Anti-pol IgG levels were determined by an ELISA assay using RT as a surrogate antigen. Cellular response were quantified via IFNγ ELISpot assay against pools of pol-epitope containing peptides. The results of these assays are summarized in Table 10. The results indicate that the mouse vaccinees exhibited detectable anti-RT IgGs with an adenovector dose as low as 10^7 vp. The humoral responses are highly dose-dependent and are boostable with a second immunization. One or two doses of either pol vectors elicit high frequencies of antigen-specific $CD4^+$ and $CD8^+$ T cells; the responses are weakly dose-dependent but are boostable with a second immunization.

TABLE 10

Immunogenicity of MRKAd5pol Vectors in BALB/c mice.

| | | | | | | | SFC/10^6 cells[c] | | |
|---|---|---|---|---|---|---|---|---|---|
| | | | No. of | Anti-RT IgG Titers[a] | | | | CD4+ peptide | CD8+ peptide |
| Group | Vaccine | Dose | Doses | GMT | +SE | −SE | Medium | pool | pool |
| 1 | MRKAd5hCMVFLpol (E3+) | 10^7 vp | 2 | 310419 | 301785 | 153020 | 1(1) | 75(4) | 2313(67) |
| | | | 1 | 919 | 372 | 265 | 1(1) | 72(9) | 533(41) |
| 2 | MRKAd5hCMVFLpol (E3+) | 10^9 vp | 2 | 1638400[b] | 0 | 0 | 2(2) | 114(9) | 2063(182) |
| | | | 1 | 713155 | 528520 | 303555 | 1(1) | 48(7) | 733(89) |
| 3 | MRKAd5hCMVFLpol (E3−) | 10^7 vp | 2 | 310419 | 386218 | 172097 | 0(0) | 223(7) | 2607(27) |
| | | | 1 | 6400 | 14013 | 4393 | 10(8) | 141(21) | 409(28) |
| 4 | MRKAd5hCMVFLpol (E3−) | 10^9 vp | 2 | 1638400[b] | 0 | 0 | 1(1) | 160(13) | 2385(11) |
| | | | 1 | 1241675[b] | 396725 | 300661 | 0(0) | 39(13) | 833(83) |
| 5 | Naïve | none | none | 57 | 9 | 7 | 9(2) | 11(4) | 10(1) |

[a]GMT, geometric mean titer of the cohort of 5 mice; SE, standard error of the gemetric mean
[b]Near or at the upper limit of the serial dilution; hence, could be greater than this value
[c]No. of Spot-forming Cells per million splecnoytes; mean values of triplicates are reported along with standard errors in parenthesis.

C57/BL6 mice were immunized once or twice with varying doses of MRKAd5hCMV-nef(G2A,LLAA) (E3+), MRKAd5mCMV-nef(G2A,LLAA) (E3+) at either 10^7 vp and(3) MRKAd5mCMV-tpanef(LLAA) (E3+) at either 10^7 vp and 10^9 vp. The immune response were analyzed using similar protocols and the results are listed in Table 11. While anti-nef IgG responses could not be detected in this model system with any of the constructs, there are strong indications of a cellular immunity generated against nef using the ELIspot assay.

TABLE 11

Immunogenicity of MRKAd5nef Vectors in C57/BL6 mice.

| Group | Vaccine | Dose | No. of Doses | Anti-nef IgG Titers[a] GMT | +SE | −SE | SFC/10^6 cells[b] Medium | aa51–70 CD8+ | aa81–100 CD4+ |
|---|---|---|---|---|---|---|---|---|---|
| 1 | MRKAd5hCMVFLnef (E3+) | 10^7 vp | 2 | 174 | 70 | 50 | 1(1) | 23(1) | 1(1) |
| | | | 1 | 132 | 42 | 32 | 0(0) | 0(0) | 0(0) |
| 2 | MRKAd5hCMVFLnef (E3+) | 10^9 vp | 2 | 174 | 70 | 50 | 0(0) | 61(7) | 4(2) |
| | | | 1 | 132 | 42 | 32 | 1(1) | 62(7) | 3(1) |
| 3 | MRKAd5mCMVFLnef (E3+) | 10^7 vp | 2 | 132 | 42 | 32 | 3(1) | 15(5) | 5(2) |
| | | | 1 | 115 | 46 | 33 | 3(2) | 3(2) | 4(2) |
| 4 | MRKAd5mCMVFLnef (E3+) | 10^9 vp | 2 | 132 | 42 | 32 | 4(2) | 83(13) | 5(1) |
| | | | 1 | 132 | 42 | 32 | 2(1) | 29(2) | 4(0) |
| 5 | MRKAd5mCMVtpanef (E3+) | 10^7 vp | 2 | 132 | 42 | 32 | 3(2) | 14(2) | 5(1) |
| | | | 1 | 100 | 0 | 0 | 3(1) | 13(4) | 10(3) |
| 6 | MRKAd5mCMVtpanef (E3+) | 10^9 vp | 2 | 230 | 170 | 98 | 3(2) | 145(29) | 4(0) |
| | | | 1 | 115 | 46 | 33 | 7(1) | 151(14) | 10(0) |
| 7 | Naïve | none | none | 152 | 78 | 52 | 21(2) | 18(6) | 26(3) |

[a]GMT, geometric mean titer of the cohort of 5 mice; SE, standard error of the gemetric mean
[b]No. of spot-forming cells per million splecnoytes; mean values of triplicates are reported along with standard errors in parenthesis Monkey Studies—Cohorts of 3 rhesus macaques were immunized with 2 doses of MRKAd5hCMV-IApol(E3+) and MRKAd5hCMV-IApol(E3−). The number of antigen-specific T cells (per million PBMCs) were enumerated using one of two peptide pools (L and R) that cover the entire pol sequence; the results are listed in Table 12. Moderate-to-strong T cell responses were detected in the vaccinees using either constructs even at a low dose of 10^9 vp. Longitudinal analyses of the anti-RT antibody titers in the animals suggest that the pol transgene product is expressed efficiently to elicit a humoral response (Table 13). It would appear that generally higher immune responses were observed in animals that received the E3− construct compared to the E3+ virus.

TABLE 12

Pol-specific T Cell Responses in MRKAd5pol Immunized Rhesus Macaques.

| Vaccine (T = 0, 4 wks) | Monk # | Prebleed Mock | Prebleed Pol L | Prebleed Pol R | T = 4 Mock | T = 4 Pol L | T = 4 Pol R | T = 7 Mock | T = 7 Pol L | T = 7 Pol R | T = 16 Mock | T = 16 Pol L | T = 16 Pol R |
|---|---|---|---|---|---|---|---|---|---|---|---|---|---|
| MRKAd5hCMV-I Apol(E3+) | 99C100 | 1 | 0 | 0 | 1 | 38 | 31 | 0 | 52 | 146 | 0 | 49 | 715 |
| 10^11 vp | 99C215 | 1 | 2 | 2 | 10 | 98 | 249 | 1 | 109 | 305 | 22 | 88 | 250 |
| | 99D201 | 5 | 5 | 4 | 6 | 149 | 95 | 0 | 40 | 35 | 0 | 35 | 18 |
| MRKAd5hCMV-I Apol(E3+) | 99D212 | 0 | 2 | 0 | 4 | 331 | 114 | 0 | 58 | 14 | 0 | 6 | 6 |
| 10^9 vp | 99D180 | 0 | 4 | 2 | 0 | 19 | 192 | 4 | 36 | 156 | 5 | 38 | 106 |
| | 99C201 | 8 | 5 | 21 | 6 | 62 | 62 | 0 | 18 | 32 | 1 | 14 | 65 |
| MRKAd5hCMV-I Apol(E3−) | 99D239 | 5 | 2 | 2 | 20 | 82 | 172 | 1 | 66 | 114 | 9 | 21 | 40 |
| 10^11 vp | 99C186 | 4 | 12 | 6 | 5 | 120 | 421 | 2 | 271 | 489 | 16 | 875 | 530 |
| | 99C084 | 1 | 8 | 9 | 8 | 84 | 464 | 0 | 14 | 236 | 1 | 24 | 264 |
| MRKAd5hCMV-I Apol(E3−) | CC7C | 10 | 10 | 8 | 12 | 724 | 745 | 4 | 322 | 376 | 4 | 188 | 176 |
| 10^9 vp | CD1G | 2 | 0 | 1 | 5 | 474 | 468 | 0 | 232 | 212 | 0 | 101 | 121 |
| | CD11 | 6 | 6 | 12 | 10 | 98 | 110 | 5 | 60 | 80 | 8 | 25 | 34 |
| Naïve | 083Q | nd | nd | nd | nd | nd | nd | 4 | 2 | 2 | 2 | 1 | 2 |

nd, not determined
Reported are SFC per million PBMCs; mean of duplicate wells

TABLE 13

Anti-RT Ig Levels in MRKAd5pol Immunized macaques.

RT ANTIBODY ASSAY TITERS IN mMU/mL

| Vaccine/Monkey Tag | T = 4 | T = 7 | T = 12 | T = 16 |
|---|---|---|---|---|
| MRKAd5hCMV-IApol(E3+), 10^11 vp | | | | |
| 99C100 | 61 | 1999 | 5928 | 4768 |
| 99C215 | 81 | 1541 | 2356 | 2767 |
| 99D201 | 53 | 336 | 539 | 387 |
| MRKAd5hCMV-IApol(E3+), 10^9 vp | | | | |
| 99D212 | 10 | 40 | 49 | 68 |
| 99D180 | <10 | 36 | 79 | 93 |
| 99C201 | <10 | 37 | 71 | 76 |
| MRKAd5hCMV-IApol(E3–), 10^11 vp | | | | |
| 99D239 | 44 | 460 | 1234 | 1015 |
| 99C186 | 21 | 233 | 480 | 345 |
| 99C084 | 235 | 2637 | 2858 | 1626 |
| MRKAd5hCMV-IApol(E3–), 10^9 vp | | | | |
| CC7C | 32 | 175 | 306 | 235 |
| CD1G | 20 | 140 | 273 | 419 |
| CD11 | 15 | 112 | 149 | 237 |

When rhesus macaques were immunized i.m. with two doses of MRKAd5nef constructs, vigorous T cell responses ranging from 100 to as high as 1100 per million were observed in 8 of 12 vaccinees (Table 14). The efficacies of the mCMV- and hCMV-driven nef constructs are comparable on the basis of the data generated thus far.

TABLE 14

Nef-specific T cell Responses in MRKAd5nef Immunized Rhesus Macaques.

| | | Pre | | T = 4 | | T = 7 | | T = 16 | |
|---|---|---|---|---|---|---|---|---|---|
| Vaccine (T = 0,4 wks) | Monk # | Mock | Nef | Mock | Nef | Mock | Nef | Mock | Nef |
| MRKAd5hCMV-nef(G2A,LLAA) (E3+) | CD2D | 0 | 4 | 31 | 440 | 4 | 368 | 1 | 251 |
| 10^11 vp | CC7B | 0 | 0 | 2 | 521 | 0 | 178 | 1 | 1522 |
| | CC61 | 2 | 9 | 31 | 112 | 0 | 108 | 11 | 100 |
| MRKAd5hCMV-nef(G2A,LLAA) (E3+) | CC2K | 9 | 9 | 6 | 52 | 0 | 35 | 0 | 15 |
| 10^9 vp | CD15 | 5 | 4 | 30 | 998 | 2 | 586 | 0 | 434 |
| | CD16 | 6 | 1 | 6 | 1146 | 0 | 369 | 1 | 212 |
| MRKAd5mCMV-nef(G2A,LLAA) (E3+) | 99D191 | 1 | 5 | 4 | 614 | 0 | 298 | 2 | 419 |
| 10^11 vp | 99D144 | 4 | 6 | 5 | 434 | 0 | 1100 | 2 | 932 |
| | 99C193 | 1 | 2 | 1 | 58 | 1 | 22 | 0 | 64 |
| MRKAd5mCMV-nef(G2A,LLAA) (E3+) | 99D224 | 1 | 11 | 14 | 231 | 1 | 125 | 0 | 70 |
| 10^9 vp | 99D250 | 8 | 9 | 4 | 108 | 0 | 54 | 0 | 5 |
| | 99C120 | 1 | 6 | 20 | 299 | 0 | 92 | 0 | 79 |
| Naive | 083Q | nd | nd | 18 | 22 | 4 | 5 | 2 | 1 |

EXAMPLE 25

Comparison of Clade B vs. Clade C T Cell Responses in HIV-Infected Subjects

Figure 24:
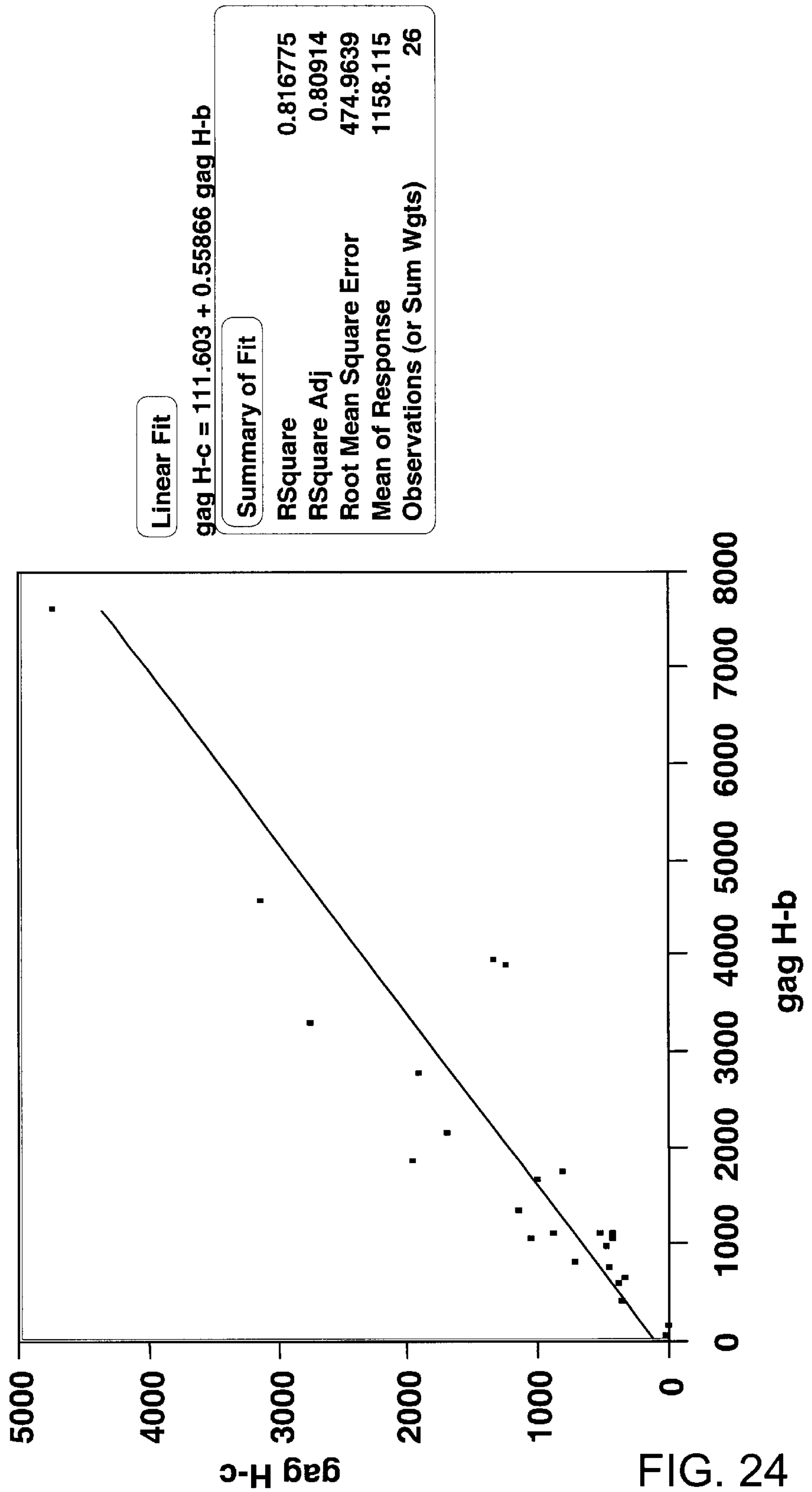
Figure 25:
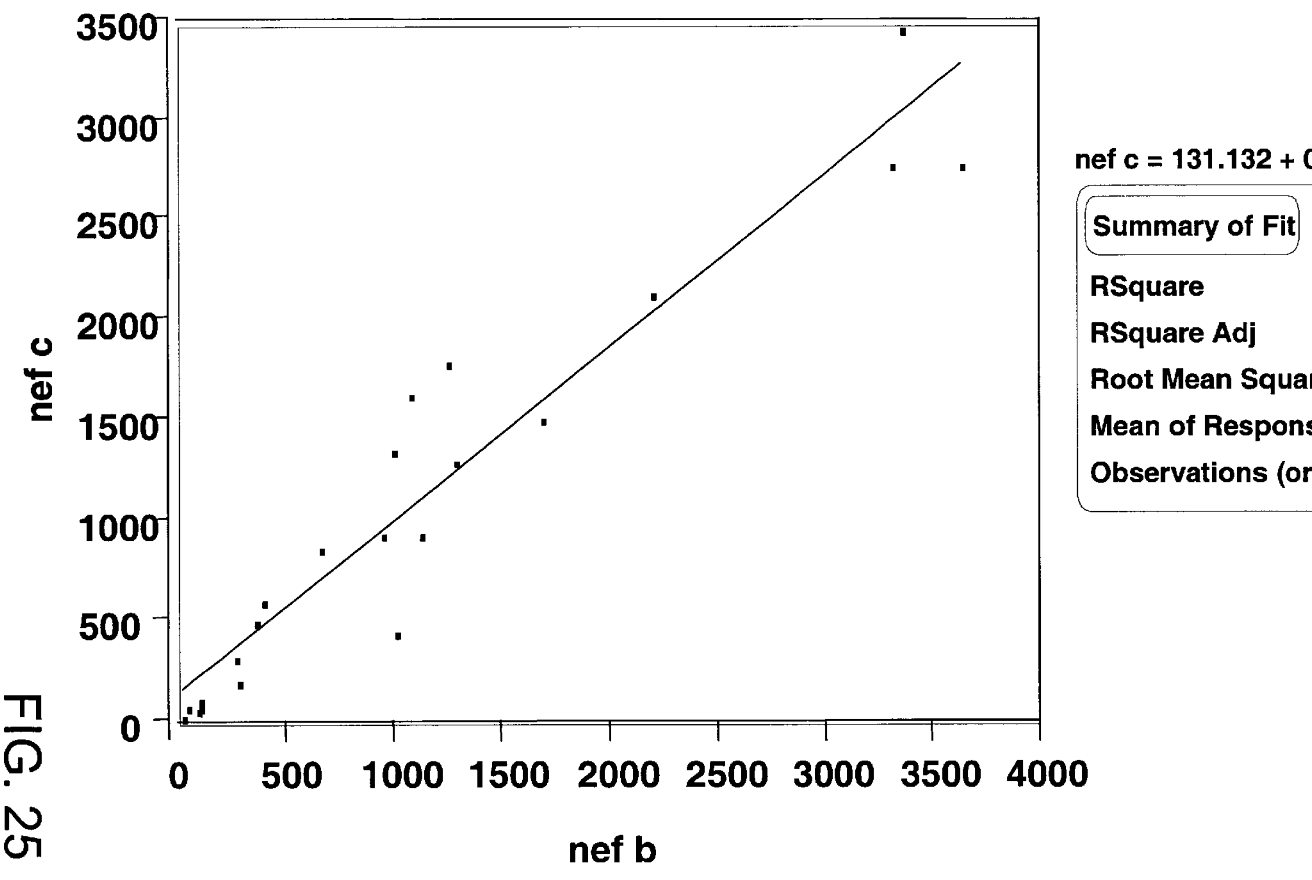

PBMC samples collected from two dozens of patients infected with HIV-1 in US were tested in ELISPOT assays with peptide pools of 20-mer peptides overlapping by 10 amino acids. Four different peptide pools were tested for cross-clade recognition, and they were either derived from a lade B-based isolate (gag H-b; nef-b) or a clade C-based isolate (gag H-c, nef-c). Data in Table 15 shows that T cells from these patients presumably infected with lade B HIV-1 could recognize clade C gag and nef antigens in ELISPOT assay. Correlation analysis further demonstrated that these T cell responses against lade C gag peptide pool were about 60% of the clade B counterpart (FIG. 24), while the T cell responses against lade C nef were about 85% of the clade B counterpart (FIG. 25). These results suggest that cellular immune responses generated in patients infected with lade B HIV-1 can recognize gag and nef antigens derived from clade C HIV-1. These data show that a HIV vaccine, such as a DNA or MRKAd5-based adenoviral vaccine expressing a clade B gag and/or nef antigen will potentially have the ability to provide a prophylactic and/or therapetic advantage on a global scale.

TABLE 15

Responses Shown as the Number of gIFN-Secreting T Cells per Million PBMCs

| subject | bleed date | gag epitope # (from mapping) | mock | gag H-b | gagH-c | nef-b | nef-c |
|---|---|---|---|---|---|---|---|
| #100 | 19-Jul-99 | 12 | 10 | 3950 | 1385 | 1295 | 1300 |
| #101 | 25-Jul-99 | 3 | 15 | 3885 | 1280 | na | 1020 |
| #102 | 25-Jul-99 | 4 | 15 | 1740 | 850 | 1255 | 1785 |
| #104 | 7-Jun-99 | 2 | 5 | 1355 | 1185 | na | 1060 |
| #107 | 11-Oct-99 | 2 | 25 | 3305 | 2795 | 670 | 870 |
| #405 | 11-Jul-99 | 2 | 15 | 4575 | 3180 | 1700 | 1500 |
| #501 | 19-Jul-99 | 2 | 15 | 1100 | 570 | 3365 | 3460 |
| #505 | 18-Jul-99 | 5 | 10 | 2145 | 1725 | 1235 | na |
| #506 | 28-Feb-99 | 2 | 25 | 150 | 45 | 400 | 610 |
| #701 | 28-Mar-99 | 5 | 30 | 7620 | 4775 | 3320 | 2780 |
| #709 | 17-May-99 | 3 | 15 | 2785 | 1945 | 1090 | 1630 |
| #710 | 24-May-99 | 4 | 5 | 1055 | 1080 | 2210 | 2140 |

EXAMPLE 26

Characterization and Production of MRKAd5pol and MRKAd5nef Vectors in Roller Bottles Expansion of Nef and Pol Adenovectors—Nef and pol CsCl purified MRKAd5 seeds were used to infect roller bottles to produce P4 virus to be used as a seed for further experiments. P4 MRKAd5 pol and nef vectors were used to infect roller bottles at an MOI 280 vp/cell, except for hCMV-tpa-nef [E3+] which was infected at an MOI of 125 due to low titers of seed obtained at P4.

TABLE 16

Viral particle concentrations for P5 nef and pol adenovectors

| Adenovector | AEX Titer ($10^{10}$ vp/ml culture) | AEX Titer ($10^4$ vp/cell) | Amplification Ratio |
|---|---|---|---|
| hCMV-FL-nef [E3+] | 1.1 | 0.9 | 30 |
| mCMV-FL-nef [E3+] | 2.2 | 2.1 | 75 |

TABLE 16-continued

Viral particle concentrations for P5 nef and pol adenovectors

| Adenovector | AEX Titer ($10^{10}$ vp/ml culture) | AEX Titer ($10^4$ vp/cell) | Amplification Ratio |
|---|---|---|---|
| hCMV-tpa-nef [E3+] | 0.07 | 0.1 | 5 |
| mCMV-tpa-nef [E3+] | 1.3 | 0.9 | 35 |
| hCMV-FL-pol [E3+] | 2.7 | 2.1 | 75 |
| hCMV-FL-pol [E3−] | 1.9 | 1.3 | 45 |

Roller Bottle Passaging—Passaging of the pol and nef constructs continued through passage seven. Cell-associated (freeze/thaw lysis) and whole broth (triton-lysis) titers obtained in all passages were very consistent. In general, MRKAd5pol is ca. 70% as productive as MRKAd5gag while MRKAd5nef is ca. 25% as productive as MRKAd5gag. Samples of P7 virus for both constructs were analyzed by V&CB by restriction digest analysis and did not show any rearrangements.

TABLE 17

Passage Six Viral Productivity for MRKAd5pol and MRKAd5nef

| | | Xviable ($10^6$ cells/ml), Viability (%) | | Cell Passage | AEX Titer (Cell Associated) | Titer | Amplification | Triton Lysis Titer |
|---|---|---|---|---|---|---|---|---|
| | | Infection | Harvest | Number | $10^{10}$ vp/ml culture | $10^4$ vp/cell | Ratio | $10^{10}$ vp/ml culture |
| hCMV-FL-nef [E3+] | pool | 1.22, 85% | | 62 | 0.8 | 0.7 | 25 | 1.6 |
| | 1 | | 0.99, 62% | | | | | |
| | 2 | | 1.10, 72% | | | | | |
| hCMV-FL-pol [E3+] | pool | 1.42, 89% | | 62 | 4.5 | 3.2 | 115 | 7.0 |
| | 1 | | 1.22, 70% | | | | | |
| | 2 | | 1.42, 74% | | | | | |

TABLE 18

Passage Seven Viral Productivity for MRKAd5pol and MRKAd5nef

| | | Xviable ($10^6$ cells/ml), Viability (%) | | Cell Passage | AEX Titer (Cell Associated) | Titer | Amplification | Triton Lysis Titer |
|---|---|---|---|---|---|---|---|---|
| | | Infection | Harvest | Number | $10^{10}$ vp/ml culture | $10^4$ vp/cell | Ratio | $10^{10}$ vp/ml culture |
| hCMV-FL-nef [E3+] | Pool | 1.33, 90% | | 66 | 1.0 | 0.8 | 29 | 2.1 |

TABLE 18-continued

Passage Seven Viral Productivity for MRKAd5pol and MRKAd5nef

| | | Xviable ($10^6$ cells/ml), Viability (%) | | Cell Passage | AEX Titer (Cell Associated) | Titer | Amplification | Triton Lysis Titer |
|---|---|---|---|---|---|---|---|---|
| | | Infection | Harvest | Number | $10^{10}$ vp/ml culture | $10^4$ vp/cell | Ratio | $10^{10}$ vp/ml culture |
| | 1 | | 0.96, 70% | | | | | |
| | 2 | | 1.18, 73% | | | | | |
| hCMV-FL-pol [E3+] | Pool | 0.90*, 90% | | 56 | 4.2 | 4.7 | 168 | 6.5 |
| | 1 | | 1.18, 88% | | | | | |
| | 2 | | 1.04, 80% | | | | | |

Figure 29A:
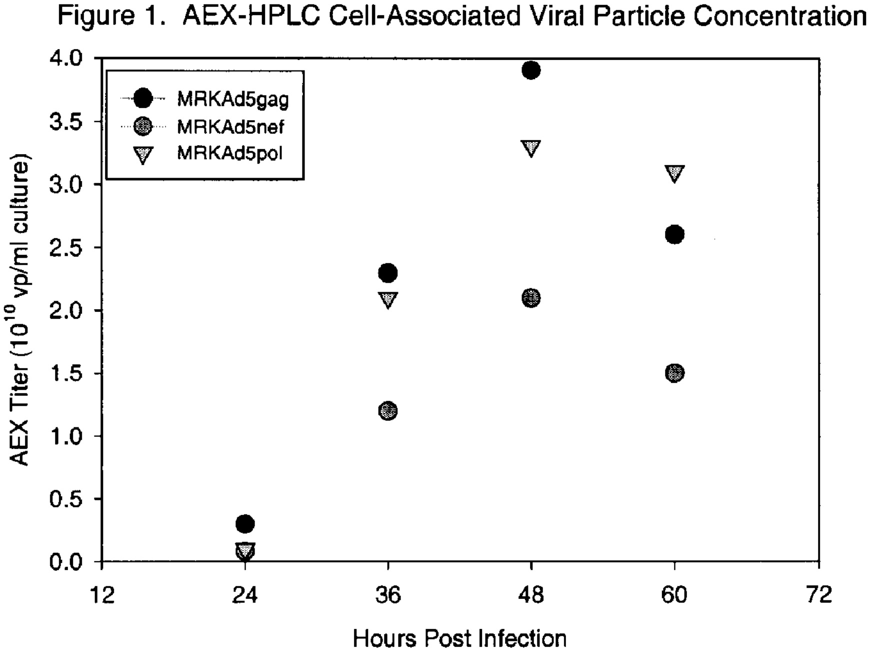
FIGS. 29A and B shows the anion-exchange HPLC viral particle concentrations of the freeze-thaw recovered cell associated virus at the 24, 36, 48, and 60 hpi time points (FIG. 29A) and the timcourse QPA supernatant titers (FIG. 29B) for MRKAd5gag, MRKAd5pol and MRKAd5nef.
Figure 29B:
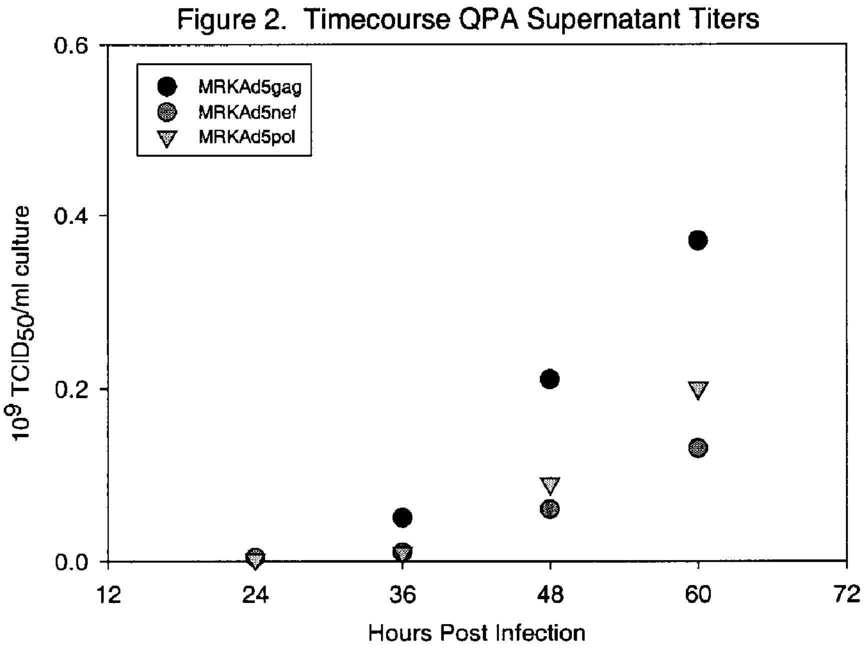

MRKAd5nef and MRKAd5pol Viral Production Kinetics—A timecourse experiment was carried out in roller bottles to determine if the viral production kinetics of the MRKAd5pol and MRKAd5nef vectors were similar to those of MRKAd5gag. PER.C6® cells in roller bottle cultures were infected at an MOI of 280 vp/cells with P5 MRKAd5pol, PS MRKAd5nef and P7 MRKAd5gag; for each adenovector, two infected bottles were sampled at 24, 36, 48, and 60 hours post infection. In addition, two bottles were left unsampled until 48 hpi when they were harvested under the Phase I process conditions. The anion-exchange HPLC viral particle concentrations of the freeze-thaw recovered cell associated virus at the 24, 36, 48, and 60 hpi timepoints are shown in FIGS. 29A–B. The QPA titers show a similar trend (data not shown).

Comparison of hCMV- and mCMV-FL-nef—As the titers obtained with the MRKAd5nef construct (hCMV-FL-nef) were lower than those obtained with MRKAd5gag or MRKAd5pol, a viral productivity comparison experiment was performed with mCMV-FL-nef. For each of the two adenovectors (hCMV- and mCMV-FL-nef), two roller bottles were infected at an MOI of 280 vp/cell with passage five clarified lysate. The macroscopic and microscopic observations of the four roller bottles were identical at the time of harvest. Analysis of the clarified lysate produced indicated a higher viral particle concentration in the bottles infected with mCMV-FL-nef, as shown in Table 19. It is stipulated that the higher productivity with mCMV promoter driven nef vector is due to lower nef expression levels in PER.C6® cells-experiments are underway at V&CB to measure nef expression levels.

EXAMPLE 27

Characterization and Large Scale Production of MRKAd5nef Virus in Bioreactors Materials and Methods—The experiment of the present example was run twice under the following conditions: 36.5° C., DO 30%, pH 7.30, 150rpm agitation rate, no sparging, Life Technologies (Gibco, Invitrogen) 293 SFM II (with 6 mM L-glutamine), 0.5M NaOH as base for pH control. During the first run (B20010115), two 10L stirred vessel bioreactors were inoculated with PER.C6® cells at a concentration of $0.2\times10^6$ cells/ml. Cells were grown until they reached a cell concentration of approximately $1\times10^6$ cells/ml. The cells were infected with uncloned MRKAd5nef (G2A,LLAA) at a MOI of 280 virus particles (vp)/cell. For the second batch (B20010202), the same procedure as the first run was used, except the cells were infected with cloned MRAd5nef. During both runs, the bioreactors were harvested 48 hours post-infection. Samples were taken and virus concentrations were determined from whole broth (with triton lysis), supernatant, and cell pellets (3× freeze/thaw) with the AEX and QPA assays. Metabolites were measured with BioProfile 250 throughout the process.

TABLE 20

| Experimental Conditions | |
|---|---|
| Temperature | 36.5° C. |
| DO | 30% |
| PH | 7.30 |
| Agitation | 150 rpm |
| Sparging | None |

TABLE 19

Passage Six Viral Productivity Comparison of hCMV- and mCMV-FL-nef

| | | Xv ($10^6$ cells/ml), Viability (%) | | Cell Passage | AEX Titer | Titer | Amplification | Triton Lysis Titer |
|---|---|---|---|---|---|---|---|---|
| | | Infection | Harvest | Number | $10^{10}$ vp/ml culture | $10^4$ vp/cell | Ratio | $10^{10}$ vp/ml culture |
| hCMV-FL-nef | Pool | 1.11, 91% | | 60 | 1.5 | 1.4 | 50 | 2.8 |
| (MRKAd5nef) | 1 | | 1.23, 75% | | | | | |
| | 2 | | 1.34, 74% | | | | | |
| mCMV-FL-nef | Pool | 1.11, 91% | | 60 | 2.3 | 2.1 | 75 | 4.6 |
| | 1 | | 1.49, 84% | | | | | |
| | 2 | | 1.18, 77% | | | | | |

TABLE 21

| Virus source used for experiments. | | | |
|---|---|---|---|
| Run | Batch ID | Cloned/Uncloned MRKAd5nef | MOI (vp/cells) |
| #1 | B20010115-1 | Uncloned | 280 |
| | B20010115-2 | Uncloned | 280 |
| #2 | B20010202-1 | Cloned | 280 |
| | B20010202-2 | Cloned | 280 |

Results—Table 22 and 23 show an the ability to scale up production of MRKAd5nef by growth in a bioreactor.

TABLE 22

| Virus Concentration as measured by the AEX assay | | | | | | |
|---|---|---|---|---|---|---|
| | | Cloned/Uncloned | Virus Concentration @ 48 hpi ($1 \times 10^{13}$ vp/L) | | | |
| Run | Batch ID | MRKAd5nef | Supernatant | Clarified Lysate | Total | Triton Lysate |
| #1 | B20010115-1 | Uncloned | 0.72 | 3.26 | 3.98 | 5.76 |
| | B20010115-2 | Uncloned | 0.38 | 1.67 | 2.05 | 2.46 |
| #2 | B20010202-1 | Cloned | 0.80 | 6.00 | 6.80 | 8.88 |
| | B20010202-2 | Cloned | 0.50 | 6.00 | 6.50 | 8.47 |

TABLE 23

| Virus Titers as measured by the QPA assay | | | | | | | |
|---|---|---|---|---|---|---|---|
| | | | Virus Concentration @ 48 hpi ($1 \times 10^{11}$ IU/L) | | | | |
| Run | Batch ID | Cloned/Uncloned MRKAd5nef | Whole Broth | Supernatant | Clarified Lysate | Total | Triton Lysate |
| #1 | B20010115-1 | Uncloned | 0.13 | 1.12 | 1.76 | 2.88 | 11.28 |
| | B20010115-2 | Uncloned | 0.14 | 0.73 | 1.54 | 2.27 | 5.86 |
| #2 | B20010202-1 | Cloned | 0.14 | 0.97 | 1.62 | 2.69 | 11.89 |
| | B20010202-2 | Cloned | 0.14 | 1.17 | 1.70 | 2.97 | 12.47 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

EXAMPLE 28

MRKAd5HIV-1gag Boosting of DNA-Primed Animals

Figure 32:
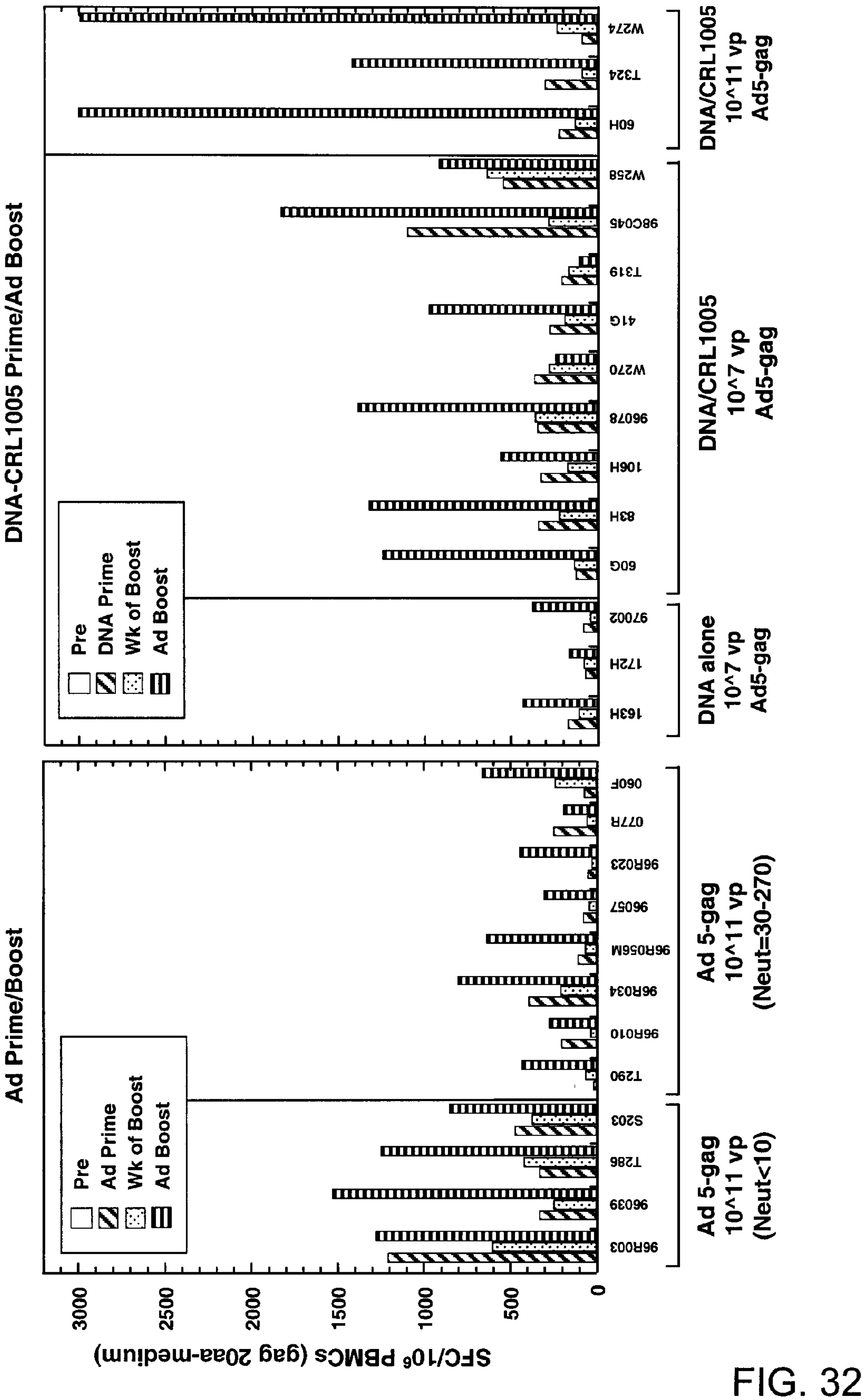

Groups of 3–5 rhesus macaques were immunized with (a) 5 mgs of V1Jns-Flgag (pV1JnsCMV(no intron)-FL-gag-bGHpA), (b) 5 mgs of V1Jns-Flgag formulated with 45 mgs of a non-ionic block copolymer CRL1005, or (c) 5 mgs of V1Jns-Flgag formulated with 7.5 mgs of CRL1005 and 0.6 mM benzalkonium chloride at weeks 0, 4, and 8. All animals received a single dose of 10e7 viral particles (vp) of the MRKAd5HIV-1gag at week 26. Note: 10e7 is too low to prime or boost effectively when used as a single modality (dose is selected to mimic preexposure to adenovirus); see FIG. 32.

Blood samples were collected from all animals at several time points and peripheral blood mononuclear cells (PBMCs) were prepared using standard Ficoll method. The PBMCs were counted and analyzed for gamma-interferon secretion using the ELISpot assay (Table 24). For each monkey, the PBMCs were incubated overnight either in the absence (medium) or presence of a pool (called "gag H") of 50 20-aa long peptides that encompass the entire HIV-1 gag sequence.

The results indicate that MRKAd5HIV-1gag was very effective in boosting the T cell immune responses in these monkeys. At week 28 or 2 weeks after the viral boost, the number of gag-specific T cells per million PBMCs increased 2–48 fold compared to the levels observed at week 24 or 2 weeks prior to the boost.

Figure 31:
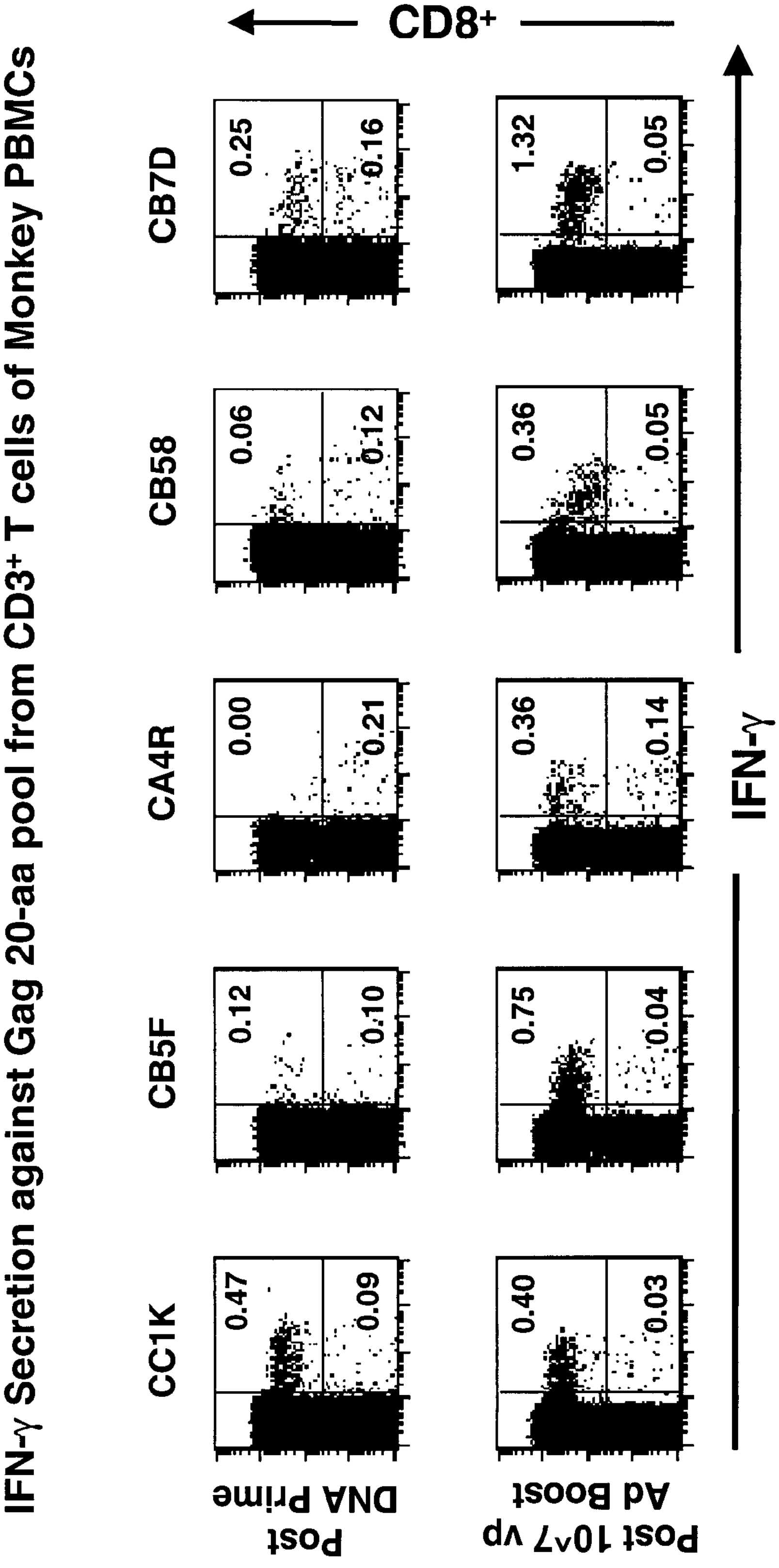

The PBMCs were also analyzed by intracellular gamma-interferon staining prior to (at week 10) and after the MRKAd5gag boost (at week 30). The results for select animals are shown on FIG. 31. The results indicate that (a) immunization with DNA/adjuvant formulation elicited T cell responses which can either be balanced, $CD4^+$-biased or $CD8^+$-biased, and (b) boosting with the MRKAd5gag construct produced in all cases a strongly $CD8^+$-biased response. These results suggest that boosting with MRKAd5HIV-1gag construct is able to improve the levels of antigen-specific $CD8^+$ T cells.

TABLE 24

Boosting of DNA/Adjuvant-Primed Rhesus Monkeys with MRKAd5gag
Number of SFC/million PBMCs

| | Priming | Boost | | T = 0 | | T = 4 | | T = 6 | | T = 10 | |
|---|---|---|---|---|---|---|---|---|---|---|---|
| Grp # | T = 0, 4, 8 wks | T = 26 wks | Monk # | Medium | gag H | Medium | gag H | Medium | gag H | Medium | gag H |
| 1 | DNA/5 mgs | MRKAd5gag(E3+) | CB5H | NA | NA | 3 | 35 | 15 | 71 | 4 | 224 |
| | PBS | 10^7 vp | CC6X | 0 | 0 | 0 | 15 | 0 | 46 | 0 | 58 |
| | (D101) | | AW3G | 5 | 11 | 0 | 36 | 3 | 51 | 3 | 46 |
| 2 | DNA/5 mgs + | MRKAd5gag(E3+) | CC1C | 0 | 4 | 1 | 60 | 0 | 111 | 5 | 270 |
| | CRL1005/45 mgs | 10^7 vp | CC1K | 4 | 0 | 1 | 101 | 0 | 254 | 0 | 791 |
| | | | AW3P | 9 | 8 | 1 | 10 | 4 | 71 | 4 | 154 |
| | | | CB5F | NA | NA | 0 | 31 | 0 | 288 | 0 | 530 |
| | | | AK8B | 9 | 12 | 4 | 36 | 1 | 119 | 0 | 439 |
| 3 | DNA/5 mgs+ | MRKAd5gag(E3+) | AW20 | 10 | 4 | 1 | 59 | 5 | 264 | 19 | 425 |
| | CRL1005/7.5 mgs + 0.6 mM BAK | 10^7 vp | CA4R | 1 | 0 | 3 | 121 | 1 | 135 | 1 | 270 |
| | | | CB58 | 8 | 6 | 0 | 6 | 3 | 119 | 0 | 274 |
| | | | CB5W | 4 | 3 | 0 | 26 | 1 | 91 | 0 | 139 |
| | | | CB7D | 1 | 0 | 0 | 136 | 0 | 316 | 1 | 609 |
| 4 | none | None | 98D201 | 3 | 0 | 0 | 0 | 1 | 0 | 0 | 0 |

| | Priming | Boost | | T = 17 | | T = 24 | | T = 28 | | T = 30 | |
|---|---|---|---|---|---|---|---|---|---|---|---|
| Grp # | T = 0, 4, 8 wks | T = 26 wks | Monk # | Medium | gag H | Medium | gag H | Medium | gag H | Medium | gag H |
| 1 | DNA/5 mgs | MRKAd5gag(E3+) | CB5H | 8 | 115 | 6 | 85 | 19 | 956 | 0 | 316 |
| | PBS | 10^7 vp | CC6X | 0 | 75 | 0 | 35 | 3 | 1705 | 1 | 755 |
| | (D101) | | AW3G | 2 | 89 | 8 | 65 | 10 | 989 | 0 | 395 |
| 2 | DNA/5 mgs + | MRKAd5gag(E3+) | CC1C | 4 | 280 | 8 | 232 | 3 | 959 | 19 | 1345 |
| | CRL1005/45 mgs | 10^7 vp | CC1K | 5 | 452 | 0 | 321 | 0 | 1915 | 1 | 1099 |
| | | | AW3P | 8 | 104 | 5 | 85 | 11 | 836 | 6 | 241 |
| | | | CB5F | 19 | 374 | 9 | 251 | 8 | 1549 | 20 | 1734 |
| | | | AK8B | 0 | 425 | 0 | 316 | 4 | 1229 | 5 | 1354 |
| 3 | DNA/5 mgs+ | MRKAd5gag(E3+) | AW20 | 6 | 105 | 9 | 205 | 18 | 565 | 8 | 404 |
| | CRL1005/7.5 mgs + 0.6 mM BAK | 10^7 vp | CA4R | 5 | 130 | 1 | 105 | 14 | 1384 | 10 | 978 |
| | | | CB58 | 6 | 282 | 1 | 208 | 0 | 636 | 1 | 828 |
| | | | CB5W | 0 | 164 | 1 | 62 | 5 | 543 | 1 | 349 |
| | | | CB7D | 5 | 626 | 1 | 759 | 0 | 2278 | 4 | 1831 |
| 4 | none | None | 98D201 | 0 | 1 | 1 | 2 | 3 | 0 | 0 | 0 |

NA, not available

EXAMPLE 29

Construction of Gagpol Fusion for MRKAd5Gagpol Fusion Constructs

The open reading frames for the codon-optimized HIV-1 gag gene was fused directly to the open reading frame of the IA pol gene (consisting of RT, RNAseH and integrase domains) by stepwise PCR. Because the gene (SEQ ID NO:34) does not include the protease gene and the frameshift sequence, it encodes a single polypeptide of the combined size of p55, RT, RNAse H and integrase (1350 amino acids; SEQ ID NO:35).

The fragment that extends from the BstEII site within the gag gene to the last non-stop codon was ligated via PCR to a fragment that extends from the start codon of the IApol to a unique BamHI site. This fragment was digested with BstEII and BamHI. Construction of gag-IApol fusion was achieved via three-fragment ligation involving the PstI-BstEII gag digestion fragment, the BstEII/BamHI digested PCR product and long PstI/BamHI V1R-FLpol backbone fragment.

The MRKAd5-gagpol adenovirus vector was constructed using the BglII fragment of the V1R-gagpol containing the entire ORF of gag-IApol fusion gene.

EXAMPLE 30

Immunogenicity Studies in Non-Human Primates

Cohorts of three (3) macaques were immunized with 10e8 or 10e10 viral particles (vp) of one of the following MRKAd5 HIV-1 vaccines: (1) MRKAd5gag; (2) MRKAd5pol; (3) MRKAd5nef; (4) a mixture containing equal amounts of MRKAd5gag, MRKAd5pol, and MRKAd5nef, or (5) a mixture of equal amounts of MRKAd5gagpol and MRKAd5nef. The vaccines were administered at weeks 0 and 4.

The T cell responses against each of the HIV-1 antigens were assayed by IFN-gamma ELISpot assay using pools of 20-aa peptides that encompass the entire protein sequence of each antigen. The results (Table 25) are expressed as the number of spot-forming cells (sfc) per million peripheral blood mononuclear cells (PBMC) that respond to each of the peptide pools.

Results indicate the following observations: (1) each of the single gene constructs (MRKAd5gag, MRKAd5pol, or MRKAd5nef) is able to elicit high levels of antigen-specific T cells in monkeys; (2) the single-gene MRKAd5 constructs can be mixed as a multi-cocktail formulation capable of eliciting very broad T cell responses against gag, pol, and nef; (3) the MRKAd5 vector expressing the fusion protein of gag plus IA pol is capable of inducing strong T cell responses to both gag and pol.

TABLE 25

Evaluation of Mixtures of MRKAd5 vectors expressing humanized HIV-1 gag, pol, gagpol, nef in rhesus macaques

| Grp # | Vaccine T = 0, 4 wks | Monk # | T = 6 wks Mock | Gag H | Pol-1 | Pol-2 | Nef |
|---|---|---|---|---|---|---|---|
| 1 | MRKAd5 gag | CB9V | 0 | 15 | — | — | — |
| | 10^10 vp | CD19 | 0 | 374 | — | — | — |
| | | 109H | 1 | 843 | — | — | — |
| 2 | MRKAd5 gag | 99D130 | 1 | 948 | — | — | — |
| | 10^8 vp | W277 | 16 | 324 | — | — | — |
| | | 143H | 4 | 595 | — | — | — |
| 3 | MRKAd5 pol | CC1X | 4 | — | 46 | 256 | — |
| | 10^10 vp | AW3W | 3 | — | 463 | 550 | — |
| | | AV43 | 6 | — | 95 | 1333 | — |
| 4 | MRKAd5 pol | AW38 | 1 | — | 19 | 30 | — |
| | 10^8 vp | CC8K | 0 | — | 50 | 995 | — |
| | | CC21 | 1 | — | 33 | 436 | — |
| 5 | MRKAd5 nef | 076Q | 9 | — | — | — | 1204 |
| | 10^10 vp | 091Q | 4 | — | — | — | 85 |
| | | 083Q | 0 | — | — | — | 176 |
| 6 | MRKAd5 nef | 00C029 | 1 | — | — | — | 114 |
| | 10^8 vp | 98D022 | 6 | — | — | — | 170 |
| | | 98D160 | 3 | — | — | — | 198 |
| 7 | MRKAd5gag + MRKAd5pol + MRKAd5nef | 99D251 | 3 | 206 | 15 | 193 | 120 |
| | 10^10 vp each | 05H | 3 | 135 | 21 | 9 | 638 |
| | | 00C016 | 3 | 26 | 4 | 51 | 23 |
| 8 | MRKAd5gag + MRKAd5pol + MRKAd5nef | 99D215 | 1 | 171 | 18 | 193 | 240 |
| | 10^8 vp each | 81H | 5 | 73 | 6 | 14 | 243 |
| | | 12H | 8 | 1140 | 115 | 811 | 719 |
| 9 | MRKAd5gagpol + MRKAd5 nef | 99D211 | 0 | 83 | 56 | 838 | 725 |
| | 10^10 vp each | 22H | 4 | 385 | 119 | 1194 | 1915 |
| | | 61H | 4 | 343 | 11 | 765 | 853 |
| 10 | MRKAd5gagpol + MRKAd5 nef | 34H | 3 | 78 | 19 | 5 | 75 |
| | 10^8 vp each | 48H | 1 | 65 | 105 | 46 | 43 |
| | | 70H | 5 | 158 | 15 | 220 | 191 |

Indicated are numbers of spot-forming cells per million PBMCS against the peptide pools. Mock, no peptides; gag H, fifty 20-aa peptides encompassing p55 sequence; pol-1, 20-aa peptides representing N-terminal half of IA pol; pol-2, 20-aa peptides representing the carboxy-terminal half of IA pol; nef, 20-aa peptides encompassing the entire wild-type nef sequence. Responses to the antigens prior to the first immunization did not exceed 40 sfc/10^6 PBMC.

What is claimed is:

1. A recombinant adenoviral vector at least partially deleted in E1 and devoid of E1 activity, comprising:

a) an adenovirus cis-acting packaging region corresponding to from about base pair 1 to between from about base pair 400 to about base pair 458 of a wildtype adenovirus genome; and b) at least one gene encoding an HIV protein selected from the group consisting of HIV gag, nef, pol, and immunologically relevant modifications thereof.

2. A vector in accordance with claim 1 comprising a packaging region corresponding to from about base pair 1 to about base pair 450 of a wildtype adenovirus genome.

3. A vector in accordance with claim 1 further comprising nucleotides corresponding to between from about base pair 3511 to about 3524 to about base pair 5798 of a wildtype adenovirus genome.

4. A vector in accordance with claim 3 comprising base pairs corresponding to 1–450 and 3511–5798 of a wildtype adenovirus genome.

5. A vector in accordance with claim 4 which is deleted of base pairs 451–3510.

6. A vector in accordance with claim 1 which is at least partially deleted in E3.

7. A vector in accordance with claim 6 wherein the E3 deleted region is from base pairs 28,133–30,818.

8. A vector in accordance with claim 1 wherein the gene encoding the HIV protein or modification thereof comprises codons optimized for expression in a human.

9. A vector in accordance with claim 1 wherein the vector comprises a gene expression cassette comprising:

a) a nucleic acid encoding a protein;

b) a heterologous promoter operatively linked to the nucleic acid encoding the protein; and (c) a transcription termination sequence.

10. A vector in accordance with claim 9 wherein the gene expression cassette is inserted into the E1 region.

11. An adenoviral vector in accordance with claim 9 wherein the gene expression cassette is in an E1 parallel orientation.

12. An adenoviral vector in accordance with claim 9 wherein the gene expression cassette is in an E1 antiparallel orientation.

13. An adenoviral vector in accordance with claim 9 wherein the promoter is a cytomegalovirus promoter devoid of intronic sequences.

14. An adenoviral vector in accordance with claim 13 wherein the promoter is an immediate early human cytomegalovirus promoter.

15. An adenoviral vector in accordance with claim 9 wherein the promoter is a murine cytomegalovirus promoter.

16. An adenoviral vector in accordance with claim 9 wherein the transcription termination sequence is a bovine growth hormone polyadenylation and transcription termination sequence.

17. An adenoviral vector in accordance with claim 9 wherein the transcription termination sequence is a synthetic polyadenylation signal (SPA).

18. A cell comprising the adenoviral vector of claim 1.

19. Recombinant, replication-defective adenovirus particles harvested and purified subsequent to transfection of the adenoviral vector of claim 1 into a cell line which expresses adenovirus E1 protein at complementing levels.

20. A method of producing recombinant, replication defective adenovirus particles containing the adenoviral genome of the adenoviral vector of claim 1 which comprises introducing the adenoviral vector into a host cell which expresses adenoviral E1 protein, and harvesting the resultant recombinant, replication-defective adenovirus.

21. A method according to claim 20 wherein the cell expresses a transgene inclusive of nucleotides 459–3510 of adenovirus serotype 5.

22. An adenoviral vector in accordance with claim 1 wherein the HIV protein is HIV gag or an immunologically relevant modification thereof.

23. An adenoviral vector in accordance with claim 9 wherein the gene expression cassette comprises an open reading frame encoding an HIV gag protein or immunologically relevant modification thereof.

24. A recombinant adenoviral vector at least partially deleted in E1 and devoid of E1 activity, comprising:

a) an adenovirus cis-acting packaging region corresponding to from about base pair 1 to about base pair 450 of a wildtype adenovirus genome;

b) a region corresponding to from about base pair 3511 to about base pair 5798 of a wildtype adenovirus genome; and c) a gene expression cassette comprising i) SEQ ID NO: 27;

ii) a heterologous promoter operatively linked to i); and iii) a transcription termination sequence;

wherein the vector has a deletion corresponding to from about base pair 451 to about base pair 3510 of a wildtype adenovirus genome.

25. An adenoviral vector in accordance with claim 24 wherein the gene expression cassette is in an E1 parallel orientation.

26. An adenoviral vector in accordance with claim 24 wherein the gene expression cassette is in an E1 antiparallel orientation.

27. An adenoviral vector in accordance with claim 24 wherein the promoter is a cytomegalovirus promoter devoid of intronic sequences.

28. An adenoviral vector in accordance with claim 24 wherein the transcription termination sequence is a bovine growth hormone polyadenylation and transcription termination sequence.

29. An adenoviral vector in accordance with claim 24 which is at least partially deleted in E3.

30. A cell comprising the adenoviral vector of claim 24.

31. Recombinant, replication-defective adenovirus particles harvested and purified subsequent to transfection of the adenoviral vector of claim 24 into a cell line which expresses adenovirus E1 protein at complementing levels.

32. A method of producing recombinant, replication defective adenovirus particles containing the adenoviral genome of the adenoviral vector of claim 24 which comprises introducing the adenoviral vector into a host cell which expresses adenoviral E1 protein, and harvesting the resultant recombinant, replication-defective adenovirus.

33. A method according to claim 32 wherein the cell expresses a transgene inclusive of nucleotides 459–3510 of adenovirus serotype 5.

34. An adenoviral vector in accordance with claim 1 wherein the HIV protein is HIV pol or an immunologically relevant modification thereof.

35. An adenoviral vector in accordance with claim 9 wherein the gene expression cassette comprises an open reading frame encoding an HIV pol protein or immunologically relevant modification thereof.

36. A recombinant adenoviral vector at least partially deleted in E1 and devoid of E1 activity, comprising:

a) an adenovirus cis-acting packaging region corresponding to from about base pair 1 to about base pair 450 of a wildtype adenovirus genome;

b) a region corresponding to from about base pair 3511 to about base pair 5798 of a wildtype adenovirus genome; and c) a gene expression cassette comprising i) a nucleotide sequence selected the group consisting of SEQ ID NO: 1, SEQ ID NO: 5 and SEQ ID NO: 7;

ii) a heterologous promoter operatively linked to i); and iii) a transcription termination sequence;

wherein the vector has a deletion corresponding to from about base pair 451 to about base pair 3510 of a wildtype adenovirus genome.

37. An adenoviral vector in accordance with claim 36 wherein the gene expression cassette is in an E1 parallel orientation.

38. An adenoviral vector in accordance with claim 36 wherein the gene expression cassette is in an E1 antiparallel orientation.

39. An adenoviral vector in accordance with claim 36 wherein the promoter is a cytomegalovirus promoter devoid of intronic sequences.

40. An adenoviral vector in accordance with claim 36 wherein the transcription termination sequence is a bovine growth hormone polyadenylation and transcription termination sequence.

41. An adenoviral vector in accordance with claim 36 which is at least partially deleted in E3.

42. A cell comprising the adenoviral vector of claim 36.

43. Recombinant, replication-defective adenovirus particles harvested and purified subsequent to transfection of the adenoviral vector of claim 36 into a cell line which expresses adenovirus E1 protein at complementing levels.

44. A method of producing recombinant, replication defective adenovirus particles containing the adenoviral genome of the adenoviral vector of claim 36 which comprises introducing the adenoviral vector into a host cell which expresses adenoviral E1 protein, and harvesting the resultant recombinant, replication-defective adenovirus.

45. A method according to claim 44 wherein the cell expresses a transgene inclusive of nucleotides 459–3510 of adenovirus serotype 5.

46. An adenoviral vector in accordance with claim 1 wherein the HIV protein is HIV nef or an immunologically relevant modification thereof.

47. An adenoviral vector in accordance with claim 9 wherein the gene expression cassette comprises an open reading frame encoding an HIV nef protein or immunologically relevant modification thereof.

48. A recombinant adenoviral vector at least partially deleted in E1 and devoid of E1 activity, comprising:

a) an adenovirus cis-acting packaging region corresponding to from about base pair 1 to about base pair 450 of a wildtype adenovirus genome;

b) a region corresponding to from about base pair 3511 to about base pair 5798 of a wildtype adenovirus genome; and c) a gene expression cassette comprising i) a nucleotide sequence selected the group consisting of SEQ ID NO: 9, SEQ ID NO: 11, SEQ ID NO: 13 and SEQ ID NO: 15;

ii) a heterologous promoter operatively linked to i); and iii) a transcription termination sequence;

wherein the vector has a deletion corresponding to from about base pair 451 to about base pair 3510 of a wildtype adenovirus genome.

49. An adenoviral vector in accordance with claim 48 wherein the gene expression cassette is in an E1 parallel orientation.

50. An adenoviral vector in accordance with claim 48 wherein the gene expression cassette is in an E1 antiparallel orientation.

51. An adenoviral vector in accordance with claim 48 wherein the promoter is a cytomegalovirus promoter devoid of intronic sequences.

52. An adenoviral vector in accordance with claim 48 wherein the transcription termination sequence is a bovine growth hormone polyadenylation and transcription termination sequence.

53. An adenoviral vector in accordance with claim 48 which is at least partially deleted in E3.

54. A cell comprising the adenoviral vector of claim 48.

55. Recombinant, replication-defective adenovirus particles harvested and purified subsequent to transfection of the adenoviral vector of claim 48 into a cell line which expresses adenovirus E1 protein at complementing levels.

56. A method of producing recombinant, replication defective adenovirus particles containing the adenoviral genome of the adenoviral vector of claim 48 which comprises introducing the adenoviral vector into a host cell which expresses adenoviral E1 protein, and harvesting the resultant recombinant, replication-defective adenovirus.

57. A method according to claim 56 wherein the cell expresses a transgene inclusive of nucleotides 459–3510 of adenovirus serotype 5.

* * * * *

SEQUENCE LISTING

<160> NUMBER OF SEQ ID NOS: 38

<210> SEQ ID NO 1
<211> LENGTH: 2577
<212> TYPE: DNA
<213> ORGANISM: Artificial Sequence
<220> FEATURE:
<223> OTHER INFORMATION: Codon optimized DNA encoding modified wt pol

<400> SEQUENCE: 1

```
agatctacca tggcccccat ctcccccatt gagactgtgc ctgtgaagct gaagcctggc      60

atggatggcc ccaaggtgaa gcagtggccc ctgactgagg agaagatcaa ggccctggtg     120

gaaatctgca ctgagatgga gaaggagggc aaaatctcca agattggccc cgagaacccc     180

tacaacaccc ctgtgtttgc catcaagaag aaggactcca ccaagtggag gaagctggtg     240

gacttcaggg agctgaacaa gaggacccag gacttctggg aggtgcagct gggcatcccc     300

cacccccgctg gcctgaagaa gaagaagtct gtgactgtgc tggatgtggg ggatgcctac     360

ttctctgtgc ccctggatga ggacttcagg aagtacactg ccttcaccat cccctccatc     420

aacaatgaga cccctggcat caggtaccag tacaatgtgc tgccccaggg ctggaagggc     480

tcccctgcca tcttccagtc ctccatgacc aagatcctgg agcccttcag gaagcagaac     540
```

-continued

```
cctgacattg tgatctacca gtacatggat gacctgtatg tgggctctga cctggagatt    600
gggcagcaca ggaccaagat tgaggagctg aggcagcacc tgctgaggtg gggcctgacc    660
accccctgaca agaagcacca gaaggagccc cccttcctgt ggatgggcta tgagctgcac   720
cccgacaagt ggactgtgca gcccattgtg ctgcctgaga aggactcctg gactgtgaat    780
gacatccaga agctggtggg caagctgaac tgggcctccc aaatctaccc tggcatcaag    840
gtgaggcagc tgtgcaagct gctgaggggc accaaggccc tgactgaggt gatccccctg    900
actgaggagg ctgagctgga gctggctgag aacagggaga tcctgaagga gcctgtgcat    960
ggggtgtact atgacccctc caaggacctg attgctgaga tccagaagca gggccagggc   1020
cagtggacct accaaatcta ccaggagccc ttcaagaacc tgaagactgg caagtatgcc   1080
aggatgaggg gggcccacac caatgatgtg aagcagctga ctgaggctgt gcagaagatc   1140
accactgagt ccattgtgat ctggggcaag acccccaagt tcaagctgcc catccagaag   1200
gagacctggg agacctggtg gactgagtac tggcaggcca cctggatccc tgagtgggag   1260
tttgtgaaca cccccccccct ggtgaagctg tggtaccagc tggagaagga gcccattgtg   1320
ggggctgaga ccttctatgt ggatggggct gccaacaggg agaccaagct gggcaaggct   1380
ggctatgtga ccaacagggg caggcagaag gtggtgaccc tgactgacac caccaaccag   1440
aagactgagc tccaggccat ctacctggcc ctccaggact ctggcctgga ggtgaacatt   1500
gtgactgact cccagtatgc cctgggcatc atccaggccc agcctgatca gtctgagtct   1560
gagctggtga accagatcat tgagcagctg atcaagaagg agaaggtgta cctggcctgg   1620
gtgcctgccc acaagggcat tggggggcaat gagcaggtgg acaagctggt gtctgctggc  1680
atcaggaagg tgctgttcct ggatggcatt gacaaggccc aggatgagca tgagaagtac   1740
cactccaact ggagggctat ggcctctgac ttcaacctgc cccctgtggt ggctaaggag   1800
attgtggcct cctgtgacaa gtgccagctg aaggggggagg ccatgcatgg gcaggtggac  1860
tgctcccctg gcatctggca gctggactgc acccacctgg agggcaaggt gatcctggtg   1920
gctgtgcatg tggcctccgg ctacattgag gctgaggtga tccctgctga gacaggccag   1980
gagactgcct acttcctgct gaagctggct ggcaggtggc ctgtgaagac catccacact   2040
gacaatggct ccaacttcac tggggccaca gtgagggctg cctgctggtg ggctggcatc   2100
aagcaggagt ttggcatccc ctacaacccc cagtcccagg gggtggtgga gtccatgaac   2160
aaggagctga agaagatcat tgggcaggtg agggaccagg ctgagcacct gaagacagct   2220
gtgcagatgg ctgtgttcat ccacaacttc aagaggaagg ggggcatcgg gggctactcc   2280
gctggggaga ggattgtgga catcattgcc acagacatcc agaccaagga gctccagaag   2340
cagatcacca agatccagaa cttcagggtg tactacaggg actccaggaa ccccctgtgg   2400
aagggccctg ccaagctgct gtggaagggg gagggggctg tggtgatcca ggacaactct   2460
gacatcaagg tggtgcccag gaggaaggcc aagatcatca gggactatgg caagcagatg   2520
gctggggatg actgtgtggc ctccaggcag gatgaggact aaagcccggg cagatct      2577
```

<210> SEQ ID NO 2
<211> LENGTH: 850
<212> TYPE: PRT
<213> ORGANISM: Artificial Sequence
<220> FEATURE:
<223> OTHER INFORMATION: Codon optimized HIV-1 pol

<400> SEQUENCE: 2

-continued

```
Met Ala Pro Ile Ser Pro Ile Glu Thr Val Pro Val Lys Leu Lys Pro
 1               5                  10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Asp
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
        275                 280                 285

Lys Ala Leu Thr Glu Val Ile Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
```

-continued

```
            420                 425                 430

Lys Glu Pro Ile Val Gly Ala Glu Thr Phe Tyr Val Asp Gly Ala Ala
        435                 440                 445

Asn Arg Glu Thr Lys Leu Gly Lys Ala Gly Tyr Val Thr Asn Arg Gly
    450                 455                 460

Arg Gln Lys Val Val Thr Leu Thr Asp Thr Thr Asn Gln Lys Thr Glu
465                 470                 475                 480

Leu Gln Ala Ile Tyr Leu Ala Leu Gln Asp Ser Gly Leu Glu Val Asn
                485                 490                 495

Ile Val Thr Asp Ser Gln Tyr Ala Leu Gly Ile Ile Gln Ala Gln Pro
            500                 505                 510

Asp Gln Ser Glu Ser Glu Leu Val Asn Gln Ile Ile Glu Gln Leu Ile
        515                 520                 525

Lys Lys Glu Lys Val Tyr Leu Ala Trp Val Pro Ala His Lys Gly Ile
    530                 535                 540

Gly Gly Asn Glu Gln Val Asp Lys Leu Val Ser Ala Gly Ile Arg Lys
545                 550                 555                 560

Val Leu Phe Leu Asp Gly Ile Asp Lys Ala Gln Asp Glu His Glu Lys
                565                 570                 575

Tyr His Ser Asn Trp Arg Ala Met Ala Ser Asp Phe Asn Leu Pro Pro
            580                 585                 590

Val Val Ala Lys Glu Ile Val Ala Ser Cys Asp Lys Cys Gln Leu Lys
        595                 600                 605

Gly Glu Ala Met His Gly Gln Val Asp Cys Ser Pro Gly Ile Trp Gln
    610                 615                 620

Leu Asp Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Asp Asn Gly Ser Asn Phe Thr Gly Ala Thr Val
        675                 680                 685

Arg Ala Ala Cys Trp Trp Ala Gly Ile Lys Gln Glu Phe Gly Ile Pro
    690                 695                 700

Tyr Asn Pro Gln Ser Gln Gly Val Val Glu Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Gly Tyr Ser Ala Gly Glu Arg Ile Val Asp Ile Ile Ala Thr
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asn Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845
```

-continued

Glu Asp
850

<210> SEQ ID NO 3
<211> LENGTH: 2577
<212> TYPE: DNA
<213> ORGANISM: Artificial Sequence
<220> FEATURE:
<223> OTHER INFORMATION: Codon optimized DNA encoding inactivated Pol (IA-Pol)

<400> SEQUENCE: 3
agatctacca tggcccccat ctcccccatt gagactgtgc ctgtgaagct gaagcctggc 60
atggatggcc ccaaggtgaa gcagtggccc ctgactgagg agaagatcaa ggccctggtg 120
gaaatctgca ctgagatgga gaaggagggc aaaatctcca agattggccc cgagaacccc 180
tacaacaccc ctgtgtttgc catcaagaag aaggactcca ccaagtggag gaagctggtg 240
gacttcaggg agctgaacaa gaggacccag gacttctggg aggtgcagct gggcatcccc 300
caccccgctg gcctgaagaa gaagaagtct gtgactgtgc tggctgtggg ggatgcctac 360
ttctctgtgc ccctggatga ggacttcagg aagtacactg ccttcaccat cccctccatc 420
aacaatgaga cccctggcat caggtaccag tacaatgtgc tgccccaggg ctggaagggc 480
tcccctgcca tcttccagtc ctccatgacc aagatcctgg agcccttcag gaagcagaac 540
cctgacattg tgatctacca gtacatggct gccctgtatg tgggctctga cctggagatt 600
gggcagcaca ggaccaagat tgaggagctg aggcagcacc tgctgaggtg gggcctgacc 660
acccctgaca agaagcacca gaaggagccc cccttcctgt ggatgggcta tgagctgcac 720
cccgacaagt ggactgtgca gcccattgtg ctgcctgaga aggactcctg gactgtgaat 780
gacatccaga agctggtggg caagctgaac tgggcctccc aaatctaccc tggcatcaag 840
gtgaggcagc tgtgcaagct gctgaggggc accaaggccc tgactgaggt gatcccccctg 900 actgaggagg ctgagctgga gctggctgag aacagggaga tcctgaagga gcctgtgcat 960
ggggtgtact atgacccctc caaggacctg attgctgaga tccagaagca gggccagggc 1020
cagtggacct accaaatcta ccaggagccc ttcaagaacc tgaagactgg caagtatgcc 1080
aggatgaggg gggcccacac caatgatgtg aagcagctga ctgaggctgt gcagaagatc 1140
accactgagt ccattgtgat ctggggcaag acccccaagt tcaagctgcc catccagaag 1200
gagacctggg agacctggtg gactgagtac tggcaggcca cctggatccc tgagtgggag 1260
tttgtgaaca cccccccct ggtgaagctg tggtaccagc tggagaagga gcccattgtg 1320
ggggctgaga ccttctatgt ggctggggct gccaacaggg agaccaagct gggcaaggct 1380
ggctatgtga ccaacagggg caggcagaag gtggtgaccc tgactgacac caccaaccag 1440
aagactgccc tccaggccat ctacctggcc ctccaggact ctggcctgga ggtgaacatt 1500
gtgactgcct cccagtatgc cctgggcatc atccaggccc agcctgatca gtctgagtct 1560
gagctggtga accagatcat tgagcagctg atcaagaagg agaaggtgta cctggcctgg 1620
gtgcctgccc acaagggcat tgggggcaat gagcaggtgg acaagctggt gtctgctggc 1680
atcaggaagg tgctgttcct ggatggcatt gacaaggccc aggatgagca tgagaagtac 1740
cactccaact ggagggctat ggcctctgac ttcaacctgc cccctgtggt ggctaaggag 1800
attgtggcct cctgtgacaa gtgccagctg aagggggagg ccatgcatgg gcaggtggac 1860
tgctcccctg gcatctggca gctggcctgc acccacctgg agggcaaggt gatcctggtg 1920

-continued

```
gctgtgcatg tggcctccgg ctacattgag gctgaggtga tccctgctga gacaggccag   1980

gagactgcct acttcctgct gaagctggct ggcaggtggc ctgtgaagac catccacact   2040

gccaatggct ccaacttcac tggggccaca gtgagggctg cctgctggtg ggctggcatc   2100

aagcaggagt ttggcatccc ctacaacccc cagtcccagg gggtggtggc ctccatgaac   2160

aaggagctga agaagatcat tgggcaggtg agggaccagg ctgagcacct gaagacagct   2220

gtgcagatgg ctgtgttcat ccacaacttc aagaggaagg ggggcatcgg gggctactcc   2280

gctggggaga ggattgtgga catcattgcc acagacatcc agaccaagga gctccagaag   2340

cagatcacca agatccagaa cttcagggtg tactacaggg actccaggaa ccccctgtgg   2400

aagggccctg ccaagctgct gtggaagggg gagggggctg tggtgatcca ggacaactct   2460

gacatcaagg tggtgcccag gaggaaggcc aagatcatca gggactatgg caagcagatg   2520

gctggggatg actgtgtggc ctccaggcag gatgaggact aaagcccggg cagatct      2577
```

<210> SEQ ID NO 4
<211> LENGTH: 850
<212> TYPE: PRT
<213> ORGANISM: Artificial Sequence
<220> FEATURE:
<223> OTHER INFORMATION: Codon optimized DNA inactivated Pol (IA-Pol)

<400> SEQUENCE: 4

```
Met Ala Pro Ile Ser Pro Ile Glu Thr Val Pro Val Lys Leu Lys Pro
 1               5                  10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Ala
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255
```

-continued

```
Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
        275                 280                 285

Lys Ala Leu Thr Glu Val Ile Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val Gly Ala Glu Thr Phe Tyr Val Ala Gly Ala Ala
        435                 440                 445

Asn Arg Glu Thr Lys Leu Gly Lys Ala Gly Tyr Val Thr Asn Arg Gly
    450                 455                 460

Arg Gln Lys Val Val Thr Leu Thr Asp Thr Thr Asn Gln Lys Thr Ala
465                 470                 475                 480

Leu Gln Ala Ile Tyr Leu Ala Leu Gln Asp Ser Gly Leu Glu Val Asn
                485                 490                 495

Ile Val Thr Ala Ser Gln Tyr Ala Leu Gly Ile Ile Gln Ala Gln Pro
            500                 505                 510

Asp Gln Ser Glu Ser Glu Leu Val Asn Gln Ile Ile Glu Gln Leu Ile
        515                 520                 525

Lys Lys Glu Lys Val Tyr Leu Ala Trp Val Pro Ala His Lys Gly Ile
    530                 535                 540

Gly Gly Asn Glu Gln Val Asp Lys Leu Val Ser Ala Gly Ile Arg Lys
545                 550                 555                 560

Val Leu Phe Leu Asp Gly Ile Asp Lys Ala Gln Asp Glu His Glu Lys
                565                 570                 575

Tyr His Ser Asn Trp Arg Ala Met Ala Ser Asp Phe Asn Leu Pro Pro
            580                 585                 590

Val Val Ala Lys Glu Ile Val Ala Ser Cys Asp Lys Cys Gln Leu Lys
        595                 600                 605

Gly Glu Ala Met His Gly Gln Val Asp Cys Ser Pro Gly Ile Trp Gln
    610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670
```

-continued

```
Lys Thr Ile His Thr Ala Asn Gly Ser Asn Phe Thr Gly Ala Thr Val
        675                 680                 685

Arg Ala Ala Cys Trp Trp Ala Gly Ile Lys Gln Glu Phe Gly Ile Pro
    690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Gly Tyr Ser Ala Gly Glu Arg Ile Val Asp Ile Ile Ala Thr
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asn Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845

Glu Asp
    850


<210> SEQ ID NO 5
<211> LENGTH: 2650
<212> TYPE: DNA
<213> ORGANISM: Artificial Sequence
<220> FEATURE:
<223> OTHER INFORMATION: Codon optimized DNA encoding modified HIV-1 pol
      fused to an amino terminal localized leader
      sequence

<400> SEQUENCE: 5

gatcaccatg gatgcaatga agagagggct ctgctgtgtg ctgctgctgt gtggagcagt      60

cttcgtttcg cccagcgaga tctccgcccc catctccccc attgagactg tgcctgtgaa     120

gctgaagcct ggcatggatg gccccaaggt gaagcagtgg cccctgactg aggagaagat     180

caaggccctg gtggaaatct gcactgagat ggagaaggag ggcaaaatct ccaagattgg     240

ccccgagaac ccctacaaca cccctgtgtt tgccatcaag aagaaggact ccaccaagtg     300

gaggaagctg gtggacttca gggagctgaa caagaggacc caggacttct gggaggtgca     360

gctgggcatc cccccacccg ctggcctgaa gaagaagaag tctgtgactg tgctggatgt     420

gggggatgcc tacttctctg tgcccctgga tgaggacttc aggaagtaca ctgccttcac     480

catcccctcc atcaacaatg agacccctgg catcaggtac cagtacaatg tgctgcccca     540

gggctggaag ggctcccctg ccatcttcca gtcctccatg accaagatcc tggagccctt     600

caggaagcag aaccctgaca ttgtgatcta ccagtacatg gatgacctgt atgtgggctc     660

tgacctggag attgggcagc acaggaccaa gattgaggag ctgaggcagc acctgctgag     720

gtggggcctg accacccctg acaagaagca ccagaaggag cccccccttcc tgtggatggg     780

ctatgagctg caccccgaca agtggactgt gcagcccatt gtgctgcctg agaaggactc     840

ctggactgtg aatgacatcc agaagctggt gggcaagctg aactgggcct cccaaatcta     900

ccctggcatc aaggtgaggc agctgtgcaa gctgctgagg ggcaccaagg ccctgactga     960
```

-continued

```
ggtgatcccc ctgactgagg aggctgagct ggagctggct gagaacaggg agatcctgaa   1020

ggagcctgtg catggggtgt actatgaccc ctccaaggac ctgattgctg agatccagaa   1080

gcagggccag ggccagtgga cctaccaaat ctaccaggag cccttcaaga acctgaagac   1140

tggcaagtat gccaggatga gggggcccca caccaatgat gtgaagcagc tgactgaggc   1200

tgtgcagaag atcaccactg agtccattgt gatctggggc aagacccccca agttcaagct   1260

gcccatccag aaggagacct gggagacctg gtggactgag tactggcagg ccacctggat   1320

ccctgagtgg gagtttgtga acaccccccc cctggtgaag ctgtggtacc agctggagaa   1380

ggagcccatt gtgggggctg agaccttcta tgtggatggg gctgccaaca gggagaccaa   1440

gctgggcaag gctggctatg tgaccaacag gggcaggcag aaggtggtga ccctgactga   1500

caccaccaac cagaagactg agctccaggc catctacctg gccctccagg actctggcct   1560

ggaggtgaac attgtgactg actcccagta tgccctgggc atcatccagg cccagcctga   1620

tcagtctgag tctgagctgg tgaaccagat cattgagcag ctgatcaaga aggagaaggt   1680

gtacctggcc tgggtgcctg cccacaaggg cattgggggc aatgagcagg tggacaagct   1740

ggtgtctgct ggcatcagga aggtgctgtt cctggatggc attgacaagg cccaggatga   1800

gcatgagaag taccactcca actggagggc tatggcctct gacttcaacc tgccccctgt   1860

ggtggctaag gagattgtgg cctcctgtga caagtgccag ctgaaggggg aggccatgca   1920

tgggcaggtg gactgctccc ctggcatctg gcagctggac tgcacccacc tggagggcaa   1980

ggtgatcctg gtggctgtgc atgtggcctc cggctacatt gaggctgagg tgatccctgc   2040

tgagacaggc caggagactg cctacttcct gctgaagctg gctggcaggt ggcctgtgaa   2100

gaccatccac actgacaatg gctccaactt cactggggcc acagtgaggg ctgcctgctg   2160

gtgggctggc atcaagcagg agtttggcat cccctacaac ccccagtccc aggggggtggt   2220

ggagtccatg aacaaggagc tgaagaagat cattgggcag gtgagggacc aggctgagca   2280

cctgaagaca gctgtgcaga tggctgtgtt catccacaac ttcaagagga aggggggcat   2340

cgggggctac tccgctgggg agaggattgt ggacatcatt gccacagaca tccagaccaa   2400

ggagctccag aagcagatca ccaagatcca gaacttcagg gtgtactaca gggactccag   2460

gaaccccctg tggaagggcc ctgccaagct gctgtggaag ggggaggggg ctgtggtgat   2520

ccaggacaac tctgacatca aggtggtgcc caggaggaag gccaagatca tcagggacta   2580

tggcaagcag atggctgggg atgactgtgt ggcctccagg caggatgagg actaaagccc   2640

gggcagatct                                                          2650
```

<210> SEQ ID NO 6
<211> LENGTH: 875
<212> TYPE: PRT
<213> ORGANISM: Artificial Sequence
<220> FEATURE:
<223> OTHER INFORMATION: Codon optimized HIV-1 pol fused to an amino terminal localized leader sequence

<400> SEQUENCE: 6

```
Met Asp Ala Met Lys Arg Gly Leu Cys Cys Val Leu Leu Leu Cys Gly
 1               5                  10                  15

Ala Val Phe Val Ser Pro Ser Glu Ile Ser Ala Pro Ile Ser Pro Ile
            20                  25                  30

Glu Thr Val Pro Val Lys Leu Lys Pro Gly Met Asp Gly Pro Lys Val
        35                  40                  45
```

-continued

```
Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser Val Thr Val Leu Asp Val Gly Asp Ala Tyr Phe Ser
    130                 135                 140

Val Pro Leu Asp Glu Asp Phe Arg Lys Tyr Thr Ala Phe Thr Ile Pro
145                 150                 155                 160

Ser Ile Asn Asn Glu Thr Pro Gly Ile Arg Tyr Gln Tyr Asn Val Leu
                165                 170                 175

Pro Gln Gly Trp Lys Gly Ser Pro Ala Ile Phe Gln Ser Ser Met Thr
            180                 185                 190

Lys Ile Leu Glu Pro Phe Arg Lys Gln Asn Pro Asp Ile Val Ile Tyr
        195                 200                 205

Gln Tyr Met Asp Asp Leu Tyr Val Gly Ser Asp Leu Glu Ile Gly Gln
    210                 215                 220

His Arg Thr Lys Ile Glu Glu Leu Arg Gln His Leu Leu Arg Trp Gly
225                 230                 235                 240

Leu Thr Thr Pro Asp Lys Lys His Gln Lys Glu Pro Pro Phe Leu Trp
                245                 250                 255

Met Gly Tyr Glu Leu His Pro Asp Lys Trp Thr Val Gln Pro Ile Val
            260                 265                 270

Leu Pro Glu Lys Asp Ser Trp Thr Val Asn Asp Ile Gln Lys Leu Val
        275                 280                 285

Gly Lys Leu Asn Trp Ala Ser Gln Ile Tyr Pro Gly Ile Lys Val Arg
    290                 295                 300

Gln Leu Cys Lys Leu Leu Arg Gly Thr Lys Ala Leu Thr Glu Val Ile
305                 310                 315                 320

Pro Leu Thr Glu Glu Ala Glu Leu Glu Leu Ala Glu Asn Arg Glu Ile
                325                 330                 335

Leu Lys Glu Pro Val His Gly Val Tyr Tyr Asp Pro Ser Lys Asp Leu
            340                 345                 350

Ile Ala Glu Ile Gln Lys Gln Gly Gln Gly Gln Trp Thr Tyr Gln Ile
        355                 360                 365

Tyr Gln Glu Pro Phe Lys Asn Leu Lys Thr Gly Lys Tyr Ala Arg Met
    370                 375                 380

Arg Gly Ala His Thr Asn Asp Val Lys Gln Leu Thr Glu Ala Val Gln
385                 390                 395                 400

Lys Ile Thr Thr Glu Ser Ile Val Ile Trp Gly Lys Thr Pro Lys Phe
                405                 410                 415

Lys Leu Pro Ile Gln Lys Glu Thr Trp Glu Thr Trp Trp Thr Glu Tyr
            420                 425                 430

Trp Gln Ala Thr Trp Ile Pro Glu Trp Glu Phe Val Asn Thr Pro Pro
        435                 440                 445

Leu Val Lys Leu Trp Tyr Gln Leu Glu Lys Glu Pro Ile Val Gly Ala
    450                 455                 460

Glu Thr Phe Tyr Val Asp Gly Ala Ala Asn Arg Glu Thr Lys Leu Gly
```

-continued

```
465                 470                 475                 480

Lys Ala Gly Tyr Val Thr Asn Arg Gly Arg Gln Lys Val Val Thr Leu
                485                 490                 495

Thr Asp Thr Thr Asn Gln Lys Thr Glu Leu Gln Ala Ile Tyr Leu Ala
            500                 505                 510

Leu Gln Asp Ser Gly Leu Glu Val Asn Ile Val Thr Asp Ser Gln Tyr
        515                 520                 525

Ala Leu Gly Ile Ile Gln Ala Gln Pro Asp Gln Ser Glu Ser Glu Leu
    530                 535                 540

Val Asn Gln Ile Ile Glu Gln Leu Ile Lys Lys Glu Lys Val Tyr Leu
545                 550                 555                 560

Ala Trp Val Pro Ala His Lys Gly Ile Gly Gly Asn Glu Gln Val Asp
                565                 570                 575

Lys Leu Val Ser Ala Gly Ile Arg Lys Val Leu Phe Leu Asp Gly Ile
            580                 585                 590

Asp Lys Ala Gln Asp Glu His Glu Lys Tyr His Ser Asn Trp Arg Ala
        595                 600                 605

Met Ala Ser Asp Phe Asn Leu Pro Pro Val Val Ala Lys Glu Ile Val
    610                 615                 620

Ala Ser Cys Asp Lys Cys Gln Leu Lys Gly Glu Ala Met His Gly Gln
625                 630                 635                 640

Val Asp Cys Ser Pro Gly Ile Trp Gln Leu Asp Cys Thr His Leu Glu
                645                 650                 655

Gly Lys Val Ile Leu Val Ala Val His Val Ala Ser Gly Tyr Ile Glu
            660                 665                 670

Ala Glu Val Ile Pro Ala Glu Thr Gly Gln Glu Thr Ala Tyr Phe Leu
        675                 680                 685

Leu Lys Leu Ala Gly Arg Trp Pro Val Lys Thr Ile His Thr Asp Asn
    690                 695                 700

Gly Ser Asn Phe Thr Gly Ala Thr Val Arg Ala Ala Cys Trp Trp Ala
705                 710                 715                 720

Gly Ile Lys Gln Glu Phe Gly Ile Pro Tyr Asn Pro Gln Ser Gln Gly
                725                 730                 735

Val Val Glu Ser Met Asn Lys Glu Leu Lys Lys Ile Ile Gly Gln Val
            740                 745                 750

Arg Asp Gln Ala Glu His Leu Lys Thr Ala Val Gln Met Ala Val Phe
        755                 760                 765

Ile His Asn Phe Lys Arg Lys Gly Gly Ile Gly Gly Tyr Ser Ala Gly
    770                 775                 780

Glu Arg Ile Val Asp Ile Ile Ala Thr Asp Ile Gln Thr Lys Glu Leu
785                 790                 795                 800

Gln Lys Gln Ile Thr Lys Ile Gln Asn Phe Arg Val Tyr Tyr Arg Asp
                805                 810                 815

Ser Arg Asn Pro Leu Trp Lys Gly Pro Ala Lys Leu Leu Trp Lys Gly
            820                 825                 830

Glu Gly Ala Val Val Ile Gln Asp Asn Ser Asp Ile Lys Val Val Pro
        835                 840                 845

Arg Arg Lys Ala Lys Ile Ile Arg Asp Tyr Gly Lys Gln Met Ala Gly
    850                 855                 860

Asp Asp Cys Val Ala Ser Arg Gln Asp Glu Asp
865                 870                 875
```

<210> SEQ ID NO 7

-continued

<211> LENGTH: 2650
<212> TYPE: DNA
<213> ORGANISM: Artificial Sequence
<220> FEATURE:
<223> OTHER INFORMATION: Codon optimized DNA encoding human tPA leader fused to the IA-Pol protein

<400> SEQUENCE: 7
gatcaccatg gatgcaatga agagagggct ctgctgtgtg ctgctgctgt gtggagcagt 60
cttcgtttcg cccagcgaga tctccgcccc catctccccc attgagactg tgcctgtgaa 120
gctgaagcct ggcatggatg gccccaaggt gaagcagtgg cccctgactg aggagaagat 180
caaggccctg gtggaaatct gcactgagat ggagaaggag ggcaaaatct ccaagattgg 240
ccccgagaac ccctacaaca cccctgtgtt tgccatcaag aagaaggact ccaccaagtg 300
gaggaagctg gtggacttca gggagctgaa caagaggacc caggacttct gggaggtgca 360
gctgggcatc ccccaccccg ctggcctgaa gaagaagaag tctgtgactg tgctggctgt 420
gggggatgcc tacttctctg tgcccctgga tgaggacttc aggaagtaca ctgccttcac 480
catcccctcc atcaacaatg agacccctgg catcaggtac cagtacaatg tgctgcccca 540
gggctggaag ggctcccctg ccatcttcca gtcctccatg accaagatcc tggagccctt 600
caggaagcag aaccctgaca ttgtgatcta ccagtacatg gctgccctgt atgtgggctc 660
tgacctggag attgggcagc acaggaccaa gattgaggag ctgaggcagc acctgctgag 720
gtggggcctg accacccctg acaagaagca ccagaaggag ccccccttcc tgtggatggg 780
ctatgagctg caccccgaca agtggactgt gcagcccatt gtgctgcctg agaaggactc 840
ctggactgtg aatgacatcc agaagctggt gggcaagctg aactgggcct cccaaatcta 900
ccctggcatc aaggtgaggc agctgtgcaa gctgctgagg ggcaccaagg ccctgactga 960
ggtgatcccc ctgactgagg aggctgagct ggagctggct gagaacaggg agatcctgaa 1020
ggagcctgtg catggggtgt actatgaccc ctccaaggac ctgattgctg agatccagaa 1080
gcagggccag ggccagtgga cctaccaaat ctaccaggag cccttcaaga acctgaagac 1140
tggcaagtat gccaggatga gggggcccca caccaatgat gtgaagcagc tgactgaggc 1200
tgtgcagaag atcaccactg agtccattgt gatctggggc aagaccccca agttcaagct 1260
gcccatccag aaggagacct gggagacctg gtggactgag tactggcagg ccacctggat 1320
ccctgagtgg gagtttgtga acaccccccc cctggtgaag ctgtggtacc agctggagaa 1380
ggagcccatt gtgggggctg agaccttcta tgtggctggg gctgccaaca gggagaccaa 1440
gctgggcaag gctggctatg tgaccaacag gggcaggcag aaggtggtga ccctgactga 1500
caccaccaac cagaagactg ccctccaggc catctacctg gccctccagg actctggcct 1560
ggaggtgaac attgtgactg cctcccagta tgccctgggc atcatccagg cccagcctga 1620
tcagtctgag tctgagctgg tgaaccagat cattgagcag ctgatcaaga aggagaaggt 1680
gtacctggcc tgggtgcctg cccacaaggg cattgggggc aatgagcagg tggacaagct 1740
ggtgtctgct ggcatcagga aggtgctgtt cctggatggc attgacaagg cccaggatga 1800
gcatgagaag taccactcca actggagggc tatggcctct gacttcaacc tgccccctgt 1860
ggtggctaag gagattgtgg cctcctgtga caagtgccag ctgaaggggg aggccatgca 1920
tgggcaggtg gactgctccc ctggcatctg gcagctggcc tgcacccacc tggagggcaa 1980
ggtgatcctg gtggctgtgc atgtggcctc cggctacatt gaggctgagg tgatccctgc 2040
tgagacaggc caggagactg cctacttcct gctgaagctg gctggcaggt ggcctgtgaa 2100

-continued

```
gaccatccac actgccaatg gctccaactt cactggggcc acagtgaggg ctgcctgctg   2160

gtgggctggc atcaagcagg agtttggcat cccctacaac ccccagtccc agggggtggt   2220

ggcctccatg aacaaggagc tgaagaagat cattgggcag gtgagggacc aggctgagca   2280

cctgaagaca gctgtgcaga tggctgtgtt catccacaac ttcaagagga agggggcat    2340

cgggggctac tccgctgggg agaggattgt ggacatcatt gccacagaca tccagaccaa   2400

ggagctccag aagcagatca ccaagatcca gaacttcagg gtgtactaca gggactccag   2460

gaaccccctg tggaagggcc ctgccaagct gctgtggaag gggggagggg ctgtggtgat   2520

ccaggacaac tctgacatca aggtggtgcc caggaggaag gccaagatca tcagggacta   2580

tggcaagcag atggctgggg atgactgtgt ggcctccagg caggatgagg actaaagccc   2640

gggcagatct                                                          2650
```

<210> SEQ ID NO 8
<211> LENGTH: 875
<212> TYPE: PRT
<213> ORGANISM: Artificial Sequence
<220> FEATURE:
<223> OTHER INFORMATION: Codon optimized human tPA leader fused to the IA-Pol protein

<400> SEQUENCE: 8

```
Met Asp Ala Met Lys Arg Gly Leu Cys Cys Val Leu Leu Leu Cys Gly
 1               5                  10                  15

Ala Val Phe Val Ser Pro Ser Glu Ile Ser Ala Pro Ile Ser Pro Ile
            20                  25                  30

Glu Thr Val Pro Val Lys Leu Lys Pro Gly Met Asp Gly Pro Lys Val
        35                  40                  45

Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser Val Thr Val Leu Ala Val Gly Asp Ala Tyr Phe Ser
    130                 135                 140

Val Pro Leu Asp Glu Asp Phe Arg Lys Tyr Thr Ala Phe Thr Ile Pro
145                 150                 155                 160

Ser Ile Asn Asn Glu Thr Pro Gly Ile Arg Tyr Gln Tyr Asn Val Leu
                165                 170                 175

Pro Gln Gly Trp Lys Gly Ser Pro Ala Ile Phe Gln Ser Ser Met Thr
            180                 185                 190

Lys Ile Leu Glu Pro Phe Arg Lys Gln Asn Pro Asp Ile Val Ile Tyr
        195                 200                 205

Gln Tyr Met Ala Ala Leu Tyr Val Gly Ser Asp Leu Glu Ile Gly Gln
    210                 215                 220

His Arg Thr Lys Ile Glu Glu Leu Arg Gln His Leu Leu Arg Trp Gly
225                 230                 235                 240

Leu Thr Thr Pro Asp Lys Lys His Gln Lys Glu Pro Pro Phe Leu Trp
                245                 250                 255
```

-continued

```
Met Gly Tyr Glu Leu His Pro Asp Lys Trp Thr Val Gln Pro Ile Val
            260                 265                 270

Leu Pro Glu Lys Asp Ser Trp Thr Val Asn Asp Ile Gln Lys Leu Val
        275                 280                 285

Gly Lys Leu Asn Trp Ala Ser Gln Ile Tyr Pro Gly Ile Lys Val Arg
    290                 295                 300

Gln Leu Cys Lys Leu Leu Arg Gly Thr Lys Ala Leu Thr Glu Val Ile
305                 310                 315                 320

Pro Leu Thr Glu Glu Ala Glu Leu Glu Leu Ala Glu Asn Arg Glu Ile
                325                 330                 335

Leu Lys Glu Pro Val His Gly Val Tyr Tyr Asp Pro Ser Lys Asp Leu
            340                 345                 350

Ile Ala Glu Ile Gln Lys Gln Gly Gln Gly Gln Trp Thr Tyr Gln Ile
        355                 360                 365

Tyr Gln Glu Pro Phe Lys Asn Leu Lys Thr Gly Lys Tyr Ala Arg Met
    370                 375                 380

Arg Gly Ala His Thr Asn Asp Val Lys Gln Leu Thr Glu Ala Val Gln
385                 390                 395                 400

Lys Ile Thr Thr Glu Ser Ile Val Ile Trp Gly Lys Thr Pro Lys Phe
                405                 410                 415

Lys Leu Pro Ile Gln Lys Glu Thr Trp Glu Thr Trp Trp Thr Glu Tyr
            420                 425                 430

Trp Gln Ala Thr Trp Ile Pro Glu Trp Glu Phe Val Asn Thr Pro Pro
        435                 440                 445

Leu Val Lys Leu Trp Tyr Gln Leu Glu Lys Glu Pro Ile Val Gly Ala
    450                 455                 460

Glu Thr Phe Tyr Val Ala Gly Ala Ala Asn Arg Glu Thr Lys Leu Gly
465                 470                 475                 480

Lys Ala Gly Tyr Val Thr Asn Arg Gly Arg Gln Lys Val Val Thr Leu
                485                 490                 495

Thr Asp Thr Thr Asn Gln Lys Thr Ala Leu Gln Ala Ile Tyr Leu Ala
            500                 505                 510

Leu Gln Asp Ser Gly Leu Glu Val Asn Ile Val Thr Ala Ser Gln Tyr
        515                 520                 525

Ala Leu Gly Ile Ile Gln Ala Gln Pro Asp Gln Ser Glu Ser Glu Leu
    530                 535                 540

Val Asn Gln Ile Ile Glu Gln Leu Ile Lys Lys Glu Lys Val Tyr Leu
545                 550                 555                 560

Ala Trp Val Pro Ala His Lys Gly Ile Gly Gly Asn Glu Gln Val Asp
                565                 570                 575

Lys Leu Val Ser Ala Gly Ile Arg Lys Val Leu Phe Leu Asp Gly Ile
            580                 585                 590

Asp Lys Ala Gln Asp Glu His Glu Lys Tyr His Ser Asn Trp Arg Ala
        595                 600                 605

Met Ala Ser Asp Phe Asn Leu Pro Pro Val Val Ala Lys Glu Ile Val
    610                 615                 620

Ala Ser Cys Asp Lys Cys Gln Leu Lys Gly Glu Ala Met His Gly Gln
625                 630                 635                 640

Val Asp Cys Ser Pro Gly Ile Trp Gln Leu Ala Cys Thr His Leu Glu
                645                 650                 655

Gly Lys Val Ile Leu Val Ala Val His Val Ala Ser Gly Tyr Ile Glu
            660                 665                 670

Ala Glu Val Ile Pro Ala Glu Thr Gly Gln Glu Thr Ala Tyr Phe Leu
```

-continued

```
        675                 680                 685

Leu Lys Leu Ala Gly Arg Trp Pro Val Lys Thr Ile His Thr Ala Asn
    690                 695                 700

Gly Ser Asn Phe Thr Gly Ala Thr Val Arg Ala Ala Cys Trp Trp Ala
705                 710                 715                 720

Gly Ile Lys Gln Glu Phe Gly Ile Pro Tyr Asn Pro Gln Ser Gln Gly
                725                 730                 735

Val Val Ala Ser Met Asn Lys Glu Leu Lys Lys Ile Ile Gly Gln Val
            740                 745                 750

Arg Asp Gln Ala Glu His Leu Lys Thr Ala Val Gln Met Ala Val Phe
        755                 760                 765

Ile His Asn Phe Lys Arg Lys Gly Gly Ile Gly Gly Tyr Ser Ala Gly
    770                 775                 780

Glu Arg Ile Val Asp Ile Ile Ala Thr Asp Ile Gln Thr Lys Glu Leu
785                 790                 795                 800

Gln Lys Gln Ile Thr Lys Ile Gln Asn Phe Arg Val Tyr Tyr Arg Asp
                805                 810                 815

Ser Arg Asn Pro Leu Trp Lys Gly Pro Ala Lys Leu Leu Trp Lys Gly
            820                 825                 830

Glu Gly Ala Val Val Ile Gln Asp Asn Ser Asp Ile Lys Val Val Pro
        835                 840                 845

Arg Arg Lys Ala Lys Ile Ile Arg Asp Tyr Gly Lys Gln Met Ala Gly
    850                 855                 860

Asp Asp Cys Val Ala Ser Arg Gln Asp Glu Asp
865                 870                 875


<210> SEQ ID NO 9
<211> LENGTH: 671
<212> TYPE: DNA
<213> ORGANISM: Artificial Sequence
<220> FEATURE:
<223> OTHER INFORMATION: Codon optimized DNA encoding  HIV-1 nef from
      the HIV-1 jfrl isolate

<400> SEQUENCE: 9

gatctgccac catgggcggc aagtggtcca agaggtccgt gcccggctgg tccaccgtga     60

gggagaggat gaggagggcc gagcccgccg ccgacagggt gaggaggacc gagcccgccg    120

ccgtgggcgt gggcgccgtg tccagggacc tggagaagca cggcgccatc acctcctcca    180

acaccgccgc caccaacgcc gactgcgcct ggctggaggc ccaggaggac gaggaggtgg    240

gcttccccgt gaggccccag gtgcccctga ggcccatgac ctacaagggc gccgtggacc    300

tgtcccactt cctgaaggag aagggcggcc tggagggcct gatccactcc cagaagaggc    360

aggacatcct ggacctgtgg gtgtaccaca cccagggcta cttccccgac tggcagaact    420

acaccccccgg ccccggcatc aggttccccc tgaccttcgg ctggtgcttc aagctggtgc    480

ccgtggagcc cgagaaggtg gaggaggcca acgagggcga gaacaactgc ctgctgcacc    540

ccatgtccca gcacggcatc gaggaccccg agaaggaggt gctggagtgg aggttcgact    600

ccaagctggc cttccaccac gtggccaggg agctgcaccc cgagtactac aaggactgct    660

aaagcccggg c                                                          671


<210> SEQ ID NO 10
<211> LENGTH: 216
<212> TYPE: PRT
<213> ORGANISM: Artificial Sequence
<220> FEATURE:
```

-continued

<223> OTHER INFORMATION: Codon optimized HIV-1 nef from the HIV-1 jfrl isolate

<400> SEQUENCE: 10

```
Met Gly Gly Lys Trp Ser Lys Arg Ser Val Pro Gly Trp Ser Thr Val
 1               5                  10                  15

Arg Glu Arg Met Arg Arg Ala Glu Pro Ala Ala Asp Arg Val Arg Arg
            20                  25                  30

Thr Glu Pro Ala Ala Val Gly Val Gly Ala Val Ser Arg Asp Leu Glu
        35                  40                  45

Lys His Gly Ala Ile Thr Ser Ser Asn Thr Ala Ala Thr Asn Ala Asp
    50                  55                  60

Cys Ala Trp Leu Glu Ala Gln Glu Asp Glu Glu Val Gly Phe Pro Val
65                  70                  75                  80

Arg Pro Gln Val Pro Leu Arg Pro Met Thr Tyr Lys Gly Ala Val Asp
                85                  90                  95

Leu Ser His Phe Leu Lys Glu Lys Gly Gly Leu Glu Gly Leu Ile His
            100                 105                 110

Ser Gln Lys Arg Gln Asp Ile Leu Asp Leu Trp Val Tyr His Thr Gln
        115                 120                 125

Gly Tyr Phe Pro Asp Trp Gln Asn Tyr Thr Pro Gly Pro Gly Ile Arg
    130                 135                 140

Phe Pro Leu Thr Phe Gly Trp Cys Phe Lys Leu Val Pro Val Glu Pro
145                 150                 155                 160

Glu Lys Val Glu Glu Ala Asn Glu Gly Glu Asn Asn Cys Leu Leu His
                165                 170                 175

Pro Met Ser Gln His Gly Ile Glu Asp Pro Glu Lys Glu Val Leu Glu
            180                 185                 190

Trp Arg Phe Asp Ser Lys Leu Ala Phe His His Val Ala Arg Glu Leu
        195                 200                 205

His Pro Glu Tyr Tyr Lys Asp Cys
    210                 215
```

<210> SEQ ID NO 11
<211> LENGTH: 719
<212> TYPE: DNA
<213> ORGANISM: Artificial Sequence
<220> FEATURE:
<223> OTHER INFORMATION: Codon optimized DNA encoding human plasminogen activator (tPA) leader fused with the NH2-terminus of HIV-1 nef

<400> SEQUENCE: 11

```
catggatgca atgaagagag ggctctgctg tgtgctgctg ctgtgtggag cagtcttcgt     60

ttcgcccagc gagatctcct ccaagaggtc cgtgcccggc tggtccaccg tgagggagag    120

gatgaggagg gccgagcccg ccgccgacag ggtgaggagg accgagcccg ccgccgtggg    180

cgtgggcgcc gtgtccaggg acctggagaa gcacggcgcc atcacctcct ccaacaccgc    240

cgccaccaac gccgactgcg cctggctgga ggcccaggag gacgaggagg tgggcttccc    300

cgtgaggccc caggtgcccc tgaggcccat gacctacaag ggcgccgtgg acctgtccca    360

cttcctgaag gagaagggcg gcctggaggg cctgatccac tcccagaaga ggcaggacat    420

cctggacctg tgggtgtacc acacccaggg ctacttcccc gactggcaga actacacccc    480

cggccccggc atcaggttcc ccctgacctt cggctggtgc ttcaagctgg tgcccgtgga    540

gcccgagaag gtggaggagg ccaacgaggg cgagaacaac tgcctgctgc accccatgtc    600
```

-continued

```
ccagcacggc atcgaggacc ccgagaagga ggtgctggag tggaggttcg actccaagct    660

ggccttccac cacgtggcca gggagctgca ccccgagtac tacaaggact gctaaagcc     719


<210> SEQ ID NO 12
<211> LENGTH: 237
<212> TYPE: PRT
<213> ORGANISM: Artificial Sequence
<220> FEATURE:
<223> OTHER INFORMATION: Codon optimized DNA for human plasminogen
      activator (tPA) leader fused with the NH2-terminus
      of HIV-1 nef

<400> SEQUENCE: 12

Met Asp Ala Met Lys Arg Gly Leu Cys Cys Val Leu Leu Leu Cys Gly
 1               5                  10                  15

Ala Val Phe Val Ser Pro Ser Glu Ile Ser Ser Lys Arg Ser Val Pro
            20                  25                  30

Gly Trp Ser Thr Val Arg Glu Arg Met Arg Arg Ala Glu Pro Ala Ala
        35                  40                  45

Asp Arg Val Arg Arg Thr Glu Pro Ala Ala Val Gly Val Gly Ala Val
    50                  55                  60

Ser Arg Asp Leu Glu Lys His Gly Ala Ile Thr Ser Ser Asn Thr Ala
65                  70                  75                  80

Ala Thr Asn Ala Asp Cys Ala Trp Leu Glu Ala Gln Glu Asp Glu Glu
                85                  90                  95

Val Gly Phe Pro Val Arg Pro Gln Val Pro Leu Arg Pro Met Thr Tyr
            100                 105                 110

Lys Gly Ala Val Asp Leu Ser His Phe Leu Lys Glu Lys Gly Gly Leu
        115                 120                 125

Glu Gly Leu Ile His Ser Gln Lys Arg Gln Asp Ile Leu Asp Leu Trp
    130                 135                 140

Val Tyr His Thr Gln Gly Tyr Phe Pro Asp Trp Gln Asn Tyr Thr Pro
145                 150                 155                 160

Gly Pro Gly Ile Arg Phe Pro Leu Thr Phe Gly Trp Cys Phe Lys Leu
                165                 170                 175

Val Pro Val Glu Pro Glu Lys Val Glu Glu Ala Asn Glu Gly Glu Asn
            180                 185                 190

Asn Cys Leu Leu His Pro Met Ser Gln His Gly Ile Glu Asp Pro Glu
        195                 200                 205

Lys Glu Val Leu Glu Trp Arg Phe Asp Ser Lys Leu Ala Phe His His
    210                 215                 220

Val Ala Arg Glu Leu His Pro Glu Tyr Tyr Lys Asp Cys
225                 230                 235


<210> SEQ ID NO 13
<211> LENGTH: 671
<212> TYPE: DNA
<213> ORGANISM: Artificial Sequence
<220> FEATURE:
<223> OTHER INFORMATION: DNA encoding optimized modified HIV-1 nef

<400> SEQUENCE: 13

gatctgccac catggccggc aagtggtcca agaggtccgt gcccggctgg tccaccgtga     60

gggagaggat gaggagggcc gagcccgccg ccgacagggt gaggaggacc gagcccgccg    120

ccgtgggcgt gggcgccgtg tccagggacc tggagaagca cggcgccatc acctcctcca    180

acaccgccgc caccaacgcc gactgcgcct ggctggaggc ccaggaggac gaggaggtgg    240
```

-continued

```
gcttccccgt gaggccccag gtgcccctga ggcccatgac ctacaagggc gccgtggacc    300

tgtcccactt cctgaaggag aagggcggcc tggagggcct gatccactcc cagaagaggc    360

aggacatcct ggacctgtgg gtgtaccaca cccagggcta cttccccgac tggcagaact    420

acaccccgg ccccggcatc aggttccccc tgaccttcgg ctggtgcttc aagctggtgc     480

ccgtggagcc cgagaaggtg gaggaggcca acgagggcga gaacaactgc gccgcccacc    540

ccatgtccca gcacggcatc gaggaccccg agaaggaggt gctggagtgg aggttcgact    600

ccaagctggc cttccaccac gtggccaggg agctgcaccc cgagtactac aaggactgct    660

aaagcccggg c                                                         671
```

```
<210> SEQ ID NO 14
<211> LENGTH: 217
<212> TYPE: PRT
<213> ORGANISM: Artificial Sequence
<220> FEATURE:
<223> OTHER INFORMATION: Codon optimized modified HIV-1 nef

<400> SEQUENCE: 14

Met Ala Gly Lys Trp Ser Lys Arg Ser Val Pro Gly Trp Ser Thr Val
 1               5                  10                  15

Arg Glu Arg Met Arg Arg Ala Glu Pro Ala Ala Asp Arg Val Arg Arg
            20                  25                  30

Thr Glu Pro Ala Ala Val Gly Val Gly Ala Val Ser Arg Asp Leu Glu
        35                  40                  45

Lys His Gly Ala Ile Thr Ser Ser Asn Thr Ala Ala Thr Asn Ala Asp
    50                  55                  60

Cys Ala Trp Leu Glu Ala Gln Glu Asp Glu Glu Val Gly Phe Pro Val
65                  70                  75                  80

Arg Pro Gln Val Pro Leu Arg Pro Met Thr Tyr Lys Gly Ala Val Asp
                85                  90                  95

Leu Ser His Phe Leu Lys Glu Lys Gly Gly Leu Glu Gly Leu Ile His
            100                 105                 110

Ser Gln Lys Arg Gln Asp Ile Leu Asp Leu Trp Val Tyr His Thr Gln
        115                 120                 125

Gly Tyr Phe Pro Asp Trp Gln Asn Tyr Thr Pro Gly Pro Gly Ile Arg
    130                 135                 140

Phe Pro Leu Thr Phe Gly Trp Cys Phe Lys Leu Val Pro Val Glu Pro
145                 150                 155                 160

Glu Lys Val Glu Glu Ala Asn Glu Gly Glu Asn Asn Cys Ala Ala His
                165                 170                 175

Pro Met Ser Gln His Gly Ile Glu Asp Pro Glu Lys Glu Val Leu Glu
            180                 185                 190

Trp Arg Phe Asp Ser Lys Leu Ala Phe His His Val Ala Arg Glu Leu
        195                 200                 205

His Pro Glu Tyr Tyr Lys Asp Cys Ser
    210                 215


<210> SEQ ID NO 15
<211> LENGTH: 720
<212> TYPE: DNA
<213> ORGANISM: Artificial Sequence
<220> FEATURE:
<223> OTHER INFORMATION: Codon optimized DNA encoding modified HIV-1nef
      fused to a leader sequence

<400> SEQUENCE: 15
```

-continued

```
catggatgca atgaagagag ggctctgctg tgtgctgctg ctgtgtggag cagtcttcgt     60

ttcgcccagc gagatctcct ccaagaggtc cgtgcccggc tggtccaccg tgagggagag    120

gatgaggagg gccgagcccg ccgccgacag ggtgaggagg accgagcccg ccgccgtggg    180

cgtgggcgcc gtgtccaggg acctggagaa gcacggcgcc atcacctcct ccaacaccgc    240

cgccaccaac gccgactgcg cctggctgga ggcccaggag gacgaggagg tgggcttccc    300

cgtgaggccc caggtgcccc tgaggcccat gacctacaag ggcgccgtgg acctgtccca    360

cttcctgaag gagaagggcg gcctggaggg cctgatccac tcccagaaga ggcaggacat    420

cctggacctg tgggtgtacc acacccaggg ctacttcccc gactggcaga actacacccc    480

cggccccggc atcaggttcc ccctgacctt cggctggtgc ttcaagctgg tgcccgtgga    540

gcccgagaag gtggaggagg ccaacgaggg cgagaacaac tgcgccgccc accccatgtc    600

ccagcacggc atcgaggacc ccgagaagga ggtgctggag tggaggttcg actccaagct    660

ggccttccac cacgtggcca gggagctgca ccccgagtac tacaaggact gctaaagccc    720
```

```
<210> SEQ ID NO 16
<211> LENGTH: 237
<212> TYPE: PRT
<213> ORGANISM: Artificial Sequence
<220> FEATURE:
<223> OTHER INFORMATION: Codon optimized modified HIV-1 nef fused to a
      leader sequence

<400> SEQUENCE: 16

Met Asp Ala Met Lys Arg Gly Leu Cys Cys Val Leu Leu Leu Cys Gly
 1               5                  10                  15

Ala Val Phe Val Ser Pro Ser Glu Ile Ser Ser Lys Arg Ser Val Pro
            20                  25                  30

Gly Trp Ser Thr Val Arg Glu Arg Met Arg Arg Ala Glu Pro Ala Ala
        35                  40                  45

Asp Arg Val Arg Arg Thr Glu Pro Ala Ala Val Gly Val Gly Ala Val
    50                  55                  60

Ser Arg Asp Leu Glu Lys His Gly Ala Ile Thr Ser Ser Asn Thr Ala
65                  70                  75                  80

Ala Thr Asn Ala Asp Cys Ala Trp Leu Glu Ala Gln Glu Asp Glu Glu
                85                  90                  95

Val Gly Phe Pro Val Arg Pro Gln Val Pro Leu Arg Pro Met Thr Tyr
            100                 105                 110

Lys Gly Ala Val Asp Leu Ser His Phe Leu Lys Glu Lys Gly Gly Leu
        115                 120                 125

Glu Gly Leu Ile His Ser Gln Lys Arg Gln Asp Ile Leu Asp Leu Trp
    130                 135                 140

Val Tyr His Thr Gln Gly Tyr Phe Pro Asp Trp Gln Asn Tyr Thr Pro
145                 150                 155                 160

Gly Pro Gly Ile Arg Phe Pro Leu Thr Phe Gly Trp Cys Phe Lys Leu
                165                 170                 175

Val Pro Val Glu Pro Glu Lys Val Glu Glu Ala Asn Glu Gly Glu Asn
            180                 185                 190

Asn Cys Ala Ala His Pro Met Ser Gln His Gly Ile Glu Asp Pro Glu
        195                 200                 205

Lys Glu Val Leu Glu Trp Arg Phe Asp Ser Lys Leu Ala Phe His His
    210                 215                 220

Val Ala Arg Glu Leu His Pro Glu Tyr Tyr Lys Asp Cys
225                 230                 235
```

-continued

<210> SEQ ID NO 17
<211> LENGTH: 27
<212> TYPE: PRT
<213> ORGANISM: Artificial Sequence
<220> FEATURE:
<223> OTHER INFORMATION: Amino acid sequence of human tPA leader

<400> SEQUENCE: 17

Met Asp Ala Met Lys Arg Gly Leu Cys Cys Val Leu Leu Leu Cys Gly
1 5 10 15

Ala Val Phe Val Ser Pro Ser Glu Ile Ser Ser
20 25

<210> SEQ ID NO 18
<211> LENGTH: 49
<212> TYPE: DNA
<213> ORGANISM: Artificial Sequence
<220> FEATURE:
<223> OTHER INFORMATION: Short synthetic polyA signal (SPA)

<400> SEQUENCE: 18
aataaaagat ctttattttc attagatctg tgtgttggtt ttttgtgtg 49

<210> SEQ ID NO 19
<211> LENGTH: 651
<212> TYPE: DNA
<213> ORGANISM: Human Immunodeficiency Virus

<400> SEQUENCE: 19
atgggtggca agtggtcaaa acgtagtgtg cctggatggt ctactgtaag ggaaagaatg 60
agacgagctg agccagcagc agatagggtg agacgaactg agccagcagc agtaggggtg 120
ggagcagtat ctcgagacct ggaaaaacat ggagcaatca caagtagcaa tacagcagct 180
accaatgctg attgtgcctg gctagaagca caagaggatg aggaagtggg ttttccagtc 240
agacctcagg tacctttaag accaatgact tacaagggag ctgtagatct tagccacttt 300
ttaaaagaaa aggggggact ggaagggcta attcactcac agaaaagaca agatatcctt 360
gatctgtggg tctaccacac acaaggctac ttccctgatt ggcagaacta cacaccaggg 420
ccaggaatca gatttccatt gacctttgga tggtgcttca agctagtacc agttgagcca 480
gaaaaggtag aagaggccaa tgaaggagag aacaactgct tgttacaccc tatgagccag 540
catgggatag aggacccgga gaaggaagtg ttagagtgga ggtttgacag caagctagca 600
tttcatcacg tggcccgaga gctgcatccg gagtactaca aggactgctg a 651

<210> SEQ ID NO 20
<211> LENGTH: 35
<212> TYPE: DNA
<213> ORGANISM: Artificial Sequence
<220> FEATURE:
<223> OTHER INFORMATION: PCR primer

<400> SEQUENCE: 20
ataagaatgc ggccgccata tactgagtca ttagg 35

<210> SEQ ID NO 21
<211> LENGTH: 31
<212> TYPE: DNA
<213> ORGANISM: Artificial Sequence
<220> FEATURE:
<223> OTHER INFORMATION: PCR primer -continued

<400> SEQUENCE: 21
aaggaagatc taccgacgct ggtcgcgcct c 31

<210> SEQ ID NO 22
<211> LENGTH: 34
<212> TYPE: DNA
<213> ORGANISM: Artificial Sequence
<220> FEATURE:
<223> OTHER INFORMATION: PCR primer

<400> SEQUENCE: 22
ataagaatgg cgcgccatat actgagtcat tagg 34

<210> SEQ ID NO 23
<211> LENGTH: 31
<212> TYPE: DNA
<213> ORGANISM: Artificial Sequence
<220> FEATURE:
<223> OTHER INFORMATION: PCR primer

<400> SEQUENCE: 23
aaggaagatc taccgacgct ggtcgcgcct c 31

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24
attggatcca tggatgcaat gaagagaggg 30

<210> SEQ ID NO 25
<211> LENGTH: 37474
<212> TYPE: DNA
<213> ORGANISM: Artificial Sequence
<220> FEATURE:
<223> OTHER INFORMATION: DNA encoding pMRKAd5 HIV-1 gag, coding

<400> SEQUENCE: 25
ttcttaatta acatcatcaa taatatacct tattttggat tgaagccaat atgataatga 60
gggggtggag tttgtgacgt ggcgcggggc gtgggaacgg ggcgggtgac gtagtagtgt 120
ggcggaagtg tgatgttgca agtgtggcgg aacacatgta agcgacggat gtggcaaaag 180
tgacgttttt ggtgtgcgcc ggtgtacaca ggaagtgaca attttcgcgc ggttttaggc 240
ggatgttgta gtaaatttgg gcgtaaccga gtaagatttg gccattttcg cgggaaaact 300
gaataagagg aagtgaaatc tgaataattt tgtgttactc atagcgcgta atatttgtct 360
agggccgcgg ggactttgac cgtttacgtg gagactcgcc caggtgtttt tctcaggtgt 420
tttccgcgtt ccgggtcaaa gttggcgttt tattattata ggcggccgcg atccattgca 480
tacgttgtat ccatatcata atatgtacat ttatattggc tcatgtccaa cattaccgcc 540
atgttgacat tgattattga ctagttatta atagtaatca attacggggt cattagttca 600
tagcccatat atggagttcc gcgttacata acttacggta aatggcccgc ctggctgacc 660
gcccaacgac ccccgcccat tgacgtcaat aatgacgtat gttcccatag taacgccaat 720
agggactttc cattgacgtc aatgggtgga gtatttacgg taaactgccc acttggcagt 780
acatcaagtg tatcatatgc caagtacgcc ccctattgac gtcaatgacg gtaaatggcc 840
cgcctggcat tatgcccagt acatgacctt atgggacttt cctacttggc agtacatcta 900

-continued

```
cgtattagtc atcgctatta ccatggtgat gcggttttgg cagtacatca atgggcgtgg    960
atagcggttt gactcacggg gatttccaag tctccacccc attgacgtca atgggagttt   1020
gttttggcac caaaatcaac gggactttcc aaaatgtcgt aacaactccg ccccattgac   1080
gcaaatgggc ggtaggcgtg tacggtggga ggtctatata agcagagctc gtttagtgaa   1140
ccgtcagatc gcctggagac gccatccacg ctgttttgac ctccatagaa gacaccggga   1200
ccgatccagc ctccgcggcc gggaacggtg cattggaacg cggattcccc gtgccaagag   1260
tgagatctac catgggtgct agggcttctg tgctgtctgg tggtgagctg gacaagtggg   1320
agaagatcag gctgaggcct ggtggcaaga agaagtacaa gctaaagcac attgtgtggg   1380
cctccaggga gctggagagg tttgctgtga accctggcct gctggagacc tctgaggggt   1440
gcaggcagat cctgggccag ctccagccct ccctgcaaac aggctctgag gagctgaggt   1500
ccctgtacaa cacagtggct accctgtact gtgtgcacca gaagattgat gtgaaggaca   1560
ccaaggaggc cctggagaag attgaggagg agcagaacaa gtccaagaag aaggcccagc   1620
aggctgctgc tggcacaggc aactccagcc aggtgtccca gaactacccc attgtgcaga   1680
acctccaggg ccagatggtg caccaggcca tctccccccg gaccctgaat gcctgggtga   1740
aggtggtgga ggagaaggcc ttctcccctg aggtgatccc catgttctct gccctgtctg   1800
agggtgccac cccccaggac ctgaacacca tgctgaacac agtgggggc catcaggctg   1860
ccatgcagat gctgaaggag accatcaatg aggaggctgc tgagtgggac aggctgcatc   1920
ctgtgcacgc tggccccatt gcccccggcc agatgaggga gcccaggggc tctgacattg   1980
ctggcaccac ctccaccctc caggagcaga ttggctggat gaccaacaac ccccccatcc   2040
ctgtggggga aatctacaag aggtggatca tcctgggcct gaacaagatt gtgaggatgt   2100
actcccccac ctccatcctg gacatcaggc agggccccaa ggagcccttc agggactatg   2160
tggacaggtt ctacaagacc ctgagggctg agcaggcctc ccaggaggtg aagaactgga   2220
tgacagagac cctgctggtg cagaatgcca accctgactg caagaccatc ctgaaggccc   2280
tgggccctgc tgccaccctg gaggagatga tgacagcctg ccaggggggtg gggggccctg   2340
gtcacaaggc cagggtgctg gctgaggcca tgtcccaggt gaccaactcc gccaccatca   2400
tgatgcagag gggcaacttc aggaaccaga ggaagacagt gaagtgcttc aactgtggca   2460
aggtgggcca cattgccaag aactgtaggg cccccaggaa gaagggctgc tggaagtgtg   2520
gcaaggaggg ccaccagatg aaggactgca atgagaggca ggccaacttc ctgggcaaaa   2580
tctggccctc ccacaagggc aggcctggca acttcctcca gtccaggcct gagcccacag   2640
cccctcccga ggagtccttc aggtttgggg aggagaagac cacccccagc cagaagcagg   2700
agcccattga caaggagctg taccccctgg cctccctgag gtccctgttt ggcaacgacc   2760
cctcctccca gtaaaataaa gcccgggcag atctgctgtg ccttctagtt gccagccatc   2820
tgttgtttgc ccctcccccg tgccttcctt gaccctggaa ggtgccactc ccactgtcct   2880
ttcctaataa aatgaggaaa ttgcatcgca ttgtctgagt aggtgtcatt ctattctggg   2940
gggtggggtg gggcaggaca gcaaggggga ggattgggaa gacaatagca ggcatgctgg   3000
ggatgcggtg ggctctatgg ccgatcggcg cgccgtactg aaatgtgtgg gcgtggctta   3060
agggtgggaa agaatatata aggtgggggt cttatgtagt tttgtatctg ttttgcagca   3120
gccgccgccg ccatgagcac caactcgttt gatggaagca ttgtgagctc atatttgaca   3180
acgcgcatgc ccccatgggc cggggtgcgt cagaatgtga tgggctccag cattgatggt   3240
```

-continued

```
cgccccgtcc tgcccgcaaa ctctactacc ttgacctacg agaccgtgtc tggaacgccg   3300
ttggagactg cagcctccgc cgccgcttca gccgctgcag ccaccgcccg cgggattgtg   3360
actgactttg ctttcctgag cccgcttgca aacagtgcag cttcccgttc atccgcccgc   3420
gatgacaagt tgacggctct tttggcacaa ttggattctt tgacccggga acttaatgtc   3480
gtttctcagc agctgttgga tctgcgccag caggtttctg ccctgaaggc ttcctcccct   3540
cccaatgcgg tttaaaacat aaataaaaaa ccagactctg tttggatttg gatcaagcaa   3600
gtgtcttgct gtctttattt aggggttttg cgcgcgcggt aggcccggga ccagcggtct   3660
cggtcgttga gggtcctgtg tatttttttcc aggacgtggt aaaggtgact ctggatgttc   3720
agatacatgg gcataagccc gtctctgggg tggaggtagc accactgcag agcttcatgc   3780
tgcggggtgg tgttgtagat gatccagtcg tagcaggagc gctgggcgtg gtgcctaaaa   3840
atgtctttca gtagcaagct gattgccagg ggcaggccct tggtgtaagt gtttacaaag   3900
cggttaagct gggatgggtg catacgtggg gatatgagat gcatcttgga ctgtattttt   3960
aggttggcta tgttcccagc catatccctc cggggattca tgttgtgcag aaccaccagc   4020
acagtgtatc cggtgcactt gggaaatttg tcatgtagct tagaaggaaa tgcgtggaag   4080
aacttggaga cgcccttgtg acctccaaga ttttccatgc attcgtccat aatgatggca   4140
atgggcccac gggcggcggc ctgggcgaag atatttctgg gatcactaac gtcatagttg   4200
tgttccagga tgagatcgtc ataggccatt tttacaaagc gcgggcggag ggtgccagac   4260
tgcggtataa tggttccatc cggcccaggg gcgtagttac cctcacagat ttgcatttcc   4320
cacgctttga gttcagatgg ggggatcatg tctacctgcg gggcgatgaa gaaaacggtt   4380
tccggggtag gggagatcag ctgggaagaa agcaggttcc tgagcagctg cgacttaccg   4440
cagccggtgg gcccgtaaat cacacctatt accggctgca actggtagtt aagagagctg   4500
cagctgccgt catccctgag caggggggcc acttcgttaa gcatgtccct gactcgcatg   4560
ttttccctga ccaaatccgc cagaaggcgc tcgccgccca gcgatagcag ttcttgcaag   4620
gaagcaaagt ttttcaacgg tttgagaccg tccgccgtag gcatgctttt gagcgtttga   4680
ccaagcagtt ccaggcggtc ccacagctcg gtcacctgct ctacggcatc tcgatccagc   4740
atatctcctc gtttcgcggg ttggggcggc tttcgctgta cggcagtagt cggtgctcgt   4800
ccagacgggc cagggtcatg tctttccacg ggcgcagggt cctcgtcagc gtagtctggg   4860
tcacggtgaa ggggtgcgct ccgggctgcg cgctggccag ggtgcgcttg aggctggtcc   4920
tgctggtgct gaagcgctgc cggtcttcgc cctgcgcgtc ggccaggtag catttgacca   4980
tggtgtcata gtccagcccc tccgcggcgt ggcccttggc gcgcagcttg cccttggagg   5040
aggcgccgca cgaggggcag tgcagacttt tgagggcgta gagcttgggc gcgagaaata   5100
ccgattccgg ggagtaggca tccgcgccgc aggccccgca gacggtctcg cattccacga   5160
gccaggtgag ctctggccgt tcggggtcaa aaaccaggtt tcccccatgc tttttgatgc   5220
gtttcttacc tctggtttcc atgagccggt gtccacgctc ggtgacgaaa aggctgtccg   5280
tgtccccgta tacagacttg agaggcctgt cctcgagcgg tgttccgcgg tcctcctcgt   5340
atagaaactc ggaccactct gagacaaagg ctcgcgtcca ggccagcacg aaggaggcta   5400
agtgggaggg gtagcggtcg ttgtccacta gggggtccac tcgctccagg gtgtgaagac   5460
acatgtcgcc ctcttcggca tcaaggaagg tgattggttt gtaggtgtag gccacgtgac   5520
cgggtgttcc tgaagggggg ctataaaagg gggtgggggc gcgttcgtcc tcactctctt   5580
ccgcatcgct gtctgcgagg gccagctgtt ggggtgagta ctccctctga aaagcgggca   5640
```

-continued

```
tgacttctgc gctaagattg tcagtttcca aaaacgagga ggatttgata ttcacctggc   5700
ccgcggtgat gcctttgagg gtggccgcat ccatctggtc agaaaagaca atctttttgt   5760
tgtcaagctt ggtggcaaac gacccgtaga gggcgttgga cagcaacttg gcgatggagc   5820
gcagggtttg gtttttgtcg cgatcggcgc gctccttggc cgcgatgttt agctgcacgt   5880
attcgcgcgc aacgcaccgc cattcgggaa agacggtggt gcgctcgtcg ggcaccaggt   5940
gcacgcgcca accgcggttg tgcagggtga caaggtcaac gctggtggct acctctccgc   6000
gtaggcgctc gttggtccag cagaggcggc cgcccttgcg cgagcagaat ggcggtaggg   6060
ggtctagctg cgtctcgtcc ggggggtctg cgtccacggt aaagaccccg ggcagcaggc   6120
gcgcgtcgaa gtagtctatc ttgcatcctt gcaagtctag cgcctgctgc catgcgcggg   6180
cggcaagcgc gcgctcgtat gggttgagtg ggggacccca tggcatgggg tgggtgagcg   6240
cggaggcgta catgccgcaa atgtcgtaaa cgtagagggg ctctctgagt attccaagat   6300
atgtagggta gcatcttcca ccgcggatgc tggcgcgcac gtaatcgtat agttcgtgcg   6360
agggagcgag gaggtcggga ccgaggttgc tacgggcggg ctgctctgct cggaagacta   6420
tctgcctgaa gatggcatgt gagttggatg atatggttgg acgctggaag acgttgaagc   6480
tggcgtctgt gagacctacc gcgtcacgca cgaaggaggc gtaggagtcg cgcagcttgt   6540
tgaccagctc ggcggtgacc tgcacgtcta gggcgcagta gtccagggtt tccttgatga   6600
tgtcatactt atcctgtccc ttttttttcc acagctcgcg gttgaggaca aactcttcgc   6660
ggtctttcca gtactcttgg atcggaaacc cgtcggcctc cgaacggtaa gagcctagca   6720
tgtagaactg gttgacggcc tggtaggcgc agcatccctt ttctacgggt agcgcgtatg   6780
cctgcgcggc cttccggagc gaggtgtggg tgagcgcaaa ggtgtccctg accatgactt   6840
tgaggtactg gtatttgaag tcagtgtcgt cgcatccgcc ctgctcccag agcaaaaagt   6900
ccgtgcgctt tttggaacgc ggatttggca gggcgaaggt gacatcgttg aagagtatct   6960
ttcccgcgcg aggcataaag ttgcgtgtga tgcggaaggg tcccggcacc tcggaacggt   7020
tgttaattac ctgggcggcg agcacgatct cgtcaaagcc gttgatgttg tggcccacaa   7080
tgtaaagttc caagaagcgc gggatgccct tgatggaagg caattttta agttcctcgt   7140
aggtgagctc ttcaggggag ctgagcccgt gctctgaaag ggcccagtct gcaagatgag   7200
ggttggaagc gacgaatgag ctccacaggt cacgggccat tagcatttgc aggtggtcgc   7260
gaaaggtcct aaactggcga cctatggcca tttttctgg ggtgatgcag tagaaggtaa   7320
gcgggtcttg ttcccagcgg tcccatccaa ggttcgcggc taggtctcgc gcggcagtca   7380
ctagaggctc atctccgccg aacttcatga ccagcatgaa gggcacgagc tgcttcccaa   7440
aggcccccat ccaagtatag gtctctacat cgtaggtgac aaagagacgc tcggtgcgag   7500
gatgcgagcc gatcgggaag aactggatct cccgccacca attggaggag tggctattga   7560
tgtggtgaaa gtagaagtcc ctgcgacggg ccgaacactc gtgctggctt ttgtaaaaac   7620
gtgcgcagta ctggcagcgg tgcacgggct gtacatcctg cacgaggttg acctgacgac   7680
cgcgcacaag gaagcagagt gggaatttga gcccctcgcc tggcgggttt ggctggtggt   7740
cttctacttc ggctgcttgt ccttgaccgt ctggctgctc gaggggagtt acggtggatc   7800
ggaccaccac gccgcgcgag cccaaagtcc agatgtccgc gcgcggcggt cggagcttga   7860
tgacaacatc gcgcagatgg gagctgtcca tggtctggag ctcccgcggc gtcaggtcag   7920
gcgggagctc ctgcaggttt acctcgcata gacgggtcag ggcgcgggct agatccaggt   7980
```

-continued gatacctaat ttccaggggc tggttggtgg cggcgtcgat ggcttgcaag aggccgcatc 8040
cccgcggcgc gactacggta ccgcgcggcg ggcggtgggc cgcgggggtg tccttggatg 8100
atgcatctaa aagcggtgac gcgggcgagc ccccggaggt aggggggggct ccggacccgc 8160
cgggagaggg ggcaggggca cgtcggcgcc gcgcgcgggc aggagctggt gctgcgcgcg 8220
taggttgctg gcgaacgcga cgacgcggcg gttgatctcc tgaatctggc gcctctgcgt 8280
gaagacgacg ggcccggtga gcttgaacct gaaagagagt tcgacagaat caatttcggt 8340
gtcgttgacg gcggcctggc gcaaaatctc ctgcacgtct cctgagttgt cttgataggc 8400
gatctcggcc atgaactgct cgatctcttc ctcctggaga tctccgcgtc cggctcgctc 8460
cacggtggcg gcgaggtcgt tggaaatgcg ggccatgagc tgcgagaagg cgttgaggcc 8520
tccctcgttc cagacgcggc tgtagaccac gccccccttcg gcatcgcggg cgcgcatgac 8580
cacctgcgcg agattgagct ccacgtgccg ggcgaagacg gcgtagtttc gcaggcgctg 8640
aaagaggtag ttgagggtgg tggcggtgtg ttctgccacg aagaagtaca taacccagcg 8700
tcgcaacgtg gattcgttga tatcccccaa ggcctcaagg cgctccatgg cctcgtagaa 8760
gtccacggcg aagttgaaaa actgggagtt gcgcgccgac acggttaact cctcctccag 8820
aagacggatg agctcggcga cagtgtcgcg cacctcgcgc tcaaaggcta caggggcctc 8880
ttcttcttct tcaatctcct cttccataag ggcctcccct tcttcttctt ctggcggcgg 8940
tgggggaggg gggacacggc ggcgacgacg gcgcaccggg aggcggtcga caaagcgctc 9000
gatcatctcc ccgcggcgac ggcgcatggt ctcggtgacg gcgcggccgt tctcgcgggg 9060
gcgcagttgg aagacgccgc ccgtcatgtc ccggttatgg gttggcgggg ggctgccatg 9120
cggcagggat acggcgctaa cgatgcatct caacaattgt tgtgtaggta ctccgccgcc 9180
gagggacctg agcgagtccg catcgaccgg atcggaaaac ctctcgagaa aggcgtctaa 9240
ccagtcacag tcgcaaggta ggctgagcac cgtggcgggc ggcagcgggc ggcggtcggg 9300
gttgtttctg gcggaggtgc tgctgatgat gtaattaaag taggcggtct tgagacggcg 9360
gatggtcgac agaagcacca tgtccttggg tccggcctgc tgaatgcgca ggcggtcggc 9420
catgccccag gcttcgtttt gacatcggcg caggtctttg tagtagtctt gcatgagcct 9480
ttctaccggc acttcttctt ctccttcctc ttgtcctgca tctcttgcat ctatcgctgc 9540
ggcggcggcg gagtttggcc gtaggtggcg ccctcttcct cccatgcgtg tgaccccgaa 9600
gcccctcatc ggctgaagca gggctaggtc ggcgacaacg cgctcggcta atatggcctg 9660
ctgcacctgc gtgagggtag actggaagtc atccatgtcc acaaagcggt ggtatgcgcc 9720
cgtgttgatg gtgtaagtgc agttggccat aacggaccag ttaacggtct ggtgacccgg 9780
ctgcgagagc tcggtgtacc tgagacgcga gtaagccctc gagtcaaata cgtagtcgtt 9840
gcaagtccgc accaggtact ggtatcccac caaaaagtgc ggcggcggct ggcggtagag 9900
gggccagcgt agggtggccg gggctccggg ggcgagatct tccaacataa ggcgatgata 9960
tccgtagatg tacctggaca tccaggtgat gccggcggcg gtggtggagg cgcgcggaaa 10020
gtcgcggacg cggttccaga tgttgcgcag cggcaaaaag tgctccatgg tcgggacgct 10080
ctggccggtc aggcgcgcgc aatcgttgac gctctagacc gtgcaaaagg agagcctgta 10140
agcgggcact cttccgtggt ctggtggata aattcgcaag ggtatcatgg cggacgaccg 10200
gggttcgagc cccgtatccg gccgtccgcc gtgatccatg cggttaccgc ccgcgtgtcg 10260
aacccaggtg tgcgacgtca gacaacgggg gagtgctcct tttggcttcc ttccaggcgc 10320
ggcggctgct gcgctagctt ttttggccac tggccgcgcg cagcgtaagc ggttaggctg 10380

-continued gaaagcgaaa gcattaagtg gctcgctccc tgtagccgga gggttatttt ccaagggttg 10440
agtcgcggga cccccggttc gagtctcgga ccggccggac tgcggcgaac gggggtttgc 10500
ctccccgtca tgcaagaccc cgcttgcaaa ttcctccgga aacagggacg agcccctttt 10560
ttgcttttcc cagatgcatc cggtgctgcg gcagatgcgc ccccctcctc agcagcggca 10620
agagcaagag cagcggcaga catgcagggc accctcccct cctcctaccg cgtcaggagg 10680
ggcgacatcc gcggttgacg cggcagcaga tggtgattac gaacccccgc ggcgccgggc 10740
ccggcactac ctggacttgg aggagggcga gggcctggcg cggctaggag cgccctctcc 10800
tgagcggcac ccaagggtgc agctgaagcg tgatacgcgt gaggcgtacg tgccgcggca 10860
gaacctgttt cgcgaccgcg agggagagga gcccgaggag atgcgggatc gaaagttcca 10920
cgcagggcgc gagctgcggc atggcctgaa tcgcgagcgg ttgctgcgcg aggaggactt 10980
tgagcccgac gcgcgaaccg ggattagtcc cgcgcgcgca cacgtggcgg ccgccgacct 11040
ggtaaccgca tacgagcaga cggtgaacca ggagattaac tttcaaaaaa gctttaacaa 11100
ccacgtgcgt acgcttgtgg cgcgcgagga ggtggctata ggactgatgc atctgtggga 11160
ctttgtaagc gcgctggagc aaaacccaaa tagcaagccg ctcatggcgc agctgttcct 11220
tatagtgcag cacagcaggg acaacgaggc attcagggat gcgctgctaa acatagtaga 11280
gcccgagggc cgctggctgc tcgatttgat aaacatcctg cagagcatag tggtgcagga 11340
gcgcagcttg agcctggctg acaaggtggc cgccatcaac tattccatgc ttagcctggg 11400
caagttttac gcccgcaaga tataccatac cccttacgtt cccatagaca aggaggtaaa 11460
gatcgagggg ttctacatgc gcatggcgct gaaggtgctt accttgagcg acgacctggg 11520
cgtttatcgc aacgagcgca tccacaaggc cgtgagcgtg agccggcggc gcgagctcag 11580
cgaccgcgag ctgatgcaca gcctgcaaag ggccctggct ggcacgggca gcggcgatag 11640
agaggccgag tcctactttg acgcgggcgc tgacctgcgc tgggccccaa gccgacgcgc 11700
cctggaggca gctggggccg gacctgggct ggcggtggca cccgcgcgcg ctggcaacgt 11760
cggcggcgtg gaggaatatg acgaggacga tgagtacgag ccagaggacg gcgagtacta 11820
agcggtgatg tttctgatca gatgatgcaa gacgcaacgg acccggcggt gcgggcggcg 11880
ctgcagagcc agccgtccgg ccttaactcc acggacgact ggcgccaggt catggaccgc 11940
atcatgtcgc tgactgcgcg caatcctgac gcgttccggc agcagccgca ggccaaccgg 12000
ctctccgcaa ttctggaagc ggtggtcccg gcgcgcgcaa accccacgca cgagaaggtg 12060
ctggcgatcg taaacgcgct ggccgaaaac agggccatcc ggcccgacga ggccggcctg 12120
gtctacgacg cgctgcttca gcgcgtggct cgttacaaca gcggcaacgt gcagaccaac 12180
ctggaccggc tggtgggga tgtgcgcgag gccgtggcgc agcgtgagcg cgcgcagcag 12240
cagggcaacc tgggctccat ggttgcacta aacgccttcc tgagtacaca gcccgccaac 12300
gtgccgcggg gacaggagga ctacaccaac tttgtgagcg cactgcggct aatggtgact 12360
gagacaccgc aaagtgaggt gtaccagtct gggccagact attttttcca gaccagtaga 12420
caaggcctgc agaccgtaaa cctgagccag gctttcaaaa acttgcaggg gctgtggggg 12480
gtgcgggctc ccacaggcga ccgcgcgacc gtgtctagct tgctgacgcc caactcgcgc 12540
ctgttgctgc tgctaatagc gcccttcacg gacagtggca gcgtgtcccg ggacacatac 12600
ctaggtcact tgctgacact gtaccgcgag gccataggtc aggcgcatgt ggacgagcat 12660
actttccagg agattacaag tgtcagccgc gcgctggggc aggaggacac gggcagcctg 12720

-continued

```
gaggcaaccc taaactacct gctgaccaac cggcggcaga agatcccctc gttgcacagt  12780
ttaaacagcg aggaggagcg cattttgcgc tacgtgcagc agagcgtgag ccttaacctg  12840
atgcgcgacg gggtaacgcc cagcgtggcg ctggacatga ccgcgcgcaa catggaaccg  12900
ggcatgtatg cctcaaaccg gccgtttatc aaccgcctaa tggactactt gcatcgcgcg  12960
gccgccgtga accccgagta tttcaccaat gccatcttga acccgcactg gctaccgccc  13020
cctggtttct acaccggggg attcgaggtg cccgagggta acgatggatt cctctgggac  13080
gacatagacg acagcgtgtt ttccccgcaa ccgcagaccc tgctagagtt gcaacagcgc  13140
gagcaggcag aggcggcgct gcgaaaggaa agcttccgca ggccaagcag cttgtccgat  13200
ctaggcgctg cggccccgcg gtcagatgct agtagcccat ttccaagctt gatagggtct  13260
cttaccagca ctcgcaccac ccgcccgcgc ctgctgggcg aggaggagta cctaaacaac  13320
tcgctgctgc agccgcagcg cgaaaaaaac ctgcctccgg catttcccaa caacgggata  13380
gagagcctag tggacaagat gagtagatgg aagacgtacg cgcaggagca cagggacgtg  13440
ccaggcccgc gcccgcccac ccgtcgtcaa aggcacgacc gtcagcgggg tctggtgtgg  13500
gaggacgatg actcggcaga cgacagcagc gtcctggatt tgggagggag tggcaacccg  13560
tttgcgcacc ttcgccccag gctggggaga atgttttaaa aaaaaaaaaa gcatgatgca  13620
aaataaaaaa ctcaccaagg ccatggcacc gagcgttggt tttcttgtat tccccttagt  13680
atgcggcgcg cggcgatgta tgaggaaggt cctcctccct cctacgagag tgtggtgagc  13740
gcggcgccag tggcggcggc gctgggttct cccttcgatg ctcccctgga cccgccgttt  13800
gtgcctccgc ggtacctgcg gcctaccggg gggagaaaca gcatccgtta ctctgagttg  13860
gcacccctat tcgacaccac ccgtgtgtac ctggtggaca acaagtcaac ggatgtggca  13920
tccctgaact accagaacga ccacagcaac tttctgacca cggtcattca aaacaatgac  13980
tacagcccgg gggaggcaag cacacagacc atcaatcttg acgaccggtc gcactggggc  14040
ggcgacctga aaaccatcct gcataccaac atgccaaatg tgaacgagtt catgtttacc  14100
aataagttta aggcgcgggt gatggtgtcg cgcttgccta ctaaggacaa tcaggtggag  14160
ctgaaatacg agtgggtgga gttcacgctg cccgagggca actactccga gaccatgacc  14220
atagacctta tgaacaacgc gatcgtggag cactacttga aagtgggcag acagaacggg  14280
gttctggaaa gcgacatcgg ggtaaagttt gacacccgca acttcagact ggggtttgac  14340
cccgtcactg gtcttgtcat gcctggggta tatacaaacg aagccttcca tccagacatc  14400
attttgctgc caggatgcgg ggtggacttc acccacagcc gcctgagcaa cttgttgggc  14460
atccgcaagc ggcaaccctt ccaggagggc tttaggatca cctacgatga tctggagggt  14520
ggtaacattc ccgcactgtt ggatgtggac gcctaccagg cgagcttgaa agatgacacc  14580
gaacagggcg ggggtggcgc aggcggcagc aacagcagtg gcagcggcgc ggaagagaac  14640
tccaacgcgg cagccgcggc aatgcagccg gtggaggaca tgaacgatca tgccattcgc  14700
ggcgacacct ttgccacacg ggctgaggag aagcgcgctg aggccgaagc agcggccgaa  14760
gctgccgccc ccgctgcgca acccgaggtc gagaagcctc agaagaaacc ggtgatcaaa  14820
cccctgacag aggacagcaa gaaacgcagt tacaacctaa taagcaatga cagcaccttc  14880
acccagtacc gcagctggta ccttgcatac aactacggcg accctcagac cggaatccgc  14940
tcatggaccc tgctttgcac tcctgacgta acctgcggct cggagcaggt ctactggtcg  15000
ttgccagaca tgatgcaaga ccccgtgacc ttccgctcca cgcgccagat cagcaacttt  15060
ccggtggtgg gcgccgagct gttgcccgtg cactccaaga gcttctacaa cgaccaggcc  15120
```

-continued

```
gtctactccc aactcatccg ccagtttacc tctctgaccc acgtgttcaa tcgctttccc  15180
gagaaccaga ttttggcgcg cccgccagcc cccaccatca ccaccgtcag tgaaaacgtt  15240
cctgctctca cagatcacgg gacgctaccg ctgcgcaaca gcatcggagg agtccagcga  15300
gtgaccatta ctgacgccag acgccgcacc tgcccctacg tttacaaggc cctgggcata  15360
gtctcgccgc gcgtcctatc gagccgcact ttttgagcaa gcatgtccat ccttatatcg  15420
cccagcaata acacaggctg ggcctgcgc ttcccaagca agatgtttgg cggggccaag  15480
aagcgctccg accaacaccc agtgcgcgtg cgcgggcact accgcgcgcc ctggggcgcg  15540
cacaaacgcg gccgcactgg gcgcaccacc gtcgatgacg ccatcgacgc ggtggtggag  15600
gaggcgcgca actacacgcc cacgccgcca ccagtgtcca cagtggacgc ggccattcag  15660
accgtggtgc gcggagcccg gcgctatgct aaaatgaaga gacggcggag gcgcgtagca  15720
cgtcgccacc gccgccgacc cggcactgcc gcccaacgcg cggcggcggc cctgcttaac  15780
cgcgcacgtc gcaccggccg acgggcggcc atgcgggccg ctcgaaggct ggccgcgggt  15840
attgtcactg tgccccccag gtccaggcga cgagcggccg ccgcagcagc cgcggccatt  15900
agtgctatga ctcagggtcg caggggcaac gtgtattggg tgcgcgactc ggttagcggc  15960
ctgcgcgtgc ccgtgcgcac ccgccccccg cgcaactaga ttgcaagaaa aaactactta  16020
gactcgtact gttgtatgta tccagcggcg gcggcgcgca acgaagctat gtccaagcgc  16080
aaaatcaaag aagagatgct ccaggtcatc gcgccggaga tctatggccc cccgaagaag  16140
gaagagcagg attacaagcc ccgaaagcta aagcgggtca aaaagaaaaa gaaagatgat  16200
gatgatgaac ttgacgacga ggtggaactg ctgcacgcta ccgcgcccag gcgacgggta  16260
cagtggaaag gtcgacgcgt aaaacgtgtt ttgcgacccg gcaccaccgt agtctttacg  16320
cccggtgagc gctccacccg cacctacaag cgcgtgtatg atgaggtgta cggcgacgag  16380
gacctgcttg agcaggccaa cgagcgcctc ggggagtttg cctacggaaa gcggcataag  16440
gacatgctgg cgttgccgct ggacgagggc aacccaacac ctagcctaaa gcccgtaaca  16500
ctgcagcagg tgctgcccgc gcttgcaccg tccgaagaaa agcgcggcct aaagcgcgag  16560
tctggtgact tggcacccac cgtgcagctg atggtaccca agcgccagcg actggaagat  16620
gtcttggaaa aaatgaccgt ggaacctggg ctggagcccg aggtccgcgt gcggccaatc  16680
aagcaggtgg cgccgggact gggcgtgcag accgtggacg ttcagatacc cactaccagt  16740
agcaccagta ttgccaccgc cacagagggc atggagacac aaacgtcccc ggttgcctca  16800
gcggtggcgg atgccgcggt gcaggcggtc gctgcggccg cgtccaagac ctctacggag  16860
gtgcaaacgg acccgtggat gtttcgcgtt tcagcccccc ggcgcccgcg ccgttcgagg  16920
aagtacggcg ccgccagcgc gctactgccc gaatatgccc tacatccttc cattgcgcct  16980
acccccggct atcgtggcta cacctaccgc cccagaagac gagcaactac ccgacgccga  17040
accaccactg gaacccgccg ccgccgtcgc cgtcgccagc ccgtgctggc cccgatttcc  17100
gtgcgcaggg tggctcgcga aggaggcagg accctggtgc tgccaacagc gcgctaccac  17160
cccagcatcg tttaaaagcc ggtctttgtg gttcttgcag atatggccct cacctgccgc  17220
ctccgtttcc cggtgccggg attccgagga agaatgcacc gtaggagggg catggccggc  17280
cacggcctga cgggcggcat gcgtcgtgcg caccaccggc ggcggcgcgc gtcgcaccgt  17340
cgcatgcgcg gcggtatcct gcccctcctt attccactga tcgccgcggc gattggcgcc  17400
gtgcccggaa ttgcatccgt ggccttgcag gcgcagagac actgattaaa aacaagttgc  17460
```

-continued atgtggaaaa atcaaaataa aaagtctgga ctctcacgct cgcttggtcc tgtaactatt 17520
ttgtagaatg gaagacatca actttgcgtc tctggccccg cgacacggct cgcgcccgtt 17580
catgggaaac tggcaagata tcggcaccag caatatgagc ggtggcgcct tcagctgggg 17640
ctcgctgtgg agcggcatta aaaatttcgg ttccaccgtt aagaactatg gcagcaaggc 17700
ctggaacagc agcacaggcc agatgctgag ggataagttg aaagagcaaa atttccaaca 17760
aaaggtggta gatggcctgg cctctggcat tagcggggtg gtggacctgg ccaaccaggc 17820
agtgcaaaat aagattaaca gtaagcttga tccccgccct cccgtagagg agcctccacc 17880
ggccgtggag acagtgtctc cagaggggcg tggcgaaaag cgtccgcgcc ccgacaggga 17940
agaaactctg gtgacgcaaa tagacgagcc tccctcgtac gaggaggcac taaagcaagg 18000
cctgcccacc acccgtccca tcgcgcccat ggctaccgga gtgctgggcc agcacacacc 18060
cgtaacgctg gacctgcctc cccccgccga cacccagcag aaacctgtgc tgccaggccc 18120
gaccgccgtt gttgtaaccc gtcctagccg cgcgtccctg cgccgcgccg ccagcggtcc 18180
gcgatcgttg cggcccgtag ccagtggcaa ctggcaaagc acactgaaca gcatcgtggg 18240
tctgggggtg caatccctga agcgccgacg atgcttctga tagctaacgt gtcgtatgtg 18300
tgtcatgtat gcgtccatgt cgccgccaga ggagctgctg agccgccgcg cgcccgcttt 18360
ccaagatggc taccccttcg atgatgccgc agtggtctta catgcacatc tcgggccagg 18420
acgcctcgga gtacctgagc cccgggctgg tgcagtttgc ccgcgccacc gagacgtact 18480
tcagcctgaa taacaagttt agaaacccca cggtggcgcc tacgcacgac gtgaccacag 18540
accggtccca gcgtttgacg ctgcggttca tccctgtgga ccgtgaggat actgcgtact 18600
cgtacaaggc gcggttcacc ctagctgtgg gtgataaccg tgtgctggac atggcttcca 18660
cgtactttga catccgcggc gtgctggaca ggggccctac ttttaagccc tactctggca 18720
ctgcctacaa cgccctggct cccaagggtg ccccaaatcc ttgcgaatgg gatgaagctg 18780
ctactgctct tgaaataaac ctagaagaag aggacgatga caacgaagac gaagtagacg 18840
agcaagctga gcagcaaaaa actcacgtat ttgggcaggc gccttattct ggtataaata 18900
ttacaaagga gggtattcaa ataggtgtcg aaggtcaaac acctaaatat gccgataaaa 18960
catttcaacc tgaacctcaa ataggagaat ctcagtggta cgaaacagaa attaatcatg 19020
cagctgggag agtcctaaaa aagactaccc caatgaaacc atgttacggt tcatatgcaa 19080
aacccacaaa tgaaaatgga gggcaaggca ttcttgtaaa gcaacaaaat ggaaagctag 19140
aaagtcaagt ggaaatgcaa tttttctcaa ctactgaggc agccgcaggc aatggtgata 19200
acttgactcc taaagtggta ttgtacagtg aagatgtaga tatagaaacc ccagacactc 19260
atatttctta catgcccact attaaggaag gtaactcacg agaactaatg ggccaacaat 19320
ctatgcccaa caggcctaat tacattgctt ttagggacaa ttttattggt ctaatgtatt 19380
acaacagcac gggtaatatg ggtgttctgg cgggccaagc atcgcagttg aatgctgttg 19440
tagatttgca agacagaaac acagagcttt cataccagct tttgcttgat tccattggtg 19500
atagaaccag gtacttttct atgtggaatc aggctgttga cagctatgat ccagatgtta 19560
gaattattga aaatcatgga actgaagatg aacttccaaa ttactgcttt ccactgggag 19620
gtgtgattaa tacagagact cttaccaagg taaaacctaa aacaggtcag gaaaatggat 19680
gggaaaaaga tgctacagaa ttttcagata aaaatgaaat aagagttgga aataattttg 19740
ccatggaaat caatctaaat gccaacctgt ggagaaattt cctgtactcc aacatagcgc 19800
tgtatttgcc cgacaagcta aagtacagtc cttccaacgt aaaaatttct gataacccaa 19860

-continued acacctacga ctacatgaac aagcgagtgg tggctcccgg gctagtggac tgctacatta 19920
accttggagc acgctggtcc cttgactata tggacaacgt caacccattt aaccaccacc 19980
gcaatgctgg cctgcgctac cgctcaatgt tgctgggcaa tggtcgctat gtgcccttcc 20040
acatccaggt gcctcagaag ttctttgcca ttaaaaacct ccttctcctg ccgggctcat 20100
acacctacga gtggaacttc aggaaggatg ttaacatggt tctgcagagc tccctaggaa 20160
atgacctaag ggttgacgga gccagcatta agtttgatag catttgcctt tacgccacct 20220
tcttccccat ggcccacaac accgcctcca cgcttgaggc catgcttaga aacgacacca 20280
acgaccagtc ctttaacgac tatctctccg ccgccaacat gctctaccct atacccgcca 20340
acgctaccaa cgtgcccata tccatcccct cccgcaactg ggcggctttc cgcggctggg 20400
ccttcacgcg ccttaagact aaggaaaccc catcactggg ctcgggctac gacccttatt 20460
acacctactc tggctctata ccctacctag atggaacctt ttacctcaac cacaccttta 20520
agaaggtggc cattaccttt gactcttctg tcagctggcc tggcaatgac cgcctgctta 20580
cccccaacga gtttgaaatt aagcgctcag ttgacgggga gggttacaac gttgcccagt 20640
gtaacatgac caaagactgg ttcctggtac aaatgctagc taactataac attggctacc 20700
agggcttcta tatcccagag agctacaagg accgcatgta ctccttcttt agaaacttcc 20760
agcccatgag ccgtcaggtg gtggatgata ctaaatacaa ggactaccaa caggtgggca 20820
tcctacacca acacaacaac tctggatttg ttggctacct tgcccccacc atgcgcgaag 20880
gacaggccta ccctgctaac ttcccctatc cgcttatagg caagaccgca gttgacagca 20940
ttacccagaa aaagtttctt tgcgatcgca ccctttggcg catcccattc tccagtaact 21000
ttatgtccat gggcgcactc acagacctgg gccaaaacct tctctacgcc aactccgccc 21060
acgcgctaga catgactttt gaggtggatc ccatggacga gcccaccctt ctttatgttt 21120
tgtttgaagt ctttgacgtg gtccgtgtgc accagccgca ccgcggcgtc atcgaaaccg 21180
tgtacctgcg cacgcccttc tcggccggca acgccacaac ataaagaagc aagcaacatc 21240
aacaacagct gccgccatgg gctccagtga gcaggaactg aaagccattg tcaaagatct 21300
tggttgtggg ccatattttt tgggcaccta tgacaagcgc tttccaggct ttgtttctcc 21360
acacaagctc gcctgcgcca tagtcaatac ggccggtcgc gagactgggg gcgtacactg 21420
gatggccttt gcctggaacc cgcactcaaa aacatgctac ctctttgagc cctttggctt 21480
ttctgaccag cgactcaagc aggtttacca gtttgagtac gagtcactcc tgcgccgtag 21540
cgccattgct tcttcccccg accgctgtat aacgctggaa aagtccaccc aaagcgtaca 21600
ggggcccaac tcggccgcct gtggactatt ctgctgcatg tttctccacg cctttgccaa 21660
ctggccccaa actcccatgg atcacaaccc caccatgaac cttattaccg gggtacccaa 21720
ctccatgctc aacagtcccc aggtacagcc caccctgcgt cgcaaccagg aacagctcta 21780
cagcttcctg gagcgccact cgccctactt ccgcagccac agtgcgcaga ttaggagcgc 21840
cacttctttt tgtcacttga aaaacatgta aaaataatgt actagagaca ctttcaataa 21900
aggcaaatgc ttttatttgt acactctcgg gtgattattt acccccaccc ttgccgtctg 21960
cgccgtttaa aaatcaaagg ggttctgccg cgcatcgcta tgcgccactg gcagggacac 22020
gttgcgatac tggtgtttag tgctccactt aaactcaggc acaaccatcc gcggcagctc 22080
ggtgaagttt tcactccaca ggctgcgcac catcaccaac gcgtttagca ggtcgggcgc 22140
cgatatcttg aagtcgcagt tggggcctcc gccctgcgcg cgcgagttgc gatacacagg 22200

-continued

```
gttgcagcac tggaacacta tcagcgccgg gtggtgcacg ctggccagca cgctcttgtc  22260
ggagatcaga tccgcgtcca ggtcctccgc gttgctcagg gcgaacggag tcaactttgg  22320
tagctgcctt cccaaaaagg gcgcgtgccc aggctttgag ttgcactcgc accgtagtgg  22380
catcaaaagg tgaccgtgcc cggtctgggc gttaggatac agcgcctgca taaaagcctt  22440
gatctgctta aaagccacct gagcctttgc gccttcagag aagaacatgc cgcaagactt  22500
gccggaaaac tgattggccg gacaggccgc gtcgtgcacg cagcaccttg cgtcggtgtt  22560
ggagatctgc accacatttc ggccccaccg gttcttcacg atcttggcct tgctagactg  22620
ctccttcagc gcgcgctgcc cgttttcgct cgtcacatcc atttcaatca cgtgctcctt  22680
atttatcata atgcttccgt gtagacactt aagctcgcct tcgatctcag cgcagcggtg  22740
cagccacaac gcgcagcccg tgggctcgtg atgcttgtag gtcacctctg caaacgactg  22800
caggtacgcc tgcaggaatc gccccatcat cgtcacaaag gtcttgttgc tggtgaaggt  22860
cagctgcaac ccgcggtgct cctcgttcag ccaggtcttg catacggccg ccagagcttc  22920
cacttggtca ggcagtagtt tgaagttcgc ctttagatcg ttatccacgt ggtacttgtc  22980
catcagcgcg cgcgcagcct ccatgccctt ctcccacgca gacacgatcg gcacactcag  23040
cgggttcatc accgtaattt cactttccgc ttcgctgggc tcttcctctt cctcttgcgt  23100
ccgcatacca cgcgccactg ggtcgtcttc attcagccgc cgcactgtgc gcttacctcc  23160
tttgccatgc ttgattagca ccggtgggtt gctgaaaccc accatttgta gcgccacatc  23220
ttctctttct tcctcgctgt ccacgattac ctctggtgat ggcgggcgct cgggcttggg  23280
agaagggcgc ttcttttct tcttgggcgc aatggccaaa tccgccgccg aggtcgatgg  23340
ccgcgggctg ggtgtgcgcg gcaccagcgc gtcttgtgat gagtcttcct cgtcctcgga  23400
ctcgatacgc cgcctcatcc gcttttttgg gggcgcccgg ggaggcggcg gcgacgggga  23460
cggggacgac acgtcctcca tggttggggg acgtcgcgcc gcaccgcgtc cgcgctcggg  23520
ggtggtttcg cgctgctcct cttcccgact ggccatttcc ttctcctata ggcagaaaaa  23580
gatcatggag tcagtcgaga agaaggacag cctaaccgcc ccctctgagt tcgccaccac  23640
cgcctccacc gatgccgcca acgcgcctac caccttcccc gtcgaggcac ccccgcttga  23700
ggaggaggaa gtgattatcg agcaggaccc aggttttgta agcgaagacg acgaggaccg  23760
ctcagtacca acagaggata aaaagcaaga ccaggacaac gcagaggcaa acgaggaaca  23820
agtcgggcgg ggggacgaaa ggcatggcga ctacctagat gtgggagacg acgtgctgtt  23880
gaagcatctg cagcgccagt gcgccattat ctgcgacgcg ttgcaagagc gcagcgatgt  23940
gcccctcgcc atagcggatg tcagccttgc ctacgaacgc cacctattct caccgcgcgt  24000
accccccaaa cgccaagaaa acggcacatg cgagcccaac ccgcgcctca acttctaccc  24060
cgtatttgcc gtgccagagg tgcttgccac ctatcacatc tttttccaaa actgcaagat  24120
acccctatcc tgccgtgcca accgcagccg agcggacaag cagctggcct tgcggcaggg  24180
cgctgtcata cctgatatcg cctcgctcaa cgaagtgcca aaaatctttg agggtcttgg  24240
acgcgacgag aagcgcgcgg caaacgctct gcaacaggaa aacagcgaaa atgaaagtca  24300
ctctggagtg ttggtggaac tcgagggtga caacgcgcgc ctagccgtac taaaacgcag  24360
catcgaggtc acccactttg cctacccggc acttaaccta ccccccaagg tcatgagcac  24420
agtcatgagt gagctgatcg tgcgccgtgc gcagcccctg gagagggatg caaatttgca  24480
agaacaaaca gaggagggcc tacccgcagt tggcgacgag cagctagcgc gctggcttca  24540
aacgcgcgag cctgccgact tggaggagcg acgcaaacta atgatggccg cagtgctcgt  24600
```

-continued taccgtggag cttgagtgca tgcagcggtt ctttgctgac ccggagatgc agcgcaagct 24660
agaggaaaca ttgcactaca cctttcgaca gggctacgta cgccaggcct gcaagatctc 24720
caacgtggag ctctgcaacc tggtctccta ccttggaatt ttgcacgaaa accgccttgg 24780
gcaaaacgtg cttcattcca cgctcaaggg cgaggcgcgc cgcgactacg tccgcgactg 24840
cgtttactta tttctatgct acacctggca gacggccatg ggcgtttggc agcagtgctt 24900
ggaggagtgc aacctcaagg agctgcagaa actgctaaag caaaacttga aggacctatg 24960
gacggccttc aacgagcgct ccgtggccgc gcacctggcg gacatcattt tccccgaacg 25020
cctgcttaaa accctgcaac agggtctgcc agacttcacc agtcaaagca tgttgcagaa 25080
ctttaggaac tttatcctag agcgctcagg aatcttgccc gccacctgct gtgcacttcc 25140
tagcgacttt gtgcccatta agtaccgcga atgccctccg ccgctttggg gccactgcta 25200
ccttctgcag ctagccaact accttgccta ccactctgac ataatggaag acgtgagcgg 25260
tgacggtcta ctggagtgtc actgtcgctg caacctatgc accccgcacc gctccctggt 25320
ttgcaattcg cagctgctta acgaaagtca aattatcggt acctttgagc tgcagggtcc 25380
ctcgcctgac gaaaagtccg cggctccggg gttgaaactc actccggggc tgtggacgtc 25440
ggcttacctt cgcaaatttg tacctgagga ctaccacgcc cacgagatta ggttctacga 25500
agaccaatcc cgcccgccta atgcggagct taccgcctgc gtcattaccc agggccacat 25560
tcttggccaa ttgcaagcca tcaacaaagc ccgccaagag tttctgctac gaaagggacg 25620
gggggtttac ttggaccccc agtccggcga ggagctcaac ccaatccccc cgccgccgca 25680
gccctatcag cagcagccgc gggcccttgc ttcccaggat ggcacccaaa aagaagctgc 25740
agctgccgcc gccacccacg gacgaggagg aatactggga cagtcaggca gaggaggttt 25800
tggacgagga ggaggaggac atgatggaag actgggagag cctagacgag gaagcttccg 25860
aggtcgaaga ggtgtcagac gaaacaccgt caccctcggt cgcattcccc tcgccggcgc 25920
cccagaaatc ggcaaccggt tccagcatgg ctacaacctc cgctcctcag gcgccgccgg 25980
cactgcccgt tcgccgaccc aaccgtagat gggacaccac tggaaccagg gccggtaagt 26040
ccaagcagcc gccgccgtta gcccaagagc aacaacagcg ccaaggctac cgctcatggc 26100
gcgggcacaa gaacgccata gttgcttgct tgcaagactg tgggggcaac atctccttcg 26160
cccgccgctt tcttctctac catcacggcg tggccttccc ccgtaacatc ctgcattact 26220
accgtcatct ctacagccca tactgcaccg gcggcagcgg cagcaacagc agcggccaca 26280
cagaagcaaa ggcgaccgga tagcaagact ctgacaaagc ccaagaaatc cacagcggcg 26340
gcagcagcag gaggaggagc gctgcgtctg gcgcccaacg aacccgtatc gacccgcgag 26400
cttagaaaca ggatttttcc cactctgtat gctatatttc aacagagcag gggccaagaa 26460
caagagctga aaataaaaaa caggtctctg cgatccctca cccgcagctg cctgtatcac 26520
aaaagcgaag atcagcttcg gcgcacgctg gaagacgcgg aggctctctt cagtaaatac 26580
tgcgcgctga ctcttaagga ctagtttcgc gccctttctc aaatttaagc gcgaaaacta 26640
cgtcatctcc agcggccaca cccggcgcca gcacctgttg tcagcgccat tatgagcaag 26700
gaaattccca cgccctacat gtggagttac cagccacaaa tgggacttgc ggctggagct 26760
gcccaagact actcaacccg aataaactac atgagcgcgg gaccccacat gatatcccgg 26820
gtcaacggaa tacgcgccca ccgaaaccga attctcctgg aacaggcggc tattaccacc 26880
acacctcgta ataaccttaa tccccgtagt tggcccgctg ccctggtgta ccaggaaagt 26940

-continued

```
cccgctccca ccactgtggt acttcccaga gacgcccagg ccgaagttca gatgactaac  27000
tcaggggcgc agcttgcggg cggctttcgt cacagggtgc ggtcgcccgg gcagggtata  27060
actcacctga caatcagagg gcgaggtatt cagctcaacg acgagtcggt gagctcctcg  27120
cttggtctcc gtccggacgg gacatttcag atcggcggcg ccggccgctc ttcattcacg  27180
cctcgtcagg caatcctaac tctgcagacc tcgtcctctg agccgcgctc tggaggcatt  27240
ggaactctgc aatttattga ggagtttgtg ccatcggtct actttaaccc cttctcggga  27300
cctcccggcc actatccgga tcaatttatt cctaactttg acgcggtaaa ggactcggcg  27360
gacggctacg actgaatgtt aagtggagag gcagagcaac tgcgcctgaa acacctggtc  27420
cactgtcgcc gccacaagtg ctttgcccgc gactccggtg agttttgcta ctttgaattg  27480
cccgaggatc atatcgaggg cccggcgcac ggcgtccggc ttaccgccca gggagagctt  27540
gcccgtagcc tgattcggga gtttacccag cgcccccctgc tagttgagcg ggacagggga  27600
ccctgtgttc tcactgtgat ttgcaactgt cctaaccctg gattacatca agatctttgt  27660
tgccatctct gtgctgagta taataaatac agaaattaaa atatactggg gctcctatcg  27720
ccatcctgta aacgccaccg tcttcacccg cccaagcaaa ccaaggcgaa ccttacctgg  27780
tacttttaac atctctccct ctgtgattta caacagtttc aacccagacg gagtgagtct  27840
acgagagaac ctctccgagc tcagctactc catcagaaaa aacaccaccc tccttacctg  27900
ccgggaacgt acgagtgcgt caccggccgc tgcaccacac ctaccgcctg accgtaaacc  27960
agactttttc cggacagacc tcaataactc tgtttaccag aacaggaggt gagcttagaa  28020
aacccttagg gtattaggcc aaaggcgcag ctactgtggg gtttatgaac aattcaagca  28080
actctacggg ctattctaat tcaggtttct ctagaatcgg ggttggggtt attctctgtc  28140
ttgtgattct ctttattctt atactaacgc ttctctgcct aaggctcgcc gcctgctgtg  28200
tgcacatttg catttattgt cagcttttta aacgctgggg tcgccaccca agatgattag  28260
gtacataatc ctaggtttac tcacccttgc gtcagcccac ggtaccaccc aaaaggtgga  28320
ttttaaggag ccagcctgta atgttacatt cgcagctgaa gctaatgagt gcaccactct  28380
tataaaatgc accacagaac atgaaaagct gcttattcgc cacaaaaaca aaattggcaa  28440
gtatgctgtt tatgctattt ggcagccagg tgacactaca gagtataatg ttacagtttt  28500
ccagggtaaa agtcataaaa cttttatgta tacttttcca ttttatgaaa tgtgcgacat  28560
taccatgtac atgagcaaac agtataagtt gtggcccccca caaaattgtg tggaaaacac  28620
tggcactttc tgctgcactg ctatgctaat tacagtgctc gctttggtct gtaccctact  28680
ctatattaaa tacaaaagca gacgcagctt tattgaggaa aagaaaatgc cttaatttac  28740
taagttacaa agctaatgtc accactaact gctttactcg ctgcttgcaa aacaaattca  28800
aaaagttagc attataatta gaataggatt taaacccccc ggtcatttcc tgctcaatac  28860
cattcccctg aacaattgac tctatgtggg atatgctcca gcgctacaac cttgaagtca  28920
ggcttcctgg atgtcagcat ctgactttgg ccagcacctg tcccgcggat ttgttccagt  28980
ccaactacag cgacccaccc taacagagat gaccaacaca accaacgcgg ccgccgctac  29040
cggacttaca tctaccacaa atacacccca agtttctgcc tttgtcaata actgggataa  29100
cttgggcatg tggtggttct ccatagcgct tatgtttgta tgccttatta ttatgtggct  29160
catctgctgc ctaaagcgca aacgcgcccg accacccatc tatagtccca tcattgtgct  29220
acacccaaac aatgatggaa tccatagatt ggacggactg aaacacatgt tcttttctct  29280
tacagtatga ttaaatgaga catgattcct cgagttttta tattactgac ccttgttgcg  29340
```

-continued

```
cttttttgtg cgtgctccac attggctgcg gtttctcaca tcgaagtaga ctgcattcca  29400
gccttcacag tctatttgct ttacggattt gtcaccctca cgctcatctg cagcctcatc  29460
actgtggtca tcgcctttat ccagtgcatt gactgggtct gtgtgcgctt tgcatatctc  29520
agacaccatc cccagtacag ggacaggact atagctgagc ttcttagaat tctttaatta  29580
tgaaatttac tgtgactttt ctgctgatta tttgcaccct atctgcgttt tgttccccga  29640
cctccaagcc tcaaagacat atatcatgca gattcactcg tatatggaat attccaagtt  29700
gctacaatga aaaaagcgat ctttccgaag cctggttata tgcaatcatc tctgttatgg  29760
tgttctgcag taccatctta gccctagcta tatatcccta ccttgacatt ggctggaacg  29820
caatagatgc catgaaccac ccaactttcc ccgcgcccgc tatgcttcca ctgcaacaag  29880
ttgttgccgg cggctttgtc ccagccaatc agcctcgccc accttctccc acccccactg  29940
aaatcagcta ctttaatcta acaggaggag atgactgaca ccctagatct agaaatggac  30000
ggaattatta cagagcagcg cctgctagaa agacgcaggg cagcggccga gcaacagcgc  30060
atgaatcaag agctccaaga catggttaac ttgcaccagt gcaaaagggg tatcttttgt  30120
ctcgtaaagc aggccaaagt cacctacgac agtaatacca ccggacaccg ccttagctac  30180
aagttgccaa ccaagcgtca gaaattggtg gtcatggtgg gagaaaagcc cattaccata  30240
actcagcact cggtagaaac cgaaggctgc attcactcac cttgtcaagg acctgaggat  30300
ctctgcaccc ttattaagac cctgtgcggt ctcaaagatc ttattccctt taactaataa  30360
aaaaaaataa taaagcatca cttacttaaa atcagttagc aaatttctgt ccagtttatt  30420
cagcagcacc tccttgccct cctcccagct ctggtattgc agcttcctcc tggctgcaaa  30480
ctttctccac aatctaaatg gaatgtcagt ttcctcctgt tcctgtccat ccgcacccac  30540
tatcttcatg ttgttgcaga tgaagcgcgc aagaccgtct gaagatacct tcaaccccgt  30600
gtatccatat gacacggaaa ccggtcctcc aactgtgcct ttcttactc ctccctttgt  30660
atcccccaat gggtttcaag agagtccccc tggggtactc tctttgcgcc tatccgaacc  30720
tctagttacc tccaatggca tgcttgcgct caaaatgggc aacggcctct ctctggacga  30780
ggccggcaac cttacctccc aaaatgtaac cactgtgagc ccacctctca aaaaaaccaa  30840
gtcaaacata aacctggaaa tatctgcacc cctcacagtt acctcagaag ccctaactgt  30900
ggctgccgcc gcacctctaa tggtcgcggg caacacactc accatgcaat cacaggcccc  30960
gctaaccgtg cacgactcca aacttagcat tgccacccaa ggacccctca cagtgtcaga  31020
aggaaagcta gccctgcaaa catcaggccc cctcaccacc accgatagca gtacccttac  31080
tatcactgcc tcacccccct taactactgc cactggtagc ttgggcattg acttgaaaga  31140
gcccatttat acacaaaatg gaaaactagg actaaagtac ggggctcctt tgcatgtaac  31200
agacgaccta aacactttga ccgtagcaac tggtccaggt gtgactatta ataatacttc  31260
cttgcaaact aaagttactg gagccttggg ttttgattca caaggcaata tgcaacttaa  31320
tgtagcagga ggactaagga ttgattctca aaacagacgc cttatacttg atgttagtta  31380
tccgtttgat gctcaaaacc aactaaatct aagactagga cagggccctc tttttataaa  31440
ctcagcccac aacttggata ttaactacaa caaaggcctt tacttgttta cagcttcaaa  31500
caattccaaa aagcttgagg ttaacctaag cactgccaag gggttgatgt ttgacgctac  31560
agccatagcc attaatgcag gagatgggct tgaatttggt tcacctaatg caccaaacac  31620
aaatcccctc aaaacaaaaa ttggccatgg cctagaattt gattcaaaca aggctatggt  31680
```

```
tcctaaacta ggaactggcc ttagttttga cagcacaggt gccattacag taggaaacaa   31740

aaataatgat aagctaactt tgtggaccac accagctcca tctcctaact gtagactaaa   31800

tgcagagaaa gatgctaaac tcactttggt cttaacaaaa tgtggcagtc aaatacttgc   31860

tacagtttca gttttggctg ttaaaggcag tttggctcca atatctggaa cagttcaaag   31920

tgctcatctt attataagat ttgacgaaaa tggagtgcta ctaaacaatt ccttcctgga   31980

cccagaatat tggaacttta gaaatggaga tcttactgaa ggcacagcct atacaaacgc   32040

tgttggattt atgcctaacc tatcagctta tccaaaatct cacggtaaaa ctgccaaaag   32100

taacattgtc agtcaagttt acttaaacgg agacaaaact aaacctgtaa cactaaccat   32160

tacactaaac ggtacacagg aaacaggaga cacaactcca agtgcatact ctatgtcatt   32220

ttcatgggac tggtctggcc acaactacat taatgaaata tttgccacat cctcttacac   32280

tttttcatac attgcccaag aataaagaat cgtttgtgtt atgtttcaac gtgtttattt   32340

ttcaattgca gaaaatttca agtcattttt cattcagtag tatagcccca ccaccacata   32400

gcttatacag atcaccgtac cttaatcaaa ctcacagaac cctagtattc aacctgccac   32460

ctccctccca acacacagag tacacagtcc tttctccccg gctggcctta aaaagcatca   32520

tatcatgggt aacagacata ttcttaggtg ttatattcca cacggtttcc tgtcgagcca   32580

aacgctcatc agtgatatta ataaactccc cgggcagctc acttaagttc atgtcgctgt   32640

ccagctgctg agccacaggc tgctgtccaa cttgcggttg cttaacgggc ggcgaaggag   32700

aagtccacgc ctacatgggg gtagagtcat aatcgtgcat caggataggg cggtggtgct   32760

gcagcagcgc gcgaataaac tgctgccgcc gccgctccgt cctgcaggaa tacaacatgg   32820

cagtggtctc ctcagcgatg attcgcaccg cccgcagcat aaggcgcctt gtcctccggg   32880

cacagcagcg caccctgatc tcacttaaat cagcacagta actgcagcac agcaccacaa   32940

tattgttcaa aatcccacag tgcaaggcgc tgtatccaaa gctcatggcg gggaccacag   33000

aacccacgtg gccatcatac cacaagcgca ggtagattaa gtggcgaccc ctcataaaca   33060

cgctggacat aaacattacc tcttttggca tgttgtaatt caccacctcc cggtaccata   33120

taaacctctg attaaacatg gcgccatcca ccaccatcct aaaccagctg gccaaaacct   33180

gcccgccggc tatacactgc agggaaccgg gactggaaca atgacagtgg agagcccagg   33240

actcgtaacc atggatcatc atgctcgtca tgatatcaat gttggcacaa cacaggcaca   33300

cgtgcataca cttcctcagg attacaagct cctcccgcgt tagaaccata tcccagggaa   33360

caacccattc ctgaatcagc gtaaatccca cactgcaggg aagacctcgc acgtaactca   33420

cgttgtgcat tgtcaaagtg ttacattcgg gcagcagcgg atgatcctcc agtatggtag   33480

cgcgggtttc tgtctcaaaa ggaggtagac gatccctact gtacggagtg cgccgagaca   33540

accgagatcg tgttggtcgt agtgtcatgc caaatggaac gccggacgta gtcatatttc   33600

ctgaagcaaa accaggtgcg ggcgtgacaa acagatctgc gtctccggtc tcgccgctta   33660

gatcgctctg tgtagtagtt gtagtatatc cactctctca aagcatccag gcgcccctg    33720

gcttcgggtt ctatgtaaac tccttcatgc gccgctgccc tgataacatc caccaccgca   33780

gaataagcca cacccagcca acctacacat tcgttctgcg agtcacacac gggaggagcg   33840

ggaagagctg gaagaaccat gttttttttt ttattccaaa agattatcca aaacctcaaa   33900

atgaagatct attaagtgaa cgcgctcccc tccggtggcg tggtcaaact ctacagccaa   33960

agaacagata atggcatttg taagatgttg cacaatggct tccaaaaggc aaacggccct   34020

cacgtccaag tggacgtaaa ggctaaaccc ttcagggtga atctcctcta taaacattcc   34080
```

-continued

```
agcaccttca accatgccca aataattctc atctcgccac cttctcaata tatctctaag  34140
caaatcccga atattaagtc cggccattgt aaaaatctgc tccagagcgc cctccacctt  34200
cagcctcaag cagcgaatca tgattgcaaa aattcaggtt cctcacagac ctgtataaga  34260
ttcaaaagcg gaacattaac aaaaataccg cgatcccgta ggtcccttcg cagggccagc  34320
tgaacataat cgtgcaggtc tgcacggacc agcgcggcca cttccccgcc aggaaccatg  34380
acaaaagaac ccacactgat tatgacacgc atactcggag ctatgctaac cagcgtagcc  34440
ccgatgtaag cttgttgcat gggcggcgat ataaaatgca aggtgctgct caaaaaatca  34500
ggcaaagcct cgcgcaaaaa agaaagcaca tcgtagtcat gctcatgcag ataaaggcag  34560
gtaagctccg gaaccaccac agaaaaagac accatttttc tctcaaacat gtctgcgggt  34620
ttctgcataa acacaaaata aaataacaaa aaaacattta aacattagaa gcctgtctta  34680
caacaggaaa aacaaccctt ataagcataa gacggactac ggccatgccg gcgtgaccgt  34740
aaaaaaactg gtcaccgtga ttaaaaagca ccaccgacag ctcctcggtc atgtccggag  34800
tcataatgta agactcggta aacacatcag gttgattcac atcggtcagt gctaaaaagc  34860
gaccgaaata gcccggggga atacataccc gcaggcgtag agacaacatt acagccccca  34920
taggaggtat aacaaaatta ataggagaga aaaacacata aacacctgaa aaaccctcct  34980
gcctaggcaa aatagcaccc tcccgctcca gaacaacata cagcgcttcc acagcggcag  35040
ccataacagt cagccttacc agtaaaaaag aaaacctatt aaaaaaacac cactcgacac  35100
ggcaccagct caatcagtca cagtgtaaaa aagggccaag tgcagagcga gtatatatag  35160
gactaaaaaa tgacgtaacg gttaaagtcc acaaaaaaca cccagaaaac cgcacgcgaa  35220
cctacgccca gaaacgaaag ccaaaaaacc cacaacttcc tcaaatcgtc acttccgttt  35280
tcccacgtta cgtcacttcc cattttaaga aaactacaat tcccaacaca tacaagttac  35340
tccgccctaa aacctacgtc acccgccccg ttcccacgcc ccgcgccacg tcacaaactc  35400
cacccccctca ttatcatatt ggcttcaatc caaaataagg tatattattg atgatgttaa  35460
ttaagaattc ggatctgcga cgcgaggctg gatggccttc cccattatga ttcttctcgc  35520
ttccggcggc atcgggatgc ccgcgttgca ggccatgctg tccaggcagg tagatgacga  35580
ccatcaggga cagcttcaag gccagcaaaa ggccaggaac cgtaaaaagg ccgcgttgct  35640
ggcgtttttc cataggctcc gcccccctga cgagcatcac aaaaatcgac gctcaagtca  35700
gaggtggcga aacccgacag gactataaag ataccaggcg tttccccctg gaagctccct  35760
cgtgcgctct cctgttccga ccctgccgct taccggatac ctgtccgcct ttctcccttc  35820
gggaagcgtg gcgctttctc atagctcacg ctgtaggtat ctcagttcgg tgtaggtcgt  35880
tcgctccaag ctgggctgtg tgcacgaacc ccccgttcag cccgaccgct gcgccttatc  35940
cggtaactat cgtcttgagt ccaacccggt aagacacgac ttatcgccac tggcagcagc  36000
cactggtaac aggattagca gagcgaggta tgtaggcggt gctacagagt tcttgaagtg  36060
gtggcctaac tacggctaca ctagaaggac agtatttggt atctgcgctc tgctgaagcc  36120
agttaccttc ggaaaaagag ttggtagctc ttgatccggc aaacaaacca ccgctggtag  36180
cggtggtttt tttgtttgca agcagcagat tacgcgcaga aaaaaaggat ctcaagaaga  36240
tcctttgatc ttttctacgg ggtctgacgc tcagtggaac gaaaactcac gttaagggat  36300
tttggtcatg agattatcaa aaggatcttc acctagatcc ttttaaatc aatctaaagt  36360
atatatgagt aaacttggtc tgacagttac caatgcttaa tcagtgaggc acctatctca  36420
```

-continued

```
gcgatctgtc tatttcgttc atccatagtt gcctgactcc ccgtcgtgta gataactacg  36480
atacgggagg gcttaccatc tggccccagt gctgcaatga taccgcgaga cccacgctca  36540
ccggctccag atttatcagc aataaaccag ccagccggaa gggccgagcg cagaagtggt  36600
cctgcaactt tatccgcctc catccagtct attaattgtt gccgggaagc tagagtaagt  36660
agttcgccag ttaatagttt gcgcaacgtt gttgccattg ctacaggcat cgtggtgtca  36720
cgctcgtcgt ttggtatggc ttcattcagc tccggttccc aacgatcaag gcgagttaca  36780
tgatccccca tgttgtgcaa aaaagcggtt agctccttcg gtcctccgat cgttgtcaga  36840
agtaagttgg ccgcagtgtt atcactcatg gttatggcag cactgcataa ttctcttact  36900
gtcatgccat ccgtaagatg cttttctgtg actggtgagt actcaaccaa gtcattctga  36960
gaatagtgta tgcggcgacc gagttgctct tgcccggcgt caacacggga taataccgcg  37020
ccacatagca gaactttaaa agtgctcatc attggaaaac gttcttcggg gcgaaaactc  37080
tcaaggatct taccgctgtt gagatccagt tcgatgtaac ccactcgtgc acccaactga  37140
tcttcagcat cttttacttt caccagcgtt tctgggtgag caaaaacagg aaggcaaaat  37200
gccgcaaaaa agggaataag ggcgacacgg aaatgttgaa tactcatact cttccttttt  37260
caatattatt gaagcattta tcagggttat tgtctcatga gcggatacat atttgaatgt  37320
atttagaaaa ataaacaaat aggggttccg cgcacatttc cccgaaaagt gccacctgac  37380
gtctaagaaa ccattattat catgacatta acctataaaa ataggcgtat cacgaggccc  37440
tttcgtcttc aagaattgga tccgaattct taat                              37474
```

```
<210> SEQ ID NO 26
<211> LENGTH: 37474
<212> TYPE: DNA
<213> ORGANISM: Artificial Sequence
<220> FEATURE:
<223> OTHER INFORMATION: DNA encoding pMRKAd5 HIV-1 gag, noncoding

<400> SEQUENCE: 26
```

```
aagaattaat tgtagtagtt attatatgga ataaaaccta acttcggtta tactattact     60
cccccacctc aaacactgca ccgcgccccg cacccttgcc ccgcccactg catcatcaca    120
ccgccttcac actacaacgt tcacaccgcc ttgtgtacat tcgctgccta caccgttttc    180
actgcaaaaa ccacacgcgg ccacatgtgt ccttcactgt taaaagcgcg ccaaaatccg    240
cctacaacat catttaaacc cgcattggct cattctaaac cggtaaaagc gcccttttga    300
cttattctcc ttcactttag acttattaaa acacaatgag tatcgcgcat tataaacaga    360
tcccggcgcc cctgaaactg gcaaatgcac ctctgagcgg gtccacaaaa agagtccaca    420
aaaggcgcaa ggcccagttt caaccgcaaa ataataatat ccgccggcgc taggtaacgt    480
atgcaacata ggtatagtat tatacatgta aatataaccg agtacaggtt gtaatggcgg    540
tacaactgta actaataact gatcaataat tatcattagt taatgcccca gtaatcaagt    600
atcgggtata tacctcaagg cgcaatgtat tgaatgccat ttaccgggcg gaccgactgg    660
cgggttgctg gggcgggta actgcagtta ttactgcata caagggtatc attgcggtta    720
tccctgaaag gtaactgcag ttacccacct cataaatgcc atttgacggg tgaaccgtca    780
tgtagttcac atagtatacg gttcatgcgg gggataactg cagttactgc catttaccgg    840
gcggaccgta atacgggtca tgtactggaa taccctgaaa ggatgaaccg tcatgtagat    900
gcataatcag tagcgataat ggtaccacta cgccaaaacc gtcatgtagt tacccgcacc    960
tatcgccaaa ctgagtgccc ctaaaggttc agaggtgggg taactgcagt taccctcaaa   1020
```

-continued

```
caaaaccgtg gttttagttg ccctgaaagg ttttacagca ttgttgaggc ggggtaactg   1080
cgtttacccg ccatccgcac atgccaccct ccagatatat tcgtctcgag caaatcactt   1140
ggcagtctag cggacctctg cggtaggtgc gacaaaactg gaggtatctt ctgtggccct   1200
ggctaggtcg gaggcgccgg cccttgccac gtaaccttgc gcctaagggg cacggttctc   1260
actctagatg gtacccacga tcccgaagac acgacagacc accactcgac ctgttcaccc   1320
tcttctagtc cgactccgga ccaccgttct tcttcatgtt cgatttcgtg taacacaccc   1380
ggaggtccct cgacctctcc aaacgacact tgggaccgga cgacctctgg agactcccca   1440
cgtccgtcta ggacccggtc gaggtcggga gggacgtttg tccgagactc ctcgactcca   1500
gggacatgtt gtgtcaccga tgggacatga cacacgtggt cttctaacta cacttcctgt   1560
ggttcctccg ggacctcttc taactcctcc tcgtcttgtt caggttcttc ttccgggtcg   1620
tccgacgacg accgtgtccg ttgaggtcgg tccacagggt cttgatgggg taacacgtct   1680
tggaggtccc ggtctaccac gtggtccggt agagggggc ctgggactta cggacccact   1740
tccaccacct cctcttccgg aagaggggac tccactaggg gtacaagaga cgggacagac   1800
tcccacggtg gggggtcctg gacttgtggt acgacttgtg tcacccccg gtagtccgac   1860
ggtacgtcta cgacttcctc tggtagttac tcctccgacg actcaccctg tccgacgtag   1920
gacacgtgcg accggggtaa cgggggccgg tctactccct cgggtccccg agactgtaac   1980
gaccgtggtg gaggtgggag gtcctcgtct aaccgaccta ctggttgttg ggggggtagg   2040
gacaccccct ttagatgttc tccacctagt aggacccgga cttgttctaa cactcctaca   2100
tgagggggtg gaggtaggac ctgtagtccg tcccggggtt cctcgggaag tccctgatac   2160
acctgtccaa gatgttctgg gactcccgac tcgtccggag ggtcctccac ttcttgacct   2220
actgtctctg ggacgaccac gtcttacggt tgggactgac gttctggtag gacttccggg   2280
acccgggacg acggtgggac ctcctctact actgtcggac ggtcccccac cccccgggac   2340
cagtgttccg gtcccacgac cgactccggt acagggtcca ctggttgagg cggtggtagt   2400
actacgtctc cccgttgaag tccttggtct ccttctgtca cttcacgaag ttgacaccgt   2460
tccacccggt gtaacggttc ttgacatccc gggggtcctt cttcccgacg accttcacac   2520
cgttcctccc ggtggtctac ttcctgacgt tactctccgt ccggttgaag gacccgtttt   2580
agaccgggag ggtgttcccg tccggaccgt tgaaggaggt caggtccgga ctcgggtgtc   2640
ggggagggct cctcaggaag tccaaacccc tcctcttctg gtgggggtcg gtcttcgtcc   2700
tcgggtaact gttcctcgac atgggggacc ggagggactc cagggacaaa ccgttgctgg   2760
ggaggagggt cattttattt cggcccgtc tagacgacac ggaagatcaa cggtcggtag   2820
acaacaaacg gggaggggc acggaaggaa ctgggacctt ccacggtgag ggtgacagga   2880
aaggattatt ttactccttt aacgtagcgt aacagactca tccacagtaa gataagaccc   2940
cccaccccac cccgtcctgt cgttccccct cctaaccctt ctgttatcgt ccgtacgacc   3000
cctacgccac ccgagatacc ggctagccgc gcggcatgac tttacacacc cgcaccgaat   3060
tcccaccctt tcttatatat tccaccccca gaatacatca aaacatagac aaaacgtcgt   3120
cggcggcggc ggtactcgtg gttgagcaaa ctaccttcgt aacactcgag tataaactgt   3180
tgcgcgtacg gggtacccg gccccacgca gtcttacact acccgaggtc gtaactacca   3240
gcggggcagg acgggcgttt gagatgatgg aactggatgc tctggcacag accttgcggc   3300
aacctctgac gtcggaggcg gcggcgaagt cggcgacgtc ggtggcgggc gccctaacac   3360
```

-continued

```
tgactgaaac gaaaggactc gggcgaacgt ttgtcacgtc gaagggcaag taggcgggcg   3420
ctactgttca actgccgaga aaaccgtgtt aacctaagaa actgggccct tgaattacag   3480
caaagagtcg tcgacaacct agacgcggtc gtccaaagac gggacttccg aaggagggga   3540
gggttacgcc aaattttgta tttatttttt ggtctgagac aaacctaaac ctagttcgtt   3600
cacagaacga cagaaataaa tccccaaaac gcgcgcgcca tccgggccct ggtcgccaga   3660
gccagcaact cccaggacac ataaaaaagg tcctgcacca tttccactga gacctacaag   3720
tctatgtacc cgtattcggg cagagacccc acctccatcg tggtgacgtc tcgaagtacg   3780
acgccccacc acaacatcta ctaggtcagc atcgtcctcg cgacccgcac cacggatttt   3840
tacagaaagt catcgttcga ctaacggtcc ccgtccggga accacattca caaatgtttc   3900
gccaattcga ccctacccac gtatgcaccc ctatactcta cgtagaacct gacataaaaa   3960
tccaaccgat acaagggtcg gtatagggag gcccctaagt acaacacgtc ttggtggtcg   4020
tgtcacatag gccacgtgaa ccctttaaac agtacatcga atcttccttt acgcaccttc   4080
ttgaacctct gcgggaacac tggaggttct aaaaggtacg taagcaggta ttactaccgt   4140
tacccgggtg cccgccgccg gacccgcttc tataaagacc ctagtgattg cagtatcaac   4200
acaaggtcct actctagcag tatccggtaa aaatgtttcg cgcccgcctc ccacggtctg   4260
acgccatatt accaaggtag gccgggtccc cgcatcaatg ggagtgtcta aacgtaaagg   4320
gtgcgaaact caagtctacc cccctagtac agatggacgc cccgctactt cttttgccaa   4380
aggccccatc ccctctagtc gacccttctt tcgtccaagg actcgtcgac gctgaatggc   4440
gtcggccacc cgggcattta gtgtggataa tggccgacgt tgaccatcaa ttctctcgac   4500
gtcgacggca gtagggactc gtcccccgg tgaagcaatt cgtacaggga ctgagcgtac   4560
aaaagggact ggtttaggcg gtcttccgcg agcggcgggt cgctatcgtc aagaacgttc   4620
cttcgtttca aaaagttgcc aaactctggc aggcggcatc cgtacgaaaa ctcgcaaact   4680
ggttcgtcaa ggtccgccag ggtgtcgagc cagtggacga gatgccgtag agctaggtcg   4740
tatagaggag caaagcgccc aaccccgccg aaagcgacat gccgtcatca gccacgagca   4800
ggtctgcccg gtcccagtac agaaaggtgc ccgcgtccca ggagcagtcg catcagaccc   4860
agtgccactt ccccacgcga ggcccgacgc gcgaccggtc ccacgcgaac tccgaccagg   4920
acgaccacga cttcgcgacg gccagaagcg ggacgcgcag ccggtccatc gtaaactggt   4980
accacagtat caggtcgggg aggcgccgca ccgggaaccg cgcgtcgaac gggaacctcc   5040
tccgcggcgt gctccccgtc acgtctgaaa actcccgcat ctcgaacccg cgctctttat   5100
ggctaaggcc cctcatccgt aggcgcggcg tccggggcgt ctgccagagc gtaaggtgct   5160
cggtccactc gagaccggca agccccagtt tttggtccaa agggggtacg aaaaactacg   5220
caaagaatgg agaccaaagg tactcggcca caggtgcgag ccactgcttt tccgacaggc   5280
acaggggcat atgtctgaac tctccggaca ggagctcgcc acaaggcgcc aggaggagca   5340
tatctttgag cctggtgaga ctctgtttcc gagcgcaggt ccggtcgtgc ttcctccgat   5400
tcaccctccc catcgccagc aacaggtgat cccccaggtg agcgaggtcc cacacttctg   5460
tgtacagcgg gagaagccgt agttccttcc actaaccaaa catccacatc cggtgcactg   5520
gcccacaagg acttcccccc gatattttcc cccacccccg cgcaagcagg agtgagagaa   5580
ggcgtagcga cagacgctcc cggtcgacaa ccccactcat gagggagact tttcgcccgt   5640
actgaagacg cgattctaac agtcaaaggt tttgctcct cctaaactat aagtggaccg    5700
ggcgccacta cggaaactcc caccggcgta ggtagaccag tcttttctgt tagaaaaaca   5760
```

-continued

```
acagttcgaa ccaccgtttg ctgggcatct cccgcaacct gtcgttgaac cgctacctcg   5820
cgtcccaaac caaaaacagc gctagccgcg cgaggaaccg gcgctacaaa tcgacgtgca   5880
taagcgcgcg ttgcgtggcg gtaagccctt tctgccacca cgcgagcagc ccgtggtcca   5940
cgtgcgcggt tggcgccaac acgtcccact gttccagttg cgaccaccga tggagaggcg   6000
catccgcgag caaccaggtc gtctccgccg gcgggaacgc gctcgtctta ccgccatccc   6060
ccagatcgac gcagagcagg ccccccagac gcaggtgcca tttctggggc ccgtcgtccg   6120
cgcgcagctt catcagatag aacgtaggaa cgttcagatc gcggacgacg gtacgcgccc   6180
gccgttcgcg cgcgagcata cccaactcac cccctggggt accgtacccc acccactcgc   6240
gcctccgcat gtacggcgtt tacagcattt gcatctcccc gagagactca taaggttcta   6300
tacatcccat cgtagaaggt ggcgcctacg accgcgcgtg cattagcata tcaagcacgc   6360
tccctcgctc ctccagccct ggctccaacg atgcccgccc gacgagacga gccttctgat   6420
agacggactt ctaccgtaca ctcaacctac tataccaacc tgcgaccttc tgcaacttcg   6480
accgcagaca ctctggatgg cgcagtgcgt gcttcctccg catcctcagc gcgtcgaaca   6540
actggtcgag ccgccactgg acgtgcagat cccgcgtcat caggtcccaa aggaactact   6600
acagtatgaa taggacaggg aaaaaaaagg tgtcgagcgc caactcctgt ttgagaagcg   6660
ccagaaaggt catgagaacc tagcctttgg gcagccggag gcttgccatt ctcggatcgt   6720
acatcttgac caactgccgg accatccgcg tcgtagggaa aagatgccca tcgcgcatac   6780
ggacgcgccg gaaggcctcg ctccacaccc actcgcgttt ccacagggac tggtactgaa   6840
actccatgac cataaacttc agtcacagca gcgtaggcgg gacgagggtc tcgtttttca   6900
ggcacgcgaa aaaccttgcg cctaaaccgt cccgcttcca ctgtagcaac ttctcataga   6960
aagggcgcgc tccgtatttc aacgcacact acgccttccc agggccgtgg agccttgcca   7020
acaattaatg gacccgccgc tcgtgctaga gcagtttcgg caactacaac accgggtgtt   7080
acatttcaag gttcttcgcg ccctacggga actaccttcc gttaaaaaat tcaaggagca   7140
tccactcgag aagtcccctc gactcgggca cgagactttc ccgggtcaga cgttctactc   7200
ccaaccttcg ctgcttactc gaggtgtcca gtgcccggta atcgtaaacg tccaccagcg   7260
ctttccagga tttgaccgct ggataccggt aaaaaagacc ccactacgtc atcttccatt   7320
cgcccagaac aagggtcgcc agggtaggtt ccaagcgccg atccagagcg cgccgtcagt   7380
gatctccgag tagaggcggc ttgaagtact ggtcgtactt cccgtgctcg acgaagggtt   7440
tccgggggta ggttcatatc cagagatgta gcatccactg tttctctgcg agccacgctc   7500
ctacgctcgg ctagcccttc ttgacctaga gggcggtggt taacctcctc accgataact   7560
acaccacttt catcttcagg gacgctgccc ggcttgtgag cacgaccgaa aacatttttg   7620
cacgcgtcat gaccgtcgcc acgtgcccga catgtaggac gtgctccaac tggactgctg   7680
gcgcgtgttc cttcgtctca cccttaaact cggggagcgg accgcccaaa ccgaccacca   7740
gaagatgaag ccgacgaaca ggaactggca gaccgacgag ctcccctcaa tgccacctag   7800
cctggtggtg cggcgcgctc gggtttcagg tctacaggcg cgcgccgcca gcctcgaact   7860
actgttgtag cgcgtctacc ctcgacaggt accagacctc gagggcgccg cagtccagtc   7920
cgccctcgag gacgtccaaa tggagcgtat ctgcccagtc ccgcgcccga tctaggtcca   7980
ctatggatta aaggtccccg accaaccacc gccgcagcta ccgaacgttc tccggcgtag   8040
gggcgccgcg ctgatgccat ggcgcgccgc ccgccacccg gcgcccccac aggaacctac   8100
```

-continued

```
tacgtagatt ttcgccactg cgcccgctcg ggggcctcca tccccccga ggcctgggcg   8160
gccctctccc ccgtccccgt gcagccgcgg cgcgcgcccg tcctcgacca cgacgcgcgc   8220
atccaacgac cgcttgcgct gctgcgccgc caactagagg acttagaccg cggagacgca   8280
cttctgctgc ccgggccact cgaacttgga ctttctctca agctgtctta gttaaagcca   8340
cagcaactgc cgccggaccg cgttttagag gacgtgcaga ggactcaaca gaactatccg   8400
ctagagccgg tacttgacga gctagagaag gaggacctct agaggcgcag gccgagcgag   8460
gtgccaccgc cgctccagca acctttacgc ccggtactcg acgctcttcc gcaactccgg   8520
agggagcaag gtctgcgccg acatctggtg cgggggaagc cgtagcgccc gcgcgtactg   8580
gtggacgcgc tctaactcga ggtgcacggc ccgcttctgc cgcatcaaag cgtccgcgac   8640
tttctccatc aactcccacc accgccacac aagacggtgc ttcttcatgt attgggtcgc   8700
agcgttgcac ctaagcaact atagggggtt ccggagttcc gcgaggtacc ggagcatctt   8760
caggtgccgc ttcaactttt tgaccctcaa cgcgcggctg tgccaattga ggaggaggtc   8820
ttctgcctac tcgagccgct gtcacagcgc gtggagcgcg agtttccgat gtccccggag   8880
aagaagaaga agttagagga gaaggtattc ccggagggga agaagaagaa gaccgccgcc   8940
accccctccc ccctgtgccg ccgctgctgc cgcgtggccc tccgccagct gtttcgcgag   9000
ctagtagagg ggcgccgctg ccgcgtacca gagccactgc cgcgccggca agagcgcccc   9060
cgcgtcaacc ttctgcggcg ggcagtacag ggccaatacc caaccgcccc ccgacggtac   9120
gccgtcccta tgccgcgatt gctacgtaga gttgttaaca acacatccat gaggcggcgg   9180
ctccctggac tcgctcaggc gtagctggcc tagccttttg gagagctctt tccgcagatt   9240
ggtcagtgtc agcgttccat ccgactcgtg gcaccgcccg ccgtcgcccg ccgccagccc   9300
caacaaagac cgcctccacg acgactacta cattaatttc atccgccaga actctgccgc   9360
ctaccagctg tcttcgtggt acaggaaccc aggccggacg acttacgcgt ccgccagccg   9420
gtacggggtc cgaagcaaaa ctgtagccgc gtccagaaac atcatcagaa cgtactcgga   9480
aagatggccg tgaagaagaa gaggaaggag aacaggacgt agagaacgta gatagcgacg   9540
ccgccgccgc ctcaaaccgg catccaccgc gggagaagga gggtacgcac actggggctt   9600
cggggagtag ccgacttcgt cccgatccag ccgctgttgc gcgagccgat tataccggac   9660
gacgtggacg cactcccatc tgaccttcag taggtacagg tgtttcgcca ccatacgcgg   9720
gcacaactac cacattcacg tcaaccggta ttgcctggtc aattgccaga ccactgggcc   9780
gacgctctcg agccacatgg actctgcgct cattcgggag ctcagtttat gcatcagcaa   9840
cgttcaggcg tggtccatga ccatagggtg gtttttcacg ccgccgccga ccgccatctc   9900
cccggtcgca tcccaccggc cccgaggccc ccgctctaga aggttgtatt ccgctactat   9960
aggcatctac atggacctgt aggtccacta cggccgccgc caccacctcc gcgcgccttt  10020
cagcgcctgc gccaaggtct acaacgcgtc gccgtttttc acgaggtacc agccctgcga  10080
gaccggccag tccgcgcgcg ttagcaactg cgagatctgg cacgttttcc tctcggacat  10140
tcgcccgtga gaaggcacca gaccacctat ttaagcgttc ccatagtacc gcctgctggc  10200
cccaagctcg gggcataggc cggcaggcgg cactaggtac gccaatggcg ggcgcacagc  10260
ttgggtccac acgctgcagt ctgttgcccc ctcacgagga aaaccgaagg aaggtccgcg  10320
ccgccgacga cgcgatcgaa aaaaccggtg accggcgcgc gtcgcattcg ccaatccgac  10380
ctttcgcttt cgtaattcac cgagcgaggg acatcggcct cccaataaaa ggttcccaac  10440
tcagcgccct gggggccaag ctcagagcct ggccggcctg acgccgcttg cccccaaacg  10500
```

-continued

```
gaggggcagt acgttctggg gcgaacgttt aaggaggcct ttgtccctgc tcggggaaaa  10560
aacgaaaagg gtctacgtag gccacgacgc cgtctacgcg gggggaggag tcgtcgccgt  10620
tctcgttctc gtcgccgtct gtacgtcccg tgggagggga ggaggatggc gcagtcctcc  10680
ccgctgtagg cgccaactgc gccgtcgtct accactaatg cttgggggcg ccgcggcccg  10740
ggccgtgatg gacctgaacc tcctcccgct cccggaccgc gccgatcctc gcgggagagg  10800
actcgccgtg ggttcccacg tcgacttcgc actatgcgca ctccgcatgc acggcgccgt  10860
cttggacaaa gcgctggcgc tccctctcct cgggctcctc tacgccctag ctttcaaggt  10920
gcgtcccgcg ctcgacgccg taccggactt agcgctcgcc aacgacgcgc tcctcctgaa  10980
actcgggctg cgcgcttggc cctaatcagg gcgcgcgcgt gtgcaccgcc ggcggctgga  11040
ccattggcgt atgctcgtct gccacttggt cctctaattg aaagtttttt cgaaattgtt  11100
ggtgcacgca tgcgaacacc gcgcgctcct ccaccgatat cctgactacg tagacaccct  11160
gaaacattcg cgcgacctcg ttttgggttt atcgttcggc gagtaccgcg tcgacaagga  11220
atatcacgtc gtgtcgtccc tgttgctccg taagtcccta cgcgacgatt tgtatcatct  11280
cgggctcccg gcgaccgacg agctaaacta tttgtaggac gtctcgtatc accacgtcct  11340
cgcgtcgaac tcggaccgac tgttccaccg gcggtagttg ataaggtacg aatcggaccc  11400
gttcaaaatg cgggcgttct atatggtatg gggaatgcaa gggtatctgt tcctccattt  11460
ctagctcccc aagatgtacg cgtaccgcga cttccacgaa tggaactcgc tgctggaccc  11520
gcaaatagcg ttgctcgcgt aggtgttccg gcactcgcac tcggccgccg cgctcgagtc  11580
gctggcgctc gactacgtgt cggacgtttc ccgggaccga ccgtgcccgt cgccgctatc  11640
tctccggctc aggatgaaac tgcgcccgcg actggacgcg acccggggtt cggctgcgcg  11700
ggacctccgt cgaccccggc ctggacccga ccgccaccgt gggcgcgcgc gaccgttgca  11760
gccgccgcac ctccttatac tgctcctgct actcatgctc ggtctcctgc cgctcatgat  11820
tcgccactac aaagactagt ctactacgtt ctgcgttgcc tgggccgcca cgcccgccgc  11880
gacgtctcgg tcggcaggcc ggaattgagg tgcctgctga ccgcggtcca gtacctggcg  11940
tagtacagcg actgacgcgc gttaggactg cgcaaggccg tcgtcggcgt ccggttggcc  12000
gagaggcgtt aagaccttcg ccaccagggc cgcgcgcgtt tggggtgcgt gctcttccac  12060
gaccgctagc atttgcgcga ccggcttttg tcccggtagg ccgggctgct ccggccggac  12120
cagatgctgc gcgacgaagt cgcgcaccga gcaatgttgt cgccgttgca cgtctggttg  12180
gacctggccg accacccct acacgcgctc cggcaccgcg tcgcactcgc gcgcgtcgtc  12240
gtcccgttgg acccgaggta ccaacgtgat ttgcggaagg actcatgtgt cgggcggttg  12300
cacggcgccc ctgtcctcct gatgtggttg aaacactcgc gtgacgccga ttaccactga  12360
ctctgtggcg tttcactcca catggtcaga cccggtctga taaaaaaggt ctggtcatct  12420
gttccggacg tctggcattt ggactcggtc cgaaagtttt tgaacgtccc cgacacccc  12480
cacgcccgag ggtgtccgct ggcgcgctgg cacagatcga acgactgcgg gttgagcgcg  12540
gacaacgacg acgattatcg cgggaagtgc ctgtcaccgt cgcacagggc cctgtgtatg  12600
gatccagtga acgactgtga catggcgctc cggtatccag tccgcgtaca cctgctcgta  12660
tgaaaggtcc tctaatgttc acagtcggcg cgcgaccccg tcctcctgtg cccgtcggac  12720
ctccgttggg atttgatgga cgactggttg gccgccgtct tctaggggag caacgtgtca  12780
aatttgtcgc tcctcctcgc gtaaaacgcg atgcacgtcg tctcgcactc ggaattggac  12840
```

-continued

```
tacgcgctgc cccattgcgg gtcgcaccgc gacctgtact ggcgcgcgtt gtaccttggc  12900
ccgtacatac ggagtttggc cggcaaatag ttggcggatt acctgatgaa cgtagcgcgc  12960
cggcggcact tggggctcat aaagtggtta cggtagaact tgggcgtgac cgatggcggg  13020
ggaccaaaga tgtggccccc taagctccac gggctcccat tgctacctaa ggagaccctg  13080
ctgtatctgc tgtcgcacaa aaggggcgtt ggcgtctggg acgatctcaa cgttgtcgcg  13140
ctcgtccgtc tccgccgcga cgctttcctt tcgaaggcgt ccggttcgtc gaacaggcta  13200
gatccgcgac gccggggcgc cagtctacga tcatcgggta aaggttcgaa ctatcccaga  13260
gaatggtcgt gagcgtggtg ggcgggcgcg gacgacccgc tcctcctcat ggatttgttg  13320
agcgacgacg tcggcgtcgc gctttttttg gacggaggcc gtaaagggtt gttgccctat  13380
ctctcggatc acctgttcta ctcatctacc ttctgcatgc gcgtcctcgt gtccctgcac  13440
ggtccgggcg cgggcgggtg ggcagcagtt tccgtgctgg cagtcgcccc agaccacacc  13500
ctcctgctac tgagccgtct gctgtcgtcg caggacctaa accctccctc accgttgggc  13560
aaacgcgtgg aagcggggtc cgacccctct tacaaaattt tttttttttt cgtactacgt  13620
tttatttttt gagtggttcc ggtaccgtgg ctcgcaacca aaagaacata aggggaatca  13680
tacgccgcgc gccgctacat actccttcca ggaggaggga ggatgctctc acaccactcg  13740
cgccgcggtc accgccgccg cgacccaaga gggaagctac gaggggacct gggcggcaaa  13800
cacggaggcg ccatggacgc cggatggccc ccctctttgt cgtaggcaat gagactcaac  13860
cgtggggata agctgtggtg ggcacacatg gaccacctgt tgttcagttg cctacaccgt  13920
agggacttga tggtcttgct ggtgtcgttg aaagactggt gccagtaagt tttgttactg  13980
atgtcgggcc ccctccgttc gtgtgtctgg tagttagaac tgctggccag cgtgaccccg  14040
ccgctggact tttggtagga cgtatggttg tacggtttac acttgctcaa gtacaaatgg  14100
ttattcaaat tccgcgccca ctaccacagc gcgaacggat gattcctgtt agtccacctc  14160
gactttatgc tcacccacct caagtgcgac gggctcccgt tgatgaggct ctggtactgg  14220
tatctggaat acttgttgcg ctagcacctc gtgatgaact ttcacccgtc tgtcttgccc  14280
caagaccttt cgctgtagcc ccatttcaaa ctgtgggcgt tgaagtctga ccccaaactg  14340
gggcagtgac cagaacagta cggaccccat atatgtttgc ttcggaaggt aggtctgtag  14400
taaaacgacg gtcctacgcc ccacctgaag tgggtgtcgg cggactcgtt gaacaacccg  14460
taggcgttcg ccgttgggaa ggtcctcccg aaatcctagt ggatgctact agacctccca  14520
ccattgtaag ggcgtgacaa cctacacctg cggatggtcc gctcgaactt tctactgtgg  14580
cttgtcccgc ccccaccgcg tccgccgtcg ttgtcgtcac cgtcgccgcg ccttctcttg  14640
aggttgcgcc gtcggcgccg ttacgtcggc cacctcctgt acttgctagt acggtaagcg  14700
ccgctgtgga aacggtgtgc ccgactcctc ttcgcgcgac tccggcttcg tcgccggctt  14760
cgacggcggg ggcgacgcgt tgggctccag ctcttcggag tcttctttgg ccactagttt  14820
ggggactgtc tcctgtcgtt ctttgcgtca atgttggatt attcgttact gtcgtggaag  14880
tgggtcatgg cgtcgaccat ggaacgtatg ttgatgccgc tgggagtctg gccttaggcg  14940
agtacctggg acgaaacgtg aggactgcat tggacgccga gcctcgtcca gatgaccagc  15000
aacggtctgt actacgttct ggggcactgg aaggcgaggt gcgcggtcta gtcgttgaaa  15060
ggccaccacc cgcggctcga caacgggcac gtgaggttct cgaagatgtt gctggtccgg  15120
cagatgaggg ttgagtaggc ggtcaaatgg agagactggg tgcacaagtt agcgaaaggg  15180
ctcttggtct aaaaccgcgc gggcggtcgg gggtggtagt ggtggcagtc acttttgcaa  15240
```

-continued

```
ggacgagagt gtctagtgcc ctgcgatggc gacgcgttgt cgtagcctcc tcaggtcgct  15300
cactggtaat gactgcggtc tgcggcgtgg acggggatgc aaatgttccg ggacccgtat  15360
cagagcggcg cgcaggatag ctcggcgtga aaaactcgtt cgtacaggta ggaatatagc  15420
gggtcgttat tgtgtccgac cccggacgcg aagggttcgt tctacaaacc gccccggttc  15480
ttcgcgaggc tggttgtggg tcacgcgcac gcgcccgtga tggcgcgcgg gaccccgcgc  15540
gtgtttgcgc cggcgtgacc cgcgtggtgg cagctactgc ggtagctgcg ccaccacctc  15600
ctccgcgcgt tgatgtgcgg gtgcggcggt ggtcacaggt gtcacctgcg ccggtaagtc  15660
tggcaccacg cgcctcgggc cgcgatacga ttttacttct ctgccgcctc cgcgcatcgt  15720
gcagcggtgg cggcggctgg gccgtgacgg cgggttgcgc gccgccgccg ggacgaattg  15780
gcgcgtgcag cgtggccggc tgcccgccgg tacgcccggc gagcttccga ccggcgccca  15840
taacagtgac acggggggtc caggtccgct gctcgccggc ggcgtcgtcg gcgccggtaa  15900
tcacgatact gagtcccagc gtccccgttg cacataaccc acgcgctgag ccaatcgccg  15960
gacgcgcacg ggcacgcgtg ggcgggggc gcgttgatct aacgttcttt tttgatgaat  16020
ctgagcatga caacatacat aggtcgccgc cgccgcgcgt tgcttcgata caggttcgcg  16080
ttttagtttc ttctctacga ggtccagtag cgcggcctct agataccggg gggcttcttc  16140
cttctcgtcc taatgttcgg ggctttcgat ttcgcccagt ttttcttttt ctttctacta  16200
ctactacttg aactgctgct ccaccttgac gacgtgcgat ggcgcgggtc cgctgcccat  16260
gtcacctttc cagctgcgca ttttgcacaa aacgctgggc cgtggtggca tcagaaatgc  16320
gggccactcg cgaggtgggc gtggatgttc gcgcacatac tactccacat gccgctgctc  16380
ctggacgaac tcgtccggtt gctcgcggag cccctcaaac ggatgccttt cgccgtattc  16440
ctgtacgacc gcaacggcga cctgctcccg ttgggttgtg gatcggattt cgggcattgt  16500
gacgtcgtcc acgacgggcg cgaacgtggc aggcttcttt tcgcgccgga tttcgcgctc  16560
agaccactga accgtgggtg gcacgtcgac taccatgggt tcgcggtcgc tgaccttcta  16620
cagaaccttt tttactggca ccttggaccc gacctcgggc tccaggcgca cgccggttag  16680
ttcgtccacc gcggccctga cccgcacgtc tggcacctgc aagtctatgg gtgatggtca  16740
tcgtggtcat aacggtggcg gtgtctcccg tacctctgtg tttgcagggg ccaacggagt  16800
cgccaccgcc tacggcgcca cgtccgccag cgacgccggc gcaggttctg gagatgcctc  16860
cacgtttgcc tgggcaccta caaagcgcaa agtcgggggg ccgcgggcgc ggcaagctcc  16920
ttcatgccgc ggcggtcgcg cgatgacggg cttatacggg atgtaggaag gtaacgcgga  16980
tgggggccga tagcaccgat gtggatggcg gggtcttctg ctcgttgatg ggctgcggct  17040
tggtggtgac cttgggcggc ggcggcagcg gcagcggtcg ggcacgaccg gggctaaagg  17100
cacgcgtccc accgagcgct tcctccgtcc tgggaccacg acggttgtcg cgcgatggtg  17160
gggtcgtagc aaattttcgg ccagaaacac caagaacgtc tataccggga gtggacggcg  17220
gaggcaaagg gccacggccc taaggctcct tcttacgtgg catcctcccc gtaccggccg  17280
gtgccggact gcccgccgta cgcagcacgc gtggtggccg ccgccgcgcg cagcgtggca  17340
gcgtacgcgc cgccatagga cggggaggaa taaggtgact agcggcgccg ctaaccgcgg  17400
cacgggcctt aacgtaggca ccggaacgtc cgcgtctctg tgactaattt ttgttcaacg  17460
tacacctttt tagttttatt tttcagacct gagagtgcga gcgaaccagg acattgataa  17520
aacatcttac cttctgtagt tgaaacgcag agaccggggc gctgtgccga gcgcgggcaa  17580
```

-continued

```
gtaccctttg accgttctat agccgtggtc gttatactcg ccaccgcgga agtcgacccc  17640
gagcgacacc tcgccgtaat ttttaaagcc aaggtggcaa ttcttgatac cgtcgttccg  17700
gaccttgtcg tcgtgtccgg tctacgactc cctattcaac tttctcgttt taaaggttgt  17760
tttccaccat ctaccggacc ggagaccgta atcgccccac cacctggacc ggttggtccg  17820
tcacgtttta ttctaattgt cattcgaact aggggcggga gggcatctcc tcggaggtgg  17880
ccggcacctc tgtcacagag gtctccccgc accgcttttc gcaggcgcgg ggctgtccct  17940
tctttgagac cactgcgttt atctgctcgg agggagcatg ctcctccgtg atttcgttcc  18000
ggacgggtgg tgggcagggt agcgcgggta ccgatggcct cacgacccgg tcgtgtgtgg  18060
gcattgcgac ctggacggag gggggcggct gtgggtcgtc tttggacacg acggtccggg  18120
ctggcggcaa caacattggg caggatcggc gcgcagggac gcggcgcggc ggtcgccagg  18180
cgctagcaac gccgggcatc ggtcaccgtt gaccgtttcg tgtgacttgt cgtagcaccc  18240
agacccccac gttagggact tcgcggctgc tacgaagact atcgattgca cagcatacac  18300
acagtacata cgcaggtaca gcggcggtct cctcgacgac tcggcggcgc gcgggcgaaa  18360
ggttctaccg atggggaagc tactacggcg tcaccagaat gtacgtgtag agcccggtcc  18420
tgcggagcct catggactcg gggcccgacc acgtcaaacg ggcgcggtgg ctctgcatga  18480
agtcggactt attgttcaaa tctttggggt gccaccgcgg atgcgtgctg cactggtgtc  18540
tggccagggt cgcaaactgc gacgccaagt agggacacct ggcactccta tgacgcatga  18600
gcatgttccg cgccaagtgg gatcgacacc cactattggc acacgacctg taccgaaggt  18660
gcatgaaact gtaggcgccg cacgacctgt ccccgggatg aaaattcggg atgagaccgt  18720
gacggatgtt gcgggaccga gggttcccac ggggtttagg aacgcttacc ctacttcgac  18780
gatgacgaga actttatttg gatcttcttc tcctgctact gttgcttctg cttcatctgc  18840
tcgttcgact cgtcgttttt tgagtgcata aacccgtccg cggaataaga ccatatttat  18900
aatgtttcct cccataagtt tatccacagc ttccagtttg tggatttata cggctatttt  18960
gtaaagttgg acttggagtt tatcctctta gagtcaccat gctttgtctt taattagtac  19020
gtcgaccctc tcaggatttt ttctgatggg gttactttgg tacaatgcca agtatacgtt  19080
ttgggtgttt acttttacct cccgttccgt aagaacattt cgttgtttta cctttcgatc  19140
tttcagttca cctttacgtt aaaaagagtt gatgactccg tcggcgtccg ttaccactat  19200
tgaactgagg atttcaccat aacatgtcac ttctacatct atatctttgg ggtctgtgag  19260
tataaagaat gtacgggtga taattccttc cattgagtgc tcttgattac ccggttgtta  19320
gatacgggtt gtccggatta atgtaacgaa aatccctgtt aaaataacca gattacataa  19380
tgttgtcgtg cccattatac ccacaagacc gcccggttcg tagcgtcaac ttacgacaac  19440
atctaaacgt tctgtctttg tgtctcgaaa gtatggtcga aaacgaacta aggtaaccac  19500
tatcttggtc catgaaaaga tacaccttag tccgacaact gtcgatacta ggtctacaat  19560
cttaataact tttagtacct tgacttctac ttgaaggttt aatgacgaaa ggtgaccctc  19620
cacactaatt atgtctctga gaatggttcc attttggatt ttgtccagtc cttttaccta  19680
ccctttttct acgatgtctt aaaagtctat ttttacttta ttctcaacct ttattaaaac  19740
ggtaccttta gttagattta cggttggaca cctctttaaa ggacatgagg ttgtatcgcg  19800
acataaacgg gctgttcgat ttcatgtcag gaaggttgca tttttaaaga ctattgggtt  19860
tgtggatgct gatgtacttg ttcgctcacc accgagggcc cgatcacctg acgatgtaat  19920
tggaacctcg tgcgaccagg gaactgatat acctgttgca gttgggtaaa ttggtggtgg  19980
```

-continued

```
cgttacgacc ggacgcgatg gcgagttaca acgacccgtt accagcgata cacgggaagg  20040
tgtaggtcca cggagtcttc aagaaacggt aatttttgga ggaagaggac ggcccgagta  20100
tgtggatgct caccttgaag tccttcctac aattgtacca agacgtctcg agggatcctt  20160
tactggattc ccaactgcct cggtcgtaat tcaaactatc gtaaacggaa atgcggtgga  20220
agaaggggta ccgggtgttg tggcggaggt gcgaactccg gtacgaatct ttgctgtggt  20280
tgctggtcag gaaattgctg atagagaggc ggcggttgta cgagatggga tatgggcggt  20340
tgcgatggtt gcacgggtat aggtagggga gggcgttgac ccgccgaaag gcgccgaccc  20400
ggaagtgcgc ggaattctga ttcctttggg gtagtgaccc gagcccgatg ctgggaataa  20460
tgtggatgag accgagatat gggatggatc taccttggaa aatggagttg gtgtggaaat  20520
tcttccaccg gtaatggaaa ctgagaagac agtcgaccgg accgttactg gcggacgaat  20580
gggggttgct caaactttaa ttcgcgagtc aactgcccct cccaatgttg caacgggtca  20640
cattgtactg gtttctgacc aaggaccatg tttacgatcg attgatattg taaccgatgg  20700
tcccgaagat atagggtctc tcgatgttcc tggcgtacat gaggaagaaa tctttgaagg  20760
tcgggtactc ggcagtccac cacctactat gatttatgtt cctgatggtt gtccacccgt  20820
aggatgtggt tgtgttgttg agacctaaac aaccgatgga acgggggtgg tacgcgcttc  20880
ctgtccggat gggacgattg aaggggatag gcgaatatcc gttctggcgt caactgtcgt  20940
aatgggtctt tttcaaagaa acgctagcgt gggaaaccgc gtagggtaag aggtcattga  21000
aatacaggta cccgcgtgag tgtctggacc cggttttgga agagatgcgg ttgaggcggg  21060
tgcgcgatct gtactgaaaa ctccacctag ggtacctgct cgggtgggaa gaaatacaaa  21120
acaaacttca gaaactgcac caggcacacg tggtcggcgt ggcgccgcag tagctttggc  21180
acatggacgc gtgcgggaag agccggccgt tgcggtgttg tatttcttcg ttcgttgtag  21240
ttgttgtcga cggcggtacc cgaggtcact cgtccttgac tttcggtaac agtttctaga  21300
accaacaccc ggtataaaaa acccgtggat actgttcgcg aaaggtccga aacaaagagg  21360
tgtgttcgag cggacgcggt atcagttatg ccggccagcg ctctgacccc cgcatgtgac  21420
ctaccggaaa cggaccttgg gcgtgagttt ttgtacgatg gagaaactcg ggaaaccgaa  21480
aagactggtc gctgagttcg tccaaatggt caaactcatg ctcagtgagg acgcggcatc  21540
gcggtaacga agaagggggc tggcgacata ttgcgacctt ttcaggtggg tttcgcatgt  21600
ccccgggttg agccggcgga cacctgataa gacgacgtac aaagaggtgc ggaaacggtt  21660
gaccggggtt tgagggtacc tagtgttggg gtggtacttg gaataatggc cccatgggtt  21720
gaggtacgag ttgtcagggg tccatgtcgg gtgggacgca gcgttggtcc ttgtcgagat  21780
gtcgaaggac ctcgcggtga gcgggatgaa ggcgtcggtg tcacgcgtct aatcctcgcg  21840
gtgaagaaaa acagtgaact ttttgtacat ttttattaca tgatctctgt gaaagttatt  21900
tccgtttacg aaaataaaca tgtgagagcc cactaataaa tgggggtggg aacggcagac  21960
gcggcaaatt tttagtttcc ccaagacggc gcgtagcgat acgcggtgac cgtccctgtg  22020
caacgctatg accacaaatc acgaggtgaa tttgagtccg tgttggtagg cgccgtcgag  22080
ccacttcaaa agtgaggtgt ccgacgcgtg gtagtggttg cgcaaatcgt ccagcccgcg  22140
gctatagaac ttcagcgtca accccggagg cgggacgcgc gcgctcaacg ctatgtgtcc  22200
caacgtcgtg accttgtgat agtcgcggcc caccacgtgc gaccggtcgt gcgagaacag  22260
cctctagtct aggcgcaggt ccaggaggcg caacgagtcc cgcttgcctc agttgaaacc  22320
```

-continued

```
atcgacggaa gggtttttcc cgcgcacggg tccgaaactc aacgtgagcg tggcatcacc  22380
gtagttttcc actggcacgg gccagacccg caatcctatg tcgcggacgt attttcggaa  22440
ctagacgaat tttcggtgga ctcggaaacg cggaagtctc ttcttgtacg gcgttctgaa  22500
cggccttttg actaaccggc ctgtccggcg cagcacgtgc gtcgtggaac gcagccacaa  22560
cctctagacg tggtgtaaag ccggggtggc caagaagtgc tagaaccgga acgatctgac  22620
gaggaagtcg cgcgcgacgg gcaaaagcga gcagtgtagg taaagttagt gcacgaggaa  22680
taaatagtat tacgaaggca catctgtgaa ttcgagcgga agctagagtc gcgtcgccac  22740
gtcggtgttg cgcgtcgggc acccgagcac tacgaacatc cagtggagac gtttgctgac  22800
gtccatgcgg acgtccttag cggggtagta gcagtgtttc cagaacaacg accacttcca  22860
gtcgacgttg ggcgccacga ggagcaagtc ggtccagaac gtatgccggc ggtctcgaag  22920
gtgaaccagt ccgtcatcaa acttcaagcg gaaatctagc aataggtgca ccatgaacag  22980
gtagtcgcgc gcgcgtcgga ggtacgggaa gagggtgcgt ctgtgctagc cgtgtgagtc  23040
gcccaagtag tggcattaaa gtgaaaggcg aagcgacccg agaaggagaa ggagaacgca  23100
ggcgtatggt gcgcggtgac ccagcagaag taagtcggcg gcgtgacacg cgaatggagg  23160
aaacggtacg aactaatcgt ggccacccaa cgactttggg tggtaaacat cgcggtgtag  23220
aagagaaaga aggagcgaca ggtgctaatg gagaccacta ccgcccgcga gcccgaaccc  23280
tcttcccgcg aagaaaaaga agaacccgcg ttaccggttt aggcggcggc tccagctacc  23340
ggcgcccgac ccacacgcgc cgtggtcgcg cagaacacta ctcagaagga gcaggagcct  23400
gagctatgcg gcggagtagg cgaaaaaacc cccgcgggcc cctccgccgc cgctgcccct  23460
gcccctgctg tgcaggaggt accaacccc tgcagcgcgg cgtggcgcag gcgcgagccc  23520
ccaccaaagc gcgacgagga gaagggctga ccggtaaagg aagaggatat ccgtcttttt  23580
ctagtacctc agtcagctct tcttcctgtc ggattggcgg gggagactca agcggtggtg  23640
gcggaggtgg ctacggcggt tgcgcggatg gtggaagggg cagctccgtg ggggcgaact  23700
cctcctcctt cactaatagc tcgtcctggg tccaaaacat tcgcttctgc tgctcctggc  23760
gagtcatggt tgtctcctat ttttcgttct ggtcctgttg cgtctccgtt tgctccttgt  23820
tcagcccgcc cccctgcttt ccgtaccgct gatggatcta caccctctgc tgcacgacaa  23880
cttcgtagac gtcgcggtca cgcggtaata gacgctgcgc aacgttctcg cgtcgctaca  23940
cggggagcgg tatcgcctac agtcggaacg gatgcttgcg gtggataaga gtggcgcgca  24000
tgggggggttt gcggttcttt tgccgtgtac gctcgggttg ggcgcggagt tgaagatggg  24060
gcataaacgg cacggtctcc acgaacggtg gatagtgtag aaaaaggttt tgacgttcta  24120
tggggatagg acggcacggt tggcgtcggc tcgcctgttc gtcgaccgga acgccgtccc  24180
gcgacagtat ggactatagc ggagcgagtt gcttcacggt ttttagaaac tcccagaacc  24240
tgcgctgctc ttcgcgcgcc gtttgcgaga cgttgtcctt ttgtcgcttt tactttcagt  24300
gagacctcac aaccaccttg agctcccact gttgcgcgcg gatcggcatg attttgcgtc  24360
gtagctccag tgggtgaaac ggatgggccg tgaattggat ggggggttcc agtactcgtg  24420
tcagtactca ctcgactagc acgcggcacg cgtcggggac ctctccctac gtttaaacgt  24480
tcttgtttgt ctcctcccgg atgggcgtca accgctgctc gtcgatcgcg cgaccgaagt  24540
ttgcgcgctc ggacggctga acctcctcgc tgcgtttgat tactaccggc gtcacgagca  24600
atggcacctc gaactcacgt acgtcgccaa gaaacgactg ggcctctacg tcgcgttcga  24660
tctcctttgt aacgtgatgt ggaaagctgt cccgatgcat gcggtccgga cgttctagag  24720
```

-continued gttgcacctc gagacgttgg accagaggat ggaaccttaa aacgtgcttt tggcggaacc 24780
cgttttgcac gaagtaaggt gcgagttccc gctccgcgcg gcgctgatgc aggcgctgac 24840
gcaaatgaat aaagatacga tgtggaccgt ctgccggtac ccgcaaaccg tcgtcacgaa 24900
cctcctcacg ttggagttcc tcgacgtctt tgacgatttc gttttgaact tcctggatac 24960
ctgccggaag ttgctcgcga ggcaccggcg cgtggaccgc ctgtagtaaa aggggcttgc 25020
ggacgaattt tgggacgttg tcccagacgg tctgaagtgg tcagtttcgt acaacgtctt 25080
gaaatccttg aaataggatc tcgcgagtcc ttagaacggg cggtggacga cacgtgaagg 25140
atcgctgaaa cacgggtaat tcatggcgct tacgggaggc ggcgaaaccc cggtgacgat 25200
ggaagacgtc gatcggttga tggaacggat ggtgagactg tattaccttc tgcactcgcc 25260
actgccagat gacctcacag tgacagcgac gttggatacg tggggcgtgg cgagggacca 25320
aacgttaagc gtcgacgaat tgctttcagt ttaatagcca tggaaactcg acgtcccagg 25380
gagcggactg cttttcaggc gccgaggccc caactttgag tgaggccccg acacctgcag 25440
ccgaatggaa gcgtttaaac atggactcct gatggtgcgg gtgctctaat ccaagatgct 25500
tctggttagg gcgggcggat tacgcctcga atggcggacg cagtaatggg tcccggtgta 25560
agaaccggtt aacgttcggt agttgtttcg ggcggttctc aaagacgatg ctttccctgc 25620
cccccaaatg aacctggggg tcaggccgct cctcgagttg ggttaggggg gcggcggcgt 25680
cgggatagtc gtcgtcggcg cccgggaacg aagggtccta ccgtgggttt ttcttcgacg 25740
tcgacggcgg cggtgggtgc ctgctcctcc ttatgaccct gtcagtccgt ctcctccaaa 25800
acctgctcct cctcctcctg tactaccttc tgaccctctc ggatctgctc cttcgaaggc 25860
tccagcttct ccacagtctg ctttgtggca gtgggagcca gcgtaagggg agcggccgcg 25920
gggtctttag ccgttggcca aggtcgtacc gatgttggag gcgaggagtc cgcggcggcc 25980
gtgacgggca agcggctggg ttggcatcta ccctgtggtg accttggtcc cggccattca 26040
ggttcgtcgg cggcggcaat cgggttctcg ttgttgtcgc ggttccgatg gcgagtaccg 26100
cgcccgtgtt cttgcggtat caacgaacga acgttctgac acccccgttg tagaggaagc 26160
gggcggcgaa agaagagatg gtagtgccgc accggaaggg ggcattgtag gacgtaatga 26220
tggcagtaga gatgtcgggt atgacgtggc cgccgtcgcc gtcgttgtcg tcgccggtgt 26280
gtcttcgttt ccgctggcct atcgttctga gactgtttcg ggttctttag gtgtcgccgc 26340
cgtcgtcgtc ctcctcctcg cgacgcagac cgcgggttgc ttgggcatag ctgggcgctc 26400
gaatctttgt cctaaaaagg gtgagacata cgatataaag ttgtctcgtc cccggttctt 26460
gttctcgact tttatttttt gtccagagac gctagggagt gggcgtcgac ggacatagtg 26520
ttttcgcttc tagtcgaagc cgcgtgcgac cttctgcgcc tccgagagaa gtcatttatg 26580
acgcgcgact gagaattcct gatcaaagcg cgggaaagag tttaaattcg cgcttttgat 26640
gcagtagagg tcgccggtgt gggccgcggt cgtggacaac agtcgcggta atactcgttc 26700
ctttaagggt gcgggatgta cacctcaatg gtcggtgttt accctgaacg ccgacctcga 26760
cgggttctga tgagttgggc ttatttgatg tactcgcgcc ctggggtgta ctatagggcc 26820
cagttgcctt atgcgcgggt ggctttggct taagaggacc ttgtccgccg ataatggtgg 26880
tgtggagcat tattggaatt aggggcatca accgggcgac gggaccacat ggtcctttca 26940
gggcgagggt ggtgacacca tgaagggtct ctgcgggtcc ggcttcaagt ctactgattg 27000
agtccccgcg tcgaacgccc gccgaaagca gtgtcccacg ccagcgggcc cgtcccatat 27060

-continued

```
tgagtggact gttagtctcc cgctccataa gtcgagttgc tgctcagcca ctcgaggagc  27120
gaaccagagg caggcctgcc ctgtaaagtc tagccgccgc ggccggcgag aagtaagtgc  27180
ggagcagtcc gttaggattg agacgtctgg agcaggagac tcggcgcgag acctccgtaa  27240
ccttgagacg ttaaataact cctcaaacac ggtagccaga tgaaattggg gaagagccct  27300
ggagggccgg tgataggcct agttaaataa ggattgaaac tgcgccattt cctgagccgc  27360
ctgccgatgc tgacttacaa ttcacctctc cgtctcgttg acgcggactt tgtggaccag  27420
gtgacagcgg cggtgttcac gaaacgggcg ctgaggccac tcaaaacgat gaaacttaac  27480
gggctcctag tatagctccc gggccgcgtg ccgcaggccg aatggcgggt ccctctcgaa  27540
cgggcatcgg actaagccct caaatgggtc gcgggggacg atcaactcgc cctgtcccct  27600
gggacacaag agtgacacta aacgttgaca ggattgggac ctaatgtagt tctagaaaca  27660
acggtagaga cacgactcat attatttatg tctttaattt tatatgaccc cgaggatagc  27720
ggtaggacat ttgcggtggc agaagtgggc gggttcgttt ggttccgctt ggaatggacc  27780
atgaaaattg tagagaggga gacactaaat gttgtcaaag ttgggtctgc ctcactcaga  27840
tgctctcttg gagaggctcg agtcgatgag gtagtctttt ttgtggtggg aggaatggac  27900
ggcccttgca tgctcacgca gtggccggcg acgtggtgtg gatggcggac tggcatttgg  27960
tctgaaaaag gcctgtctgg agttattgag acaaatggtc ttgtcctcca ctcgaatctt  28020
ttgggaatcc cataatccgg tttccgcgtc gatgacaccc caaatacttg ttaagttcgt  28080
tgagatgccc gataagatta agtccaaaga gatcttagcc ccaaccccaa taagagacag  28140
aacactaaga gaaataagaa tatgattgcg aagagacgga ttccgagcgg cggacgacac  28200
acgtgtaaac gtaaataaca gtcgaaaaat ttgcgacccc agcggtgggt tctactaatc  28260
catgtattag gatccaaatg agtgggaacg cagtcgggtg ccatggtggg ttttccacct  28320
aaaattcctc ggtcggacat tacaatgtaa gcgtcgactt cgattactca cgtggtgaga  28380
atattttacg tggtgtcttg tacttttcga cgaataagcg gtgtttttgt tttaaccgtt  28440
catacgacaa atacgataaa ccgtcggtcc actgtgatgt ctcatattac aatgtcaaaa  28500
ggtcccattt tcagtatttt gaaaatacat atgaaaaggt aaaatacttt acacgctgta  28560
atggtacatg tactcgtttg tcatattcaa caccgggggt gttttaacac accttttgtg  28620
accgtgaaag acgacgtgac gatacgatta atgtcacgag cgaaaccaga catgggatga  28680
gatataattt atgttttcgt ctgcgtcgaa ataactcctt ttcttttacg gaattaaatg  28740
attcaatgtt tcgattacag tggtgattga cgaaatgagc gacgaacgtt ttgtttaagt  28800
ttttcaatcg taatattaat cttatcctaa atttgggggg ccagtaaagg acgagttatg  28860
gtaaggggac ttgttaactg agatacaccc tatacgaggt cgcgatgttg gaacttcagt  28920
ccgaaggacc tacagtcgta gactgaaacc ggtcgtggac agggcgccta aacaaggtca  28980
ggttgatgtc gctgggtggg attgtctcta ctggttgtgt tggttgcgcc ggcggcgatg  29040
gcctgaatgt agatggtgtt tatgtggggt tcaaagacgg aaacagttat tgaccctatt  29100
gaacccgtac accaccaaga ggtatcgcga atacaaacat acggaataat aatacaccga  29160
gtagacgacg gatttcgcgt ttgcgcgggc tggtgggtag atatcagggt agtaacacga  29220
tgtgggtttg ttactacctt aggtatctaa cctgcctgac tttgtgtaca agaaaagaga  29280
atgtcatact aatttactct gtactaagga gctcaaaaat ataatgactg ggaacaacgc  29340
gaaaaaacac gcacgaggtg taaccgacgc caaagagtgt agcttcatct gacgtaaggt  29400
cggaagtgtc agataaacga aatgcctaaa cagtgggagt gcgagtagac gtcggagtag  29460
```

-continued

```
tgacaccagt agcggaaata ggtcacgtaa ctgacccaga cacacgcgaa acgtatagag  29520
tctgtggtag ggtcatgtc cctgtcctga tatcgactcg aagaatctta agaaattaat  29580
actttaaatg acactgaaaa gacgactaat aaacgtggga tagacgcaaa acaaggggct  29640
ggaggttcgg agtttctgta tatagtacgt ctaagtgagc atataccttta taaggttcaa  29700
cgatgttact tttttcgcta gaaaggcttc ggaccaatat acgttagtag agacaatacc  29760
acaagacgtc atggtagaat cgggatcgat atatagggat ggaactgtaa ccgaccttgc  29820
gttatctacg gtacttggtg ggttgaaagg ggcgcgggcg atacgaaggt gacgttgttc  29880
aacaacggcc gccgaaacag ggtcggttag tcggagcggg tggaagaggg tgggggtgac  29940
tttagtcgat gaaattagat tgtcctcctc tactgactgt gggatctaga tctttacctg  30000
ccttaataat gtctcgtcgc ggacgatctt tctgcgtccc gtcgccggct cgttgtcgcg  30060
tacttagttc tcgaggttct gtaccaattg aacgtggtca cgttttcccc atagaaaaca  30120
gagcatttcg tccggtttca gtggatgctg tcattatggt ggcctgtggc ggaatcgatg  30180
ttcaacggtt ggttcgcagt ctttaaccac cagtaccacc ctcttttcgg gtaatggtat  30240
tgagtcgtga gccatctttg gcttccgacg taagtgagtg gaacagttcc tggactccta  30300
gagacgtggg aataattctg ggacacgcca gagtttctag aataagggaa attgattatt  30360
ttttttatt atttcgtagt gaatgaattt tagtcaatcg tttaaagaca ggtcaaataa  30420
gtcgtcgtgg aggaacggga ggagggtcga gaccataacg tcgaaggagg accgacgttt  30480
gaaagaggtg ttagatttac cttacagtca aaggaggaca aggacaggta ggcgtgggtg  30540
atagaagtac aacaacgtct acttcgcgcg ttctggcaga cttctatgga agttggggca  30600
cataggtata ctgtgccttt ggccaggagg ttgacacgga aaagaatgag gagggaaaca  30660
taggggggtta cccaaagttc tctcaggggg accccatgag agaaacgcgg ataggcttgg  30720
agatcaatgg aggttaccgt acgaacgcga gttttacccg ttgccggaga gagacctgct  30780
ccggccgttg gaatggaggg ttttacattg gtgacactcg ggtggagagt ttttttggtt  30840
cagtttgtat ttggaccttt atagacgtgg ggagtgtcaa tggagtcttc gggattgaca  30900
ccgacggcgg cgtggagatt accagcgccc gttgtgtgag tggtacgtta gtgtccgggg  30960
cgattggcac gtgctgaggt ttgaatcgta acggtgggtt cctggggagt gtcacagtct  31020
tcctttcgat cgggacgttt gtagtccggg ggagtggtgg tggctatcgt catgggaatg  31080
atagtgacgg agtgggggaa attgatgacg gtgaccatcg aacccgtaac tgaactttct  31140
cgggtaaata tgtgttttac cttttgatcc tgatttcatg ccccgaggaa acgtacattg  31200
tctgctggat ttgtgaaact ggcatcgttg accaggtcca cactgataat tattatgaag  31260
gaacgtttga tttcaatgac ctcggaaccc aaaactaagt gttccgttat acgttgaatt  31320
acatcgtcct cctgattcct aactaagagt tttgtctgcg gaatatgaac tacaatcaat  31380
aggcaaacta cgagttttgg ttgatttaga ttctgatcct gtcccgggag aaaaatattt  31440
gagtcgggtg ttgaacctat aattgatgtt gtttccggaa atgaacaaat gtcgaagttt  31500
gttaaggttt ttcgaactcc aattggattc gtgacggttc cccaactaca aactgcgatg  31560
tcggtatcgg taattacgtc ctctacccga acttaaacca agtggattac gtggtttgtg  31620
tttaggggag ttttgttttt aaccggtacc ggatcttaaa ctaagtttgt tccgatacca  31680
aggatttgat ccttgaccgg aatcaaaact gtcgtgtcca cggtaatgtc atcctttgtt  31740
tttattacta ttcgattgaa acacctggtg tggtcgaggt agaggattga catctgattt  31800
```

-continued

```
acgtctcttt ctacgatttg agtgaaacca gaattgtttt acaccgtcag tttatgaacg  31860
atgtcaaagt caaaaccgac aatttccgtc aaaccgaggt tatagacctt gtcaagtttc  31920
acgagtagaa taatattcta aactgctttt acctcacgat gatttgttaa ggaaggacct  31980
gggtcttata accttgaaat ctttacctct agaatgactt ccgtgtcgga tatgtttgcg  32040
acaacctaaa tacggattgg atagtcgaat aggttttaga gtgccatttt gacggttttc  32100
attgtaacag tcagttcaaa tgaatttgcc tctgttttga tttggacatt gtgattggta  32160
atgtgatttg ccatgtgtcc tttgtcctct gtgttgaggt tcacgtatga gatacagtaa  32220
aagtaccctg accagaccgg tgttgatgta attactttat aaacggtgta ggagaatgtg  32280
aaaaagtatg taacgggttc ttatttctta gcaaacacaa tacaaagttg cacaaataaa  32340
aagttaacgt cttttaaagt tcagtaaaaa gtaagtcatc atatcggggt ggtggtgtat  32400
cgaatatgtc tagtggcatg gaattagttt gagtgtcttg ggatcataag ttggacggtg  32460
gagggagggt tgtgtgtctc atgtgtcagg aaagaggggc cgaccggaat ttttcgtagt  32520
atagtaccca ttgtctgtat aagaatccac aatataaggt gtgccaaagg acagctcggt  32580
ttgcgagtag tcactataat tatttgaggg gcccgtcgag tgaattcaag tacagcgaca  32640
ggtcgacgac tcggtgtccg acgacaggtt gaacgccaac gaattgcccg ccgcttcctc  32700
ttcaggtgcg gatgtacccc catctcagta ttagcacgta gtcctatccc gccaccacga  32760
cgtcgtcgcg cgcttatttg acgacggcgg cggcgaggca ggacgtcctt atgttgtacc  32820
gtcaccagag gagtcgctac taagcgtggc gggcgtcgta ttccgcggaa caggaggccc  32880
gtgtcgtcgc gtgggactag agtgaattta gtcgtgtcat tgacgtcgtg tcgtggtgtt  32940
ataacaagtt ttagggtgtc acgttccgcg acataggttt cgagtaccgc ccctggtgtc  33000
ttgggtgcac cggtagtatg gtgttcgcgt ccatctaatt caccgctggg gagtatttgt  33060
gcgacctgta tttgtaatgg agaaaaccgt acaacattaa gtggtggagg gccatggtat  33120
atttggagac taatttgtac cgcggtaggt ggtggtagga tttggtcgac cggttttgga  33180
cgggcggccg atatgtgacg tcccttggcc ctgaccttgt tactgtcacc tctcgggtcc  33240
tgagcattgg tacctagtag tacgagcagt actatagtta caaccgtgtt gtgtccgtgt  33300
gcacgtatgt gaaggagtcc taatgttcga ggagggcgca atcttggtat agggtccctt  33360
gttgggtaag gacttagtcg catttagggt gtgacgtccc ttctggagcg tgcattgagt  33420
gcaacacgta acagtttcac aatgtaagcc cgtcgtcgcc tactaggagg tcataccatc  33480
gcgcccaaag acagagtttt cctccatctg ctagggatga catgcctcac gcggctctgt  33540
tggctctagc acaaccagca tcacagtacg gtttaccttg cggcctgcat cagtataaag  33600
gacttcgttt tggtccacgc ccgcactgtt tgtctagacg cagaggccag agcggcgaat  33660
ctagcgagac acatcatcaa catcatatag gtgagagagt ttcgtaggtc cgcgggggac  33720
cgaagcccaa gatacatttg aggaagtacg cggcgacggg actattgtag gtggtggcgt  33780
cttattcggt gtgggtcggt tggatgtgta agcaagacgc tcagtgtgtg ccctcctcgc  33840
ccttctcgac cttcttggta caaaaaaaaa aataaggttt tctaataggt tttggagttt  33900
tacttctaga taattcactt gcgcgagggg aggccaccgc accagtttga gatgtcggtt  33960
tcttgtctat taccgtaaac attctacaac gtgttaccga aggttttccg tttgccggga  34020
gtgcaggttc acctgcattt ccgatttggg aagtcccact tagaggagat atttgtaagg  34080
tcgtggaagt tggtacgggt ttattaagag tagagcggtg gaagagttat atagagattc  34140
gtttagggct tataattcag gccggtaaca tttttagacg aggtctcgcg ggaggtggaa  34200
```

-continued

```
gtcggagttc gtcgcttagt actaacgttt ttaagtccaa ggagtgtctg gacatattct  34260
aagttttcgc cttgtaattg tttttatggc gctagggcat ccagggaagc gtcccggtcg  34320
acttgtatta gcacgtccag acgtgcctgg tcgcgccggt gaaggggcgg tccttggtac  34380
tgttttcttg ggtgtgacta atactgtgcg tatgagcctc gatacgattg gtcgcatcgg  34440
ggctacattc gaacaacgta cccgccgcta tattttacgt tccacgacga gttttttagt  34500
ccgtttcgga gcgcgttttt tctttcgtgt agcatcagta cgagtacgtc tatttccgtc  34560
cattcgaggc cttggtggtg tctttttctg tggtaaaaag agagtttgta cagacgccca  34620
aagacgtatt tgtgttttat tttattgttt ttttgtaaat ttgtaatctt cggacagaat  34680
gttgtccttt ttgttgggaa tattcgtatt ctgcctgatg ccggtacggc cgcactggca  34740
tttttttgac cagtggcact aatttttcgt ggtggctgtc gaggagccag tacaggcctc  34800
agtattacat tctgagccat ttgtgtagtc caactaagtg tagccagtca cgatttttcg  34860
ctggctttat cgggccccct tatgtatggg cgtccgcatc tctgttgtaa tgtcgggggt  34920
atcctccata ttgttttaat tatcctctct ttttgtgtat ttgtggactt tttgggagga  34980
cggatccgtt ttatcgtggg agggcgaggt cttgttgtat gtcgcgaagg tgtcgccgtc  35040
ggtattgtca gtcggaatgg tcattttttc ttttggataa tttttttgtg gtgagctgtg  35100
ccgtggtcga gttagtcagt gtcacatttt ttcccggttc acgtctcgct catatatatc  35160
ctgatttttt actgcattgc caatttcagg tgttttttgt gggtcttttg gcgtgcgctt  35220
ggatgcgggt ctttgctttc ggttttttgg gtgttgaagg agtttagcag tgaaggcaaa  35280
agggtgcaat gcagtgaagg gtaaaattct tttgatgtta agggttgtgt atgttcaatg  35340
aggcgggatt ttggatgcag tgggcggggc aagggtgcgg ggcgcggtgc agtgtttgag  35400
gtgggggagt aatagtataa ccgaagttag gttttattcc atataataac tactacaatt  35460
aattcttaag cctagacgct gcgctccgac ctaccggaag gggtaatact aagaagagcg  35520
aaggccgccg tagccctacg ggcgcaacgt ccggtacgac aggtccgtcc atctactgct  35580
ggtagtccct gtcgaagttc cggtcgtttt ccggtccttg gcatttttcc ggcgcaacga  35640
ccgcaaaaag gtatccgagg cggggggact gctcgtagtg tttttagctg cgagttcagt  35700
ctccaccgct ttgggctgtc ctgatatttc tatggtccgc aaagggggac cttcgaggga  35760
gcacgcgaga ggacaaggct gggacggcga atggcctatg gacaggcgga aagagggaag  35820
cccttcgcac cgcgaaagag tatcgagtgc gacatccata gagtcaagcc acatccagca  35880
agcgaggttc gacccgacac acgtgcttgg ggggcaagtc gggctggcga cgcggaatag  35940
gccattgata gcagaactca ggttgggcca ttctgtgctg aatagcggtg accgtcgtcg  36000
gtgaccattg tcctaatcgt ctcgctccat acatccgcca cgatgtctca agaacttcac  36060
caccggattg atgccgatgt gatcttcctg tcataaacca tagacgcgag acgacttcgg  36120
tcaatggaag ccttttttctc aaccatcgag aactaggccg tttgtttggt ggcgaccatc  36180
gccaccaaaa aaacaaacgt tcgtcgtcta atgcgcgtct ttttttccta gagttcttct  36240
aggaaactag aaaagatgcc ccagactgcg agtcaccttg cttttgagtg caattcccta  36300
aaaccagtac tctaatagtt tttcctagaa gtggatctag gaaaatttag ttagatttca  36360
tatatactca tttgaaccag actgtcaatg gttacgaatt agtcactccg tggatagagt  36420
cgctagacag ataaagcaag taggtatcaa cggactgagg ggcagcacat ctattgatgc  36480
tatgccctcc cgaatggtag accggggtca cgacgttact atggcgctct gggtgcgagt  36540
```

-continued

```
ggccgaggtc taaatagtcg ttatttggtc ggtcggcctt cccggctcgc gtcttcacca  36600

ggacgttgaa ataggcggag gtaggtcaga taattaacaa cggcccttcg atctcattca  36660

tcaagcggtc aattatcaaa cgcgttgcaa caacggtaac gatgtccgta gcaccacagt  36720

gcgagcagca aaccataccg aagtaagtcg aggccaaggg ttgctagttc cgctcaatgt  36780

actagggggt acaacacgtt ttttcgccaa tcgaggaagc caggaggcta gcaacagtct  36840

tcattcaacc ggcgtcacaa tagtgagtac caataccgtc gtgacgtatt aagagaatga  36900

cagtacggta ggcattctac gaaaagacac tgaccactca tgagttggtt cagtaagact  36960

cttatcacat acgccgctgg ctcaacgaga acgggccgca gttgtgccct attatggcgc  37020

ggtgtatcgt cttgaaattt tcacgagtag taaccttttg caagaagccc cgcttttgag  37080

agttcctaga atggcgacaa ctctaggtca agctacattg ggtgagcacg tgggttgact  37140

agaagtcgta gaaaatgaaa gtggtcgcaa agacccactc gtttttgtcc ttccgtttta  37200

cggcgttttt tcccttattc ccgctgtgcc tttacaactt atgagtatga gaaggaaaaa  37260

gttataataa cttcgtaaat agtcccaata acagagtact cgcctatgta taaacttaca  37320

taaatctttt tatttgttta tccccaaggc gcgtgtaaag ggcttttca cggtggactg  37380

cagattcttt ggtaataata gtactgtaat tggatatttt tatccgcata gtgctccggg  37440

aaagcagaag ttcttaacct aggcttaaga atta                              37474
```

<210> SEQ ID NO 27
<211> LENGTH: 1521
<212> TYPE: DNA
<213> ORGANISM: Artificial Sequence
<220> FEATURE:
<223> OTHER INFORMATION: Codon optimized DNA encoding human HIV-1 gag

<400> SEQUENCE: 27

```
atgggtgcta gggcttctgt gctgtctggt ggtgagctgg acaagtggga gaagatcagg    60

ctgaggcctg gtggcaagaa gaagtacaag ctaaagcaca ttgtgtgggc ctccagggag   120

ctggagaggt ttgctgtgaa ccctggcctg ctggagacct ctgaggggtg caggcagatc   180

ctgggccagc tccagccctc cctgcaaaca ggctctgagg agctgaggtc cctgtacaac   240

acagtggcta ccctgtactg tgtgcaccag aagattgatg tgaaggacac caaggaggcc   300

ctggagaaga ttgaggagga gcagaacaag tccaagaaga aggcccagca ggctgctgct   360

ggcacaggca actccagcca ggtgtcccag aactacccca ttgtgcagaa cctccagggc   420

cagatggtgc accaggccat ctccccccgg accctgaatg cctgggtgaa ggtggtggag   480

gagaaggcct tctccccctga ggtgatcccc atgttctctg ccctgtctga gggtgccacc   540

ccccaggacc tgaacaccat gctgaacaca gtgggggggcc atcaggctgc catgcagatg   600

ctgaaggaga ccatcaatga ggaggctgct gagtgggaca ggctgcatcc tgtgcacgct   660

ggccccattg cccccggcca gatgagggag cccaggggct ctgacattgc tggcaccacc   720

tccaccctcc aggagcagat tggctggatg accaacaacc cccccatccc tgtgggggaa   780

atctacaaga ggtggatcat cctgggcctg aacaagattg tgaggatgta ctcccccacc   840

tccatcctgg acatcaggca gggccccaag gagcccttca gggactatgt ggacaggttc   900

tacaagaccc tgagggctga gcaggcctcc caggaggtga agaactggat gacagagacc   960

ctgctggtgc agaatgccaa ccctgactgc aagaccatcc tgaaggccct gggccctgct  1020

gccaccctgg aggagatgat gacagcctgc caggggggtgg ggggccctgg tcacaaggcc  1080

agggtgctgg ctgaggccat gtcccaggtg accaactccg ccaccatcat gatgcagagg  1140
```

-continued

```
ggcaacttca ggaaccagag gaagacagtg aagtgcttca actgtggcaa ggtgggccac   1200

attgccaaga actgtagggc ccccaggaag aagggctgct ggaagtgtgg caaggagggc   1260

caccagatga aggactgcaa tgagaggcag gccaacttcc tgggcaaaat ctggccctcc   1320

cacaagggca ggcctggcaa cttcctccag tccaggcctg agcccacagc ccctcccgag   1380

gagtccttca ggtttgggga ggagaagacc acccccagcc agaagcagga gcccattgac   1440

aaggagctgt accccctggc ctccctgagg tccctgtttg gcaacgaccc ctcctcccag   1500

taaaataaag cccgggcaga t                                              1521
```

<210> SEQ ID NO 28
<211> LENGTH: 38519
<212> TYPE: DNA
<213> ORGANISM: Artificial Sequence
<220> FEATURE:
<223> OTHER INFORMATION: Codon optimized DNA encoding pMRKAd5HIV-1 pol, coding

<400> SEQUENCE: 28

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag gcggccgcga tccattgcat acgttgtatc    480

catatcataa tatgtacatt tatattggct catgtccaac attaccgcca tgttgacatt    540

gattattgac tagttattaa tagtaatcaa ttacggggtc attagttcat agcccatata    600

tggagttccg cgttacataa cttacggtaa atggcccgcc tggctgaccg cccaacgacc    660

cccgcccatt gacgtcaata atgacgtatg ttcccatagt aacgccaata gggactttcc    720

attgacgtca atgggtggag tatttacggt aaactgccca cttggcagta catcaagtgt    780

atcatatgcc aagtacgccc cctattgacg tcaatgacgg taaatggccc gcctggcatt    840

atgcccagta catgacctta tgggactttc ctacttggca gtacatctac gtattagtca    900

tcgctattac catggtgatg cggttttggc agtacatcaa tgggcgtgga tagcggtttg    960

actcacgggg atttccaagt ctccacccca ttgacgtcaa tgggagtttg ttttggcacc   1020

aaaatcaacg ggactttcca aaatgtcgta acaactccgc cccattgacg caaatgggcg   1080

gtaggcgtgt acggtgggag gtctatataa gcagagctcg tttagtgaac cgtcagatcg   1140

cctggagacg ccatccacgc tgttttgacc tccatagaag acaccgggac cgatccagcc   1200

tccgcggccg ggaacggtgc attggaacgc ggattccccg tgccaagagt gagatctacc   1260

atggccccca tctcccccat tgagactgtg cctgtgaagc tgaagcctgg catggatggc   1320

cccaaggtga agcagtggcc cctgactgag gagaagatca aggccctggt ggaaatctgc   1380

actgagatgg agaaggaggg caaaatctcc aagattggcc ccgagaaccc ctacaacacc   1440

cctgtgtttg ccatcaagaa gaaggactcc accaagtgga ggaagctggt ggacttcagg   1500

gagctgaaca agaggaccca ggacttctgg gaggtgcagc tgggcatccc ccaccccgct   1560

ggcctgaaga agaagaagtc tgtgactgtg ctggctgtgg gggatgccta cttctctgtg   1620
```

-continued

```
ccccctggatg aggacttcag gaagtacact gccttcacca tcccctccat caacaatgag   1680
acccctggca tcaggtacca gtacaatgtg ctgccccagg gctggaaggg ctcccctgcc   1740
atcttccagt cctccatgac caagatcctg gagcccttca ggaagcagaa ccctgacatt   1800
gtgatctacc agtacatggc tgccctgtat gtgggctctg acctggagat tgggcagcac   1860
aggaccaaga ttgaggagct gaggcagcac ctgctgaggt ggggcctgac cacccctgac   1920
aagaagcacc agaaggagcc ccccttcctg tggatgggct atgagctgca ccccgacaag   1980
tggactgtgc agcccattgt gctgcctgag aaggactcct ggactgtgaa tgacatccag   2040
aagctggtgg gcaagctgaa ctgggcctcc caaatctacc ctggcatcaa ggtgaggcag   2100
ctgtgcaagc tgctgagggg caccaaggcc ctgactgagg tgatcccccct gactgaggag   2160
gctgagctgg agctggctga gaacagggag atcctgaagg agcctgtgca tggggtgtac   2220
tatgacccct ccaaggacct gattgctgag atccagaagc agggccaggg ccagtggacc   2280
taccaaatct accaggagcc cttcaagaac ctgaagactg gcaagtatgc caggatgagg   2340
ggggcccaca ccaatgatgt gaagcagctg actgaggctg tgcagaagat caccactgag   2400
tccattgtga tctggggcaa gacccccaag ttcaagctgc ccatccagaa ggagacctgg   2460
gagacctggt ggactgagta ctggcaggcc acctggatcc ctgagtggga gtttgtgaac   2520
acccccccccc tggtgaagct gtggtaccag ctggagaagg agcccattgt gggggctgag   2580
accttctatg tggctggggc tgccaacagg gagaccaagc tgggcaaggc tggctatgtg   2640
accaacaggg gcaggcagaa ggtggtgacc ctgactgaca ccaccaacca gaagactgcc   2700
ctccaggcca tctacctggc cctccaggac tctggcctgg aggtgaacat tgtgactgcc   2760
tcccagtatg ccctgggcat catccaggcc cagcctgatc agtctgagtc tgagctggtg   2820
aaccagatca ttgagcagct gatcaagaag gagaaggtgt acctggcctg ggtgcctgcc   2880
cacaagggca ttgggggcaa tgagcaggtg gacaagctgg tgtctgctgg catcaggaag   2940
gtgctgttcc tggatggcat tgacaaggcc caggatgagc atgagaagta ccactccaac   3000
tggagggcta tggcctctga cttcaacctg ccccctgtgg tggctaagga gattgtggcc   3060
tcctgtgaca agtgccagct gaagggggag gccatgcatg ggcaggtgga ctgctcccct   3120
ggcatctggc agctggcctg cacccacctg gagggcaagg tgatcctggt ggctgtgcat   3180
gtggcctccg gctacattga ggctgaggtg atccctgctg agacaggcca ggagactgcc   3240
tacttcctgc tgaagctggc tggcaggtgg cctgtgaaga ccatccacac tgccaatggc   3300
tccaacttca ctggggccac agtgagggct gcctgctggt gggctggcat caagcaggag   3360
tttggcatcc cctacaaccc ccagtcccag ggggtggtgg cctccatgaa caaggagctg   3420
aagaagatca ttgggcaggt gagggaccag gctgagcacc tgaagacagc tgtgcagatg   3480
gctgtgttca tccacaactt caagaggaag gggggcatcg gggggctactc cgctggggag   3540
aggattgtgg acatcattgc cacagacatc cagaccaagg agctccagaa gcagatcacc   3600
aagatccaga acttcagggt gtactacagg gactccagga acccccctgtg gaagggccct   3660
gccaagctgc tgtggaaggg ggagggggct gtggtgatcc aggacaactc tgacatcaag   3720
gtggtgccca ggaggaaggc caagatcatc agggactatg gcaagcagat ggctggggat   3780
gactgtgtgg cctccaggca ggatgaggac taaagcccgg gcagatctgc tgtgccttct   3840
agttgccagc catctgttgt ttgcccctcc cccgtgcctt ccttgaccct ggaaggtgcc   3900
actcccactg tcctttccta ataaaatgag gaaattgcat cgcattgtct gagtaggtgt   3960
```

-continued

```
cattctattc tggggggtgg ggtggggcag gacagcaagg gggaggattg ggaagacaat   4020
agcaggcatg ctggggatgc ggtgggctct atggccgatc ggcgcgccgt actgaaatgt   4080
gtgggcgtgg cttaagggtg ggaaagaata tataaggtgg gggtcttatg tagttttgta   4140
tctgttttgc agcagccgcc gccgccatga gcaccaactc gtttgatgga agcattgtga   4200
gctcatattt gacaacgcgc atgcccccat gggccggggt gcgtcagaat gtgatgggct   4260
ccagcattga tggtcgcccc gtcctgcccg caaactctac taccttgacc tacgagaccg   4320
tgtctggaac gccgttggag actgcagcct ccgccgccgc ttcagccgct gcagccaccg   4380
cccgcgggat tgtgactgac tttgctttcc tgagcccgct tgcaaacagt gcagcttccc   4440
gttcatccgc ccgcgatgac aagttgacgg ctcttttggc acaattggat tctttgaccc   4500
gggaacttaa tgtcgtttct cagcagctgt tggatctgcg ccagcaggtt tctgccctga   4560
aggcttcctc ccctcccaat gcggtttaaa acataaataa aaaaccagac tctgtttgga   4620
tttggatcaa gcaagtgtct tgctgtcttt atttaggggt tttgcgcgcg cggtaggccc   4680
gggaccagcg gtctcggtcg ttgagggtcc tgtgtatttt ttccaggacg tggtaaaggt   4740
gactctggat gttcagatac atgggcataa gcccgtctct ggggtggagg tagcaccact   4800
gcagagcttc atgctgcggg gtggtgttgt agatgatcca gtcgtagcag gagcgctggg   4860
cgtggtgcct aaaaatgtct ttcagtagca agctgattgc caggggcagg cccttggtgt   4920
aagtgtttac aaagcggtta agctgggatg ggtgcatacg tggggatatg agatgcatct   4980
tggactgtat ttttaggttg gctatgttcc cagccatatc cctccgggga ttcatgttgt   5040
gcagaaccac cagcacagtg tatccggtgc acttgggaaa tttgtcatgt agcttagaag   5100
gaaatgcgtg gaagaacttg gagacgccct tgtgacctcc aagattttcc atgcattcgt   5160
ccataatgat ggcaatgggc ccacgggcgg cggcctgggc gaagatattt ctgggatcac   5220
taacgtcata gttgtgttcc aggatgagat cgtcataggc catttttaca aagcgcgggc   5280
ggagggtgcc agactgcggt ataatggttc catccggccc aggggcgtag ttaccctcac   5340
agatttgcat ttcccacgct ttgagttcag atggggggat catgtctacc tgcggggcga   5400
tgaagaaaac ggtttccggg gtaggggaga tcagctggga agaaagcagg ttcctgagca   5460
gctgcgactt accgcagccg gtgggcccgt aaatcacacc tattaccggc tgcaactggt   5520
agttaagaga gctgcagctg ccgtcatccc tgagcagggg ggccacttcg ttaagcatgt   5580
ccctgactcg catgttttcc ctgaccaaat ccgccagaag gcgctcgccg cccagcgata   5640
gcagttcttg caaggaagca aagtttttca acggtttgag accgtccgcc gtaggcatgc   5700
ttttgagcgt ttgaccaagc agttccaggc ggtcccacag ctcggtcacc tgctctacgg   5760
catctcgatc cagcatatct cctcgtttcg cgggttgggg cggctttcgc tgtacggcag   5820
tagtcggtgc tcgtccagac gggccagggt catgtctttc cacgggcgca gggtcctcgt   5880
cagcgtagtc tgggtcacgg tgaaggggtg cgctccgggc tgcgcgctgg ccagggtgcg   5940
cttgaggctg gtcctgctgg tgctgaagcg ctgccggtct tcgccctgcg cgtcggccag   6000
gtagcatttg accatggtgt catagtccag cccctccgcg gcgtggccct tggcgcgcag   6060
cttgcccttg gaggaggcgc cgcacgaggg gcagtgcaga cttttgaggg cgtagagctt   6120
gggcgcgaga aataccgatt ccggggagta ggcatccgcg ccgcaggccc cgcagacggt   6180
ctcgcattcc acgagccagg tgagctctgg ccgttcgggg tcaaaaacca ggtttccccc   6240
atgctttttg atgcgtttct tacctctggt ttccatgagc cggtgtccac gctcggtgac   6300
gaaaaggctg tccgtgtccc cgtatacaga cttgagaggc ctgtcctcga gcggtgttcc   6360
```

-continued

```
gcggtcctcc tcgtatagaa actcggacca ctctgagaca aaggctcgcg tccaggccag   6420
cacgaaggag gctaagtggg aggggtagcg gtcgttgtcc actagggggt ccactcgctc   6480
cagggtgtga agacacatgt cgccctcttc ggcatcaagg aaggtgattg gtttgtaggt   6540
gtaggccacg tgaccgggtg ttcctgaagg ggggctataa aagggggtgg gggcgcgttc   6600
gtcctcactc tcttccgcat cgctgtctgc gagggccagc tgttggggtg agtactccct   6660
ctgaaaagcg ggcatgactt ctgcgctaag attgtcagtt tccaaaaacg aggaggattt   6720
gatattcacc tggcccgcgg tgatgccttt gagggtggcc gcatccatct ggtcagaaaa   6780
gacaatcttt ttgttgtcaa gcttggtggc aaacgacccg tagagggcgt tggacagcaa   6840
cttggcgatg gagcgcaggg tttggttttt gtcgcgatcg gcgcgctcct tggccgcgat   6900
gtttagctgc acgtattcgc gcgcaacgca ccgccattcg ggaaagacgg tggtgcgctc   6960
gtcgggcacc aggtgcacgc gccaaccgcg gttgtgcagg gtgacaaggt caacgctggt   7020
ggctacctct ccgcgtaggc gctcgttggt ccagcagagg cggccgccct tgcgcgagca   7080
gaatggcggt aggggtcta gctgcgtctc gtccgggggg tctgcgtcca cggtaaagac   7140
cccgggcagc aggcgcgcgt cgaagtagtc tatcttgcat ccttgcaagt ctagcgcctg   7200
ctgccatgcg cgggcggcaa gcgcgcgctc gtatgggttg agtgggggac cccatggcat   7260
ggggtgggtg agcgcggagg cgtacatgcc gcaaatgtcg taaacgtaga ggggctctct   7320
gagtattcca agatatgtag ggtagcatct tccaccgcgg atgctggcgc gcacgtaatc   7380
gtatagttcg tgcgagggag cgaggaggtc gggaccgagg ttgctacggg cgggctgctc   7440
tgctcggaag actatctgcc tgaagatggc atgtgagttg gatgatatgg ttggacgctg   7500
gaagacgttg aagctggcgt ctgtgagacc taccgcgtca cgcacgaagg aggcgtagga   7560
gtcgcgcagc ttgttgacca gctcggcggt gacctgcacg tctagggcgc agtagtccag   7620
ggtttccttg atgatgtcat acttatcctg tccctttttt ttccacagct cgcggttgag   7680
gacaaactct tcgcggtctt tccagtactc ttggatcgga aacccgtcgg cctccgaacg   7740
gtaagagcct agcatgtaga actggttgac ggcctggtag gcgcagcatc ccttttctac   7800
gggtagcgcg tatgcctgcg cggccttccg gagcgaggtg tgggtgagcg caaaggtgtc   7860
cctgaccatg actttgaggt actggtattt gaagtcagtg tcgtcgcatc cgccctgctc   7920
ccagagcaaa aagtccgtgc gctttttgga acgcggattt ggcagggcga aggtgacatc   7980
gttgaagagt atctttcccg cgcgaggcat aaagttgcgt gtgatgcgga agggtcccgg   8040
cacctcggaa cggttgttaa ttacctgggc ggcgagcacg atctcgtcaa agccgttgat   8100
gttgtggccc acaatgtaaa gttccaagaa gcgcgggatg cccttgatgg aaggcaattt   8160
tttaagttcc tcgtaggtga gctcttcagg ggagctgagc ccgtgctctg aaagggccca   8220
gtctgcaaga tgagggttgg aagcgacgaa tgagctccac aggtcacggg ccattagcat   8280
ttgcaggtgg tcgcgaaagg tcctaaactg gcgacctatg gccatttttt ctggggtgat   8340
gcagtagaag gtaagcgggt cttgttccca gcggtcccat ccaaggttcg cggctaggtc   8400
tcgcgcggca gtcactagag gctcatctcc gccgaacttc atgaccagca tgaagggcac   8460
gagctgcttc ccaaaggccc ccatccaagt ataggtctct acatcgtagg tgacaaagag   8520
acgctcggtg cgaggatgcg agccgatcgg gaagaactgg atctcccgcc accaattgga   8580
ggagtggcta ttgatgtggt gaaagtagaa gtccctgcga cgggccgaac actcgtgctg   8640
gcttttgtaa aaacgtgcgc agtactggca gcggtgcacg ggctgtacat cctgcacgag   8700
```

-continued

```
gttgacctga cgaccgcgca caaggaagca gagtgggaat ttgagcccct cgcctggcgg   8760
gtttggctgg tggtcttcta cttcggctgc ttgtccttga ccgtctggct gctcgagggg   8820
agttacggtg gatcggacca ccacgccgcg cgagcccaaa gtccagatgt ccgcgcgcgg   8880
cggtcggagc ttgatgacaa catcgcgcag atgggagctg tccatggtct ggagctcccg   8940
cggcgtcagg tcaggcggga gctcctgcag gtttacctcg catagacggg tcagggcgcg   9000
ggctagatcc aggtgatacc taatttccag gggctggttg gtggcggcgt cgatggcttg   9060
caagaggccg catccccgcg gcgcgactac ggtaccgcgc ggcgggcggt gggccgcggg   9120
ggtgtccttg gatgatgcat ctaaaagcgg tgacgcgggc gagccccgg aggtaggggg   9180
ggctccggac ccgccgggag agggggcagg ggcacgtcgg cgccgcgcgc gggcaggagc   9240
tggtgctgcg cgcgtaggtt gctggcgaac gcgacgacgc ggcggttgat ctcctgaatc   9300
tggcgcctct gcgtgaagac gacgggcccg gtgagcttga acctgaaaga gagttcgaca   9360
gaatcaattt cggtgtcgtt gacggcggcc tggcgcaaaa tctcctgcac gtctcctgag   9420
ttgtcttgat aggcgatctc ggccatgaac tgctcgatct cttcctcctg gagatctccg   9480
cgtccggctc gctccacggt ggcggcgagg tcgttggaaa tgcgggccat gagctgcgag   9540
aaggcgttga ggcctccctc gttccagacg cggctgtaga ccacgccccc ttcggcatcg   9600
cgggcgcgca tgaccacctg cgcgagattg agctccacgt gccgggcgaa gacggcgtag   9660
tttcgcaggc gctgaaagag gtagttgagg gtggtggcgg tgtgttctgc cacgaagaag   9720
tacataaccc agcgtcgcaa cgtggattcg ttgatatccc ccaaggcctc aaggcgctcc   9780
atggcctcgt agaagtccac ggcgaagttg aaaaactggg agttgcgcgc cgacacggtt   9840
aactcctcct ccagaagacg gatgagctcg gcgacagtgt cgcgcacctc gcgctcaaag   9900
gctacagggg cctcttcttc ttcttcaatc tcctcttcca taagggcctc cccttcttct   9960
tcttctggcg gcggtggggg agggggggaca cggcggcgac gacggcgcac cgggaggcgg  10020
tcgacaaagc gctcgatcat ctccccgcgg cgacggcgca tggtctcggt gacggcgcgg  10080
ccgttctcgc gggggcgcag ttggaagacg ccgcccgtca tgtcccggtt atgggttggc  10140
ggggggctgc catgcggcag ggatacggcg ctaacgatgc atctcaacaa ttgttgtgta  10200
ggtactccgc cgccgaggga cctgagcgag tccgcatcga ccggatcgga aaacctctcg  10260
agaaaggcgt ctaaccagtc acagtcgcaa ggtaggctga gcaccgtggc gggcggcagc  10320
gggcggcggt cggggttgtt tctggcggag gtgctgctga tgatgtaatt aaagtaggcg  10380
gtcttgagac ggcggatggt cgacagaagc accatgtcct tgggtccggc ctgctgaatg  10440
cgcaggcggt cggccatgcc ccaggcttcg ttttgacatc ggcgcaggtc tttgtagtag  10500
tcttgcatga gcctttctac cggcacttct tcttctcctt cctcttgtcc tgcatctctt  10560
gcatctatcg ctgcggcggc ggcggagttt ggccgtaggt ggcgccctct tcctcccatg  10620
cgtgtgaccc cgaagcccct catcggctga agcagggcta ggtcggcgac aacgcgctcg  10680
gctaatatgg cctgctgcac ctgcgtgagg gtagactgga agtcatccat gtccacaaag  10740
cggtggtatg cgcccgtgtt gatggtgtaa gtgcagttgg ccataacgga ccagttaacg  10800
gtctggtgac ccggctgcga gagctcggtg tacctgagac gcgagtaagc cctcgagtca  10860
aatacgtagt cgttgcaagt ccgcaccagg tactggtatc ccaccaaaaa gtgcggcggc  10920
ggctggcggt agaggggcca gcgtagggtg gccggggctc cgggggcgag atcttccaac  10980
ataaggcgat gatatccgta gatgtacctg gacatccagg tgatgccggc ggcggtggtg  11040
gaggcgcgcg gaaagtcgcg gacgcggttc cagatgttgc gcagcggcaa aaagtgctcc  11100
```

-continued atggtcggga cgctctggcc ggtcaggcgc gcgcaatcgt tgacgctcta gaccgtgcaa 11160
aaggagagcc tgtaagcggg cactcttccg tggtctggtg gataaattcg caagggtatc 11220
atggcggacg accggggttc gagccccgta tccggccgtc cgccgtgatc catgcggtta 11280
ccgcccgcgt gtcgaaccca ggtgtgcgac gtcagacaac gggggagtgc tccttttggc 11340
ttccttccag gcgcggcggc tgctgcgcta gctttttttgg ccactggccg cgcgcagcgt 11400
aagcggttag gctggaaagc gaaagcatta agtggctcgc tccctgtagc cggagggtta 11460
ttttccaagg gttgagtcgc gggacccccg gttcgagtct cggaccggcc ggactgcggc 11520
gaacgggggt ttgcctcccc gtcatgcaag accccgcttg caaattcctc cggaaacagg 11580
gacgagcccc ttttttgctt ttcccagatg catccggtgc tgcggcagat gcgccccccct 11640 cctcagcagc ggcaagagca agagcagcgg cagacatgca gggcaccctc ccctcctcct 11700
accgcgtcag gaggggcgac atccgcggtt gacgcggcag cagatggtga ttacgaaccc 11760
ccgcggcgcc gggcccggca ctacctggac ttggaggagg gcgagggcct ggcgcggcta 11820
ggagcgccct ctcctgagcg gcacccaagg gtgcagctga agcgtgatac gcgtgaggcg 11880
tacgtgccgc ggcagaacct gtttcgcgac cgcgagggag aggagcccga ggagatgcgg 11940
gatcgaaagt tccacgcagg gcgcgagctg cggcatggcc tgaatcgcga gcggttgctg 12000
cgcgaggagg actttgagcc cgacgcgcga accgggatta gtcccgcgcg cgcacacgtg 12060
gcggccgccg acctggtaac cgcatacgag cagacggtga accaggagat taactttcaa 12120
aaaagcttta acaaccacgt gcgtacgctt gtggcgcgcg aggaggtggc tataggactg 12180
atgcatctgt gggactttgt aagcgcgctg gagcaaaacc caaatagcaa gccgctcatg 12240
gcgcagctgt tccttatagt gcagcacagc agggacaacg aggcattcag ggatgcgctg 12300
ctaaacatag tagagcccga gggccgctgg ctgctcgatt tgataaacat cctgcagagc 12360
atagtggtgc aggagcgcag cttgagcctg gctgacaagg tggccgccat caactattcc 12420
atgcttagcc tgggcaagtt ttacgcccgc aagatatacc atacccctta cgttcccata 12480
gacaaggagg taaagatcga ggggttctac atgcgcatgg cgctgaaggt gcttaccttg 12540
agcgacgacc tgggcgttta tcgcaacgag cgcatccaca aggccgtgag cgtgagccgg 12600
cggcgcgagc tcagcgaccg cgagctgatg cacagcctgc aaagggccct ggctggcacg 12660
ggcagcggcg atagagaggc cgagtcctac tttgacgcgg gcgctgacct gcgctgggcc 12720
ccaagccgac gcgccctgga ggcagctggg gccggacctg ggctggcggt ggcacccgcg 12780
cgcgctggca acgtcggcgg cgtggaggaa tatgacgagg acgatgagta cgagccagag 12840
gacggcgagt actaagcggt gatgtttctg atcagatgat gcaagacgca acggacccgg 12900
cggtgcgggc ggcgctgcag agccagccgt ccggccttaa ctccacggac gactggcgcc 12960
aggtcatgga ccgcatcatg tcgctgactg cgcgcaatcc tgacgcgttc cggcagcagc 13020
cgcaggccaa ccggctctcc gcaattctgg aagcggtggt cccggcgcgc gcaaacccca 13080
cgcacgagaa ggtgctggcg atcgtaaacg cgctggccga aaacagggcc atccggcccg 13140
acgaggccgg cctggtctac gacgcgctgc ttcagcgcgt ggctcgttac aacagcggca 13200
acgtgcagac caacctggac cggctggtgg gggatgtgcg cgaggccgtg gcgcagcgtg 13260
agcgcgcgca gcagcagggc aacctgggct ccatggttgc actaaacgcc ttcctgagta 13320
cacagcccgc caacgtgccg cggggacagg aggactacac caactttgtg agcgcactgc 13380
ggctaatggt gactgagaca ccgcaaagtg aggtgtacca gtctgggcca gactattttt 13440

-continued

```
tccagaccag tagacaaggc ctgcagaccg taaacctgag ccaggctttc aaaaacttgc  13500
aggggctgtg gggggtgcgg gctcccacag gcgaccgcgc gaccgtgtct agcttgctga  13560
cgcccaactc gcgcctgttg ctgctgctaa tagcgccctt cacggacagt ggcagcgtgt  13620
cccgggacac atacctaggt cacttgctga cactgtaccg cgaggccata ggtcaggcgc  13680
atgtggacga gcatactttc caggagatta caagtgtcag ccgcgcgctg gggcaggagg  13740
acacgggcag cctggaggca accctaaact acctgctgac caaccggcgg cagaagatcc  13800
cctcgttgca cagtttaaac agcgaggagg agcgcatttt gcgctacgtg cagcagagcg  13860
tgagccttaa cctgatgcgc gacggggtaa cgcccagcgt ggcgctggac atgaccgcgc  13920
gcaacatgga accgggcatg tatgcctcaa accggccgtt tatcaaccgc ctaatggact  13980
acttgcatcg cgcggccgcc gtgaaccccg agtatttcac caatgccatc ttgaacccgc  14040
actggctacc gcccctggt ttctacaccg ggggattcga ggtgcccgag ggtaacgatg  14100
gattcctctg ggacgacata gacgacagcg tgttttcccc gcaaccgcag accctgctag  14160
agttgcaaca gcgcgagcag gcagaggcgg cgctgcgaaa ggaaagcttc cgcaggccaa  14220
gcagcttgtc cgatctaggc gctgcggccc cgcggtcaga tgctagtagc ccatttccaa  14280
gcttgatagg gtctcttacc agcactcgca ccacccgccc gcgcctgctg ggcgaggagg  14340
agtacctaaa caactcgctg ctgcagccgc agcgcgaaaa aaacctgcct ccggcatttc  14400
ccaacaacgg gatagagagc ctagtggaca agatgagtag atggaagacg tacgcgcagg  14460
agcacaggga cgtgccaggc ccgcgcccgc ccacccgtcg tcaaaggcac gaccgtcagc  14520
ggggtctggt gtgggaggac gatgactcgg cagacgacag cagcgtcctg gatttgggag  14580
ggagtggcaa cccgtttgcg caccttcgcc ccaggctggg gagaatgttt taaaaaaaaa  14640
aaaagcatga tgcaaaataa aaaactcacc aaggccatgg caccgagcgt tggttttctt  14700
gtattcccct tagtatgcgg cgcgcggcga tgtatgagga aggtcctcct ccctcctacg  14760
agagtgtggt gagcgcggcg ccagtggcgg cggcgctggg ttctcccttc gatgctcccc  14820
tggacccgcc gtttgtgcct ccgcggtacc tgcggcctac cggggggaga aacagcatcc  14880
gttactctga gttggcaccc ctattcgaca ccacccgtgt gtacctggtg gacaacaagt  14940
caacggatgt ggcatccctg aactaccaga acgaccacag caactttctg accacggtca  15000
ttcaaaacaa tgactacagc ccgggggagg caagcacaca gaccatcaat cttgacgacc  15060
ggtcgcactg ggcggcgac ctgaaaacca tcctgcatac caacatgcca aatgtgaacg  15120
agttcatgtt taccaataag tttaaggcgc gggtgatggt gtcgcgcttg cctactaagg  15180
acaatcaggt ggagctgaaa tacgagtggg tggagttcac gctgcccgag ggcaactact  15240
ccgagaccat gaccatagac cttatgaaca acgcgatcgt ggagcactac ttgaaagtgg  15300
gcagacagaa cggggttctg gaaagcgaca tcggggtaaa gtttgacacc cgcaacttca  15360
gactggggtt tgaccccgtc actggtcttg tcatgcctgg ggtatataca aacgaagcct  15420
tccatccaga catcattttg ctgccaggat gcggggtgga cttcacccac agccgcctga  15480
gcaacttgtt gggcatccgc aagcggcaac ccttccagga gggctttagg atcacctacg  15540
atgatctgga gggtggtaac attcccgcac tgttggatgt ggacgcctac caggcgagct  15600
tgaaagatga caccgaacag ggcgggggtg gcgcaggcgg cagcaacagc agtggcagcg  15660
gcgcggaaga gaactccaac gcggcagccg cggcaatgca gccggtggag gacatgaacg  15720
atcatgccat tcgcggcgac acctttgcca cacgggctga ggagaagcgc gctgaggccg  15780
aagcagcggc cgaagctgcc gcccccgctg cgcaacccga ggtcgagaag cctcagaaga  15840
```

-continued

```
aaccggtgat caaacccctg acagaggaca gcaagaaacg cagttacaac ctaataagca  15900
atgacagcac cttcacccag taccgcagct ggtaccttgc atacaactac ggcgaccctc  15960
agaccggaat ccgctcatgg accctgcttt gcactcctga cgtaacctgc ggctcggagc  16020
aggtctactg gtcgttgcca gacatgatgc aagaccccgt gaccttccgc tccacgcgcc  16080
agatcagcaa ctttccggtg gtgggcgccg agctgttgcc cgtgcactcc aagagcttct  16140
acaacgacca ggccgtctac tcccaactca tccgccagtt tacctctctg acccacgtgt  16200
tcaatcgctt tcccgagaac cagattttgg cgcgcccgcc agcccccacc atcaccaccg  16260
tcagtgaaaa cgttcctgct ctcacagatc acgggacgct accgctgcgc aacagcatcg  16320
gaggagtcca gcgagtgacc attactgacg ccagacgccg cacctgcccc tacgtttaca  16380
aggccctggg catagtctcg ccgcgcgtcc tatcgagccg cactttttga gcaagcatgt  16440
ccatccttat atcgcccagc aataacacag gctggggcct gcgcttccca agcaagatgt  16500
ttggcggggc caagaagcgc tccgaccaac acccagtgcg cgtgcgcggg cactaccgcg  16560
cgccctgggg cgcgcacaaa cgcggccgca ctgggcgcac caccgtcgat gacgccatcg  16620
acgcggtggt ggaggaggcg cgcaactaca cgcccacgcc gccaccagtg tccacagtgg  16680
acgcggccat tcagaccgtg gtgcgcggag cccggcgcta tgctaaaatg aagagacggc  16740
ggaggcgcgt agcacgtcgc caccgccgcc gacccggcac tgccgcccaa cgcgcggcgg  16800
cggccctgct taaccgcgca cgtcgcaccg gccgacgggc ggccatgcgg gccgctcgaa  16860
ggctggccgc gggtattgtc actgtgcccc ccaggtccag gcgacgagcg gccgccgcag  16920
cagccgcggc cattagtgct atgactcagg gtcgcagggg caacgtgtat tgggtgcgcg  16980
actcggttag cggcctgcgc gtgcccgtgc gcacccgccc cccgcgcaac tagattgcaa  17040
gaaaaaacta cttagactcg tactgttgta tgtatccagc ggcggcggcg cgcaacgaag  17100
ctatgtccaa gcgcaaaatc aaagaagaga tgctccaggt catcgcgccg gagatctatg  17160
gcccccgaa gaaggaagag caggattaca agccccgaaa gctaaagcgg gtcaaaaaga  17220
aaaagaaaga tgatgatgat gaacttgacg acgaggtgga actgctgcac gctaccgcgc  17280
ccaggcgacg ggtacagtgg aaaggtcgac gcgtaaaacg tgttttgcga cccggcacca  17340
ccgtagtctt tacgcccggt gagcgctcca cccgcaccta caagcgcgtg tatgatgagg  17400
tgtacggcga cgaggacctg cttgagcagg ccaacgagcg cctcggggag tttgcctacg  17460
gaaagcggca taaggacatg ctggcgttgc cgctggacga gggcaaccca acacctagcc  17520
taaagcccgt aacactgcag caggtgctgc ccgcgcttgc accgtccgaa gaaaagcgcg  17580
gcctaaagcg cgagtctggt gacttggcac ccaccgtgca gctgatggta cccaagcgcc  17640
agcgactgga agatgtcttg gaaaaaatga ccgtggaacc tgggctggag cccgaggtcc  17700
gcgtgcggcc aatcaagcag gtggcgccgg gactgggcgt gcagaccgtg gacgttcaga  17760
tacccactac cagtagcacc agtattgcca ccgccacaga gggcatggag acacaaacgt  17820
ccccggttgc ctcagcggtg gcggatgccg cggtgcaggc ggtcgctgcg gccgcgtcca  17880
agacctctac ggaggtgcaa acggacccgt ggatgtttcg cgtttcagcc ccccggcgcc  17940
cgcgccgttc gaggaagtac ggcgccgcca gcgcgctact gcccgaatat gccctacatc  18000
cttccattgc gcctaccccc ggctatcgtg gctacaccta ccgccccaga agacgagcaa  18060
ctacccgacg ccgaaccacc actggaaccc gccgccgccg tcgccgtcgc cagcccgtgc  18120
tggccccgat ttccgtgcgc agggtggctc gcgaaggagg caggaccctg gtgctgccaa  18180
```

-continued

```
cagcgcgcta ccaccccagc atcgtttaaa agccggtctt tgtggttctt gcagatatgg  18240
ccctcacctg ccgcctccgt ttcccggtgc cgggattccg aggaagaatg caccgtagga  18300
ggggcatggc cggccacggc ctgacgggcg gcatgcgtcg tgcgcaccac cggcggcggc  18360
gcgcgtcgca ccgtcgcatg cgcggcggta tcctgcccct ccttattcca ctgatcgccg  18420
cggcgattgg cgccgtgccc ggaattgcat ccgtggcctt gcaggcgcag agacactgat  18480
taaaaacaag ttgcatgtgg aaaaatcaaa ataaaaagtc tggactctca cgctcgcttg  18540
gtcctgtaac tattttgtag aatggaagac atcaactttg cgtctctggc cccgcgacac  18600
ggctcgcgcc cgttcatggg aaactggcaa gatatcggca ccagcaatat gagcggtggc  18660
gccttcagct ggggctcgct gtggagcggc attaaaaatt tcggttccac cgttaagaac  18720
tatggcagca aggcctggaa cagcagcaca ggccagatgc tgagggataa gttgaaagag  18780
caaaatttcc aacaaaaggt ggtagatggc ctggcctctg gcattagcgg ggtggtggac  18840
ctggccaacc aggcagtgca aaataagatt aacagtaagc ttgatccccg ccctcccgta  18900
gaggagcctc caccggccgt ggagacagtg tctccagagg ggcgtggcga aaagcgtccg  18960
cgccccgaca gggaagaaac tctggtgacg caaatagacg agcctccctc gtacgaggag  19020
gcactaaagc aaggcctgcc caccacccgt cccatcgcgc ccatggctac cggagtgctg  19080
ggccagcaca cacccgtaac gctggacctg cctcccccg ccgacaccca gcagaaacct  19140
gtgctgccag gcccgaccgc cgttgttgta acccgtccta gccgcgcgtc cctgcgccgc  19200
gccgccagcg gtccgcgatc gttgcggccc gtagccagtg gcaactggca aagcacactg  19260
aacagcatcg tgggtctggg ggtgcaatcc ctgaagcgcc gacgatgctt ctgatagcta  19320
acgtgtcgta tgtgtgtcat gtatgcgtcc atgtcgccgc cagaggagct gctgagccgc  19380
cgcgcgcccg ctttccaaga tggctacccc ttcgatgatg ccgcagtggt cttacatgca  19440
catctcgggc caggacgcct cggagtacct gagccccggg ctggtgcagt ttgcccgcgc  19500
caccgagacg tacttcagcc tgaataacaa gtttagaaac cccacggtgg cgcctacgca  19560
cgacgtgacc acagaccggt cccagcgttt gacgctgcgg ttcatccctg tggaccgtga  19620
ggatactgcg tactcgtaca aggcgcggtt caccctagct gtgggtgata accgtgtgct  19680
ggacatggct tccacgtact ttgacatccg cggcgtgctg gacaggggcc ctacttttaa  19740
gccctactct ggcactgcct acaacgccct ggctcccaag ggtgccccaa atccttgcga  19800
atgggatgaa gctgctactg ctcttgaaat aaacctagaa gaagaggacg atgacaacga  19860
agacgaagta gacgagcaag ctgagcagca aaaaactcac gtatttgggc aggcgcctta  19920
ttctggtata aatattacaa aggagggtat tcaaataggt gtcgaaggtc aaacacctaa  19980
atatgccgat aaaacatttc aacctgaacc tcaaatagga gaatctcagt ggtacgaaac  20040
agaaattaat catgcagctg ggagagtcct aaaaaagact accccaatga aaccatgtta  20100
cggttcatat gcaaaaccca caaatgaaaa tggagggcaa ggcattcttg taaagcaaca  20160
aaatggaaag ctagaaagtc aagtggaaat gcaatttttc tcaactactg aggcagccgc  20220
aggcaatggt gataacttga ctcctaaagt ggtattgtac agtgaagatg tagatataga  20280
aaccccagac actcatattt cttacatgcc cactattaag gaaggtaact cacgagaact  20340
aatgggccaa caatctatgc ccaacaggcc taattacatt gcttttaggg acaattttat  20400
tggtctaatg tattacaaca gcacgggtaa tatgggtgtt ctggcgggcc aagcatcgca  20460
gttgaatgct gttgtagatt tgcaagacag aaacacagag ctttcatacc agcttttgct  20520
tgattccatt ggtgatagaa ccaggtactt ttctatgtgg aatcaggctg ttgacagcta  20580
```

-continued tgatccagat gttagaatta ttgaaaatca tggaactgaa gatgaacttc caaattactg 20640
ctttccactg ggaggtgtga ttaatacaga gactcttacc aaggtaaaac ctaaaacagg 20700
tcaggaaaat ggatgggaaa aagatgctac agaattttca gataaaaatg aaataagagt 20760
tggaaataat tttgccatgg aaatcaatct aaatgccaac ctgtggagaa atttcctgta 20820
ctccaacata gcgctgtatt tgcccgacaa gctaaagtac agtccttcca acgtaaaaat 20880
ttctgataac ccaaacacct acgactacat gaacaagcga gtggtggctc ccgggctagt 20940
ggactgctac attaaccttg gagcacgctg gtcccttgac tatatggaca acgtcaaccc 21000
atttaaccac caccgcaatg ctggcctgcg ctaccgctca atgttgctgg gcaatggtcg 21060
ctatgtgccc ttccacatcc aggtgcctca gaagttcttt gccattaaaa acctccttct 21120
cctgccgggc tcatacacct acgagtggaa cttcaggaag gatgttaaca tggttctgca 21180
gagctcccta ggaaatgacc taagggttga cggagccagc attaagtttg atagcatttg 21240
cctttacgcc accttcttcc ccatggccca caacaccgcc tccacgcttg aggccatgct 21300
tagaaacgac accaacgacc agtcctttaa cgactatctc tccgccgcca acatgctcta 21360
ccctataccc gccaacgcta ccaacgtgcc catatccatc ccctcccgca actgggcggc 21420
tttccgcggc tgggccttca cgcgccttaa gactaaggaa accccatcac tgggctcggg 21480
ctacgaccct tattacacct actctggctc tataccctac ctagatggaa ccttttacct 21540
caaccacacc tttaagaagg tggccattac ctttgactct tctgtcagct ggcctggcaa 21600
tgaccgcctg cttacccccca acgagtttga aattaagcgc tcagttgacg gggagggtta 21660
caacgttgcc cagtgtaaca tgaccaaaga ctggttcctg gtacaaatgc tagctaacta 21720
taacattggc taccagggct tctatatccc agagagctac aaggaccgca tgtactcctt 21780
ctttagaaac ttccagccca tgagccgtca ggtggtggat gatactaaat acaaggacta 21840
ccaacaggtg ggcatcctac accaacacaa caactctgga tttgttggct accttgcccc 21900
caccatgcgc gaaggacagg cctaccctgc taacttcccc tatccgctta taggcaagac 21960
cgcagttgac agcattaccc agaaaaagtt tctttgcgat cgcacccttt ggcgcatccc 22020
attctccagt aactttatgt ccatgggcgc actcacagac ctgggccaaa accttctcta 22080
cgccaactcc gcccacgcgc tagacatgac ttttgaggtg gatcccatgg acgagcccac 22140
ccttctttat gttttgtttg aagtctttga cgtggtccgt gtgcaccagc cgcaccgcgg 22200
cgtcatcgaa accgtgtacc tgcgcacgcc cttctcggcc ggcaacgcca caacataaag 22260
aagcaagcaa catcaacaac agctgccgcc atgggctcca gtgagcagga actgaaagcc 22320
attgtcaaag atcttggttg tgggccatat tttttgggca cctatgacaa gcgctttcca 22380
ggctttgttt ctccacacaa gctcgcctgc gccatagtca atacggccgg tcgcgagact 22440
gggggcgtac actggatggc ctttgcctgg aacccgcact caaaaacatg ctacctcttt 22500
gagccctttg gcttttctga ccagcgactc aagcaggttt accagtttga gtacgagtca 22560
ctcctgcgcc gtagcgccat tgcttcttcc cccgaccgct gtataacgct ggaaaagtcc 22620
acccaaagcg tacaggggcc caactcggcc gcctgtggac tattctgctg catgtttctc 22680
cacgcctttg ccaactggcc ccaaactccc atggatcaca accccaccat gaaccttatt 22740
accggggtac ccaactccat gctcaacagt ccccaggtac agcccaccct gcgtcgcaac 22800
caggaacagc tctacagctt cctggagcgc cactcgccct acttccgcag ccacagtgcg 22860
cagattagga gcgccacttc tttttgtcac ttgaaaaaca tgtaaaaata atgtactaga 22920

-continued

```
gacactttca ataaaggcaa atgcttttat ttgtacactc tcgggtgatt atttaccccc  22980
acccttgccg tctgcgccgt ttaaaaatca aaggggttct gccgcgcatc gctatgcgcc  23040
actggcaggg acacgttgcg atactggtgt ttagtgctcc acttaaactc aggcacaacc  23100
atccgcggca gctcggtgaa gttttcactc cacaggctgc gcaccatcac caacgcgttt  23160
agcaggtcgg gcgccgatat cttgaagtcg cagttggggc ctccgccctg cgcgcgcgag  23220
ttgcgataca cagggttgca gcactggaac actatcagcg ccgggtggtg cacgctggcc  23280
agcacgctct tgtcggagat cagatccgcg tccaggtcct ccgcgttgct cagggcgaac  23340
ggagtcaact ttggtagctg ccttcccaaa aagggcgcgt gcccaggctt tgagttgcac  23400
tcgcaccgta gtggcatcaa aaggtgaccg tgcccggtct gggcgttagg atacagcgcc  23460
tgcataaaag ccttgatctg cttaaaagcc acctgagcct ttgcgccttc agagaagaac  23520
atgccgcaag acttgccgga aaactgattg gccggacagg ccgcgtcgtg cacgcagcac  23580
cttgcgtcgg tgttggagat ctgcaccaca tttcggcccc accggttctt cacgatcttg  23640
gccttgctag actgctcctt cagcgcgcgc tgcccgtttt cgctcgtcac atccatttca  23700
atcacgtgct ccttatttat cataatgctt ccgtgtagac acttaagctc gccttcgatc  23760
tcagcgcagc ggtgcagcca caacgcgcag cccgtgggct cgtgatgctt gtaggtcacc  23820
tctgcaaacg actgcaggta cgcctgcagg aatcgcccca tcatcgtcac aaaggtcttg  23880
ttgctggtga aggtcagctg caacccgcgg tgctcctcgt tcagccaggt cttgcatacg  23940
gccgccagag cttccacttg gtcaggcagt agtttgaagt tcgcctttag atcgttatcc  24000
acgtggtact tgtccatcag cgcgcgcgca gcctccatgc ccttctccca cgcagacacg  24060
atcggcacac tcagcgggtt catcaccgta atttcacttt ccgcttcgct gggctcttcc  24120
tcttcctctt gcgtccgcat accacgcgcc actgggtcgt cttcattcag ccgccgcact  24180
gtgcgcttac ctcctttgcc atgcttgatt agcaccggtg ggttgctgaa acccaccatt  24240
tgtagcgcca catcttctct ttcttcctcg ctgtccacga ttacctctgg tgatggcggg  24300
cgctcgggct tgggagaagg gcgcttcttt ttcttcttgg gcgcaatggc caaatccgcc  24360
gccgaggtcg atggccgcgg gctgggtgtg cgcggcacca gcgcgtcttg tgatgagtct  24420
tcctcgtcct cggactcgat acgccgcctc atccgctttt ttgggggcgc ccggggaggc  24480
ggcggcgacg gggacgggga cgacacgtcc tccatggttg gggggacgtcg cgccgcaccg  24540
cgtccgcgct cgggggtggt ttcgcgctgc tcctcttccc gactggccat ttccttctcc  24600
tataggcaga aaaagatcat ggagtcagtc gagaagaagg acagcctaac cgccccctct  24660
gagttcgcca ccaccgcctc caccgatgcc gccaacgcgc ctaccacctt ccccgtcgag  24720
gcacccccgc ttgaggagga ggaagtgatt atcgagcagg acccaggttt tgtaagcgaa  24780
gacgacgagg accgctcagt accaacagag gataaaaagc aagaccagga caacgcagag  24840
gcaaacgagg aacaagtcgg gcgggggggac gaaaggcatg gcgactacct agatgtggga  24900
gacgacgtgc tgttgaagca tctgcagcgc cagtgcgcca ttatctgcga cgcgttgcaa  24960
gagcgcagcg atgtgcccct cgccatagcg gatgtcagcc ttgcctacga acgccaccta  25020
ttctcaccgc gcgtaccccc caaacgccaa gaaaacggca catgcgagcc caacccgcgc  25080
ctcaacttct accccgtatt tgccgtgcca gaggtgcttg ccacctatca catctttttc  25140
caaaactgca agatacccct atcctgccgt gccaaccgca gccgagcgga caagcagctg  25200
gccttgcggc agggcgctgt catacctgat atcgcctcgc tcaacgaagt gccaaaaatc  25260
tttgagggtc ttggacgcga cgagaagcgc gcggcaaacg ctctgcaaca ggaaaacagc  25320
```

-continued gaaaatgaaa gtcactctgg agtgttggtg gaactcgagg gtgacaacgc gcgcctagcc 25380
gtactaaaac gcagcatcga ggtcacccac tttgcctacc cggcacttaa cctacccccc 25440
aaggtcatga gcacagtcat gagtgagctg atcgtgcgcc gtgcgcagcc cctggagagg 25500
gatgcaaatt tgcaagaaca aacagaggag ggcctacccg cagttggcga cgagcagcta 25560
gcgcgctggc ttcaaacgcg cgagcctgcc gacttggagg agcgacgcaa actaatgatg 25620
gccgcagtgc tcgttaccgt ggagcttgag tgcatgcagc ggttctttgc tgacccggag 25680
atgcagcgca agctagagga aacattgcac tacacctttc gacagggcta cgtacgccag 25740
gcctgcaaga tctccaacgt ggagctctgc aacctggtct cctaccttgg aattttgcac 25800
gaaaaccgcc ttgggcaaaa cgtgcttcat tccacgctca agggcgaggc gcgccgcgac 25860
tacgtccgcg actgcgttta cttatttcta tgctacacct ggcagacggc catgggcgtt 25920
tggcagcagt gcttggagga gtgcaacctc aaggagctgc agaaactgct aaagcaaaac 25980
ttgaaggacc tatggacggc cttcaacgag cgctccgtgg ccgcgcacct ggcggacatc 26040
attttccccg aacgcctgct taaaaccctg caacagggtc tgccagactt caccagtcaa 26100
agcatgttgc agaactttag gaactttatc ctagagcgct caggaatctt gcccgccacc 26160
tgctgtgcac ttcctagcga ctttgtgccc attaagtacc gcgaatgccc tccgccgctt 26220
tggggccact gctaccttct gcagctagcc aactaccttg cctaccactc tgacataatg 26280
gaagacgtga gcggtgacgg tctactggag tgtcactgtc gctgcaacct atgcaccccg 26340
caccgctccc tggtttgcaa ttcgcagctg cttaacgaaa gtcaaattat cggtaccttt 26400
gagctgcagg gtccctcgcc tgacgaaaag tccgcggctc cggggttgaa actcactccg 26460
gggctgtgga cgtcggctta ccttcgcaaa tttgtacctg aggactacca cgcccacgag 26520
attaggttct acgaagacca atcccgcccg cctaatgcgg agcttaccgc ctgcgtcatt 26580
acccaggcc acattcttgg ccaattgcaa gccatcaaca aagcccgcca agagtttctg 26640
ctacgaaagg gacggggggt ttacttggac ccccagtccg gcgaggagct caacccaatc 26700
cccccgccgc cgcagcccta tcagcagcag ccgcgggccc ttgcttccca ggatggcacc 26760
caaaaagaag ctgcagctgc cgccgccacc cacggacgag gaggaatact gggacagtca 26820
ggcagaggag gttttggacg aggaggagga ggacatgatg gaagactggg agagcctaga 26880
cgaggaagct tccgaggtcg aagaggtgtc agacgaaaca ccgtcaccct cggtcgcatt 26940
cccctcgccg gcgccccaga aatcggcaac cggttccagc atggctacaa cctccgctcc 27000
tcaggcgccg ccggcactgc ccgttcgccg acccaaccgt agatgggaca ccactggaac 27060
cagggccggt aagtccaagc agccgccgcc gttagcccaa gagcaacaac agcgccaagg 27120
ctaccgctca tggcgcgggc acaagaacgc catagttgct tgcttgcaag actgtggggg 27180
caacatctcc ttcgcccgcc gctttcttct ctaccatcac ggcgtggcct tcccccgtaa 27240
catcctgcat tactaccgtc atctctacag cccatactgc accggcggca gcggcagcaa 27300
cagcagcggc cacacagaag caaaggcgac cggatagcaa gactctgaca aagcccaaga 27360
aatccacagc ggcggcagca gcaggaggag gagcgctgcg tctggcgccc aacgaacccg 27420
tatcgacccg cgagcttaga aacaggattt ttcccactct gtatgctata tttcaacaga 27480
gcaggggcca agaacaagag ctgaaaataa aaaacaggtc tctgcgatcc ctcacccgca 27540
gctgcctgta tcacaaaagc gaagatcagc ttcggcgcac gctggaagac gcggaggctc 27600
tcttcagtaa atactgcgcg ctgactctta aggactagtt tcgcgccctt tctcaaattt 27660

-continued

```
aagcgcgaaa actacgtcat ctccagcggc cacacccggc gccagcacct gttgtcagcg  27720
ccattatgag caaggaaatt cccacgccct acatgtggag ttaccagcca caaatgggac  27780
ttgcggctgg agctgcccaa gactactcaa cccgaataaa ctacatgagc gcgggacccc  27840
acatgatatc ccgggtcaac ggaatacgcg cccaccgaaa ccgaattctc ctggaacagg  27900
cggctattac caccacacct cgtaataacc ttaatccccg tagttggccc gctgccctgg  27960
tgtaccagga aagtcccgct cccaccactg tggtacttcc cagagacgcc caggccgaag  28020
ttcagatgac taactcaggg gcgcagcttg cgggcggctt tcgtcacagg gtgcggtcgc  28080
ccgggcaggg tataactcac ctgacaatca gagggcgagg tattcagctc aacgacgagt  28140
cggtgagctc ctcgcttggt ctccgtccgg acgggacatt tcagatcggc ggcgccggcc  28200
gctcttcatt cacgcctcgt caggcaatcc taactctgca gacctcgtcc tctgagccgc  28260
gctctggagg cattggaact ctgcaattta ttgaggagtt tgtgccatcg gtctacttta  28320
acccccttctc gggacctccc ggccactatc cggatcaatt tattcctaac tttgacgcgg  28380
taaaggactc ggcggacggc tacgactgaa tgttaagtgg agaggcagag caactgcgcc  28440
tgaaacacct ggtccactgt cgccgccaca agtgctttgc ccgcgactcc ggtgagtttt  28500
gctactttga attgcccgag gatcatatcg agggcccggc gcacggcgtc cggcttaccg  28560
cccagggaga gcttgcccgt agcctgattc gggagtttac ccagcgcccc ctgctagttg  28620
agcgggacag gggaccctgt gttctcactg tgatttgcaa ctgtcctaac cctggattac  28680
atcaagatct ttgttgccat ctctgtgctg agtataataa atacagaaat taaaatatac  28740
tggggctcct atcgccatcc tgtaaacgcc accgtcttca cccgcccaag caaaccaagg  28800
cgaaccttac ctggtacttt taacatctct ccctctgtga tttacaacag tttcaaccca  28860
gacggagtga gtctacgaga gaacctctcc gagctcagct actccatcag aaaaaacacc  28920
accctcctta cctgccggga acgtacgagt gcgtcaccgg ccgctgcacc acacctaccg  28980
cctgaccgta aaccagactt tttccggaca gacctcaata actctgttta ccagaacagg  29040
aggtgagctt agaaaaccct tagggtatta ggccaaaggc gcagctactg tggggtttat  29100
gaacaattca agcaactcta cgggctattc taattcaggt ttctctagaa tcggggttgg  29160
ggttattctc tgtcttgtga ttctctttat tcttatacta acgcttctct gcctaaggct  29220
cgccgcctgc tgtgtgcaca tttgcattta ttgtcagctt tttaaacgct ggggtcgcca  29280
cccaagatga ttaggtacat aatcctaggt ttactcaccc ttgcgtcagc ccacggtacc  29340
acccaaaagg tggattttaa ggagccagcc tgtaatgtta cattcgcagc tgaagctaat  29400
gagtgcacca ctcttataaa atgcaccaca gaacatgaaa agctgcttat tcgccacaaa  29460
aacaaaattg gcaagtatgc tgtttatgct atttggcagc caggtgacac tacagagtat  29520
aatgttacag ttttccaggg taaaagtcat aaaactttta tgtatacttt tccattttat  29580
gaaatgtgcg acattaccat gtacatgagc aaacagtata agttgtggcc cccacaaaat  29640
tgtgtggaaa acactggcac tttctgctgc actgctatgc taattacagt gctcgctttg  29700
gtctgtaccc tactctatat taaatacaaa agcagacgca gctttattga ggaaaagaaa  29760
atgccttaat ttactaagtt acaaagctaa tgtcaccact aactgcttta ctcgctgctt  29820
gcaaaacaaa ttcaaaaagt tagcattata attagaatag gatttaaacc ccccggtcat  29880
ttcctgctca ataccattcc cctgaacaat tgactctatg tgggatatgc tccagcgcta  29940
caaccttgaa gtcaggcttc ctggatgtca gcatctgact ttggccagca cctgtcccgc  30000
ggatttgttc cagtccaact acagcgaccc accctaacag agatgaccaa cacaaccaac  30060
```

-continued gcggccgccg ctaccggact tacatctacc acaaatacac cccaagtttc tgcctttgtc 30120
aataactggg ataacttggg catgtggtgg ttctccatag cgcttatgtt tgtatgcctt 30180
attattatgt ggctcatctg ctgcctaaag cgcaaacgcg cccgaccacc catctatagt 30240
cccatcattg tgctacaccc aaacaatgat ggaatccata gattggacgg actgaaacac 30300
atgttctttt ctcttacagt atgattaaat gagacatgat tcctcgagtt tttatattac 30360
tgacccttgt tgcgcttttt tgtgcgtgct ccacattggc tgcggtttct cacatcgaag 30420
tagactgcat tccagccttc acagtctatt tgctttacgg atttgtcacc ctcacgctca 30480
tctgcagcct catcactgtg gtcatcgcct ttatccagtg cattgactgg gtctgtgtgc 30540
gctttgcata tctcagacac catccccagt acagggacag gactatagct gagcttctta 30600
gaattcttta attatgaaat ttactgtgac ttttctgctg attatttgca ccctatctgc 30660
gttttgttcc ccgacctcca agcctcaaag acatatatca tgcagattca ctcgtatatg 30720
gaatattcca agttgctaca atgaaaaaag cgatctttcc gaagcctggt tatatgcaat 30780
catctctgtt atggtgttct gcagtaccat cttagcccta gctatatatc cctaccttga 30840
cattggctgg aacgcaatag atgccatgaa ccacccaact ttccccgcgc ccgctatgct 30900
tccactgcaa caagttgttg ccggcggctt tgtcccagcc aatcagcctc gcccaccttc 30960
tcccaccccc actgaaatca gctactttaa tctaacagga ggagatgact gacaccctag 31020
atctagaaat ggacggaatt attacagagc agcgcctgct agaaagacgc agggcagcgg 31080
ccgagcaaca gcgcatgaat caagagctcc aagacatggt taacttgcac cagtgcaaaa 31140
ggggtatctt ttgtctcgta aagcaggcca aagtcaccta cgacagtaat accaccggac 31200
accgccttag ctacaagttg ccaaccaagc gtcagaaatt ggtggtcatg gtgggagaaa 31260
agcccattac cataactcag cactcggtag aaaccgaagg ctgcattcac tcaccttgtc 31320
aaggacctga ggatctctgc acccttatta agaccctgtg cggtctcaaa gatcttattc 31380
cctttaacta ataaaaaaaa ataataaagc atcacttact taaaatcagt tagcaaattt 31440
ctgtccagtt tattcagcag cacctccttg ccctcctccc agctctggta ttgcagcttc 31500
ctcctggctg caaactttct ccacaatcta aatggaatgt cagtttcctc ctgttcctgt 31560
ccatccgcac ccactatctt catgttgttg cagatgaagc gcgcaagacc gtctgaagat 31620
accttcaacc ccgtgtatcc atatgacacg gaaaccggtc ctccaactgt gccttttctt 31680
actcctccct ttgtatcccc caatgggttt caagagagtc cccctggggt actctctttg 31740
cgcctatccg aacctctagt tacctccaat ggcatgcttg cgctcaaaat gggcaacggc 31800
ctctctctgg acgaggccgg caaccttacc tcccaaaatg taaccactgt gagcccacct 31860
ctcaaaaaaa ccaagtcaaa cataaacctg gaaatatctg cacccctcac agttacctca 31920
gaagccctaa ctgtggctgc cgccgcacct ctaatggtcg cgggcaacac actcaccatg 31980
caatcacagg ccccgctaac cgtgcacgac tccaaactta gcattgccac ccaaggaccc 32040
ctcacagtgt cagaaggaaa gctagccctg caaacatcag gccccctcac caccaccgat 32100
agcagtaccc ttactatcac tgcctcaccc cctctaacta ctgccactgg tagcttgggc 32160
attgacttga aagagcccat ttatacacaa aatggaaaac taggactaaa gtacggggct 32220
cctttgcatg taacagacga cctaaacact ttgaccgtag caactggtcc aggtgtgact 32280
attaataata cttccttgca aactaaagtt actggagcct tgggttttga ttcacaaggc 32340
aatatgcaac ttaatgtagc aggaggacta aggattgatt ctcaaaacag acgccttata 32400

-continued

```
cttgatgtta gttatccgtt tgatgctcaa aaccaactaa atctaagact aggacagggc  32460

cctcttttta taaactcagc ccacaacttg gatattaact acaacaaagg cctttacttg  32520

tttacagctt caaacaattc caaaaagctt gaggttaacc taagcactgc caaggggttg  32580

atgtttgacg ctacagccat agccattaat gcaggagatg ggcttgaatt tggttcacct  32640

aatgcaccaa acacaaatcc cctcaaaaca aaaattggcc atggcctaga atttgattca  32700

aacaaggcta tggttcctaa actaggaact ggccttagtt ttgacagcac aggtgccatt  32760

acagtaggaa acaaaaataa tgataagcta actttgtgga ccacaccagc tccatctcct  32820

aactgtagac taaatgcaga gaaagatgct aaactcactt tggtcttaac aaaatgtggc  32880

agtcaaatac ttgctacagt ttcagttttg gctgttaaag gcagtttggc tccaatatct  32940

ggaacagttc aaagtgctca tcttattata agatttgacg aaaatggagt gctactaaac  33000

aattccttcc tggacccaga atattggaac tttagaaatg gagatcttac tgaaggcaca  33060

gcctatacaa acgctgttgg atttatgcct aacctatcag cttatccaaa atctcacggt  33120

aaaactgcca aaagtaacat tgtcagtcaa gtttacttaa acggagacaa aactaaacct  33180

gtaacactaa ccattacact aaacggtaca caggaaacag gagacacaac tccaagtgca  33240

tactctatgt cattttcatg ggactggtct ggccacaact acattaatga aatatttgcc  33300

acatcctctt acactttttc atacattgcc caagaataaa gaatcgtttg tgttatgttt  33360

caacgtgttt atttttcaat tgcagaaaat ttcaagtcat ttttcattca gtagtatagc  33420

cccaccacca catagcttat acagatcacc gtaccttaat caaactcaca gaaccctagt  33480

attcaacctg ccacctccct cccaacacac agagtacaca gtcctttctc cccggctggc  33540

cttaaaaagc atcatatcat gggtaacaga catattctta ggtgttatat tccacacggt  33600

ttcctgtcga gccaaacgct catcagtgat attaataaac tccccgggca gctcacttaa  33660

gttcatgtcg ctgtccagct gctgagccac aggctgctgt ccaacttgcg gttgcttaac  33720

gggcggcgaa ggagaagtcc acgcctacat gggggtagag tcataatcgt gcatcaggat  33780

agggcggtgg tgctgcagca gcgcgcgaat aaactgctgc cgccgccgct ccgtcctgca  33840

ggaatacaac atggcagtgg tctcctcagc gatgattcgc accgcccgca gcataaggcg  33900

ccttgtcctc cgggcacagc agcgcaccct gatctcactt aaatcagcac agtaactgca  33960

gcacagcacc acaatattgt tcaaaatccc acagtgcaag gcgctgtatc caaagctcat  34020

ggcggggacc acagaaccca cgtggccatc ataccacaag cgcaggtaga ttaagtggcg  34080

acccctcata aacacgctgg acataaacat tacctctttt ggcatgttgt aattcaccac  34140

ctcccggtac catataaacc tctgattaaa catggcgcca tccaccacca tcctaaacca  34200

gctggccaaa acctgcccgc cggctataca ctgcagggaa ccgggactgg aacaatgaca  34260

gtggagagcc caggactcgt aaccatggat catcatgctc gtcatgatat caatgttggc  34320

acaacacagg cacacgtgca tacacttcct caggattaca agctcctccc gcgttagaac  34380

catatcccag ggaacaaccc attcctgaat cagcgtaaat cccacactgc agggaagacc  34440

tcgcacgtaa ctcacgttgt gcattgtcaa agtgttacat tcgggcagca gcggatgatc  34500

ctccagtatg gtagcgcggg tttctgtctc aaaaggaggt agacgatccc tactgtacgg  34560

agtgcgccga gacaaccgag atcgtgttgg tcgtagtgtc atgccaaatg gaacgccgga  34620

cgtagtcata tttcctgaag caaaaccagg tgcgggcgtg acaaacagat ctgcgtctcc  34680

ggtctcgccg cttagatcgc tctgtgtagt agttgtagta tatccactct ctcaaagcat  34740

ccaggcgccc cctggcttcg ggttctatgt aaactccttc atgcgccgct gccctgataa  34800
```

-continued

```
catccaccac cgcagaataa gccacaccca gccaacctac acattcgttc tgcgagtcac  34860
acacgggagg agcgggaaga gctggaagaa ccatgttttt ttttttattc caaaagatta  34920
tccaaaacct caaaatgaag atctattaag tgaacgcgct cccctccggt ggcgtggtca  34980
aactctacag ccaaagaaca gataatggca tttgtaagat gttgcacaat ggcttccaaa  35040
aggcaaacgg ccctcacgtc caagtggacg taaaggctaa acccttcagg gtgaatctcc  35100
tctataaaca ttccagcacc ttcaaccatg cccaaataat tctcatctcg ccaccttctc  35160
aatatatctc taagcaaatc ccgaatatta agtccggcca ttgtaaaaat ctgctccaga  35220
gcgccctcca ccttcagcct caagcagcga atcatgattg caaaaattca ggttcctcac  35280
agacctgtat aagattcaaa agcggaacat taacaaaaat accgcgatcc cgtaggtccc  35340
ttcgcagggc cagctgaaca taatcgtgca ggtctgcacg gaccagcgcg gccacttccc  35400
cgccaggaac catgacaaaa gaacccacac tgattatgac acgcatactc ggagctatgc  35460
taaccagcgt agccccgatg taagcttgtt gcatgggcgg cgatataaaa tgcaaggtgc  35520
tgctcaaaaa atcaggcaaa gcctcgcgca aaaaagaaag cacatcgtag tcatgctcat  35580
gcagataaag gcaggtaagc tccggaacca ccacagaaaa agacaccatt tttctctcaa  35640
acatgtctgc gggtttctgc ataaacacaa aataaaataa caaaaaaaca tttaaacatt  35700
agaagcctgt cttacaacag gaaaaacaac ccttataagc ataagacgga ctacggccat  35760
gccggcgtga ccgtaaaaaa actggtcacc gtgattaaaa agcaccaccg acagctcctc  35820
ggtcatgtcc ggagtcataa tgtaagactc ggtaaacaca tcaggttgat tcacatcggt  35880
cagtgctaaa aagcgaccga aatagcccgg gggaatacat acccgcaggc gtagagacaa  35940
cattacagcc cccataggag gtataacaaa attaatagga gagaaaaaca cataaacacc  36000
tgaaaaaccc tcctgcctag gcaaaatagc accctcccgc tccagaacaa catacagcgc  36060
ttccacagcg gcagccataa cagtcagcct taccagtaaa aaagaaaacc tattaaaaaa  36120
acaccactcg acacggcacc agctcaatca gtcacagtgt aaaaaagggc caagtgcaga  36180
gcgagtatat ataggactaa aaaatgacgt aacggttaaa gtccacaaaa aacacccaga  36240
aaaccgcacg cgaacctacg cccagaaacg aaagccaaaa aacccacaac ttcctcaaat  36300
cgtcacttcc gttttcccac gttacgtcac ttcccatttt aagaaaacta caattcccaa  36360
cacatacaag ttactccgcc ctaaaaccta cgtcacccgc cccgttccca cgccccgcgc  36420
cacgtcacaa actccacccc ctcattatca tattggcttc aatccaaaat aaggtatatt  36480
attgatgatg ttaattaaga attcggatct gcgacgcgag gctggatggc cttccccatt  36540
atgattcttc tcgcttccgg cggcatcggg atgcccgcgt tgcaggccat gctgtccagg  36600
caggtagatg acgaccatca gggacagctt caaggccagc aaaaggccag gaaccgtaaa  36660
aaggccgcgt tgctggcgtt tttccatagg ctccgccccc ctgacgagca tcacaaaaat  36720
cgacgctcaa gtcagaggtg gcgaaacccg acaggactat aaagatacca ggcgtttccc  36780
cctggaagct ccctcgtgcg ctctcctgtt ccgaccctgc cgcttaccgg atacctgtcc  36840
gcctttctcc cttcgggaag cgtggcgctt tctcatagct cacgctgtag gtatctcagt  36900
tcggtgtagg tcgttcgctc caagctgggc tgtgtgcacg aaccccccgt tcagcccgac  36960
cgctgcgcct tatccggtaa ctatcgtctt gagtccaacc cggtaagaca cgacttatcg  37020
ccactggcag cagccactgg taacaggatt agcagagcga ggtatgtagg cggtgctaca  37080
gagttcttga agtggtggcc taactacggc tacactagaa ggacagtatt tggtatctgc  37140
```

-continued

```
gctctgctga agccagttac cttcggaaaa agagttggta gctcttgatc cggcaaacaa  37200

accaccgctg gtagcggtgg tttttttgtt tgcaagcagc agattacgcg cagaaaaaaa  37260

ggatctcaag aagatccttt gatcttttct acggggtctg acgctcagtg gaacgaaaac  37320

tcacgttaag ggattttggt catgagatta tcaaaaagga tcttcaccta gatcctttta  37380

aatcaatcta aagtatatat gagtaaactt ggtctgacag ttaccaatgc ttaatcagtg  37440

aggcacctat ctcagcgatc tgtctatttc gttcatccat agttgcctga ctccccgtcg  37500

tgtagataac tacgatacgg gagggcttac catctggccc cagtgctgca atgataccgc  37560

gagacccacg ctcaccggct ccagatttat cagcaataaa ccagccagcc ggaagggccg  37620

agcgcagaag tggtcctgca actttatccg cctccatcca gtctattaat tgttgccggg  37680

aagctagagt aagtagttcg ccagttaata gtttgcgcaa cgttgttgcc attgctacag  37740

gcatcgtggt gtcacgctcg tcgtttggta tggcttcatt cagctccggt tcccaacgat  37800

caaggcgagt tacatgatcc cccatgttgt gcaaaaaagc ggttagctcc ttcggtcctc  37860

cgatcgttgt cagaagtaag ttggccgcag tgttatcact catggttatg gcagcactgc  37920

ataattctct tactgtcatg ccatccgtaa gatgcttttc tgtgactggt gagtactcaa  37980

ccaagtcatt ctgagaatag tgtatgcggc gaccgagttg ctcttgcccg gcgtcaacac  38040

gggataatac cgcgccacat agcagaactt taaaagtgct catcattgga aaacgttctt  38100

cggggcgaaa actctcaagg atcttaccgc tgttgagatc cagttcgatg taacccactc  38160

gtgcacccaa ctgatcttca gcatctttta ctttcaccag cgtttctggg tgagcaaaaa  38220

caggaaggca aaatgccgca aaaaagggaa taagggcgac acggaaatgt tgaatactca  38280

tactcttcct ttttcaatat tattgaagca tttatcaggg ttattgtctc atgagcggat  38340

acatatttga atgtatttag aaaaataaac aaataggggt tccgcgcaca tttccccgaa  38400

aagtgccacc tgacgtctaa gaaaccatta ttatcatgac attaacctat aaaaataggc  38460

gtatcacgag gccctttcgt cttcaagaat tggatccgaa ttcttaattt cttaattaa   38519
```

<210> SEQ ID NO 29
<211> LENGTH: 38519
<212> TYPE: DNA
<213> ORGANISM: Artificial Sequence
<220> FEATURE:
<223> OTHER INFORMATION: Codon optimized DNA encoding pMRKAd5HIV-1 pol, noncoding

<400> SEQUENCE: 29

```
gtagtagtta ttatatggaa taaaacctaa cttcggttat actattactc ccccacctca     60

aacactgcac cgcgccccgc acccttgccc cgcccactgc atcatcacac cgccttcaca    120

ctacaacgtt cacaccgcct tgtgtacatt cgctgcctac accgttttca ctgcaaaaac    180

cacacgcggc cacatgtgtc cttcactgtt aaaagcgcgc caaaatccgc ctacaacatc    240

atttaaaccc gcattggctc attctaaacc ggtaaaagcg ccctttttgac ttattctcct    300

tcactttaga cttattaaaa cacaatgagt atcgcgcatt ataaacagat cccggcgccc    360

ctgaaactgg caaatgcacc tctgagcggg tccacaaaaa gagtccacaa aaggcgcaag    420

gcccagtttc aaccgcaaaa taataatatc cgccggcgct aggtaacgta tgcaacatag    480

gtatagtatt atacatgtaa atataaccga gtacaggttg taatggcggt acaactgtaa    540

ctaataactg atcaataatt atcattagtt aatgccccag taatcaagta tcgggtatat    600

acctcaaggc gcaatgtatt gaatgccatt taccgggcgg accgactggc gggttgctgg    660
```

-continued

```
gggcgggtaa ctgcagttat tactgcatac aagggtatca ttgcggttat ccctgaaagg    720
taactgcagt tacccacctc ataaatgcca tttgacgggt gaaccgtcat gtagttcaca    780
tagtatacgg ttcatgcggg ggataactgc agttactgcc atttaccggg cggaccgtaa    840
tacgggtcat gtactggaat accctgaaag gatgaaccgt catgtagatg cataatcagt    900
agcgataatg gtaccactac gccaaaaccg tcatgtagtt acccgcacct atcgccaaac    960
tgagtgcccc taaaggttca gaggtggggt aactgcagtt accctcaaac aaaaccgtgg   1020
ttttagttgc cctgaaaggt tttacagcat tgttgaggcg gggtaactgc gtttacccgc   1080
catccgcaca tgccaccctc cagatatatt cgtctcgagc aaatcacttg gcagtctagc   1140
ggacctctgc ggtaggtgcg acaaaactgg aggtatcttc tgtggccctg gctaggtcgg   1200
aggcgccggc ccttgccacg taaccttgcg cctaaggggc acggttctca ctctagatgg   1260
taccgggggt agagggggta actctgacac ggacacttcg acttcggacc gtacctaccg   1320
gggttccact tcgtcaccgg ggactgactc ctcttctagt tccgggacca cctttagacg   1380
tgactctacc tcttcctccc gttttagagg ttctaaccgg ggctcttggg gatgttgtgg   1440
ggacacaaac ggtagttctt cttcctgagg tggttcacct ccttcgacca cctgaagtcc   1500
ctcgacttgt tctcctgggt cctgaagacc ctccacgtcg acccgtaggg ggtggggcga   1560
ccggacttct tcttcttcag acactgacac gaccgacacc ccctacggat gaagagacac   1620
ggggacctac tcctgaagtc cttcatgtga cggaagtggt aggggaggta gttgttactc   1680
tggggaccgt agtccatggt catgttacac gacggggtcc cgaccttccc gaggggacgg   1740
tagaaggtca ggaggtactg gttctaggac ctcgggaagt ccttcgtctt gggactgtaa   1800
cactagatgg tcatgtaccg acgggacata cacccgagac tggacctcta acccgtcgtg   1860
tcctggttct aactcctcga ctccgtcgtg gacgactcca ccccggactg gtggggactg   1920
ttcttcgtgg tcttcctcgg ggggaaggac acctacccga tactcgacgt ggggctgttc   1980
acctgacacg tcgggtaaca cgacggactc ttcctgagga cctgacactt actgtaggtc   2040
ttcgaccacc cgttcgactt gacccggagg gtttagatgg gaccgtagtt ccactccgtc   2100
gacacgttcg acgactcccc gtggttccgg gactgactcc actaggggga ctgactcctc   2160
cgactcgacc tcgaccgact cttgtccctc taggacttcc tcggacacgt accccacatg   2220
atactgggga ggttcctgga ctaacgactc taggtcttcg tcccggtccc ggtcacctgg   2280
atggtttaga tggtcctcgg gaagttcttg gacttctgac cgttcatacg gtcctactcc   2340
ccccgggtgt ggttactaca cttcgtcgac tgactccgac acgtcttcta gtggtgactc   2400
aggtaacact agaccccgtt ctggggggttc aagttcgacg ggtaggtctt cctctggacc   2460
ctctggacca cctgactcat gaccgtccgg tggacctagg gactcaccct caaacacttg   2520
tggggggggg accacttcga caccatggtc gacctcttcc tcgggtaaca cccccgactc   2580
tggaagatac accgaccccg acggttgtcc ctctggttcg acccgttccg accgatacac   2640
tggttgtccc cgtccgtctt ccaccactgg gactgactgt ggtggttggt cttctgacgg   2700
gaggtccggt agatggaccg ggaggtcctg agaccggacc tccacttgta acactgacgg   2760
agggtcatac gggacccgta gtaggtccgg gtcggactag tcagactcag actcgaccac   2820
ttggtctagt aactcgtcga ctagttcttc ctcttccaca tggaccggac ccacggacgg   2880
gtgttcccgt aacccccgtt actcgtccac ctgttcgacc acagacgacc gtagtccttc   2940
cacgacaagg acctaccgta actgttccgg gtcctactcg tactcttcat ggtgaggttg   3000
acctcccgat accggagact gaagttggac gggggacacc accgattcct ctaacaccgg   3060
```

-continued

```
aggacactgt tcacggtcga cttccccctc cggtacgtac ccgtccacct gacgagggga   3120
ccgtagaccg tcgaccggac gtgggtggac ctcccgttcc actaggacca ccgacacgta   3180
caccggaggc cgatgtaact ccgactccac tagggacgac tctgtccggt cctctgacgg   3240
atgaaggacg acttcgaccg accgtccacc ggacacttct ggtaggtgtg acggttaccg   3300
aggttgaagt gaccccggtg tcactcccga cggacgacca cccgaccgta gttcgtcctc   3360
aaaccgtagg ggatgttggg ggtcagggtc ccccaccacc ggaggtactt gttcctcgac   3420
ttcttctagt aacccgtcca ctccctggtc cgactcgtgg acttctgtcg acacgtctac   3480
cgacacaagt aggtgttgaa gttctccttc cccccgtagc ccccgatgag gcgacccctc   3540
tcctaacacc tgtagtaacg gtgtctgtag gtctggttcc tcgaggtctt cgtctagtgg   3600
ttctaggtct tgaagtccca catgatgtcc ctgaggtcct tgggggacac cttcccggga   3660
cggttcgacg acaccttccc cctcccccga caccactagg tcctgttgag actgtagttc   3720
caccacgggt cctccttccg gttctagtag tccctgatac cgttcgtcta ccgaccccta   3780
ctgacacacc ggaggtccgt cctactcctg atttcgggcc cgtctagacg acacggaaga   3840
tcaacggtcg gtagacaaca aacggggagg gggcacggaa ggaactggga ccttccacgg   3900
tgagggtgac aggaaaggat tattttactc ctttaacgta gcgtaacaga ctcatccaca   3960
gtaagataag accccccacc ccaccccgtc ctgtcgttcc ccctcctaac ccttctgtta   4020
tcgtccgtac gacccctacg ccacccgaga taccggctag ccgcgcggca tgactttaca   4080
cacccgcacc gaattcccac cctttcttat atattccacc cccagaatac atcaaaacat   4140
agacaaaacg tcgtcggcgg cggcggtact cgtggttgag caaactacct tcgtaacact   4200
cgagtataaa ctgttgcgcg tacgggggta cccggcccca cgcagtctta cactacccga   4260
ggtcgtaact accagcgggg caggacgggc gtttgagatg atggaactgg atgctctggc   4320
acagaccttg cggcaacctc tgacgtcgga ggcggcggcg aagtcggcga cgtcggtggc   4380
gggcgcccta acactgactg aaacgaaagg actcgggcga acgtttgtca cgtcgaaggg   4440
caagtaggcg ggcgctactg ttcaactgcc gagaaaaccg tgttaaccta agaaactggg   4500
cccttgaatt acagcaaaga gtcgtcgaca acctagacgc ggtcgtccaa agacgggact   4560
tccgaaggag gggagggtta cgccaaattt tgtatttatt ttttggtctg agacaaacct   4620
aaacctagtt cgttcacaga acgacagaaa taaatcccca aaacgcgcgc gccatccggg   4680
ccctggtcgc cagagccagc aactcccagg acacataaaa aaggtcctgc accatttcca   4740
ctgagaccta caagtctatg tacccgtatt cgggcagaga ccccacctcc atcgtggtga   4800
cgtctcgaag tacgacgccc caccacaaca tctactaggt cagcatcgtc ctcgcgaccc   4860
gcaccacgga tttttacaga aagtcatcgt tcgactaacg gtccccgtcc gggaaccaca   4920
ttcacaaatg tttcgccaat tcgaccctac ccacgtatgc accccctatac tctacgtaga   4980
acctgacata aaaatccaac cgatacaagg gtcggtatag ggaggcccct aagtacaaca   5040
cgtcttggtg gtcgtgtcac ataggccacg tgaacccttt aaacagtaca tcgaatcttc   5100
ctttacgcac cttcttgaac ctctgcggga acactggagg ttctaaaagg tacgtaagca   5160
ggtattacta ccgttacccg ggtgcccgcc gccggacccg cttctataaa gaccctagtg   5220
attgcagtat caacacaagg tcctactcta gcagtatccg gtaaaaatgt ttcgcgcccg   5280
cctcccacgg tctgacgcca tattaccaag gtaggccggg tccccgcatc aatgggagtg   5340
tctaaacgta aagggtgcga aactcaagtc taccccccta gtacagatgg acgccccgct   5400
```

-continued

```
acttcttttg ccaaaggccc catcccctct agtcgaccct tctttcgtcc aaggactcgt   5460
cgacgctgaa tggcgtcggc cacccgggca tttagtgtgg ataatggccg acgttgacca   5520
tcaattctct cgacgtcgac ggcagtaggg actcgtcccc ccggtgaagc aattcgtaca   5580
gggactgagc gtacaaaagg gactggttta ggcggtcttc cgcgagcggc gggtcgctat   5640
cgtcaagaac gttccttcgt ttcaaaaagt tgccaaactc tggcaggcgg catccgtacg   5700
aaaactcgca aactggttcg tcaaggtccg ccagggtgtc gagccagtgg acgagatgcc   5760
gtagagctag gtcgtataga ggagcaaagc gcccaacccc gccgaaagcg acatgccgtc   5820
atcagccacg agcaggtctg cccggtccca gtacagaaag gtgcccgcgt cccaggagca   5880
gtcgcatcag acccagtgcc acttccccac gcgaggcccg acgcgcgacc ggtcccacgc   5940
gaactccgac caggacgacc acgacttcgc gacggccaga agcgggacgc gcagccggtc   6000
catcgtaaac tggtaccaca gtatcaggtc ggggaggcgc cgcaccggga accgcgcgtc   6060
gaacgggaac ctcctccgcg gcgtgctccc cgtcacgtct gaaaactccc gcatctcgaa   6120
cccgcgctct ttatggctaa ggcccctcat ccgtaggcgc ggcgtccggg gcgtctgcca   6180
gagcgtaagg tgctcggtcc actcgagacc ggcaagcccc agtttttggt ccaaaggggg   6240
tacgaaaaac tacgcaaaga atggagacca aaggtactcg gccacaggtg cgagccactg   6300
cttttccgac aggcacaggg gcatatgtct gaactctccg gacaggagct cgccacaagg   6360
cgccaggagg agcatatctt tgagcctggt gagactctgt ttccgagcgc aggtccggtc   6420
gtgcttcctc cgattcaccc tccccatcgc cagcaacagg tgatccccca ggtgagcgag   6480
gtcccacact tctgtgtaca gcgggagaag ccgtagttcc ttccactaac caaacatcca   6540
catccggtgc actggcccac aaggacttcc ccccgatatt ttcccccacc cccgcgcaag   6600
caggagtgag agaaggcgta gcgacagacg ctcccggtcg acaaccccac tcatgaggga   6660
gacttttcgc ccgtactgaa gacgcgattc taacagtcaa aggtttttgc tcctcctaaa   6720
ctataagtgg accgggcgcc actacggaaa ctcccaccgg cgtaggtaga ccagtctttt   6780
ctgttagaaa aacaacagtt cgaaccaccg tttgctgggc atctcccgca acctgtcgtt   6840
gaaccgctac ctcgcgtccc aaaccaaaaa cagcgctagc cgcgcgagga accggcgcta   6900
caaatcgacg tgcataagcg cgcgttgcgt ggcggtaagc cctttctgcc accacgcgag   6960
cagcccgtgg tccacgtgcg cggttggcgc caacacgtcc cactgttcca gttgcgacca   7020
ccgatggaga ggcgcatccg cgagcaacca ggtcgtctcc gccggcggga acgcgctcgt   7080
cttaccgcca tcccccagat cgacgcagag caggcccccc agacgcaggt gccatttctg   7140
gggcccgtcg tccgcgcgca gcttcatcag atagaacgta ggaacgttca gatcgcggac   7200
gacggtacgc gcccgccgtt cgcgcgcgag catacccaac tcaccccctg gggtaccgta   7260
ccccacccac tcgcgcctcc gcatgtacgg cgtttacagc atttgcatct ccccgagaga   7320
ctcataaggt tctatacatc ccatcgtaga aggtggcgcc tacgaccgcg cgtgcattag   7380
catatcaagc acgctccctc gctcctccag ccctggctcc aacgatgccc gcccgacgag   7440
acgagccttc tgatagacgg acttctaccg tacactcaac ctactatacc aacctgcgac   7500
cttctgcaac ttcgaccgca gacactctgg atggcgcagt gcgtgcttcc tccgcatcct   7560
cagcgcgtcg aacaactggt cgagccgcca ctggacgtgc agatcccgcg tcatcaggtc   7620
ccaaaggaac tactacagta tgaataggac agggaaaaaa aaggtgtcga gcgccaactc   7680
ctgtttgaga agcgccagaa aggtcatgag aacctagcct ttgggcagcc ggaggcttgc   7740
cattctcgga tcgtacatct tgaccaactg ccggaccatc cgcgtcgtag ggaaaagatg   7800
```

-continued

```
cccatcgcgc atacggacgc gccggaaggc ctcgctccac acccactcgc gtttccacag   7860
ggactggtac tgaaactcca tgaccataaa cttcagtcac agcagcgtag gcgggacgag   7920
ggtctcgttt ttcaggcacg cgaaaaacct tgcgcctaaa ccgtcccgct tccactgtag   7980
caacttctca tagaaagggc gcgctccgta tttcaacgca cactacgcct tcccagggcc   8040
gtggagcctt gccaacaatt aatggacccg ccgctcgtgc tagagcagtt tcggcaacta   8100
caacaccggg tgttacattt caaggttctt cgcgccctac gggaactacc ttccgttaaa   8160
aaattcaagg agcatccact cgagaagtcc cctcgactcg ggcacgagac tttcccgggt   8220
cagacgttct actcccaacc ttcgctgctt actcgaggtg tccagtgccc ggtaatcgta   8280
aacgtccacc agcgctttcc aggatttgac cgctggatac cggtaaaaaa gaccccacta   8340
cgtcatcttc cattcgccca gaacaagggt cgccagggta ggttccaagc gccgatccag   8400
agcgcgccgt cagtgatctc cgagtagagg cggcttgaag tactggtcgt acttcccgtg   8460
ctcgacgaag ggtttccggg ggtaggttca tatccagaga tgtagcatcc actgtttctc   8520
tgcgagccac gctcctacgc tcggctagcc cttcttgacc tagagggcgg tggttaacct   8580
cctcaccgat aactacacca ctttcatctt cagggacgct gcccggcttg tgagcacgac   8640
cgaaaacatt tttgcacgcg tcatgaccgt cgccacgtgc ccgacatgta ggacgtgctc   8700
caactggact gctggcgcgt gttccttcgt ctcaccctta aactcgggga gcggaccgcc   8760
caaaccgacc accagaagat gaagccgacg aacaggaact ggcagaccga cgagctcccc   8820
tcaatgccac ctagcctggt ggtgcggcgc gctcgggttt caggtctaca ggcgcgcgcc   8880
gccagcctcg aactactgtt gtagcgcgtc taccctcgac aggtaccaga cctcgagggc   8940
gccgcagtcc agtccgccct cgaggacgtc caaatggagc gtatctgccc agtcccgcgc   9000
ccgatctagg tccactatgg attaaaggtc cccgaccaac caccgccgca gctaccgaac   9060
gttctccggc gtaggggcgc cgcgctgatg ccatggcgcg ccgcccgcca cccggcgccc   9120
ccacaggaac ctactacgta gattttcgcc actgcgcccg ctcgggggcc tccatccccc   9180
ccgaggcctg ggcggccctc tccccgtcc ccgtgcagcc gcggcgcgcg cccgtcctcg   9240
accacgacgc gcgcatccaa cgaccgcttg cgctgctgcg ccgccaacta gaggacttag   9300
accgcggaga cgcacttctg ctgcccgggc cactcgaact tggactttct ctcaagctgt   9360
cttagttaaa gccacagcaa ctgccgccgg accgcgtttt agaggacgtg cagaggactc   9420
aacagaacta tccgctagag ccggtacttg acgagctaga gaaggaggac ctctagaggc   9480
gcaggccgag cgaggtgcca ccgccgctcc agcaaccttt acgcccggta ctcgacgctc   9540
ttccgcaact ccggagggag caaggtctgc gccgacatct ggtgcggggg aagccgtagc   9600
gcccgcgcgt actggtggac gcgctctaac tcgaggtgca cggcccgctt ctgccgcatc   9660
aaagcgtccg cgactttctc catcaactcc caccaccgcc acacaagacg gtgcttcttc   9720
atgtattggg tcgcagcgtt gcacctaagc aactataggg ggttccggag ttccgcgagg   9780
taccggagca tcttcaggtg ccgcttcaac tttttgaccc tcaacgcgcg gctgtgccaa   9840
ttgaggagga ggtcttctgc ctactcgagc cgctgtcaca gcgcgtggag cgcgagtttc   9900
cgatgtcccc ggagaagaag aagaagttag aggagaaggt attcccggag gggaagaaga   9960
agaagaccgc cgccaccccc tccccctgt gccgccgctg ctgccgcgtg gccctccgcc  10020
agctgtttcg cgagctagta gaggggcgcc gctgccgcgt accagagcca ctgccgcgcc  10080
ggcaagagcg cccccgcgtc aaccttctgc ggcgggcagt acagggccaa tacccaaccg  10140
```

-continued cccccgacg gtacgccgtc cctatgccgc gattgctacg tagagttgtt aacaacacat 10200
ccatgaggcg gcggctccct ggactcgctc aggcgtagct ggcctagcct tttggagagc 10260
tctttccgca gattggtcag tgtcagcgtt ccatccgact cgtggcaccg cccgccgtcg 10320
cccgccgcca gccccaacaa agaccgcctc cacgacgact actacattaa tttcatccgc 10380
cagaactctg ccgcctacca gctgtcttcg tggtacagga acccaggccg gacgacttac 10440
gcgtccgcca gccggtacgg ggtccgaagc aaaactgtag ccgcgtccag aaacatcatc 10500
agaacgtact cggaaagatg gccgtgaaga agaagaggaa ggagaacagg acgtagagaa 10560
cgtagatagc gacgccgccg ccgcctcaaa ccggcatcca ccgcgggaga aggagggtac 10620
gcacactggg gcttcgggga gtagccgact tcgtcccgat ccagccgctg ttgcgcgagc 10680
cgattatacc ggacgacgtg gacgcactcc catctgacct tcagtaggta caggtgtttc 10740
gccaccatac gcgggcacaa ctaccacatt cacgtcaacc ggtattgcct ggtcaattgc 10800
cagaccactg ggccgacgct ctcgagccac atggactctg cgctcattcg ggagctcagt 10860
ttatgcatca gcaacgttca ggcgtggtcc atgaccatag ggtggttttt cacgccgccg 10920
ccgaccgcca tctccccggt cgcatcccac cggccccgag gccccccgctc tagaaggttg 10980
tattccgcta ctataggcat ctacatggac ctgtaggtcc actacggccg ccgccaccac 11040
ctccgcgcgc ctttcagcgc ctgcgccaag gtctacaacg cgtcgccgtt tttcacgagg 11100
taccagccct gcgagaccgg ccagtccgcg cgcgttagca actgcgagat ctggcacgtt 11160
ttcctctcgg acattcgccc gtgagaaggc accagaccac ctatttaagc gttcccatag 11220
taccgcctgc tggccccaag ctcggggcat aggccggcag gcggcactag gtacgccaat 11280
ggcgggcgca cagcttgggt ccacacgctg cagtctgttg ccccctcacg aggaaaaccg 11340
aaggaaggtc cgcgccgccg acgacgcgat cgaaaaaacc ggtgaccggc gcgcgtcgca 11400
ttcgccaatc cgacctttcg ctttcgtaat tcaccgagcg agggacatcg gcctcccaat 11460
aaaaggttcc caactcagcg ccctgggggc caagctcaga gcctggccgg cctgacgccg 11520
cttgcccccca aacggagggg cagtacgttc tggggcgaac gtttaaggag gcctttgtcc 11580
ctgctcgggg aaaaaacgaa aagggtctac gtaggccacg acgccgtcta cgcgggggga 11640
ggagtcgtcg ccgttctcgt tctcgtcgcc gtctgtacgt cccgtgggag gggaggagga 11700
tggcgcagtc ctccccgctg taggcgccaa ctgcgccgtc gtctaccact aatgcttggg 11760
ggcgccgcgg cccgggccgt gatggacctg aacctcctcc cgctcccgga ccgcgccgat 11820
cctcgcggga gaggactcgc cgtgggttcc cacgtcgact tcgcactatg cgcactccgc 11880
atgcacggcg ccgtcttgga caaagcgctg gcgctccctc tcctcgggct cctctacgcc 11940
ctagctttca aggtgcgtcc cgcgctcgac gccgtaccgg acttagcgct cgccaacgac 12000
gcgctcctcc tgaaactcgg gctgcgcgct tggccctaat cagggcgcgc gcgtgtgcac 12060
cgccggcggc tggaccattg gcgtatgctc gtctgccact tggtcctcta attgaaagtt 12120
ttttcgaaat tgttggtgca cgcatgcgaa caccgcgcgc tcctccaccg atatcctgac 12180
tacgtagaca ccctgaaaca ttcgcgcgac ctcgttttgg gtttatcgtt cggcgagtac 12240
cgcgtcgaca aggaatatca cgtcgtgtcg tccctgttgc tccgtaagtc cctacgcgac 12300
gatttgtatc atctcgggct cccggcgacc gacgagctaa actatttgta ggacgtctcg 12360
tatcaccacg tcctcgcgtc gaactcggac cgactgttcc accggcggta gttgataagg 12420
tacgaatcgg acccgttcaa aatgcgggcg ttctatatgg tatggggaat gcaagggtat 12480
ctgttcctcc atttctagct ccccaagatg tacgcgtacc gcgacttcca cgaatggaac 12540

-continued tcgctgctgg acccgcaaat agcgttgctc gcgtaggtgt tccggcactc gcactcggcc 12600
gccgcgctcg agtcgctggc gctcgactac gtgtcggacg tttcccggga ccgaccgtgc 12660
ccgtcgccgc tatctctccg gctcaggatg aaactgcgcc cgcgactgga cgcgacccgg 12720
ggttcggctg cgcgggacct ccgtcgaccc cggcctggac ccgaccgcca ccgtgggcgc 12780
gcgcgaccgt tgcagccgcc gcacctcctt atactgctcc tgctactcat gctcggtctc 12840
ctgccgctca tgattcgcca ctacaaagac tagtctacta cgttctgcgt tgcctgggcc 12900
gccacgcccg ccgcgacgtc tcggtcggca ggccggaatt gaggtgcctg ctgaccgcgg 12960
tccagtacct ggcgtagtac agcgactgac gcgcgttagg actgcgcaag gccgtcgtcg 13020
gcgtccggtt ggccgagagg cgttaagacc ttcgccacca gggccgcgcg cgtttggggt 13080
gcgtgctctt ccacgaccgc tagcatttgc gcgaccggct tttgtcccgg taggccgggc 13140
tgctccggcc ggaccagatg ctgcgcgacg aagtcgcgca ccgagcaatg ttgtcgccgt 13200
tgcacgtctg gttggacctg gccgaccacc ccctacacgc gctccggcac cgcgtcgcac 13260
tcgcgcgcgt cgtcgtcccg ttggacccga ggtaccaacg tgatttgcgg aaggactcat 13320
gtgtcgggcg gttgcacggc gcccctgtcc tcctgatgtg gttgaaacac tcgcgtgacg 13380
ccgattacca ctgactctgt ggcgtttcac tccacatggt cagacccggt ctgataaaaa 13440
aggtctggtc atctgttccg gacgtctggc atttggactc ggtccgaaag tttttgaacg 13500
tccccgacac cccccacgcc cgagggtgtc cgctggcgcg ctggcacaga tcgaacgact 13560
gcgggttgag cgcggacaac gacgacgatt atcgcgggaa gtgcctgtca ccgtcgcaca 13620
gggccctgtg tatggatcca gtgaacgact gtgacatggc gctccggtat ccagtccgcg 13680
tacacctgct cgtatgaaag gtcctctaat gttcacagtc ggcgcgcgac cccgtcctcc 13740
tgtgcccgtc ggacctccgt tgggatttga tggacgactg gttggccgcc gtcttctagg 13800
ggagcaacgt gtcaaatttg tcgctcctcc tcgcgtaaaa cgcgatgcac gtcgtctcgc 13860
actcggaatt ggactacgcg ctgccccatt gcgggtcgca ccgcgacctg tactggcgcg 13920
cgttgtacct tggcccgtac atacggagtt tggccggcaa atagttggcg gattacctga 13980
tgaacgtagc gcgccggcgg cacttggggc tcataaagtg gttacggtag aacttgggcg 14040
tgaccgatgg cgggggacca aagatgtggc cccctaagct ccacgggctc ccattgctac 14100
ctaaggagac cctgctgtat ctgctgtcgc acaaaagggg cgttggcgtc tgggacgatc 14160
tcaacgttgt cgcgctcgtc cgtctccgcc gcgacgcttt cctttcgaag gcgtccggtt 14220
cgtcgaacag gctagatccg cgacgccggg gcgccagtct acgatcatcg ggtaaaggtt 14280
cgaactatcc cagagaatgg tcgtgagcgt ggtgggcggg cgcggacgac ccgctcctcc 14340
tcatggattt gttgagcgac gacgtcggcg tcgcgctttt tttggacgga ggccgtaaag 14400
ggttgttgcc ctatctctcg gatcacctgt tctactcatc taccttctgc atgcgcgtcc 14460
tcgtgtccct gcacggtccg ggcgcgggcg ggtgggcagc agtttccgtg ctggcagtcg 14520
ccccagacca caccctcctg ctactgagcc gtctgctgtc gtcgcaggac ctaaaccctc 14580
cctcaccgtt gggcaaacgc gtggaagcgg ggtccgaccc ctcttacaaa attttttttt 14640
ttttcgtact acgttttatt ttttgagtgg ttccggtacc gtggctcgca accaaaagaa 14700
cataagggga atcatacgcc gcgcgccgct acatactcct tccaggagga gggaggatgc 14760
tctcacacca ctcgcgccgc ggtcaccgcc gccgcgaccc aagagggaag ctacgagggg 14820
acctgggcgg caaacacgga ggcgccatgg acgccggatg gccccccctct ttgtcgtagg 14880

-continued

```
caatgagact caaccgtggg gataagctgt ggtgggcaca catggaccac ctgttgttca  14940
gttgcctaca ccgtagggac ttgatggtct tgctggtgtc gttgaaagac tggtgccagt  15000
aagttttgtt actgatgtcg ggccccctcc gttcgtgtgt ctggtagtta gaactgctgg  15060
ccagcgtgac cccgccgctg gacttttggt aggacgtatg gttgtacggt ttacacttgc  15120
tcaagtacaa atggttattc aaattccgcg cccactacca cagcgcgaac ggatgattcc  15180
tgttagtcca cctcgacttt atgctcaccc acctcaagtg cgacgggctc ccgttgatga  15240
ggctctggta ctggtatctg gaatacttgt tgcgctagca cctcgtgatg aactttcacc  15300
cgtctgtctt gccccaagac ctttcgctgt agccccattt caaactgtgg gcgttgaagt  15360
ctgaccccaa actggggcag tgaccagaac agtacggacc ccatatatgt ttgcttcgga  15420
aggtaggtct gtagtaaaac gacggtccta cgcccccacct gaagtgggtg tcggcggact  15480
cgttgaacaa cccgtaggcg ttcgccgttg ggaaggtcct cccgaaatcc tagtggatgc  15540
tactagacct cccaccattg taagggcgtg acaacctaca cctgcggatg gtccgctcga  15600
actttctact gtggcttgtc ccgcccccac cgcgtccgcc gtcgttgtcg tcaccgtcgc  15660
cgcgccttct cttgaggttg cgccgtcggc gccgttacgt cggccacctc ctgtacttgc  15720
tagtacggta agcgccgctg tggaaacggt gtgcccgact cctcttcgcg cgactccggc  15780
ttcgtcgccg gcttcgacgg cgggggcgac gcgttgggct ccagctcttc ggagtcttct  15840
ttggccacta gtttggggac tgtctcctgt cgttctttgc gtcaatgttg gattattcgt  15900
tactgtcgtg gaagtgggtc atggcgtcga ccatggaacg tatgttgatg ccgctgggag  15960
tctggcctta ggcgagtacc tgggacgaaa cgtgaggact gcattggacg ccgagcctcg  16020
tccagatgac cagcaacggt ctgtactacg ttctggggca ctggaaggcg aggtgcgcgg  16080
tctagtcgtt gaaaggccac cacccgcggc tcgacaacgg gcacgtgagg ttctcgaaga  16140
tgttgctggt ccggcagatg agggttgagt aggcggtcaa atggagagac tgggtgcaca  16200
agttagcgaa agggctcttg gtctaaaacc gcgcgggcgg tcgggggtgg tagtggtggc  16260
agtcactttt gcaaggacga gagtgtctag tgccctgcga tggcgacgcg ttgtcgtagc  16320
ctcctcaggt cgctcactgg taatgactgc ggtctgcggc gtggacgggg atgcaaatgt  16380
tccgggaccc gtatcagagc ggcgcgcagg atagctcggc gtgaaaaact cgttcgtaca  16440
ggtaggaata tagcgggtcg ttattgtgtc cgaccccgga cgcgaagggt tcgttctaca  16500
aaccgccccg gttcttcgcg aggctggttg tgggtcacgc gcacgcgccc gtgatggcgc  16560
gcgggacccc gcgcgtgttt gcgccggcgt gacccgcgtg gtggcagcta ctgcggtagc  16620
tgcgccacca cctcctccgc gcgttgatgt gcgggtgcgg cggtggtcac aggtgtcacc  16680
tgcgccggta agtctggcac cacgcgcctc gggccgcgat acgattttac ttctctgccg  16740
cctccgcgca tcgtgcagcg gtggcggcgg ctgggccgtg acggcgggtt gcgcgccgcc  16800
gccgggacga attggcgcgt gcagcgtggc cggctgcccg ccggtacgcc cggcgagctt  16860
ccgaccggcg cccataacag tgacacgggg ggtccaggtc cgctgctcgc cggcggcgtc  16920
gtcggcgccg gtaatcacga tactgagtcc cagcgtcccc gttgcacata acccacgcgc  16980
tgagccaatc gccggacgcg cacgggcacg cgtgggcggg gggcgcgttg atctaacgtt  17040
ctttttttgat gaatctgagc atgacaacat acataggtcg ccgccgccgc gcgttgcttc  17100
gatacaggtt cgcgttttag tttcttctct acgaggtcca gtagcgcggc ctctagatac  17160
cggggggctt cttccttctc gtcctaatgt tcggggcttt cgatttcgcc cagtttttct  17220
ttttctttct actactacta cttgaactgc tgctccacct tgacgacgtg cgatggcgcg  17280
```

-continued

```
ggtccgctgc ccatgtcacc tttccagctg cgcattttgc acaaaacgct gggccgtggt  17340
ggcatcagaa atgcgggcca ctcgcgaggt gggcgtggat gttcgcgcac atactactcc  17400
acatgccgct gctcctggac gaactcgtcc ggttgctcgc ggagcccctc aaacggatgc  17460
ctttcgccgt attcctgtac gaccgcaacg gcgacctgct cccgttgggt tgtggatcgg  17520
atttcgggca ttgtgacgtc gtccacgacg ggcgcgaacg tggcaggctt cttttcgcgc  17580
cggatttcgc gctcagacca ctgaaccgtg ggtggcacgt cgactaccat gggttcgcgg  17640
tcgctgacct tctacagaac ctttttttact ggcaccttgg acccgacctc gggctccagg  17700
cgcacgccgg ttagttcgtc caccgcggcc ctgacccgca cgtctggcac ctgcaagtct  17760
atgggtgatg gtcatcgtgg tcataacggt ggcggtgtct cccgtacctc tgtgtttgca  17820
ggggccaacg gagtcgccac cgcctacggc gccacgtccg ccagcgacgc cggcgcaggt  17880
tctggagatg cctccacgtt tgcctgggca cctacaaagc gcaaagtcgg ggggccgcgg  17940
gcgcggcaag ctccttcatg ccgcggcggt cgcgcgatga cgggcttata cgggatgtag  18000
gaaggtaacg cggatggggg ccgatagcac cgatgtggat ggcggggtct tctgctcgtt  18060
gatgggctgc ggcttggtgg tgaccttggg cggcggcggc agcggcagcg gtcgggcacg  18120
accggggcta aaggcacgcg tcccaccgag cgcttcctcc gtcctgggac cacgacggtt  18180
gtcgcgcgat ggtggggtcg tagcaaattt tcggccagaa acaccaagaa cgtctatacc  18240
gggagtggac ggcggaggca aagggccacg gccctaaggc tccttcttac gtggcatcct  18300
ccccgtaccg gccggtgccg gactgcccgc cgtacgcagc acgcgtggtg gccgccgccg  18360
cgcgcagcgt ggcagcgtac gcgccgccat aggacgggga ggaataaggt gactagcggc  18420
gccgctaacc gcggcacggg ccttaacgta ggcaccggaa cgtccgcgtc tctgtgacta  18480
atttttgttc aacgtacacc tttttagttt tatttttcag acctgagagt gcgagcgaac  18540
caggacattg ataaaacatc ttaccttctg tagttgaaac gcagagaccg ggcgctgtg  18600
ccgagcgcgg gcaagtaccc tttgaccgtt ctatagccgt ggtcgttata ctcgccaccg  18660
cggaagtcga ccccgagcga cacctcgccg taatttttaa agccaaggtg gcaattcttg  18720
ataccgtcgt tccggacctt gtcgtcgtgt ccggtctacg actccctatt caactttctc  18780
gttttaaagg ttgttttcca ccatctaccg gaccggagac cgtaatcgcc ccaccacctg  18840
gaccggttgg tccgtcacgt tttattctaa ttgtcattcg aactaggggc gggagggcat  18900
ctcctcggag gtggccggca cctctgtcac agaggtctcc ccgcaccgct tttcgcaggc  18960
gcggggctgt cccttctttg agaccactgc gtttatctgc tcggagggag catgctcctc  19020
cgtgatttcg ttccggacgg gtggtgggca gggtagcgcg ggtaccgatg gcctcacgac  19080
ccggtcgtgt gtgggcattg cgacctggac ggaggggggc ggctgtgggt cgtctttgga  19140
cacgacggtc cgggctggcg gcaacaacat tgggcaggat cggcgcgcag ggacgcggcg  19200
cggcggtcgc caggcgctag caacgccggg catcggtcac cgttgaccgt ttcgtgtgac  19260
ttgtcgtagc acccagaccc ccacgttagg gacttcgcgg ctgctacgaa gactatcgat  19320
tgcacagcat acacacagta catacgcagg tacagcggcg gtctcctcga cgactcggcg  19380
gcgcgcgggc gaaaggttct accgatgggg aagctactac ggcgtcacca gaatgtacgt  19440
gtagagcccg gtcctgcgga gcctcatgga ctcggggccc gaccacgtca aacgggcgcg  19500
gtggctctgc atgaagtcgg acttattgtt caaatctttg gggtgccacc gcggatgcgt  19560
gctgcactgg tgtctggcca gggtcgcaaa ctgcgacgcc aagtagggac acctggcact  19620
```

-continued

```
cctatgacgc atgagcatgt tccgcgccaa gtgggatcga cacccactat tggcacacga  19680
cctgtaccga aggtgcatga aactgtaggc gccgcacgac ctgtccccgg gatgaaaatt  19740
cgggatgaga ccgtgacgga tgttgcggga ccgagggttc ccacggggtt taggaacgct  19800
taccctactt cgacgatgac gagaacttta tttggatctt cttctcctgc tactgttgct  19860
tctgcttcat ctgctcgttc gactcgtcgt tttttgagtg cataaacccg tccgcggaat  19920
aagaccatat ttataatgtt tcctcccata agtttatcca cagcttccag tttgtggatt  19980
tatacggcta ttttgtaaag ttggacttgg agtttatcct cttagagtca ccatgctttg  20040
tctttaatta gtacgtcgac cctctcagga ttttttctga tggggttact ttggtacaat  20100
gccaagtata cgttttgggt gtttactttt acctcccgtt ccgtaagaac atttcgttgt  20160
tttacctttc gatctttcag ttcaccttta cgttaaaaag agttgatgac tccgtcggcg  20220
tccgttacca ctattgaact gaggatttca ccataacatg tcacttctac atctatatct  20280
ttggggtctg tgagtataaa gaatgtacgg gtgataattc cttccattga gtgctcttga  20340
ttacccggtt gttagatacg ggttgtccgg attaatgtaa cgaaaatccc tgttaaaata  20400
accagattac ataatgttgt cgtgcccatt atacccacaa gaccgcccgg ttcgtagcgt  20460
caacttacga caacatctaa acgttctgtc tttgtgtctc gaaagtatgg tcgaaaacga  20520
actaaggtaa ccactatctt ggtccatgaa aagatacacc ttagtccgac aactgtcgat  20580
actaggtcta caatcttaat aacttttagt accttgactt ctacttgaag gtttaatgac  20640
gaaaggtgac cctccacact aattatgtct ctgagaatgg ttccattttg gattttgtcc  20700
agtcctttta cctacccttt ttctacgatg tcttaaaagt ctatttttac tttattctca  20760
acctttatta aaacggtacc tttagttaga tttacggttg gacacctctt taaaggacat  20820
gaggttgtat cgcgacataa acgggctgtt cgatttcatg tcaggaaggt tgcattttta  20880
aagactattg ggtttgtgga tgctgatgta cttgttcgct caccaccgag ggcccgatca  20940
cctgacgatg taattggaac ctcgtgcgac cagggaactg atatacctgt tgcagttggg  21000
taaattggtg gtggcgttac gaccggacgc gatggcgagt tacaacgacc cgttaccagc  21060
gatacacggg aaggtgtagg tccacggagt cttcaagaaa cggtaatttt tggaggaaga  21120
ggacggcccg agtatgtgga tgctcacctt gaagtccttc ctacaattgt accaagacgt  21180
ctcgagggat cctttactgg attcccaact gcctcggtcg taattcaaac tatcgtaaac  21240
ggaaatgcgg tggaagaagg ggtaccgggt gttgtggcgg aggtgcgaac tccggtacga  21300
atctttgctg tggttgctgg tcaggaaatt gctgatagag aggcggcggt tgtacgagat  21360
gggatatggg cggttgcgat ggttgcacgg gtataggtag gggagggcgt tgacccgccg  21420
aaaggcgccg acccggaagt gcgcggaatt ctgattcctt tggggtagtg acccgagccc  21480
gatgctggga ataatgtgga tgagaccgag atatgggatg gatctacctt ggaaaatgga  21540
gttggtgtgg aaattcttcc accggtaatg gaaactgaga agacagtcga ccggaccgtt  21600
actggcggac gaatgggggt tgctcaaact ttaattcgcg agtcaactgc ccctcccaat  21660
gttgcaacgg gtcacattgt actggtttct gaccaaggac catgtttacg atcgattgat  21720
attgtaaccg atggtcccga agatataggg tctctcgatg ttcctggcgt acatgaggaa  21780
gaaatctttg aaggtcgggt actcggcagt ccaccaccta ctatgattta tgttcctgat  21840
ggttgtccac ccgtaggatg tggttgtgtt gttgagacct aaacaaccga tggaacgggg  21900
gtggtacgcg cttcctgtcc ggatgggacg attgaagggg ataggcgaat atccgttctg  21960
gcgtcaactg tcgtaatggg tctttttcaa agaaacgcta gcgtgggaaa ccgcgtaggg  22020
```

-continued

```
taagaggtca ttgaaataca ggtacccgcg tgagtgtctg gacccggttt tggaagagat  22080
gcggttgagg cgggtgcgcg atctgtactg aaaactccac ctagggtacc tgctcgggtg  22140
ggaagaaata caaaacaaac ttcagaaact gcaccaggca cacgtggtcg gcgtggcgcc  22200
gcagtagctt tggcacatgg acgcgtgcgg gaagagccgg ccgttgcggt gttgtatttc  22260
ttcgttcgtt gtagttgttg tcgacggcgg tacccgaggt cactcgtcct tgactttcgg  22320
taacagtttc tagaaccaac acccggtata aaaaacccgt ggatactgtt cgcgaaaggt  22380
ccgaaacaaa gaggtgtgtt cgagcggacg cggtatcagt tatgccggcc agcgctctga  22440
cccccgcatg tgacctaccg gaaacggacc ttgggcgtga gtttttgtac gatggagaaa  22500
ctcgggaaac cgaaaagact ggtcgctgag ttcgtccaaa tggtcaaact catgctcagt  22560
gaggacgcgg catcgcggta acgaagaagg gggctggcga catattgcga ccttttcagg  22620
tgggtttcgc atgtccccgg gttgagccgg cggacacctg ataagacgac gtacaaagag  22680
gtgcggaaac ggttgaccgg ggtttgaggg tacctagtgt tggggtggta cttggaataa  22740
tggccccatg ggttgaggta cgagttgtca ggggtccatg tcgggtggga cgcagcgttg  22800
gtccttgtcg agatgtcgaa ggacctcgcg gtgagcggga tgaaggcgtc ggtgtcacgc  22860
gtctaatcct cgcggtgaag aaaaacagtg aactttttgt acatttttat tacatgatct  22920
ctgtgaaagt tatttccgtt tacgaaaata aacatgtgag agcccactaa taaatggggg  22980
tgggaacggc agacgcggca aatttttagt ttccccaaga cggcgcgtag cgatacgcgg  23040
tgaccgtccc tgtgcaacgc tatgaccaca aatcacgagg tgaatttgag tccgtgttgg  23100
taggcgccgt cgagccactt caaaagtgag gtgtccgacg cgtggtagtg gttgcgcaaa  23160
tcgtccagcc cgcggctata gaacttcagc gtcaaccccg gaggcgggac gcgcgcgctc  23220
aacgctatgt gtcccaacgt cgtgaccttg tgatagtcgc ggcccaccac gtgcgaccgg  23280
tcgtgcgaga acagcctcta gtctaggcgc aggtccagga ggcgcaacga gtcccgcttg  23340
cctcagttga aaccatcgac ggaagggttt ttcccgcgca cgggtccgaa actcaacgtg  23400
agcgtggcat caccgtagtt ttccactggc acgggccaga cccgcaatcc tatgtcgcgg  23460
acgtattttc ggaactagac gaattttcgg tggactcgga aacgcggaag tctcttcttg  23520
tacggcgttc tgaacggcct tttgactaac cggcctgtcc ggcgcagcac gtgcgtcgtg  23580
gaacgcagcc acaacctcta gacgtggtgt aaagccgggg tggccaagaa gtgctagaac  23640
cggaacgatc tgacgaggaa gtcgcgcgcg acgggcaaaa gcgagcagtg taggtaaagt  23700
tagtgcacga ggaataaata gtattacgaa ggcacatctg tgaattcgag cggaagctag  23760
agtcgcgtcg ccacgtcggt gttgcgcgtc gggcacccga gcactacgaa catccagtgg  23820
agacgtttgc tgacgtccat gcggacgtcc ttagcggggt agtagcagtg tttccagaac  23880
aacgaccact tccagtcgac gttgggcgcc acgaggagca agtcggtcca gaacgtatgc  23940
cggcggtctc gaaggtgaac cagtccgtca tcaaacttca agcggaaatc tagcaatagg  24000
tgcaccatga acaggtagtc gcgcgcgcgt cggaggtacg ggaagagggt gcgtctgtgc  24060
tagccgtgtg agtcgcccaa gtagtggcat taaagtgaaa ggcgaagcga cccgagaagg  24120
agaaggagaa cgcaggcgta tggtgcgcgg tgacccagca gaagtaagtc ggcggcgtga  24180
cacgcgaatg gaggaaacgg tacgaactaa tcgtggccac ccaacgactt tgggtggtaa  24240
acatcgcggt gtagaagaga aagaaggagc gacaggtgct aatggagacc actaccgccc  24300
gcgagcccga accctcttcc cgcgaagaaa aagaagaacc cgcgttaccg gtttaggcgg  24360
```

-continued

```
cggctccagc taccggcgcc cgacccacac gcgccgtggt cgcgcagaac actactcaga  24420
aggagcagga gcctgagcta tgcggcggag taggcgaaaa aacccccgcg ggcccctccg  24480
ccgccgctgc ccctgcccct gctgtgcagg aggtaccaac cccctgcagc gcggcgtggc  24540
gcaggcgcga gcccccacca aagcgcgacg aggagaaggg ctgaccggta aaggaagagg  24600
atatccgtct ttttctagta cctcagtcag ctcttcttcc tgtcggattg gcgggggaga  24660
ctcaagcggt ggtggcggag gtggctacgg cggttgcgcg gatggtggaa ggggcagctc  24720
cgtgggggcg aactcctcct ccttcactaa tagctcgtcc tgggtccaaa acattcgctt  24780
ctgctgctcc tggcgagtca tggttgtctc ctatttttcg ttctggtcct gttgcgtctc  24840
cgtttgctcc ttgttcagcc cgccccccctg ctttccgtac cgctgatgga tctacaccct  24900
ctgctgcacg acaacttcgt agacgtcgcg gtcacgcggt aatagacgct gcgcaacgtt  24960
ctcgcgtcgc tacacgggga gcggtatcgc ctacagtcgg aacggatgct tgcggtggat  25020
aagagtggcg cgcatggggg gtttgcggtt cttttgccgt gtacgctcgg gttgggcgcg  25080
gagttgaaga tggggcataa acggcacggt ctccacgaac ggtggatagt gtagaaaaag  25140
gttttgacgt tctatgggga taggacggca cggttggcgt cggctcgcct gttcgtcgac  25200
cggaacgccg tcccgcgaca gtatggacta tagcggagcg agttgcttca cggtttttag  25260
aaactcccag aacctgcgct gctcttcgcg cgccgtttgc gagacgttgt ccttttgtcg  25320
cttttacttt cagtgagacc tcacaaccac cttgagctcc cactgttgcg cgcggatcgg  25380
catgattttg cgtcgtagct ccagtgggtg aaacggatgg gccgtgaatt ggatgggggg  25440
ttccagtact cgtgtcagta ctcactcgac tagcacgcgg cacgcgtcgg ggacctctcc  25500
ctacgtttaa acgttcttgt ttgtctcctc ccggatgggc gtcaaccgct gctcgtcgat  25560
cgcgcgaccg aagtttgcgc gctcggacgg ctgaacctcc tcgctgcgtt tgattactac  25620
cggcgtcacg agcaatggca cctcgaactc acgtacgtcg ccaagaaacg actgggcctc  25680
tacgtcgcgt tcgatctcct ttgtaacgtg atgtggaaag ctgtcccgat gcatgcggtc  25740
cggacgttct agaggttgca cctcgagacg ttggaccaga ggatggaacc ttaaaacgtg  25800
cttttggcgg aacccgtttt gcacgaagta aggtgcgagt tcccgctccg cgcggcgctg  25860
atgcaggcgc tgacgcaaat gaataaagat acgatgtgga ccgtctgccg gtacccgcaa  25920
accgtcgtca cgaacctcct cacgttggag ttcctcgacg tctttgacga tttcgttttg  25980
aacttcctgg atacctgccg gaagttgctc gcgaggcacc ggcgcgtgga ccgcctgtag  26040
taaaaggggc ttgcggacga attttgggac gttgtcccag acggtctgaa gtggtcagtt  26100
tcgtacaacg tcttgaaatc cttgaaatag gatctcgcga gtccttagaa cgggcggtgg  26160
acgacacgtg aaggatcgct gaaacacggg taattcatgg cgcttacggg aggcggcgaa  26220
accccggtga cgatggaaga cgtcgatcgg ttgatggaac ggatggtgag actgtattac  26280
cttctgcact cgccactgcc agatgacctc acagtgacag cgacgttgga tacgtggggc  26340
gtggcgaggg accaaacgtt aagcgtcgac gaattgcttt cagtttaata gccatggaaa  26400
ctcgacgtcc cagggagcgg actgcttttc aggcgccgag gccccaactt tgagtgaggc  26460
cccgacacct gcagccgaat ggaagcgttt aaacatggac tcctgatggt gcgggtgctc  26520
taatccaaga tgcttctggt tagggcgggc ggattacgcc tcgaatggcg gacgcagtaa  26580
tgggtcccgg tgtaagaacc ggttaacgtt cggtagttgt ttcgggcggt tctcaaagac  26640
gatgctttcc ctgcccccca aatgaacctg gggtcaggc cgctcctcga gttgggttag  26700
gggggcggcg gcgtcgggat agtcgtcgtc ggcgcccggg aacgaagggt cctaccgtgg  26760
```

-continued gtttttcttc gacgtcgacg gcggcggtgg gtgcctgctc ctccttatga ccctgtcagt 26820
ccgtctcctc caaaacctgc tcctcctcct cctgtactac cttctgaccc tctcggatct 26880
gctccttcga aggctccagc ttctccacag tctgctttgt ggcagtggga gccagcgtaa 26940
ggggagcggc cgcggggtct ttagccgttg gccaaggtcg taccgatgtt ggaggcgagg 27000
agtccgcggc ggccgtgacg ggcaagcggc tgggttggca tctaccctgt ggtgaccttg 27060
gtcccggcca ttcaggttcg tcggcggcgg caatcgggtt ctcgttgttg tcgcggttcc 27120
gatggcgagt accgcgcccg tgttcttgcg gtatcaacga acgaacgttc tgacaccccc 27180
gttgtagagg aagcgggcgg cgaaagaaga gatggtagtg ccgcaccgga agggggcatt 27240
gtaggacgta atgatggcag tagagatgtc gggtatgacg tggccgccgt cgccgtcgtt 27300
gtcgtcgccg gtgtgtcttc gtttccgctg gcctatcgtt ctgagactgt ttcgggttct 27360
ttaggtgtcg ccgccgtcgt cgtcctcctc ctcgcgacgc agaccgcggg ttgcttgggc 27420
atagctgggc gctcgaatct ttgtcctaaa aagggtgaga catacgatat aaagttgtct 27480
cgtccccggt tcttgttctc gacttttatt ttttgtccag agacgctagg gagtgggcgt 27540
cgacggacat agtgttttcg cttctagtcg aagccgcgtg cgaccttctg cgcctccgag 27600
agaagtcatt tatgacgcgc gactgagaat tcctgatcaa agcgcgggaa agagtttaaa 27660
ttcgcgcttt tgatgcagta gaggtcgccg gtgtgggccg cggtcgtgga caacagtcgc 27720
ggtaatactc gttcctttaa gggtgcggga tgtacacctc aatggtcggt gtttaccctg 27780
aacgccgacc tcgacgggtt ctgatgagtt gggcttattt gatgtactcg cgccctgggg 27840
tgtactatag ggcccagttg ccttatgcgc gggtggcttt ggcttaagag gaccttgtcc 27900
gccgataatg gtggtgtgga gcattattgg aattaggggc atcaaccggg cgacgggacc 27960
acatggtcct ttcagggcga gggtggtgac accatgaagg gtctctgcgg gtccggcttc 28020
aagtctactg attgagtccc cgcgtcgaac gcccgccgaa agcagtgtcc cacgccagcg 28080
ggcccgtccc atattgagtg gactgttagt ctcccgctcc ataagtcgag ttgctgctca 28140
gccactcgag gagcgaacca gaggcaggcc tgccctgtaa agtctagccg ccgcggccgg 28200
cgagaagtaa gtgcggagca gtccgttagg attgagacgt ctggagcagg agactcggcg 28260
cgagacctcc gtaaccttga gacgttaaat aactcctcaa acacggtagc cagatgaaat 28320
tggggaagag ccctggaggg ccggtgatag gcctagttaa ataaggattg aaactgcgcc 28380
atttcctgag ccgcctgccg atgctgactt acaattcacc tctccgtctc gttgacgcgg 28440
actttgtgga ccaggtgaca gcggcggtgt tcacgaaacg ggcgctgagg ccactcaaaa 28500
cgatgaaact taacgggctc ctagtatagc tcccgggccg cgtgccgcag gccgaatggc 28560
gggtccctct cgaacgggca tcggactaag ccctcaaatg ggtcgcgggg gacgatcaac 28620
tcgccctgtc ccctgggaca caagagtgac actaaacgtt gacaggattg ggacctaatg 28680
tagttctaga aacaacggta gagacacgac tcatattatt tatgtcttta attttatatg 28740
accccgagga tagcggtagg acatttgcgg tggcagaagt gggcgggttc gtttggttcc 28800
gcttggaatg gaccatgaaa attgtagaga gggagacact aaatgttgtc aaagttgggt 28860
ctgcctcact cagatgctct cttggagagg ctcgagtcga tgaggtagtc ttttttgtgg 28920
tgggaggaat ggacggccct tgcatgctca cgcagtggcc ggcgacgtgg tgtggatggc 28980
ggactggcat ttggtctgaa aaaggcctgt ctggagttat tgagacaaat ggtcttgtcc 29040
tccactcgaa tcttttggga atcccataat ccggtttccg cgtcgatgac accccaaata 29100

-continued

```
cttgttaagt tcgttgagat gcccgataag attaagtcca aagagatctt agccccaacc  29160
ccaataagag acagaacact aagagaaata agaatatgat tgcgaagaga cggattccga  29220
gcggcggacg acacacgtgt aaacgtaaat aacagtcgaa aaatttgcga ccccagcggt  29280
gggttctact aatccatgta ttaggatcca aatgagtggg aacgcagtcg ggtgccatgg  29340
tgggttttcc acctaaaatt cctcggtcgg acattacaat gtaagcgtcg acttcgatta  29400
ctcacgtggt gagaatattt tacgtggtgt cttgtacttt tcgacgaata agcggtgttt  29460
ttgttttaac cgttcatacg acaaatacga taaaccgtcg gtccactgtg atgtctcata  29520
ttacaatgtc aaaaggtccc attttcagta ttttgaaaat acatatgaaa aggtaaaata  29580
ctttacacgc tgtaatggta catgtactcg tttgtcatat tcaacaccgg gggtgtttta  29640
acacaccttt tgtgaccgtg aaagacgacg tgacgatacg attaatgtca cgagcgaaac  29700
cagacatggg atgagatata atttatgttt tcgtctgcgt cgaaataact ccttttcttt  29760
tacggaatta aatgattcaa tgtttcgatt acagtggtga ttgacgaaat gagcgacgaa  29820
cgttttgttt aagtttttca atcgtaatat taatcttatc ctaaatttgg ggggccagta  29880
aaggacgagt tatggtaagg ggacttgtta actgagatac accctatacg aggtcgcgat  29940
gttggaactt cagtccgaag gacctacagt cgtagactga aaccggtcgt ggacagggcg  30000
cctaaacaag gtcaggttga tgtcgctggg tgggattgtc tctactggtt gtgttggttg  30060
cgccggcggc gatggcctga atgtagatgg tgtttatgtg gggttcaaag acggaaacag  30120
ttattgaccc tattgaaccc gtacaccacc aagaggtatc gcgaatacaa acatacggaa  30180
taataataca ccgagtagac gacggatttc gcgtttgcgc gggctggtgg gtagatatca  30240
gggtagtaac acgatgtggg tttgttacta ccttaggtat ctaacctgcc tgactttgtg  30300
tacaagaaaa gagaatgtca tactaattta ctctgtacta aggagctcaa aaatataatg  30360
actgggaaca acgcgaaaaa acacgcacga ggtgtaaccg acgccaaaga gtgtagcttc  30420
atctgacgta aggtcggaag tgtcagataa acgaaatgcc taaacagtgg gagtgcgagt  30480
agacgtcgga gtagtgacac cagtagcgga aataggtcac gtaactgacc cagacacacg  30540
cgaaacgtat agagtctgtg gtaggggtca tgtccctgtc ctgatatcga ctcgaagaat  30600
cttaagaaat taatacttta aatgacactg aaaagacgac taataaacgt gggatagacg  30660
caaaacaagg ggctggaggt tcggagtttc tgtatatagt acgtctaagt gagcatatac  30720
cttataaggt tcaacgatgt tacttttttc gctagaaagg cttcggacca atatacgtta  30780
gtagagacaa taccacaaga cgtcatggta gaatcgggat cgatatatag ggatggaact  30840
gtaaccgacc ttgcgttatc tacggtactt ggtgggttga aaggggcgcg ggcgatacga  30900
aggtgacgtt gttcaacaac ggccgccgaa acagggtcgg ttagtcggag cgggtggaag  30960
agggtggggg tgactttagt cgatgaaatt agattgtcct cctctactga ctgtgggatc  31020
tagatcttta cctgccttaa taatgtctcg tcgcggacga tctttctgcg tcccgtcgcc  31080
ggctcgttgt cgcgtactta gttctcgagg ttctgtacca attgaacgtg gtcacgtttt  31140
ccccatagaa aacagagcat ttcgtccggt ttcagtggat gctgtcatta tggtggcctg  31200
tggcggaatc gatgttcaac ggttggttcg cagtctttaa ccaccagtac caccctcttt  31260
tcgggtaatg gtattgagtc gtgagccatc tttggcttcc gacgtaagtg agtggaacag  31320
ttcctggact cctagagacg tgggaataat tctgggacac gccagagttt ctagaataag  31380
ggaaattgat tatttttttt tattatttcg tagtgaatga attttagtca atcgtttaaa  31440
gacaggtcaa ataagtcgtc gtggaggaac gggaggaggg tcgagaccat aacgtcgaag  31500
```

-continued gaggaccgac gtttgaaaga ggtgttagat ttaccttaca gtcaaaggag gacaaggaca 31560
ggtaggcgtg ggtgatagaa gtacaacaac gtctacttcg cgcgttctgg cagacttcta 31620
tggaagttgg ggcacatagg tatactgtgc ctttggccag gaggttgaca cggaaaagaa 31680
tgaggaggga aacatagggg gttacccaaa gttctctcag ggggacccca tgagagaaac 31740
gcggataggc ttggagatca atggaggtta ccgtacgaac gcgagtttta cccgttgccg 31800
gagagagacc tgctccggcc gttggaatgg agggttttac attggtgaca ctcgggtgga 31860
gagttttttt ggttcagttt gtatttggac ctttatagac gtggggagtg tcaatggagt 31920
cttcgggatt gacaccgacg gcggcgtgga gattaccagc gcccgttgtg tgagtggtac 31980
gttagtgtcc ggggcgattg gcacgtgctg aggtttgaat cgtaacggtg ggttcctggg 32040
gagtgtcaca gtcttccttt cgatcgggac gtttgtagtc cgggggagtg gtggtggcta 32100
tcgtcatggg aatgatagtg acggagtggg ggagattgat gacggtgacc atcgaacccg 32160
taactgaact ttctcgggta aatatgtgtt ttaccttttg atcctgattt catgccccga 32220
ggaaacgtac attgtctgct ggatttgtga aactggcatc gttgaccagg tccacactga 32280
taattattat gaaggaacgt ttgatttcaa tgacctcgga acccaaaact aagtgttccg 32340
ttatacgttg aattacatcg tcctcctgat tcctaactaa gagttttgtc tgcggaatat 32400
gaactacaat caataggcaa actacgagtt ttggttgatt tagattctga tcctgtcccg 32460
ggagaaaaat atttgagtcg ggtgttgaac ctataattga tgttgtttcc ggaaatgaac 32520
aaatgtcgaa gtttgttaag gtttttcgaa ctccaattgg attcgtgacg gttccccaac 32580
tacaaactgc gatgtcggta tcggtaatta cgtcctctac ccgaacttaa accaagtgga 32640
ttacgtggtt tgtgtttagg ggagttttgt ttttaaccgg taccggatct taaactaagt 32700
ttgttccgat accaaggatt tgatccttga ccggaatcaa aactgtcgtg tccacggtaa 32760
tgtcatcctt tgtttttatt actattcgat tgaaacacct ggtgtggtcg aggtagagga 32820
ttgacatctg atttacgtct ctttctacga tttgagtgaa accagaattg ttttacaccg 32880
tcagtttatg aacgatgtca aagtcaaaac cgacaatttc cgtcaaaccg aggttataga 32940
ccttgtcaag tttcacgagt agaataatat tctaaactgc ttttacctca cgatgatttg 33000
ttaaggaagg acctgggtct tataaccttg aaatctttac ctctagaatg acttccgtgt 33060
cggatatgtt tgcgacaacc taaatacgga ttggatagtc gaataggttt tagagtgcca 33120
ttttgacggt tttcattgta acagtcagtt caaatgaatt tgcctctgtt ttgatttgga 33180
cattgtgatt ggtaatgtga tttgccatgt gtcctttgtc ctctgtgttg aggttcacgt 33240
atgagataca gtaaaagtac cctgaccaga ccggtgttga tgtaattact ttataaacgg 33300
tgtaggagaa tgtgaaaaag tatgtaacgg gttcttattt cttagcaaac acaatacaaa 33360
gttgcacaaa taaaaagtta acgtctttta aagttcagta aaaagtaagt catcatatcg 33420
gggtggtggt gtatcgaata tgtctagtgg catggaatta gtttgagtgt cttgggatca 33480
taagttggac ggtggaggga gggttgtgtg tctcatgtgt caggaaagag gggccgaccg 33540
gaatttttcg tagtatagta cccattgtct gtataagaat ccacaatata aggtgtgcca 33600
aaggacagct cggtttgcga gtagtcacta taattatttg aggggcccgt cgagtgaatt 33660
caagtacagc gacaggtcga cgactcggtg tccgacgaca ggttgaacgc caacgaattg 33720
cccgccgctt cctcttcagg tgcggatgta cccccatctc agtattagca cgtagtccta 33780
tcccgccacc acgacgtcgt cgcgcgctta tttgacgacg gcggcggcga ggcaggacgt 33840

-continued

```
ccttatgttg taccgtcacc agaggagtcg ctactaagcg tggcgggcgt cgtattccgc  33900
ggaacaggag gcccgtgtcg tcgcgtggga ctagagtgaa tttagtcgtg tcattgacgt  33960
cgtgtcgtgg tgttataaca agttttaggg tgtcacgttc cgcgacatag gtttcgagta  34020
ccgcccctgg tgtcttgggt gcaccggtag tatggtgttc gcgtccatct aattcaccgc  34080
tggggagtat ttgtgcgacc tgtatttgta atggagaaaa ccgtacaaca ttaagtggtg  34140
gagggccatg gtatatttgg agactaattt gtaccgcggt aggtggtggt aggatttggt  34200
cgaccggttt tggacgggcg gccgatatgt gacgtccctt ggccctgacc ttgttactgt  34260
cacctctcgg gtcctgagca ttggtaccta gtagtacgag cagtactata gttacaaccg  34320
tgttgtgtcc gtgtgcacgt atgtgaagga gtcctaatgt tcgaggaggg cgcaatcttg  34380
gtatagggtc ccttgttggg taaggactta gtcgcattta gggtgtgacg tcccttctgg  34440
agcgtgcatt gagtgcaaca cgtaacagtt tcacaatgta agcccgtcgt cgcctactag  34500
gaggtcatac catcgcgccc aaagacagag ttttcctcca tctgctaggg atgacatgcc  34560
tcacgcggct ctgttggctc tagcacaacc agcatcacag tacggtttac cttgcggcct  34620
gcatcagtat aaaggacttc gttttggtcc acgcccgcac tgtttgtcta gacgcagagg  34680
ccagagcggc gaatctagcg agacacatca tcaacatcat ataggtgaga gagtttcgta  34740
ggtccgcggg ggaccgaagc ccaagataca tttgaggaag tacgcggcga cgggactatt  34800
gtaggtggtg gcgtcttatt cggtgtgggt cggttggatg tgtaagcaag acgctcagtg  34860
tgtgccctcc tcgcccttct cgaccttctt ggtacaaaaa aaaaaataag gttttctaat  34920
aggttttgga gttttacttc tagataattc acttgcgcga ggggaggcca ccgcaccagt  34980
ttgagatgtc ggtttcttgt ctattaccgt aaacattcta caacgtgtta ccgaaggttt  35040
tccgtttgcc gggagtgcag gttcacctgc atttccgatt tgggaagtcc cacttagagg  35100
agatatttgt aaggtcgtgg aagttggtac gggtttatta agagtagagc ggtggaagag  35160
ttatatagag attcgtttag ggcttataat tcaggccggt aacattttta gacgaggtct  35220
cgcgggaggt ggaagtcgga gttcgtcgct tagtactaac gtttttaagt ccaaggagtg  35280
tctggacata ttctaagttt tcgccttgta attgttttta tggcgctagg gcatccaggg  35340
aagcgtcccg gtcgacttgt attagcacgt ccagacgtgc ctggtcgcgc cggtgaaggg  35400
gcggtccttg gtactgtttt cttgggtgtg actaatactg tgcgtatgag cctcgatacg  35460
attggtcgca tcggggctac attcgaacaa cgtacccgcc gctatatttt acgttccacg  35520
acgagttttt tagtccgttt cggagcgcgt tttttctttc gtgtagcatc agtacgagta  35580
cgtctatttc cgtccattcg aggccttggt ggtgtctttt tctgtggtaa aaagagagtt  35640
tgtacagacg cccaaagacg tatttgtgtt ttattttatt gtttttttgt aaatttgtaa  35700
tcttcggaca gaatgttgtc ctttttgttg ggaatattcg tattctgcct gatgccggta  35760
cggccgcact ggcatttttt tgaccagtgg cactaatttt tcgtggtggc tgtcgaggag  35820
ccagtacagg cctcagtatt acattctgag ccatttgtgt agtccaacta agtgtagcca  35880
gtcacgattt ttcgctggct ttatcgggcc cccttatgta tgggcgtccg catctctgtt  35940
gtaatgtcgg gggtatcctc catattgttt taattatcct ctctttttgt gtatttgtgg  36000
actttttggg aggacggatc cgttttatcg tgggagggcg aggtcttgtt gtatgtcgcg  36060
aaggtgtcgc cgtcggtatt gtcagtcgga atggtcattt tttcttttgg ataatttttt  36120
tgtggtgagc tgtgccgtgg tcgagttagt cagtgtcaca ttttttcccg gttcacgtct  36180
cgctcatata tatcctgatt ttttactgca ttgccaattt caggtgtttt ttgtgggtct  36240
```

-continued

```
tttggcgtgc gcttggatgc gggtctttgc tttcggtttt ttgggtgttg aaggagttta  36300
gcagtgaagg caaaagggtg caatgcagtg aagggtaaaa ttcttttgat gttaagggtt  36360
gtgtatgttc aatgaggcgg gattttggat gcagtgggcg gggcaagggt gcggggcgcg  36420
gtgcagtgtt tgaggtgggg gagtaatagt ataaccgaag ttaggtttta ttccatataa  36480
taactactac aattaattct taagcctaga cgctgcgctc cgacctaccg gaaggggtaa  36540
tactaagaag agcgaaggcc gccgtagccc tacgggcgca acgtccggta cgacaggtcc  36600
gtccatctac tgctggtagt ccctgtcgaa gttccggtcg ttttccggtc cttggcattt  36660
ttccggcgca acgaccgcaa aaaggtatcc gaggcggggg gactgctcgt agtgttttta  36720
gctgcgagtt cagtctccac cgctttgggc tgtcctgata tttctatggt ccgcaaaggg  36780
ggaccttcga gggagcacgc gagaggacaa ggctgggacg gcgaatggcc tatggacagg  36840
cggaaagagg gaagcccttc gcaccgcgaa agagtatcga gtgcgacatc catagagtca  36900
agccacatcc agcaagcgag gttcgacccg acacacgtgc ttgggggGca agtcgggctg  36960
gcgacgcgga ataggccatt gatagcagaa ctcaggttgg gccattctgt gctgaatagc  37020
ggtgaccgtc gtcggtgacc attgtcctaa tcgtctcgct ccatacatcc gccacgatgt  37080
ctcaagaact tcaccaccgg attgatgccg atgtgatctt cctgtcataa accatagacg  37140
cgagacgact tcggtcaatg gaagcctttt tctcaaccat cgagaactag gccgtttgtt  37200
tggtggcgac catcgccacc aaaaaaacaa acgttcgtcg tctaatgcgc gtcttttttt  37260
cctagagttc ttctaggaaa ctagaaaaga tgccccagac tgcgagtcac cttgcttttg  37320
agtgcaattc cctaaaacca gtactctaat agtttttcct agaagtggat ctaggaaaat  37380
ttagttagat ttcatatata ctcatttgaa ccagactgtc aatggttacg aattagtcac  37440
tccgtggata gagtcgctag acagataaag caagtaggta tcaacggact gaggggcagc  37500
acatctattg atgctatgcc ctcccgaatg gtagaccggg gtcacgacgt tactatggcg  37560
ctctgggtgc gagtggccga ggtctaaata gtcgttattt ggtcggtcgg ccttcccggc  37620
tcgcgtcttc accaggacgt tgaaataggc ggaggtaggt cagataatta acaacggccc  37680
ttcgatctca ttcatcaagc ggtcaattat caaacgcgtt gcaacaacgg taacgatgtc  37740
cgtagcacca cagtgcgagc agcaaaccat accgaagtaa gtcgaggcca agggttgcta  37800
gttccgctca atgtactagg gggtacaaca cgtttttttcg ccaatcgagg aagccaggag  37860
gctagcaaca gtcttcattc aaccggcgtc acaatagtga gtaccaatac cgtcgtgacg  37920
tattaagaga atgacagtac ggtaggcatt ctacgaaaag acactgacca ctcatgagtt  37980
ggttcagtaa gactcttatc acatacgccg ctggctcaac gagaacgggc cgcagttgtg  38040
ccctattatg gcgcggtgta tcgtcttgaa attttcacga gtagtaacct tttgcaagaa  38100
gccccgcttt tgagagttcc tagaatggcg acaactctag gtcaagctac attgggtgag  38160
cacgtgggtt gactagaagt cgtagaaaat gaaagtggtc gcaaagaccc actcgttttt  38220
gtccttccgt tttacggcgt tttttccctt attcccgctg tgcctttaca acttatgagt  38280
atgagaagga aaaagttata ataacttcgt aaatagtccc aataacagag tactcgccta  38340
tgtataaact tacataaatc tttttatttg tttatcccca aggcgcgtgt aaaggggctt  38400
ttcacggtgg actgcagatt ctttggtaat aatagtactg taattggata tttttatccg  38460
catagtgctc cgggaaagca gaagttctta acctaggctt aagaattaaa gaattaatt   38519
```

<210> SEQ ID NO 30

-continued

<211> LENGTH: 36620
<212> TYPE: DNA
<213> ORGANISM: Artificial Sequence
<220> FEATURE:
<223> OTHER INFORMATION: Codon optimized DNA encoding pMRKAd5HIV-1 nef, coding

<400> SEQUENCE: 30
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag gcggccgcga tccattgcat acgttgtatc 480
catatcataa tatgtacatt tatattggct catgtccaac attaccgcca tgttgacatt 540
gattattgac tagttattaa tagtaatcaa ttacggggtc attagttcat agcccatata 600
tggagttccg cgttacataa cttacggtaa atggcccgcc tggctgaccg cccaacgacc 660
cccgcccatt gacgtcaata atgacgtatg ttcccatagt aacgccaata gggactttcc 720
attgacgtca atgggtggag tatttacggt aaactgccca cttggcagta catcaagtgt 780
atcatatgcc aagtacgccc cctattgacg tcaatgacgg taaatggccc gcctggcatt 840
atgcccagta catgacctta tgggactttc ctacttggca gtacatctac gtattagtca 900
tcgctattac catggtgatg cggttttggc agtacatcaa tgggcgtgga tagcggtttg 960
actcacgggg atttccaagt ctccacccca ttgacgtcaa tgggagtttg ttttggcacc 1020
aaaatcaacg ggactttcca aaatgtcgta acaactccgc cccattgacg caaatgggcg 1080
gtaggcgtgt acggtgggag gtctatataa gcagagctcg tttagtgaac cgtcagatcg 1140
cctggagacg ccatccacgc tgttttgacc tccatagaag acaccgggac cgatccagcc 1200
tccgcggccg ggaacggtgc attggaacgc ggattccccg tgccaagagt gagatctgcc 1260
accatggccg gcaagtggtc caagaggtcc gtgcccggct ggtccaccgt gagggagagg 1320
atgaggaggg ccgagcccgc cgccgacagg gtgaggagga ccgagcccgc cgcagtgggc 1380
gtgggcgccg tgtccaggga cctggagaag cacggcgcca tcacctcctc caacaccgcc 1440
gccaccaacg ccgactgcgc ctggctggag gcccaggagg acgaggaggt gggcttcccc 1500
gtgaggcccc aggtgcccct gaggcccatg acctacaagg gcgccgtgga cctgtcccac 1560
ttcctgaagg agaagggcgg cctggagggc ctgatccact cccagaagag gcaggacatc 1620
ctggacctgt gggtgtacca cacccagggc tacttccccg actggcagaa ctacaccccc 1680
ggccccggca tcaggttccc cctgaccttc ggctggtgct tcaagctggt gcccgtggag 1740
cccgagaagg tggaggaggc caacgagggc gagaacaact gcgccgccca ccccatgtcc 1800
cagcacggca tcgaggaccc cgagaaggag gtgctggagt ggaggttcga ctccaagctg 1860
gccttccacc acgtggccag ggagctgcac cccgagtact acaaggactg ctaaagcccg 1920
ggcagatctg ctgtgccttc tagttgccag ccatctgttg tttgcccctc ccccgtgcct 1980
tccttgaccc tggaaggtgc cactcccact gtcctttcct aataaaatga ggaaattgca 2040
tcgcattgtc tgagtaggtg tcattctatt ctggggggtg gggtggggca ggacagcaag 2100

-continued

```
ggggaggatt gggaagacaa tagcaggcat gctggggatg cggtgggctc tatggccgat   2160
cggcgcgccg tactgaaatg tgtgggcgtg gcttaagggt gggaaagaat atataaggtg   2220
ggggtcttat gtagttttgt atctgttttg cagcagccgc cgccgccatg agcaccaact   2280
cgtttgatgg aagcattgtg agctcatatt tgacaacgcg catgccccca tgggccgggg   2340
tgcgtcagaa tgtgatgggc tccagcattg atggtcgccc cgtcctgccc gcaaactcta   2400
ctaccttgac ctacgagacc gtgtctggaa cgccgttgga gactgcagcc tccgccgccg   2460
cttcagccgc tgcagccacc gcccgcggga ttgtgactga ctttgctttc ctgagcccgc   2520
ttgcaaacag tgcagcttcc cgttcatccg cccgcgatga caagttgacg gctcttttgg   2580
cacaattgga ttctttgacc cgggaactta atgtcgtttc tcagcagctg ttggatctgc   2640
gccagcaggt ttctgccctg aaggcttcct cccctcccaa tgcggtttaa aacataaata   2700
aaaaaccaga ctctgtttgg atttggatca agcaagtgtc ttgctgtctt tatttagggg   2760
ttttgcgcgc gcggtaggcc cgggaccagc ggtctcggtc gttgagggtc ctgtgtattt   2820
tttccaggac gtggtaaagg tgactctgga tgttcagata catgggcata agcccgtctc   2880
tggggtggag gtagcaccac tgcagagctt catgctgcgg ggtggtgttg tagatgatcc   2940
agtcgtagca ggagcgctgg gcgtggtgcc taaaaatgtc tttcagtagc aagctgattg   3000
ccaggggcag gcccttggtg taagtgttta caaagcggtt aagctgggat gggtgcatac   3060
gtggggatat gagatgcatc ttggactgta tttttaggtt ggctatgttc ccagccatat   3120
ccctccgggg attcatgttg tgcagaacca ccagcacagt gtatccggtg cacttgggaa   3180
atttgtcatg tagcttagaa ggaaatgcgt ggaagaactt ggagacgccc ttgtgacctc   3240
caagattttc catgcattcg tccataatga tggcaatggg cccacgggcg gcggcctggg   3300
cgaagatatt tctgggatca ctaacgtcat agttgtgttc caggatgaga tcgtcatagg   3360
ccatttttac aaagcgcggg cggagggtgc cagactgcgg tataatggtt ccatccggcc   3420
caggggcgta gttaccctca cagatttgca tttcccacgc tttgagttca gatgggggga   3480
tcatgtctac ctgcggggcg atgaagaaaa cggtttccgg ggtaggggag atcagctggg   3540
aagaaagcag gttcctgagc agctgcgact taccgcagcc ggtgggcccg taaatcacac   3600
ctattaccgg ctgcaactgg tagttaagag agctgcagct gccgtcatcc ctgagcaggg   3660
gggccacttc gttaagcatg tccctgactc gcatgttttc cctgaccaaa tccgccagaa   3720
ggcgctcgcc gcccagcgat agcagttctt gcaaggaagc aaagtttttc aacggtttga   3780
gaccgtccgc cgtaggcatg cttttgagcg tttgaccaag cagttccagg cggtcccaca   3840
gctcggtcac ctgctctacg gcatctcgat ccagcatatc tcctcgtttc gcgggttggg   3900
gcggctttcg ctgtacggca gtagtcggtg ctcgtccaga cgggccaggg tcatgtcttt   3960
ccacgggcgc agggtcctcg tcagcgtagt ctgggtcacg gtgaaggggt gcgctccggg   4020
ctgcgcgctg gccagggtgc gcttgaggct ggtcctgctg gtgctgaagc gctgccggtc   4080
ttcgccctgc gcgtcggcca ggtagcattt gaccatggtg tcatagtcca gcccctccgc   4140
ggcgtggccc ttggcgcgca gcttgccctt ggaggaggcg ccgcacgagg ggcagtgcag   4200
acttttgagg gcgtagagct tgggcgcgag aaataccgat tccggggagt aggcatccgc   4260
gccgcaggcc ccgcagacgg tctcgcattc cacgagccag gtgagctctg gccgttcggg   4320
gtcaaaaacc aggtttcccc catgcttttt gatgcgtttc ttacctctgg tttccatgag   4380
ccggtgtcca cgctcggtga cgaaaaggct gtccgtgtcc ccgtatacag acttgagagg   4440
cctgtcctcg agcggtgttc cgcggtcctc ctcgtataga aactcggacc actctgagac   4500
```

-continued

```
aaaggctcgc gtccaggcca gcacgaagga ggctaagtgg gaggggtagc ggtcgttgtc   4560
cactaggggg tccactcgct ccagggtgtg aagacacatg tcgccctctt cggcatcaag   4620
gaaggtgatt ggtttgtagg tgtaggccac gtgaccgggt gttcctgaag gggggctata   4680
aaagggggtg ggggcgcgtt cgtcctcact ctcttccgca tcgctgtctg cgagggccag   4740
ctgttggggt gagtactccc tctgaaaagc gggcatgact tctgcgctaa gattgtcagt   4800
ttccaaaaac gaggaggatt tgatattcac ctggcccgcg gtgatgcctt tgagggtggc   4860
cgcatccatc tggtcagaaa agacaatctt tttgttgtca agcttggtgg caaacgaccc   4920
gtagagggcg ttggacagca acttggcgat ggagcgcagg gtttggtttt tgtcgcgatc   4980
ggcgcgctcc ttggccgcga tgtttagctg cacgtattcg cgcgcaacgc accgccattc   5040
gggaaagacg gtggtgcgct cgtcgggcac caggtgcacg cgccaaccgc ggttgtgcag   5100
ggtgacaagg tcaacgctgg tggctacctc tccgcgtagg cgctcgttgg tccagcagag   5160
gcggccgccc ttgcgcgagc agaatggcgg tagggggtct agctgcgtct cgtccggggg   5220
gtctgcgtcc acggtaaaga ccccgggcag caggcgcgcg tcgaagtagt ctatcttgca   5280
tccttgcaag tctagcgcct gctgccatgc gcgggcggca agcgcgcgct cgtatgggtt   5340
gagtggggga ccccatggca tggggtgggt gagcgcggag gcgtacatgc cgcaaatgtc   5400
gtaaacgtag aggggctctc tgagtattcc aagatatgta gggtagcatc ttccaccgcg   5460
gatgctggcg cgcacgtaat cgtatagttc gtgcgaggga gcgaggaggt cgggaccgag   5520
gttgctacgg gcgggctgct ctgctcggaa gactatctgc ctgaagatgg catgtgagtt   5580
ggatgatatg gttggacgct ggaagacgtt gaagctggcg tctgtgagac ctaccgcgtc   5640
acgcacgaag gaggcgtagg agtcgcgcag cttgttgacc agctcggcgg tgacctgcac   5700
gtctagggcg cagtagtcca gggtttcctt gatgatgtca tacttatcct gtcccttttt   5760
tttccacagc tcgcggttga ggacaaactc ttcgcggtct ttccagtact cttggatcgg   5820
aaacccgtcg gcctccgaac ggtaagagcc tagcatgtag aactggttga cggcctggta   5880
ggcgcagcat cccttttcta cgggtagcgc gtatgcctgc gcggccttcc ggagcgaggt   5940
gtgggtgagc gcaaaggtgt ccctgaccat gactttgagg tactggtatt tgaagtcagt   6000
gtcgtcgcat ccgccctgct cccagagcaa aaagtccgtg cgctttttgg aacgcggatt   6060
tggcagggcg aaggtgacat cgttgaagag tatctttccc gcgcgaggca taaagttgcg   6120
tgtgatgcgg aagggtcccg gcacctcgga acggttgtta attacctggg cggcgagcac   6180
gatctcgtca aagccgttga tgttgtggcc cacaatgtaa agttccaaga agcgcgggat   6240
gcccttgatg gaaggcaatt ttttaagttc ctcgtaggtg agctcttcag gggagctgag   6300
cccgtgctct gaaagggccc agtctgcaag atgagggttg gaagcgacga atgagctcca   6360
caggtcacgg gccattagca tttgcaggtg gtcgcgaaag gtcctaaact ggcgacctat   6420
ggccattttt tctggggtga tgcagtagaa ggtaagcggg tcttgttccc agcggtccca   6480
tccaaggttc gcggctaggt ctcgcgcggc agtcactaga ggctcatctc cgccgaactt   6540
catgaccagc atgaagggca cgagctgctt cccaaaggcc cccatccaag tataggtctc   6600
tacatcgtag gtgacaaaga gacgctcggt gcgaggatgc gagccgatcg ggaagaactg   6660
gatctcccgc caccaattgg aggagtggct attgatgtgg tgaaagtaga agtccctgcg   6720
acgggccgaa cactcgtgct ggcttttgta aaaacgtgcg cagtactggc agcggtgcac   6780
gggctgtaca tcctgcacga ggttgacctg acgaccgcgc acaaggaagc agagtgggaa   6840
```

-continued

```
tttgagcccc tcgcctggcg ggtttggctg gtggtcttct acttcggctg cttgtccttg   6900
accgtctggc tgctcgaggg gagttacggt ggatcggacc accacgccgc gcgagcccaa   6960
agtccagatg tccgcgcgcg gcggtcggag cttgatgaca acatcgcgca gatgggagct   7020
gtccatggtc tggagctccc gcggcgtcag gtcaggcggg agctcctgca ggtttacctc   7080
gcatagacgg gtcagggcgc gggctagatc caggtgatac ctaatttcca ggggctggtt   7140
ggtggcggcg tcgatggctt gcaagaggcc gcatccccgc ggcgcgacta cggtaccgcg   7200
cggcgggcgg tgggccgcgg gggtgtcctt ggatgatgca tctaaaagcg gtgacgcggg   7260
cgagcccccg gaggtagggg gggctccgga cccgccggga gagggggcag gggcacgtcg   7320
gcgccgcgcg cgggcaggag ctggtgctgc gcgcgtaggt tgctggcgaa cgcgacgacg   7380
cggcggttga tctcctgaat ctggcgcctc tgcgtgaaga cgacgggccc ggtgagcttg   7440
aacctgaaag agagttcgac agaatcaatt tcggtgtcgt tgacggcggc ctggcgcaaa   7500
atctcctgca cgtctcctga gttgtcttga taggcgatct cggccatgaa ctgctcgatc   7560
tcttcctcct ggagatctcc gcgtccggct cgctccacgg tggcggcgag gtcgttggaa   7620
atgcgggcca tgagctgcga gaaggcgttg aggcctccct cgttccagac gcggctgtag   7680
accacgcccc cttcggcatc gcgggcgcgc atgaccacct gcgcgagatt gagctccacg   7740
tgccgggcga agacggcgta gtttcgcagg cgctgaaaga ggtagttgag ggtggtggcg   7800
gtgtgttctg ccacgaagaa gtacataacc cagcgtcgca acgtggattc gttgatatcc   7860
cccaaggcct caaggcgctc catggcctcg tagaagtcca cggcgaagtt gaaaaactgg   7920
gagttgcgcg ccgacacggt taactcctcc tccagaagac ggatgagctc ggcgacagtg   7980
tcgcgcacct cgcgctcaaa ggctacaggg gcctcttctt cttcttcaat ctcctcttcc   8040
ataagggcct cccct tcttc ttcttctggc ggcggtgggg gaggggggac acggcggcga   8100
cgacggcgca ccgggaggcg gtcgacaaag cgctcgatca tctccccgcg gcgacggcgc   8160
atggtctcgg tgacggcgcg gccgttctcg cgggggcgca gttggaagac gccgcccgtc   8220
atgtcccggt tatgggttgg cgggggcgtg ccatgcggca gggatacggc gctaacgatg   8280
catctcaaca attgttgtgt aggtactccg ccgccgaggg acctgagcga gtccgcatcg   8340
accggatcgg aaaacctctc gagaaaggcg tctaaccagt cacagtcgca aggtaggctg   8400
agcaccgtgg cgggcggcag cgggcggcgg tcggggttgt ttctggcgga ggtgctgctg   8460
atgatgtaat taaagtaggc ggtcttgaga cggcggatgg tcgacagaag caccatgtcc   8520
ttgggtccgg cctgctgaat gcgcaggcgg tcggccatgc cccaggcttc gttttgacat   8580
cggcgcaggt ctttgtagta gtcttgcatg agcctttcta ccggcacttc ttcttctcct   8640
tcctcttgtc ctgcatctct tgcatctatc gctgcggcgg cggcggagtt tggccgtagg   8700
tggcgccctc ttcctcccat gcgtgtgacc ccgaagcccc tcatcggctg aagcagggct   8760
aggtcggcga caacgcgctc ggctaatatg gcctgctgca cctgcgtgag ggtagactgg   8820
aagtcatcca tgtccacaaa gcggtggtat gcgcccgtgt tgatggtgta agtgcagttg   8880
gccataacgg accagttaac ggtctggtga cccggctgcg agagctcggt gtacctgaga   8940
cgcgagtaag ccctcgagtc aaatacgtag tcgttgcaag tccgcaccag gtactggtat   9000
cccaccaaaa agtgcggcgg cggctggcgg tagaggggcc agcgtagggt ggccggggct   9060
ccgggggcga gatcttccaa cataaggcga tgatatccgt agatgtacct ggacatccag   9120
gtgatgccgg cggcggtggt ggaggcgcgc ggaaagtcgc ggacgcggtt ccagatgttg   9180
cgcagcggca aaaagtgctc catggtcggg acgctctggc cggtcaggcg cgcgcaatcg   9240
```

-continued

```
ttgacgctct agaccgtgca aaaggagagc ctgtaagcgg gcactcttcc gtggtctggt   9300
ggataaattc gcaagggtat catggcggac gaccggggtt cgagccccgt atccggccgt   9360
ccgccgtgat ccatgcggtt accgcccgcg tgtcgaaccc aggtgtgcga cgtcagacaa   9420
cgggggagtg ctccttttgg cttccttcca ggcgcggcgg ctgctgcgct agcttttttg   9480
gccactggcc gcgcgcagcg taagcggtta ggctggaaag cgaaagcatt aagtggctcg   9540
ctccctgtag ccggagggtt attttccaag ggttgagtcg cgggaccccc ggttcgagtc   9600
tcggaccggc cggactgcgg cgaacggggg tttgcctccc cgtcatgcaa gaccccgctt   9660
gcaaattcct ccggaaacag ggacgagccc ctttttgct  tttcccagat gcatccggtg   9720
ctgcggcaga tgcgcccccc tcctcagcag cggcaagagc aagagcagcg gcagacatgc   9780
agggcaccct cccctcctcc taccgcgtca ggaggggcga catccgcggt tgacgcggca   9840
gcagatggtg attacgaacc cccgcggcgc cgggcccggc actacctgga cttggaggag   9900
ggcgagggcc tggcgcggct aggagcgccc tctcctgagc ggcacccaag ggtgcagctg   9960
aagcgtgata cgcgtgaggc gtacgtgccg cggcagaacc tgtttcgcga ccgcgaggga  10020
gaggagcccg aggagatgcg ggatcgaaag ttccacgcag ggcgcgagct gcggcatggc  10080
ctgaatcgcg agcggttgct gcgcgaggag gactttgagc ccgacgcgcg aaccgggatt  10140
agtcccgcgc gcgcacacgt ggcggccgcc gacctggtaa ccgcatacga gcagacggtg  10200
aaccaggaga ttaactttca aaaaagcttt aacaaccacg tgcgtacgct tgtggcgcgc  10260
gaggaggtgg ctataggact gatgcatctg tgggactttg taagcgcgct ggagcaaaac  10320
ccaaatagca agccgctcat ggcgcagctg ttccttatag tgcagcacag cagggacaac  10380
gaggcattca gggatgcgct gctaaacata gtagagcccg agggccgctg gctgctcgat  10440
ttgataaaca tcctgcagag catagtggtg caggagcgca gcttgagcct ggctgacaag  10500
gtggccgcca tcaactattc catgcttagc ctgggcaagt tttacgcccg caagatatac  10560
catacccctt acgttcccat agacaaggag gtaaagatcg aggggttcta catgcgcatg  10620
gcgctgaagg tgcttacctt gagcgacgac ctgggcgttt atcgcaacga gcgcatccac  10680
aaggccgtga gcgtgagccg gcggcgcgag ctcagcgacc gcgagctgat gcacagcctg  10740
caaagggccc tggctggcac gggcagcggc gatagagagg ccgagtccta ctttgacgcg  10800
ggcgctgacc tgcgctgggc cccaagccga cgcgccctgg aggcagctgg ggccggacct  10860
gggctggcgg tggcacccgc gcgcgctggc aacgtcggcg gcgtggagga atatgacgag  10920
gacgatgagt acgagccaga ggacggcgag tactaagcgg tgatgtttct gatcagatga  10980
tgcaagacgc aacggacccg gcggtgcggg cggcgctgca gagccagccg tccggcctta  11040
actccacgga cgactggcgc caggtcatgg accgcatcat gtcgctgact gcgcgcaatc  11100
ctgacgcgtt ccggcagcag ccgcaggcca accggctctc cgcaattctg gaagcggtgg  11160
tcccggcgcg cgcaaacccc acgcacgaga aggtgctggc gatcgtaaac gcgctggccg  11220
aaaacagggc catccggccc gacgaggccg gcctggtcta cgacgcgctg cttcagcgcg  11280
tggctcgtta caacagcggc aacgtgcaga ccaacctgga ccggctggtg ggggatgtgc  11340
gcgaggccgt ggcgcagcgt gagcgcgcgc agcagcaggg caacctgggc tccatggttg  11400
cactaaacgc cttcctgagt acacagcccg ccaacgtgcc gcggggacag gaggactaca  11460
ccaactttgt gagcgcactg cggctaatgg tgactgagac accgcaaagt gaggtgtacc  11520
agtctgggcc agactatttt ttccagacca gtagacaagg cctgcagacc gtaaacctga  11580
```

-continued gccaggcttt caaaaacttg caggggctgt ggggggtgcg ggctcccaca ggcgaccgcg 11640
cgaccgtgtc tagcttgctg acgcccaact cgcgcctgtt gctgctgcta atagcgccct 11700
tcacggacag tggcagcgtg tcccgggaca catacctagg tcacttgctg acactgtacc 11760
gcgaggccat aggtcaggcg catgtggacg agcatacttt ccaggagatt acaagtgtca 11820
gccgcgcgct ggggcaggag gacacgggca gcctggaggc aaccctaaac tacctgctga 11880
ccaaccggcg gcagaagatc ccctcgttgc acagtttaaa cagcgaggag gagcgcattt 11940
tgcgctacgt gcagcagagc gtgagcctta acctgatgcg cgacggggta acgcccagcg 12000
tggcgctgga catgaccgcg cgcaacatgg aaccgggcat gtatgcctca aaccggccgt 12060
ttatcaaccg cctaatggac tacttgcatc gcgcggccgc cgtgaacccc gagtatttca 12120
ccaatgccat cttgaacccg cactggctac cgccccctgg tttctacacc gggggattcg 12180
aggtgcccga gggtaacgat ggattcctct gggacgacat agacgacagc gtgttttccc 12240
cgcaaccgca gaccctgcta gagttgcaac agcgcgagca ggcagaggcg gcgctgcgaa 12300
aggaaagctt ccgcaggcca agcagcttgt ccgatctagg cgctgcggcc ccgcggtcag 12360
atgctagtag cccatttcca agcttgatag ggtctcttac cagcactcgc accacccgcc 12420
cgcgcctgct gggcgaggag gagtacctaa acaactcgct gctgcagccg cagcgcgaaa 12480
aaaacctgcc tccggcattt cccaacaacg ggatagagag cctagtggac aagatgagta 12540
gatggaagac gtacgcgcag gagcacaggg acgtgccagg cccgcgcccg cccacccgtc 12600
gtcaaaggca cgaccgtcag cggggtctgg tgtgggagga cgatgactcg gcagacgaca 12660
gcagcgtcct ggatttggga gggagtggca acccgtttgc gcaccttcgc cccaggctgg 12720
ggagaatgtt ttaaaaaaaa aaaaagcatg atgcaaaata aaaaactcac caaggccatg 12780
gcaccgagcg ttggttttct tgtattcccc ttagtatgcg gcgcgcggcg atgtatgagg 12840
aaggtcctcc tccctcctac gagagtgtgg tgagcgcggc gccagtggcg gcggcgctgg 12900
gttctccctt cgatgctccc ctggacccgc cgtttgtgcc tccgcggtac ctgcggccta 12960
ccggggggag aaacagcatc cgttactctg agttggcacc cctattcgac accacccgtg 13020
tgtacctggt ggacaacaag tcaacggatg tggcatccct gaactaccag aacgaccaca 13080
gcaactttct gaccacggtc attcaaaaca atgactacag cccgggggag gcaagcacac 13140
agaccatcaa tcttgacgac cggtcgcact ggggcggcga cctgaaaacc atcctgcata 13200
ccaacatgcc aaatgtgaac gagttcatgt ttaccaataa gtttaaggcg cgggtgatgg 13260
tgtcgcgctt gcctactaag gacaatcagg tggagctgaa atacgagtgg gtggagttca 13320
cgctgcccga gggcaactac tccgagacca tgaccataga ccttatgaac aacgcgatcg 13380
tggagcacta cttgaaagtg ggcagacaga acggggttct ggaaagcgac atcggggtaa 13440
agtttgacac ccgcaacttc agactggggt ttgaccccgt cactggtctt gtcatgcctg 13500
ggtatatac aaacgaagcc ttccatccag acatcatttt gctgccagga tgcggggtgg 13560
acttcaccca cagccgcctg agcaacttgt tgggcatccg caagcggcaa cccttccagg 13620
agggctttag gatcacctac gatgatctgg agggtggtaa cattcccgca ctgttggatg 13680
tggacgccta ccaggcgagc ttgaaagatg acaccgaaca gggcgggggt ggcgcaggcg 13740
gcagcaacag cagtggcagc ggcgcggaag agaactccaa cgcggcagcc gcggcaatgc 13800
agccggtgga ggacatgaac gatcatgcca ttcgcggcga cacctttgcc acacgggctg 13860
aggagaagcg cgctgaggcc gaagcagcgg ccgaagctgc cgcccccgct gcgcaacccg 13920
aggtcgagaa gcctcagaag aaaccggtga tcaaacccct gacagaggac agcaagaaac 13980

-continued

```
gcagttacaa cctaataagc aatgacagca ccttcaccca gtaccgcagc tggtaccttg  14040
catacaacta cggcgaccct cagaccggaa tccgctcatg gaccctgctt tgcactcctg  14100
acgtaacctg cggctcggag caggtctact ggtcgttgcc agacatgatg caagaccccg  14160
tgaccttccg ctccacgcgc cagatcagca actttccggt ggtgggcgcc gagctgttgc  14220
ccgtgcactc caagagcttc tacaacgacc aggccgtcta ctcccaactc atccgccagt  14280
ttacctctct gacccacgtg ttcaatcgct ttcccgagaa ccagattttg gcgcgcccgc  14340
cagcccccac catcaccacc gtcagtgaaa acgttcctgc tctcacagat cacgggacgc  14400
taccgctgcg caacagcatc ggaggagtcc agcgagtgac cattactgac gccagacgcc  14460
gcacctgccc ctacgtttac aaggccctgg gcatagtctc gccgcgcgtc ctatcgagcc  14520
gcacttttg agcaagcatg tccatcctta tatcgcccag caataacaca ggctggggcc  14580
tgcgcttccc aagcaagatg tttggcgggg ccaagaagcg ctccgaccaa cacccagtgc  14640
gcgtgcgcgg gcactaccgc gcgccctggg gcgcgcacaa acgcggccgc actgggcgca  14700
ccaccgtcga tgacgccatc gacgcggtgg tggaggaggc gcgcaactac acgcccacgc  14760
cgccaccagt gtccacagtg gacgcggcca ttcagaccgt ggtgcgcgga gcccggcgct  14820
atgctaaaat gaagagacgg cggaggcgcg tagcacgtcg ccaccgccgc cgacccggca  14880
ctgccgccca acgcgcggcg gcggccctgc ttaaccgcgc acgtcgcacc ggccgacggg  14940
cggccatgcg ggccgctcga aggctggccg cgggtattgt cactgtgccc cccaggtcca  15000
ggcgacgagc ggccgccgca gcagccgcgg ccattagtgc tatgactcag ggtcgcaggg  15060
gcaacgtgta ttgggtgcgc gactcggtta gcggcctgcg cgtgcccgtg cgcacccgcc  15120
ccccgcgcaa ctagattgca agaaaaaact acttagactc gtactgttgt atgtatccag  15180
cggcggcggc gcgcaacgaa gctatgtcca agcgcaaaat caaagaagag atgctccagg  15240
tcatcgcgcc ggagatctat ggccccccga agaaggaaga gcaggattac aagccccgaa  15300
agctaaagcg ggtcaaaaag aaaaagaaag atgatgatga tgaacttgac gacgaggtgg  15360
aactgctgca cgctaccgcg cccaggcgac gggtacagtg gaaaggtcga cgcgtaaaac  15420
gtgttttgcg acccggcacc accgtagtct ttacgcccgg tgagcgctcc acccgcacct  15480
acaagcgcgt gtatgatgag gtgtacggcg acgaggacct gcttgagcag gccaacgagc  15540
gcctcgggga gtttgcctac ggaaagcggc ataaggacat gctggcgttg ccgctggacg  15600
agggcaaccc aacacctagc ctaaagcccg taacactgca gcaggtgctg cccgcgcttg  15660
caccgtccga agaaaagcgc ggcctaaagc gcgagtctgg tgacttggca cccaccgtgc  15720
agctgatggt acccaagcgc cagcgactgg aagatgtctt ggaaaaaatg accgtggaac  15780
ctgggctgga gcccgaggtc cgcgtgcggc caatcaagca ggtggcgccg ggactgggcg  15840
tgcagaccgt ggacgttcag atacccacta ccagtagcac cagtattgcc accgccacag  15900
agggcatgga gacacaaacg tccccggttg cctcagcggt ggcggatgcc gcggtgcagg  15960
cggtcgctgc ggccgcgtcc aagacctcta cggaggtgca aacggacccg tggatgtttc  16020
gcgtttcagc cccccggcgc ccgcgccgtt cgaggaagta cggcgccgcc agcgcgctac  16080
tgcccgaata tgccctacat ccttccattg cgcctacccc cggctatcgt ggctacacct  16140
accgccccag aagacgagca actacccgac gccgaaccac cactggaacc cgccgccgcc  16200
gtcgccgtcg ccagcccgtg ctggccccga tttccgtgcg cagggtggct cgcgaaggag  16260
gcaggaccct ggtgctgcca acagcgcgct accaccccag catcgtttaa aagccggtct  16320
```

-continued

```
ttgtggttct tgcagatatg gccctcacct gccgcctccg tttcccggtg ccgggattcc  16380
gaggaagaat gcaccgtagg aggggcatgg ccggccacgg cctgacgggc ggcatgcgtc  16440
gtgcgcacca ccggcggcgg cgcgcgtcgc accgtcgcat gcgcggcggt atcctgcccc  16500
tccttattcc actgatcgcc gcggcgattg gcgccgtgcc cggaattgca tccgtggcct  16560
tgcaggcgca gagacactga ttaaaaacaa gttgcatgtg gaaaaatcaa aataaaaagt  16620
ctggactctc acgctcgctt ggtcctgtaa ctattttgta gaatggaaga catcaacttt  16680
gcgtctctgg ccccgcgaca cggctcgcgc ccgttcatgg gaaactggca agatatcggc  16740
accagcaata tgagcggtgg cgccttcagc tggggctcgc tgtggagcgg cattaaaaat  16800
ttcggttcca ccgttaagaa ctatggcagc aaggcctgga acagcagcac aggccagatg  16860
ctgagggata agttgaaaga gcaaaatttc caacaaaagg tggtagatgg cctggcctct  16920
ggcattagcg gggtggtgga cctggccaac caggcagtgc aaaataagat taacagtaag  16980
cttgatcccc gccctcccgt agaggagcct ccaccggccg tggagacagt gtctccagag  17040
gggcgtggcg aaaagcgtcc gcgccccgac agggaagaaa ctctggtgac gcaaatagac  17100
gagcctccct cgtacgagga ggcactaaag caaggcctgc ccaccacccg tcccatcgcg  17160
cccatggcta ccggagtgct gggccagcac acacccgtaa cgctggacct gcctcccccc  17220
gccgacaccc agcagaaacc tgtgctgcca ggcccgaccg ccgttgttgt aacccgtcct  17280
agccgcgcgt ccctgcgccg cgccgccagc ggtccgcgat cgttgcggcc cgtagccagt  17340
ggcaactggc aaagcacact gaacagcatc gtgggtctgg gggtgcaatc cctgaagcgc  17400
cgacgatgct tctgatagct aacgtgtcgt atgtgtgtca tgtatgcgtc catgtcgccg  17460
ccagaggagc tgctgagccg ccgcgcgccc gctttccaag atggctaccc cttcgatgat  17520
gccgcagtgg tcttacatgc acatctcggg ccaggacgcc tcggagtacc tgagccccgg  17580
gctggtgcag tttgcccgcg ccaccgagac gtacttcagc ctgaataaca agtttagaaa  17640
ccccacggtg gcgcctacgc acgacgtgac cacagaccgg tcccagcgtt tgacgctgcg  17700
gttcatccct gtggaccgtg aggatactgc gtactcgtac aaggcgcggt tcaccctagc  17760
tgtgggtgat aaccgtgtgc tggacatggc ttccacgtac tttgacatcc gcggcgtgct  17820
ggacaggggc cctactttta agccctactc tggcactgcc tacaacgccc tggctcccaa  17880
gggtgcccca aatccttgcg aatgggatga agctgctact gctcttgaaa taaacctaga  17940
agaagaggac gatgacaacg aagacgaagt agacgagcaa gctgagcagc aaaaaactca  18000
cgtatttggg caggcgcctt attctggtat aaatattaca aaggagggta ttcaaatagg  18060
tgtcgaaggt caaacaccta aatatgccga taaaacattt caacctgaac ctcaaatagg  18120
agaatctcag tggtacgaaa cagaaattaa tcatgcagct gggagagtcc taaaaaagac  18180
taccccaatg aaaccatgtt acggttcata tgcaaaaccc acaaatgaaa atggagggca  18240
aggcattctt gtaaagcaac aaaatggaaa gctagaaagt caagtggaaa tgcaattttt  18300
ctcaactact gaggcagccg caggcaatgg tgataacttg actcctaaag tggtattgta  18360
cagtgaagat gtagatatag aaaccccaga cactcatatt tcttacatgc ccactattaa  18420
ggaaggtaac tcacgagaac taatgggcca acaatctatg cccaacaggc ctaattacat  18480
tgcttttagg gacaatttta ttggtctaat gtattacaac agcacgggta atatgggtgt  18540
tctggcgggc caagcatcgc agttgaatgc tgttgtagat ttgcaagaca gaaacacaga  18600
gctttcatac cagcttttgc ttgattccat tggtgataga accaggtact tttctatgtg  18660
gaatcaggct gttgacagct atgatccaga tgttagaatt attgaaaatc atggaactga  18720
```

-continued

```
agatgaactt ccaaattact gctttccact gggaggtgtg attaatacag agactcttac  18780
caaggtaaaa cctaaaacag gtcaggaaaa tggatgggaa aaagatgcta cagaattttc  18840
agataaaaat gaaataagag ttggaaataa ttttgccatg gaaatcaatc taaatgccaa  18900
cctgtggaga aatttcctgt actccaacat agcgctgtat ttgcccgaca agctaaagta  18960
cagtccttcc aacgtaaaaa tttctgataa cccaaacacc tacgactaca tgaacaagcg  19020
agtggtggct cccgggctag tggactgcta cattaacctt ggagcacgct ggtcccttga  19080
ctatatggac aacgtcaacc catttaacca ccaccgcaat gctggcctgc gctaccgctc  19140
aatgttgctg ggcaatggtc gctatgtgcc cttccacatc caggtgcctc agaagttctt  19200
tgccattaaa aacctccttc tcctgccggg ctcatacacc tacgagtgga acttcaggaa  19260
ggatgttaac atggttctgc agagctccct aggaaatgac ctaagggttg acggagccag  19320
cattaagttt gatagcattt gcctttacgc caccttcttc cccatggccc acaacaccgc  19380
ctccacgctt gaggccatgc ttagaaacga caccaacgac cagtccttta acgactatct  19440
ctccgccgcc aacatgctct accctatacc cgccaacgct accaacgtgc ccatatccat  19500
cccctcccgc aactgggcgg ctttccgcgg ctgggccttc acgcgcctta agactaagga  19560
aaccccatca ctgggctcgg gctacgaccc ttattacacc tactctggct ctataccctta  19620
cctagatgga accttttacc tcaaccacac ctttaagaag gtggccatta cctttgactc  19680
ttctgtcagc tggcctggca atgaccgcct gcttaccccc aacgagtttg aaattaagcg  19740
ctcagttgac ggggagggtt acaacgttgc ccagtgtaac atgaccaaag actggttcct  19800
ggtacaaatg ctagctaact ataacattgg ctaccagggc ttctatatcc cagagagcta  19860
caaggaccgc atgtactcct tctttagaaa cttccagccc atgagccgtc aggtggtgga  19920
tgatactaaa tacaaggact accaacaggt gggcatccta caccaacaca acaactctgg  19980
atttgttggc taccttgccc ccaccatgcg cgaaggacag gcctaccctg ctaacttccc  20040
ctatccgctt ataggcaaga ccgcagttga cagcattacc cagaaaaagt ttctttgcga  20100
tcgcaccctt tggcgcatcc cattctccag taactttatg tccatgggcg cactcacaga  20160
cctgggccaa aaccttctct acgccaactc cgcccacgcg ctagacatga cttttgaggt  20220
ggatcccatg gacgagccca cccttcttta tgttttgttt gaagtctttg acgtggtccg  20280
tgtgcaccag ccgcaccgcg gcgtcatcga aaccgtgtac ctgcgcacgc ccttctcggc  20340
cggcaacgcc acaacataaa gaagcaagca acatcaacaa cagctgccgc catgggctcc  20400
agtgagcagg aactgaaagc cattgtcaaa gatcttggtt gtgggccata ttttttgggc  20460
acctatgaca agcgctttcc aggctttgtt tctccacaca agctcgcctg cgccatagtc  20520
aatacggccg gtcgcgagac tgggggcgta cactggatgg cctttgcctg gaacccgcac  20580
tcaaaaacat gctacctctt tgagcccttt ggcttttctg accagcgact caagcaggtt  20640
taccagtttg agtacgagtc actcctgcgc cgtagcgcca ttgcttcttc ccccgaccgc  20700
tgtataacgc tggaaaagtc cacccaaagc gtacaggggc ccaactcggc cgcctgtgga  20760
ctattctgct gcatgtttct ccacgccttt gccaactggc cccaaactcc catggatcac  20820
aaccccacca tgaaccttat taccggggta cccaactcca tgctcaacag tccccaggta  20880
cagcccaccc tgcgtcgcaa ccaggaacag ctctacagct tcctggagcg ccactcgccc  20940
tacttccgca gccacagtgc gcagattagg agcgccactt ctttttgtca cttgaaaaac  21000
atgtaaaaat aatgtactag agacactttc aataaaggca aatgctttta tttgtacact  21060
```

-continued

```
ctcgggtgat tatttacccc caccccttgcc gtctgcgccg tttaaaaatc aaaggggttc  21120
tgccgcgcat cgctatgcgc cactggcagg gacacgttgc gatactggtg tttagtgctc  21180
cacttaaact caggcacaac catccgcggc agctcggtga agttttcact ccacaggctg  21240
cgcaccatca ccaacgcgtt tagcaggtcg ggcgccgata tcttgaagtc gcagttgggg  21300
cctccgccct gcgcgcgcga gttgcgatac acagggttgc agcactggaa cactatcagc  21360
gccgggtggt gcacgctggc cagcacgctc ttgtcggaga tcagatccgc gtccaggtcc  21420
tccgcgttgc tcagggcgaa cggagtcaac tttggtagct gccttcccaa aaagggcgcg  21480
tgcccaggct ttgagttgca ctcgcaccgt agtggcatca aaaggtgacc gtgcccggtc  21540
tgggcgttag gatacagcgc ctgcataaaa gccttgatct gcttaaaagc cacctgagcc  21600
tttgcgcctt cagagaagaa catgccgcaa gacttgccgg aaaactgatt ggccggacag  21660
gccgcgtcgt gcacgcagca ccttgcgtcg gtgttggaga tctgcaccac atttcggccc  21720
caccggttct tcacgatctt ggccttgcta gactgctcct tcagcgcgcg ctgcccgttt  21780
tcgctcgtca catccatttc aatcacgtgc tccttattta tcataatgct tccgtgtaga  21840
cacttaagct cgccttcgat ctcagcgcag cggtgcagcc acaacgcgca gcccgtgggc  21900
tcgtgatgct tgtaggtcac ctctgcaaac gactgcaggt acgcctgcag gaatcgcccc  21960
atcatcgtca caaaggtctt gttgctggtg aaggtcagct gcaacccgcg gtgctcctcg  22020
ttcagccagg tcttgcatac ggccgccaga gcttccactt ggtcaggcag tagtttgaag  22080
ttcgccttta gatcgttatc cacgtggtac ttgtccatca gcgcgcgcgc agcctccatg  22140
cccttctccc acgcagacac gatcggcaca ctcagcgggt tcatcaccgt aatttcactt  22200
tccgcttcgc tgggctcttc ctcttcctct tgcgtccgca taccacgcgc cactgggtcg  22260
tcttcattca gccgccgcac tgtgcgctta cctcctttgc catgcttgat tagcaccggt  22320
gggttgctga aacccaccat ttgtagcgcc acatcttctc tttcttcctc gctgtccacg  22380
attacctctg gtgatggcgg gcgctcgggc ttgggagaag ggcgcttctt tttcttcttg  22440
ggcgcaatgg ccaaatccgc cgccgaggtc gatggccgcg ggctgggtgt gcgcggcacc  22500
agcgcgtctt gtgatgagtc ttcctcgtcc tcggactcga tacgccgcct catccgcttt  22560
tttgggggcg cccggggagg cggcggcgac ggggacgggg acgacacgtc ctccatggtt  22620
gggggacgtc gcgccgcacc gcgtccgcgc tcgggggtgg tttcgcgctg ctcctcttcc  22680
cgactggcca tttccttctc ctataggcag aaaaagatca tggagtcagt cgagaagaag  22740
gacagcctaa ccgcccccctc tgagttcgcc accaccgcct ccaccgatgc cgccaacgcg  22800
cctaccacct tccccgtcga ggcacccccg cttgaggagg aggaagtgat tatcgagcag  22860
gacccaggtt ttgtaagcga agacgacgag gaccgctcag taccaacaga ggataaaaag  22920
caagaccagg acaacgcaga ggcaaacgag gaacaagtcg ggcgggggga cgaaaggcat  22980
ggcgactacc tagatgtggg agacgacgtg ctgttgaagc atctgcagcg ccagtgcgcc  23040
attatctgcg acgcgttgca agagcgcagc gatgtgcccc tcgccatagc ggatgtcagc  23100
cttgcctacg aacgccacct attctcaccg cgcgtacccc ccaaacgcca agaaaacggc  23160
acatgcgagc ccaacccgcg cctcaacttc taccccgtat ttgccgtgcc agaggtgctt  23220
gccacctatc acatcttttt ccaaaactgc aagataccc tatcctgccg tgccaaccgc  23280
agccgagcgg acaagcagct ggccttgcgg cagggcgctg tcatacctga tatcgcctcg  23340
ctcaacgaag tgccaaaaat ctttgagggt cttggacgcg acgagaagcg cgcggcaaac  23400
gctctgcaac aggaaaacag cgaaaatgaa agtcactctg gagtgttggt ggaactcgag  23460
```

-continued

```
ggtgacaacg cgcgcctagc cgtactaaaa cgcagcatcg aggtcaccca ctttgcctac  23520
ccggcactta acctacccccc caaggtcatg agcacagtca tgagtgagct gatcgtgcgc  23580
cgtgcgcagc ccctggagag ggatgcaaat ttgcaagaac aaacagagga gggcctaccc  23640
gcagttggcg acgagcagct agcgcgctgg cttcaaacgc gcgagcctgc cgacttggag  23700
gagcgacgca aactaatgat ggccgcagtg ctcgttaccg tggagcttga gtgcatgcag  23760
cggttctttg ctgacccgga gatgcagcgc aagctagagg aaacattgca ctacaccttt  23820
cgacagggct acgtacgcca ggcctgcaag atctccaacg tggagctctg caacctggtc  23880
tcctaccttg gaattttgca cgaaaaccgc cttgggcaaa acgtgcttca ttccacgctc  23940
aagggcgagg cgcgccgcga ctacgtccgc gactgcgttt acttatttct atgctacacc  24000
tggcagacgg ccatgggcgt ttggcagcag tgcttggagg agtgcaacct caaggagctg  24060
cagaaactgc taaagcaaaa cttgaaggac ctatggacgg ccttcaacga gcgctccgtg  24120
gccgcgcacc tggcggacat cattttcccc gaacgcctgc ttaaaaccct gcaacagggt  24180
ctgccagact tcaccagtca aagcatgttg cagaacttta ggaactttat cctagagcgc  24240
tcaggaatct tgcccgccac ctgctgtgca cttcctagcg actttgtgcc cattaagtac  24300
cgcgaatgcc ctccgccgct ttggggccac tgctaccttc tgcagctagc caactacctt  24360
gcctaccact ctgacataat ggaagacgtg agcggtgacg gtctactgga gtgtcactgt  24420
cgctgcaacc tatgcacccc gcaccgctcc ctggtttgca attcgcagct gcttaacgaa  24480
agtcaaatta tcggtacctt tgagctgcag ggtccctcgc ctgacgaaaa gtccgcggct  24540
ccggggttga aactcactcc ggggctgtgg acgtcggctt accttcgcaa atttgtacct  24600
gaggactacc acgcccacga gattaggttc tacgaagacc aatcccgccc gcctaatgcg  24660
gagcttaccg cctgcgtcat tacccagggc cacattcttg gccaattgca agccatcaac  24720
aaagcccgcc aagagtttct gctacgaaag ggacgggggg tttacttgga cccccagtcc  24780
ggcgaggagc tcaacccaat ccccccgccg ccgcagccct atcagcagca gccgcgggcc  24840
cttgcttccc aggatggcac ccaaaaagaa gctgcagctg ccgccgccac ccacggacga  24900
ggaggaatac tgggacagtc aggcagagga ggttttggac gaggaggagg aggacatgat  24960
ggaagactgg gagagcctag acgaggaagc ttccgaggtc gaagaggtgt cagacgaaac  25020
accgtcaccc tcggtcgcat tcccctcgcc ggcgccccag aaatcggcaa ccggttccag  25080
catggctaca acctccgctc ctcaggcgcc gccggcactg cccgttcgcc gacccaaccg  25140
tagatgggac accactggaa ccagggccgg taagtccaag cagccgccgc cgttagccca  25200
agagcaacaa cagcgccaag gctaccgctc atggcgcggg cacaagaacg ccatagttgc  25260
ttgcttgcaa gactgtgggg gcaacatctc cttcgcccgc cgctttcttc tctaccatca  25320
cggcgtggcc ttcccccgta acatcctgca ttactaccgt catctctaca gcccatactg  25380
caccggcggc agcggcagca acagcagcgg ccacacagaa gcaaaggcga ccggatagca  25440
agactctgac aaagcccaag aaatccacag cggcggcagc agcaggagga ggagcgctgc  25500
gtctggcgcc caacgaaccc gtatcgaccc gcgagcttag aaacaggatt tttcccactc  25560
tgtatgctat atttcaacag agcaggggcc aagaacaaga gctgaaaata aaaaacaggt  25620
ctctgcgatc cctcacccgc agctgcctgt atcacaaaag cgaagatcag cttcggcgca  25680
cgctggaaga cgcggaggct ctcttcagta aatactgcgc gctgactctt aaggactagt  25740
ttcgcgccct ttctcaaatt taagcgcgaa aactacgtca tctccagcgg ccacacccgg  25800
```

-continued cgccagcacc tgttgtcagc gccattatga gcaaggaaat tcccacgccc tacatgtgga 25860
gttaccagcc acaaatggga cttgcggctg gagctgccca agactactca acccgaataa 25920
actacatgag cgcgggaccc cacatgatat cccgggtcaa cggaatacgc gcccaccgaa 25980
accgaattct cctggaacag gcggctatta ccaccacacc tcgtaataac cttaatcccc 26040
gtagttggcc cgctgccctg gtgtaccagg aaagtcccgc tcccaccact gtggtacttc 26100
ccagagacgc ccaggccgaa gttcagatga ctaactcagg ggcgcagctt gcgggcggct 26160
ttcgtcacag ggtgcggtcg cccgggcagg gtataactca cctgacaatc agagggcgag 26220
gtattcagct caacgacgag tcggtgagct cctcgcttgg tctccgtccg gacgggacat 26280
ttcagatcgg cggcgccggc cgctcttcat tcacgcctcg tcaggcaatc ctaactctgc 26340
agacctcgtc ctctgagccg cgctctggag gcattggaac tctgcaattt attgaggagt 26400
ttgtgccatc ggtctacttt aaccccttct cgggacctcc cggccactat ccggatcaat 26460
ttattcctaa ctttgacgcg gtaaaggact cggcggacgg ctacgactga atgttaagtg 26520
gagaggcaga gcaactgcgc ctgaaacacc tggtccactg tcgccgccac aagtgctttg 26580
cccgcgactc cggtgagttt tgctactttg aattgcccga ggatcatatc gagggcccgg 26640
cgcacggcgt ccggcttacc gcccagggag agcttgcccg tagcctgatt cgggagttta 26700
cccagcgccc cctgctagtt gagcgggaca ggggaccctg tgttctcact gtgatttgca 26760
actgtcctaa ccctggatta catcaagatc tttgttgcca tctctgtgct gagtataata 26820
aatacagaaa ttaaaatata ctggggctcc tatcgccatc ctgtaaacgc caccgtcttc 26880
acccgcccaa gcaaaccaag gcgaacctta cctggtactt ttaacatctc tccctctgtg 26940
atttacaaca gtttcaaccc agacggagtg agtctacgag agaacctctc cgagctcagc 27000
tactccatca gaaaaaacac caccctcctt acctgccggg aacgtacgag tgcgtcaccg 27060
gccgctgcac cacacctacc gcctgaccgt aaaccagact ttttccggac agacctcaat 27120
aactctgttt accagaacag gaggtgagct tagaaaaccc ttagggtatt aggccaaagg 27180
cgcagctact gtggggttta tgaacaattc aagcaactct acgggctatt ctaattcagg 27240
tttctctaga atcggggttg gggttattct ctgtcttgtg attctcttta ttcttatact 27300
aacgcttctc tgcctaaggc tcgccgcctg ctgtgtgcac atttgcattt attgtcagct 27360
ttttaaacgc tggggtcgcc acccaagatg attaggtaca taatcctagg tttactcacc 27420
cttgcgtcag cccacggtac cacccaaaag gtggatttta aggagccagc ctgtaatgtt 27480
acattcgcag ctgaagctaa tgagtgcacc actcttataa aatgcaccac agaacatgaa 27540
aagctgctta ttcgccacaa aaacaaaatt ggcaagtatg ctgtttatgc tatttggcag 27600
ccaggtgaca ctacagagta taatgttaca gttttccagg gtaaaagtca taaaactttt 27660
atgtatactt ttccatttta tgaaatgtgc gacattacca tgtacatgag caaacagtat 27720
aagttgtggc ccccacaaaa ttgtgtggaa aacactggca ctttctgctg cactgctatg 27780
ctaattacag tgctcgcttt ggtctgtacc ctactctata ttaaatacaa aagcagacgc 27840
agctttattg aggaaaagaa aatgccttaa tttactaagt tacaaagcta atgtcaccac 27900
taactgcttt actcgctgct tgcaaaacaa attcaaaaag ttagcattat aattagaata 27960
ggatttaaac cccccggtca tttcctgctc aataccattc ccctgaacaa ttgactctat 28020
gtgggatatg ctccagcgct acaaccttga agtcaggctt cctggatgtc agcatctgac 28080
tttggccagc acctgtcccg cggatttgtt ccagtccaac tacagcgacc caccctaaca 28140
gagatgacca acacaaccaa cgcggccgcc gctaccggac ttacatctac cacaaataca 28200

-continued

```
ccccaagttt ctgcctttgt caataactgg gataacttgg gcatgtggtg gttctccata  28260
gcgcttatgt ttgtatgcct tattattatg tggctcatct gctgcctaaa gcgcaaacgc  28320
gcccgaccac ccatctatag tcccatcatt gtgctacacc caaacaatga tggaatccat  28380
agattggacg gactgaaaca catgttcttt tctcttacag tatgattaaa tgagacatga  28440
ttcctcgagt ttttatatta ctgacccttg ttgcgctttt ttgtgcgtgc tccacattgg  28500
ctgcggtttc tcacatcgaa gtagactgca ttccagcctt cacagtctat ttgctttacg  28560
gatttgtcac cctcacgctc atctgcagcc tcatcactgt ggtcatcgcc tttatccagt  28620
gcattgactg ggtctgtgtg cgctttgcat atctcagaca ccatccccag tacagggaca  28680
ggactatagc tgagcttctt agaattcttt aattatgaaa tttactgtga cttttctgct  28740
gattatttgc accctatctg cgttttgttc cccgacctcc aagcctcaaa gacatatatc  28800
atgcagattc actcgtatat ggaatattcc aagttgctac aatgaaaaaa gcgatctttc  28860
cgaagcctgg ttatatgcaa tcatctctgt tatggtgttc tgcagtacca tcttagccct  28920
agctatatat ccctaccttg acattggctg gaacgcaata gatgccatga accacccaac  28980
tttccccgcg cccgctatgc ttccactgca acaagttgtt gccggcggct ttgtcccagc  29040
caatcagcct cgcccacctt ctcccacccc cactgaaatc agctacttta atctaacagg  29100
aggagatgac tgacacccta gatctagaaa tggacggaat tattacagag cagcgcctgc  29160
tagaaagacg cagggcagcg gccgagcaac agcgcatgaa tcaagagctc caagacatgg  29220
ttaacttgca ccagtgcaaa aggggtatct tttgtctcgt aaagcaggcc aaagtcacct  29280
acgacagtaa taccaccgga caccgcctta gctacaagtt gccaaccaag cgtcagaaat  29340
tggtggtcat ggtgggagaa aagcccatta ccataactca gcactcggta gaaaccgaag  29400
gctgcattca ctcaccttgt caaggacctg aggatctctg cacccttatt aagaccctgt  29460
gcggtctcaa agatcttatt ccctttaact aataaaaaaa aataataaag catcacttac  29520
ttaaaatcag ttagcaaatt tctgtccagt ttattcagca gcacctcctt gccctcctcc  29580
cagctctggt attgcagctt cctcctggct gcaaactttc tccacaatct aaatggaatg  29640
tcagtttcct cctgttcctg tccatccgca cccactatct tcatgttgtt gcagatgaag  29700
cgcgcaagac cgtctgaaga taccttcaac cccgtgtatc catatgacac ggaaaccggt  29760
cctccaactg tgccttttct tactcctccc tttgtatccc ccaatgggtt tcaagagagt  29820
ccccctgggg tactctcttt gcgcctatcc gaacctctag ttacctccaa tggcatgctt  29880
gcgctcaaaa tgggcaacgg cctctctctg gacgaggccg gcaaccttac ctcccaaaat  29940
gtaaccactg tgagcccacc tctcaaaaaa accaagtcaa acataaacct ggaaatatct  30000
gcacccctca cagttacctc agaagcccta actgtggctg ccgccgcacc tctaatggtc  30060
gcgggcaaca cactcaccat gcaatcacag gccccgctaa ccgtgcacga ctccaaactt  30120
agcattgcca cccaaggacc cctcacagtg tcagaaggaa agctagccct gcaaacatca  30180
ggccccctca ccaccaccga tagcagtacc cttactatca ctgcctcacc ccctctaact  30240
actgccactg gtagcttggg cattgacttg aaagagccca tttatacaca aaatggaaaa  30300
ctaggactaa agtacggggc tcctttgcat gtaacagacg acctaaacac tttgaccgta  30360
gcaactggtc caggtgtgac tattaataat acttccttgc aaactaaagt tactggagcc  30420
ttgggttttg attcacaagg caatatgcaa cttaatgtag caggaggact aaggattgat  30480
tctcaaaaca gacgccttat acttgatgtt agttatccgt ttgatgctca aaaccaacta  30540
```

-continued

```
aatctaagac taggacaggg ccctcttttt ataaactcag cccacaactt ggatattaac  30600
tacaacaaag gcctttactt gtttacagct tcaaacaatt ccaaaaagct tgaggttaac  30660
ctaagcactg ccaaggggtt gatgtttgac gctacagcca tagccattaa tgcaggagat  30720
gggcttgaat ttggttcacc taatgcacca aacacaaatc ccctcaaaac aaaaattggc  30780
catggcctag aatttgattc aaacaaggct atggttccta aactaggaac tggccttagt  30840
tttgacagca caggtgccat tacagtagga aacaaaaata atgataagct aactttgtgg  30900
accacaccag ctccatctcc taactgtaga ctaaatgcag agaaagatgc taaactcact  30960
ttggtcttaa caaaatgtgg cagtcaaata cttgctacag tttcagtttt ggctgttaaa  31020
ggcagtttgg ctccaatatc tggaacagtt caaagtgctc atcttattat aagatttgac  31080
gaaaatggag tgctactaaa caattccttc ctggacccag aatattggaa ctttagaaat  31140
ggagatctta ctgaaggcac agcctataca aacgctgttg gatttatgcc taacctatca  31200
gcttatccaa aatctcacgg taaaactgcc aaaagtaaca ttgtcagtca agtttactta  31260
aacggagaca aaactaaacc tgtaacacta accattacac taaacggtac acaggaaaca  31320
ggagacacaa ctccaagtgc atactctatg tcattttcat gggactggtc tggccacaac  31380
tacattaatg aaatatttgc cacatcctct tacacttttt catacattgc ccaagaataa  31440
agaatcgttt gtgttatgtt tcaacgtgtt tatttttcaa ttgcagaaaa tttcaagtca  31500
tttttcattc agtagtatag ccccaccacc acatagctta tacagatcac cgtaccttaa  31560
tcaaactcac agaaccctag tattcaacct gccacctccc tcccaacaca cagagtacac  31620
agtcctttct ccccggctgg ccttaaaaag catcatatca tgggtaacag acatattctt  31680
aggtgttata ttccacacgg tttcctgtcg agccaaacgc tcatcagtga tattaataaa  31740
ctccccgggc agctcactta agttcatgtc gctgtccagc tgctgagcca caggctgctg  31800
tccaacttgc ggttgcttaa cgggcggcga aggagaagtc cacgcctaca tgggggtaga  31860
gtcataatcg tgcatcagga tagggcggtg gtgctgcagc agcgcgcgaa taaactgctg  31920
ccgccgccgc tccgtcctgc aggaatacaa catggcagtg gtctcctcag cgatgattcg  31980
caccgcccgc agcataaggc gccttgtcct ccgggcacag cagcgcaccc tgatctcact  32040
taaatcagca cagtaactgc agcacagcac cacaatattg ttcaaaatcc cacagtgcaa  32100
ggcgctgtat ccaaagctca tggcggggac cacagaaccc acgtggccat cataccacaa  32160
gcgcaggtag attaagtggc gacccctcat aaacacgctg gacataaaca ttacctcttt  32220
tggcatgttg taattcacca cctcccggta ccatataaac ctctgattaa acatggcgcc  32280
atccaccacc atcctaaacc agctggccaa aacctgcccg ccggctatac actgcaggga  32340
accgggactg gaacaatgac agtggagagc ccaggactcg taaccatgga tcatcatgct  32400
cgtcatgata tcaatgttgg cacaacacag gcacacgtgc atacacttcc tcaggattac  32460
aagctcctcc cgcgttagaa ccatatccca gggaacaacc cattcctgaa tcagcgtaaa  32520
tcccacactg cagggaagac ctcgcacgta actcacgttg tgcattgtca aagtgttaca  32580
ttcgggcagc agcggatgat cctccagtat ggtagcgcgg gtttctgtct caaaaggagg  32640
tagacgatcc ctactgtacg gagtgcgccg agacaaccga gatcgtgttg gtcgtagtgt  32700
catgccaaat ggaacgccgg acgtagtcat atttcctgaa gcaaaaccag gtgcgggcgt  32760
gacaaacaga tctgcgtctc cggtctcgcc gcttagatcg ctctgtgtag tagttgtagt  32820
atatccactc tctcaaagca tccaggcgcc ccctggcttc gggttctatg taaactcctt  32880
catgcgccgc tgccctgata acatccacca ccgcagaata agccacaccc agccaaccta  32940
```

-continued

```
cacattcgtt ctgcgagtca cacacgggag gagcgggaag agctggaaga accatgtttt  33000
tttttttatt ccaaaagatt atccaaaacc tcaaaatgaa gatctattaa gtgaacgcgc  33060
tcccctccgg tggcgtggtc aaactctaca gccaaagaac agataatggc atttgtaaga  33120
tgttgcacaa tggcttccaa aaggcaaacg gccctcacgt ccaagtggac gtaaaggcta  33180
aacccttcag ggtgaatctc ctctataaac attccagcac cttcaaccat gcccaaataa  33240
ttctcatctc gccaccttct caatatatct ctaagcaaat cccgaatatt aagtccggcc  33300
attgtaaaaa tctgctccag agcgccctcc accttcagcc tcaagcagcg aatcatgatt  33360
gcaaaaattc aggttcctca cagacctgta taagattcaa aagcggaaca ttaacaaaaa  33420
taccgcgatc ccgtaggtcc cttcgcaggg ccagctgaac ataatcgtgc aggtctgcac  33480
ggaccagcgc ggccacttcc ccgccaggaa ccatgacaaa agaacccaca ctgattatga  33540
cacgcatact cggagctatg ctaaccagcg tagccccgat gtaagcttgt tgcatgggcg  33600
gcgatataaa atgcaaggtg ctgctcaaaa aatcaggcaa agcctcgcgc aaaaaagaaa  33660
gcacatcgta gtcatgctca tgcagataaa ggcaggtaag ctccggaacc accacagaaa  33720
aagacaccat ttttctctca aacatgtctg cgggtttctg cataaacaca aaataaaata  33780
acaaaaaaac atttaaacat tagaagcctg tcttacaaca ggaaaaacaa cccttataag  33840
cataagacgg actacggcca tgccggcgtg accgtaaaaa aactggtcac cgtgattaaa  33900
aagcaccacc gacagctcct cggtcatgtc cggagtcata atgtaagact cggtaaacac  33960
atcaggttga ttcacatcgg tcagtgctaa aaagcgaccg aaatagcccg gggggaatac a  34020
tacccgcagg cgtagagaca acattacagc cccatagga ggtataacaa aattaatagg  34080
agagaaaaac acataaacac ctgaaaaacc ctcctgccta ggcaaaatag caccctcccg  34140
ctccagaaca acatacagcg cttccacagc ggcagccata acagtcagcc ttaccagtaa  34200
aaaagaaaac ctattaaaaa aacaccactc gacacggcac cagctcaatc agtcacagtg  34260
taaaaaaggg ccaagtgcag agcgagtata tataggacta aaaaatgacg taacggttaa  34320
agtccacaaa aaacacccag aaaaccgcac gcgaacctac gcccagaaac gaaagccaaa  34380
aaacccacaa cttcctcaaa tcgtcacttc cgttttccca cgttacgtca cttcccattt  34440
taagaaaact acaattccca acacatacaa gttactccgc cctaaaacct acgtcacccg  34500
ccccgttccc acgccccgcg ccacgtcaca aactccaccc cctcattatc atattggctt  34560
caatccaaaa taaggtatat tattgatgat gttaattaag aattcggatc tgcgacgcga  34620
ggctggatgg ccttccccat tatgattctt ctcgcttccg gcggcatcgg gatgcccgcg  34680
ttgcaggcca tgctgtccag gcaggtagat gacgaccatc agggacagct tcaaggccag  34740
caaaaggcca ggaaccgtaa aaaggccgcg ttgctggcgt ttttccatag gctccgcccc  34800
cctgacgagc atcacaaaaa tcgacgctca agtcagaggt ggcgaaaccc gacaggacta  34860
taaagatacc aggcgtttcc ccctggaagc tccctcgtgc gctctcctgt tccgaccctg  34920
ccgcttaccg gatacctgtc cgcctttctc ccttcgggaa gcgtggcgct ttctcatagc  34980
tcacgctgta ggtatctcag ttcggtgtag gtcgttcgct ccaagctggg ctgtgtgcac  35040
gaaccccccg ttcagcccga ccgctgcgcc ttatccggta actatcgtct tgagtccaac  35100
ccggtaagac acgacttatc gccactggca gcagccactg gtaacaggat tagcagagcg  35160
aggtatgtag gcggtgctac agagttcttg aagtggtggc ctaactacgg ctacactaga  35220
aggacagtat ttggtatctg cgctctgctg aagccagtta ccttcggaaa aagagttggt  35280
```

-continued

```
agctcttgat ccggcaaaca aaccaccgct ggtagcggtg gtttttttgt ttgcaagcag  35340

cagattacgc gcagaaaaaa aggatctcaa gaagatcctt tgatcttttc tacggggtct  35400

gacgctcagt ggaacgaaaa ctcacgttaa gggattttgg tcatgagatt atcaaaaagg  35460

atcttcacct agatcctttt aaatcaatct aaagtatata tgagtaaact tggtctgaca  35520

gttaccaatg cttaatcagt gaggcaccta tctcagcgat ctgtctattt cgttcatcca  35580

tagttgcctg actccccgtc gtgtagataa ctacgatacg ggagggctta ccatctggcc  35640

ccagtgctgc aatgataccg cgagacccac gctcaccggc tccagattta tcagcaataa  35700

accagccagc cggaagggcc gagcgcagaa gtggtcctgc aactttatcc gcctccatcc  35760

agtctattaa ttgttgccgg gaagctagag taagtagttc gccagttaat agtttgcgca  35820

acgttgttgc cattgctaca ggcatcgtgg tgtcacgctc gtcgtttggt atggcttcat  35880

tcagctccgg ttcccaacga tcaaggcgag ttacatgatc ccccatgttg tgcaaaaaag  35940

cggttagctc cttcggtcct ccgatcgttg tcagaagtaa gttggccgca gtgttatcac  36000

tcatggttat ggcagcactg cataattctc ttactgtcat gccatccgta agatgctttt  36060

ctgtgactgg tgagtactca accaagtcat tctgagaata gtgtatgcgg cgaccgagtt  36120

gctcttgccc ggcgtcaaca cgggataata ccgcgccaca tagcagaact ttaaaagtgc  36180

tcatcattgg aaaacgttct tcggggcgaa aactctcaag gatcttaccg ctgttgagat  36240

ccagttcgat gtaacccact cgtgcaccca actgatcttc agcatctttt actttcacca  36300

gcgtttctgg gtgagcaaaa acaggaaggc aaaatgccgc aaaaaaggga ataagggcga  36360

cacggaaatg ttgaatactc atactcttcc tttttcaata ttattgaagc atttatcagg  36420

gttattgtct catgagcgga tacatatttg aatgtattta gaaaaataaa caaatagggg  36480

ttccgcgcac atttccccga aaagtgccac ctgacgtcta agaaaccatt attatcatga  36540

cattaaccta taaaaatagg cgtatcacga ggccctttcg tcttcaagaa ttggatccga  36600

attcttaatt tcttaattaa                                              36620
```

<210> SEQ ID NO 31
<211> LENGTH: 36620
<212> TYPE: DNA
<213> ORGANISM: Artificial Sequence
<220> FEATURE:
<223> OTHER INFORMATION: Codon optimized DNA encoding pMRKAd5HIV-1 nef, noncoding

<400> SEQUENCE: 31

```
gtagtagtta ttatatggaa taaaacctaa cttcggttat actattactc ccccacctca     60

aacactgcac cgcgccccgc acccttgccc cgcccactgc atcatcacac cgccttcaca    120

ctacaacgtt cacaccgcct tgtgtacatt cgctgcctac accgttttca ctgcaaaaac    180

cacacgcggc cacatgtgtc cttcactgtt aaaagcgcgc caaaatccgc ctacaacatc    240

atttaaaccc gcattggctc attctaaacc ggtaaaagcg cccttttgac ttattctcct    300

tcactttaga cttattaaaa cacaatgagt atcgcgcatt ataaacagat cccggcgccc    360

ctgaaactgg caaatgcacc tctgagcggg tccacaaaaa gagtccacaa aaggcgcaag    420

gcccagtttc aaccgcaaaa taataatatc cgccggcgct aggtaacgta tgcaacatag    480

gtatagtatt atacatgtaa atataaccga gtacaggttg taatggcggt acaactgtaa    540

ctaataactg atcaataatt atcattagtt aatgccccag taatcaagta tcgggtatat    600

acctcaaggc gcaatgtatt gaatgccatt taccgggcgg accgactggc gggttgctgg    660
```

-continued

```
gggcgggtaa ctgcagttat tactgcatac aagggtatca ttgcggttat ccctgaaagg    720
taactgcagt tacccacctc ataaatgcca tttgacgggt gaaccgtcat gtagttcaca    780
tagtatacgg ttcatgcggg ggataactgc agttactgcc atttaccggg cggaccgtaa    840
tacgggtcat gtactggaat accctgaaag gatgaaccgt catgtagatg cataatcagt    900
agcgataatg gtaccactac gccaaaaccg tcatgtagtt acccgcacct atcgccaaac    960
tgagtgcccc taaaggttca gaggtggggt aactgcagtt accctcaaac aaaaccgtgg   1020
ttttagttgc cctgaaaggt tttacagcat tgttgaggcg gggtaactgc gtttacccgc   1080
catccgcaca tgccaccctc cagatatatt cgtctcgagc aaatcacttg gcagtctagc   1140
ggacctctgc ggtaggtgcg acaaaactgg aggtatcttc tgtggccctg gctaggtcgg   1200
aggcgccggc ccttgccacg taaccttgcg cctaaggggc acggttctca ctctagacgg   1260
tggtaccggc cgttcaccag gttctccagg cacgggccga ccaggtggca ctccctctcc   1320
tactcctccc ggctcgggcg gcggctgtcc cactcctcct ggctcgggcg gcgtcacccg   1380
cacccgcggc acaggtccct ggacctcttc gtgccgcggt agtggaggag gttgtggcgg   1440
cggtggttgc ggctgacgcg gaccgacctc cgggtcctcc tgctcctcca cccgaagggg   1500
cactccgggg tccacgggga ctccgggtac tggatgttcc cgcggcacct ggacagggtg   1560
aaggacttcc tcttcccgcc ggacctcccg gactaggtga gggtcttctc cgtcctgtag   1620
gacctggaca cccacatggt gtgggtcccg atgaaggggc tgaccgtctt gatgtggggg   1680
ccggggccgt agtccaaggg ggactggaag ccgaccacga agttcgacca cgggcacctc   1740
gggctcttcc acctcctccg gttgctcccg ctcttgttga cgcggcgggt ggggtacagg   1800
gtcgtgccgt agctcctggg gctcttcctc cacgacctca cctccaagct gaggttcgac   1860
cggaaggtgg tgcaccggtc cctcgacgtg gggctcatga tgttcctgac gatttcgggc   1920
ccgtctagac gacacggaag atcaacggtc ggtagacaac aaacggggag ggggcacgga   1980
aggaactggg accttccacg gtgagggtga caggaaagga ttattttact cctttaacgt   2040
agcgtaacag actcatccac agtaagataa gacccccac cccaccccgt cctgtcgttc    2100
cccctcctaa cccttctgtt atcgtccgta cgacccctac gccacccgag ataccggcta   2160
gccgcgcggc atgactttac acacccgcac cgaattccca ccctttctta tatattccac   2220
ccccagaata catcaaaaca tagacaaaac gtcgtcggcg gcggcggtac tcgtggttga   2280
gcaaactacc ttcgtaacac tcgagtataa actgttgcgc gtacggggt acccggcccc    2340
acgcagtctt acactacccg aggtcgtaac taccagcggg gcaggacggg cgtttgagat   2400
gatggaactg gatgctctgg cacagacctt gcggcaacct ctgacgtcgg aggcggcggc   2460
gaagtcggcg acgtcggtgg cgggcgccct aacactgact gaaacgaaag gactcgggcg   2520
aacgtttgtc acgtcgaagg gcaagtaggc gggcgctact gttcaactgc cgagaaaacc   2580
gtgttaacct aagaaactgg gcccttgaat tacagcaaag agtcgtcgac aacctagacg   2640
cggtcgtcca aagacgggac ttccgaagga ggggagggtt acgccaaatt ttgtatttat   2700
tttttggtct gagacaaacc taaacctagt tcgttcacag aacgacagaa ataaatcccc   2760
aaaacgcgcg cgccatccgg gccctggtcg ccagagccag caactcccag gacacataaa   2820
aaaggtcctg caccatttcc actgagacct acaagtctat gtacccgtat tcgggcagag   2880
accccacctc catcgtggtg acgtctcgaa gtacgacgcc ccaccacaac atctactagg   2940
tcagcatcgt cctcgcgacc cgcaccacgg atttttacag aaagtcatcg ttcgactaac   3000
ggtccccgtc cgggaaccac attcacaaat gtttcgccaa ttcgacccta cccacgtatg   3060
```

-continued

```
caccccctata ctctacgtag aacctgacat aaaaatccaa ccgatacaag ggtcggtata   3120
gggaggcccc taagtacaac acgtcttggt ggtcgtgtca cataggccac gtgaaccctt   3180
taaacagtac atcgaatctt cctttacgca ccttcttgaa cctctgcggg aacactggag   3240
gttctaaaag gtacgtaagc aggtattact accgttaccc gggtgcccgc cgccggaccc   3300
gcttctataa agaccctagt gattgcagta tcaacacaag gtcctactct agcagtatcc   3360
ggtaaaaatg tttcgcgccc gcctcccacg gtctgacgcc atattaccaa ggtaggccgg   3420
gtccccgcat caatgggagt gtctaaacgt aaagggtgcg aaactcaagt ctaccccccct   3480
agtacagatg gacgccccgc tacttctttt gccaaaggcc ccatcccctc tagtcgaccc   3540
ttctttcgtc caaggactcg tcgacgctga atggcgtcgg ccacccgggc atttagtgtg   3600
gataatggcc gacgttgacc atcaattctc tcgacgtcga cggcagtagg gactcgtccc   3660
cccggtgaag caattcgtac agggactgag cgtacaaaag ggactggttt aggcggtctt   3720
ccgcgagcgg cgggtcgcta tcgtcaagaa cgttccttcg tttcaaaaag ttgccaaact   3780
ctggcaggcg gcatccgtac gaaaactcgc aaactggttc gtcaaggtcc gccagggtgt   3840
cgagccagtg gacgagatgc cgtagagcta ggtcgtatag aggagcaaag cgcccaaccc   3900
cgccgaaagc gacatgccgt catcagccac gagcaggtct gcccggtccc agtacagaaa   3960
ggtgcccgcg tcccaggagc agtcgcatca gacccagtgc cacttcccca cgcgaggccc   4020
gacgcgcgac cggtcccacg cgaactccga ccaggacgac cacgacttcg cgacggccag   4080
aagcgggacg cgcagccggt ccatcgtaaa ctggtaccac agtatcaggt cggggaggcg   4140
ccgcaccggg aaccgcgcgt cgaacgggaa cctcctccgc ggcgtgctcc ccgtcacgtc   4200
tgaaaactcc cgcatctcga acccgcgctc tttatggcta aggcccctca tccgtaggcg   4260
cggcgtccgg ggcgtctgcc agagcgtaag gtgctcggtc cactcgagac cggcaagccc   4320
cagtttttgg tccaaagggg gtacgaaaaa ctacgcaaag aatggagacc aaaggtactc   4380
ggccacaggt gcgagccact gcttttccga caggcacagg ggcatatgtc tgaactctcc   4440
ggacaggagc tcgccacaag gcgccaggag gagcatatct ttgagcctgg tgagactctg   4500
tttccgagcg caggtccggt cgtgcttcct ccgattcacc ctccccatcg ccagcaacag   4560
gtgatccccc aggtgagcga ggtcccacac ttctgtgtac agcgggagaa gccgtagttc   4620
cttccactaa ccaaacatcc acatccggtg cactggccca caaggacttc cccccgatat   4680
tttcccccac ccccgcgcaa gcaggagtga gagaaggcgt agcgacagac gctcccggtc   4740
gacaacccca ctcatgaggg agacttttcg cccgtactga agacgcgatt ctaacagtca   4800
aaggtttttg ctcctcctaa actataagtg gaccgggcgc cactacggaa actcccaccg   4860
gcgtaggtag accagtcttt tctgttagaa aaacaacagt tcgaaccacc gtttgctggg   4920
catctcccgc aacctgtcgt tgaaccgcta cctcgcgtcc caaaccaaaa acagcgctag   4980
ccgcgcgagg aaccggcgct acaaatcgac gtgcataagc gcgcgttgcg tggcggtaag   5040
ccctttctgc caccacgcga gcagcccgtg gtccacgtgc gcggttggcg ccaacacgtc   5100
ccactgttcc agttgcgacc accgatggag aggcgcatcc gcgagcaacc aggtcgtctc   5160
cgccggcggg aacgcgctcg tcttaccgcc atcccccaga tcgacgcaga gcaggccccc   5220
cagacgcagg tgccatttct ggggcccgtc gtccgcgcgc agcttcatca gatagaacgt   5280
aggaacgttc agatcgcgga cgacggtacg cgcccgccgt tcgcgcgcga gcatacccaa   5340
ctcacccccct ggggtaccgt accccaccca ctcgcgcctc cgcatgtacg gcgtttacag   5400
```

-continued catttgcatc tccccgagag actcataagg ttctatacat cccatcgtag aaggtggcgc 5460
ctacgaccgc gcgtgcatta gcatatcaag cacgctccct cgctcctcca gccctggctc 5520
caacgatgcc cgcccgacga gacgagcctt ctgatagacg gacttctacc gtacactcaa 5580
cctactatac caacctgcga ccttctgcaa cttcgaccgc agacactctg gatggcgcag 5640
tgcgtgcttc ctccgcatcc tcagcgcgtc gaacaactgg tcgagccgcc actggacgtg 5700
cagatcccgc gtcatcaggt cccaaaggaa ctactacagt atgaatagga cagggaaaaa 5760
aaaggtgtcg agcgccaact cctgtttgag aagcgccaga aaggtcatga gaacctagcc 5820
tttgggcagc cggaggcttg ccattctcgg atcgtacatc ttgaccaact gccggaccat 5880
ccgcgtcgta gggaaaagat gcccatcgcg catacggacg cgccggaagg cctcgctcca 5940
cacccactcg cgtttccaca gggactggta ctgaaactcc atgaccataa acttcagtca 6000
cagcagcgta ggcgggacga gggtctcgtt tttcaggcac gcgaaaaacc ttgcgcctaa 6060
accgtcccgc ttccactgta gcaacttctc atagaaaggg cgcgctccgt atttcaacgc 6120
acactacgcc ttcccagggc cgtggagcct tgccaacaat taatggaccc gccgctcgtg 6180
ctagagcagt ttcggcaact acaacaccgg gtgttacatt tcaaggttct tcgcgcccta 6240
cgggaactac cttccgttaa aaaattcaag gagcatccac tcgagaagtc ccctcgactc 6300
gggcacgaga ctttcccggg tcagacgttc tactcccaac cttcgctgct tactcgaggt 6360
gtccagtgcc cggtaatcgt aaacgtccac cagcgctttc caggatttga ccgctggata 6420
ccggtaaaaa agaccccact acgtcatctt ccattcgccc agaacaaggg tcgccagggt 6480
aggttccaag cgccgatcca gagcgcgccg tcagtgatct ccgagtagag gcggcttgaa 6540
gtactggtcg tacttcccgt gctcgacgaa gggtttccgg gggtaggttc atatccagag 6600
atgtagcatc cactgtttct ctgcgagcca cgctcctacg ctcggctagc ccttcttgac 6660
ctagagggcg gtggttaacc tcctcaccga taactacacc actttcatct tcagggacgc 6720
tgcccggctt gtgagcacga ccgaaaacat ttttgcacgc gtcatgaccg tcgccacgtg 6780
cccgacatgt aggacgtgct ccaactggac tgctggcgcg tgttccttcg tctcaccctt 6840
aaactcgggg agcggaccgc ccaaaccgac caccagaaga tgaagccgac gaacaggaac 6900
tggcagaccg acgagctccc ctcaatgcca cctagcctgg tggtgcggcg cgctcgggtt 6960
tcaggtctac aggcgcgcgc cgccagcctc gaactactgt tgtagcgcgt ctaccctcga 7020
caggtaccag acctcgaggg cgccgcagtc cagtccgccc tcgaggacgt ccaaatggag 7080
cgtatctgcc cagtcccgcg cccgatctag gtccactatg gattaaaggt ccccgaccaa 7140
ccaccgccgc agctaccgaa cgttctccgg cgtaggggcg ccgcgctgat gccatggcgc 7200
gccgcccgcc acccggcgcc cccacaggaa cctactacgt agattttcgc cactgcgccc 7260
gctcggggc ctccatcccc cccgaggcct gggcggccct ctcccccgtc cccgtgcagc 7320
cgcggcgcgc gcccgtcctc gaccacgacg cgcgcatcca acgaccgctt gcgctgctgc 7380
gccgccaact agaggactta gaccgcggag acgcacttct gctgcccggg ccactcgaac 7440
ttggactttc tctcaagctg tcttagttaa agccacagca actgccgccg gaccgcgttt 7500
tagaggacgt gcagaggact caacagaact atccgctaga gccggtactt gacgagctag 7560
agaaggagga cctctagagg cgcaggccga gcgaggtgcc accgccgctc cagcaacctt 7620
tacgcccggt actcgacgct cttccgcaac tccggaggga gcaaggtctg cgccgacatc 7680
tggtgcgggg gaagccgtag cgcccgcgcg tactggtgga cgcgctctaa ctcgaggtgc 7740
acggcccgct tctgccgcat caaagcgtcc gcgactttct ccatcaactc ccaccaccgc 7800

-continued cacacaagac ggtgcttctt catgtattgg gtcgcagcgt tgcacctaag caactatagg 7860
gggttccgga gttccgcgag gtaccggagc atcttcaggt gccgcttcaa ctttttgacc 7920
ctcaacgcgc ggctgtgcca attgaggagg aggtcttctg cctactcgag ccgctgtcac 7980
agcgcgtgga gcgcgagttt ccgatgtccc cggagaagaa gaagaagtta gaggagaagg 8040
tattcccgga ggggaagaag aagaagaccg ccgccacccc ctcccccctg tgccgccgct 8100
gctgccgcgt ggccctccgc cagctgtttc gcgagctagt agaggggcgc cgctgccgcg 8160
taccagagcc actgccgcgc cggcaagagc gcccccgcgt caaccttctg cggcgggcag 8220
tacagggcca atacccaacc gccccccgac ggtacgccgt ccctatgccg cgattgctac 8280
gtagagttgt taacaacaca tccatgaggc ggcggctccc tggactcgct caggcgtagc 8340
tggcctagcc ttttggagag ctctttccgc agattggtca gtgtcagcgt tccatccgac 8400
tcgtggcacc gcccgccgtc gcccgccgcc agccccaaca aagaccgcct ccacgacgac 8460
tactacatta atttcatccg ccagaactct gccgcctacc agctgtcttc gtggtacagg 8520
aacccaggcc ggacgactta cgcgtccgcc agccggtacg gggtccgaag caaaactgta 8580
gccgcgtcca gaaacatcat cagaacgtac tcggaaagat ggccgtgaag aagaagagga 8640
aggagaacag gacgtagaga acgtagatag cgacgccgcc gccgcctcaa accggcatcc 8700
accgcgggag aaggagggta cgcacactgg ggcttcgggg agtagccgac ttcgtcccga 8760
tccagccgct gttgcgcgag ccgattatac cggacgacgt ggacgcactc ccatctgacc 8820
ttcagtaggt acaggtgttt cgccaccata cgcgggcaca actaccacat tcacgtcaac 8880
cggtattgcc tggtcaattg ccagaccact gggccgacgc tctcgagcca catggactct 8940
gcgctcattc gggagctcag tttatgcatc agcaacgttc aggcgtggtc catgaccata 9000
gggtggtttt tcacgccgcc gccgaccgcc atctccccgg tcgcatccca ccggccccga 9060
ggcccccgct ctagaaggtt gtattccgct actataggca tctacatgga cctgtaggtc 9120
cactacggcc gccgccacca cctccgcgcg cctttcagcg cctgcgccaa ggtctacaac 9180
gcgtcgccgt ttttcacgag gtaccagccc tgcgagaccg gccagtccgc gcgcgttagc 9240
aactgcgaga tctggcacgt tttcctctcg gacattcgcc cgtgagaagg caccagacca 9300
cctatttaag cgttcccata gtaccgcctg ctggccccaa gctcggggca taggccggca 9360
ggcggcacta ggtacgccaa tggcgggcgc acagcttggg tccacacgct gcagtctgtt 9420
gccccctcac gaggaaaacc gaaggaaggt ccgcgccgcc gacgacgcga tcgaaaaaac 9480
cggtgaccgg cgcgcgtcgc attcgccaat ccgacctttc gctttcgtaa ttcaccgagc 9540
gagggacatc ggcctcccaa taaaaggttc ccaactcagc gccctggggg ccaagctcag 9600
agcctggccg gcctgacgcc gcttgccccc aaacggaggg gcagtacgtt ctggggcgaa 9660
cgtttaagga ggcctttgtc cctgctcggg gaaaaaacga aaagggtcta cgtaggccac 9720
gacgccgtct acgcgggggg aggagtcgtc gccgttctcg ttctcgtcgc cgtctgtacg 9780
tcccgtggga ggggaggagg atggcgcagt cctccccgct gtaggcgcca actgcgccgt 9840
cgtctaccac taatgcttgg gggcgccgcg gcccgggccg tgatggacct gaacctcctc 9900
ccgctcccgg accgcgccga tcctcgcggg agaggactcg ccgtgggttc ccacgtcgac 9960
ttcgcactat gcgcactccg catgcacggc gccgtcttgg acaaagcgct ggcgctccct 10020
ctcctcgggc tcctctacgc cctagctttc aaggtgcgtc ccgcgctcga cgccgtaccg 10080
gacttagcgc tcgccaacga cgcgctcctc ctgaaactcg ggctgcgcgc ttggccctaa 10140

-continued tcagggcgcg cgcgtgtgca ccgccggcgg ctggaccatt ggcgtatgct cgtctgccac 10200
ttggtcctct aattgaaagt tttttcgaaa ttgttggtgc acgcatgcga acaccgcgcg 10260
ctcctccacc gatatcctga ctacgtagac accctgaaac attcgcgcga cctcgttttg 10320
ggtttatcgt tcggcgagta ccgcgtcgac aaggaatatc acgtcgtgtc gtccctgttg 10380
ctccgtaagt ccctacgcga cgatttgtat catctcgggc tcccggcgac cgacgagcta 10440
aactatttgt aggacgtctc gtatcaccac gtcctcgcgt cgaactcgga ccgactgttc 10500
caccggcggt agttgataag gtacgaatcg gacccgttca aaatgcgggc gttctatatg 10560
gtatggggaa tgcaagggta tctgttcctc catttctagc tccccaagat gtacgcgtac 10620
cgcgacttcc acgaatggaa ctcgctgctg gacccgcaaa tagcgttgct cgcgtaggtg 10680
ttccggcact cgcactcggc cgccgcgctc gagtcgctgg cgctcgacta cgtgtcggac 10740
gtttcccggg accgaccgtg cccgtcgccg ctatctctcc ggctcaggat gaaactgcgc 10800
ccgcgactgg acgcgacccg gggttcggct gcgcgggacc tccgtcgacc ccggcctgga 10860
cccgaccgcc accgtgggcg cgcgcgaccg ttgcagccgc cgcacctcct tatactgctc 10920
ctgctactca tgctcggtct cctgccgctc atgattcgcc actacaaaga ctagtctact 10980
acgttctgcg ttgcctgggc cgccacgccc gccgcgacgt ctcggtcggc aggccggaat 11040
tgaggtgcct gctgaccgcg gtccagtacc tggcgtagta cagcgactga cgcgcgttag 11100
gactgcgcaa ggccgtcgtc ggcgtccggt tggccgagag gcgttaagac cttcgccacc 11160
agggccgcgc gcgtttgggg tgcgtgctct tccacgaccg ctagcatttg cgcgaccggc 11220
ttttgtcccg gtaggccggg ctgctccggc cggaccagat gctgcgcgac gaagtcgcgc 11280
accgagcaat gttgtcgccg ttgcacgtct ggttggacct ggccgaccac cccctacacg 11340
cgctccggca ccgcgtcgca ctcgcgcgcg tcgtcgtccc gttggacccg aggtaccaac 11400
gtgatttgcg gaaggactca tgtgtcgggc ggttgcacgg cgcccctgtc ctcctgatgt 11460
ggttgaaaca ctcgcgtgac gccgattacc actgactctg tggcgtttca ctccacatgg 11520
tcagacccgg tctgataaaa aaggtctggt catctgttcc ggacgtctgg catttggact 11580
cggtccgaaa gtttttgaac gtccccgaca ccccccacgc ccgagggtgt ccgctggcgc 11640
gctggcacag atcgaacgac tgcgggttga gcgcggacaa cgacgacgat tatcgcggga 11700
agtgcctgtc accgtcgcac agggccctgt gtatggatcc agtgaacgac tgtgacatgg 11760
cgctccggta tccagtccgc gtacacctgc tcgtatgaaa ggtcctctaa tgttcacagt 11820
cggcgcgcga ccccgtcctc ctgtgcccgt cggacctccg ttgggatttg atggacgact 11880
ggttggccgc cgtcttctag gggagcaacg tgtcaaattt gtcgctcctc ctcgcgtaaa 11940
acgcgatgca cgtcgtctcg cactcggaat tggactacgc gctgccccat tgcgggtcgc 12000
accgcgacct gtactggcgc gcgttgtacc ttggcccgta catacggagt ttggccggca 12060
aatagttggc ggattacctg atgaacgtag cgcgccggcg gcacttgggg ctcataaagt 12120
ggttacggta gaacttgggc gtgaccgatg gcgggggacc aaagatgtgg ccccctaagc 12180
tccacgggct cccattgcta cctaaggaga ccctgctgta tctgctgtcg cacaaaaggg 12240
gcgttggcgt ctgggacgat ctcaacgttg tcgcgctcgt ccgtctccgc cgcgacgctt 12300
tcctttcgaa ggcgtccggt tcgtcgaaca ggctagatcc gcgacgccgg ggcgccagtc 12360
tacgatcatc gggtaaaggt tcgaactatc ccagagaatg gtcgtgagcg tggtgggcgg 12420
gcgcggacga cccgctcctc ctcatggatt tgttgagcga cgacgtcggc gtcgcgcttt 12480
ttttggacgg aggccgtaaa gggttgttgc cctatctctc ggatcacctg ttctactcat 12540

-continued

```
ctaccttctg catgcgcgtc ctcgtgtccc tgcacggtcc gggcgcgggc gggtgggcag  12600
cagtttccgt gctggcagtc gccccagacc acaccctcct gctactgagc cgtctgctgt  12660
cgtcgcagga cctaaaccct ccctcaccgt tgggcaaacg cgtggaagcg gggtccgacc  12720
cctcttacaa aattttttt tttttcgtac tacgttttat tttttgagtg gttccggtac  12780
cgtggctcgc aaccaaaaga acataagggg aatcatacgc cgcgcgccgc tacatactcc  12840
ttccaggagg agggaggatg ctctcacacc actcgcgccg cggtcaccgc cgccgcgacc  12900
caagagggaa gctacgaggg gacctgggcg gcaaacacgg aggcgccatg gacgccggat  12960
ggccccccctc tttgtcgtag gcaatgagac tcaaccgtgg ggataagctg tggtgggcac  13020
acatggacca cctgttgttc agttgcctac accgtaggga cttgatggtc ttgctggtgt  13080
cgttgaaaga ctggtgccag taagttttgt tactgatgtc gggcccccctc cgttcgtgtg  13140
tctggtagtt agaactgctg gccagcgtga ccccgccgct ggacttttgg taggacgtat  13200
ggttgtacgg tttacacttg ctcaagtaca aatggttatt caaattccgc gcccactacc  13260
acagcgcgaa cggatgattc ctgttagtcc acctcgactt tatgctcacc cacctcaagt  13320
gcgacgggct cccgttgatg aggctctggt actggtatct ggaatacttg ttgcgctagc  13380
acctcgtgat gaactttcac ccgtctgtct tgccccaaga cctttcgctg tagccccatt  13440
tcaaactgtg ggcgttgaag tctgacccca aactggggca gtgaccagaa cagtacggac  13500
cccatatatg tttgcttcgg aaggtaggtc tgtagtaaaa cgacggtcct acgccccacc  13560
tgaagtgggt gtcggcggac tcgttgaaca acccgtaggc gttcgccgtt gggaaggtcc  13620
tcccgaaatc ctagtggatg ctactagacc tcccaccatt gtaagggcgt gacaacctac  13680
acctgcggat ggtccgctcg aactttctac tgtggcttgt cccgccccca ccgcgtccgc  13740
cgtcgttgtc gtcaccgtcg ccgcgccttc tcttgaggtt gcgccgtcgg cgccgttacg  13800
tcggccacct cctgtacttg ctagtacggt aagcgccgct gtggaaacgg tgtgcccgac  13860
tcctcttcgc gcgactccgg cttcgtcgcc ggcttcgacg gcgggggcga cgcgttgggc  13920
tccagctctt cggagtcttc tttggccact agtttgggga ctgtctcctg tcgttctttg  13980
cgtcaatgtt ggattattcg ttactgtcgt ggaagtgggt catggcgtcg accatggaac  14040
gtatgttgat gccgctggga gtctggcctt aggcgagtac ctgggacgaa acgtgaggac  14100
tgcattggac gccgagcctc gtccagatga ccagcaacgg tctgtactac gttctggggc  14160
actggaaggc gaggtgcgcg gtctagtcgt tgaaaggcca ccacccgcgg ctcgacaacg  14220
ggcacgtgag gttctcgaag atgttgctgg tccggcagat gagggttgag taggcggtca  14280
aatggagaga ctgggtgcac aagttagcga aagggctctt ggtctaaaac cgcgcgggcg  14340
gtcgggggtg gtagtggtgg cagtcacttt tgcaaggacg agagtgtcta gtgccctgcg  14400
atggcgacgc gttgtcgtag cctcctcagg tcgctcactg gtaatgactg cggtctgcgg  14460
cgtggacggg gatgcaaatg ttccgggacc cgtatcagag cggcgcgcag gatagctcgg  14520
cgtgaaaaac tcgttcgtac aggtaggaat atagcgggtc gttattgtgt ccgaccccgg  14580
acgcgaaggg ttcgttctac aaaccgcccc ggttcttcgc gaggctggtt gtgggtcacg  14640
cgcacgcgcc cgtgatggcg cgcgggaccc cgcgcgtgtt tgcgccggcg tgacccgcgt  14700
ggtggcagct actgcggtag ctgcgccacc acctcctccg cgcgttgatg tgcgggtgcg  14760
gcggtggtca caggtgtcac ctgcgccggt aagtctggca ccacgcgcct cgggccgcga  14820
tacgatttta cttctctgcc gcctccgcgc atcgtgcagc ggtggcggcg gctgggccgt  14880
```

-continued

```
gacggcgggt tgcgcgccgc cgccgggacg aattggcgcg tgcagcgtgg ccggctgccc  14940
gccggtacgc ccggcgagct tccgaccggc gcccataaca gtgacacggg gggtccaggt  15000
ccgctgctcg ccggcggcgt cgtcggcgcc ggtaatcacg atactgagtc ccagcgtccc  15060
cgttgcacat aacccacgcg ctgagccaat cgccggacgc gcacgggcac gcgtgggcgg  15120
ggggcgcgtt gatctaacgt tctttttga tgaatctgag catgacaaca tacataggtc  15180
gccgccgccg cgcgttgctt cgatacaggt tcgcgtttta gtttcttctc tacgaggtcc  15240
agtagcgcgg cctctagata ccggggggct tcttccttct cgtcctaatg ttcggggctt  15300
tcgatttcgc ccagtttttc tttttctttc tactactact acttgaactg ctgctccacc  15360
ttgacgacgt gcgatggcgc gggtccgctg cccatgtcac ctttccagct gcgcattttg  15420
cacaaaacgc tgggccgtgg tggcatcaga aatgcgggcc actcgcgagg tgggcgtgga  15480
tgttcgcgca catactactc cacatgccgc tgctcctgga cgaactcgtc cggttgctcg  15540
cggagcccct caaacggatg cctttcgccg tattcctgta cgaccgcaac ggcgacctgc  15600
tcccgttggg ttgtggatcg gatttcgggc attgtgacgt cgtccacgac gggcgcgaac  15660
gtggcaggct tcttttcgcg ccggatttcg cgctcagacc actgaaccgt gggtggcacg  15720
tcgactacca tgggttcgcg gtcgctgacc ttctacagaa cctttttac tggcaccttg  15780
gacccgacct cgggctccag gcgcacgccg gttagttcgt ccaccgcggc cctgacccgc  15840
acgtctggca cctgcaagtc tatgggtgat ggtcatcgtg gtcataacgg tggcggtgtc  15900
tcccgtacct ctgtgtttgc aggggccaac ggagtcgcca ccgcctacgg cgccacgtcc  15960
gccagcgacg ccggcgcagg ttctggagat gcctccacgt ttgcctgggc acctacaaag  16020
cgcaaagtcg gggggccgcg ggcgcggcaa gctccttcat gccgcggcgg tcgcgcgatg  16080
acgggcttat acgggatgta ggaaggtaac gcggatgggg gccgatagca ccgatgtgga  16140
tggcggggtc ttctgctcgt tgatgggctg cggcttggtg gtgaccttgg gcggcggcgg  16200
cagcggcagc ggtcgggcac gaccggggct aaaggcacgc gtcccaccga gcgcttcctc  16260
cgtcctggga ccacgacggt tgtcgcgcga tggtggggtc gtagcaaatt ttcggccaga  16320
aacaccaaga acgtctatac cgggagtgga cggcggaggc aaagggccac ggccctaagg  16380
ctccttctta cgtggcatcc tccccgtacc ggccggtgcc ggactgcccg ccgtacgcag  16440
cacgcgtggt ggccgccgcc gcgcgcagcg tggcagcgta cgcgccgcca taggacgggg  16500
aggaataagg tgactagcgg cgccgctaac cgcggcacgg gccttaacgt aggcaccgga  16560
acgtccgcgt ctctgtgact aatttttgtt caacgtacac ctttttagtt ttatttttca  16620
gacctgagag tgcgagcgaa ccaggacatt gataaaacat cttaccttct gtagttgaaa  16680
cgcagagacc ggggcgctgt gccgagcgcg ggcaagtacc ctttgaccgt tctatagccg  16740
tggtcgttat actcgccacc gcggaagtcg accccgagcg acacctcgcc gtaattttta  16800
aagccaaggt ggcaattctt gataccgtcg ttccggacct tgtcgtcgtg tccggtctac  16860
gactccctat tcaactttct cgttttaaag gttgttttcc accatctacc ggaccggaga  16920
ccgtaatcgc cccaccacct ggaccggttg gtccgtcacg ttttattcta attgtcattc  16980
gaactagggg cgggagggca tctcctcgga ggtggccggc acctctgtca cagaggtctc  17040
cccgcaccgc ttttcgcagg cgcggggctg tcccttcttt gagaccactg cgtttatctg  17100
ctcggaggga gcatgctcct ccgtgatttc gttccggacg ggtggtgggc agggtagcgc  17160
gggtaccgat ggcctcacga cccggtcgtg tgtgggcatt gcgacctgga cggagggggg  17220
cggctgtggg tcgtctttgg acacgacggt ccgggctggc ggcaacaaca ttgggcagga  17280
```

-continued

```
tcggcgcgca gggacgcggc gcggcggtcg ccaggcgcta gcaacgccgg gcatcggtca  17340
ccgttgaccg tttcgtgtga cttgtcgtag cacccagacc cccacgttag ggacttcgcg  17400
gctgctacga agactatcga ttgcacagca tacacacagt acatacgcag gtacagcggc  17460
ggtctcctcg acgactcggc ggcgcgcggg cgaaaggttc taccgatggg gaagctacta  17520
cggcgtcacc agaatgtacg tgtagagccc ggtcctgcgg agcctcatgg actcggggcc  17580
cgaccacgtc aaacgggcgc ggtggctctg catgaagtcg gacttattgt tcaaatcttt  17640
ggggtgccac cgcggatgcg tgctgcactg gtgtctggcc agggtcgcaa actgcgacgc  17700
caagtaggga cacctggcac tcctatgacg catgagcatg ttccgcgcca agtgggatcg  17760
acacccacta ttggcacacg acctgtaccg aaggtgcatg aaactgtagg cgccgcacga  17820
cctgtccccg ggatgaaaat tcgggatgag accgtgacgg atgttgcggg accgagggtt  17880
cccacggggt ttaggaacgc ttaccctact tcgacgatga cgagaacttt atttggatct  17940
tcttctcctg ctactgttgc ttctgcttca tctgctcgtt cgactcgtcg tttttgagt  18000
gcataaaccc gtccgcggaa taagaccata tttataatgt ttcctcccat aagtttatcc  18060
acagcttcca gtttgtggat ttatacggct attttgtaaa gttggacttg gagtttatcc  18120
tcttagagtc accatgcttt gtctttaatt agtacgtcga ccctctcagg attttttctg  18180
atggggttac tttggtacaa tgccaagtat acgttttggg tgtttacttt tacctcccgt  18240
tccgtaagaa catttcgttg ttttaccttt cgatctttca gttcaccttt acgttaaaaa  18300
gagttgatga ctccgtcggc gtccgttacc actattgaac tgaggatttc accataacat  18360
gtcacttcta catctatatc tttggggtct gtgagtataa agaatgtacg ggtgataatt  18420
ccttccattg agtgctcttg attacccggt tgttagatac gggttgtccg gattaatgta  18480
acgaaaatcc ctgttaaaat aaccagatta cataatgttg tcgtgcccat tatacccaca  18540
agaccgcccg gttcgtagcg tcaacttacg acaacatcta aacgttctgt ctttgtgtct  18600
cgaaagtatg gtcgaaaacg aactaaggta accactatct tggtccatga aaagatacac  18660
cttagtccga caactgtcga tactaggtct acaatcttaa taacttttag taccttgact  18720
tctacttgaa ggtttaatga cgaaaggtga ccctccacac taattatgtc tctgagaatg  18780
gttccatttt ggattttgtc cagtcctttt acctaccctt tttctacgat gtcttaaaag  18840
tctattttta ctttattctc aacctttatt aaaacggtac ctttagttag atttacggtt  18900
ggacacctct ttaaaggaca tgaggttgta tcgcgacata aacgggctgt tcgatttcat  18960
gtcaggaagg ttgcattttt aaagactatt gggtttgtgg atgctgatgt acttgttcgc  19020
tcaccaccga gggcccgatc acctgacgat gtaattggaa cctcgtgcga ccagggaact  19080
gatatacctg ttgcagttgg gtaaattggt ggtggcgtta cgaccggacg cgatggcgag  19140
ttacaacgac ccgttaccag cgatacacgg gaaggtgtag gtccacggag tcttcaagaa  19200
acggtaattt ttggaggaag aggacggccc gagtatgtgg atgctcacct tgaagtcctt  19260
cctacaattg taccaagacg tctcgaggga tcctttactg gattcccaac tgcctcggtc  19320
gtaattcaaa ctatcgtaaa cggaaatgcg gtggaagaag gggtaccggg tgttgtggcg  19380
gaggtgcgaa ctccggtacg aatctttgct gtggttgctg gtcaggaaat tgctgataga  19440
gaggcggcgg ttgtacgaga tgggatatgg gcggttgcga tggttgcacg ggtataggta  19500
ggggagggcg ttgacccgcc gaaaggcgcc gacccggaag tgcgcggaat tctgattcct  19560
ttggggtagt gacccgagcc cgatgctggg aataatgtgg atgagaccga gatatgggat  19620
```

-continued

```
ggatctacct tggaaaatgg agttggtgtg gaaattcttc caccggtaat ggaaactgag  19680
aagacagtcg accggaccgt tactggcgga cgaatggggg ttgctcaaac tttaattcgc  19740
gagtcaactg cccctcccaa tgttgcaacg ggtcacattg tactggtttc tgaccaagga  19800
ccatgtttac gatcgattga tattgtaacc gatggtcccg aagatatagg gtctctcgat  19860
gttcctggcg tacatgagga agaaatcttt gaaggtcggg tactcggcag tccaccacct  19920
actatgattt atgttcctga tggttgtcca cccgtaggat gtggttgtgt tgttgagacc  19980
taaacaaccg atggaacggg ggtggtacgc gcttcctgtc cggatgggac gattgaaggg  20040
gataggcgaa tatccgttct ggcgtcaact gtcgtaatgg gtctttttca aagaaacgct  20100
agcgtgggaa accgcgtagg gtaagaggtc attgaaatac aggtacccgc gtgagtgtct  20160
ggacccggtt ttggaagaga tgcggttgag gcgggtgcgc gatctgtact gaaaactcca  20220
cctagggtac ctgctcgggt gggaagaaat acaaaacaaa cttcagaaac tgcaccaggc  20280
acacgtggtc ggcgtggcgc cgcagtagct ttggcacatg gacgcgtgcg ggaagagccg  20340
gccgttgcgg tgttgtattt cttcgttcgt tgtagttgtt gtcgacggcg gtacccgagg  20400
tcactcgtcc ttgactttcg gtaacagttt ctagaaccaa cacccggtat aaaaaacccg  20460
tggatactgt tcgcgaaagg tccgaaacaa agaggtgtgt tcgagcggac gcggtatcag  20520
ttatgccggc cagcgctctg acccccgcat gtgacctacc ggaaacggac cttgggcgtg  20580
agtttttgta cgatggagaa actcgggaaa ccgaaaagac tggtcgctga gttcgtccaa  20640
atggtcaaac tcatgctcag tgaggacgcg gcatcgcggt aacgaagaag ggggctggcg  20700
acatattgcg accttttcag gtgggtttcg catgtccccg ggttgagccg gcggacacct  20760
gataagacga cgtacaaaga ggtgcggaaa cggttgaccg gggtttgagg gtacctagtg  20820
ttggggtggt acttggaata atggccccat gggttgaggt acgagttgtc aggggtccat  20880
gtcgggtggg acgcagcgtt ggtccttgtc gagatgtcga aggacctcgc ggtgagcggg  20940
atgaaggcgt cggtgtcacg cgtctaatcc tcgcggtgaa gaaaaacagt gaactttttg  21000
tacattttta ttacatgatc tctgtgaaag ttatttccgt ttacgaaaat aaacatgtga  21060
gagcccacta ataaatgggg gtgggaacgg cagacgcggc aaatttttag tttccccaag  21120
acggcgcgta gcgatacgcg gtgaccgtcc ctgtgcaacg ctatgaccac aaatcacgag  21180
gtgaatttga gtccgtgttg gtaggcgccg tcgagccact tcaaaagtga ggtgtccgac  21240
gcgtggtagt ggttgcgcaa atcgtccagc ccgcggctat agaacttcag cgtcaacccc  21300
ggaggcggga cgcgcgcgct caacgctatg tgtcccaacg tcgtgacctt gtgatagtcg  21360
cggcccacca cgtgcgaccg gtcgtgcgag aacagcctct agtctaggcg caggtccagg  21420
aggcgcaacg agtcccgctt gcctcagttg aaaccatcga cggaagggtt tttcccgcgc  21480
acgggtccga aactcaacgt gagcgtggca tcaccgtagt tttccactgg cacgggccag  21540
acccgcaatc ctatgtcgcg gacgtatttt cggaactaga cgaattttcg gtggactcgg  21600
aaacgcggaa gtctcttctt gtacggcgtt ctgaacggcc ttttgactaa ccggcctgtc  21660
cggcgcagca cgtgcgtcgt ggaacgcagc cacaacctct agacgtggtg taaagccggg  21720
gtggccaaga agtgctagaa ccggaacgat ctgacgagga agtcgcgcgc gacgggcaaa  21780
agcgagcagt gtaggtaaag ttagtgcacg aggaataaat agtattacga aggcacatct  21840
gtgaattcga gcggaagcta gagtcgcgtc gccacgtcgg tgttgcgcgt cgggcacccg  21900
agcactacga acatccagtg gagacgtttg ctgacgtcca tgcggacgtc cttagcgggg  21960
tagtagcagt gtttccagaa caacgaccac ttccagtcga cgttgggcgc cacgaggagc  22020
```

-continued aagtcggtcc agaacgtatg ccggcggtct cgaaggtgaa ccagtccgtc atcaaacttc 22080
aagcggaaat ctagcaatag gtgcaccatg aacaggtagt cgcgcgcgcg tcggaggtac 22140
gggaagaggg tgcgtctgtg ctagccgtgt gagtcgccca agtagtggca ttaaagtgaa 22200
aggcgaagcg acccgagaag gagaaggaga acgcaggcgt atggtgcgcg gtgacccagc 22260
agaagtaagt cggcggcgtg acacgcgaat ggaggaaacg gtacgaacta atcgtggcca 22320
cccaacgact ttgggtggta aacatcgcgg tgtagaagag aaagaaggag cgacaggtgc 22380
taatggagac cactaccgcc cgcgagcccg aaccctcttc ccgcgaagaa aaagaagaac 22440
ccgcgttacc ggtttaggcg gcggctccag ctaccggcgc ccgacccaca cgcgccgtgg 22500
tcgcgcagaa cactactcag aaggagcagg agcctgagct atgcggcgga gtaggcgaaa 22560
aaacccccgc gggcccctcc gccgccgctg cccctgcccc tgctgtgcag gaggtaccaa 22620
ccccctgcag cgcggcgtgg cgcaggcgcg agccccccacc aaagcgcgac gaggagaagg 22680
gctgaccggt aaaggaagag gatatccgtc tttttctagt acctcagtca gctcttcttc 22740
ctgtcggatt ggcgggggag actcaagcgg tggtggcgga ggtggctacg gcggttgcgc 22800
ggatggtgga aggggcagct ccgtgggggc gaactcctcc tccttcacta atagctcgtc 22860
ctgggtccaa aacattcgct tctgctgctc ctggcgagtc atggttgtct cctatttttc 22920
gttctggtcc tgttgcgtct ccgtttgctc cttgttcagc ccgccccccct gctttccgta 22980
ccgctgatgg atctacaccc tctgctgcac gacaacttcg tagacgtcgc ggtcacgcgg 23040
taatagacgc tgcgcaacgt tctcgcgtcg ctacacgggg agcggtatcg cctacagtcg 23100
gaacggatgc ttgcggtgga taagagtggc gcgcatgggg ggtttgcggt tcttttgccg 23160
tgtacgctcg ggttgggcgc ggagttgaag atggggcata aacggcacgg tctccacgaa 23220
cggtggatag tgtagaaaaa ggttttgacg ttctatgggg ataggacggc acggttggcg 23280
tcggctcgcc tgttcgtcga ccggaacgcc gtcccgcgac agtatggact atagcggagc 23340
gagttgcttc acggttttta gaaactccca gaacctgcgc tgctcttcgc gcgccgtttg 23400
cgagacgttg tccttttgtc gcttttactt tcagtgagac ctcacaacca ccttgagctc 23460
ccactgttgc gcgcggatcg gcatgatttt gcgtcgtagc tccagtgggt gaaacggatg 23520
ggccgtgaat tggatggggg gttccagtac tcgtgtcagt actcactcga ctagcacgcg 23580
gcacgcgtcg ggacctctc cctacgttta aacgttcttg tttgtctcct cccggatggg 23640
cgtcaaccgc tgctcgtcga tcgcgcgacc gaagtttgcg cgctcggacg gctgaacctc 23700
ctcgctgcgt ttgattacta ccggcgtcac gagcaatggc acctcgaact cacgtacgtc 23760
gccaagaaac gactgggcct ctacgtcgcg ttcgatctcc tttgtaacgt gatgtggaaa 23820
gctgtcccga tgcatgcggt ccggacgttc tagaggttgc acctcgagac gttggaccag 23880
aggatggaac cttaaaacgt gcttttggcg gaacccgttt tgcacgaagt aaggtgcgag 23940
ttcccgctcc gcgcggcgct gatgcaggcg ctgacgcaaa tgaataaaga tacgatgtgg 24000
accgtctgcc ggtacccgca aaccgtcgtc acgaacctcc tcacgttgga gttcctcgac 24060
gtctttgacg atttcgtttt gaacttcctg gatacctgcc ggaagttgct cgcgaggcac 24120
cggcgcgtgg accgcctgta gtaaaagggg cttgcggacg aattttggga cgttgtccca 24180
gacggtctga agtggtcagt ttcgtacaac gtcttgaaat ccttgaaata ggatctcgcg 24240
agtccttaga acgggcggtg gacgacacgt gaaggatcgc tgaaacacgg gtaattcatg 24300
gcgcttacgg gaggcggcga aaccccggtg acgatggaag acgtcgatcg gttgatggaa 24360

-continued

```
cggatggtga gactgtatta ccttctgcac tcgccactgc cagatgacct cacagtgaca  24420
gcgacgttgg atacgtgggg cgtggcgagg gaccaaacgt taagcgtcga cgaattgctt  24480
tcagtttaat agccatggaa actcgacgtc ccagggagcg gactgctttt caggcgccga  24540
ggccccaact ttgagtgagg ccccgacacc tgcagccgaa tggaagcgtt taaacatgga  24600
ctcctgatgg tgcgggtgct ctaatccaag atgcttctgg ttagggcggg cggattacgc  24660
ctcgaatggc ggacgcagta atgggtcccg gtgtaagaac cggttaacgt tcggtagttg  24720
tttcgggcgg ttctcaaaga cgatgctttc cctgcccccc aaatgaacct gggggtcagg  24780
ccgctcctcg agttgggtta ggggggcggc ggcgtcggga tagtcgtcgt cggcgcccgg  24840
gaacgaaggg tcctaccgtg ggtttttctt cgacgtcgac ggcggcggtg ggtgcctgct  24900
cctccttatg accctgtcag tccgtctcct ccaaaacctg ctcctcctcc tcctgtacta  24960
ccttctgacc ctctcggatc tgctccttcg aaggctccag cttctccaca gtctgctttg  25020
tggcagtggg agccagcgta aggggagcgg ccgcggggtc tttagccgtt ggccaaggtc  25080
gtaccgatgt tggaggcgag gagtccgcgg cggccgtgac gggcaagcgg ctgggttggc  25140
atctaccctg tggtgacctt ggtcccggcc attcaggttc gtcggcggcg gcaatcgggt  25200
tctcgttgtt gtcgcggttc cgatggcgag taccgcgccc gtgttcttgc ggtatcaacg  25260
aacgaacgtt ctgacacccc cgttgtagag gaagcgggcg gcgaaagaag agatggtagt  25320
gccgcaccgg aagggggcat tgtaggacgt aatgatggca gtagagatgt cgggtatgac  25380
gtggccgccg tcgccgtcgt tgtcgtcgcc ggtgtgtctt cgtttccgct ggcctatcgt  25440
tctgagactg tttcgggttc tttaggtgtc gccgccgtcg tcgtcctcct cctcgcgacg  25500
cagaccgcgg gttgcttggg catagctggg cgctcgaatc tttgtcctaa aaagggtgag  25560
acatacgata taaagttgtc tcgtccccgg ttcttgttct cgacttttat tttttgtcca  25620
gagacgctag ggagtgggcg tcgacggaca tagtgttttc gcttctagtc gaagccgcgt  25680
gcgaccttct gcgcctccga gagaagtcat ttatgacgcg cgactgagaa ttcctgatca  25740
aagcgcggga aagagtttaa attcgcgctt ttgatgcagt agaggtcgcc ggtgtgggcc  25800
gcggtcgtgg acaacagtcg cggtaatact cgttccttta agggtgcggg atgtacacct  25860
caatggtcgg tgtttaccct gaacgccgac ctcgacgggt tctgatgagt tgggcttatt  25920
tgatgtactc gcgccctggg gtgtactata gggcccagtt gccttatgcg cgggtggctt  25980
tggcttaaga ggaccttgtc cgccgataat ggtggtgtgg agcattattg gaattagggg  26040
catcaaccgg gcgacgggac cacatggtcc tttcagggcg agggtggtga caccatgaag  26100
ggtctctgcg ggtccggctt caagtctact gattgagtcc ccgcgtcgaa cgcccgccga  26160
aagcagtgtc ccacgccagc gggcccgtcc catattgagt ggactgttag tctcccgctc  26220
cataagtcga gttgctgctc agccactcga ggagcgaacc agaggcaggc ctgccctgta  26280
aagtctagcc gccgcggccg gcgagaagta agtgcggagc agtccgttag gattgagacg  26340
tctggagcag gagactcggc gcgagacctc cgtaaccttg agacgttaaa taactcctca  26400
aacacggtag ccagatgaaa ttggggaaga gccctggagg gccggtgata ggcctagtta  26460
aataaggatt gaaactgcgc catttcctga gccgcctgcc gatgctgact tacaattcac  26520
ctctccgtct cgttgacgcg gactttgtgg accaggtgac agcggcggtg ttcacgaaac  26580
gggcgctgag gccactcaaa acgatgaaac ttaacgggct cctagtatag ctcccgggcc  26640
gcgtgccgca ggccgaatgg cgggtccctc tcgaacgggc atcggactaa gccctcaaat  26700
gggtcgcggg ggacgatcaa ctcgccctgt cccctgggac acaagagtga cactaaacgt  26760
```

-continued

```
tgacaggatt gggacctaat gtagttctag aaacaacggt agagacacga ctcatattat  26820
ttatgtcttt aattttatat gaccccgagg atagcggtag gacatttgcg gtggcagaag  26880
tgggcgggtt cgtttggttc cgcttggaat ggaccatgaa aattgtagag agggagacac  26940
taaatgttgt caaagttggg tctgcctcac tcagatgctc tcttggagag gctcgagtcg  27000
atgaggtagt ctttttgtg gtgggaggaa tggacggccc ttgcatgctc acgcagtggc  27060
cggcgacgtg gtgtggatgg cggactggca tttggtctga aaaaggcctg tctggagtta  27120
ttgagacaaa tggtcttgtc ctccactcga atcttttggg aatcccataa tccggtttcc  27180
gcgtcgatga caccccaaat acttgttaag ttcgttgaga tgcccgataa gattaagtcc  27240
aaagagatct tagccccaac cccaataaga gacagaacac taagagaaat aagaatatga  27300
ttgcgaagag acggattccg agcggcggac gacacacgtg taaacgtaaa taacagtcga  27360
aaaatttgcg accccagcgg tgggttctac taatccatgt attaggatcc aaatgagtgg  27420
gaacgcagtc gggtgccatg gtgggttttc cacctaaaat tcctcggtcg gacattacaa  27480
tgtaagcgtc gacttcgatt actcacgtgg tgagaatatt ttacgtggtg tcttgtactt  27540
ttcgacgaat aagcggtgtt tttgttttaa ccgttcatac gacaaatacg ataaaccgtc  27600
ggtccactgt gatgtctcat attacaatgt caaaaggtcc cattttcagt attttgaaaa  27660
tacatatgaa aaggtaaaat actttacacg ctgtaatggt acatgtactc gtttgtcata  27720
ttcaacaccg gggtgtttt aacacacctt ttgtgaccgt gaaagacgac gtgacgatac  27780
gattaatgtc acgagcgaaa ccagacatgg gatgagatat aatttatgtt ttcgtctgcg  27840
tcgaaataac tccttttctt ttacggaatt aaatgattca atgtttcgat tacagtggtg  27900
attgacgaaa tgagcgacga acgttttgtt taagtttttc aatcgtaata ttaatcttat  27960
cctaaatttg gggggccagt aaaggacgag ttatggtaag gggacttgtt aactgagata  28020
caccctatac gaggtcgcga tgttggaact tcagtccgaa ggacctacag tcgtagactg  28080
aaaccggtcg tggacagggc gcctaaacaa ggtcaggttg atgtcgctgg gtgggattgt  28140
ctctactggt tgtgttggtt gcgccggcgg cgatggcctg aatgtagatg gtgtttatgt  28200
ggggttcaaa gacggaaaca gttattgacc ctattgaacc cgtacaccac caagaggtat  28260
cgcgaataca aacatacgga ataataatac accgagtaga cgacggattt cgcgtttgcg  28320
cgggctggtg ggtagatatc agggtagtaa cacgatgtgg gtttgttact accttaggta  28380
tctaacctgc ctgactttgt gtacaagaaa agagaatgtc atactaattt actctgtact  28440
aaggagctca aaaatataat gactgggaac aacgcgaaaa aacacgcacg aggtgtaacc  28500
gacgccaaag agtgtagctt catctgacgt aaggtcggaa gtgtcagata aacgaaatgc  28560
ctaaacagtg ggagtgcgag tagacgtcgg agtagtgaca ccagtagcgg aaataggtca  28620
cgtaactgac ccagacacac gcgaaacgta tagagtctgt ggtaggggtc atgtccctgt  28680
cctgatatcg actcgaagaa tcttaagaaa ttaatacttt aaatgacact gaaaagacga  28740
ctaataaacg tgggatagac gcaaaacaag gggctggagg ttcggagttt ctgtatatag  28800
tacgtctaag tgagcatata ccttataagg ttcaacgatg ttactttttt cgctagaaag  28860
gcttcggacc aatatacgtt agtagagaca ataccacaag acgtcatggt agaatcggga  28920
tcgatatata gggatggaac tgtaaccgac cttgcgttat ctacggtact tggtgggttg  28980
aaaggggcgc gggcgatacg aaggtgacgt tgttcaacaa cggccgccga aacagggtcg  29040
gttagtcgga gcgggtggaa gagggtgggg gtgactttag tcgatgaaat tagattgtcc  29100
```

-continued

```
tcctctactg actgtgggat ctagatcttt acctgcctta ataatgtctc gtcgcggacg  29160
atctttctgc gtcccgtcgc cggctcgttg tcgcgtactt agttctcgag gttctgtacc  29220
aattgaacgt ggtcacgttt tccccataga aaacagagca tttcgtccgg tttcagtgga  29280
tgctgtcatt atggtggcct gtggcggaat cgatgttcaa cggttggttc gcagtcttta  29340
accaccagta ccaccctctt ttcgggtaat ggtattgagt cgtgagccat ctttggcttc  29400
cgacgtaagt gagtggaaca gttcctggac tcctagagac gtgggaataa ttctgggaca  29460
cgccagagtt tctagaataa gggaaattga ttattttttt ttattatttc gtagtgaatg  29520
aattttagtc aatcgtttaa agacaggtca aataagtcgt cgtggaggaa cgggaggagg  29580
gtcgagacca taacgtcgaa ggaggaccga cgtttgaaag aggtgttaga tttaccttac  29640
agtcaaagga ggacaaggac aggtaggcgt gggtgataga agtacaacaa cgtctacttc  29700
gcgcgttctg gcagacttct atggaagttg gggcacatag gtatactgtg cctttggcca  29760
ggaggttgac acggaaaaga atgaggaggg aaacataggg ggttacccaa agttctctca  29820
gggggacccc atgagagaaa cgcggatagg cttggagatc aatggaggtt accgtacgaa  29880
cgcgagtttt acccgttgcc ggagagagac ctgctccggc cgttggaatg gagggtttta  29940
cattggtgac actcgggtgg agagtttttt tggttcagtt tgtatttgga cctttataga  30000
cgtggggagt gtcaatggag tcttcgggat tgacaccgac ggcggcgtgg agattaccag  30060
cgcccgttgt gtgagtggta cgttagtgtc cggggcgatt ggcacgtgct gaggtttgaa  30120
tcgtaacggt gggttcctgg ggagtgtcac agtcttcctt tcgatcggga cgtttgtagt  30180
ccgggggagt ggtggtggct atcgtcatgg gaatgatagt gacggagtgg gggagattga  30240
tgacggtgac catcgaaccc gtaactgaac tttctcgggt aaatatgtgt tttacctttt  30300
gatcctgatt tcatgccccg aggaaacgta cattgtctgc tggatttgtg aaactggcat  30360
cgttgaccag gtccacactg ataattatta tgaaggaacg tttgatttca atgacctcgg  30420
aacccaaaac taagtgttcc gttatacgtt gaattacatc gtcctcctga ttcctaacta  30480
agagttttgt ctgcggaata tgaactacaa tcaataggca aactacgagt tttggttgat  30540
ttagattctg atcctgtccc gggagaaaaa tatttgagtc gggtgttgaa cctataattg  30600
atgttgtttc cggaaatgaa caaatgtcga agtttgttaa ggtttttcga actccaattg  30660
gattcgtgac ggttccccaa ctacaaactg cgatgtcggt atcggtaatt acgtcctcta  30720
cccgaactta aaccaagtgg attacgtggt ttgtgtttag gggagttttg tttttaaccg  30780
gtaccggatc ttaaactaag tttgttccga taccaaggat ttgatccttg accggaatca  30840
aaactgtcgt gtccacggta atgtcatcct ttgtttttat tactattcga ttgaaacacc  30900
tggtgtggtc gaggtagagg attgacatct gatttacgtc tctttctacg atttgagtga  30960
aaccagaatt gttttacacc gtcagtttat gaacgatgtc aaagtcaaaa ccgacaattt  31020
ccgtcaaacc gaggttatag accttgtcaa gtttcacgag tagaataata ttctaaactg  31080
cttttacctc acgatgattt gttaaggaag gacctgggtc ttataacctt gaaatcttta  31140
cctctagaat gacttccgtg tcggatatgt ttgcgacaac ctaaatacgg attggatagt  31200
cgaataggtt ttagagtgcc attttgacgg ttttcattgt aacagtcagt tcaaatgaat  31260
ttgcctctgt tttgatttgg acattgtgat tggtaatgtg atttgccatg tgtcctttgt  31320
cctctgtgtt gaggttcacg tatgagatac agtaaaagta ccctgaccag accggtgttg  31380
atgtaattac tttataaacg gtgtaggaga atgtgaaaaa gtatgtaacg ggttcttatt  31440
tcttagcaaa cacaatacaa agttgcacaa ataaaaagtt aacgtctttt aaagttcagt  31500
```

-continued aaaaagtaag tcatcatatc ggggtggtgg tgtatcgaat atgtctagtg gcatggaatt 31560
agtttgagtg tcttgggatc ataagttgga cggtggaggg agggttgtgt gtctcatgtg 31620
tcaggaaaga ggggccgacc ggaatttttc gtagtatagt acccattgtc tgtataagaa 31680
tccacaatat aaggtgtgcc aaaggacagc tcggtttgcg agtagtcact ataattattt 31740
gaggggcccg tcgagtgaat tcaagtacag cgacaggtcg acgactcggt gtccgacgac 31800
aggttgaacg ccaacgaatt gcccgccgct tcctcttcag gtgcggatgt acccccatct 31860
cagtattagc acgtagtcct atcccgccac cacgacgtcg tcgcgcgctt atttgacgac 31920
ggcggcggcg aggcaggacg tccttatgtt gtaccgtcac cagaggagtc gctactaagc 31980
gtggcgggcg tcgtattccg cggaacagga ggcccgtgtc gtcgcgtggg actagagtga 32040
atttagtcgt gtcattgacg tcgtgtcgtg gtgttataac aagttttagg gtgtcacgtt 32100
ccgcgacata ggtttcgagt accgcccctg gtgtcttggg tgcaccggta gtatggtgtt 32160
cgcgtccatc taattcaccg ctggggagta tttgtgcgac ctgtatttgt aatggagaaa 32220
accgtacaac attaagtggt ggagggccat ggtatatttg gagactaatt tgtaccgcgg 32280
taggtggtgg taggatttgg tcgaccggtt ttggacgggc ggccgatatg tgacgtccct 32340
tggccctgac cttgttactg tcacctctcg ggtcctgagc attggtacct agtagtacga 32400
gcagtactat agttacaacc gtgttgtgtc cgtgtgcacg tatgtgaagg agtcctaatg 32460
ttcgaggagg gcgcaatctt ggtatagggt cccttgttgg gtaaggactt agtcgcattt 32520
agggtgtgac gtcccttctg gagcgtgcat tgagtgcaac acgtaacagt ttcacaatgt 32580
aagcccgtcg tcgcctacta ggaggtcata ccatcgcgcc caaagacaga gttttcctcc 32640
atctgctagg gatgacatgc ctcacgcggc tctgttggct ctagcacaac cagcatcaca 32700
gtacggttta ccttgcggcc tgcatcagta taaaggactt cgttttggtc cacgcccgca 32760
ctgtttgtct agacgcagag gccagagcgg cgaatctagc gagacacatc atcaacatca 32820
tataggtgag agagtttcgt aggtccgcgg gggaccgaag cccaagatac atttgaggaa 32880
gtacgcggcg acgggactat tgtaggtggt ggcgtcttat tcggtgtggg tcggttggat 32940
gtgtaagcaa gacgctcagt gtgtgccctc ctcgcccttc tcgaccttct tggtacaaaa 33000
aaaaaaataa ggttttctaa taggttttgg agttttactt ctagataatt cacttgcgcg 33060
aggggaggcc accgcaccag tttgagatgt cggtttcttg tctattaccg taaacattct 33120
acaacgtgtt accgaaggtt ttccgtttgc cgggagtgca ggttcacctg catttccgat 33180
ttgggaagtc ccacttagag gagatatttg taaggtcgtg gaagttggta cgggtttatt 33240
aagagtagag cggtggaaga gttatataga gattcgttta gggcttataa ttcaggccgg 33300
taacattttt agacgaggtc tcgcgggagg tggaagtcgg agttcgtcgc ttagtactaa 33360
cgtttttaag tccaaggagt gtctggacat attctaagtt ttcgccttgt aattgttttt 33420
atggcgctag ggcatccagg gaagcgtccc ggtcgacttg tattagcacg tccagacgtg 33480
cctggtcgcg ccggtgaagg ggcggtcctt ggtactgttt tcttgggtgt gactaatact 33540
gtgcgtatga gcctcgatac gattggtcgc atcggggcta cattcgaaca acgtacccgc 33600
cgctatattt tacgttccac gacgagtttt ttagtccgtt tcggagcgcg ttttttcttt 33660
cgtgtagcat cagtacgagt acgtctattt ccgtccattc gaggccttgg tggtgtcttt 33720
ttctgtggta aaaagagagt ttgtacagac gcccaaagac gtatttgtgt tttattttat 33780
tgttttttg taaatttgta atcttcggac agaatgttgt ccttttgtt gggaatattc 33840

-continued

```
gtattctgcc tgatgccggt acggccgcac tggcattttt ttgaccagtg gcactaattt  33900
ttcgtggtgg ctgtcgagga gccagtacag gcctcagtat tacattctga gccatttgtg  33960
tagtccaact aagtgtagcc agtcacgatt tttcgctggc tttatcgggc cccccttatgt  34020
atgggcgtcc gcatctctgt tgtaatgtcg ggggtatcct ccatattgtt ttaattatcc  34080
tctcttttttg tgtatttgtg gactttttgg gaggacggat ccgttttatc gtgggagggc  34140
gaggtcttgt tgtatgtcgc gaaggtgtcg ccgtcggtat tgtcagtcgg aatggtcatt  34200
ttttcttttg gataattttt ttgtggtgag ctgtgccgtg gtcgagttag tcagtgtcac  34260
attttttccc ggttcacgtc tcgctcatat atatcctgat tttttactgc attgccaatt  34320
tcaggtgttt tttgtgggtc ttttggcgtg cgcttggatg cgggtctttg ctttcggttt  34380
tttgggtgtt gaaggagttt agcagtgaag gcaaaagggt gcaatgcagt gaagggtaaa  34440
attcttttga tgttaagggt tgtgtatgtt caatgaggcg ggattttgga tgcagtgggc  34500
ggggcaaggg tgcggggcgc ggtgcagtgt ttgaggtggg ggagtaatag tataaccgaa  34560
gttaggtttt attccatata ataactacta caattaattc ttaagcctag acgctgcgct  34620
ccgacctacc ggaaggggta atactaagaa gagcgaaggc cgccgtagcc ctacgggcgc  34680
aacgtccggt acgacaggtc cgtccatcta ctgctggtag tccctgtcga agttccggtc  34740
gttttccggt ccttggcatt tttccggcgc aacgaccgca aaaaggtatc cgaggcgggg  34800
ggactgctcg tagtgttttt agctgcgagt tcagtctcca ccgctttggg ctgtcctgat  34860
atttctatgg tccgcaaagg gggaccttcg agggagcacg cgagaggaca aggctgggac  34920
ggcgaatggc ctatggacag gcggaaagag ggaagccctt cgcaccgcga aagagtatcg  34980
agtgcgacat ccatagagtc aagccacatc cagcaagcga ggttcgaccc gacacacgtg  35040
cttggggggc aagtcgggct ggcgacgcgg aataggccat tgatagcaga actcaggttg  35100
ggccattctg tgctgaatag cggtgaccgt cgtcggtgac cattgtccta atcgtctcgc  35160
tccatacatc cgccacgatg tctcaagaac ttcaccaccg gattgatgcc gatgtgatct  35220
tcctgtcata aaccatagac gcgagacgac ttcggtcaat ggaagccttt ttctcaacca  35280
tcgagaacta ggccgtttgt ttggtggcga ccatcgccac caaaaaaaca aacgttcgtc  35340
gtctaatgcg cgtctttttt tcctagagtt cttctaggaa actagaaaag atgccccaga  35400
ctgcgagtca ccttgctttt gagtgcaatt ccctaaaacc agtactctaa tagtttttcc  35460
tagaagtgga tctaggaaaa tttagttaga tttcatatat actcatttga accagactgt  35520
caatggttac gaattagtca ctccgtggat agagtcgcta gacagataaa gcaagtaggt  35580
atcaacggac tgaggggcag cacatctatt gatgctatgc cctcccgaat ggtagaccgg  35640
ggtcacgacg ttactatggc gctctgggtg cgagtggccg aggtctaaat agtcgttatt  35700
tggtcggtcg gccttcccgg ctcgcgtctt caccaggacg ttgaaatagg cggaggtagg  35760
tcagataatt aacaacggcc cttcgatctc attcatcaag cggtcaatta tcaaacgcgt  35820
tgcaacaacg gtaacgatgt ccgtagcacc acagtgcgag cagcaaacca taccgaagta  35880
agtcgaggcc aagggttgct gttccgctca atgtactagg gggtacaaca cgtttttttcg  35940
ccaatcgagg gaagccagga ggctagcaac agtcttcatt caaccggcgt cacaatagtg  36000
agtaccaata ccgtcgtgac gtattaagag aatgacagta cggtaggcat tctacgaaaa  36060
gacactgacc actcatgagt tggttcagta agactcttat cacatacgcc gctggctcaa  36120
cgagaacggg ccgcagttgt gccctattat ggcgcggtgt atcgtcttga aattttcacg  36180
agtagtaacc ttttgcaaga agccccgctt ttgagagttc ctagaatggc gacaactcta  36240
```

-continued

```
ggtcaagcta cattgggtga gcacgtgggt tgactagaag tcgtagaaaa tgaaagtggt  36300

cgcaaagacc cactcgtttt tgtccttccg ttttacggcg ttttttccct tattcccgct  36360

gtgcctttac aacttatgag tatgagaagg aaaaagttat aataacttcg taaatagtcc  36420

caataacaga gtactcgcct atgtataaac ttacataaat ctttttattt gtttatcccc  36480

aaggcgcgtg taaaggggct tttcacggtg gactgcagat tctttggtaa taatagtact  36540

gtaattggat atttttatcc gcatagtgct ccgggaaagc agaagttctt aacctaggct  36600

taagaattaa agaattaatt                                              36620
```

<210> SEQ ID NO 32
<211> LENGTH: 1479
<212> TYPE: DNA
<213> ORGANISM: Artificial Sequence
<220> FEATURE:
<223> OTHER INFORMATION: Codon optimized DNA encoding a tPA-gag fusion open reading frame

<400> SEQUENCE: 32

```
atggatgcaa tgaagagagg gctctgctgt gtgctgctgc tgtgtggagc agtcttcgtt     60

tcgcccagcg agatctccat tgtgtgggcc tccagggagc tggagaggtt tgctgtgaac    120

cctggcctgc tggagacctc tgaggggtgc aggcagatcc tgggccagct ccagccctcc    180

ctgcaaacag gctctgagga gctgaggtcc ctgtacaaca cagtggctac cctgtactgt    240

gtgcaccaga agattgatgt gaaggacacc aaggaggccc tggagaagat tgaggaggag    300

cagaacaagt ccaagaagaa ggcccagcag gctgctgctg gcacaggcaa ctccagccag    360

gtgtcccaga actaccccat tgtgcagaac ctccagggcc agatggtgca ccaggccatc    420

tccccccgga ccctgaatgc ctgggtgaag gtggtggagg agaaggcctt ctcccctgag    480

gtgatcccca tgttctctgc cctgtctgag ggtgccaccc cccaggacct gaacaccatg    540

ctgaacacag tgggggggcca tcaggctgcc atgcagatgc tgaaggagac catcaatgag    600

gaggctgctg agtgggacag gctgcatcct gtgcacgctg gccccattgc ccccggccag    660

atgagggagc ccaggggctc tgacattgct ggcaccacct ccaccctcca ggagcagatt    720

ggctggatga ccaacaaccc ccccatccct gtgggggaaa tctacaagag gtggatcatc    780

ctgggcctga acaagattgt gaggatgtac tcccccacct ccatcctgga catcaggcag    840

ggccccaagg agcccttcag ggactatgtg gacaggttct acaagaccct gagggctgag    900

caggcctccc aggaggtgaa gaactggatg acagagaccc tgctggtgca gaatgccaac    960

cctgactgca agaccatcct gaaggccctg ggccctgctg ccaccctgga ggagatgatg   1020

acagcctgcc agggggtggg gggccctggt cacaaggcca gggtgctggc tgaggccatg   1080

tcccaggtga ccaactccgc caccatcatg atgcagaggg gcaacttcag gaaccagagg   1140

aagacagtga agtgcttcaa ctgtggcaag gtgggccaca ttgccaagaa ctgtagggcc   1200

cccaggaaga agggctgctg gaagtgtggc aaggagggcc accagatgaa ggactgcaat   1260

gagaggcagg ccaacttcct gggcaaaatc tggccctccc acaagggcag gcctggcaac   1320

ttcctccagt ccaggcctga gcccacagcc cctcccgagg agtccttcag gtttggggag   1380

gagaagacca cccccagcca gaagcaggag cccattgaca aggagctgta ccccctggcc   1440

tccctgaggt ccctgtttgg caacgacccc tcctcccag                          1479
```

<210> SEQ ID NO 33
<211> LENGTH: 493

-continued

<212> TYPE: PRT
<213> ORGANISM: Artificial Sequence
<220> FEATURE:
<223> OTHER INFORMATION: tPA-gag fusion open reading frame

<400> SEQUENCE: 33

```
Met Asp Ala Met Lys Arg Gly Leu Cys Cys Val Leu Leu Leu Cys Gly
 1               5                  10                  15

Ala Val Phe Val Ser Pro Ser Glu Ile Ser Ile Val Trp Ala Ser Arg
            20                  25                  30

Glu Leu Glu Arg Phe Ala Val Asn Pro Gly Leu Leu Glu Thr Ser Glu
        35                  40                  45

Gly Cys Arg Gln Ile Leu Gly Gln Leu Gln Pro Ser Leu Gln Thr Gly
    50                  55                  60

Ser Glu Glu Leu Arg Ser Leu Tyr Asn Thr Val Ala Thr Leu Tyr Cys
65                  70                  75                  80

Val His Gln Lys Ile Asp Val Lys Asp Thr Lys Glu Ala Leu Glu Lys
                85                  90                  95

Ile Glu Glu Glu Gln Asn Lys Ser Lys Lys Lys Ala Gln Gln Ala Ala
            100                 105                 110

Ala Gly Thr Gly Asn Ser Ser Gln Val Ser Gln Asn Tyr Pro Ile Val
        115                 120                 125

Gln Asn Leu Gln Gly Gln Met Val His Gln Ala Ile Ser Pro Arg Thr
    130                 135                 140

Leu Asn Ala Trp Val Lys Val Val Glu Glu Lys Ala Phe Ser Pro Glu
145                 150                 155                 160

Val Ile Pro Met Phe Ser Ala Leu Ser Glu Gly Ala Thr Pro Gln Asp
                165                 170                 175

Leu Asn Thr Met Leu Asn Thr Val Gly Gly His Gln Ala Ala Met Gln
            180                 185                 190

Met Leu Lys Glu Thr Ile Asn Glu Glu Ala Ala Glu Trp Asp Arg Leu
        195                 200                 205

His Pro Val His Ala Gly Pro Ile Ala Pro Gly Gln Met Arg Glu Pro
    210                 215                 220

Arg Gly Ser Asp Ile Ala Gly Thr Thr Ser Thr Leu Gln Glu Gln Ile
225                 230                 235                 240

Gly Trp Met Thr Asn Asn Pro Pro Ile Pro Val Gly Glu Ile Tyr Lys
                245                 250                 255

Arg Trp Ile Ile Leu Gly Leu Asn Lys Ile Val Arg Met Tyr Ser Pro
            260                 265                 270

Thr Ser Ile Leu Asp Ile Arg Gln Gly Pro Lys Glu Pro Phe Arg Asp
        275                 280                 285

Tyr Val Asp Arg Phe Tyr Lys Thr Leu Arg Ala Glu Gln Ala Ser Gln
    290                 295                 300

Glu Val Lys Asn Trp Met Thr Glu Thr Leu Leu Val Gln Asn Ala Asn
305                 310                 315                 320

Pro Asp Cys Lys Thr Ile Leu Lys Ala Leu Gly Pro Ala Ala Thr Leu
                325                 330                 335

Glu Glu Met Met Thr Ala Cys Gln Gly Val Gly Gly Pro Gly His Lys
            340                 345                 350

Ala Arg Val Leu Ala Glu Ala Met Ser Gln Val Thr Asn Ser Ala Thr
        355                 360                 365

Ile Met Met Gln Arg Gly Asn Phe Arg Asn Gln Arg Lys Thr Val Lys
    370                 375                 380
```

-continued

```
Cys Phe Asn Cys Gly Lys Val Gly His Ile Ala Lys Asn Cys Arg Ala
385                 390                 395                 400

Pro Arg Lys Lys Gly Cys Trp Lys Cys Gly Lys Glu Gly His Gln Met
                405                 410                 415

Lys Asp Cys Asn Glu Arg Gln Ala Asn Phe Leu Gly Lys Ile Trp Pro
            420                 425                 430

Ser His Lys Gly Arg Pro Gly Asn Phe Leu Gln Ser Arg Pro Glu Pro
        435                 440                 445

Thr Ala Pro Pro Glu Glu Ser Phe Arg Phe Gly Glu Glu Lys Thr Thr
    450                 455                 460

Pro Ser Gln Lys Gln Glu Pro Ile Asp Lys Glu Leu Tyr Pro Leu Ala
465                 470                 475                 480

Ser Leu Arg Ser Leu Phe Gly Asn Asp Pro Ser Ser Gln
                485                 490


<210> SEQ ID NO 34
<211> LENGTH: 4053
<212> TYPE: DNA
<213> ORGANISM: Artificial Sequence
<220> FEATURE:
<223> OTHER INFORMATION: Codon optimized DNA encoding a gag-IA pol
      fusion

<400> SEQUENCE: 34

atgggtgcta gggcttctgt gctgtctggt ggtgagctgg acaagtggga gaagatcagg     60

ctgaggcctg gtggcaagaa gaagtacaag ctaaagcaca ttgtgtgggc ctccagggag    120

ctggagaggt ttgctgtgaa ccctggcctg ctggagacct ctgaggggtg caggcagatc    180

ctgggccagc tccagccctc cctgcaaaca ggctctgagg agctgaggtc cctgtacaac    240

acagtggcta ccctgtactg tgtgcaccag aagattgatg tgaaggacac caaggaggcc    300

ctggagaaga ttgaggagga gcagaacaag tccaagaaga aggcccagca ggctgctgct    360

ggcacaggca actccagcca ggtgtcccag aactacccca ttgtgcagaa cctccagggc    420

cagatggtgc accaggccat ctcccccggg accctgaatg cctgggtgaa ggtggtggag    480

gagaaggcct tctcccctga ggtgatcccc atgttctctg ccctgtctga gggtgccacc    540

ccccaggacc tgaacaccat gctgaacaca gtgggggggc atcaggctgc catgcagatg    600

ctgaaggaga ccatcaatga ggaggctgct gagtgggaca ggctgcatcc tgtgcacgct    660

ggccccattg cccccggcca gatgagggag cccaggggct ctgacattgc tggcaccacc    720

tccaccctcc aggagcagat tggctggatg accaacaacc cccccatccc tgtgggggaa    780

atctacaaga ggtggatcat cctgggcctg aacaagattg tgaggatgta ctcccccacc    840

tccatcctgg acatcaggca gggccccaag gagcccttca gggactatgt ggacaggttc    900

tacaagaccc tgagggctga gcaggcctcc caggaggtga agaactggat gacagagacc    960

ctgctggtgc agaatgccaa ccctgactgc aagaccatcc tgaaggccct gggccctgct   1020

gccaccctgg aggagatgat gacagcctgc caggggggtgg ggggccctgg tcacaaggcc   1080

agggtgctgg ctgaggccat gtcccaggtg accaactccg ccaccatcat gatgcagagg   1140

ggcaacttca ggaaccagag gaagacagtg aagtgcttca actgtggcaa ggtgggccac   1200

attgccaaga actgtagggc ccccaggaag aagggctgct ggaagtgtgg caaggagggc   1260

caccagatga aggactgcaa tgagaggcag gccaacttcc tgggcaaaat ctggccctcc   1320

cacaagggca ggcctggcaa cttcctccag tccaggcctg agcccacagc cctcccgag   1380

gagtccttca ggtttgggga ggagaagacc acccccagcc agaagcagga gcccattgac   1440
```

-continued

```
aaggagctgt acccccctggc ctccctgagg tccctgtttg gcaacgaccc ctcctcccag   1500
atggctccca tctcccccat tgagactgtg cctgtgaagc tgaagcctgg catggatggc   1560
cccaaggtga agcagtggcc cctgactgag gagaagatca aggccctggt ggaaatctgc   1620
actgagatgg agaaggaggg caaaatctcc aagattggcc ccgagaaccc ctacaacacc   1680
cctgtgtttg ccatcaagaa gaaggactcc accaagtgga ggaagctggt ggacttcagg   1740
gagctgaaca agaggaccca ggacttctgg gaggtgcagc tgggcatccc ccaccccgct   1800
ggcctgaaga agaagaagtc tgtgactgtg ctggctgtgg gggatgccta cttctctgtg   1860
cccctggatg aggacttcag gaagtacact gccttcacca tcccctccat caacaatgag   1920
acccctggca tcaggtacca gtacaatgtg ctgccccagg gctggaaggg ctcccctgcc   1980
atcttccagt cctccatgac caagatcctg gagcccttca ggaagcagaa ccctgacatt   2040
gtgatctacc agtacatggc tgccctgtat gtgggctctg acctggagat tgggcagcac   2100
aggaccaaga ttgaggagct gaggcagcac ctgctgaggt ggggcctgac cacccctgac   2160
aagaagcacc agaaggagcc cccttcctg tggatgggct atgagctgca ccccgacaag   2220
tggactgtgc agcccattgt gctgcctgag aaggactcct ggactgtgaa tgacatccag   2280
aagctggtgg gcaagctgaa ctgggcctcc caaatctacc ctggcatcaa ggtgaggcag   2340
ctgtgcaagc tgctgagggg caccaaggcc ctgactgagg tgatcccccct gactgaggag   2400
gctgagctgg agctggctga gaacagggag atcctgaagg agcctgtgca tggggtgtac   2460
tatgacccct ccaaggacct gattgctgag atccagaagc agggccaggg ccagtggacc   2520
taccaaatct accaggagcc cttcaagaac ctgaagactg gcaagtatgc caggatgagg   2580
ggggcccaca ccaatgatgt gaagcagctg actgaggctg tgcagaagat caccactgag   2640
tccattgtga tctggggcaa gacccccaag ttcaagctgc ccatccagaa ggagacctgg   2700
gagacctggt ggactgagta ctggcaggcc acctggatcc ctgagtggga gtttgtgaac   2760
accccccccc tggtgaagct gtggtaccag ctggagaagg agcccattgt gggggctgag   2820
accttctatg tggctggggc tgccaacagg gagaccaagc tgggcaaggc tggctatgtg   2880
accaacaggg gcaggcagaa ggtggtgacc ctgactgaca ccaccaacca gaagactgcc   2940
ctccaggcca tctacctggc cctccaggac tctggcctgg aggtgaacat tgtgactgcc   3000
tcccagtatg ccctgggcat catccaggcc cagcctgatc agtctgagtc tgagctggtg   3060
aaccagatca ttgagcagct gatcaagaag gagaaggtgt acctggcctg ggtgcctgcc   3120
cacaagggca ttgggggcaa tgagcaggtg gacaagctgg tgtctgctgg catcaggaag   3180
gtgctgttcc tggatggcat tgacaaggcc caggatgagc atgagaagta ccactccaac   3240
tggagggcta tggcctctga cttcaacctg ccccctgtgg tggctaagga gattgtggcc   3300
tcctgtgaca agtgccagct gaagggggag gccatgcatg ggcaggtgga ctgctcccct   3360
ggcatctggc agctggcctg cacccacctg gagggcaagg tgatcctggt ggctgtgcat   3420
gtggcctccg gctacattga ggctgaggtg atccctgctg agacaggcca ggagactgcc   3480
tacttcctgc tgaagctggc tggcaggtgg cctgtgaaga ccatccacac tgccaatggc   3540
tccaacttca ctggggccac agtgagggct gcctgctggt gggctggcat caagcaggag   3600
tttggcatcc cctacaaccc ccagtcccag gggggtggtgg cctccatgaa caaggagctg   3660
aagaagatca ttgggcaggt gagggaccag gctgagcacc tgaagacagc tgtgcagatg   3720
gctgtgttca tccacaactt caagaggaag gggggcatcg gggggctactc cgctggggag   3780
```

-continued aggattgtgg acatcattgc cacagacatc cagaccaagg agctccagaa gcagatcacc 3840
aagatccaga acttcagggt gtactacagg gactccagga accccctgtg gaagggccct 3900
gccaagctgc tgtggaaggg ggagggggct gtggtgatcc aggacaactc tgacatcaag 3960
gtggtgccca ggaggaaggc caagatcatc agggactatg gcaagcagat ggctggggat 4020
gactgtgtgg cctccaggca ggatgaggac taa 4053

<210> SEQ ID NO 35
<211> LENGTH: 1350
<212> TYPE: PRT
<213> ORGANISM: Artificial Sequence
<220> FEATURE:
<223> OTHER INFORMATION: Codon optimized gag-IA pol fusion

<400> SEQUENCE: 35

Met Gly Ala Arg Ala Ser Val Leu Ser Gly Gly Glu Leu Asp Lys Trp
1 5 10 15

Glu Lys Ile Arg Leu Arg Pro Gly Gly Lys Lys Lys Tyr Lys Leu Lys
20 25 30

His Ile Val Trp Ala Ser Arg Glu Leu Glu Arg Phe Ala Val Asn Pro
35 40 45

Gly Leu Leu Glu Thr Ser Glu Gly Cys Arg Gln Ile Leu Gly Gln Leu
50 55 60

Gln Pro Ser Leu Gln Thr Gly Ser Glu Glu Leu Arg Ser Leu Tyr Asn
65 70 75 80

Thr Val Ala Thr Leu Tyr Cys Val His Gln Lys Ile Asp Val Lys Asp
85 90 95

Thr Lys Glu Ala Leu Glu Lys Ile Glu Glu Glu Gln Asn Lys Ser Lys
100 105 110

Lys Lys Ala Gln Gln Ala Ala Ala Gly Thr Gly Asn Ser Ser Gln Val
115 120 125

Ser Gln Asn Tyr Pro Ile Val Gln Asn Leu Gln Gly Gln Met Val His
130 135 140

Gln Ala Ile Ser Pro Arg Thr Leu Asn Ala Trp Val Lys Val Val Glu
145 150 155 160

Glu Lys Ala Phe Ser Pro Glu Val Ile Pro Met Phe Ser Ala Leu Ser
165 170 175

Glu Gly Ala Thr Pro Gln Asp Leu Asn Thr Met Leu Asn Thr Val Gly
180 185 190

Gly His Gln Ala Ala Met Gln Met Leu Lys Glu Thr Ile Asn Glu Glu
195 200 205

Ala Ala Glu Trp Asp Arg Leu His Pro Val His Ala Gly Pro Ile Ala
210 215 220

Pro Gly Gln Met Arg Glu Pro Arg Gly Ser Asp Ile Ala Gly Thr Thr
225 230 235 240

Ser Thr Leu Gln Glu Gln Ile Gly Trp Met Thr Asn Asn Pro Pro Ile
245 250 255

Pro Val Gly Glu Ile Tyr Lys Arg Trp Ile Ile Leu Gly Leu Asn Lys
260 265 270

Ile Val Arg Met Tyr Ser Pro Thr Ser Ile Leu Asp Ile Arg Gln Gly
275 280 285

Pro Lys Glu Pro Phe Arg Asp Tyr Val Asp Arg Phe Tyr Lys Thr Leu
290 295 300

Arg Ala Glu Gln Ala Ser Gln Glu Val Lys Asn Trp Met Thr Glu Thr
305 310 315 320

-continued

```
Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Val Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Asn Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Lys Thr Thr Pro Ser Gln Lys Gln Glu Pro Ile Asp
465                 470                 475                 480

Lys Glu Leu Tyr Pro Leu Ala Ser Leu Arg Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Lys Val Lys Gln Trp Pro Leu
        515                 520                 525

Thr Glu Glu Lys Ile Lys Ala Leu Val Glu Ile Cys Thr Glu Met Glu
    530                 535                 540

Lys Glu Gly Lys Ile Ser Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
        595                 600                 605

Thr Val Leu Ala Val Gly Asp Ala Tyr Phe Ser Val Pro Leu Asp Glu
    610                 615                 620

Asp Phe Arg Lys Tyr Thr Ala Phe Thr Ile Pro Ser Ile Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Ser Ser Met Thr Lys Ile Leu Glu Pro
            660                 665                 670

Phe Arg Lys Gln Asn Pro Asp Ile Val Ile Tyr Gln Tyr Met Ala Ala
        675                 680                 685

Leu Tyr Val Gly Ser Asp Leu Glu Ile Gly Gln His Arg Thr Lys Ile
    690                 695                 700

Glu Glu Leu Arg Gln His Leu Leu Arg Trp Gly Leu Thr Thr Pro Asp
705                 710                 715                 720

Lys Lys His Gln Lys Glu Pro Pro Phe Leu Trp Met Gly Tyr Glu Leu
                725                 730                 735
```

-continued

```
His Pro Asp Lys Trp Thr Val Gln Pro Ile Val Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
    770                 775                 780

Leu Arg Gly Thr Lys Ala Leu Thr Glu Val Ile Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly Gln Gly Gln Trp Thr Tyr Gln Ile Tyr Gln Glu Pro Phe
        835                 840                 845

Lys Asn Leu Lys Thr Gly Lys Tyr Ala Arg Met Arg Gly Ala His Thr
    850                 855                 860

Asn Asp Val Lys Gln Leu Thr Glu Ala Val Gln Lys Ile Thr Thr Glu
865                 870                 875                 880

Ser Ile Val Ile Trp Gly Lys Thr Pro Lys Phe Lys Leu Pro Ile Gln
                885                 890                 895

Lys Glu Thr Trp Glu Thr Trp Trp Thr Glu Tyr Trp Gln Ala Thr Trp
            900                 905                 910

Ile Pro Glu Trp Glu Phe Val Asn Thr Pro Pro Leu Val Lys Leu Trp
        915                 920                 925

Tyr Gln Leu Glu Lys Glu Pro Ile Val Gly Ala Glu Thr Phe Tyr Val
    930                 935                 940

Ala Gly Ala Ala Asn Arg Glu Thr Lys Leu Gly Lys Ala Gly Tyr Val
945                 950                 955                 960

Thr Asn Arg Gly Arg Gln Lys Val Val Thr Leu Thr Asp Thr Thr Asn
                965                 970                 975

Gln Lys Thr Ala Leu Gln Ala Ile Tyr Leu Ala Leu Gln Asp Ser Gly
            980                 985                 990

Leu Glu Val Asn Ile Val Thr Ala Ser Gln Tyr Ala Leu Gly Ile Ile
        995                 1000                1005

Gln Ala Gln Pro Asp Gln Ser Glu Ser Glu Leu Val Asn Gln Ile Ile
    1010                1015                1020

Glu Gln Leu Ile Lys Lys Glu Lys Val Tyr Leu Ala Trp Val Pro Ala
1025                1030                1035                1040

His Lys Gly Ile Gly Gly Asn Glu Gln Val Asp Lys Leu Val Ser Ala
                1045                1050                1055

Gly Ile Arg Lys Val Leu Phe Leu Asp Gly Ile Asp Lys Ala Gln Asp
            1060                1065                1070

Glu His Glu Lys Tyr His Ser Asn Trp Arg Ala Met Ala Ser Asp Phe
        1075                1080                1085

Asn Leu Pro Pro Val Val Ala Lys Glu Ile Val Ala Ser Cys Asp Lys
    1090                1095                1100

Cys Gln Leu Lys Gly Glu Ala Met His Gly Gln Val Asp Cys Ser Pro
1105                1110                1115                1120

Gly Ile Trp Gln Leu Ala Cys Thr His Leu Glu Gly Lys Val Ile Leu
                1125                1130                1135

Val Ala Val His Val Ala Ser Gly Tyr Ile Glu Ala Glu Val Ile Pro
            1140                1145                1150

Ala Glu Thr Gly Gln Glu Thr Ala Tyr Phe Leu Leu Lys Leu Ala Gly
```

-continued

```
        1155                1160                1165

Arg Trp Pro Val Lys Thr Ile His Thr Ala Asn Gly Ser Asn Phe Thr
    1170                1175                1180

Gly Ala Thr Val Arg Ala Ala Cys Trp Trp Ala Gly Ile Lys Gln Glu
1185                1190                1195                1200

Phe Gly Ile Pro Tyr Asn Pro Gln Ser Gln Gly Val Val Ala Ser Met
                1205                1210                1215

Asn Lys Glu Leu Lys Lys Ile Ile Gly Gln Val Arg Asp Gln Ala Glu
            1220                1225                1230

His Leu Lys Thr Ala Val Gln Met Ala Val Phe Ile His Asn Phe Lys
        1235                1240                1245

Arg Lys Gly Gly Ile Gly Gly Tyr Ser Ala Gly Glu Arg Ile Val Asp
    1250                1255                1260

Ile Ile Ala Thr Asp Ile Gln Thr Lys Glu Leu Gln Lys Gln Ile Thr
1265                1270                1275                1280

Lys Ile Gln Asn Phe Arg Val Tyr Tyr Arg Asp Ser Arg Asn Pro Leu
                1285                1290                1295

Trp Lys Gly Pro Ala Lys Leu Leu Trp Lys Gly Glu Gly Ala Val Val
            1300                1305                1310

Ile Gln Asp Asn Ser Asp Ile Lys Val Val Pro Arg Arg Lys Ala Lys
        1315                1320                1325

Ile Ile Arg Asp Tyr Gly Lys Gln Met Ala Gly Asp Asp Cys Val Ala
    1330                1335                1340

Ser Arg Gln Asp Glu Asp
1345                1350
```

<210> SEQ ID NO 36
<211> LENGTH: 64
<212> TYPE: DNA
<213> ORGANISM: Artificial Sequence
<220> FEATURE:
<223> OTHER INFORMATION: Nucleotide sequence at junction between nef coding sequence and plasmid backbone of nef expression vector V1Jns/nef

<400> SEQUENCE: 36
caccccgagt actacaagga ctgctaaagc ccgggcagat ctgctgtgcc ttctagttgc 60
cagc 64

<210> SEQ ID NO 37
<211> LENGTH: 64
<212> TYPE: DNA
<213> ORGANISM: Artificial Sequence
<220> FEATURE:
<223> OTHER INFORMATION: Nucleotide sequence at junction between nef coding sequence and plasmid backbone of nef expression vector V1Jns/modified nef

<400> SEQUENCE: 37
caccccgagt actacaagga ctgctaaagc ccgggcagat ctgctgtgcc ttctagttgc 60
cagc 64

<210> SEQ ID NO 38
<211> LENGTH: 64
<212> TYPE: DNA
<213> ORGANISM: Artificial Sequence
<220> FEATURE:
<223> OTHER INFORMATION: Nucleotide sequence at junction between nef -continued

```
      coding sequence and plasmid backbone of nef expression
      vector V1Jns/modified nef fused to a leader
      sequence

<400> SEQUENCE: 38

caccccgagt actacaagga ctgctaaagc ccgggcagat ctgctgtgcc ttctagttgc      60

cagc                                                                   64
```